(12) United States Patent
Rajagopal et al.

(10) Patent No.: US 11,352,322 B2
(45) Date of Patent: Jun. 7, 2022

(54) CYCLOPROPYL-AMIDE COMPOUNDS AS DUAL LSD1/HDAC INHIBITORS

(71) Applicant: Jubilant Epicore LLC, Yardley, PA (US)

(72) Inventors: Sridharan Rajagopal, Yeshwanthpur Bangalore (IN); Mahanandeesha S. Hallur, Yeshwanthpur Bangalore (IN); Purushottam Dewang, Yeshwanthpur Bangalore (IN); Kannan Murugan, Yeshwanthpur Bangalore (IN); Durga Prasanna Kumar C. H., Yeshwanthpur Bangalore (IN); Pravin Iyer, Yeshwanthpur Bangalore (IN); Chandrika Mulakala, Yeshwanthpur Bangalore (IN); Dhanalakshmi Sivanandhan, Yeshwanthpur Bangalore (IN); Sreekala Nair, Yeshwanthpur Bangalore (IN); Mohd Zainuddin, Yeshwanthpur Bangalore (IN); Subramanyam Janardhan Tantry, Yeshwanthpur Bangalore (IN); Chandru Gajendran, Yeshwanthpur Bangalore (IN); Sriram Rajagopal, Yeshwanthpur Bangalore (IN)

(73) Assignee: Jubilant Epicore LLC, Yardley, PA (US)

( * ) Notice: Subject to any disclaimer, the term of this patent is extended or adjusted under 35 U.S.C. 154(b) by 525 days.

(21) Appl. No.: 16/098,341

(22) PCT Filed: May 8, 2017

(86) PCT No.: PCT/IN2017/050167
§ 371 (c)(1),
(2) Date: Nov. 1, 2018

(87) PCT Pub. No.: WO2017/195216
PCT Pub. Date: Nov. 16, 2017

(65) Prior Publication Data
US 2020/0308110 A1    Oct. 1, 2020

(30) Foreign Application Priority Data

May 9, 2016  (IN) .............................. 201641016129

(51) Int. Cl.
*C07D 205/12* (2006.01)
*A61P 35/00* (2006.01)
(Continued)

(52) U.S. Cl.
CPC ............ *C07D 205/12* (2013.01); *A61P 35/00* (2018.01); *C07C 235/56* (2013.01); *C07C 237/20* (2013.01); *C07C 259/08* (2013.01); *C07D 205/04* (2013.01); *C07D 209/44* (2013.01); *C07D 211/26* (2013.01); *C07D 217/18* (2013.01); *C07D 231/12* (2013.01); *C07D 233/64* (2013.01); *C07D 239/26* (2013.01); *C07D 249/04* (2013.01); *C07D 401/04* (2013.01); *C07D 401/14* (2013.01); *C07D 413/12* (2013.01); *C07D 413/14* (2013.01); *C07D 417/06* (2013.01); *C07D 417/12* (2013.01); *C07D 487/04* (2013.01); *C07D 495/04* (2013.01); *A61K 45/06* (2013.01)

(58) Field of Classification Search
CPC ..... C07C 53/18; C07C 259/06; C07C 237/20; C07D 261/08; C07D 239/26; C07D 401/04; C07D 487/04; C07D 401/12; C07D 211/26; C07D 413/12; C07D 401/14; C07D 231/12; C07D 249/04; C07D 205/12; C07D 205/04; C07D 403/12; C07D 417/12; C07D 233/64; C07D 217/14; C07D 217/18; C07D 495/04; C07D 209/44
See application file for complete search history.

(56) References Cited

U.S. PATENT DOCUMENTS

| 5,175,183 A | 12/1992 | Brooks et al. |
| 5,763,621 A | 6/1998 | Beckett et al. |
| 2017/0029366 A1 | 2/2017 | Cole et al. |

FOREIGN PATENT DOCUMENTS

| WO | 90/08545 A1 | 8/1990 |
| WO | 96/06074 A1 | 2/1996 |

(Continued)

OTHER PUBLICATIONS

Vaisburg. U.S. Appl. No. 62/296,193, filed Feb. 17, 2016. (Year: 2016).*

(Continued)

*Primary Examiner* — Noble E Jarrell
(74) *Attorney, Agent, or Firm* — Seed IP Law Group LLP

(57) ABSTRACT

The present disclosure describes novel compounds of the general Formula (I), their analogs, tautomeric forms, stereoisomers, polymorphs, hydrates, solvates, pharmaceutically acceptable salts, pharmaceutical compositions, metabolites, and prodrugs thereof. These compounds can inhibit both LSD and HDAC and are useful as therpeautic or ameliorating agent for diseases that are involved in cellular growth such as malignant tumors, schizophrenia, Alzheimer's disease, parkinson's disease and the like.

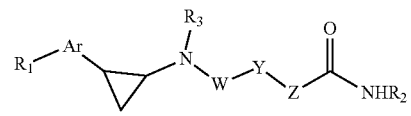

Formula I

7 Claims, 2 Drawing Sheets

(51) Int. Cl.
  C07C 235/56    (2006.01)
  C07C 237/20    (2006.01)
  C07C 259/08    (2006.01)
  C07D 205/04    (2006.01)
  C07D 211/26    (2006.01)
  C07D 217/18    (2006.01)
  C07D 231/12    (2006.01)
  C07D 233/64    (2006.01)
  C07D 239/26    (2006.01)
  C07D 249/04    (2006.01)
  C07D 401/04    (2006.01)
  C07D 401/14    (2006.01)
  C07D 413/12    (2006.01)
  C07D 413/14    (2006.01)
  C07D 417/06    (2006.01)
  C07D 417/12    (2006.01)
  C07D 487/04    (2006.01)
  C07D 495/04    (2006.01)
  C07D 209/44    (2006.01)
  A61K 45/06     (2006.01)

(56) References Cited

FOREIGN PATENT DOCUMENTS

| WO | WO 2005103003 | * | 11/2005 |
| WO | 2006/016680 A1 | | 2/2006 |
| WO | WO 2006/017216 A1 | | 2/2006 |
| WO | 2010/043721 A1 | | 4/2010 |
| WO | WO 2014/194280 A2 | | 12/2014 |
| WO | 2015/123465 A1 | | 8/2015 |
| WO | WO 2015/134973 A1 | | 9/2015 |
| WO | 2017/079476 A1 | | 5/2017 |
| WO | WO 2017079476 | * | 5/2017 |
| WO | 2017/116558 A1 | | 7/2017 |
| WO | WO 2017/116558 A1 | | 7/2017 |
| WO | 2017/157322 A1 | | 9/2017 |

OTHER PUBLICATIONS

Agrawala et al., "HDAC inhibitors: applications in oncology and beyond," *HOAJ Biology*, doi: 10.7243/2050-0874-2-2, 2013, 8 pages.

Clausen et al., "Inhibitors of histone demethylases," *Bioorganic & Medicinal Chemistry*, doi: 10.1016/j.bmc.2011.01.046, 2011, 12 pages.

Dankwardt et al., "Amino Acid Derived Sulfonamide Hydroxamates as Inhibitors of Procollagen C-Proteinase: Solid-Phase Synthesis of Ornithine Analogues," *Bioorganic & Medicinal Chemistry Letters 11*: 2085-2088, 2001.

Fiskus et al., "Highly effective combination of LSD1 (KDM1A) antagonist and pan-histone deacetylase inhibitor against human AML cells," *Leukemia* 28(11): 2155-2164. doi: 10.1038/leu.2014.119, Nov. 2014, 24 pages.

Gooden et al., "Facile synthesis of substituted trans-2-arylcyclopropylamine inhibitors of the human histone demethylase LSD1 and monoamine oxidases A and B," *Bioorg. Med. Chem. Lett.* 18(10): 3047-3051. doi:10.1016/j.bmcl.2008.01.003, May 15, 2008, 13 pages.

Højfeldt et al., "Histone lysine demethylases as targets for anticancer therapy," *Nature Reviews Drug Discovery*, AOP, published online Nov. 15, 2013; doi:10.1038/nrd4154, 14 pages.

Huang et al., "Crosstalk between lysine-specific demethylase 1 (LSD1) and histone deacetylases mediates antineoplastic efficacy of HDAC inhibitors in human breast cancer cells," *Carcinogenesis* 34(6): 1196-1207, 2013.

Jung et al., "Targeting histone methyltransferases and demethylases in clinical trials for cancer therapy," *Clinical Epigenetics 8*: 57, DOI 10.1186/s13148-016-0223-4, 2016, 16 pages.

Marks et al., "Histone Deacetylase Inhibitors: Inducers of Differentiation or Apoptosis of Transformed Cells," *Journal of the National Cancer Institute* 92(15): 1210-1216, Aug. 2, 2000.

Miyata et al., "Lysine Demethylases Inhibitors," *J. Med. Chem 54*: 8236-8250, 2011.

Singh et al., "Inhibition of LSD1 sensitizes glioblastoma cells to histone deacetylase inhibitors," *Neuro-Oncology* 13(8): 894-903, 2011.

Xu et al., "Palladium-Catalyzed Heck Reaction of Aryl Chlorides under Mild Conditions Promoted by Organic Ionic Bases," *J. Org. Chem 76*: 8036-8041, 2011.

Zhang et al., "Trend of Histone Deacetylase Inhibitors in Cancer Therapy: Isoform Selectivity or Multitargeted Strategy," *Medicinal Research Reviews*, published online in Wiley Online Library DOI 10.1002/med.21320, 2014, 21 pages.

International Search Report for International Application No. PCT/IN2017/050167, dated Oct. 27, 2017, 4 pages.

CAS Reg. Nos. 1880340-90-8, 1879286-53-9, 1869849-10-4, 1823059-14-8, 1624630-71-2, 1424537-01-8, 1375242-92-4, 1305331-60-5 1304215-09-5, 1228143-74-5, 876273-57-3, 2021. (5 pages).

* cited by examiner

CYCLOPROPYL-AMIDE COMPOUNDS AS DUAL LSD1/HDAC INHIBITORS

TECHNICAL FIELD

Described are novel derivatives of the Formula (I), their analogs, tautomeric forms, stereoisomers, geometrical isomers, polymorphs, hydrates, solvates, pharmaceutically acceptable salts, pharmaceutical compositions, metabolites, and prodrugs thereof.

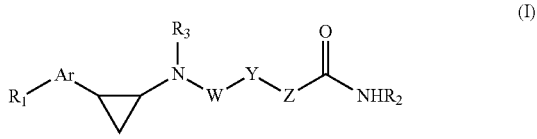

Also, described herein is the process for the preparation of the above said novel derivatives of the Formula (I), their analogs, stereoisomers, diastereomers, polymorphs, hydrates, solvates, pharmaceutically acceptable salts, pharmaceutical compositions, metabolites, prodrugs, and intermediates useful in the preparation of such compounds.

The compounds described herein are dual inhibitors of lysine specific demethylase (LSD) and histone deacetylase (HDAC) and also arrest cell growth in neoplastic cells, thereby inhibiting proliferation. These compounds can be used as prophylactic or therapeutic agents for treating cancer, schizophrenia, Alzheimer's disease, Parkinson's disease, and the like.

BACKGROUND

Transcriptional regulation is a major event in cell differentiation, proliferation and apoptosis. Transcriptional activation of a set of genes determines cellular function and is tightly regulated by a variety of factors. One of the regulatory mechanisms involved in this process is an alteration in the tertiary structure of DNA, which affects transcription factors to their target DNA regiments. Nucleosomal integrity is regulated by the acetylation status of the core histone, with the result being permissiveness to transcription. The regulations of transcription factor are thought to involve changes in the structure of chromatin. Changing the affinity of histone proteins for coiled DNA in the nucleosome alters the structure of chromatin. Hypoacetylated histones are believed to have greater affinity to the DNA and form a tightly bound DNA-histone complex and render the DNA inaccessible to transcriptional regulation. The acetylating status of the histone is governed by the balanced activities of the histone acetyl transferase (HAT) and histone deacetylase (HDAC).

Human histone deacetylases (HDACs) are classified into two distinct classes, the HDACs and sirtuins. The HDACs are divided into two subclasses based on their similarity to yeast histone deacetylases, RPD 3 (class I includes HDAC 1, 2, 3, and 8) and Hda 1 (class II includes HDAC 4, 6, 7, 9, and 10). All the HDACs have a highly conserved zinc dependent catalytic domain. There is growing evidence that the acetylation state of proteins and thus the HDAC enzyme family plays a crucial role in the modulation of several biological processes, including transcription and cell cycle. Several structural classes of HDAC inhibitors have been identified and are reviewed in Marks et al., J. Natl. Cancer Inst., 2000, 92, 1210-1215; L. Zhang, et. al., Medicinal Research Reviews, 2015, 35, 63-84; P. K. Agrawala, et. al., HOAJ Biology 2013, 2, 1-8. Other compounds that are able to inhibit HDAC activity are Trichostatin A (TSA), PXD1O1, Tropoxin (TPX), Sodium butyrate (NaB), Sodium valproate (VPA), Cyclic hydroxamic acid containing peptides (CHAPs), Depsipeptide FK-228, MGCDO103 and MS-275. The above mentioned inhibitors can also de-repress tumor suppressor genes (e.g. p21wafl/cf 1), resulting in antiproliferative effects in vitro and anti tumor effects in vivo. At present, there are four HDAC inhibitors that have been approved by FDA for the treatment of various cancers. Vorinostat, Isotdax and Belinostat have been approved for the treatment of Cutaneous T-Cell Lymphoma and panibinostat has been approved for the treatment of multiple myeloma.

Another group of enzymes known as lysine methyl transferases and lysine demethylases are involved in the modulation of histone methylation. Lysine demethylases (LSD1 and LSD2) are known to remove methyl group from mono and dimethylated Lys4 of histone H3 (H3K4me1/2) through flavin adenine dinucleotide (FAD) dependent enzymatic oxidation and releasing formaldehyde as the byproduct. LSD1 mediated demethylation is not restricted to histones; other non-histone substrates such as p53, STAT3, E2F1, and MYPT1 are also demethylated leading to a change in cellular functions. LSD1 is overexpressed in various cancer cells and tissues, neuroblastoma, prostate cancer, breast cancer, leukemia, lung cancer and bladder cancer cells. It is known that either inhibition of LSD1 with small molecule or by RNAi is associated with inhibition of cancer cell growth by modulating prosurvival gene expression and p53 transcriptional activity. Several novel irreversible inhibitors of LSD1 have been described in literature and two compounds ORY-1001 and GSK-2879552 have entered phase 1 clinical trial, (N. Miyata, et. al., J. Med. Chem, 54, 8236-8250, 2011; R. P. Clausen, et. al., Bioorg. Med. Chem., 19, 3625-3636, 2011; J. W. Hφfeldt, et. al., Nature Drug Discovery, 12, 917-930, 2013, Manfred Jung and et. al., Clinical Epigenetics (2016) 8:57).

Another recent report suggests that a cross talk between LSD1 and HDAC is associated with changes in gene expression that leads to growth inhibition and apoptosis (Huang et. al. Carcinogenesis, 34, 1196-1207, 2013). This and other similar studies suggest that the inhibition of both LSD1 and HDAC can exhibit synergyism in modulating gene expression and in inducing growth inhibition. Singh, et al., (Neuro-Oncology, 13, 894-903, 2011) have demonstrated that combined inhibition of LSD1 and HDAC can lead to cooperative regulation of key pathways of cell death in glioblastoma multiforme (GBM, a form of aggressive brain tumor). Fiskus, et al., (Leukemia, 1-10, 2014) have shown that combined treatment of LSD1 inhibitor SP2509 and HDAC inhibitor panobinostat was synergistically lethal against cultured and primary AML blasts. In mice engrafted with human AML cells, combined treatment of both SP2509 and panobinostat significantly improved the survival compared with either SP2509 or Panobinostat.

Cole, et al., have disclosed LSD1/HDAC dual inhibitors and their utility in treating various disease conditions or disorders (US2017/0029366).

Although, there are several chemotherapies and target therapies based drugs for cancer, an effective cure for cancer still remains elusive. Further, development of acquired resistance and disease relapse are major issues that still need to be addressed. Therefore, there is a need for novel mechanism-based approaches in the treatment of cancer, that would have a stronger effect on a signaling pathway and/or affect multiple pathways and mutually exclusive mechanisms in the cells. In this regard, novel dual inhibitors of LSD-1/HDAC will have better efficacy in treating multiple cancers compared to either treating with LSD-1 or HDAC inhibitors alone.

Objective

One objective herein is to provide a compound of Formula (I) their analogs, tautomeric forms, stereoisomers, polymorphs, solvates, intermediates, pharmaceutically acceptable salts, metabolites, and prodrugs thereof.

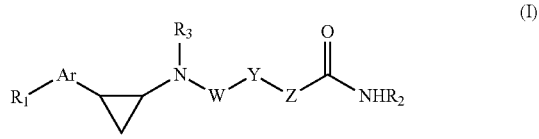

(I)

Another objective herein is to provide a pharmaceutical composition with the novel derivatives of the Formula (I).

Yet another objective herein is to provide a method of preventing or treating proliferative diseases by administering a therapeutic amount of novel compound of the Formula (I) or a pharmaceutically acceptable salt and/or prodrug.

SUMMARY

The present disclosure describes compound of Formula I

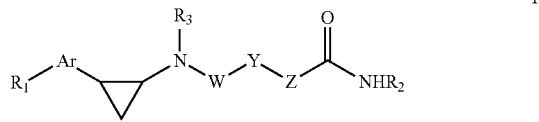

I their analogs, tautomeric forms, stereoisomers, polymorphs, solvates, intermediates, pharmaceutically acceptable salts, metabolites, and prodrugs thereof, wherein Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen, hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano; $R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION

Figure 1:
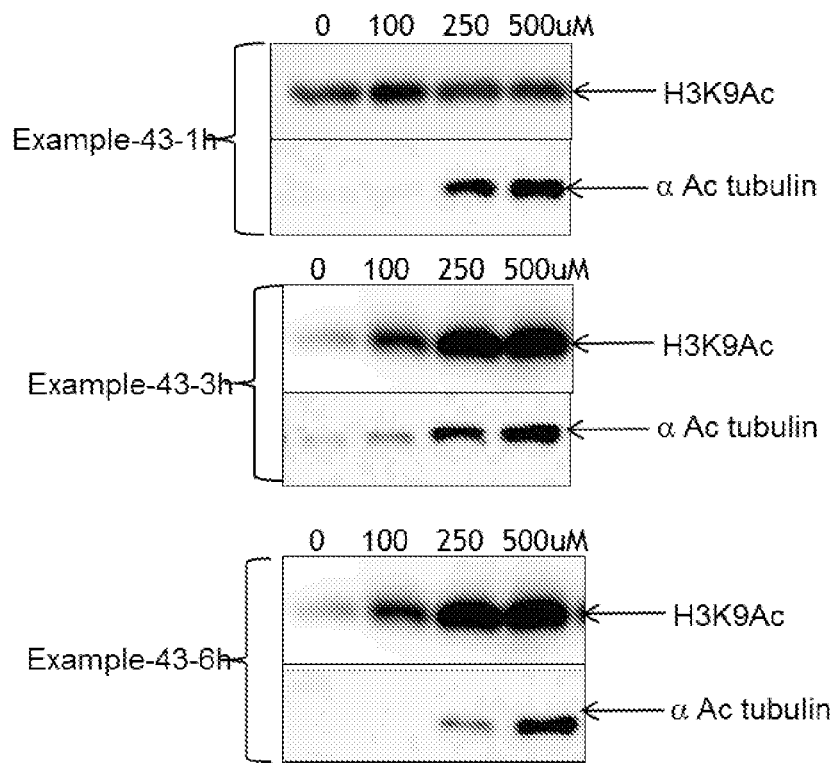
FIG. 1 depicts the modulation of Tubulin and Histone Acetylation in MM.1S cells, in accordance with an embodiment of the present disclosure.
Figure 2:
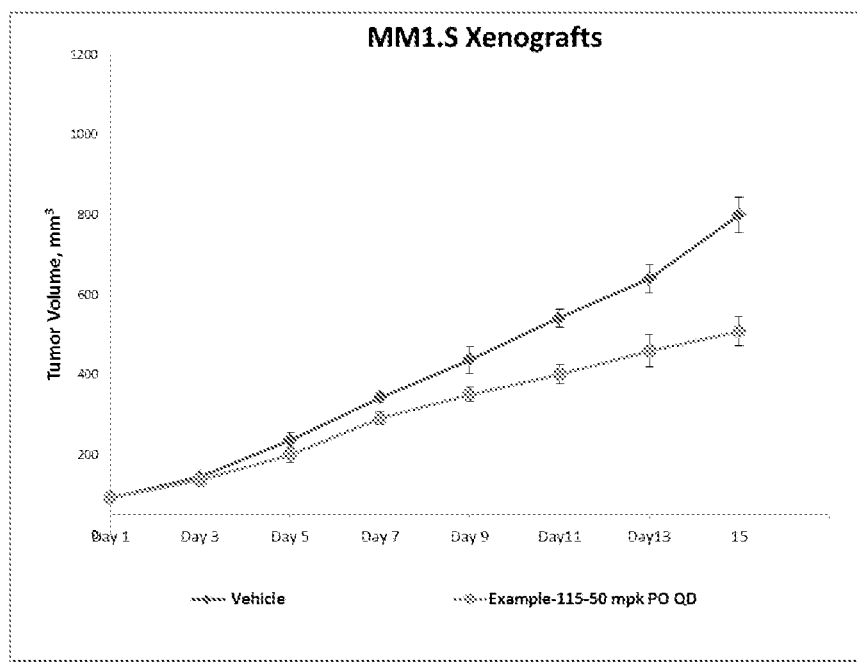
FIG. 2 depicts the efficacy study in multiple myeloma model, in accordance with an embodiment of the present disclosure.
Figure 3:
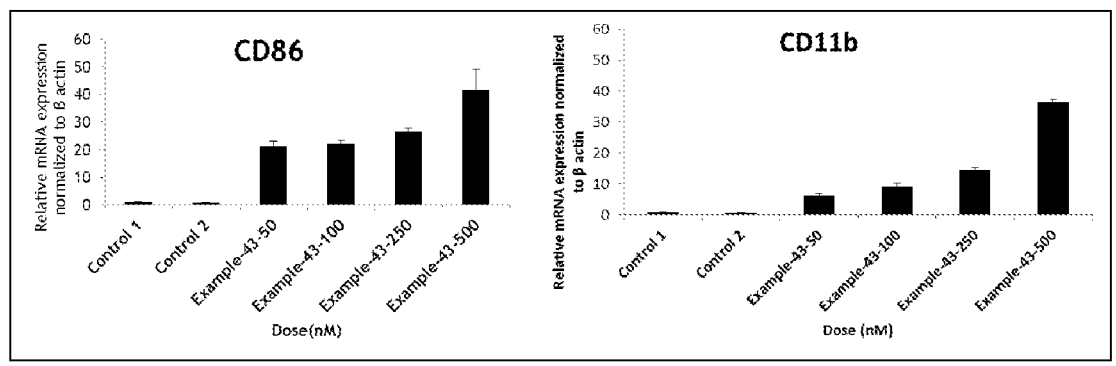
FIG. 3 depicts the modulation of CD86 and CD11b in MV411 cells, in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

Furthermore, the compound of Formula (I) can be its derivatives, analogs, tautomeric forms, stereoisomer's, diastereomers, geometrical isomers, polymorphs, solvates, intermediates, metabolites, prodrugs or pharmaceutically acceptable salts and compositions.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds. It is also understood that some isomeric form such as diastereomers, enantiomers and geometrical isomers can be separated by physical and/or chemical methods and by those skilled in the art. Pharmaceutically acceptable solvates may be hydrates or comprising of other solvents of crystallization such as alcohols, ether, and the like.

The term "solvate", as used herein, refers to a crystal lattice which contains solvent.

The term "hydrate" refers to a more specific form of solvate, wherein the solvent is water.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents, for example, include those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "prodrugs" refers to the precursor of the compound of Formula (I), which on administration undergoes chemical conversion by metabolic processes before becoming active pharmacological substances. In general, such prodrugs will be functional derivatives of a compound of the invention, which are readily convertible in vivo into a compound of the invention.

The term "alkyl" refers to straight or branched aliphatic hydrocarbon groups having the specified number of carbon atoms, which are attached to the rest of the molecule by a single atom, which may be optionally substituted by one or more substituents. Preferred alkyl groups include, without limitation, methyl, ethyl, n-propyl, isopropyl, butyl, isobutyl, t-butyl, pentyl, hexyl, heptyl, octyl and the like.

The term "aryl" refers to aromatic radicals having 6 to 14 carbon atoms, which may be optionally substituted by one or more substituents. Preferred aryl groups include, without limitation, phenyl, naphthyl, indanyl, biphenyl, and the like.

The term "arylalkyl" refers to an aryl group directly bonded to an alkyl group, which may be optionally substituted by one or more substituents. Preferred arylalkyl groups include, without limitation, $-CH_2C_6H_5$, $-C_2H_4C_6H_5$, and the like.

The term "heterocyclyl" refers to a heterocyclic ring radical which may be optionally substituted by one or more substituents. The heterocyclyl ring radical may be attached to the main structure at any heteroatom or carbon atom that results in the creation of a stable structure.

Furthermore, the term "heterocyclyl" refers to a stable 3 to 15 membered rings radical, which consists of carbon atoms and from one to five heteroatoms selected from nitrogen, phosphorus, oxygen and sulfur. For purposes of this invention the heterocyclic ring radical may be monocyclic, bicyclic or tricyclic ring systems, and the nitrogen, phosphorus, carbon, or sulfur atoms in the heterocyclic ring radical may be optionally oxidized to various oxidation states. In addition, the nitrogen atom may be optionally quaternized; and the ring radical may be partially or fully saturated. Preferred heterocyclyl groups include, without limitation, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, qunioxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl, and isochromanyl.

The term "heteroaryl" refers to an aromatic heterocyclic ring radical as defined above. The heteroaryl ring radical may be attached to the main structure at any heteroatom or carbon atom that results in the creation of stable structure.

The term "heteroarylalkyl" refers to a heteroaryl group directly bonded to an alkyl group, which may be optionally substituted by one or more substituents. Preferred heteroarylalkyl groups include, without limitation, —CH$_2$-pyridinyl, —C$_2$H$_4$-furyl and the like.

The term "fused heterocyclyl" refers to monocyclic or polycyclic ring, polycyclic ring system refers to a ring system containing 2 or more rings, preferably bicyclic or tricyclic rings, in which rings can be fused, bridged or spiro rings or any combinations thereof. A fused ring as used herein means that the two rings are linked to each other through two adjacent ring atoms common to both rings. The fused ring can contain 1-4 hetero atoms independently selected from N, O, and S. The rings can be either fused by nitrogen or —CH— group.

The term"bridged ring" as used herein means that a ring comprises a linker group (C(Rq)$_2$)p-linking together any two non-adjacent carbon or nitrogen atoms of the ring, where p is 1 or 2 and each independently is hydrogen or C$_{1-4}$ alkyl.

The term "cycloalkyl" refers to non-aromatic mono or polycyclic ring system of about 3 to 12 carbon atoms, which may be optionally substituted by one or more substituents. The polycyclic ring denotes hydrocarbon systems containing two or more ring systems with one or more ring carbon atoms in common i.e. a spiro, fused or bridged structures. Preferred cycloalkyl groups include, without limitation, cyclopropyl, cyclobutyl, cyclopentyl, cyclohexyl, cyclooctanyl, perhydronaphthyl, adamantyl, noradamantyl and norbornyl groups, bridged cyclic groups or spirobicyclic groups e.g spiro [4.4] non-2-yl and the like.

The term "alkoxy" refers to an alkyl group attached via an oxygen linkage to the rest of the molecule, which may be optionally substituted by one or more substituents. Preferred alkoxy groups include, without limitation, —OCH$_3$, —OC$_2$H$_5$ and the like.

The term "alkylthio" refers to an alkyl group attached via a sulfur linkage to the rest of the molecule, which may be optionally substituted by one or more substituents. Preferred alkylthio groups include, without limitation, —SCH$_3$, —SC$_2$H$_5$ and the like.

The term "alkylamino" refers to an alkyl group as defined above attached via amino linkage to the rest of the molecule, which may be optionally substituted by one or more substituents. Preferred alkylamino groups include, without limitation —NHCH$_3$, —N(CH$_3$)$_2$, and the like.

The term "alkenyl" refers to an aliphatic hydrocarbon group containing a carbon-carbon double bond and which may be straight or branched chain having about 2 to 10 carbon atoms, which may be optionally substituted by one or more substituents. Preferred alkenyl groups include, without limitation, ethenyl, 1-propenyl, 2-propenyl, iso-propenyl, 2-methyl-1-propenyl, 1-butenyl, 2-butenyl and the like.

The term "alkynyl" refers to a straight or branched hydrocarbyl radicals having at least one carbon-carbon triple bond and having in the range of 2-12 carbon atoms, which may be optionally substituted by one or more substituents. Preferred alkynyl groups include, without limitation, ethynyl, propynyl, butynyl and the like.

The term "alkylaryl" refers to an alkyl group directly bonded to an aryl group, which may be optionally substituted by one or more substituents. Preferred alkylaryl groups include, without limitation, —CH$_2$-phenyl, —C$_2$H$_4$-phenyl, C$_3$H$_6$-phenyl and the like.

The term "alkenylaryl" refers to an alkenyl group directly bonded to an aryl group, which may be optionally substituted by one or more substituents. Preferred alkenylaryl groups include, without limitation, —CH=CH-phenyl, —CH$_2$—CH=CH— phenyl and the like.

The term "arylalkenyl" refers to an aryl group directly bonded to an alkenyl group, which may be optionally substituted by one or more substituents. Preferred arylalkenyl groups include, without limitation, —C$_6$H$_5$—CH=CH—, —C$_6$H$_5$—CH=CH—CH$_2$ and the like.

The term "arylalkynyl" refers to an aryl group directly bonded to an alkynyl group, which may be optionally substituted by one or more substituents. Preferred arylalkenyl groups include, without limitation, —C$_6$H$_5$-ethynyl, —C$_6$H$_5$-propynyl, and the like The term "—CO-alkylaryl" refers to a carbonyl group directly attached to an alkylaryl group which may be optionally substituted by one or more substituents. Preferred "—CO-alkylaryl" groups include, without limitations, —CO—CH$_2$-phenyl, —CO—C$_2$H$_4$-phenyl and the like The term "—CO-alkenylaryl" refers to a carbonyl group directly attached to an alkenylaryl group which may be optionally substituted by one or more substituents. Preferred "—CO-alkenylaryl" groups include, without limitations, —CO—CH=CH-phenyl, —CO—CH$_2$—CH=CH-phenyl and the like.

The term "—CO-heterocyclyl" refers to a carbonyl group directly attached through the heteratom or carbon atom of a heterocyclyl group which may be optionally substituted by one or more substitutents. Preferred "—CO-heterocyclyl" groups include, without limitations, —CO-piperazinyl, —CO—N-piperdinyl (implies attachment is through the nitrogen of piperdinyl group), —CO—C-piperidinyl (implies the attachment is through the carbon of piperdinyl group) and the like The term "alkyl-O-aryl-" refers to an alkyl group attached to aryl through the oxygen linker which may be optionally substituted by one or more substitutents. Preferred groups without limitations include-(CH$_2$)$_2$—O-phenyl- and the like.

The term-"—SO$_2$alkylaryl-" refers to a —SO$_2$— group attached to alkylaryl group which may be optionally substituted by one or substitutents. Preferred '—SO$_2$alkylaryl-' groups include —SO$_2$—CH$_2$-Aryl and the like.

It is understood that included in the family of compounds of Formula (I) are isomeric forms including diastereoisomers, enantiomers, tautomers, and geometrical isomers in "E" or "Z" configurational isomer or a mixture of 'E' and 'Z' isomers. It is also understood that some isomeric form such as diastereomers, enantiomers and geometrical isomers can be separated by physical and/or chemical methods and by those skilled in the art.

Compounds disclosed herein may exist as single stereoisomers, racemates and or mixtures of enantiomers and/or diastereomers. All such single stereoisomers, racemates and mixtures thereof are intended to be within the scope of the subject matter described.

Compounds disclosed herein include isotopes of hydrogen, carbon, oxygen, fluorine, chlorine, iodine and sulfur which can be incorporated into the compounds, such as not limited to $^2H$ (D), $^3H$ (T), c $^{11}C$, $^{13}C$, $^{14}C$, $^{15}N$, $^{18}F$, $^{35}S$, $^{36}Cl$ and $^{125}I$. Compounds of this invention where in atoms were isotopically labeled for example radioisotopes such as $^3H$, $^{13}C$, $^{14}C$, and the like can be used in metabolic studies, kinetic studies and imaging techniques such as positron emission tomography used in understanding the tissue distribution of the drugs. Compounds of the invention where hydrogen is replaced with deuterium may improve the metabolic stability and pharmacokinetics properties of the drug such as in vivo half life. Compounds of the invention where isotopically labeled $^{18}F$ can be useful as PET imaging studies.

The phrase "pharmaceutically acceptable" refers to compounds or compositions that are physiologically tolerable and do not typically produce allergic or similar untoward reaction, including but not limited to gastric upset or dizziness when administered to subjects.

Pharmaceutically acceptable salts forming part of this invention include salts derived from inorganic bases such as like Li, Na, K, Ca, Mg, Fe, Cu, Zn and Mn and ammonium, substituted ammonium salts, aluminum salts and the like; salts of organic bases such as N, N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine and the like, salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, fumarates, citrates, succinates, palmoates, methanesulphonates, tosylates, benzoates, salicylates, hydroxynaphthoates, benzenesulfonates, ascorbates, glycerophosphates, ketoglutarates and the like.

Described herein are prodrugs of the compound of Formula (I), which on administration undergo chemical conversion by metabolic processes before becoming active pharmacological substances. In general, such prodrugs will be functional derivatives of a compound of the invention, which are readily convertible in vivo into a compound of the invention.

The compounds described herein can also be prepared in any solid or liquid physical form, for example the compound can be in a crystalline form, in amorphous form and have any particle size. Furthermore, the compound particles may be micronized or nanoized, or may be agglomerated, particulate granules, powders, oils, oily suspensions or any other form of solid or liquid physical forms.

The compounds described herein may also exhibit polymorphism. This invention further includes different polymorphs of the compounds of the present invention. The term polymorph refers to a particular crystalline state of a substance, having particular physical properties such as X-ray diffraction, IR spectra, melting point and the like.

The terms "histone deacetylase" and "HDAC" are intended to refer to any one of a family of enzymes that remove acetyl groups from the ε-amino groups of lysine residues at the N-terminus of a histone or tubulin. Unless otherwise indicated by context, the term "histone" is meant to refer to any histone protein, including H1, H2A, H2B, H3, H4 and H5, from any species. Human HDAC proteins or gene products include but are not limited to, HDAC-1, HDAC-2, HDAC-3, HDAC-4, HDAC-5, HDAC-6, HDAC-7, HDAC-8, HDAC-9, HDAC-10 and HDAC-11. The histone deacetylase can also be derived from a protozoal or fungal source.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone or tubulin. Preferably, such inhibition is specific, i.e. the histone deacetylase inhibitor reduces the ability of histone deacetylase to remove an acetyl group from a histone or tubulin at a concentration that is lower than the concentration of the inhibitor that is required to produce some other, unrelated biological effect.

The term "lysine demethylase inhibitor" or "inhibitor of lysine demethylase" is used to identify a compound, which is capable of interacting with a histone demethylase and inhibiting its activity, more particularly its enzymatic activity. Inhibiting histone demethylase enzymatic activity means reducing the ability of a histone demethylase to remove a methyl group from a histone. Inhibitor of histone demethylase involves removal either mono methyl or dimethyl or trimethyl group from histones. Preferably, such inhibition is specific, i.e. the histone demethylase inhibitor reduces the ability of histone demethylase to remove a methyl group from a histone at a concentration that is lower than the concentration of the inhibitor that is required to produce some other, unrelated biological effect.

The term 'Dual inhibitor of LSD-1/HDAC' is capable of removing acetyl group from histones or tublin and methyl group from histones. These inhibitors are capable of inhibiting more than one HDAC isozyme and all those isozymes are covered in addition to inhibiting LSD-1 activity The term dual inhibitor LSD1/HDAC6 is used to identify a compound which is capable of interacting selectively with HDAC6 enzymes in addition to having enzymatic interactions for LSD-1. Dual inhibitor of LSD-1/HDAC6 is capable of removing acetyl group from tublin and methyl group from histones.

The term dual inhibitor LSD1/HDAC1 is used to identify a compound which is capable of interacting selectively with HDAC1 enzymes in addition to having enzymatic interactions for LSD-1. Dual inhibitor of LSD-1/HDAC 1 is capable of removing acetyl group from histones and methyl group from histones.

The term dual inhibitor LSD1/HDAC8 is used to identify a compound which is capable of interacting selectively with HDAC8 enzymes in addition to having enzymatic interactions for LSD-1. Dual inhibitor of LSD-1/HDAC8 is capable of removing acetyl group from histones and methyl group from histones.

A term once described, the same meaning applies for it, throughout the patent.

In an embodiment of the present invention, there is provided a compound of Formula I

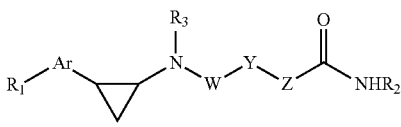

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —$OR_7$, aniline, amino $C_{5-6}$ aryl, and amino $C_{1-6}$ heteroaryl,
wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In another embodiment, the invention provides compound of Formula I

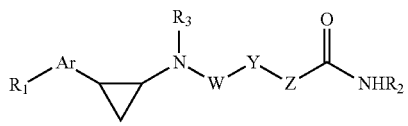

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, and substituted or unsubstituted $C_{1-8}$ alkyl;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$ alkylaryl, $C_{7-12}$ alkenylaryl, $C_{7-15}$ arylalkenyl, $C_{2-12}$ alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen, hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ hetroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclcyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclcyl, oxo (=O), $C_{3-8}$ cycloalkyl, halogen, OH, amino, and cyano;

$R_3$ is selected from the group consisting of hydrogen, and substituted or unsubstituted $C_{1-8}$ alkyl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected the group consisting of $C_{1-8}$ alkyl, $C_{5-6}$ aryl, $C_{1-6}$ heteroaryl, $C_{3-8}$cycloalkyl, and $C_{2-10}$ heterocyclyl.

In yet another embodiment, the invention relates to compound of Formula I

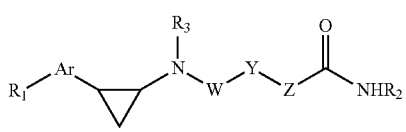

their analogs, tautomeric forms, stereoisomers, polymorphs, solvates, intermediates, pharmaceutically acceptable salts, metabolites, and prodrugs thereof;
wherein
Ar is selected from the group consisting of $C_{5-6}$ aryl, and $C_{2-10}$ heterocyclyl with heteroatoms selected from N, O, S;
W represents a bond or CR$_4$R$_5$, wherein
$R_4$ and $R_5$ are independently selected from the group consisting of hydrogen, and substituted or unsubstituted $C_{1-8}$ alkyl;
Y is a bond or is selected from the group consisting of substituted or unsubstituted $C_{1-8}$ alkyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclcyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$ alkylaryl, $C_{7-12}$ alkenylaryl, $C_{7-15}$ arylalkenyl, $C_{2-12}$ alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl or O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen, hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclcyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclcyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl;

wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided compound of Formula I

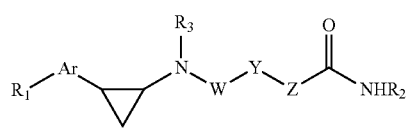

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, $C_{1-6}$ heteroaryl, and $C_{2-10}$ heterocyclyl with heteroatoms selected from N, O, S;
W represents a bond or CR$_4$R$_5$, wherein
$R_4$ and $R_5$ is hydrogen;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$ alkylaryl, $C_{7-12}$ alkenylaryl, $C_{7-15}$ arylalkenyl, $C_{2-12}$ alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclycl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl or O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, —C(O)R$_b$, —C(O)NR$_a$R$_b$, wherein R$_a$, and R$_b$ is independently selected from the group consisting of hydrogen, $C_{1-8}$ alkyl, and $C_{5-6}$ aryl; wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, oxo (=O), halogen, OH, amino, and cyano;

$R_3$ is hydrogen;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$alkyl, $C_{5-6}$aryl, $C_{2-10}$ heterocyclyl and —COR$_8$, wherein $R_8$ is selected the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In another embodiment, the invention relates to compound of Formula I

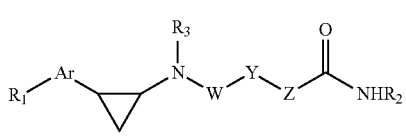

I their analogs, tautomeric forms, stereoisomers, polymorphs, solvates, intermediates, pharmaceutically acceptable salts, metabolites, and prodrugs thereof;
wherein
Ar is selected from the group consisting of $C_{5-6}$ aryl, and $C_{2-10}$ heterocyclyl with heteroatoms selected from N, O, S;
W represents a bond or CR$_4$R$_5$, wherein
$R_4$ and $R_5$ is hydrogen;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclcyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{7-12}$ alkylaryl, $C_{7-15}$ arylalkenyl, $C_{2-12}$ alkylheteroaryl, —CO— $C_{7-12}$alkylaryl, —CO—$C_{7-12}$alkenylaryl, —CONR$_6$— $C_{1-8}$alkyl, $C_{5-6}$aryl, $C_{1-6}$heteroaryl, —CO—$C_{2-10}$ heterocyclyl, —NR$_6$—$C_{5-6}$ aryl, —NR$_6$—$C_{1-6}$heteroaryl, —O—$C_{5-6}$ aryl, O—$C_{1-6}$ heteroaryl, —CONR$_6$—$C_{7-12}$ alkylaryl, —SO$_2$—$C_{5-6}$ aryl, —SO$_2$—$C_{7-12}$ alkylaryl, and —NR$_6$SO$_2$—$C_{7-12}$ alkylaryl;

$R_6$ is selected from the group consisting of hydrogen, and $C_{1-8}$ alkyl;

$R_1$ is selected from the group consisting of hydrogen, halogen, hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl,
wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein $R_8$ is selected the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In yet another embodiment, the invention relates to compound of Formula I

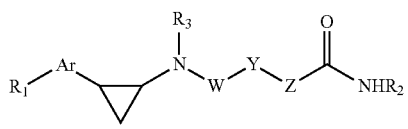

I their analogs, tautomeric forms, stereoisomers, polymorphs, solvates, intermediates, pharmaceutically acceptable salts, metabolites, and prodrugs thereof;
wherein
Ar is selected from the group consisting of $C_{5-6}$ aryl, and $C_{2-10}$ heterocyclyl with heteroatoms selected from N, O, S;
W represents a bond or CR$_4$R$_5$, wherein
$R_4$ and $R_5$ is hydrogen;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{7-12}$ alkylaryl, $C_{7-15}$ arylalkenyl, $C_{2-12}$ alkylheteroaryl, —CO—$C_{7-12}$ alkylaryl, —CO—$C_{7-12}$ alkenylaryl, —CONR$_6$—$C_{1-8}$ alkyl, $C_{5-6}$ aryl, $C_{1-6}$ heteroaryl, —CO—$C_{2-10}$ heterocyclyl, —NR$_6$—$C_{5-6}$ aryl, —NR$_6$—$C_{1-6}$ heteroaryl, —O—$C_{5-6}$ aryl, —O—$C_{1-6}$ heteroaryl, —CONR$_6$—$C_{7-12}$ alkylaryl, —SO$_2$—$C_{5-6}$ aryl, —SO$_2$—$C_{7-12}$ alkylaryl, and —NR$_6$SO$_2$—$C_{7-12}$ alkylaryl;

$R_6$ is selected from the group consisting of hydrogen, and $C_{1-8}$ alkyl;

$R_1$ is selected from the group consisting of hydrogen, halogen, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, —C(O)R$_b$, —C(O)NR$_a$R$_b$, wherein R$_a$, and R$_b$ is independently selected from the group consisting of hydrogen, $C_{1-8}$ alkyl, and $C_{5-6}$ aryl; wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, oxo (=O), halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment, there is provided compound of Formula I

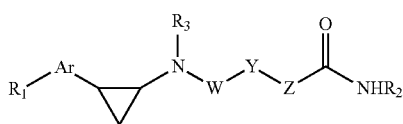

I their analogs, tautomeric forms, stereoisomers, polymorphs, solvates, intermediates, pharmaceutically acceptable salts, metabolites, and prodrugs thereof;
wherein
Ar is selected from the group consisting of $C_{5-6}$ aryl, and $C_{2-10}$ heterocyclyl with heteroatoms selected from N, O, S;
W represents a bond or CR$_4$R$_5$, wherein
$R_4$ and $R_5$ is hydrogen;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{7-12}$ alkylaryl, $C_{7-15}$ arylalkenyl, $C_{2-12}$ alkylheteroaryl, —CO—$C_{7-12}$ alkylaryl, —CO—$C_{7-12}$ alkenylaryl, —CONR$_6$—$C_{1-8}$ alkyl, $C_{5-6}$ aryl, $C_{1-6}$ heteroaryl, —CO—$C_{2-10}$ heterocyclyl, —NR$_6$—$C_{5-6}$ aryl, —NR$_6$—$C_{1-6}$ heteroaryl, —O—$C_{5-6}$ aryl, —O—$C_{1-6}$ heteroaryl, —CONR$_6$—$C_{7-12}$ alkylaryl, —SO$_2$—$C_{5-6}$ aryl, —SO$_2$—$C_{7-12}$ alkylaryl, and —NR$_6$SO$_2$—$C_{7-12}$ alkylaryl;

$R_6$ is selected from the group consisting of hydrogen, and $C_{1-8}$ alkyl;

$R_1$ is selected from the group consisting of hydrogen, halogen, hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, —NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is hydrogen;
$R_2$ is selected from the group consisting of —OR$_7$, and aniline;
wherein aniline is optionally substituted with one or more of the groups selected from $C_{1-8}$ alkyl, halogen, OH, amino, and cyano;
$R_7$ is selected from the group consisting of hydrogen, and $C_{1-8}$ alkyl.

In another embodiment, the invention relates to compound of Formula I

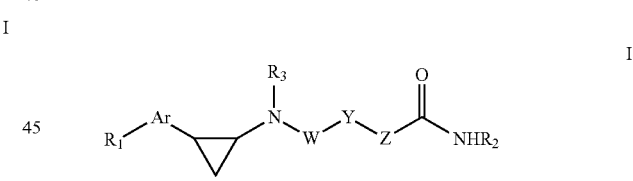

I their analogs, tautomeric forms, stereoisomers, polymorphs, solvates, intermediates, pharmaceutically acceptable salts, metabolites, and prodrugs thereof;
wherein
Ar is selected from the group consisting of $C_{5-6}$ aryl, and $C_{2-10}$ heterocyclyl with heteroatoms selected from N, O, S;
W represents a bond or CR$_4$R$_5$, wherein
$R_4$ and $R_5$ is hydrogen;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{7-12}$ alkylaryl, $C_{7-15}$ arylalkenyl, $C_{2-12}$ alkylheteroaryl, —CO—$C_{7-12}$ alkylaryl, —CO—$C_{7-12}$ alkenylaryl, —CONR$_6$—C$_{1-8}$ alkyl, C$_{5-6}$ aryl, C$_{1-6}$ heteroaryl, —CO—C$_{2-10}$ heterocyclyl, —NR$_6$—C$_{5-6}$ aryl, —NR$_6$—C$_{1-6}$ heteroaryl, —O—C$_{5-6}$ aryl, —O—C$_{1-6}$ heteroaryl, —CONR$_6$—C$_{7-12}$ alkylaryl, —SO$_2$—C$_{5-6}$ aryl, —SO$_2$—C$_{7-12}$ alkylaryl, and —NR$_6$SO$_2$—C$_{7-12}$ alkylaryl;

R$_6$ is selected from the group consisting of hydrogen, and C$_{1-8}$ alkyl;

R$_1$ is selected from the group consisting of hydrogen, halogen, hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ hetroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is hydrogen;

R$_2$ is selected from the group consisting of —OR$_7$, and aniline;

wherein aniline is optionally substituted with one or more of the groups selected from C$_{1-8}$ alkyl, halogen, OH, amino, and cyano.

In yet another embodiment, the invention relates to compound of Formula I

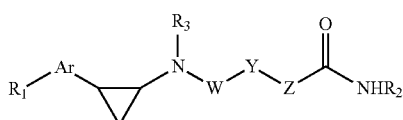

I their analogs, tautomeric forms, stereoisomers, polymorphs, solvates, intermediates, pharmaceutically acceptable salts, metabolites, and prodrugs thereof;
wherein
Ar is selected from the group consisting of C$_{5-6}$ aryl, and C$_{2-10}$ heterocyclyl with heteroatoms selected from N, O, S;
W represents a bond or CR$_4$R$_5$, wherein
R$_4$ and R$_5$ is hydrogen;
Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;
wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (=O), C$_{3-8}$ cycloalkyl, halogen, OH, and cyano;
Z represents a bond or is selected from the group consisting of C$_{1-8}$ alkyl, C$_{1-8}$ alkenyl, C$_{7-12}$-alkylaryl, C$_{7-15}$-arylalkenyl, C$_{2-12}$-alkylheteroaryl, —CO—C$_{7-12}$alkylaryl, —CO—C$_{7-12}$alkenylaryl, —CONR$_6$—C$_{1-8}$ alkyl, C$_{5-6}$ aryl, C$_{1-6}$ heteroaryl, —CO—C$_{2-10}$ heterocyclyl, —NR$_6$—C$_{5-6}$ aryl, —NR$_6$—C$_{1-6}$ heteroaryl, —O—C$_{5-6}$ aryl, —O—C$_{1-6}$ heteroaryl, —CONR$_6$—C$_{7-12}$ alkylaryl, —SO$_2$—C$_{5-6}$ aryl, —SO$_2$—C$_{7-12}$ alkylaryl, and —NR$_6$SO$_2$—C$_{7-12}$ alkylaryl;

R$_6$ is selected from the group consisting of hydrogen, and C$_{1-8}$ alkyl;

R$_1$ is selected from the group consisting of hydrogen, halogen, hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is hydrogen;
R$_2$ is selected from the group consisting of —OR$_7$, R$_7$ is selected from the group consisting of hydrogen, and C$_{1-8}$ alkyl.

In an embodiment of the present invention, there is provided a compound of Formula I

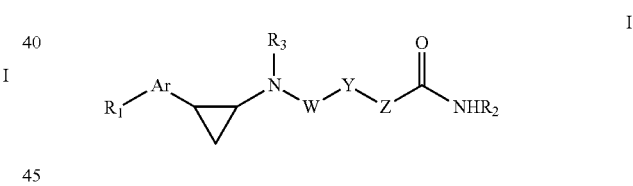

I their analogs, tautomeric forms, stereoisomers, polymorphs, solvates, intermediates, pharmaceutically acceptable salts, metabolites, and prodrugs thereof;
wherein
Ar is selected from the group consisting of C$_{5-6}$aryl, and C$_{2-10}$heterocyclyl with heteroatoms selected from N, O, S;
W represents a bond or CR$_4$R$_5$, wherein
R$_4$ and R$_5$ is hydrogen;
Y is a bond or is selected from the group consisting of substituted or unsubstituted C$_{1-8}$alkyl, C$_{1-8}$alkenyl, C$_{1-8}$alkynyl, C$_{5-6}$aryl, C$_{1-6}$heteroaryl, C$_{2-10}$heterocyclyl, C$_{3-8}$cycloalkyl, —CO—, and —CO—C$_{2-10}$heterocyclyl;
wherein C$_{1-8}$alkyl, C$_{5-6}$aryl, C$_{1-6}$heteroaryl, C$_{2-10}$heterocyclyl, C$_{3-8}$cycloalkyl, is optionally substituted with one or more of the groups selected from hydrogen, C$_{1-6}$ alkyl, oxo (=O), C$_{3-8}$ cycloalkyl, halogen, OH, and cyano;
Z represents a bond or is selected from the group consisting of C$_{1-8}$alkyl, C$_{1-8}$alkenyl, C$_{7-12}$-alkylaryl, C$_{7-15}$-arylalkenyl, C$_{2-12}$-alkylheteroaryl, —CO—C$_{7-12}$alkylaryl, —CO—C$_{7-12}$alkenylaryl, —CONR$_6$—C$_{1-8}$alkyl, C$_{5-6}$aryl, C$_{1-6}$heteroaryl, —CO—C$_{2-10}$heterocyclyl, —NR$_6$—C$_{5-6}$aryl, —NR$_6$—C$_{1-6}$heteroaryl, —O—C$_{5-6}$aryl, —O—C$_{1-6}$heteroaryl, —CONR$_6$—C$_{7-12}$alkylaryl, —SO$_2$—C$_{5-6}$aryl, —SO$_2$—C$_{7-12}$alkylaryl, and —NR$_6$SO$_2$—C$_{7-12}$alkylaryl;

R$_6$ is selected from the group consisting of hydrogen, and C$_{1-8}$ alkyl;

R$_1$ is selected from the group consisting of hydrogen, halogen, hydroxy, nitro, cyano, azido, nitroso, oxo (=O), thioxo (=S), —SO$_2$—, amino, hydrazino, formyl, C$_{1-8}$alkyl, C$_{1-8}$haloalkyl, C$_{1-8}$alkoxy, C$_{1-8}$haloalkoxy, C$_{7-12}$arylalkoxy, C$_{3-8}$cycloalkyl, C$_{3-8}$cycloalkyloxy, C$_{5-6}$aryl, C$_{2-10}$heterocyclyl, C$_{1-6}$heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$alkyl, C$_{3-8}$cycloalkyl, C$_{5-6}$aryl, C$_{7-15}$arylalkyl, C$_{2-10}$heterocyclyl, C$_{1-6}$heteroaryl, and C$_{2-12}$heteroarylalkyl with heteroatoms selected from N, O, S;

wherein C$_{7-12}$arylalkoxy, C$_{1-8}$alkyl, C$_{5-6}$aryl, C$_{1-6}$heteroaryl, C$_{2-10}$heterocyclyl, C$_{3-8}$cycloalkyl, is optionally substituted with one or more of the groups selected from hydrogen, C$_{1-6}$ alkyl, C$_{5-6}$aryl, C$_{1-6}$heteroaryl, C$_{2-10}$heterocyclyl, oxo (=O), C$_{3-8}$ cycloalkyl, halogen, OH, amino, and cyano;

R$_3$ is hydrogen;

R$_2$ is selected from the group consisting of aniline, amino C$_{5-6}$aryl, and amino C$_{1-6}$heteroaryl, wherein aniline, amino C$_{5-6}$aryl, and amino C$_{1-6}$heteroaryl, is optionally substituted with one or more of the groups selected from C$_{1-8}$ alkyl, halogen, OH, amino, and cyano.

In an embodiment of the present invention, there is provided a compound of Formula I

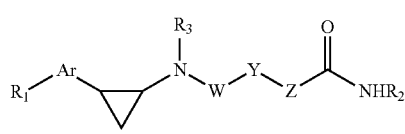

their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted C$_{5-6}$aryl, C$_{1-6}$ heteroaryl, and C$_{2-10}$ heterocyclyl with heteroatoms selected from N, O, S;

W represents a bond or CR$_4$R$_5$, wherein

R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;

Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;

wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (=O), C$_{3-8}$ cycloalkyl, halogen, OH, and cyano;

Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkylaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of

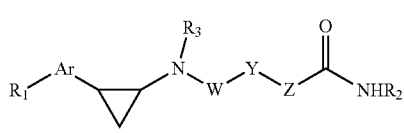

their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted C$_{5-6}$aryl, C$_{1-6}$ heteroaryl, and C$_{2-10}$ heterocyclyl with heteroatoms selected from N, O, S;

W represents a bond or CR$_4$R$_5$, wherein
R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;
Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;
wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (═O), C$_{3-8}$ cycloalkyl, halogen, OH, and cyano;
Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkylaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;
R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;
R$_1$ is selected from the group consisting of hydrogen, halogen hydroxy, nitro, cyano, azido, nitroso, oxo (═O), thioxo (═S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;
wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (═O), C$_{3-8}$ cycloalkyl, halogen, OH, amino, and cyano;
R$_3$ is selected from the group consisting of hydrogen, substituted or unsubstituted C$_{1-8}$ alkyl, and C$_{5-6}$ aryl;
R$_2$ is selected from the group consisting of —OR$_7$, aniline, amino C$_{5-6}$ aryl, and amino C$_{1-6}$ heteroaryl,
wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;
R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of

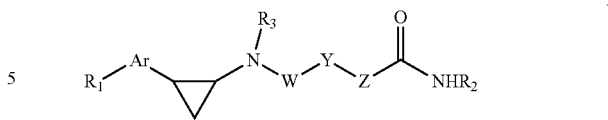

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$ aryl, C$_{1-6}$ heteroaryl, and C$_{2-10}$ heterocyclyl with heteroatoms selected from N, O, S;
W represents a bond or CR$_4$R$_5$, wherein
R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;
Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;
wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (═O), C$_{3-8}$ cycloalkyl, halogen, OH, and cyano;
Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkylaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;
R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;
R$_1$ is selected from the group consisting of hydrogen, halogen hydroxy, nitro, cyano, azido, nitroso, oxo (═O), thioxo (═S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;
wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

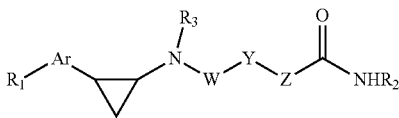

I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$ aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$— $C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$— $C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$— $C_{7-12}$ alkylaryl, $C_{1-8}$ alkyl-$CONR_6$—$C_{5-6}$ aryl, and O—CO—$NR_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

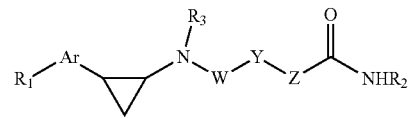

I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$— $C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

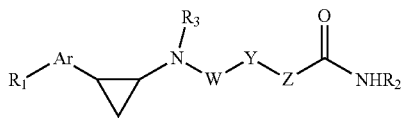

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or CR$_4$R$_5$, wherein
R$_4$ and R$_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

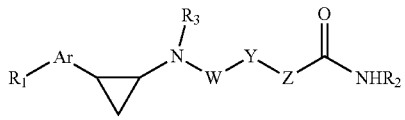

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$— $C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$— $C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$— $C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of halogen, hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$ R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S) R$_b$—, —SONR$_a$R$_b$—, —SO$_2$NR$_a$R$_b$—, —OR$_a$, —OR$_a$C (O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —OR$_7$, aniline, amino $C_{5-6}$ aryl, and amino $C_{1-6}$ heteroaryl,
wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —COR$_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

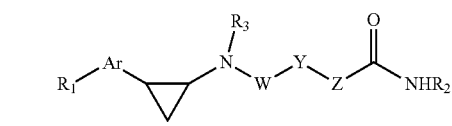

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$— $C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$— $C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$— $C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen, hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

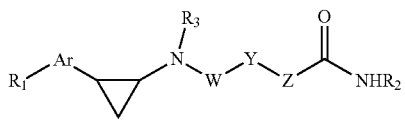

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, $C_{1-6}$ heteroaryl, and $C_{2-10}$ heterocyclyl with heteroatoms selected from N, O, S;

W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—OC—$C_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen, hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

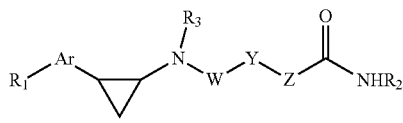

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (═O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

R$_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

R$_1$ is selected from the group consisting of hydrogen, halogen, hydroxy, nitro, cyano, azido, nitroso, oxo (═O), thioxo (═S), —SO$_2$—, amino, hydrazino, formyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (═O), $C_{3-8}$ cycloalkyl, halogen, OH, amino, and cyano;

R$_3$ is selected from the group consisting of hydrogen, substituted or unsubstituted $C_{1-8}$ alkyl, and $C_{5-6}$ aryl;

R$_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

R$_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

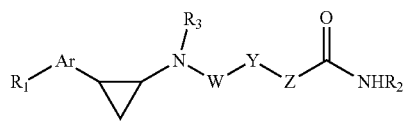

I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{1-6}$ heteroaryl, and $C_{2-10}$ heterocyclyl with heteroatoms selected from N, O, S;

W represents a bond or CR$_4$R$_5$, wherein

R$_4$ and R$_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (═O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

R$_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

R$_1$ is selected from the group consisting of hydrogen, halogen hydroxy, nitro, cyano, azido, nitroso, oxo (═O), thioxo (═S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (═O), $C_{3-8}$ cycloalkyl, halogen, OH, amino, and cyano;

R$_3$ is selected from the group consisting of hydrogen, substituted or unsubstituted $C_{1-8}$ alkyl, and $C_{5-6}$ aryl;

R$_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

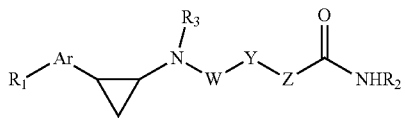

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen, hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

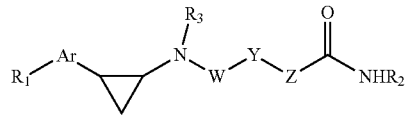

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, and $C_{1-6}$ heteroaryl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

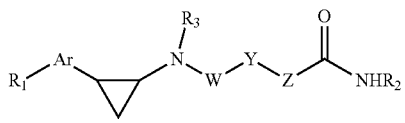

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

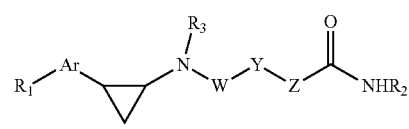

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_aR_b$, —C(S)NR$_aR_b$, —NR$_a$C(O)NR$_bR_c$, NR$_a$C(S)NR$_bR_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_aR_b$—, —SO$_2$NR$_aR_b$—, —OR$_a$, —OR$_a$C(O)OR$_b$—, —OC(O)NR$_aR_b$, OC(O)R$_a$, —OC(O)NR$_aR_b$—, —R$_a$NR$_bR_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, and $C_{5-6}$ aryl;
$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.
In an embodiment of the present invention, there is provided a compound of Formula I

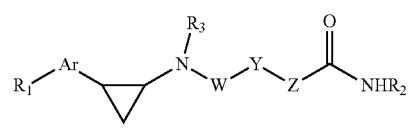

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_aR_b$, —C(S)NR$_aR_b$, —NR$_a$C(O)NR$_bR_c$, NR$_a$C(S)NR$_bR_c$, —N(R$_a$)SOR$_b$, —N(R$_a$)SO$_2$R$_b$, —NR$_a$C(O)OR$_b$, —NR$_aR_b$, —NR$_a$C(O)R$_b$—, —NR$_a$C(S)R$_b$—, —SONR$_aR_b$—, —SO$_2$NR$_aR_b$—, —OR$_a$, —OR$_a$C(O)OR$_b$—, —OC(O)NR$_aR_b$, OC(O)R$_a$, —OC(O)NR$_a$R$_b$—, —R$_a$NR$_b$R$_c$—, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (═O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

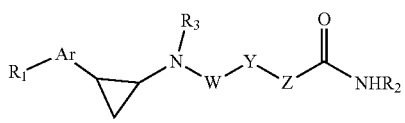

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$ aryl, C$_{1-6}$ heteroaryl, and C$_{2-10}$ heterocyclyl with heteroatoms selected from N, O, S;
W represents a bond or CR$_4$R$_5$, wherein
R$_4$ and R$_5$ are independently selected from the group consisting of substituted or unsubstituted C$_{1-8}$ alkyl, C$_{5-6}$ aryl, and C$_{1-6}$ heteroaryl with heteroatoms selected from N, O, S;
Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;
wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (═O), C$_{3-8}$ cycloalkyl, halogen, OH, and cyano;
Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkylaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (═O), thioxo (═S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (═O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl,
wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

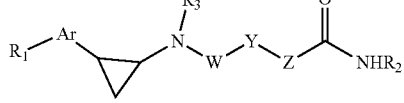

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$aryl, C$_{1-6}$ heteroaryl, and C$_{2-10}$ heterocyclyl with heteroatoms selected from N, O, S;
W represents a bond or CR$_4$R$_5$, wherein
R$_4$ and R$_5$ are independently selected from the group consisting of hydrogen, C$_{5-6}$ aryl, and C$_{1-6}$ heteroaryl with heteroatoms selected from N, O, S;
Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_8$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

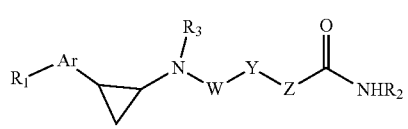

I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or CR$_4$R$_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

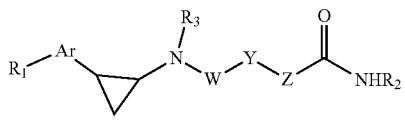

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (═O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (═O), thioxo (═S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (═O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —$OR_7$, aniline, amino $C_{5-6}$ aryl, and amino $C_{1-6}$ heteroaryl,
wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

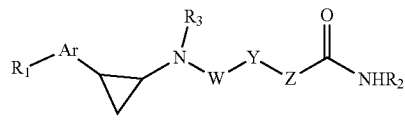

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (═O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

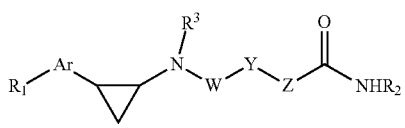

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$aryl, C$_{1-6}$ heteroaryl, and C$_{2-10}$ heterocyclyl with heteroatoms selected from N, O, S;
W represents a bond or CR$_4$R$_5$, wherein
R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;
Y is a bond or is selected from the group consisting of substituted or unsubstituted C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;

wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (=O), C$_{3-8}$ cycloalkyl, halogen, OH, and cyano;
Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkylaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

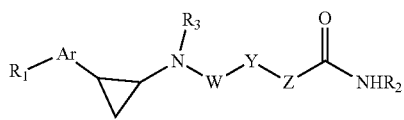

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —COR$_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

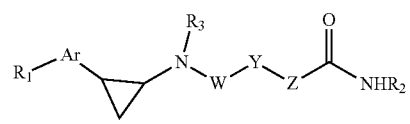

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$aryl, C$_{1-6}$ heteroaryl, and C$_{2-10}$ heterocyclyl with heteroatoms selected from N, O, S;

W represents a bond or CR$_4$R$_5$, wherein

R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;

Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, and —CO—;

wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (=O), C$_{3-8}$ cycloalkyl, halogen, OH, and cyano;

Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkylaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$aryl, C$_{1-6}$ heteroaryl, and C$_{2-10}$ heterocyclyl with heteroatoms selected from N, O, S;

W represents a bond or CR$_4$R$_5$, wherein

R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;

Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, and —CO—C$_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

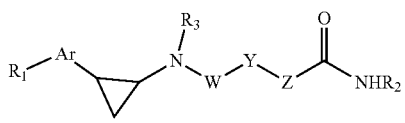

I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or CR$_4$R$_5$, wherein

R$_4$ and R$_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$8 alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

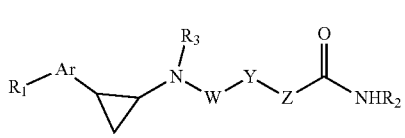

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —$OR_7$, aniline, amino $C_{5-6}$ aryl, and amino $C_{1-6}$ heteroaryl,
wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

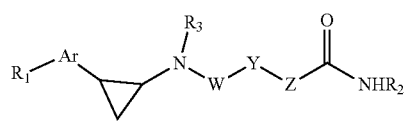

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

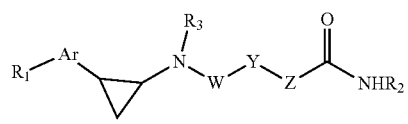

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$ aryl, $C_{1-6}$ heteroaryl, and $C_{2-10}$ heterocyclyl with heteroatoms selected from N, O, S;
W represents a bond or CR$_4$R$_5$, wherein
R$_4$ and R$_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

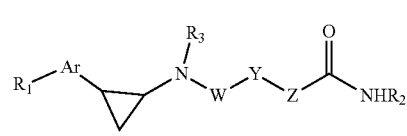

I their analogs, tautomeric forms, stereoisomers, polymorphs, solvates, intermediates, pharmaceutically acceptable salts, metabolites, and prodrugs thereof;

wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —$OR_7$, aniline, amino $C_{5-6}$ aryl, and amino $C_{1-6}$ heteroaryl,
wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

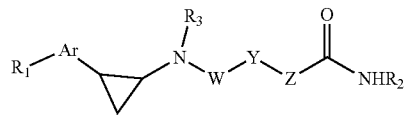

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

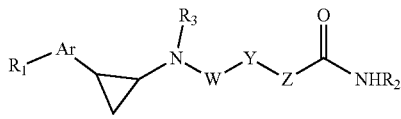

their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$ aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$SO_2$—$C_{7-12}$ alkylaryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$ aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, —CO—$C_{7-12}$ alkylaryl, —CO—$C_{7-12}$ alkenylaryl, —$CONR_6$—$C_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

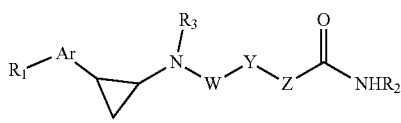

I their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$aryl, C$_{1-6}$ heteroaryl, and C$_{2-10}$ heterocyclyl with heteroatoms selected from N, O, S;
W represents a bond or CR$_4$R$_5$, wherein
R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;

Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;

wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (=O), C$_{3-8}$ cycloalkyl, halogen, OH, and cyano;

Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —NR$_6$—C$_{1-6}$ heteroaryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

I

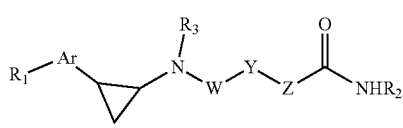

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;
wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;
$R_3$ is selected from the group consisting of hydrogen, substituted or unsubstituted $C_{1-8}$ alkyl, and $C_{5-6}$ aryl;
$R_2$ is selected from the group consisting of —OR$_7$, aniline, amino $C_{5-6}$ aryl, and amino $C_{1-6}$ heteroaryl,
wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;
$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

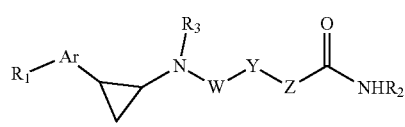

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted $C_{5-6}$aryl, $C_{1-6}$ heteroaryl, and $C_{2-10}$ heterocyclyl with heteroatoms selected from N, O, S;
W represents a bond or $CR_4R_5$, wherein
$R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;
Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;
wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;
Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;
$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;
$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O) R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

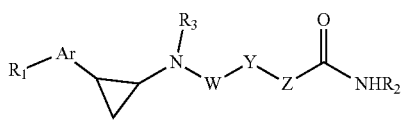

I their analogs, tautomeric forms, stereoisomers, polymorphs, solvates, intermediates, pharmaceutically acceptable salts, metabolites, and prodrugs thereof;
wherein Ar is selected from the group consisting of substituted or unsubstituted $C_{5-6}$ aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —$CONR_6$—$C_{1-8}$ alkyl, —$NR_6CO$—$C_{1-8}$ alkyl-, —$NR_6$—$C_{1-8}$ alkyl, —O—$C_{1-8}$ alkyl-, —$CONR_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —$NR_6$—CO—$OC_{1-8}$ alkyl, O—CO—$NR_6$—$C_{1-8}$ alkyl, —$NR_6CO$—$C_{5-6}$ aryl-, —$NR_6$—$C_{5-6}$ aryl, —$NR_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —$NR_6$—CO—$OC_{5-6}$ aryl, —$CONR_6$—$C_{7-12}$ alkylaryl, —$CONR_6$—$C_{7-12}$ alkenylaryl, —$SO_2$—$C_{5-6}$ aryl, —$NR_6SO_2$—$C_{7-12}$ alkylaryl, $C_{1-8}$ alkyl-$CONR_6$—$C_{5-6}$ aryl, and O—CO—$NR_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —$SO_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, —$NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —$OR_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —$COR_8$, wherein $R_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

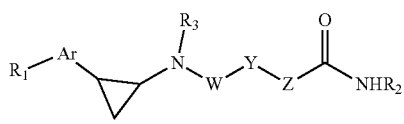

I their analogs, tautomeric forms, stereoisomers, polymorphs, solvates, intermediates, pharmaceutically acceptable salts, metabolites, and prodrugs thereof;
wherein Ar is selected from the group consisting of substituted or unsubstituted $C_{5-6}$ aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

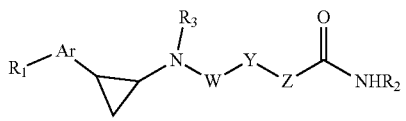

I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or CR$_4$R$_5$, wherein

R$_4$ and R$_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

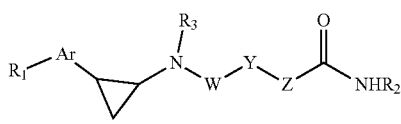

their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

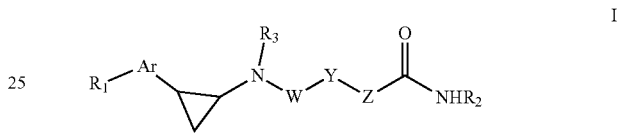

their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or $CR_4R_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

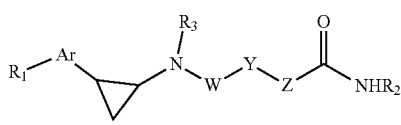

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$aryl, C$_{1-6}$ heteroaryl, and C$_{2-10}$ heterocyclyl with heteroatoms selected from N, O, S;

W represents a bond or CR$_4$R$_5$, wherein

R$_4$ and R$_5$ are independently selected from the group consisting of hydrogen, substituted or unsubstituted C$_{1-8}$ alkyl, C$_{5-6}$ aryl, and C$_{1-6}$ heteroaryl with heteroatoms selected from N, O, S;

Y is a bond or is selected from the group consisting of substituted or unsubstituted C$_{1-8}$ alkyl, C$_{1-8}$ alkenyl, C$_{1-8}$ alkynyl, C$_{5-6}$ aryl, C$_{1-6}$ heteroaryl, C$_{2-10}$ heterocyclyl, C$_{3-8}$ cycloalkyl, —CO—, and —CO—C$_{2-10}$ heterocyclyl;

wherein C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, oxo (=O), C$_{3-8}$ cycloalkyl, halogen, OH, and cyano;

Z represents a bond or is selected from the group consisting of C$_{1-8}$ alkyl, C$_{1-8}$ alkenyl, C$_{1-8}$ alkynyl, C$_{7-12}$-alkylaryl, C$_{7-12}$-alkenylaryl, C$_{7-15}$-arylalkenyl, C$_{2-12}$-alkylheteroaryl, —CO—C$_{7-12}$ alkylaryl, —CO—C$_{7-12}$ alkenylaryl, —CONR$_6$—C$_{1-8}$ alkyl, —NR$_6$CO—C$_{1-8}$ alkyl-, —NR$_6$—C$_{1-8}$ alkyl, —O—C$_{1-8}$ alkyl-, —CONR$_6$—C$_{5-6}$ aryl-, C$_{5-6}$ aryl, C$_{1-6}$ heteroaryl, C$_{2-10}$ heterocyclyl, —CO—C$_{2-10}$ heterocyclyl, —NR$_6$—CO—OC$_{1-8}$ alkyl, O—CO—NR$_6$—C$_{1-8}$ alkyl, —NR$_6$CO—C$_{5-6}$ aryl-, —NR$_6$—C$_{5-6}$ aryl, —C$_{1-8}$ alkyl-O—C$_{5-6}$ aryl, —O—C$_{5-6}$ aryl, O—C$_{1-6}$ heteroaryl, —NR$_6$—CO—OC$_{5-6}$ aryl, —CONR$_6$—C$_{7-12}$ alkylaryl, —CONR$_6$—C$_{7-12}$ alkenylaryl, —SO$_2$—C$_{5-6}$ aryl, —SO$_2$—C$_{7-12}$ alkylaryl, —NR$_6$SO$_2$—C$_{7-12}$ alkylaryl, C$_{1-8}$ alkyl-CONR$_6$—C$_{5-6}$ aryl, and O—CO—NR$_6$—C$_{5-6}$ aryl;

R$_6$ is selected from the group consisting of hydrogen, C$_{1-8}$ alkyl, C$_{1-6}$ haloalkyl, C$_{3-8}$ cycloalkyl, C$_{5-6}$ aryl, and C$_{1-6}$ heteroaryl, with heteroatoms selected from N, O, S;

R$_1$ is selected from the group consisting of hydrogen, halogen hydroxy, nitro, cyano, azido, nitroso, oxo (=O), thioxo (=S), —SO$_2$—, amino, hydrazino, formyl, C$_{1-8}$ alkyl, C$_{1-8}$ haloalkyl, C$_{1-8}$ alkoxy, C$_{1-8}$ haloalkoxy, C$_{7-12}$ arylalkoxy, C$_{3-8}$ cycloalkyl, C$_{3-8}$ cycloalkyloxy, C$_{5-6}$ aryl, C$_{2-10}$ heterocyclyl, C$_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, C$_{1-8}$ alkyl, C$_{3-8}$ cycloalkyl, C$_{5-6}$ aryl, C$_{7-15}$ arylalkyl, C$_{2-10}$ heterocyclyl, C$_{1-6}$ heteroaryl, and C$_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

In an embodiment of the present invention, there is provided a compound of Formula I

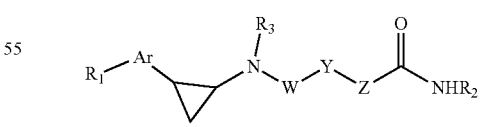

their analogs, tautomeric forms, stereoisomers, polymorphs, solvates, intermediates, pharmaceutically acceptable salts, metabolites, and prodrugs thereof;
wherein
Ar is selected from the group consisting of substituted or unsubstituted C$_{5-6}$aryl, C$_{1-6}$ heteroaryl, and C$_{2-10}$ heterocyclyl with heteroatoms selected from N, O, S;

W represents a bond or CR$_4$R$_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkylaryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein $C_{7-12}$ arylalkoxy, $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, $C_{5-6}$ aryl, $C_{1-6}$ heteroaryl, $C_{2-10}$ heterocyclyl, oxo (=O), $C_{3-8}$ cycloalkyl, halogen, OH, amino, and cyano;

$R_3$ is selected from the group consisting of hydrogen, substituted or unsubstituted $C_{1-8}$ alkyl, and $C_{5-6}$ aryl;

$R_2$ is selected from the group consisting of —OR$_7$, aniline, amino $C_{5-6}$ aryl, and amino $C_{1-6}$ heteroaryl, wherein aniline, amino $C_{5-6}$ aryl, and amino $C_{1-6}$ heteroaryl, is optionally substituted with one or more of the groups selected from $C_{1-8}$ alkyl, halogen, OH, amino, and cyano;

$R_7$ is selected from the group consisting of hydrogen, $C_{1-8}$ alkyl, $C_{5-6}$ aryl, $C_{2-10}$ heterocyclyl and —COR$_8$, wherein R$_8$ is selected from the group consisting of $C_{1-8}$ alkyl, $C_{5-6}$ aryl, $C_{1-6}$ heteroaryl, $C_{3-8}$ cycloalkyl, and $C_{2-10}$ heterocyclyl.

In an embodiment of the present invention, there is provided a compound of Formula I

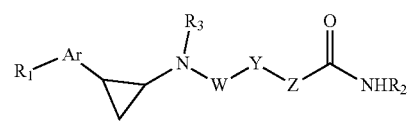

I their analogs, tautomeric forms, stereoisomers, polymorphs, solvates, intermediates, pharmaceutically acceptable salts, metabolites, and prodrugs thereof;

wherein

Ar is selected from the group consisting of substituted or unsubstituted $C_{5-6}$aryl, $C_{1-6}$ heteroaryl, and $C_{2-10}$ heterocyclyl with heteroatoms selected from N, O, S;

W represents a bond or CR$_4$R$_5$, wherein $R_4$ and $R_5$ are independently selected from the group consisting of hydrogen, substituted or unsubstituted $C_{1-8}$ alkyl, $C_{5-6}$ aryl, and $C_{1-6}$ heteroaryl with heteroatoms selected from N, O, S;

Y is a bond or is selected from the group consisting of substituted or unsubstituted $C_{1-8}$ alkyl, $C_{1-8}$ alkenyl, $C_{1-8}$ alkynyl, $C_{5-6}$ aryl, $C_{1-6}$ heteroaryl, $C_{2-10}$ heterocyclyl, $C_{3-8}$ cycloalkyl, —CO—, and —CO—$C_{2-10}$ heterocyclyl;

wherein $C_{1-8}$ alkyl, $C_{5-6}$ aryl, $C_{1-6}$ heteroaryl, $C_{2-10}$ heterocyclyl, $C_{3-8}$ cycloalkyl, is optionally substituted with one or more of the groups selected from hydrogen, $C_{1-6}$ alkyl, oxo (=O), $C_{3-8}$ cycloalkyl, halogen, OH, and cyano;

Z represents a bond or is selected from the group consisting of $C_{1-8}$ alkyl, $C_{1-8}$ alkenyl, $C_{1-8}$ alkynyl, $C_{7-12}$-alkylaryl, $C_{7-12}$-alkenylaryl, $C_{7-15}$-arylalkenyl, $C_{2-12}$-alkylheteroaryl, —CO—$C_{7-12}$ alkylaryl, —CO—$C_{7-12}$ alkenylaryl, —CONR$_6$—$C_{1-8}$ alkyl, —NR$_6$CO—$C_{1-8}$ alkyl-, —NR$_6$—$C_{1-8}$ alkyl, —O—$C_{1-8}$ alkyl-, —CONR$_6$—$C_{5-6}$ aryl-, $C_{5-6}$ aryl, $C_{1-6}$ heteroaryl, $C_{2-10}$ heterocyclyl, —CO—$C_{2-10}$ heterocyclyl, —NR$_6$—CO—OC$_{1-8}$ alkyl, O—CO—NR$_6$—$C_{1-8}$ alkyl, —NR$_6$CO—$C_{5-6}$ aryl-, —NR$_6$—$C_{5-6}$ aryl, —NR$_6$—$C_{1-6}$ heteroaryl, —$C_{1-8}$ alkyl-O—$C_{5-6}$ aryl, —O—$C_{5-6}$ aryl, O—$C_{1-6}$ heteroaryl, —NR$_6$—CO—OC$_{5-6}$ aryl, —CONR$_6$—$C_{7-12}$ alkenylaryl, —SO$_2$—$C_{5-6}$ aryl, —SO$_2$—$C_{7-12}$ alkylaryl, —NR$_6$SO$_2$—$C_{7-12}$ alkylaryl, $C_{1-8}$ alkyl-CONR$_6$—$C_{5-6}$ aryl, and O—CO—NR$_6$—$C_{5-6}$ aryl;

$R_6$ is selected from the group consisting of hydrogen, $C_{1-8}$ alkyl, $C_{1-6}$ haloalkyl, $C_{3-8}$ cycloalkyl, $C_{5-6}$ aryl, and $C_{1-6}$ heteroaryl, with heteroatoms selected from N, O, S;

$R_1$ is selected from the group consisting of hydrogen, halogen hydroxy, nitro, cyano, azido, nitroso, oxo (=O), thioxo (=S), —SO$_2$—, amino, hydrazino, formyl, $C_{1-8}$ alkyl, $C_{1-8}$ haloalkyl, $C_{1-8}$ alkoxy, $C_{1-8}$ haloalkoxy, $C_{7-12}$ arylalkoxy, $C_{3-8}$ cycloalkyl, $C_{3-8}$ cycloalkyloxy, $C_{5-6}$ aryl, $C_{2-10}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, —NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ and —SO$_2$R$_a$, wherein R$_a$, R$_b$ and R$_c$ is independently selected from the group consisting of hydrogen, $C_{1-8}$ alkyl, $C_{3-8}$ cycloalkyl, $C_{5-6}$ aryl, $C_{7-15}$ arylalkyl, $C_{2-10}$ heterocyclyl, $C_{1-6}$ heteroaryl, and $C_{2-12}$ heteroarylalkyl with heteroatoms selected from N, O, S;

wherein C$_{7-12}$ arylalkoxy, C$_{1-8}$ alkyl, C$_{5-6}$ aryl, C$_{1-6}$ heteroaryl, C$_{2-10}$ heterocyclyl, C$_{3-8}$ cycloalkyl, is optionally substituted with one or more of the groups selected from hydrogen, C$_{1-6}$ alkyl, C$_{5-6}$ aryl, C$_{1-6}$ heteroaryl, C$_{2-10}$ heterocyclyl, oxo (=O), C$_{3-8}$ cycloalkyl, halogen, OH, amino, and cyano;

R$_3$ is selected from the group consisting of hydrogen, substituted or unsubstituted C$_{1-8}$ alkyl, and C$_{5-6}$ aryl;

R$_2$ is selected from the group consisting of —OR$_7$, aniline, amino C$_{5-6}$ aryl, and amino C$_{1-6}$ heteroaryl, wherein aniline, amino C$_{5-6}$ aryl, and amino C$_{1-6}$ heteroaryl, is optionally substituted with one or more of the groups selected from C$_{1-8}$ alkyl, halogen, OH, amino, and cyano;

R$_7$ is selected from the group consisting of hydrogen, C$_{1-8}$ alkyl, C$_{5-6}$ aryl, C$_{2-10}$ heterocyclyl and —COR$_8$, wherein R$_8$ is selected from the group consisting of C$_{1-8}$ alkyl, C$_{5-6}$ aryl, C$_{1-6}$ heteroaryl, C$_{3-8}$ cycloalkyl, and C$_{2-10}$ heterocyclyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, which is selected from a group consisting of:

1) (E)3(4(((2(4-Cyclopropylphenyl)cyclopropyl)amino)methyl)phenyl)-N-hydroxyacrylamide TFA salt
2) (E)-3-(4-{[2-(4-Fluoro-phenyl)-cyclopropylamino]-methyl}-phenyl)-N-hydroxy-acrylamide TFA salt
3) (E)-3-(4-(((2-(4-((4-Fluorobenzyl)oxy)phenyl)cyclopropyl)amino)methyl)phenyl)-N-hydroxyacrylamideTFA salt
4) (E)-N-hydroxy-3-(4-(4-(((2-phenylcyclopropyl)amino)methyl)piperidin-1-yl)phenyl) acrylamideTFA salt
5) (E)-3-(4-(((2-(4'-Chloro-[1,1'-biphenyl]-4-yl)cyclopropyl)amino)methyl)phenyl)-N-hydroxyacrylamideTFA salt
6) (E)-3-(4-(((2-(4-(3,5-Dimethylisoxazol-4-yl)phenyl)cyclopropyl)amino)methyl)phenyl)-N-hydroxyacrylamide.TFA salt
7) (E)-N-hydroxy-3-(4-(((2-(4-(pyrimidin-5-yl)phenyl)cyclopropyl)amino)methyl)phenyl) acrylamide TFA salt
8) 2-(4-(((2-(4-Fluorophenyl)cyclopropyl)amino)methyl)piperidin-1-yl)-N-hydroxy pyrimidine-5-carboxamide TFA salt
9) 2-[4-(2-Phenyl-cyclopropylamino)-piperidin-1-yl]-pyrimidine-5-carboxylicacid hydroxyamide TFA salt
10) 2-{4-[2-(4-Fluorophenyl)-cyclopropylamino]-piperidin-1-yl}-pyrimidine-5-carboxylic acid hydroxyamide TFA salt
11) 2-(4-(((2-(4-((4-Fluorobenzyl)oxy)phenyl)cyclopropyl)amino)methyl)piperidin-1-yl)-N-hydroxypyrimidine-5-carboxamideTFA salt
12) 2-(4-((2-(4-((4-Fluorobenzyl)oxy)phenyl)cyclopropyl)amino)piperidin-1-yl)-N-hydroxypyrimidine-5-carboxamideTFA salt
13) 2-(4-((2-(4'-Chloro-[1,1'-biphenyl]-4-yl)cyclopropyl)amino)piperidin-1-yl)-N-hydroxypyrimidine-5-carboxamideTFA salt
14) 2-(4-(((2-(4'-Chloro-[1,1'-biphenyl]-4-yl)cyclopropyl)amino)methyl)piperidin-1-yl)-N-hydroxypyrimidine-5-carboxamide TFA salt
15) 2-(4-(((2-(4'-Fluoro-[1,1'-biphenyl]-4-yl)cyclopropyl)amino)methyl)piperidin-1-yl)-N-hydroxypyrimidine-5-carboxamide TFA salt
16) 2-(4-(((2-(4-(3,5-Dimethylisoxazol-4-yl)phenyl)cyclopropyl)amino)methyl)piperidin-1-yl)-N-hydroxypyrimidine-5-carboxamide. TFA salt
17) N-hydroxy-2-(4-(((2-(4-(pyrimidin-5-yl)phenyl)cyclopropyl)amino)methyl) piperidin-1-yl)pyrimidine-5-carboxamide.TFA salt
18) N-hydroxy-2-(4-(((2-(4-methoxyphenyl)cyclopropyl)amino)methyl)piperidin-1-yl)pyrimidine-5-carboxamide-TFA salt
19) N-hydroxy-2-(4-((2-(4-methoxyphenyl)cyclopropyl)amino)piperidin-1-yl)pyrimidine-5-carboxamide TFA salt
20) 2-(4-(((((1R,2S)-2-(4-Fluorophenyl)cyclopropyl)amino)methyl)piperidin-1-yl)-N-hydroxypyrimidine-5-carboxamide TFA salt
21) 2-(4-(((((1S,2R)-2-(4-Fluorophenyl)cyclopropyl)amino)methyl)piperidin-1-yl)-N-hydroxypyrimidine-5-carboxamide TFA salt
22) 4-(4-(((2-(4-Fluorophenyl)cyclopropyl)amino)methyl)piperidin-1-yl)-N-hydroxybenzamide TFA salt
23) N-hydroxy-2-(2-(((2-phenylcyclopropyl)amino)methyl)-5,6-dihydroimidazo[1,2-a]pyrazin-7(8H)-yl)pyrimidine-5-carboxamide TFA salt
24) N-hydroxy-2-(2-(((2-(4-methoxyphenyl)cyclopropyl)amino)methyl)-5,6-dihydroimidazo[1,2-a]pyrazin-7(8H)-yl)pyrimidine-5-carboxamide TFA salt
25) 2-(2-(((2-(4-Fluorophenyl)cyclopropyl)amino)methyl)-5,6-dihydroimidazo[1,2-a]pyrazin-7(8H)-yl)-N-hydroxypyrimidine-5-carboxamide TFA salt
26) 3-(((2-(4-Bromophenyl)cyclopropyl)amino)methyl)-N-hydroxybenzamide TFA salt
27) N-hydroxy-3-(((2-phenylcyclopropyl)amino)methyl) benzamide TFA salt
28) N-hydroxy-4-(((2-phenylcyclopropyl)amino)methyl) benzamide TFA salt
29) N-hydroxy-6-((2-phenylcyclopropyl)amino)hexanamide TFA salt
30) 4-(3-((2-(4-Fluorophenyl)cyclopropyl)amino)propyl)-N-hydroxybenzamide TFA salt
31) N-(6-Hydroxycarbamoyl-hexyl)-4-[(2-phenyl-cyclopropylamino)-methyl]-benzamide TFA salt
32) 4-(((2-(4-Fluorophenyl)cyclopropyl)amino)methyl)-N-(7-(hydroxyamino)-7-oxoheptyl)benzamide TFA salt
33) 4-(2-Phenyl-cyclopropylamino)-cyclohexanecarboxylic acid hydroxyamide TFA salt
34) (1S,4R)—N-hydroxy-4-((1S)-1-((2-phenylcyclopropyl)amino)ethyl)cyclohexanecarboxamide TFA salt
35) N-hydroxy-4-((4-(((2-(4-(1-methyl-6-oxo-1,6-dihydropyridin-3-yl)phenyl)cyclopropyl)amino)methyl)piperidin-1-yl)methyl)benzamide TFA Salt
36) N-Hydroxy-4-{4-[(2-phenyl-cyclopropylamino)-methyl]-piperidin-1-ylmethyl}-benzamide TFA salt
37) 4-((4-(((2-(4-(3,5-Dimethylisoxazol-4-yl)phenyl)cyclopropyl)amino)methyl)piperidin-1-yl) methyl)-N-hydroxybenzamide TFA salt
38) N-hydroxy-4-((4-(((2-(4-(pyrimidin-5-yl)phenyl)cyclopropyl)amino)methyl)piperidin-1-yl)methyl)benzamide TFA salt
39) 6-((4-(((2-(4-(3,5-Dimethylisoxazol-4-yl)phenyl)cyclopropyl)amino)methyl)piperidin-1-yl)methyl)-N-hydroxynicotinamide TFA salt
40) N-hydroxy-4-((4-(((2-phenylcyclopropyl)amino)methyl)-1H-pyrazol-1-yl)methyl) benzamide TFA salt
41) N-hydroxy-4-((4-(((2-phenylcyclopropyl)amino)methyl)-1H-1,2,3-triazol-1-yl) methyl)benzamide TFA salt
42) N-hydroxy-4-(2-(4-(((2-phenylcyclopropyl)amino)methyl)piperidin-1-yl)ethyl)benzamide TFA salt 43) N-hydroxy-4-(3-(4-(((2-phenylcyclopropyl)amino) methyl)piperidin-1-yl)propyl)benzamide TFA salt
44) N-hydroxy-4-(3-(4-((2-phenylcyclopropyl)amino)-piperidin-1-yl)propyl)benzamideTFA salt
45) N-hydroxy-4-(3-(4-((methyl (2-phenylcyclopropyl) amino) methyl) piperidin-1-yl) propyl)benzamide TFA salt
46) N-hydroxy-4-(3-(6-((2-phenylcyclopropyl)amino)-2-azaspiro[3.3]heptan-2-yl)propyl) benzamide TFA salt
47) 4-[3-(4-{[2-(4-Fluorophenyl)-cyclopropylamino]-methyl}-piperidin-1-yl)-propyl]-N-hydroxy-benzamide TFA salt
48) 4-(3-(3-(((2-(4-Fluorophenyl)cyclopropyl)amino) methyl)azetidin-1-yl)propyl)-N-hydroxy benzamide TFA salt
49) 4-(3-(4-(((2-(3-Fluorophenyl)cyclopropyl)amino) methyl)piperidin-1-yl)propyl)-N-hydroxy benzamide TFA salt
50) 4-(3-(4-(((2-(3,4-Difluorophenyl)cyclopropyl)amino) methyl)piperidin-1-yl)propyl)-N-hydroxybenzamide TFA salt
51) N-hydroxy-4-(3-(4-(((2-(4-methoxyphenyl)cyclopropyl)amino)methyl)piperidin-1-yl)propyl)benzamide TFA salt
52) N-hydroxy-4-(3-(4-(((2-(4-(morpholine-4-carbonyl) phenyl)cyclopropyl)amino)methyl)piperidin-1-yl)propyl) benzamide TFA salt
53) N-hydroxy-4-(3-(4-(((2-(4-(morpholine-4-carbonyl) phenyl)cyclopropyl)amino)methyl)piperidin-1-yl)propyl) benzamide TFA salt
54) N-hydroxy-4-(3-(4-(((2-(4-(piperidine-1-carbonyl)phenyl)cyclopropyl)amino)methyl)piperidin-1-yl)propyl) benzamide TFA salt
55) N-(2-(Dimethylamino)ethyl)-4-(2-(((1-(3-(4-(hydroxycarbamoyl)phenyl)propyl)piperidin-4-yl)methyl)amino) cyclopropyl)benzamide TFA salt
56) 4-(3-(4-(((2-(4'-Chloro-[1,1'-biphenyl]-4-yl)cyclopropyl)amino)methyl)piperidin-1-yl)propyl)-N-hydroxybenzamide TFA salt
57) 4-(3-(4-(((2-(4'-Fluoro-[1,1'-biphenyl]-4-yl)cyclopropyl)amino)methyl)piperidin-1-yl)propyl)-N-hydroxybenzamide TFA salt
58) 4-(3-(3-(((2-(4'-Fluoro-[1,1'-biphenyl]-4-yl)cyclopropyl)amino)methyl)azetidin-1-yl) propyl)-N-hydroxybenzamide TFA salt
59) 4-(3-(4-(((2-(4'-Cyano-[1,1'-biphenyl]-4-yl)cyclopropyl)amino)methyl)piperidin-1-yl)propyl)-N-hydroxybenzamideTFA salt
60) N-hydroxy-4-(3-(4-(((2-(4-(1-methyl-2-oxo-1,2-dihydropyridin-4-yl)phenyl)cyclopropyl)amino)methyl)piperidin-1-yl)propyl)benzamide. TFA salt
61) N-hydroxy-4-(3-(4-(((2-(4-(pyrimidin-5-yl)phenyl)cyclopropyl)amino)methyl)piperidin-1-yl)propyl)benzamide TFA salt
62) N-hydroxy-4-(3-(4-(((2-(4-(1-methyl-1H-pyrazol-4-yl) phenyl)cyclopropyl)amino) methyl)piperidin-1-yl) propyl) benzamide TFA salt
63) N-hydroxy-4-(3-(3-(((2-(4-(1-methyl-1H-pyrazol-4-yl) phenyl)cyclopropyl)amino) methyl) azetidin-1-yl)propyl) benzamide
64) 4-(3-(4-(((2-(4-(3,5-Dimethylisoxazol-4-yl)phenyl)cyclopropyl)amino)methyl)piperidin-1-yl)propyl)-N-hydroxybenzamide TFA salt
65) 3-(3-(3-(((2-(4-(3,5-Dimethylisoxazol-4-yl)phenyl)cyclopropyl)amino)methyl)azetidin-1-yl)propyl)-N-hydroxybenzamideTFA salt
66) N-hydroxy-4-(3-(4-(((2-(4-(6-(trifluoromethyl)pyridin-3-yl)phenyl)cyclopropyl)amino)methyl)piperidin-1-yl) propyl)benzamideTFA salt
67) N-hydroxy-4-(3-(4-(((2-(1-isopropyl-1H-pyrazol-4-yl) cyclopropyl)amino)methyl)piperidin-1-yl)propyl)benzamideTFA salt
68) N-hydroxy-4-(3-(4-(((2-(1-phenyl-1H-pyrazol-4-yl)cyclopropyl)amino)methyl)piperidin-1-yl)propyl)benzamideTFA salt
69) N-hydroxy-4-(3-(4-(((2-(2-methylthiazol-5-yl)cyclopropyl)amino)methyl)piperidin-1-yl)propyl)benzamide-TFA salt
70) N-hydroxy-4-(3-(4-(((2-(pyridin-3-yl)cyclopropyl) amino)methyl)piperidin-1-yl)propyl) benzamideTFA salt
71) N-hydroxy-4-(3-(2-(((2-(4-methoxyphenyl)cyclopropyl)amino)methyl)-5,6-dihydroimidazo[1,2-a]pyrazin-7 (8H)-yl)propyl)benzamide TFA salt
72) 4-(3-(2-(((2-(4-Fluorophenyl)cyclopropyl)amino) methyl)-5,6-dihydroimidazo[1,2-a] pyrazin-7(8H)-yl) propyl)-N-hydroxybenzamide TFA salt
73) 4-(3-(4-(((2-(3,4-Difluorophenyl)cyclopropyl)amino) methyl)-1H-imidazol-1-yl) propyl)-N-hydroxybenzamide TFA salt
74) N-hydroxy-4-(3-(4-(((2-phenylcyclopropyl)amino) methyl)-1H-imidazol-1-yl)propyl) benzamide TFA salt
75) N-hydroxy-4-(3-(4-(((2-phenylcyclopropyl)amino) methyl)-1H-imidazol-1-yl)propyl) benzamide
76) N-hydroxy-4-(3-(4-(((2-phenylcyclopropyl)amino) methyl)-1H-pyrazol-1-yl)propyl) benzamide TFA salt
77) N-hydroxy-4-(3-(4-(((2-phenylcyclopropyl)amino) methyl)-1H-1,2,3-triazol-1-yl)propyl)benzamide TFA salt
78) 4-(3-(6-(((2-(4-Fluorophenyl)cyclopropyl)amino) methyl)-3,4-dihydroisoquinolin-2-(1H)-yl)propyl)-N-hydroxybenzamide TFA salt
79) 4-((7-(((2-(4-Fluorophenyl)cyclopropyl)amino)methyl)-3,4-dihydroisoquinolin-2(1H)-yl)methyl)-N-hydroxybenzamide TFA salt
80) 4-((2-(((2-(4-Fluorophenyl)cyclopropyl)amino)methyl)-5,6-dihydroimidazo[1,2-a]pyrazin-7 (8H)-yl)methyl)-N-hydroxybenzamide TFA salt
81) N-hydroxy-4-(3-(4(((2-(1,3,3,-trimethyl-2-oxoindoline-5-yl)cyclopropyl)amino)methyl) piperidine-1-yl)propyl) benzamide TFA salt
82) N-hydroxy-4-(3-oxo-3-(4-(((2-phenylcyclopropyl) amino)methyl)piperidin-1-yl)propyl)benzamide TFA salt
83) N-hydroxy-4-(3-oxo-3-(4-((2-phenylcyclopropyl) amino)piperidin-1-yl)propyl)benzamide TFA salt
84) N-hydroxy-4-(2-oxo-2-(4-(((2-phenylcyclopropyl) amino)methyl)piperidin-1-yl)ethyl) benzamide TFA Salt
84A. N-hydroxy-4-(2-oxo-2-(4-(((((1R,2S)-2-phenylcyclopropyl)amino)methyl)piperidin-1-yl) ethyl)benzamide
84B. N-hydroxy-4-(2-oxo-2-(4-(((((1S,2R)-2-phenylcyclopropyl)amino)methyl)piperidin-1-yl) ethyl)benzamide
85) N-hydroxy-4-((4-(((2-phenylcyclopropyl)amino) methyl)piperidin-1-yl)sulfonyl) benzamide TFA salt
86) N-hydroxy-4-((N-(2-(4-(((2-phenylcyclopropyl)amino) methyl)piperidin-1-yl)ethyl) sulfamoyl)methyl)benzamideTFA salt
87) 4-(N-(2-(4-(((2-(4-fluorophenyl)cyclopropyl)amino) methyl)piperidin-1-yl)ethyl) sulfamoyl)-N-hydroxybenzamide
88) N-hydroxy-4-(2-((4-(((2-phenylcyclopropyl)amino) methyl)piperidin-1-yl)sulfonyl)ethyl) benzamide TFA salt
89) N-hydroxy-N4-(2-(4-(((2-phenylcyclopropyl)amino) methyl)piperidin-1-yl)ethyl) terephthalamideTFA salt 90) N1-(2-(4-(((2-(3,4-difluorophenyl)cyclopropyl)amino)methyl)piperidin-1-yl)ethyl)-N4-hydroxyterephthalamide TFA salt
91) N-hydroxy-4-((4-(2-((2-phenylcyclopropyl)amino)acetyl)piperazin-1-yl)methyl)benzamide TFA salt
92) N-hydroxy-4-(3-oxo-3-(4-(2-((2-phenylcyclopropyl)amino)acetyl)piperazin-1-yl)propyl)benzamide TFA salt
93) N-hydroxy-4-(3-(1-(2-((2-phenylcyclopropyl)amino)acetyl)piperidin-4-yl)propyl)benzamide TFA salt
94) N-hydroxy-4-(3-(2-oxo-4-(((2-phenylcyclopropyl)amino)methyl)piperidin-1-yl) propyl)benzamide TFA salt
95) N-hydroxy-4-(2-((2-phenylcyclopropyl)amino)ethoxy)benzamide TFA salt
96) 6-(2-(4-(((2-(4-fluorophenyl)cyclopropyl)amino)methyl)piperidin-1-yl)ethoxy)-N-hydroxynicotinamide TFA salt
97) N-hydroxy-6-(2-(4-(((2-phenylcyclopropyl)amino)methyl)piperidin-1-yl)ethoxy)nicotinamide TFA salt
98) 6-(2-(4-(((2-(4'-Fluoro-[1,1'-biphenyl]-4-yl)cyclopropyl)amino)methyl)piperidin-1-yl) ethoxy)-N-hydroxynicotinamide TFA salt
99) N-hydroxy-4-(2-(4-(((2-phenylcyclopropyl)amino)methyl)piperidin-1-yl)ethoxy)benzamide TFA salt
100) N-hydroxy-4-(3-(4-(((2-phenylcyclopropyl)amino)methyl)piperidin-1-yl)propoxy)benzamide TFA salt
101) N-hydroxy-4-(3-((2-phenylcyclopropyl)amino)propoxy)benzamide TFA salt
102) 2-((2-(4-(((2-(4-Fluorophenyl)cyclopropyl)amino)methyl)piperidin-1-yl)ethyl)amino)-N-hydroxypyrimidine-5-carboxamide TFA salt
103) 5-(2-((2-(4-Fluorophenyl)cyclopropyl)amino)acetyl)-N-hydroxy-4,5,6,7-tetrahydro thieno[3,2-c]pyridine-2-carboxamide TFA salt
103A) 5-(2-(((1R,2S)-2-(4-Fluorophenyl)cyclopropyl)amino)acetyl)-N-hydroxy-4,5,6,7-tetrahydrothieno[3,2-c]pyridine-2-carboxamide TFA salt
103B) 5-(2-(((1S,2R)-2-(4-Fluorophenyl)cyclopropyl)amino)acetyl)-N-hydroxy-4,5,6,7-tetrahydrothieno[3,2-c]pyridine-2-carboxamide TFA salt
104) 2-(2-((2-(4-Fluorophenyl)cyclopropyl)amino)acetyl)-N-hydroxy-1,2,3,4-tetrahydro isoquinoline-7-carboxamide TFA salt
104A) 2-(2-(((1S,2R)-2-(4-Fluorophenyl)cyclopropyl)amino)acetyl)-N-hydroxy-1,2,3,4-tetrahydroisoquinoline-7-carboxamide TFA salt
104B) 2-(2-(((1R,2S)-2-(4-Fluorophenyl)cyclopropyl)amino)acetyl)-N-hydroxy-1,2,3,4-tetrahydroisoquinoline-7-carboxamide TFA salt
105) 5-(4-((2-(4-Fluorophenyl)cyclopropyl)amino)butanoyl)-N-hydroxy-4,5,6,7-tetrahydro thieno[3,2-c]pyridine-2-carboxamide TFA salt
106) 5-(4-(4-(((2-(4-Fluorophenyl)cyclopropyl)amino)methyl)piperidin-1-yl)butanoyl)-N-hydroxy-4,5,6,7-tetrahydrothieno[3,2-c]pyridine-2-carboxamide TFA salt
107) 2-(4-((2-(4-Fluorophenyl)cyclopropyl)amino)butanoyl)-N-hydroxy-1,2,3,4-tetrahydro isoquinoline-7-carboxamide TFA salt
108) 2-(4-((2-(4-Fluorophenyl)cyclopropyl)amino)butanoyl)-N-hydroxyisoindoline-5-carboxamide TFA salt
109) N-hydroxy-2-(4-(4-(((2-phenylcyclopropyl)amino)methyl)piperidin-1-yl)butanoyl) isoindoline-5-carboxamide TFA salt
110) N-hydroxy-2-(3-(4-(((2-phenylcyclopropyl)amino)methyl)piperidin-1-yl)propyl) thiazole-4-carboxamide TFA salt
111) 2-(3-(4-(((2-(4'-Fluoro-[1,1'-biphenyl]-4-yl)cyclopropyl)amino)methyl)piperidin-1-yl)propyl)-N-hydroxythiazole-4-carboxamide TFA salt
112) N-hydroxy-2-(3-(4-(((2-phenylcyclopropyl)amino)methyl)piperidin-1-yl)propyl) thiazole-5-carboxamide TFA salt
113) N-hydroxy-2-(3-(4-(((2-phenylcyclopropyl)amino)methyl)piperidin-1-yl)propyl) oxazole-4-carboxamide TFA salt
114) (E)-N-hydroxy-4-(3-oxo-3-(4-(((2-phenylcyclopropyl)amino)methyl)piperidin-1-yl) prop-1-en-1-yl)benzamide TFA salt
114A) N-hydroxy-4-((E)-3-oxo-3-(4-((((1R,2S)-2-phenylcyclopropyl)amino)methyl) piperidin-1-yl)prop-1-en-1-yl)benzamide TFA salt
114B) N-hydroxy-4-((E)-3-oxo-3-(4-((((1S,2R)-2-phenylcyclopropyl)amino)methyl) piperidin-1-yl)prop-1-en-1-yl)benzamide TFA salt
115) 4-((E)-3-(4-((((1S,2R)-2-(4-Fluorophenyl)cyclopropyl)amino)methyl) piperidin-1-yl)-3-oxoprop-1-en-1-yl)-N-hydroxybenzamide TFA salt
115A) 4-((E)-3-(4-((((1S,2R)-2-(4-Fluorophenyl)cyclopropyl)amino)methyl) piperidin-1-yl)-3-oxoprop-1-en-1-yl)-N-hydroxybenzamide TFA salt
116) (E)-4-(3-(4-(((2-(4-(3,5-Dimethylisoxazol-4-yl)phenyl)cyclopropyl)amino)methyl) piperidin-1-yl)-3-oxoprop-1-en-1-yl)-N-hydroxybenzamide TFA salt
117) (E)-N-hydroxy-4-(3-oxo-3-(4-(((2-(4-(pyrimidin-5-yl)phenyl)cyclopropyl)amino) methyl)piperidin-1-yl)prop-1-en-1-yl)benzamide TFA salt
118) (E)-4-(3-(3-(((2-(4-Fluorophenyl)cyclopropyl)amino)methyl)azetidin-1-yl)-3-oxoprop-1-en-1-yl)-N-hydroxybenzamideTFA salt
119) (E)-N-hydroxy-4-(3-(3-(((2-(4-(1-methyl-1H-pyrazol-4-yl)phenyl)cyclopropyl)amino)methyl)azetidin-1-yl)-3-oxoprop-1-en-1-yl)benzamide TFA salt
120) (E)-N-(2-aminophenyl)-3-(4-(((2-(4-fluorophenyl)cyclopropyl)amino)methyl)phenyl)acrylamide TFA salt
121) N-(2-aminophenyl)-4-(3-(4-(((2-phenylcyclopropyl)amino)methyl)piperidin-1-yl)propyl)benzamide TFA salt
122) N-(2-aminophenyl)-4-(3-(4-(((2-(4-fluorophenyl)cyclopropyl)amino)methyl)piperidin-1-yl)propyl)benzamide TFA salt
123) N-(2-aminophenyl)-4-(3-(4-(((2-(4-methoxyphenyl) cyclopropyl)amino)methyl)piperidin-1-yl)propyl)benzamide TFA salt
124) N-(2-aminophenyl)-4-(3-(4-(((2-(3,4-difluorophenyl) cyclopropyl)amino)methyl) piperidin-1-yl)propyl)benzamide TFA salt
125) N-(2-aminophenyl)-4-(3-(4-(((2-(4-(piperidine-1-carbonyl)phenyl)cyclopropyl)amino)methyl)piperidin-1-yl)propyl)benzamide TFA salt
126) N-(2-aminophenyl)-4-(3-(3-(((2-(4-fluorophenyl)cyclopropyl)amino)methyl)azetidin-1-yl) propyl)benzamide TFA salt
127) N-(2-aminophenyl)-4-(3-(6-((2-phenylcyclopropyl)amino)-2-azaspiro[3.3]heptan-2-yl)propyl)benzamide TFA salt
128) N-(2-aminophenyl)-4-(3-(4-(((2-(1-isopropyl-1H-pyrazol-4-yl)cyclopropyl)amino)methyl)piperidin-1-yl) propyl)benzamide TFA salt
129) N-(2-aminophenyl)-4-(3-(4-(((2-(1-phenyl-1H-pyrazol-4-yl)cyclopropyl)amino)methyl)piperidin-1-yl)propyl)benzamide TFA salt
130) N-(2-aminophenyl)-4-(3-(4-(((2-(2-methylthiazol-5-yl)cyclopropyl)amino)methyl) piperidin-1-yl)propyl)benzamide TFA salt 131) N-(2-aminophenyl)-4-(3-(4-(((2-(pyridin-3-yl)cyclopropyl)amino)methyl)piperidin-1-yl)propyl)benzamide TFA salt
132) N-(2-amino-5-fluorophenyl)-4-(3-(4-(((2-(4-fluorophenyl)cyclopropyl)amino)methyl)piperidin-1-yl)propyl) benzamide TFA salt
133) N-(2-aminophenyl)-4-(3-oxo-3-(4-((2-phenylcyclopropyl)amino)piperidin-1-yl)propyl)benzamide TFA salt
134) N-(2-aminophenyl)-4-(3-oxo-3-(4-(((2-phenylcyclopropyl)amino)methyl)piperidin-1-yl)propyl)benzamide TFA salt
135) N-(2-aminophenyl)-4-(3-(4-(((2-(3,4-difluorophenyl)cyclopropyl)amino)methyl)-1H-imidazol-1-yl)propyl)benzamide TFA salt
136) N-(2-aminophenyl)-4-(3-(4-(((2-phenylcyclopropyl)amino)methyl)-1H-imidazol-1-yl)propyl)benzamide TFA salt
137) N-(2-aminophenyl)-4-(3-(4-(((2-phenylcyclopropyl)amino)methyl)-1H-1,2,3-triazol-1-yl)propyl)benzamide TFA salt
138) N-(2-aminophenyl)-4-(3-(4-(((2-phenylcyclopropyl)amino)methyl)-1H-pyrazol-1-yl)propyl)benzamide TFA salt
139) N-(2-aminophenyl)-4-(2-(4-(((2-phenylcyclopropyl)amino)methyl)piperidin-1-yl) ethyl)benzamide TFA salt
140) N-(2-aminophenyl)-4-((4-((((1R,2S)-2-phenylcyclopropyl)amino)methyl)piperidin-1-yl) methyl)benzamide TFA salt
141) N-(2-aminophenyl)-4-((4-(((2-(4-(1-methyl-6-oxo-1,6-dihydropyridin-3-yl)phenyl) cyclopropyl)amino)methyl)piperidin-1-yl)methyl)benzamide TFA salt
142) N-(2-aminophenyl)-4-((4-(((2-(4-(1-methyl-1H-pyrazol-4-yl)phenyl)cyclopropyl)amino)methyl)piperidin-1-yl)methyl)benzamide TFA salt
143) N-(2-aminophenyl)-4-((4-(((2-(4-(3,5-dimethylisoxazol-4-yl)phenyl)cyclopropyl)amino) methyl)piperidin-1-yl)methyl)benzamide TFA salt
144) N-(2-aminophenyl)-4-((4-(((2-(4-(pyrimidin-5-yl)phenyl)cyclopropyl)amino)methyl)piperidin-1-yl)methyl)benzamide TFA salt
145) N-(2-aminophenyl)-4-((4-(((2-phenylcyclopropyl)amino)methyl)-1H-pyrazol-1-yl)methyl)benzamideTFA salt
146) N-(2-aminophenyl)-4-((4-(((2-phenylcyclopropyl)amino)methyl)-1H-1,2,3-triazol-1-yl)methyl)benzamide-TFA salt
147) N-(2-aminophenyl)-4-(2-(4-(((2-(4-fluorophenyl)cyclopropyl)amino)methyl)piperidin-1-yl)-2-oxoethyl)benzamide TFA salt
148) N-(2-aminophenyl)-4-(2-((2-(4-fluorophenyl) cyclopropyl)amino) ethoxy) benzamide TFA salt
149) N-(2-aminophenyl)-6-(2-(4-(((2-(4-fluorophenyl)cyclopropyl)amino)methyl)piperidin-1-yl)ethoxy)nicotinamide TFA salt
150) N-(-2-aminophenyl)-2-((2-4(((2-(4-flurophenyl)cyclopropyl)amino)methyl)piperdine-1-yl)ethyl)amino)pyrimidine-5-carboxamide TFA salt
151) N-(2-aminophenyl)-5-((2-(4-fluorophenyl)cyclopropyl)glycyl)-4,5,6,7-tetrahydrothieno[3,2-c]pyridine-2-carboxamide TFA salt
152) N-(2-aminophenyl)-2-(2-((2-(4-fluorophenyl)cyclopropyl)amino)acetyl)-1,2,3,4-tetrahydroisoquinoline-7-carboxamide TFA salt
153) N-(2-aminophenyl)-2-(3-(4-(((2-phenylcyclopropyl)amino)methyl)piperidin-1-yl)propyl)oxazole-4-carboxamide TFA salt
154) N-(2-aminophenyl)-2-(3-(4-(((2-phenylcyclopropyl)amino)methyl)piperidin-1-yl)propyl)thiazole-5-carboxamide TFA salt
155) N-(2-aminophenyl)-4-((2-((2-(4-fluorophenyl)cyclopropyl)amino)acetamido) methyl)benzamide TFA salt
156) (E)-N-(2-aminophenyl)-4-(3-(4-(((2-(4-fluorophenyl) cyclopropyl)amino)methyl)piperidin-1-yl)-3-oxoprop-1-en-1-yl)benzamide TFA salt
157) (E)-N-(2-aminophenyl)-4-(3-(3-(((2-(4-fluorophenyl) cyclopropyl)amino)methyl)azetidin-1-yl)-3-oxoprop-1-en-1-yl)benzamide TFA salt
158) N-(4-((2-aminophenyl)carbamoyl)benzyl)-4-(((2-(4-fluorophenyl)cyclopropyl)amino)methyl)piperidine-1-carboxamide TFA salt
159) N-(2-aminophenyl)-4-(3-(2-oxo-4-(((2-phenylcyclopropyl)amino)methyl)piperidin-1-yl)propyl)benzamide TFA salt
160) N-(2-aminophenyl)-4-((4-(((2-phenylcyclopropyl)amino)methyl)piperidin-1-yl)sulfonyl) benzamide TFA salt
161) N-(2-aminophenyl)-4-(((4-(((2-phenylcyclopropyl)amino)methyl)piperidin-1-yl) sulfonyl)methyl)benzamide TFA salt
162) N-(2-aminophenyl)-4-(2-((4-(((2-phenylcyclopropyl)amino)methyl)piperidin-1-yl)sulfonyl)ethyl)benzamide TFA salt In an embodiment, the invention relates to a process of preparation of compounds of Formula (I) or its tautomers, polymorphs, stereoisomers, prodrugs, solvate, co-crystals or pharmaceutically acceptable salts thereof.

In another embodiment, the invention relates to a pharmaceutical composition comprising a compound of Formula (I) or a pharmaceutically acceptable salt thereof of together with a pharmaceutically acceptable carrier, optionally in combination with one or more other pharmaceutical compositions.

In yet another embodiment, the invention relates to the pharmaceutical composition as described herein, wherein the composition is in the form selected from the group consisting of a tablet, capsule, powder, syrup, solution, aerosol, and suspension.

In an embodiment, the invention relates to the compound of Formula I or a pharmaceutically acceptable salt thereof for use in the manufacture of a medicament for inhibiting LSD1 enzymes in a cell.

In another embodiment, the invention relates to A method of inhibiting LSD1 in a cell, comprising treating said cell with an effective amount of the compound of Formula I.

In yet another embodiment, the invention relates to a method of treating a condition mediated by LSD1 comprising administering to a subject suffering from a condition mediated by LSD1, a therapeutically effective amount of the compound of Formula I or the pharmaceutical composition described herein.

In an embodiment, the invention relates to a compound of Formula I or a pharmaceutically acceptable salt thereof for use in the manufacture of a medicament for inhibiting HDAC enzymes in a cell.

In another embodiment, the invention relates to a method of inhibiting HDAC in a cell comprising treating said cell with an effective amount of the compound of Formula I.

In yet another embodiment, the invention relates to a method of treating a condition mediated by HDAC, comprising administering to a subject suffering from a condition mediated by HDAC, a therapeutically effective amount of the compound of Formula I or the pharmaceutical composition as described herein.

In an embodiment, the invention relates to a compound of Formula I or a pharmaceutically acceptable salt thereof for use in the manufacture of a medicament for inhibiting both LSD1 and HDAC enzymes in a cell.

In another embodiment, the invention relates to a method of inhibiting both LSD1 and HDAC in a cell comprising treating said cell with an effective amount of the compound of Formula I.

In yet another embodiment, the invention relates to a method of treating a condition mediated by both LSD1 and HDAC, comprising administering to a subject suffering from a condition mediated by both LSD1 and HDAC, a therapeutically effective amount of the compound of Formula I or the pharmaceutical composition.

In an embodiment, the invention relates to a method for the treatment and/or prevention of a proliferative disorder or cancer, comprising administering to a subject suffering from the proliferative disorder or cancer a therapeutically effective amount of the compound of Formula I or the pharmaceutical composition. In another embodiment, the invention relates to the method as described herein, wherein said compound or composition is administered in combination with at least one compound selected from cytotoxic agents and non-cytotoxic agents to a subject in need thereof.

In yet another embodiment, the invention relates to use of the compounds of Formula I or the pharmaceutical composition for treatment of a condition mediated by LSD1; treatment and/or prevention of a proliferative disorder or cancer; or treatment of cancer together with other clinically relevant cytotoxic agents or non-cytotoxic agents.

In an embodiment, the invention relates to a method for the treatment and/or prevention of a condition mediated by LSD1 or a proliferative disorder or cancer, comprising administering to a subject suffering from the condition mediated by LSD1 or the proliferative disorder or cancer, a therapeutically effective amount of the compound or the pharmaceutical composition.

In another embodiment, the invention relates to use of the compounds of Formula I or the pharmaceutical composition for: treatment of a condition mediated by HDAC; treatment and/or prevention of a proliferative disorder or cancer; or treatment of cancer together with other clinically relevant cytotoxic agents or non-cytotoxic agents.

In yet another embodiment, the invention relates to a method for the treatment and/or prevention of a condition mediated by HDAC or a proliferative disorder or cancer, comprising administering to a subject suffering from the condition mediated by HDAC or the proliferative disorder or cancer, a therapeutically effective amount of the compound of Formula I or the pharmaceutical composition.

In an embodiment, the invention relates to use of the compounds of Formula I or the pharmaceutical composition for: treatment of a condition mediated by both LSD1 and HDAC; treatment and/or prevention of a proliferative disorder or cancer; or treatment of cancer together with other clinically relevant cytotoxic agents or non-cytotoxic agents.

In another embodiment, the invention relates to a method for the treatment and/or prevention of a condition mediated by both LSD1 and HDAC or a proliferative disorder or cancer, comprising administering to a subject suffering from the condition mediated by both LSD1 and HDAC or the proliferative disorder or cancer, a therapeutically effective amount of the compound of Formula I or the pharmaceutical composition.

In yet another embodiment, the invention relates to a method for the treatment of cancer, said method comprising administering a combination of the compounds of Formula I or the pharmaceutical composition, with other clinically relevant cytotoxic agents or non-cytotoxic agents to a subject in need thereof.

In an embodiment, the invention relates to a method of treatment of cancer, said method comprising administering a combination of the compounds of Formula I or the pharmaceutical composition, with other clinically relevant immune modulators agents to a subject in need of thereof.

The invention also provides a method of treatment of cancer in patients including administration of a therapeutically effective amount of a compound of Formula (I).

The invention also provides a method for treatment of proliferative conditions or cancer, comprising administering to a subject suffering from proliferative conditions or cancer, a therapeutically effective amount of a compound of Formula (I), in the presence or absence of other clinically relevant cytotoxic agents or non-cytotoxic agents to a subject in need thereof.

The present invention provides a method of treatment of a disorder caused by, associated with or accompanied by disruptions of cell proliferation and/or angiogenesis and the subsequent metastasis including administration of a therapeutically effective amount of a compound of Formula (I).

The invention provides a method of treatment of cancer in patient including administration of effective amount of compounds of Formula (I). The cancer can be either a hematologic malignancy or solid tumor. Hematological malignancy is selected from the group consisting of B-cell lymphoma, T-cell lymphoma and leukemia. In the case of solid tumors, the tumors are selected from the group consisting of breast cancer, lung cancer, ovarian cancer, prostate cancer, head cancer, neck cancer, renal cancer, gastric cancer, colon cancer, pancreatic cancer and brain cancer.

As discussed above, the compounds of the present invention are useful for treating proliferative diseases. A proliferative disease includes, for example, a tumor disease and/or metastases. Compounds of the present invention are useful for treating a proliferative disease that is refractory to the treatment with other chemotherapeutics; or a tumor that is refractory to treatment with other therapeutics due to multidrug resistance.

Compounds of the present invention are able to slow tumor growth, stop tumor growth or bring about the regression of tumors and to prevent the formation of tumor metastasis (including micrometastasis) and the growth of metastasis (including micrometastasis). In addition, they can be used in epidermal hyperproliferation.

The compound of formula I of the present invention can be used as a prophylactic or therapeutic agent for cancer. Examples of the cancer include, but not restricted to, breast cancer, prostate cancer, pancreatic cancer, gastric cancer, lung cancer, colon cancer, rectal cancer, esophagus cancer, duodenal cancer, tongue cancer, pharyngeal cancer, brain tumor, neurinoma, non-small cell lung cancer, small cell lung cancer, liver cancer, kidney cancer, bile duct cancer, uterine body cancer, cervical cancer, ovarian cancer, urinary bladder, skin cancer, hemangioma, malignant lymphoma, malignant melanoma, thyroid cancer, bone tumor, vascular fibroma, retinoblastoma, penile cancer, pediatric solid cancer, lymphoma, myeloma and leukemia (including, for example acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL) or hariy cell leukemia) or cutaneous T-cell lymphoma (CTCL).

In one embodiment, the invention provides a method of inhibiting both LSD-1 and HDAC activity comprising administering, to a patient in need of treatment, an amount of a composition comprising a compound of formula I and a pharmaceutically acceptable carrier sufficient to inhibit both LSD-1 and HDAC activity.

In one aspect of this embodiment, the invention provides a compound of formula I for use in inhibiting both LSD-1and HDAC. In a related aspect, the invention provides for the use of a compound of formula I for the manufacture of a medicament for inhibiting both LSD-1 and HDAC.

In one embodiment, the invention provides a method of treating and/or preventing a neurodegenerative disease or disorder comprising administering, to a patient in need of treatment, a therapeutically effectively amount of a composition comprising a compound of formula I and a pharmaceutically acceptable carrier.

In one aspect of this embodiment, the invention provides a compound of formula I for use in treating and/or preventing a neurodegenerative disorder or condition. In a related aspect, the invention provides for the use of a compound of formula I for the manufacture of a medicament for treating and/or preventing a neurodegenerative disorder or condition.

In another aspect, the compound may be administered in combination therapy by combining the compound of Formula (I) with one or more separate agents, not limited to targets such as DNA methyltransferase, heat shock proteins (e.g. HSP90), kinase, epigenetic and other matrix metalloproteinases.

"Combination therapy" includes the administration of the subject compounds in further combination with other biologically active ingredients (such as, but are not limited to, different antineoplastic agent) and non-drug therapies (such as, but are not limited to, surgery or radiation treatment). The compounds described herein can be used in combination with other pharmaceutically active compounds, preferably, which will enhance the effect of the compounds of the invention. The compounds can be administered simultaneously or sequentially to the other drug therapy.

In another aspect, the subject compounds may be combined with the antineoplastic agents (e.g. small molecules, cytotoxic reagents, non-cytotoxic reagents, monoclonal antibodies, antisense RNA and fusion proteins) that inhibit one or more biological targets. Such combination may enhance therapeutic efficacy over the efficacy achieved by any of the agents alone and may prevent or delay the appearance of resistant variants.

In another aspect, the subject compounds may be combined with immunoncology drugs not restricting to PDL-1, IDO, TDO, CTLA4 or any other drugs which is involved in the immune modulation.

EXAMPLES

The following examples provide the details about the synthesis, activities, and applications of the compounds of the present disclosure. It should be understood the following is representative only, and that the invention is not limited by the details set forth in these examples.

There is also provided a process as shown in the following scheme-1, for the preparation of compounds of the Formula (I), wherein all the groups are as defined earlier.

Scheme 1

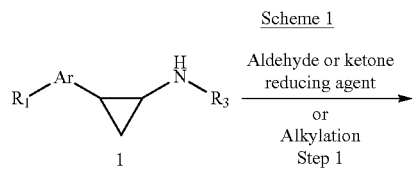

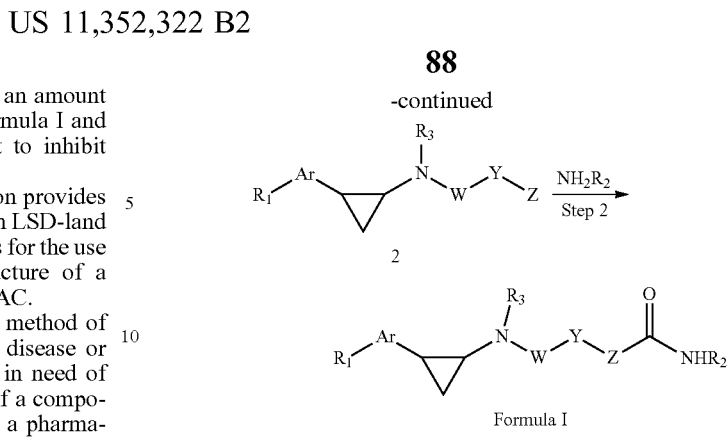

The said process for the preparation of the compounds of Formula (I) comprises of the following:

Step 1: Compound 1 were reacted with an aldehyde or ketone in protic solvents such as MeOH, etc., to give the intermediate imine which was reacted with sodium borohydride (NaBH$_4$) or its equivalent to give the compound 2 or compound of 1 were alkylated with the corresponding substituted halo compound in the presence of inorganic or organic base to give the compound 2.

Step 2: Hydrolyzing the intermediate compound 2 with an inorganic base gave the corresponding acid. Coupling the acid with activating agents such as EDCI.HCl (1 (3-dimethylaminopropyl)-3-ethylcarbodiimide hydrochloride) and HOBt (1-hydroxybenzotriazole) or (1-propylphosphonic anhydride)T$_3$P/triethylamine and the like in the presence of the respective amine NH$_2$R$_2$ to yield the compound of the general Formula (I) or alternatively reacting the intermediate compound 2 with NH$_2$R$_2$ and an inorganic base gave the compound of Formula (I)

Synthesis of Intermediates

A-1—methyl 2-(4-formylpiperidin-1-yl)pyrimidine-5-carboxylate

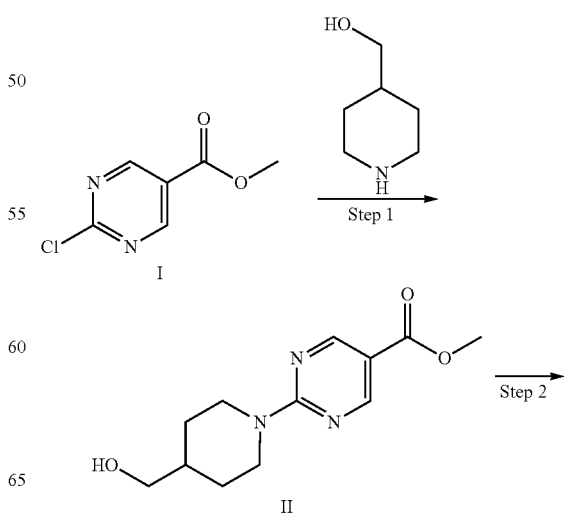

Step 1: methyl 2-(4-(hydroxymethyl) piperidin-1-yl) pyrimidine-5-carboxylate-II

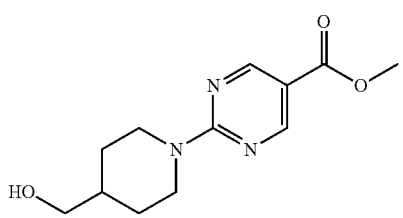

To a stirred solution of methyl 2-chloropyrimidine-5-carboxylate (I, 2.5 g, 14.53 mmol) in DMF (25 mL) was added piperidin-4-ylmethanol (2 g, 17.44 mmol) and potassium carbonate (4.01 g, 29.07 mmol) and stirred for 5 hours at room temperature. Progress of reaction followed TLC, after completion of reaction, the reaction mixture was concentrated and quenched with water (100 mL) extracted with ethyl acetate (2×150 mL). The organic portion was washed with water, brine, dried over sodium sulphate and concentrated under reduced pressure to afford the crude product which was purified by column chromatography using methanol-dichloromethane gradient to afford the titled product as off-white solid (II, 3.6 g, 83%). LC-MS m/z calcd for $C_{12}H_{17}N_3O_3$, 251.1. found 252.1[M+H]$^+$.

Step 2: methyl 2-(4-formylpiperidin-1-yl) pyrimidine-5-carboxylate-A-1

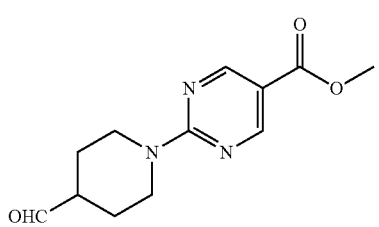

To a stirred solution of DMSO (5.6 g, 171.71 mmol) in dichloromethane (40 mL) was added oxalyl chloride (6.02 g, 47.81 mmol) at −78° C. (drop-wise) and continue stirred for 30° C., methyl 2-(4-(hydroxymethyl)piperidin-1-yl)pyrimidine-5-carboxylate (II, 3 g, 11.95 mmol) dissolved in dichloromethane (10 mL) was slowly added and continue stirred for 3 h at −78° C. (drop-wise). To the reaction mixture triethylamine (14.4 g, 143.42 mmol) was added and stirred for 12 h at room temperature. Progress of reaction followed by TLC, reaction mixture quenched with ammonium chloride (100 mL), extracted with ethylacetate (2×150 mL). The organic portion was washed with water and brine dried over sodium sulphate and concentrated under reduced pressure to afford the crude product which was purified by column chromatography using methanol-dichloromethane gradient to afford the titled product as off-white solid (A-1, 2 g, 67%). LC-MS m/z calcd for $C_{12}H_{15}N_3O_3$, 249.1. found 250.1[M+H]$^+$.

A-2 methyl (E)-3-(4-(4-formylpiperidin-1-yl)phenyl)acrylate

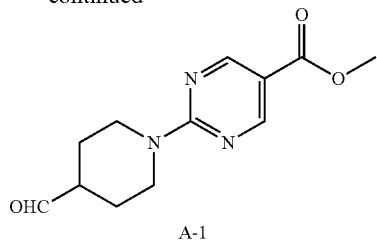

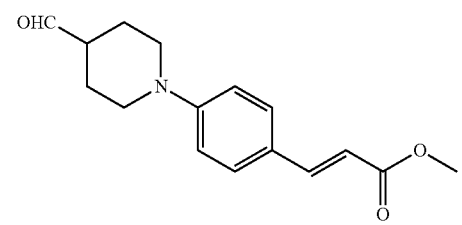 [SMILES: COC(=O)/C=C/c1ccc(N2CCC(C=O)CC2)cc1]

The intermediate A-2 was synthesized using methyl-4-fluorocinnamic acid ester and piperidin-4-yl-methanol using the procedure for synthesizing A-1. LC-MS m/z calcd for $C_{16}H_{19}NO_3$ 273.1. found 274.1[M+H]$^+$.

A-3—ethyl 2-(4-oxopiperidin-1-yl)pyrimidine-5-carboxylate

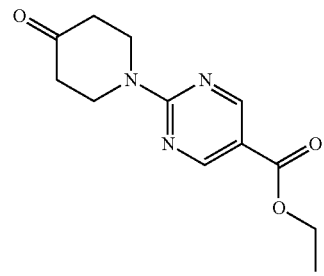 [SMILES: CCOC(=O)c1cnc(N2CCC(=O)CC2)nc1]

The intermediate A-3 was synthesized using ethyl 2-chloropyrimidine-5-carboxylate and 4-oxo-piperidine using the procedure for synthesizing A-1.

LC/MS m/z calcd for $C_{12}H_{15}N_3O_3$, 249.1. found 250.1 [M+H]$^+$.

A-4 methyl 2-(2-formyl-5,6-dihydroimidazo[1,2-a]pyrazin-7(8H)-yl)pyrimidine-5-carboxylate

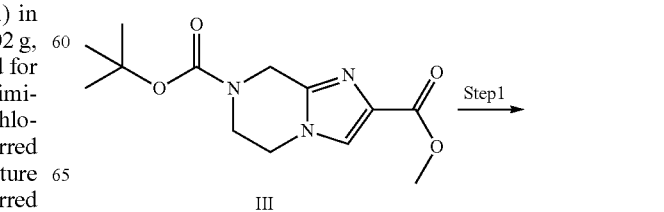

-continued

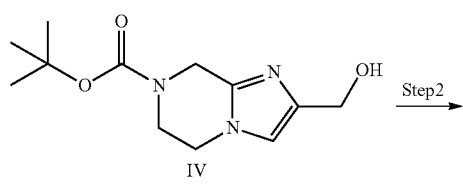

IV

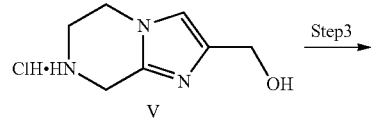

V

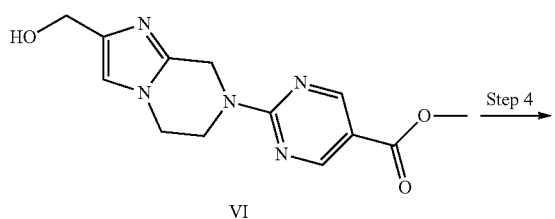

VI

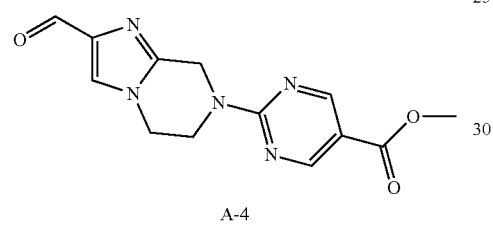

A-4

Step 1: 2-Hydroxymethyl-5,6-dihydro-8H-imidazo[1,2-a]pyrazine-7-carboxylic acid tert-butyl ester (IV)

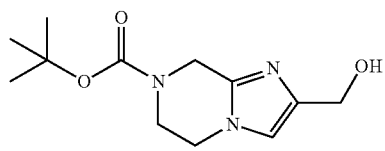 [SMILES: CC(C)(C)OC(=O)N1CCn2cc(CO)nc2C1]

To a stirred solution of 7-tert-butyl 2-methyl 5,6-dihydro-imidazo[1,2-a]pyrazine-2,7(8H)-dicarboxylate (III, 0.42 g, 1.42 mmol) in dry tetrahydrofuran (12 mL) was added diisobutylaluminium hydride (DIBAL-H) (4.97 mL, 4.98 mmol, 1M solution of THF) drop-wise at −35° C. to −40° C. After completion of addition, the reaction mixture was allowed to stir at room temperature for 3 h. The progress of the reaction was monitored by TLC. The reaction mixture was quenched with saturated ammonium chloride solution at −30° C. and was extracted with dichloromethane (3×50 mL). The combined organic extract was washed with water, brine dried over sodium sulphate and concentrated under reduced pressure to get the titled product as an off-white solid (IV, 0.34 g, 94%). LC-MS m/z calcd for $C_{12}H_{19}N_3O_3$, 253.1; found 254.4 [M+H]$^+$.

Step 2: (5,6,7,8-Tetrahydro-imidazo[1,2-a]pyrazin-2-yl)-methanol hydrochloride (V)

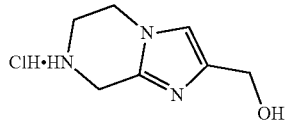

To a solution of 2-hydroxymethyl-5,6-dihydro-8H-imidazo[1,2-a]pyrazine-7-carboxylic acid tert-butyl ester (IV, 0.34 g, 1.34 mmol) in dry methanol (12 mL) was added 20% HCl in dioxane (18 mL) at 0° C. and the resulting mixture was stirred at room temperature for 16 h. The solvent was evaporated under reduced pressure to get the crude product which was triturated with diethylether to afford the titled product as a pale-yellow solid (V, 0.25 g, 95%). LC-MS m/z calcd for $C_7H_{11}N_3O$, 153.1; found 154.2 [M+H]$^+$.

Step 3: 2-(2-Hydroxymethyl-5,6-dihydro-8H-imidazo[1,2-a]pyrazin-7-yl)-pyrimidine-5-carboxylic acid methyl ester (VI)

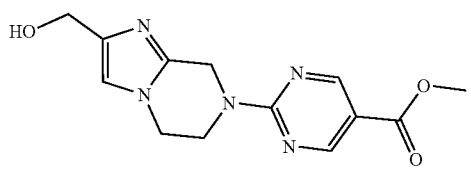 [SMILES: COC(=O)c1cnc(N2CCn3cc(CO)nc3C2)nc1]

To a suspension of (5,6,7,8-tetrahydro-imidazo[1,2-a]pyrazin-2-yl)-methanol hydrochloride (V, 0.35 g, 1.85 mmol) was added potassium carbonate (0.51 g, 3.71 mmol) at 0° C. and stirred at that temperature for 5 min. Then, 2-chloro-pyrimidine-5-carboxylic acid methyl ester (0.38 g, 2.22 mmol) was added and the resulting mixture was stirred at room temperature for 15 h. The reaction mixture was quenched with ice and the solvent was evaporated to get the residue. Water was added and precipitate formed was filtered, washed with water and n-hexane to afford the pure product as an off-white solid (VI, 0.36 g, 68%). LC-MS m/z calcd for $C_{13}H_{15}N_5O_3$, 289.1; found 290.1 [M+H]$^+$.

Step 4: 2-(2-Formyl-5,6-dihydro-8H-imidazo[1,2-a]pyrazin-7-yl)-pyrimidine-5-carboxylic acid methyl ester-Intermediate A-4

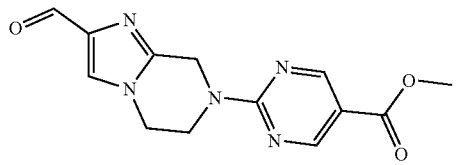 [SMILES: COC(=O)c1cnc(N2CCn3cc(C=O)nc3C2)nc1]

To a solution of 2-(2-Hydroxymethyl-5,6-dihydro-8H-imidazo[1,2-a]pyrazin-7-yl)-pyrimidine-5-carboxylic acid methyl ester (VI, 0.36 g, 1.24 mmol) in dry dichloromethane (15 mL) was added Dess-martin periodinane (1.32 g, 3.11 mmol) at 0° C. and the resulting mixture was stirred at room temperature for 2 h. The progress of the reaction was monitored by TLC. The reaction mixture was quenched with saturated sodium bicarbonate solution. Aqueous solution of sodium thiosulphate (10 mL, 10%) was added and stirred for 15 min. Then diluted with dichloromethane and the organic portion was washed with saturated sodium bicarbonate solution, water and brine solution, dried over sodium sulphate and concentrated under reduced pressure to afford the crude which was then triturated with n-pentane to afford the titled product as an off white solid (A-4, 0.35 g, 95%), LC-MS m/z calcd for $C_{13}H_{13}N_5O_3$, 287.1; found 288.1 $[M+H]^+$.

A-5-methyl 7-(4-formylbenzamido)heptanoate-procedure

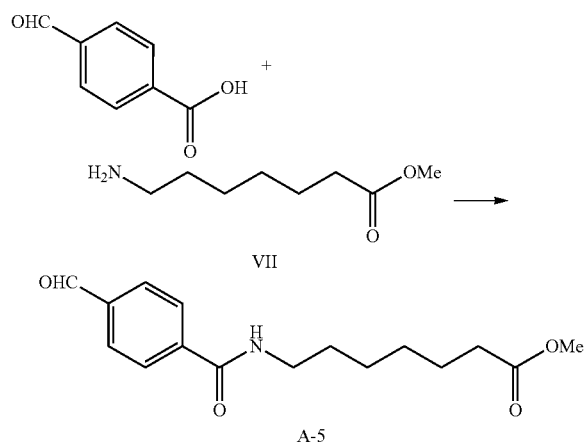

To a stirred solution of 4-formylbenzoic acid (1 g, 6.66 mmol) and methyl 7-aminoheptanoate (VII, 1.16 g, 7.33 mmol) in dichloromethane (30 mL) was added triethylamine (2.3 mL, 16.6 mmol), the reaction mixture was stirred at room temperature for 10 min and then cooled reaction mixture to 0° C. and added $T_3P$ (6.35 mL, 10 mmol) and was stirred at room temperature for 3 h. Reaction was monitored by TLC. After completion of reaction, the mixture was quenched with ice. The reaction mixture was diluted with water and extracted with dichloromethane (3×25 mL). The organic portion was washed with water, brine, dried over sodium sulphate and concentrated under reduced pressure to get the title compound as solid. (A-5, 1.8 g, 92%). LC-MS m/z calcd for $C_{16}H_{21}NO_4$, 291.1; found 292.2 $[M+H]^+$.

A-6-1-(2,2,2-trifluoroacetyl)piperidine-4-carbaldehyde

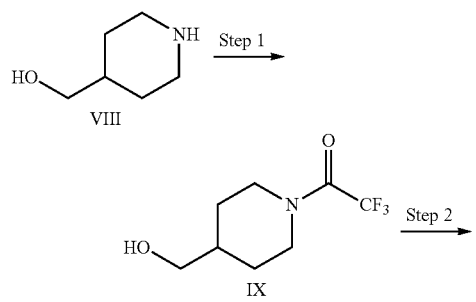

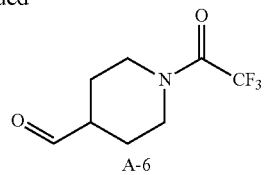

Step 1: 2,2,2-trifluoro-1-(4-(hydroxymethyl)piperidin-1-yl)ethanone (IX)

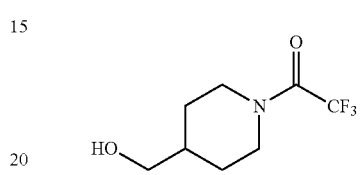

To a stirred solution of piperidin-4-ylmethanol (VIII, 5.0 g, 4.3 mmol) in dichloromethane (200 mL) was added triethylamine at 0° C. and followed by trifluoro acetic anhydride, and the reaction mixture was stirred at room temperature about 12 h. The progress of the reaction was monitored by TLC. The reaction mixture was diluted with dichloromethane, the organic portion was washed with saturated ammonium chloride, water, followed by brine solution, dried over sodium sulphate and concentrated under reduced pressure to get the product as sticky oil (IX, 8.5 g, 92%). LC-MS m/z calcd for $C_8H_{12}F_3NO$, 211.1; found 212.1 $[M+H]^+$.

Step 2: 1-(2,2,2-trifluoroacetyl)piperidine-4-carbaldehyde (A-6)

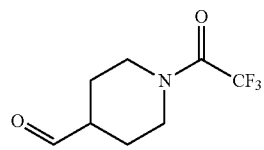 [SMILES: O=CC1CCN(C(=O)C(F)(F)F)CC1]

A solution of dimethyl sulfoxide (4 mL) and dichloromethane (60 mL) was cooled to −68° C. Oxalyl chloride (3.2 mL) was slowly added drop-wise and the reaction mixture was stirred for 30 min at −68° C. Then a solution of 2,2,2-trifluoro-1-(4-(hydroxymethyl)piperidin-1-yl)ethanone (IX, 2 g, 9.48 mmol) in 4 mL of dichloromethane and was added dropwise at −68° C., after completion of addition, the reaction mixture was stirred for 1.5 h at −68° C. and this was followed by drop-wise addition of triethylamine at −68° C. The reaction mixture was stirred at −68° C. for 4-6 h. The reaction mixture was then allowed to warm to room temperature and the stirring was continued for 16 h. The progress of the reaction was monitored by TLC. The reaction mixture was diluted with ethylacetate and the organic portion was washed with water, saturated ammonium chloride, brine, dried over sodium sulphate and concentrated under reduced pressure to get the product as sticky oil (A-6, 1.9 g, 96%), LC-MS m/z calcd for $C_8H_{10}F_3NO_2$, 209.1; found 210.1 $[M+H]^+$.

A-7: Ethyl 4-((4-formyl-1H-1,2,3-triazol-1-yl)methyl)benzoate

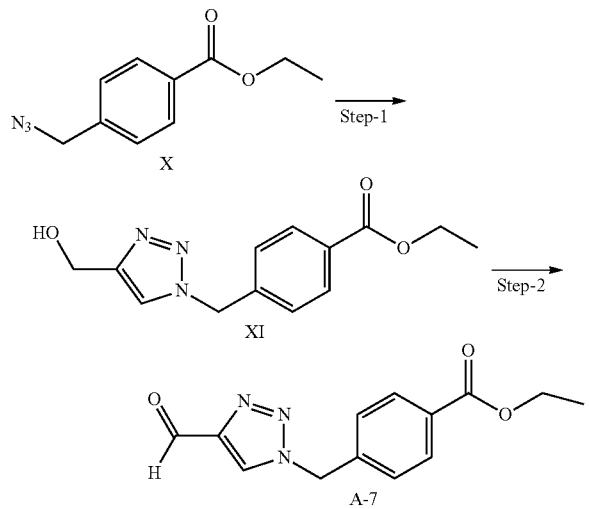

Step-1: Ethyl 4-((4-(hydroxymethyl)-1H-1,2,3-triazol-1-yl)methyl)benzoate-XI

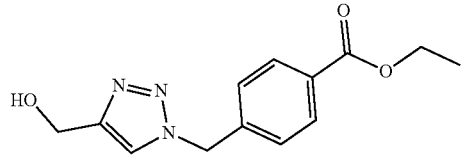 [SMILES: CCOC(=O)c1ccc(Cn2cc(CO)nn2)cc1]

To a stirred solution of ethyl 4-(azidomethyl)benzoate (X, 2 g, 9.75 mmol) in DMF (80 mL) was added propargyl alcohol (0.6 mL, 10.7 mmol) and DIPEA (2.7 mL, 14.6 mmol) and then copper (I) iodide (0.9 g, 4.87 mmol) was added. The reaction mixture was stirred for 30 min at room temperature. Saturated ammonium chloride solution with few drop of ammonia (20 mL) was added and extracted with ethylacetate (2×100 mL). The organic portion was washed with water, brine, dried over sodium sulphate and concentrated under reduced pressure to afford the crude compound which was purified by column chromatography using ethylacetate-hexane gradient as eluent to afford the titled product as sticky oil (XI, 2.1 g, 87%). LC-MS m/z calcd for $C_{13}H_{15}N_3O_3$, 261.1; found 262.1 $[M+H]^+$.

Step-2: ethyl 4-((4-formyl-1H-1,2,3-triazol-1-yl)methyl)benzoate-Intermediate A-7

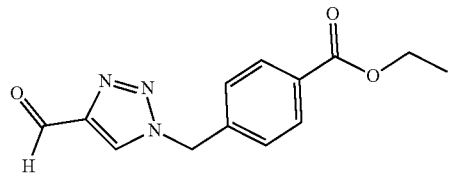 [SMILES: CCOC(=O)c1ccc(Cn2cc(C=O)nn2)cc1]

To a stirred solution of ethyl 4-((4-(hydroxymethyl)-1H-1,2,3-triazol-1-yl)methyl)benzoate (XI, 1 g, 3.83 mmol) in ethylacetate (25 mL) was added IBX (1.6 g, 5.74 mmol) and heated at 75° C. for 16 h. Water (50 mL) was added and extracted with ethyl acetate (2×50 mL). The organic portion was washed with water, brine, dried over sodium sulphate and concentrated under reduced pressure to afford the crude compound which was purified by column chromatography using ethylacetate-hexane gradient as eluent to afford the titled product as solid (A-7, 0.75 g, 76%). LC-MS m/z calcd for $C_{13}H_{13}N_3O_3$, 259.1; found 260.1 $[M+H]^+$.

A-8 and A-9: ethyl 4-(3-(4-formyl-1H-imidazol-1-yl)propyl)benzoate and ethyl 4-(3-(5-formyl-1H-imidazol-1-yl)propyl)benzoate

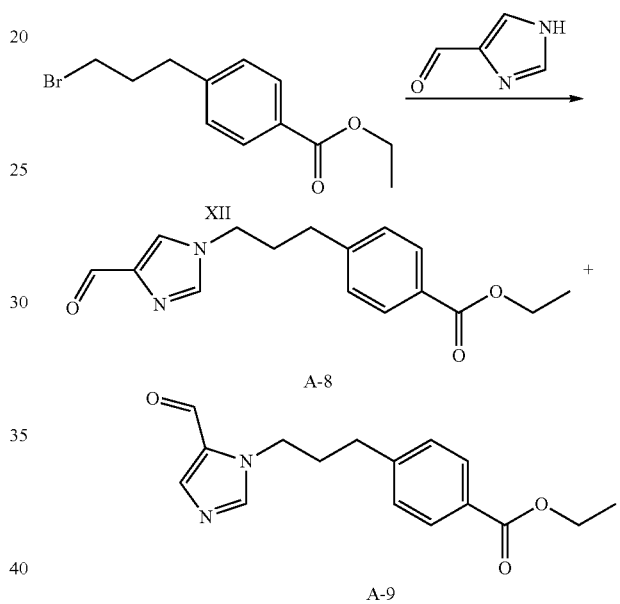

To a stirred solution of sodium hydride (0.124 g, 5.20 mmol) in THF (3.5 mL) was added 1H-imidazole-4-carbaldehyde (0.5 g, 5.20 mmol) portion wise at 0° C. After 1 h stirring, ethyl 4-(3-bromopropyl)benzoate (XII, 1.4 g, 5.20 mmol) and was 18-crown ether (0.2 g) was added at 0° C. and the temperature was allowed to warm to room temperature. The reaction mixture was then heated at 60° C. for 18 h. The reaction mixture was quenched with ice-water and extracted with ethylacetate (2×50 mL). The organic portion was washed with water, brine, dried over sodium sulphate and concentrated under reduced pressure to afford the crude compound which was purified by column chromatography using ethylacetate-hexane gradient as eluent to afford the titled product as sticky oil (A-8, 0.19 g, 13%), $^1$HNMR (400 MHz, DMSO-$d_6$): δ 9.68 (s, 1H), 8.09 (s, 1H), 7.88-7.84 (m, 3H), 7.33 (d, 2H, J=8 Hz), 4.28 (q, 2H, J=6.8 Hz), 4.06 (t, 2H, J=6.8 Hz), 2.62 (t, 2H, J=7.2 Hz), 2.13-2.06 (m, 2H), 1.29 (t, 3H, J=7.2 Hz). LC-MS m/z calcd for $C_{16}H_{18}N_2O_3$, 286.1; found 287.1 $[M+H]^+$ and stick oil (A-9, 0.2 g, 15%), $^1$HNMR (400 MHz, DMSO-$d_6$): δ 9.70 (s, 1H), 8.06 (s, 1H), 7.88 (s, 1H), 7.85 (d, 2H, J=8 Hz), 7.31 (d, 2H, J=7.6 Hz) 4.32-4.25 (m, 4H), 2.62 (t, 2H, J=8 Hz), 2.04-1.95 (m, 2H), 1.29 (t, 3H, J=7.2 Hz). LC-MS m/z calcd for $C_{16}H_{18}N_2O_3$, 286.1; found 287.1 $[M+H]^+$.

A-10: ethyl 4-((4-formyl-1H-imidazol-1-yl)methyl)benzoate

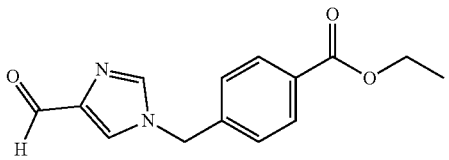 [SMILES: CCOC(=O)c1ccc(Cn2cnc(C=O)c2)cc1]

Intermediate A-10 was synthesized starting from ethyl 4-(bromomethyl)benzoate and 1H-imidazole-4-carbaldehyde following protocol given for A-8. LC-MS m/z calcd for $C_{14}H_{14}N_2O_3$, 258.1. found 259.1 $[M+H]^+$.

A-11: ethyl 4-(3-(4-formyl-1H-pyrazol-1-yl)propyl)benzoate

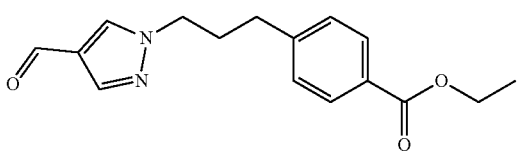 [SMILES: CCOC(=O)c1ccc(CCCn2cc(C=O)cn2)cc1]

Intermediate A-11 was synthesized starting from 1H-pyrazole-4-carbaldehyde and methyl 4-(3-bromopropyl)benzoatepyrazole following protocol given for A-8. LC-MS m/z calcd for $C_{16}H_{18}N_2O_3$, 286.1; found 287.0 $[M+H]^+$.

A-12-methyl 4-((4-formyl-1H-pyrazol-1-yl)methyl)benzoate

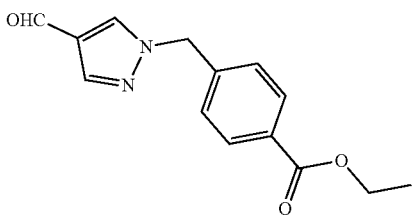 [SMILES: CCOC(=O)c1ccc(Cn2cc(C=O)cn2)cc1]

Intermediate A-12 was synthesized starting from 1H-pyrazole-4-carbaldehyde and ethyl 4-(bromomethyl)benzoate following protocol given for A-8. LC-MS m/z calcd for $C_{14}H_{14}N_2O_3$, 258.1; found 259.1 $[M+H]^+$.

A-13-methyl 4-(2-(4-formyl-1H-imidazol-1-yl)ethyl)benzoate

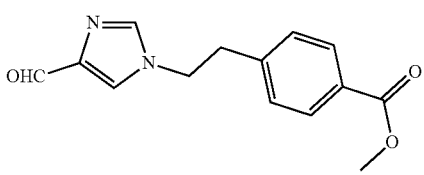 [SMILES: COC(=O)c1ccc(CCn2cnc(C=O)c2)cc1]

Intermediate A-13 was synthesized starting from 1H-pyrazole-4-carbaldehyde and methyl 4-(bromoethyl) benzoate following protocol given for A-8. LC-MS m/z calcd for $C_{14}H_{14}N_2O_3$, 258.1; found 259.1 $[M+H]^+$.

A-14: Methyl 4-((2-formyl-5,6-dihydroimidazo[1,2-a]pyrazin-7(8H)-yl)methyl)benzoate

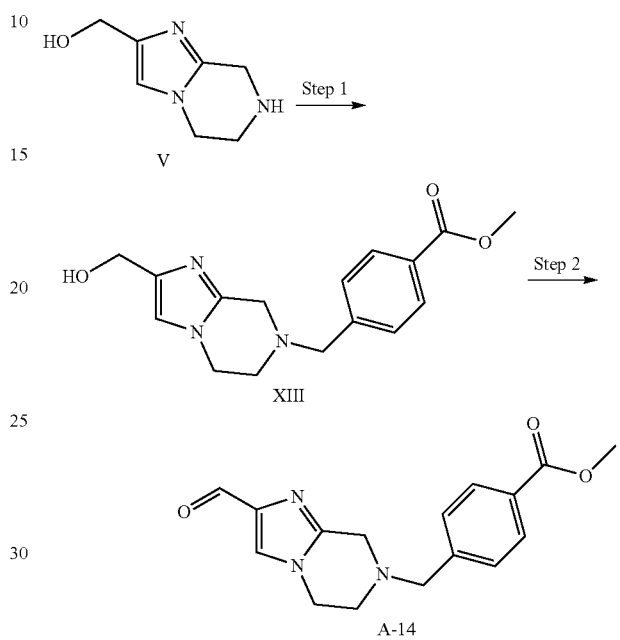

Step 1: Methyl 4-((2-(hydroxymethyl)-5,6-dihydro-imidazo[1,2-a]pyrazin-7(8H)-yl)methyl)benzoate (XIII)

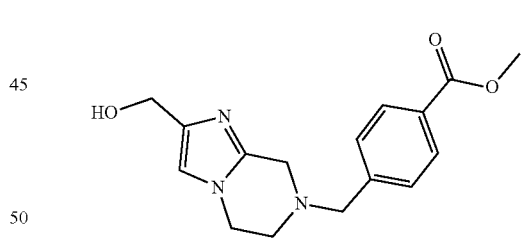

To a suspension of (5,6,7,8-Tetrahydro-imidazo[1,2-a]pyrazin-2-yl)-methanol hydrochloride (V, 0.52 g, 2.75 mmol) was added potassium carbonate (1.14 g, 8.27 mmol) at 0° C. and stirred at that temperature for 5 min. Then methyl 4-(bromomethyl)benzoate (0.69 g, 3.03 mmol) was added and the resulting mixture was stirred at room temperature for 3 h. Reaction was monitored by TLC, after completion of the reaction, the reaction mixture was quenched with ice and extracted with dichloromethane. The organic layer was washed with cold water, brine, dried over sodium sulphate and concentrated under reduced pressure to afford the required product (XIII, 0.47 g, 52%). LC-MS m/z calcd for $C_{16}H_{19}N_3O_3$, 301.1; found 302.2 $[M+H]^+$.

Step 2: Methyl 4-((2-formyl-5,6-dihydroimidazo[1,2-a]pyrazin-7(8H)-yl)methyl)benzoate-Intermediate A-14

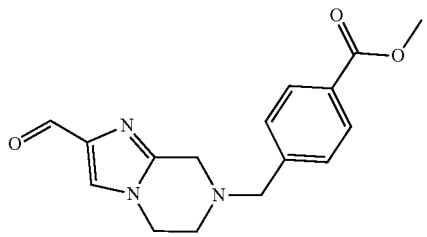 [SMILES: COC(=O)c1ccc(CN2CCn3cc(C=O)nc3C2)cc1]

To a solution of methyl 4(2-hydroxymethyl)-5,6-dihydro-imidazo[1,2-a]pyrazin-7(8H)yl)methyl)benzoate (XIII, 0.43 g, 1.42 mmol) in dry dichloromethane (15 mL) was added Dess-martin periodinane (1.51 g, 3.57 mmol) at 0° C. and the resulting mixture was stirred at room temperature for 2 h. The progress of the reaction was monitored by TLC. The reaction mixture was quenched with saturated sodium bicarbonate solution. A 10% aqueous solution of sodium thiosulphate (5 mL) was added and stirred for 15 min. Then diluted with dichloromethane and the organic portion was washed with saturated sodium bicarbonate solution, water and brine solution dried over sodium sulphate and concentrated under reduced pressure to afford the crude which was then triturated with n-pentane to afford the titled product as an off white solid (A-14, 0.41 g, 96%). LC-MS m/z calcd for $C_{16}H_{17}N_3O_3$, 299.1; found 300.1 [M+H]$^+$.

A-15-methyl 4-(2-(4-formylpiperidin-1-yl)ethyl)benzoate

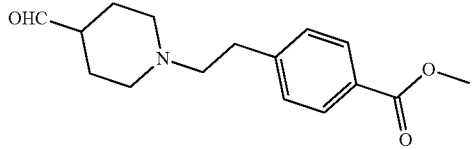 [SMILES: COC(=O)c1ccc(CCN2CCC(C=O)CC2)cc1]

Intermediate A-15 was synthesized starting from piperidin-4-yl-methanol and methyl 4-(bromoethyl)benzoate following protocol given for A-14. LC-MS m/z calcd for $C_{16}H_{21}NO_3$, 275.1; found 276.1 [M+H]$^+$.

A-16-methyl 4-(3-(4-oxopiperidin-1-yl)propyl)benzoate

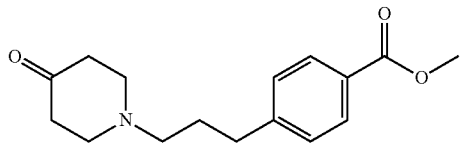 [SMILES: COC(=O)c1ccc(CCCN2CCC(=O)CC2)cc1]

Intermediate A-16 was synthesized starting from 4-oxopiperidine hydrochloride salt and methyl 4-(bromopropyl)benzoate following protocol given for A-14. LC-MS m/z calcd for $C_{16}H_{21}NO_3$, 275.1; found 276.1 [M+H]$^+$.

A-17—ethyl 4-(3-(4-formyl-2-oxopiperidin-1-yl)propyl)benzoate

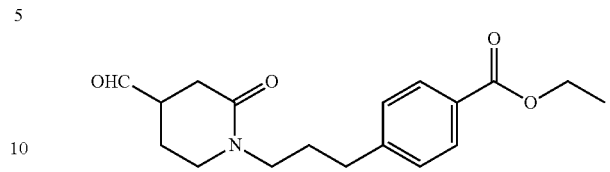

Intermediate A-17 was synthesized starting from 2-oxopiperidin-yl-4-methanol and methyl 4-(bromopropyl)benzoate following protocol given for A-14. LC-MS m/z calcd for $C_{18}H_{23}NO_4$, 317.1; found 318.0 [M+H]$^+$.

A-18-methyl 4-(3-(2-formyl-5,6-dihydroimidazo[1,2-a]pyrazin-7(8H)-yl)propyl)benzoate

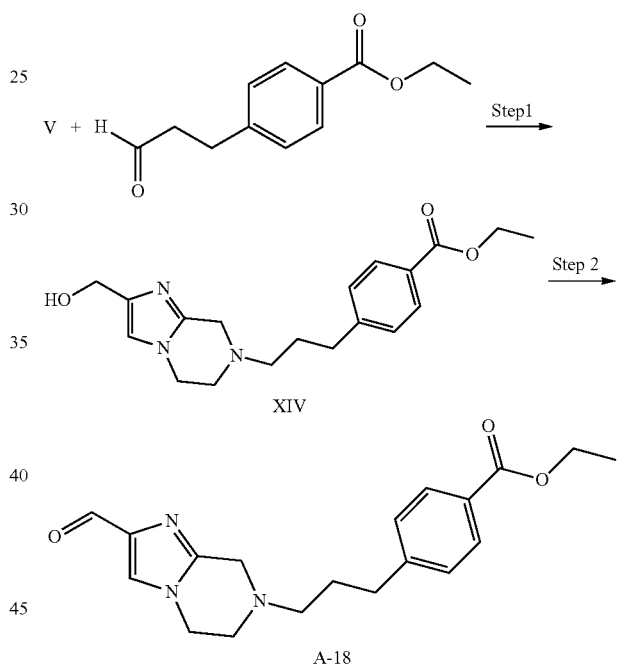

Step 1: 4-[3-(2-Hydroxymethyl-5,6-dihydro-8H-imidazo[1,2-a]pyrazin-7-yl)-propyl]-benzoic acid ethyl ester (XIV)

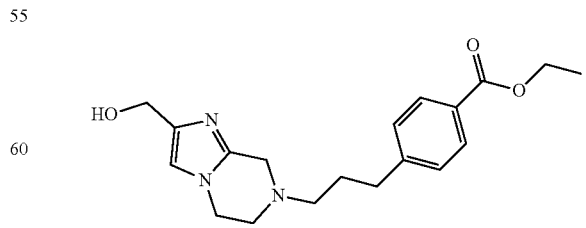

To a stirred solution of (5,6,7,8-tetrahydro-imidazo[1,2-a]pyrazin-2-yl)-methanol. HCl salt (V, 0.1 g, 0.53 mmol) in methanol (8 mL) was added 4-(3-oxo-propyl)-benzoic acid ethylester (0.13 g, 0.63 mmol) and sodium bicarbonate (0.044 g, 0.53 mmol) and molecular sieves (approx 1 g) at room temperature and the resulting mixture was heated to reflux for 30 min. Cooled to room temperature and sodium cyanoborohydride (0.036 g, 0.58 mmol) was added and stirred at room temperature for 15 h. Ice was added and the reaction mixture was filtered. The solvent was evaporated to get the residue. Water was added and extracted with dichloromethane (2×30 mL). The organic portion was washed with water and brine, dried over sodium sulphate and concentrated under reduced pressure to afford the crude compound which was purified by column chromatography to afford the titled product as a colourless oil. (XIV, 0.09 g, 50%). LC-MS m/z calcd for $C_{19}H_{25}N_3O_3$, 343.2; found 344.3 $[M+H]^+$.

Step 2: 4-[3-(2-Formyl-5,6-dihydro-8H-imidazo[1,2-a]pyrazin-7-yl)-propyl]-benzoic acid ethyl ester-Intermediate A-18

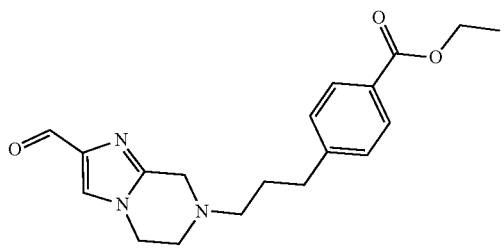 [SMILES: CCOC(=O)c1ccc(CCCN2CCn3cc(C=O)nc3C2)cc1]

To a stirred solution of 4-[3-(2-hydroxymethyl-5,6-dihydro-8H-imidazo[1,2-a]pyrazin-7-yl)-propyl]-benzoic acid ethyl ester (XIV, 0.09 g, 0.26 mmol) in dry dichloromethane (10 mL) was added Dess-martin periodinane (0.28 g, 0.65 mmol) at 0° C. and the resulting mixture was stirred at room temperature for 3 h. The progress of the reaction was monitored by TLC. The reaction mixture was quenched with saturated sodium bicarbonate solution. A 10% aqueous solution of sodium thiosulphate (1 mL) was added and stirred for 15 min, then diluted with dichloromethane (20 mL) and the organic portion was washed with saturated sodium bicarbonate solution, water and brine solution dried over sodium sulphate and concentrated under reduced pressure to afford the required product as yellow solid (A-18, 0.08 g, 90%) which was carried to next step without further purification. LC-MS m/z calcd for $C_{19}H_{23}N_3O_3$, 341.1; found 342.2 $[M+H]^+$.

A-19-methyl 4-(2-(4-formylpiperidin-1-yl)propyl)benzoate

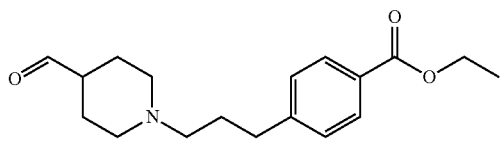 [SMILES: CCOC(=O)c1ccc(CCCN2CCC(C=O)CC2)cc1]

Intermediate A-19 was synthesized starting from piperidin-4-yl-methanol and 4-(3-Oxo-propyl)-benzoic acid ethylester following protocol given for A-18. LC-MS m/z calcd for $C_{18}H_{25}NO_3$, 303.2; found 304.1 $[M+H]^+$.

A-20-methyl 4-(3-(7-formyl-3,4-dihydroisoquinolin-2(1H)-yl)propyl)benzoate

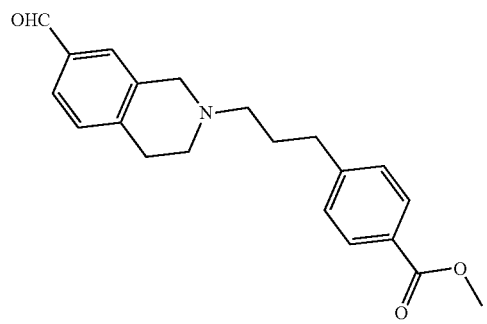 [SMILES: COC(=O)c1ccc(CCCN2CCc3ccc(C=O)cc3C2)cc1]

Intermediate A-20 was synthesized starting from (1,2,3,4-tetrahydroisoquinolin-6-yl)methanol hydrochloride and 4-(3-oxo-propyl)-benzoic acid ethylester following protocol given for A-18. LC-MS m/z calcd for $C_{21}H_{23}NO_3$, 337.2; found 338.1 $[M+H]^+$.

A-21—ethyl 4-(3-(6-formyl-3,4-dihydroisoquinolin-2(1H)-yl)propyl)benzoate

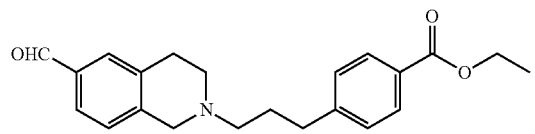 [SMILES: CCOC(=O)c1ccc(CCCN2CCc3cc(C=O)ccc3C2)cc1]

Intermediate A-21 was synthesized starting from (1,2,3,4-tetrahydroisoquinolin-7-yl)methanol hydrochloride and 4-(3-oxo-propyl)-benzoic acid ethylester following protocol given for A-18. LC-MS m/z calcd for $C_{22}H_{25}NO_3$, 351.2; found 352.2 $[M+H]^+$.

A-22-methyl 4-((7-formyl-3,4-dihydroisoquinolin-2(1H)-yl)methyl)benzoate

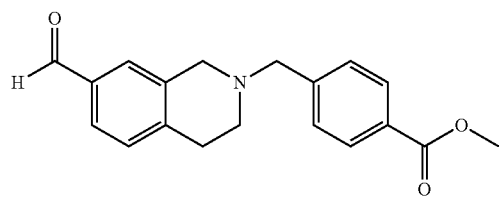 [SMILES: COC(=O)c1ccc(CN2CCc3ccc(C=O)cc3C2)cc1]

Intermediate A-22 was synthesized starting from (1,2,3,4-tetrahydroisoquinolin-7-yl)methanol hydrochloride and 4-formyl-1-benzoic acid methylester following protocol given for A-18. LC-MS m/z calcd for $C_{19}H_{19}NO_3$, 309.1; found 310.1 $[M+H]^+$.

A-23: Methyl 4-(3-oxo-3-(4-oxopiperidin-1-yl)propyl)benzoate

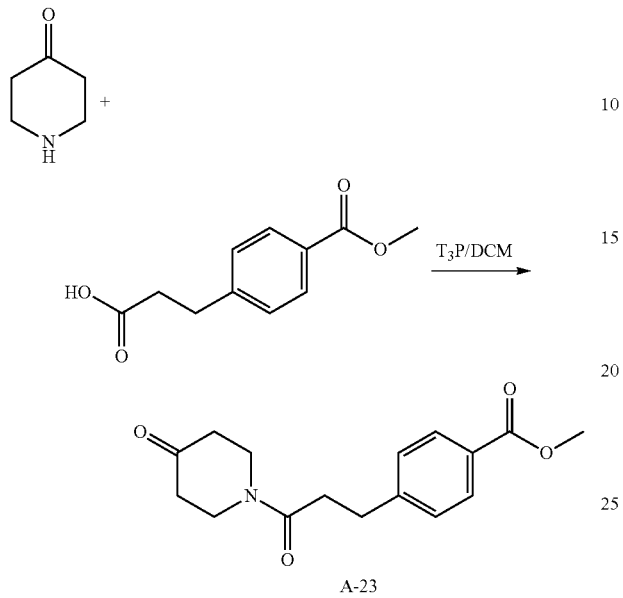

To a stirred solution of 3-(4-(methoxycarbonyl)phenyl)propanoic acid (0.6 g, 2.88 mmol) and piperidine-4-onehydrochloride (0.57 g, 5.76 mmol), in dichloromethane (15 mL) was added triethylamine (1.2 g, 8.64 mmol), the reaction was stirred at room temperature for 10 min, then cooled reaction mixture to 0° C. and added T$_3$P (2.14 mL, 7.20 mmol), and the resulting mixture was stirred at room temperature for 3 h. Reaction was monitored by TLC, after completion of reaction and the mixture was quenched with ice. The reaction mixture was diluted with water and extracted with dichloromethane (3×25 mL). The organic portion was washed with water, brine, dried over sodium sulphate and concentrated under reduced pressure to get the required product as pale-yellow oil. (A-23, 0.79 g, 94%). LC-MS m/z calcd for $C_{16}H_{19}NO_4$, 289.1; found 290.2 [M+H]$^+$.

A-24-methyl 4-(2-(4-formylpiperidin-1-yl)-2-oxoethyl)benzoate-procedure

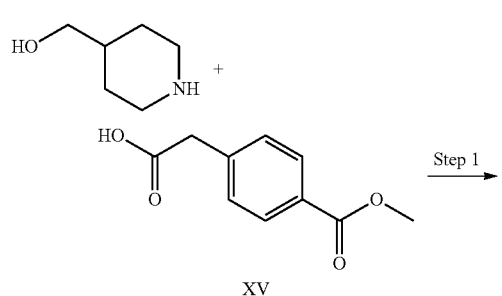

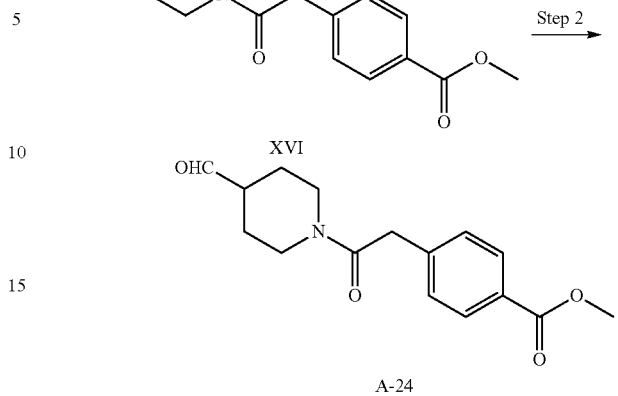

Step 1: methyl 4-(2-(4-(hydroxymethyl)piperidin-1-yl)-2-oxoethyl)benzoate-XVI

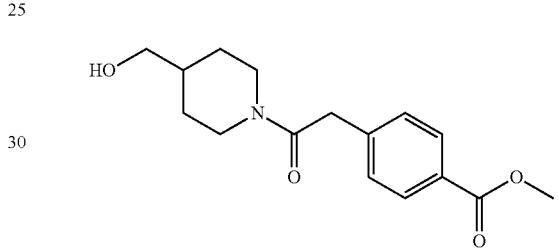

To a stirred solution of 2-(4-(methoxycarbonyl)phenyl)acetic acid (1 g, 5.15 mmol) and piperidin-4-ylmethanol (0.65 g, 5.67 mmol), in dichloromethane (25 mL) was added triethylamine (1.07 mL, 7.72 mmol), the reaction was stirred at room temperature for 10 min, then cooled reaction mixture to 0° C. and added T$_3$P (4.91 mL, 7.72 mmol), and the resulting mixture was stirred at room temperature for 3 h. Reaction was monitored by TLC, after completion of reaction, the mixture was quenched with ice. The reaction mixture was diluted with water and extracted with dichloromethane (3×25 mL). The organic portion was washed with water, brine, dried over sodium sulphate and concentrated under reduced pressure to get the title product as gummy solid. (XVI, 1.2 g, 80%). LC-MS m/z calcd for $C_{16}H_{21}NO_4$, 291.1; found 292.1 [M+H]$^+$.

Step 2: methyl 4-(2-(4-formylpiperidin-1-yl)-2-oxoethyl)benzoate-A-24

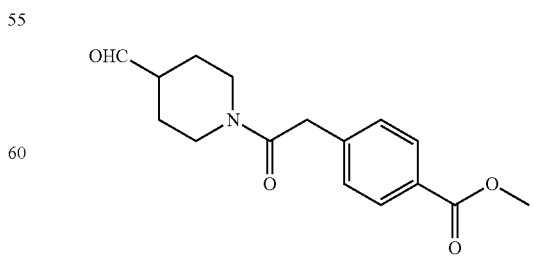

To a stirred solution of oxalyl chloride (0.23 mL, 2.69 mmol) in dry dichloromethane (5 mL) was added dried dimethylsulfoxide (0.28 mL, 4.06 mmol) dropwise at −78° C. and stirred for 15 min. A solution of methyl 4-(2-(4-(hydroxymethyl)piperidin-1-yl)-2-oxoethyl)benzoate (XVI, 0.2 g, 0.68 mmol) in dry dichloromethane was added dropwise followed by the slow addition of triethylamine (6.25 mL, 45.36 mmol) at −78° C. The resulting mixture was stirred at −78° C. for 2 h. The reaction mixture was diluted with dichloromethane (100 mL). The organic portion was washed with water, brine, dried over sodium sulphate and concentrated under reduced pressure to afford the titled product as light yellow colour oil (A-24, 0.2 g, quantitative yield). LC-MS m/z calcd for $C_{16}H_{19}NO_4$, 289.1; found 290.1 $[M+H]^+$.

A-25—ethyl 5-(4-oxobutanoyl)-4,5,6,7-tetrahydrothieno[3,2-c]pyridine-2-carboxylate

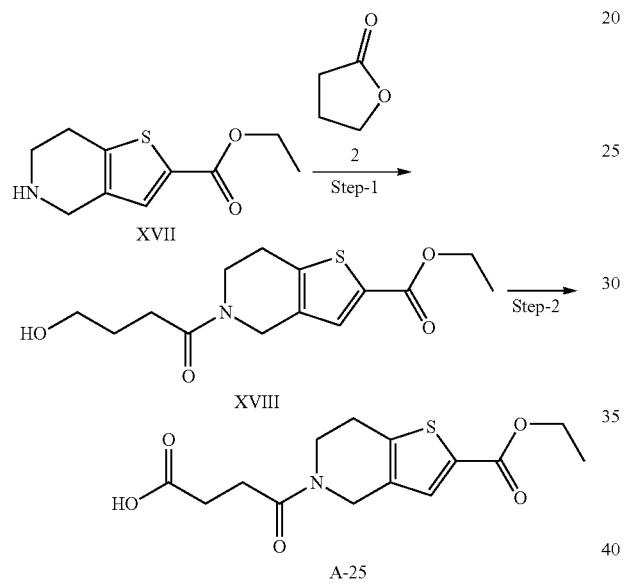

Step-1 ethyl 5-(4-hydroxybutanoyl)-4,5,6,7-tetrahydrothieno[3,2-c]pyridine-2-carboxylate-XVIII

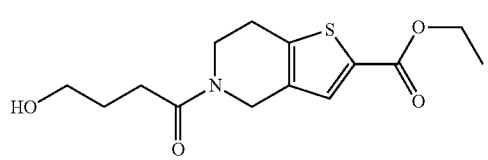 [SMILES: CCOC(=O)c1cc2c(s1)CCN(C(=O)CCCO)C2]

To a solution of ethyl 4,5,6,7-tetrahydrothieno[3,2-c]pyridine-2-carboxylate TFA salt (XVII, 0.5 g, 1.50 mmol) in triethylamine (1 mL) was added dihydrofuran-2(3H)-one (0.11 mL, 1.50 mmol) and heated at 100° C. for 16 h. The reaction mixture was diluted with dichloromethane (50 mL) and washed with 1N HCl solution, water, brine solution, dried over sodium sulphate and concentrated under vacuum to get crude product which was purified by column chromatography using methanol-dichloromethane gradient to afford the titled product as sticky oil (XVIII, 0.2 g, 44%). LC-MS m/z calcd for $C_{14}H_{19}NO_4S$, 297.1; found 298.2 $[M+H]^+$.

Step-2: ethyl 5-(4-oxobutanoyl)-4,5,6,7-tetrahydrothieno[3,2-c]pyridine-2-carboxylate-A-25

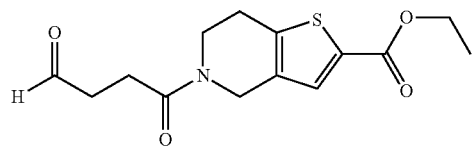 [SMILES: CCOC(=O)c1cc2c(s1)CCN(C(=O)CCC=O)C2]

To a stirred solution of oxalyl chloride (0.23 mL, 2.69 mmol) in dry dichloromethane (5 mL) was added dry dimethylsulfoxide (0.28 mL, 4.06 mmol) drop-wise at −78° C. and stirred for 15 min. A solution of ethyl 5-(4-hydroxybutanoyl)-4,5,6,7-tetrahydrothieno[3,2-c]pyridine-2-carboxylate (XVIII, 0.2 g, 0.67 mmol) in dry dichloromethane was added drop-wise followed by the slow addition of triethylamine (6.25 mL, 45.36 mmol) at −78° C. The resulting mixture was stirred at −78° C. for 2 h. The reaction mixture was diluted with dichloromethane (100 mL). The organic portion was washed with water and brine dried over sodium sulphate and concentrated under reduced pressure to afford the titled product as light yellow colour oil (A-25, 0.2 g, quantitative yield). LC-MS m/z calcd for $C_{14}H_{17}NO_4S$, 295.1; found 296.2 $[M+H]^+$.

A-26—ethyl 2-(4-oxobutanoyl)-1,2,3,4-tetrahydroisoquinoline-7-carboxylate

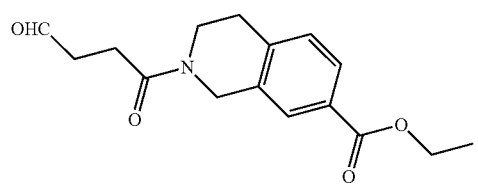 [SMILES: CCOC(=O)c1ccc2c(c1)CN(C(=O)CCC=O)CC2]

Intermediate A-26 was synthesized starting from ethyl 1,2,3,4-tetrahydroisoquinoline-7-carboxylate and dihydrofuran-2(3H)-one following protocol given for A-25. LC-MS m/z calcd for $C_{16}H_{19}NO_4$, 289.1; found 290.1 $[M+H]^+$.

A-27—ethyl 2-(4-oxobutanoyl)isoindoline-5-carboxylate

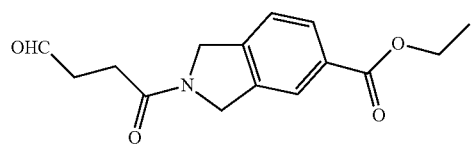 [SMILES: CCOC(=O)c1ccc2c(c1)CN(C(=O)CCC=O)C2]

Intermediate A-27 was synthesized starting from ethyl isoindoline-5-carboxylate and dihydrofuran-2(3H)-one following protocol given for A-25. LC-MS m/z calcd for $C_{15}H_{17}NO_4$, 275.1; found 276.1 $[M+H]^+$.

A-28-ethyl 4-(3-(4-formyl-1H-1,2,3-triazol-1-yl)propyl)benzoate

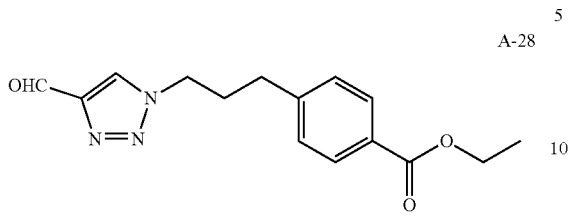

Intermediate A-28 was synthesized starting from ethyl 4-(3-azidopropyl)benzoate following protocol given for A-7. LC-MS m/z calcd for $C_{15}H_{17}N_3O_3$, 287.1; found 288.1 $[M+H]^+$.

A-29-methyl 4-(3-(4-formylpiperidin-1-yl)-3-oxopropyl)benzoate

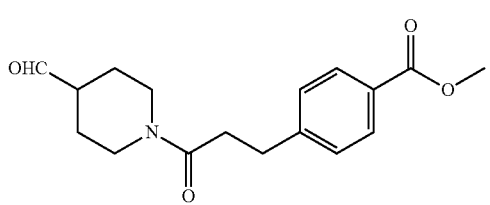

Intermediate A-29 was synthesized starting from piperidin-4-ylmethanol and 3-(4-(methoxycarbonyl)phenyl)propanoic acid following the protocol given for A-24. LC-MS m/z calcd for $C_{18}H_{23}NO_4$, 317.1; found 318.2 $[M+H]^+$.

A-30: ethyl 2-(3-oxopropyl)thiazole-4-carboxylate

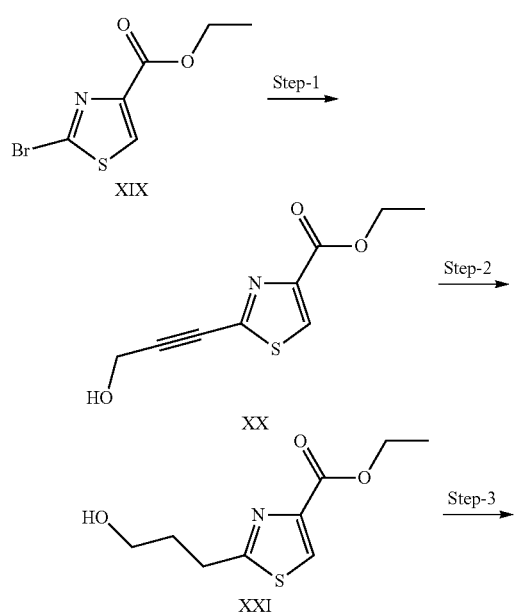

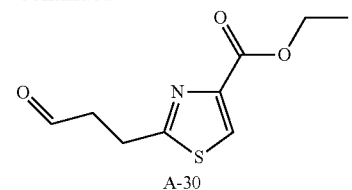

Step-1: ethyl-2(-3-hydroxyprop-1-yn-1-yl)thiazole-4-carboxylate-XX

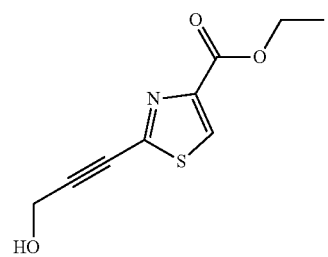

To a ethyl-2-bromothioazole-4-carboxylate (XIX, 4.0 g, 16.0 mmol) in a seal tube was added prop-2-yn-1-ol (1.07 g, 18 mmol), triethylamine (5.92 ml, 42.0 mmol), CuI (0.16 g, 0.8 mmol) and acetonitrile (60 mL) and then degassed with argon for 5 min. $PdCl_2(PPh_3)_2$ (0.59 g, 8.0 mmol) was added and heated the seal tube at 80° C. for 16 h. After completion of reaction, the reaction mixture was cooled to room temperature and filtered through celite bed. The filtrate was concentrated under vacuum to afford the crude product which was purified by flash column chromatography using ethylacetate-hexane gradient to afford title product as brown color liquid (XX, 1.3 g, 36%). LC-MS m/z calcd for $C_9H_9NO_3S$, 211.0; found 212.0 $[M+H]^+$.

Step-2: ethyl 2-(3-hydroxypropyl)thiazole-4-carboxylate-XXI

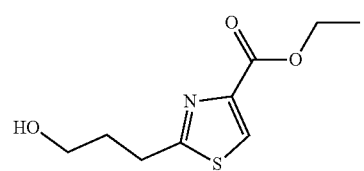

To a stirred solution of ethyl 2(-3-hydroxyprop-1-yn-1-yl)thiazole-4-carboxylate (XX, 1.3 g, 6.1 mmol) in ethanol (20 mL) was added $PtO_2$ (0.069 mg, 3.0 mmol), triethylamine (0.6 mL, 4.3 mmol) and stirred under hydrogen gas at 30 psi for 3 h. After completion of reaction, the reaction mixture was filtered through celite bed. The filtrate was concentrate under vacuum to get the crude product which was purified by flash column chromatography using ethylacetate-hexane gradient to afford the title product as yellow color liquid (XXI, 0.5 g, 50%). LC-MS m/z calcd for $C_9H_{13}NO_3S$, 215.1; found 216.1 $[M+H]^+$.

Step-3: ethyl 2-(3-oxopropyl)thiazole-4-caroboxylate-A30

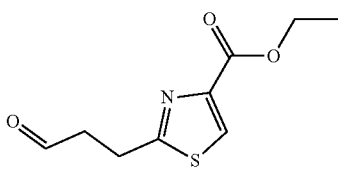

To a stirred solution of dimethylsulfoxide (0.85 mL, 20.0 mmol) in dry dichloromethane (20 mL) was added oxalyl chloride (0.71 mL, 8.3 mmol) drop-wise at −70° C. and stirred at same temperature for 30 min. Then solution of ethyl 2-(3-hydroxypropyl)thiazole-4-carboxylate (0.45 g, 2.0 mmol) in dichloromethane (4 mL) was added drop-wise. After completion of addition, the reaction mixture was stirred at −70° C. for additional 2 h. Triethylamine (3.3 mL, 24.0 mmol) was slowly added and stirred for 20 min. Then the reaction mixture was warmed to room temperature. After completion of reaction, the reaction was quenched with water, organic layer was separated. The organic layer was washed with water, brine solution, dried over sodium sulphate and concentrated to get crude which was purified by flash column chromatography using ethylacetate-hexane gradient to afford the title product as yellow liquid (A30, 0.4 g, 90%). LC-MS m/z calcd for $C_9H_{11}NO_3S$, 213.0; found 214.1 [M+H]$^+$.

A-31: ethyl 2-(3-oxopropyl)thiazole-5-carboxylate

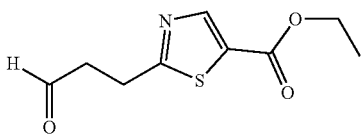

The compound was synthesized using ethyl 2-bromothiazole-5-carboxylate following the procedure for synthesis of A-30. LC-MS m/z calcd for $C_9H_{11}NO_3S$, 213.0; found 214.1 [M+H]$^+$.

A-32: methyl 2-(3-oxopropyl)oxazole-4-carboxylate

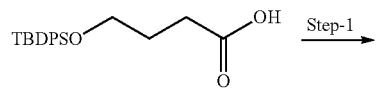

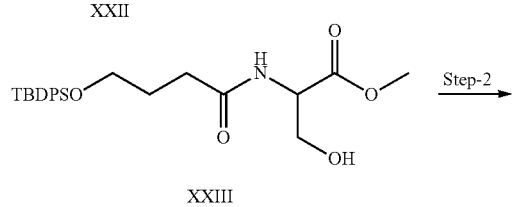

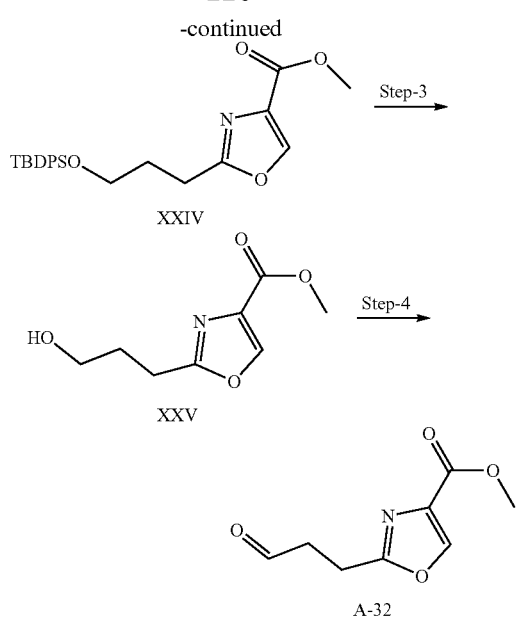

Step-1: methyl (4-((tert-butyldiphenylsilyl)oxy)butanoyl)serinate-XXIII

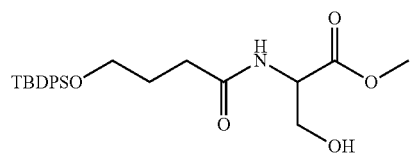

To a stirred solution of serine methyl ester (3.68 g, 23.7 mmol) in acetonitrile (60 mL) was added EDC.HCl (4.55 g, 23.7 mmol), triethylamine (3.76 mL, 26.86 mmol) and stirred for 5 min at room temperature and then 4-((tert-butyldiphenylsilyl)oxy)butanoic acid (XXII, 0.54 g, 15.8 mmol) was added and stirred for 1 h at argon atmosphere. After completion of reaction, the reaction mixture was quenched with water (100 mL) and diluted with ethylacetate. The organic layer was separated and washed with 1N HCl solution, water, brine, dried over sodium sulphate and concentrated to get crude product which was purified by flash column chromatography using ethylacetate-hexane gradient to afford the title product as colorless liquid (XXIII, 2.46 g, 63%). LC-MS m/z calcd for $C_{24}H_{33}NO_5Si$, 443.2; found 444.2 [M+H]$^+$.

Step-2: methyl 2-(3-((tert-butyldiphenylsilyl)oxy)propyl)oxazole-4-carboxylate-XXIV

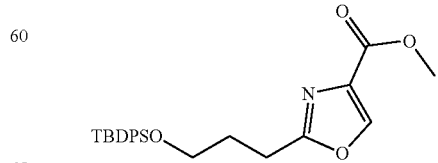

To a stirred solution of methyl (4-((tert-butyldiphenylsilyl)oxy)butanoyl)(hydroxymethyl)carbamate (XXIII, 2.46 g, 5.50 mmol) in dichloromethane (25 mL) was added diethylaminosulfur trifluoride (DAST, 0.8 mL, 6.10 mmol) at −78° C. and then stirred for 2 h. Potassium carbonate (2.27 g, 16.50 mmol) was added and then stirred at −20° C. for 1 h. After completion of reaction, the mixture was quenched with water (50 mL). The organic layer was separated, dried over sodium sulphate and concentrated under vacuum. The resultant crude product was dissolved in dichloromethane (35 mL) and then followed by addition of 1,8-Diazabicyclo (5.4.0)undec-7-ene (DBU, 2.46 mL, 16.5 mmol). The reaction mixture was cooled to 0° C. The solution of $CBrCl_3$ (1.14 mL, 11.5 mmol) in dichloromethane (4 mL) was added drop-wise and stirred for 10 h at room temperature. After completion of reaction, the mixture was diluted with ethylacetate (50 mL) and washed with 1N HCl, water, saturated aqueous sodium bicarbonate solution, brine, dried over sodium sulphate and concentrated under vacuum to get crude product which was purified by flash column chromatography using ethylacetate-hexane gradient to afford the title product colorless oil (XXIV, 0.86 g, 36%). LC-MS m/z calcd for $C_{24}H_{29}NO_4Si$, 423.3; found 424.3 $[M+H]^+$.

Step-3: methyl 2-(3-hydroxypropyl)oxazole-4-carboxylate-XXV

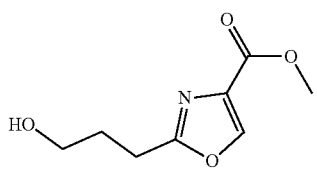

To a stirred solution of methyl 2-(3-((tert-butyldiphenylsilyl)oxy)propyl)oxazole-4-carboxylate (XXIV, 0.86 g, 2.0 mmol) in THF (5 mL) was added TBAF (4.1 mL, 4.10 mmol) and stirred for 1 h at room temperature under argon atmosphere. After completion of reaction, the mixture was quenched with brine solution and extracted with ethylacetate (25 mL×5). The organic layer was dried over sodium sulphate and concentrated under vacuum to get crude product was purified by flash column chromatography using ethylacetate-hexane gradient to afford the title product brown coloured liquid (XXV, 0.3 g, 81%). LC-MS m/z calcd for $C_8H_{11}NO_4$, 185.1; found 186.1 $[M+H]^+$.

Step-4: methyl 2-(3-oxopropyl)oxazole-4-carboxylate-A32

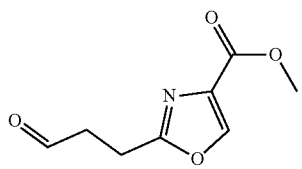

A-32

To a stirred solution of dimethylsulfoxide (0.57 mL, 8.1 mmol) in dry dichloromethane (10 mL) was added oxalyl chloride (0.46 mL, 5.0 mmol) drop-wise at −70° C. and stirred at same temperature for 30 min. Then solution of methyl 2-(3-hydroxypropyl)oxazole-4-carboxylate (0.25 g, 1.35 mmol) in dichloromethane (1 mL) was added drop-wise. After completion of addition, the reaction was stirred at −70° C. for additional 2 h. Triethylamine (2.2 mL, 24.0 mmol) was slowly added and stirred for 20 min. Then the reaction mixture was warmed to room temperature. After completion of reaction, the reaction was quenched with water, organic layer was separated. The organic layer was washed with water, brine solution, dried over sodium sulphate and concentrated to get crude product which was purified by flash column chromatography using ethylacetate-hexane gradient to afford the title product as yellow liquid (A32, 0.2 g, 81%). LC-MS m/z calcd for $C_8H_9NO_4$, 183.1; found 184.1 $[M+H]^+$.

A-33-methyl (E)-4-(3-(4-formylpiperidin-1-yl)-3-oxoprop-1-en-1-yl)benzoate

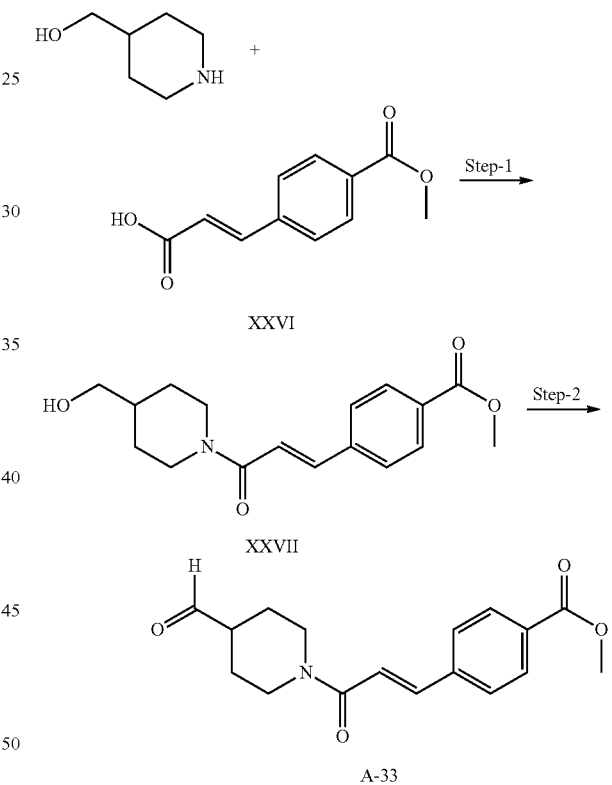

Step-1: methyl (E)-4-(3-(4-(hydroxymethyl)piperidin-1-yl)-3-oxoprop-1-en-1-yl)benzoate-XXVII

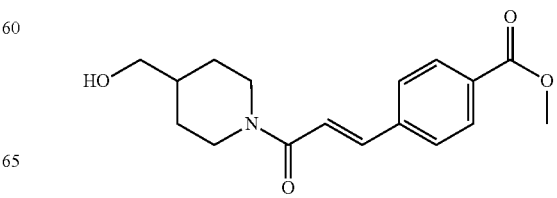

To a stirred solution of (E)-3-(4-(methoxycarbonyl)phenyl)acrylic acid (XXVI, 3 g, 14.50 mmol) and piperidin-4-yl-methanol (2.2 g, 18.9 mmol) in DMF (50 mL) was added EDC.HCl (2.5 g, 16.0 mmol), HOBt (2.1 g, 16.0 mmol) and DIPEA (3.7 mL, 29.0 mmol) at 0° C. and the resulting mixture was stirred at room temperature for 16 h. The reaction mixture was concentrated under vacuum. The resultant crude was diluted with ethylacetate and washed with water, brine, dried over sodium sulphate and concentrated under reduced pressure to get the crude product which was purified by column chromatography using methanol-dichloromethane gradient to afford the titled product as colorless solid (XXVII, 2.1 g, 48%). LC-MS m/z calcd for $C_{17}H_{21}NO_4$, 303.2; found 304.2 $[M+H]^+$.

Step-2: methyl (E)-4-(3-(4-formylpiperidin-1-yl)-3-oxoprop-1-en-1-yl)benzoate-A33

To a stirred solution of dimethylsulfoxide (2.8 mL, 39.6 mmol) in dry dichloromethane (40 mL) was added oxalyl chloride (2.2 mL, 26.0 mmol) drop-wise at −70° C. and stirred at same temperature for 30 min. Then a solution of methyl (E)-4-(3-(4-(hydroxymethyl)piperidin-1-yl)-3-oxoprop-1-en-1-yl)benzoate (XXVI, 2 g, 6.60 mmol) in dichloromethane (10 mL) was added drop-wise. After completion of addition, the reaction mixture was stirred at −70° C. for additional 2 h. Triethylamine (11 mL, 79.2 mmol) was slowly added and stirred for 20 min. Then the reaction mixture was warmed to room temperature. After completion of reaction, the reaction was quenched with water, organic layer was separated. The organic layer was washed with water, brine, dried over sodium sulphate and concentrated to afford the title product A-33 as yellow liquid (2 g, quantitative yield). LC-MS m/z calcd for $C_{17}H_{19}NO_4$, 301.1; found 302.1 $[M+H]^+$.

Synthesis of Intermediates-Amines

B-1 and B-2—(1R,2S)-2-(4-fluorophenyl)cyclopropanamine hydrochloride (I-8) and (1S,2R)-2-(4-fluorophenyl)cyclopropanamine hydrochloride (I-9)

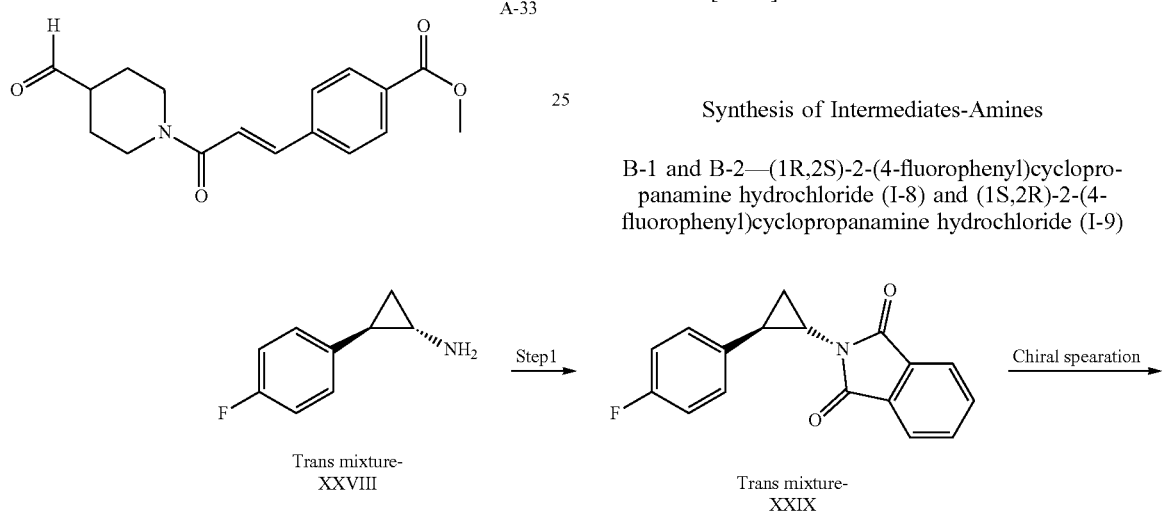

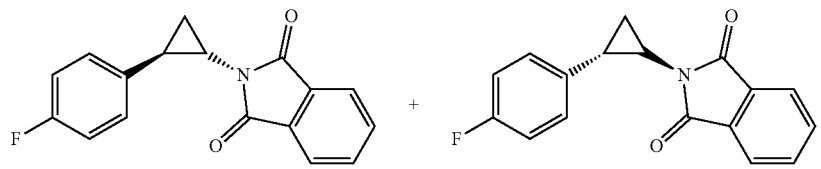

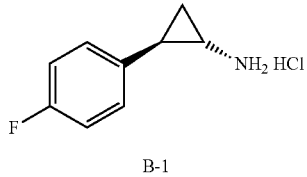

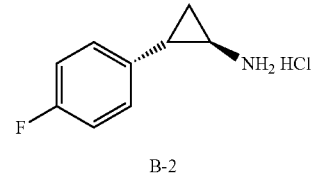

Step 1: 2-((1S,2R)-2-(4-fluorophenyl)cyclopropyl) isoindoline-1,3-dione and 2-((1R,2S)-2-(4-fluorophenyl)cyclopropyl)isoindoline-1,3-dione-XXIX

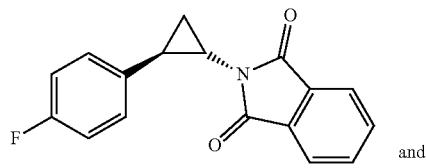

and

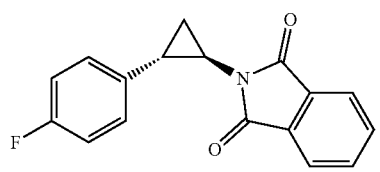

A mixture of 2-(4-fluoro-phenyl)-cyclopropylamine hydrochloride (XXVIII, 1.5 g, 7.99 mmol), isobenzofuran-1,3-dione (1.77 g, 11.99 mmol) and diisopropylethylamine (4.27 mL, 23.97 mmol) was heated in a sealed tube at 150° C. for 12 h and cooled to room temperature. The reaction mixture was diluted with ethylacetate (3×50 mL). The organic portion was washed with water and brine dried over sodium sulphate and concentrated under reduced pressure to afford the crude compound which was purified by column chromatography to afford the racemic product (1.9 g). The racemic product was separated by chiral Prep. HPLC, Chiralpak ia (250 mm×4.6 mm×5 µm) using 0.1% TFA in ACN:MeOH (20:80%) solvent to get isomer 1 (0.73 g) and isomer 2 (0.77 g). LC-MS m/z calcd for $C_{17}H_{12}FNO_2$, 281.1; found 282.2 [M+H]$^+$.

(1R,2S)-2-(4-fluorophenyl)cyclopropanamine

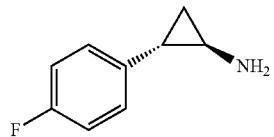 [SMILES: N[C@@H]1C[C@H]1c1ccc(F)cc1]

To a stirred solution of 2-[2-(4-fluoro-phenyl)-cyclopropyl]-isoindole-1,3-dione (isomer 2, 0.77 g, 2.73 mmol) in dichloromethane and ethanol mixture (12 mL, 5:1) was added hydrazine hydrate (0.41 mL, 8.21 mmol) at room temperature and the resulting mixture was stirred at room temperature for 3 h. The progress of the reaction was monitored by TLC. A precipitate formed which was filtered and washed with dichloromethane. The filtrate was evaporated to give the product as yellow oil (0.47 g, 95%). The crude was carried to next step without further purification. LC-MS m/z calcd for $C_9H_{10}FN$, 151.1; found 152.2 [M+H]$^+$.

B-2 (Isomer 2): (1R,2S)-2-(4-fluorophenyl)cyclopropanamine hydrochloride

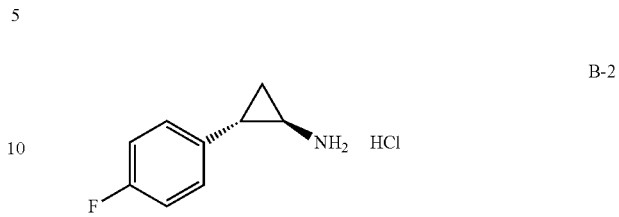

To a stirred solution of 2-(4-fluoro-phenyl)-cyclopropylamine (chirally pure, 0.47 g, 2.108 mmol) in dioxane (5 mL) was added HCl in dioxane solution (2 mL) at 0° C. and the resulting mixture was stirred at room temperature for 2 h. Cooled to room temperature and the solvent was evaporated to get the residue which was triturated with diethyl ether to afford the product as an off-white solid (B-2, 0.42 g, 72%). LC-MS m/z calcd for $C_9H_{10}FN$, 151.1; found 152.2 [M+H]$^+$.

B-1 (Isomer 1): (1S,2R)-2-(4-fluorophenyl)cyclopropanamine hydrochloride

The compound was synthesized from 2-((1R,2S)-2-(4-fluorophenyl)cyclopropyl)isoindoline-1,3-dione (B-1, isomer 1) by following the same synthesis procedure of (1R,2S)-2-(4-fluorophenyl)cyclopropanamine hydrochloride, LC-MS m/z calcd for $C_9H_{10}FN$, 151.1; found 152.2 [M+H]$^+$.

B-3—2,2,2-trifluoro-N-(2-(4-fluorophenyl)cyclopropyl)-N-(piperidin-4-ylmethyl) acetamide hydrochloride

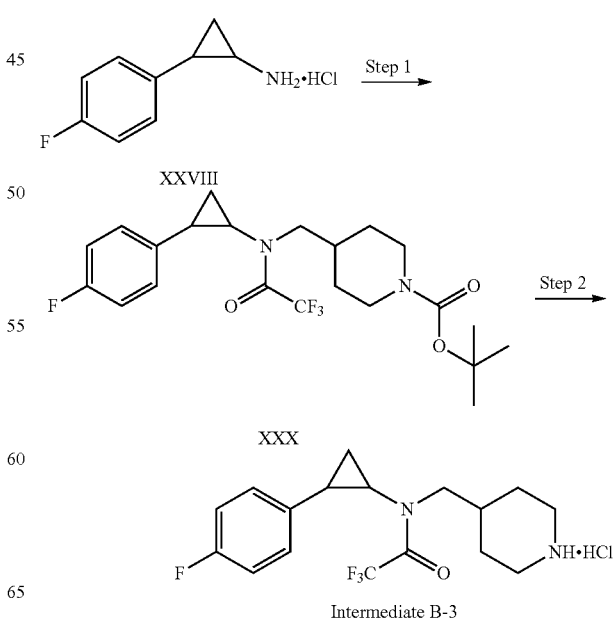

Intermediate B-3

Step 1: tert-butyl 4-((2,2,2-trifluoro-N-(2-(4-fluoro-phenyl)cyclopropyl)acetamido)methyl)piperidine-1-carboxylate-XXX

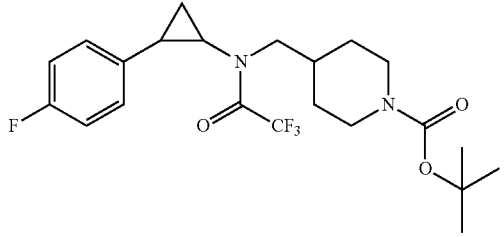 [SMILES: CC(C)(C)OC(=O)N1CCC(CN(C(=O)C(F)(F)F)C2CC2c2ccc(F)cc2)CC1]

To a stirred solution of 2-(4-fluorophenyl)cyclopropan-1-amine hydrochloride (XXVIII, 0.5 g, 2.66 mmol) in methanol (20 mL) was added tert-butyl 4-formylpiperidine-1-carboxylate (0.57 g, 2.66 mmol) and sodium bicarbonate (0.20 g, 2.30 mmol) and molecular sieves (approx. 1 g) at room temperature and the resulting mixture was heated to reflux for 2 h. Cooled to 0° C., then sodium borohydride (0.1 g, 2.66 mmol) was added and stirred at room temperature for 1 h. Ice was added and the reaction mixture was filtered. The solvent was evaporated to get the residue. Water was added and extracted with ethylacetate (2×100 mL). The organic portion was washed with water, brine, dried over sodium sulphate and concentrated under reduced pressure to afford the crude compound. To a stirred solution of crude compound in dry dichloromethane (20 mL) was added TEA (0.92 mL, 6.65 mmol) and then cooled to 0° C. Then trifluoroacetic anhydride (0.56 mL, 3.99 mmol) was added drop-wise cautiously and the resulting mixture was stirred for 2 h at that temperature. The progress of the reaction was monitored by TLC. The reaction mixture was diluted with dichloromethane and the organic portion was washed with water, brine solution, dried over sodium sulphate and concentrated under reduced pressure to get the crude product which was further purified by column chromatography using ethylacetate-hexane gradient to afford the titled product as brown colour sticky oil (XXX, 1.1 g, 93%). LC-MS m/z calcd for $C_{22}H_{28}F_4N_2O_3$, 444.2; found 445.2 [M+H]$^+$.

Step 2: 2,2,2-trifluoro-N-(2-(4-fluorophenyl)cyclopropyl)-N-(piperidin-4-ylmethyl)acetamide hydrochloride-Intermediate B-3

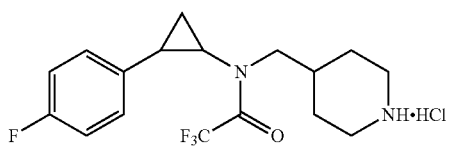

To a stirred solution of tert-butyl 4-((2,2,2-trifluoro-N-(2-(4-fluorophenyl)cyclopropyl)acetamido)methyl)piperidine-1-carboxylate (XXX, 1.1 g, 2.40 mmol) in dioxane (3 mL) was added 20% HCl in dioxane (3 mL) at 0° C. and stirred for 3 h at room temperature. The reaction mixture was concentrated under vacuum and triturated with diethyl ether. The resultant solid was dried under vacuum to afford the title product as off-white solid (B-3, 0.8 g, 94%). LC-MS m/z calcd for $C_{17}H_{20}F_4N_2O$, 344.1; found 345.1 [M+H]$^+$.

B-4—N-(azetidin-3-ylmethyl)-2,2,2-trifluoro-N-(2-(4-fluorophenyl)cyclopropyl)acetamide

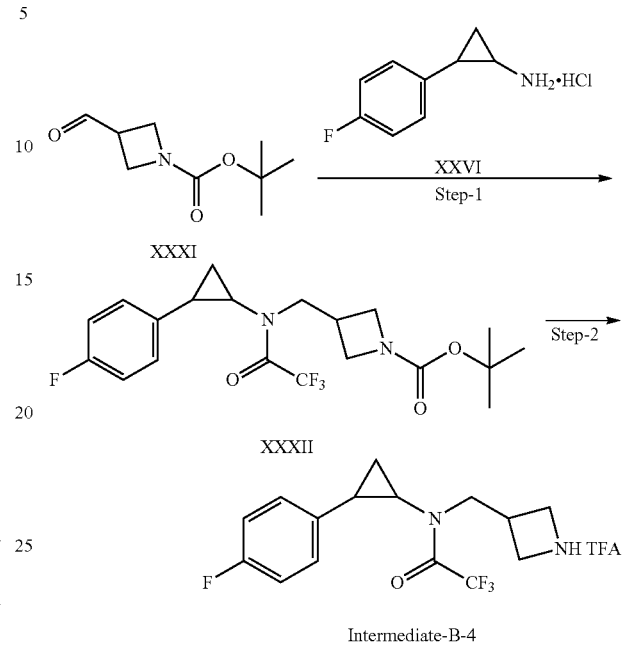

Step 1: tert-butyl 3-((2,2,2-trifluoro-N-(2-(4-fluoro-phenyl)cyclopropyl)acetamido)methyl)azetidine-1-carboxylate-XXXII

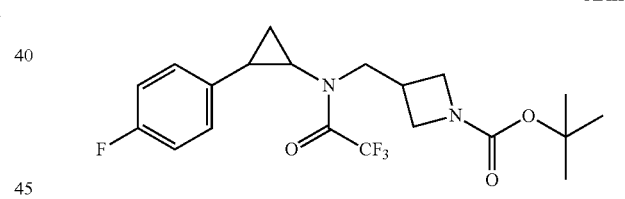

To a stirred solution of 2-(4-fluorophenyl)cyclopropan-1-amine hydrochloride (1.2 g, 6.41 mmol) in methanol (20 mL) was added tert-butyl 3-formylazetidine-1-carboxylate (XXXI, 1.2 g, 6.41 mmol) and sodium bicarbonate (0.48 g, 5.77 mmol) and molecular sieves (approx. 1 g) at room temperature and the resulting mixture was heated to reflux for 2 h. Cooled to 0° C., then sodium borohydride (0.24 g, 6.41 mmol) was added and stirred at room temperature for 1 h. Ice was added and the reaction mixture was filtered. The solvent was evaporated to get the residue. Water was added and extracted with ethylacetate (2×100 mL). The organic portion was washed with water, brine, dried over sodium sulphate and concentrated under reduced pressure to afford the crude compound. To a stirred solution of crude compound in dry dichloromethane (10 mL) was added triethylamine (2.2 mL, 16.02 mmol) and then cooled to 0° C. Then trifluoroacetic anhydride (0.98 mL, 7.05 mmol) was added drop-wise cautiously and the resulting mixture was stirred at that temperature for 2 h. The progress of the reaction was monitored by TLC. The reaction mixture was diluted with dichloromethane and the organic portion was washed with water, brine solution, dried over sodium sulphate and concentrated under reduced pressure to get the crude product which was purified by column chromatography using ethylacetate-hexane gradient to afford the titled product as sticky oil (XXXII, 2.3 g, 86%). LC-MS m/z calcd for $C_{20}H_{24}F_4N_2O_3$, 416.2; found 317.3 [M-Boc+H]$^+$.

Step-2: N-(azetidin-3-ylmethyl)-2,2,2-trifluoro-N-(2-(4-fluorophenyl)cyclopropyl) acetamide TFA salt-Intermediate B-4

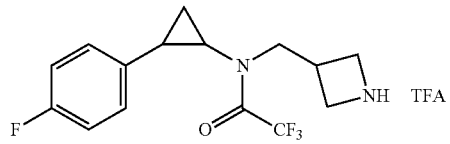 [SMILES: O=C(N(CC1CNC1)C1CC1c1ccc(F)cc1)C(F)(F)F ; "TFA"]

To solution of compound (XXXII, 2.3 g, mmole) in dichloromethane (2.5 mL) was added TFA (2.5 mL) and stirred at room temperature for 3 h. Then, the reaction mixture was concentrated under vacuum. The resultant crude product was triturated with diethyl ether and then dried under vacuum to afford the titled product as sticky oil (B-4, 1.8 g, 78%). LC-MS m/z calcd for $C_{15}H_{16}F_4N_2O$, 316.1; found 221.1 [M-TFA]$^+$.

B-5: N-(azetidin-3-ylmethyl)-2,2,2-trifluoro-N-(2-(4-iodophenyl)cyclopropyl)acetamide

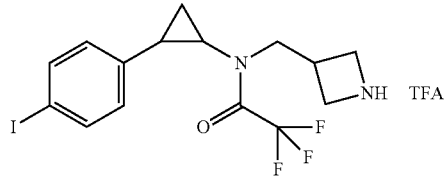 [SMILES: O=C(N(CC1CNC1)C1CC1c1ccc(I)cc1)C(F)(F)F ; "TFA"]

Intermediate B-5 was synthesized following procedure for synthesizing B-4 LC-MS m/z calcd for $C_{15}H_{16}F_3IN_2O$, 424.0; found 425.0 [M+1]$^+$.

B-6—2-(4-((4-fluorobenzyl)oxy)phenyl)cyclopropan-1-amine

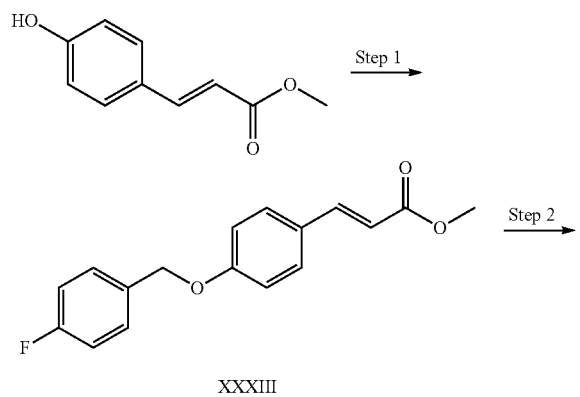

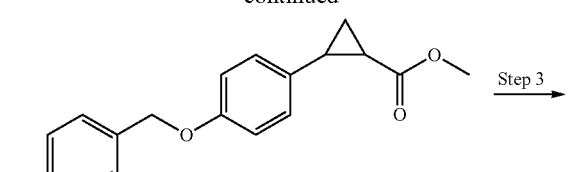

XXXIV

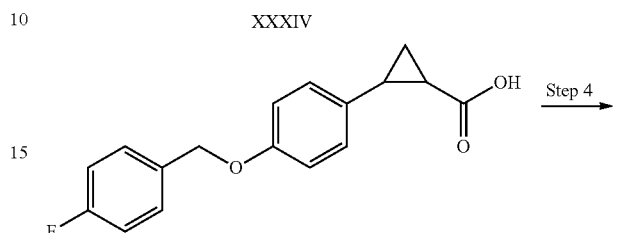

XXXV

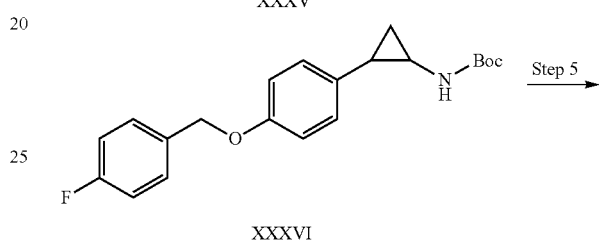

XXXVI

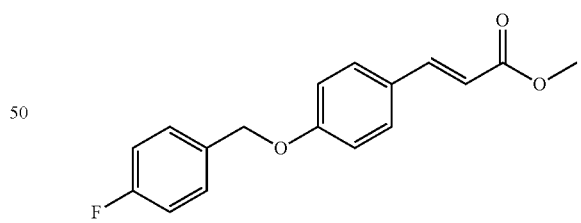

B-6

Step-1: (E)-methyl 3-(4-((4-fluorobenzyl)oxy)phenyl)acrylate-XXXIII

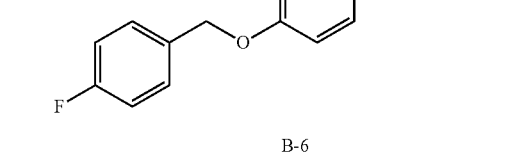

To a stirred solution of (E)-methyl 3-(4-hydroxyphenyl)acrylate (5.1 g, 28.6 mmol), in dry DMF (50 mL) was added 1-(bromomethyl)-4-fluorobenzene (6.5 g, 34.3 mmol) and potassium carbonate (11.86 g, 85.9 mmol) at room temperature and the resulting mixture was stirred at room temperature for 16 h. Ice water was added to it and then extracted with ethylacetate (3×50 mL). The combined organic extract was washed with water, brine, dried over sodium sulphate and concentrated under reduced pressure to afford the product as off-white solid (XXXIII, 8 g, 97%). LC-MS m/z calcd for $C_{17}H_{15}FO_3$, 286.1; found 287.1 [M+H]$^+$.

Step-2: methyl 2-(4-((4-fluorobenzyl)oxy)phenyl) cyclopropanecarboxylate-XXXIV

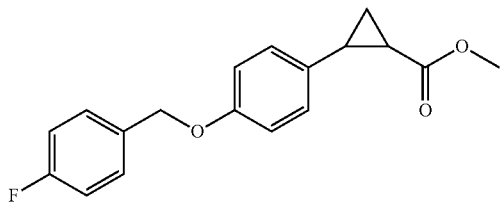 [SMILES: COC(=O)C1CC1c1ccc(OCc2ccc(F)cc2)cc1]

To a stirred solution of (E)-methyl 3-(4-((4-fluorobenzyl) oxy)phenyl)acrylate (2 g, 6.9 mmol) in diethyl ether (50 mL) was added Pd(OAc)$_2$ (0.31 g, 1.3 mmol) at 0° C. and stirred for 20 min. A freshly prepared solution of diazomethane (30 eq) in diethyl ether was then added slowly and stirred at room temperature for 16 h. The reaction mixture was filtered through celite bed and washed with dichloromethane. The filtrate was evaporated under reduced pressure to get crude product which was purified by column chromatography using ethylacetate-hexane gradient to afford the titled product as an off white solid (XXXIV, 1.96 g, 94%). LC-MS m/z calcd for $C_{18}H_{17}FO_3$, 300.1; found 301.1 [M+H]$^+$.

Step-3: 2-(4-((4-fluorobenzyl)oxy)phenyl)cyclopropanecarboxylicacid-XXXV

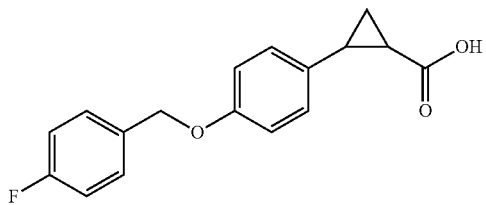 [SMILES: O=C(O)C1CC1c1ccc(OCc2ccc(F)cc2)cc1]

To a stirred solution of methyl 2-(4-((4-fluorobenzyl)oxy) phenyl)cyclopropanecarboxylate (1.86 g, 6.2 mmol) in tetrahydrofuran (10 mL) and methanol (10 mL) was added lithium hydroxide (0.52 g, 12.4 mmol). The reaction mixture was heated at 50° C. for 12 h. The reaction was concentrated under vacuum and then acidified to pH 2 with 2N aqueous HCl. The resultant solid was filtered and dried under vacuum to get the title product as a white colour solid (XXXV, 1.65 g, 93%). LC-MS m/z calcd for $C_{17}H_{15}FO_3$, 286.1; found 285.1 [M–H].

Step-4: tert-butyl (2-(4-((4-fluorobenzyl)oxy)phenyl)cyclopropyl)carbamate-XXXVI

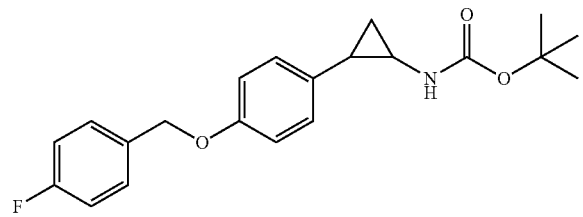 [SMILES: CC(C)(C)OC(=O)NC1CC1c1ccc(OCc2ccc(F)cc2)cc1]

To a stirred solution of 2-(4-((4-fluorobenzyl)oxy)phenyl) cyclopropanecarboxylic acid (XXXV, 1.74 g, 6 mmol) in t-butanol (50 mL) was added triethylamine (1.26 mL, 9.10 mmol) diphenylphosphorylazide (1.44 mL, 6.60 mmol) and then heated at 80° C. for 48 h. The reaction mixture was concentrated under vacuum. The resultant crude product was diluted with ethylacetate (100 mL) and washed with water, brine, dried over sodium sulphate and concentrated under reduced pressure which was purified by column chromatography using ethylacetate-hexane gradient to afford the titled product as yellow solid (XXXVI, 1.05 g, 48%), LC-MS m/z calcd for $C_{21}H_{24}FNO_3$, 357.2; found 358.2 [M+H]$^+$.

Step-5: 2-(4-((4-fluorobenzyl)oxy)phenyl)cyclopropanaminehydrochloride-B-6

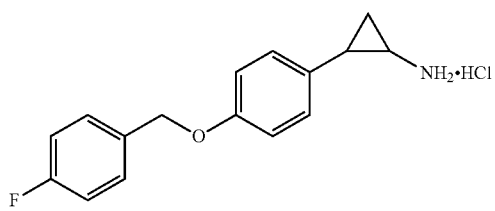

To a stirred solution of tert-butyl (2-(4-((4-fluorobenzyl) oxy)phenyl)cyclopropyl)carbamate (XXXVI, 1.05 g, 2.9 mmol) in 1,4-dioxane (10 mL) was added 20% HCl in 4-dioxane (10 mL) at 0° C. and then was heated at 50° C. for 3 h. The reaction mixture was concentrated under vacuum and the resultant solid was titurated with diethyl ether. The solid was filtered and dried under vacuum to get the titled product as white solid (B6, 0.76 g, 88%).

$^1$HNMR (400 MHz, DMSO-d$_6$): δ 8.39 (bs, 3H), 7.47-7.44 (m, 2H), 7.21-7.17 (m, 2H), 7.07 (d, 2H, J=8.8 Hz), 6.91 (d, 2H, J=8.4 Hz), 5.04 (s, 2H), 2.71-2.67 (m, 1H), 2.28-2.23 (m, 1H), 1.33-1.30 (m, 1H), 1.14-1.09 (m, 1H). LC-MS m/z calcd for $C_{16}H_{16}FNO$, 257.1. found 258.2.

B-7—2-(4-(1-methyl-1H-pyrazol-3-yl)phenyl)cyclopropan-1-amine hydrochloride

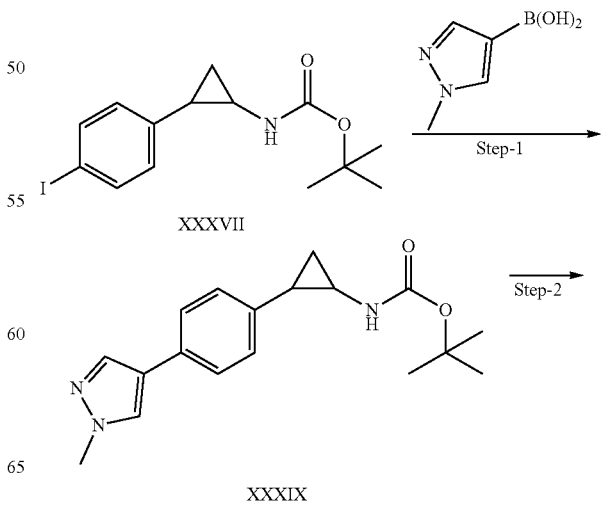

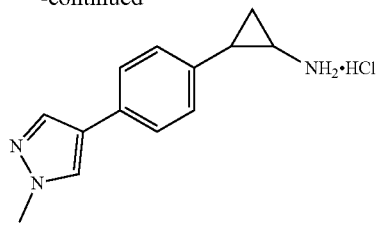

Intermediate B-7

Step 1: tert-butyl (2-(4-(1-methyl-1H-pyrazol-3-yl)phenyl)cyclopropyl)carbamate-XXXIX

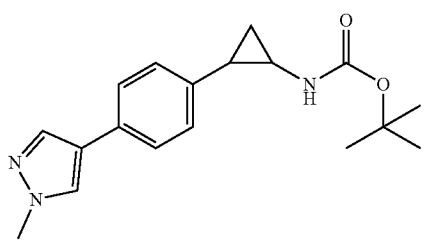 [SMILES: Cn1cc(-c2ccc(C3CC3NC(=O)OC(C)(C)C)cc2)cn1]

To a stirred solution of tert-butyl (2-(4-iodophenyl)cyclopropyl)carbamate (XXXVII, 1 g, 2.78 mmol) in mixture of dimethoxyethane (8 mL) and water (0.5 mL) was added (1-methyl-1H-pyrazol-4-yl)boronic acid (0.42 g, 3.34 mmol) and potassium carbonate (0.76 g, 5.57 mmol) and then degassed for 5 min. 1,1'-Bis(diphenylphosphino)ferrocene-palladium(II)dichloride dichloromethane complex (0.22 g, 0.27 mmol) was added and heated at 120° C. in microwave for 2 h. Water was added and extracted with ethylacetate (2×100 mL). The organic portion was washed with water, brine, dried over sodium sulphate and concentrated under reduced pressure to afford the crude product which was purified by column chromatography using methanol-dichloromethane gradient to afford the titled product as sticky oil (XXXIX, 0.29 g, 40%), LC-MS m/z calcd for $C_{18}H_{23}N_3O_2$, 313.2; found 214.2 [M-Boc+H]$^+$.

Step 2: 2-(4-(1-methyl-1H-pyrazol-3-yl)phenyl)cyclopropan-1-amine hydrochloride-Intermediate B-7

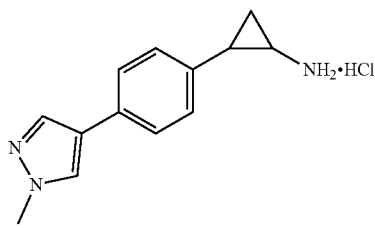

To a stirred solution of tert-butyl (2-(4-(1-methyl-1H-pyrazol-3-yl)phenyl)cyclopropyl)carbamate (XXXIX, 0.29 g, 1.11 mmol) in dioxane (15 mL) was added 20% HCl in dioxane (10 mL) at 0° C. and stirred for 3 h at room temperature. The reaction mixture was concentrated under vacuum to afford the title product as off-white solid (I-23, 0.18 g, 50%), LC-MS m/z calcd for $C_{13}H_{15}N_3$, 213.1; found 214.1 [M+H]$^+$.

B-8—2-(4-(3,5-dimethylisoxazol-4-yl)phenyl)cyclopropan-1-amine hydrochloride

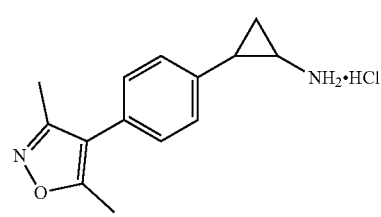

The above intermediate B-8 was synthesized by following the experiment procedure of B-7. LC-MS m/z calcd for $C_{14}H_{16}N_2O$, 228.1; found 229.1 [M+H]$^+$.

B-9—4-(4-(2-aminocyclopropyl)phenyl)-1-methylpyridin-2(1H)-one hydrochloride

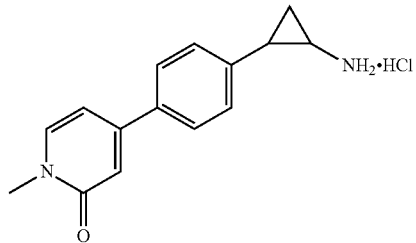

The intermediate B-9 was synthesized by following the experiment procedure of B-7. LC-MS m/z calcd for $C_{15}H_{16}N_2O$, 240.1; found 241.1 [M+H]$^+$.

B-10: 2-(4'-chloro-[1,1'-biphenyl]-4-yl)cyclopropan-1-amine

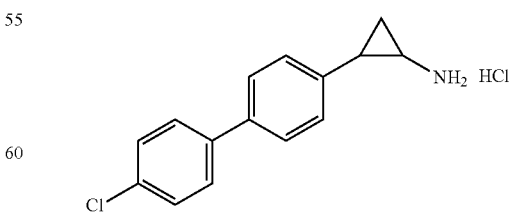

The intermediate B-10 was synthesized by following the experiment procedure of B-7. LC-MS m/z calcd for $C_{15}H_{14}ClN$, 243.1 found 244.1 [M+H]$^+$.

B-11—2-(4-(pyrimidin-5-yl)phenyl)cyclopropan-1-amine

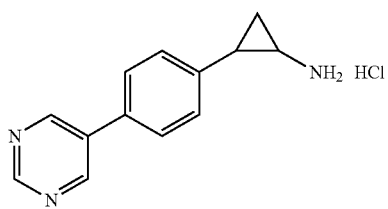 [SMILES: NC1CC1c1ccc(-c2cncnc2)cc1 ; Cl]

The intermediate B-11 was synthesized by following the experiment procedure of B-7. LC-MS m/z calcd for $C_{13}H_{13}N_3$, 211.1. found 212.1 [M+H]$^+$.

B-12—2-(4'-fluoro-[1,1'-biphenyl]-4-yl)cyclopropan-1-amine

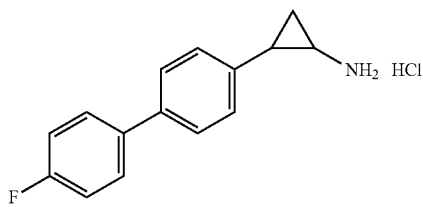 [SMILES: NC1CC1c1ccc(-c2ccc(F)cc2)cc1 ; Cl]

The intermediate B-12 was synthesized by following the experiment procedure of B-7. LC-MS m/z calcd for $C_{15}H_{14}FN$, 227.1; found 228.1[M+H]$^+$.

B-13: 2-(4'-cyano-[1,1'-biphenyl]-4-yl)cyclopropan-1-amine

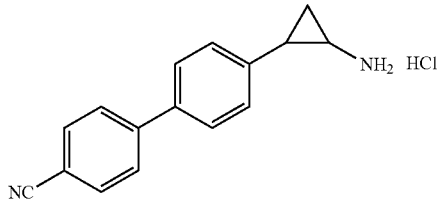 [SMILES: N#Cc1ccc(-c2ccc(C3CC3N)cc2)cc1 ; Cl]

The intermediate B-13 was synthesized by following the experiment procedure of B-7. LC-MS m/z calcd for $C_{16}H_{14}N_2$, 234.1; found 235.1 [M+H]$^+$.

B-14: 2-(4-(6-(trifluoromethyl)pyridin-3-yl)phenyl)cyclopropan-1-amine

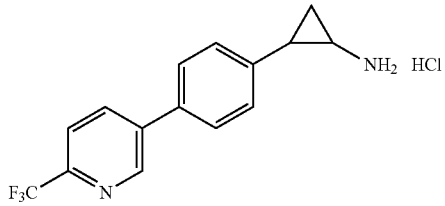 [SMILES: NC1CC1c1ccc(-c2ccc(C(F)(F)F)nc2)cc1 ; Cl]

The intermediate B-14 was synthesized by following the experiment procedure of B-7. LC-MS m/z calcd for $C_{15}H_{13}F_3N_2$, 278.1; found 279.1[M+H]$^+$.

B-15—2-(1-isopropyl-1H-pyrazol-4-yl)cyclopropan-1-amine

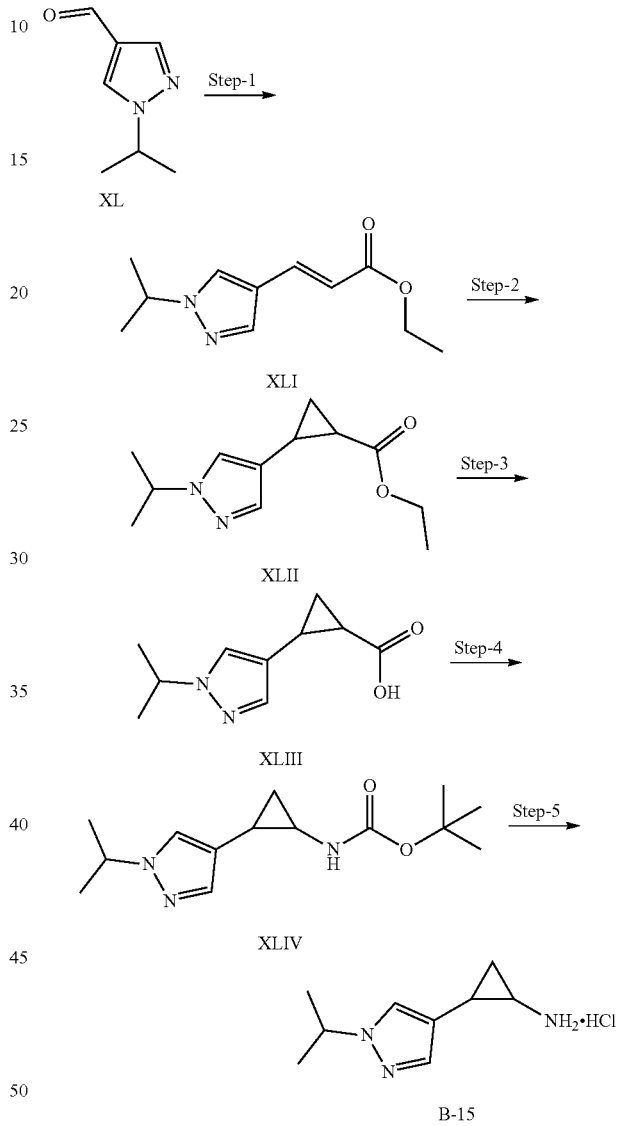

Step-1: ethyl (E)-3-(1-isopropyl-1H-pyrazol-4-yl)acrylate-XLI

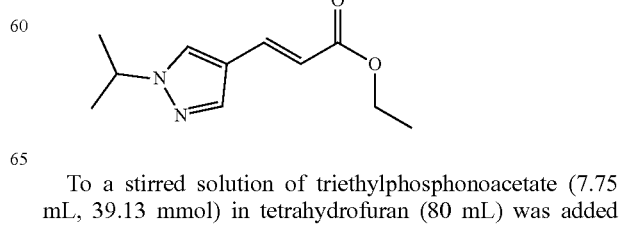

To a stirred solution of triethylphosphonoacetate (7.75 mL, 39.13 mmol) in tetrahydrofuran (80 mL) was added 60% of sodium hydride (0.94 g, 39.13 mmol) at 0° C. and then stirred for 1 h. 1-Isopropyl-1H-pyrazole-4-carbaldehyde (XL, 4.5 g, 32.57 mmol) in tetrahydrofuran (20 mL) was added and stirred for 2 h at room temperature. The reaction mixture was quenched with ice-water. Then the reaction mixture was concentrated under vacuum. The resultant crude was diluted with ethylacetate (100 mL) and washed with water, brine, dried over sodium sulphate and concentrated under reduced pressure to result in crude product which was purified by column chromatography using ethylacetate-hexane gradient to afford the titled product as colourless oil (XLI, 5.4 g, 80% yield). LC-MS m/z calcd for $C_{11}H_{16}N_2O_2$, 208.1; found 209.1 $[M+H]^+$.

Step-2: ethyl 2-(1-isopropyl-1H-pyrazol-4-yl)cyclopropane-1-carboxylate-XLII

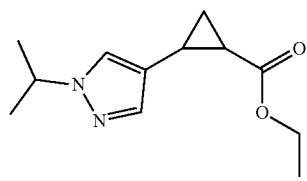 [SMILES: CCOC(=O)C1CC1c1cnn(C(C)C)c1]

To a stirred solution of ethyl (E)-3-(1-isopropyl-1H-pyrazol-4-yl)acrylate (XLI, 0.5 g, 2.40 mmol) in diethyl ether (10 mL) was added Pd(OAc)$_2$ (0.026 g, 0.12 mmol) at 0° C. and stirred for 20 min. A freshly prepared solution of diazomethane (30 eq.) in diethyl ether was then added slowly and stirred at room temperature for 16 h. The reaction mixture was filtered through celite bed and washed with dichloromethane. The filtrate was evaporated under reduced pressure to get crude product which was purified by column chromatography using ethylacetate-hexane gradient to afford the titled product as an off-white solid (XLII, 0.37 g, 69%). LC-MS m/z calcd for $C_{12}H_{18}N_2O_2$, 222.1; found 223.1 $[M+H]^+$.

Step-3: 2-(1-isopropyl-1H-pyrazol-4-yl)cyclopropane-1-carboxylic acid-XLIII

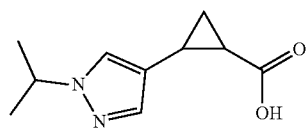

To a stirred solution of ethyl 2-(1-isopropyl-1H-pyrazol-4-yl)cyclopropane-1-carboxylate (XLII, 0.37 g, 1.78 mmol) in water (8 mL) and methanol (2 mL) was added sodium hydroxide (0.28 g, 7.11 mmol). The reaction mixture was stirred at room temperature for 2 h. The reaction was concentrated under vacuum and then acidified to pH 5 with 2N aqueous HCl. The resultant stick solid was extracted with dichloromethane (50 mL×3). The combined organic layer was washed with brine solution and concentrated under vacuum to get the title product as colourless sticky oil (XLIII, 0.3 g, 87%). LC-MS m/z calcd for $C_{10}H_{14}N_2O_2$, 194.1; found 195.1 $[M+H]^+$.

Step-4: tert-butyl (2-(1-isopropyl-1H-pyrazol-4-yl)cyclopropyl)carbamate-XLIV

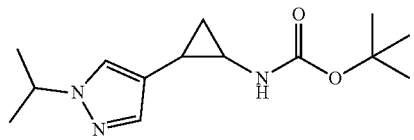 [SMILES: CC(C)n1cc(C2CC2NC(=O)OC(C)(C)C)cn1]

To a stirred solution of 2-(1-isopropyl-1H-pyrazol-4-yl)cyclopropane-1-carboxylic acid (XLIII, 0.3 g, 1.55 mmol) in t-butanol (10 mL) was added triethylamine (0.65 mL, 4.64 mmol) diphenylphosphorylazide (0.5 mL, 2.32 mmol) and then heated at 80° C. for 18 h. The reaction mixture was concentrated under vacuum. The resultant crude was diluted with ethylacetate (100 mL) and washed with water, brine solution, dried over sodium sulphate and concentrated under reduced pressure to result in crude product which was purified by column chromatography using ethylacetate-hexane gradient to afford the titled product as yellow solid (XLIV, 0.13 g, 33%). LC-MS m/z calcd for $C_{14}H_{23}N_3O_2$, 265.2; found 266.2 $[M+H]^+$.

Step-5: 2-(1-isopropyl-1H-pyrazol-4-yl)cyclopropan-1-amine hydrochloride-B15

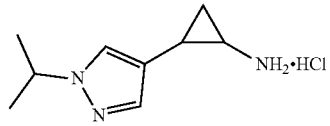

To a stirred solution of tert-butyl (2-(1-isopropyl-1H-pyrazol-4-yl)cyclopropyl)carbamate (XLIV, 0.13 g, 0.49 mmol) in 1,4-dioxane (3 mL) was added 20% HCl in 1,4-dioxane (3 mL) at 0° C. and then was heated at room temperature for 3 h. The reaction mixture was concentrated under vacuum and the resultant solid was titurated with diethyl ether. The solid was filtered out and dried under vacuum to get the titled product as white solid (B-15, 0.06 g, 61%). LC-MS m/z calcd for $C_9H_{15}N_3$, 165.1; found 166.1 $[M+H]^+$.

B-16—2-(1-phenyl-1H-pyrazol-4-yl)cyclopropan-1-amine

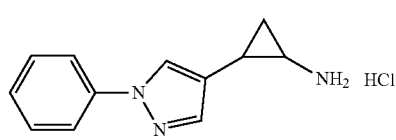 [SMILES: NC1CC1c1cnn(-c2ccccc2)c1 ; Cl]

The intermediate B-16 was synthesized starting from 1-phenyl-1H-pyrazole-4-carbaldehyde by following the experiment procedure of B-15. LC-MS m/z calcd for $C_{12}H_{13}N_3$, 199.1; found 200.1 $[M+H]^+$.

B-17—2-(2-methylthiazol-5-yl)cyclopropan-1-amine

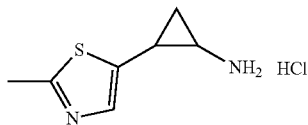

The intermediate B-17 was synthesized starting from 2-methylthiazole-5-carbaldehyde by following the experiment procedure of B-15. LC-MS m/z calcd for $C_7H_{10}N_2S$, 154.0; found 155.1[M+H]$^+$.

B-18—2-(pyridin-3-yl)cyclopropan-1-amine

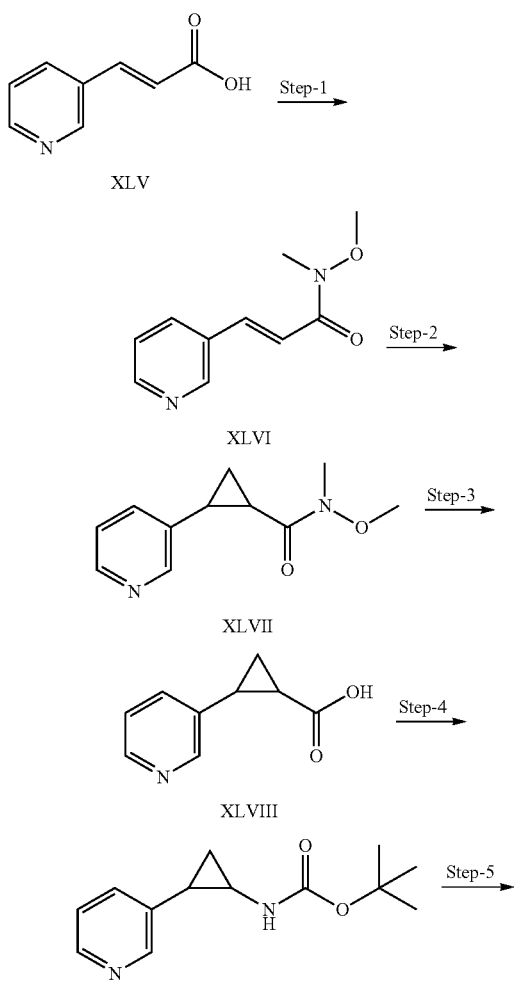

Step-1: (E)-N-methoxy-N-methyl-3-(pyridin-3-yl)acrylamide-XLVI

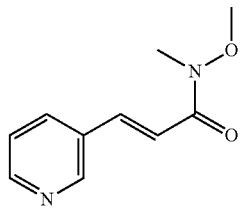

To a stirred solution of (E)-3-(pyridin-3-yl)acrylic acid (XLV, 10 g, 67.1 mmol) and N,O-dimethylhydroxylamine hydrochloride (13 g, 134 mmol) in DMF (300 mL) was added EDC.HCl (16.6 g, 87.1 mmol), HOBt (9 g, 67 mmol) and TEA (46 mL, 335 mmol) at 0° C. and the resulting mixture was stirred at room temperature for 16 h. The reaction mixture was concentrated under vacuum. The resultant crude was diluted with ethylacetate and washed with water, brine, dried over sodium sulphate and concentrated under reduced pressure to get the crude product which was purified by column chromatography using methanol-dichloromethane gradient to afford the titled product as an sticky oil (XLVI, 8.2 g, 64%). LC-MS m/z calcd for $C_{10}H_{12}N_2O_2$, 192.0; found 193.1 [M+H]$^+$.

Step-2: N-methoxy-N-methyl-2-(pyridin-3-yl)cyclopropane-1-carboxamide-XLVII

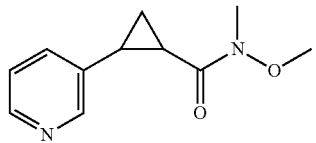

To a stirred solution of trimethylsulfoxonium iodide (2.75 g, 12.5 mmol) in dry dimethyl sulfoxide (20 mL) was added 60% of sodium hydride (12.5 g, 12.5 mmol) portion-wise at room temperature and then stirred for 3 h. (E)-N-methoxy-N-methyl-3-(pyridin-3-yl)acrylamide (1.2 g, 6.25 mmol) in dimethyl sulfoxide (10 mL) was added and stirred for 2 h at room temperature. The reaction mixture was quenched with ice-water and then extracted with ethylacetate. The combined organic layer was washed with water, brine solution, dried over sodium sulphate and concentrated under reduced pressure which was purified by column chromatography using ethylacetate-hexane gradient to afford the titled product as colourless oil (XLVII, 0.9 g, 70%), LC-MS m/z calcd for $C_{11}H_{14}N_2O_2$, 206.1; found 207.1 [M+H]$^+$.

Step-3: 2-(pyridin-3-yl)cyclopropane-1-carboxylic acid-XLVIII

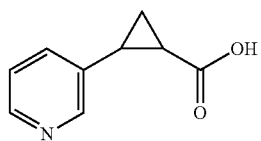 [SMILES: O=C(O)C1CC1c1cccnc1]

To a stirred solution of N-methoxy-N-methyl-2-(pyridin-3-yl)cyclopropane-1-carboxamide (XLVII, 0.9 g, 4.3 mmol) in water (2 mL) and ethanol (1 mL) was added potassium hydroxide (0.731 g, 13 mmol). The reaction mixture was stirred at room temperature for 16 h. The reaction was concentrated under vacuum and then acidified to pH 5 with 2N aqueous HCl. The resultant crude was concentrated under vacuum and then methanol (5 mL) was added to it. The resultant solid was filtrated and the filtrate was concentrated under vacuum to get the title product as colourless sticky oil (XLVIII, 0.45 g, 64%). LC-MS m/z calcd for $C_9H_9NO_2$, 163.1; found 164.1 $[M+H]^+$.

Step-4: tert-butyl (2-(pyridin-3-yl)cyclopropyl)carbamate-XLIX

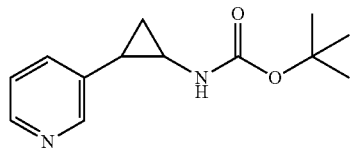 [SMILES: CC(C)(C)OC(=O)NC1CC1c1cccnc1]

To a stirred solution of 2-(pyridin-3-yl)cyclopropane-1-carboxylic acid (XLVIII, 0.4 g, 2.43 mmol) in t-butanol (20 mL) was added triethylamine (0.845 mL, 6.07 mmol), diphenylphosphorylazide (0.67 mL, 3.16 mmol) and then heated at 80° C. for 18 h. The reaction mixture was concentrated under vacuum. The resultant crude was diluted with ethylacetate (100 mL) and washed with water, brine solution, dried over sodium sulphate and concentrated under reduced pressure which was purified by column chromatography using ethylacetate-hexane gradient to afford the titled product as colourless sticky oil (XLIX, 0.11 g, 20%). LC-MS m/z calcd for $C_{13}H_{18}N_2O_2$, 234.1; found 235.1 $[M+H]^+$.

Step-5: 2-(pyridin-3-yl)cyclopropan-1-amine TFA salt-B-18

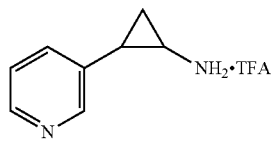

B-18

To a stirred solution of tert-butyl (2-(pyridin-3-yl)cyclopropyl)carbamate (XLIX, 0.05 g, 0.21 mmol) in dichloromethane (1 mL) was added trifluoroacetic acid (0.5 mL) at 0° C. and then was stirred at room temperature for 3 h. The reaction mixture was concentrated under vacuum and the resultant solid was titurated with diethyl ether. The solid was filtered out and dried under vacuum to get the titled product as cream colour solid (B-18, 0.03 g, 62%). LC-MS m/z calcd for $C_8H_{10}N_2$, 134.1; found 135.1 $[M+H]^+$.

B-19—5-(4-(2-aminocyclopropyl)phenyl)-1-methylpyridin-2(1H)-one hydrochloride

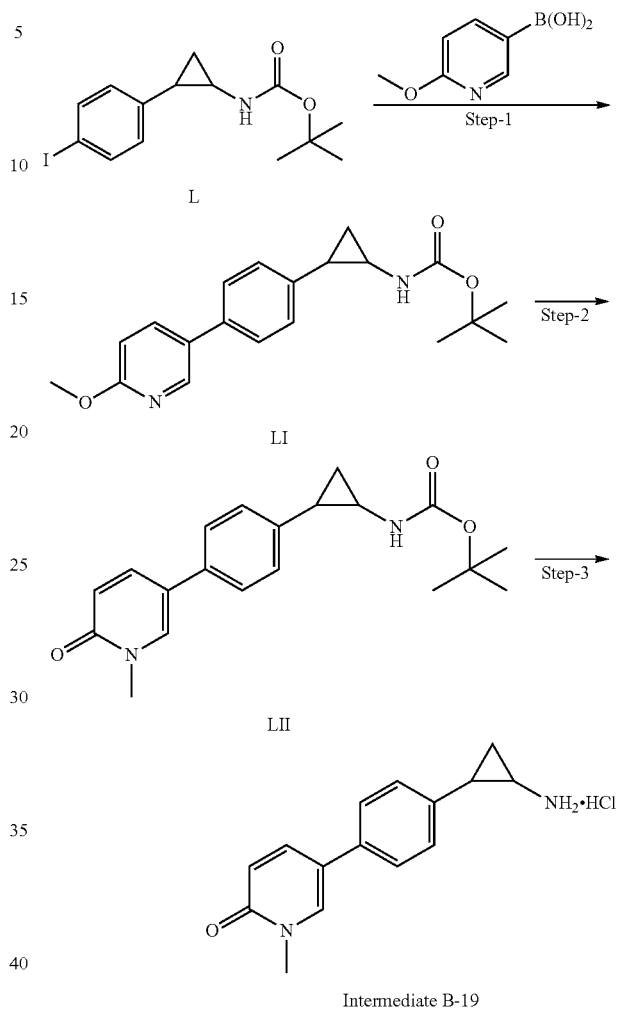

Step 1:tert-butyl (2-(4-(6-methoxypyridin-3-yl)phenyl)cyclopropyl)carbamate-LI

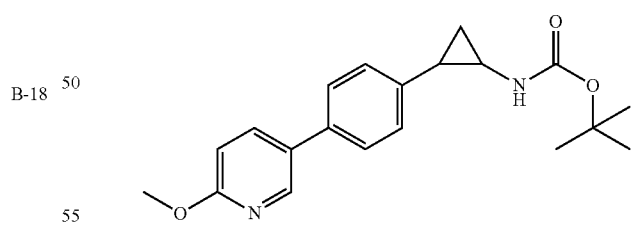

To a stirred solution of tert-butyl (2-(4-iodophenyl)cyclopropyl)carbamate (L, 1 g, 2.78 mmol) in mixture of dimethoxyethane (8 mL) and water (2 mL) was added (6-methoxypyridin-3-yl)boronic acid (0.47 g, 3.06 mmol) and potassium carbonate (0.77 g, 5.56 mmol) and then degassed for 5 min. Tetrakis(triphenylphosphine)palladium (0) (0.16 g, 1.39) was added and heated at 60° C. for 2 h. Water was added and extracted with ethylacetate (2×100 mL). The organic portion was washed with water, brine, dried over sodium sulphate and concentrated under reduced pressure to afford the crude product which was purified by column chromatography using methanol-dichloromethane to afford the titled product as sticky oil (LI, 0.84 g, 89%). LC-MS m/z calcd for $C_{20}H_{24}N_2O_3$, 340.2; found 341.2 $[M+H]^+$.

Step 2: tert-butyl (2-(4-(1-methyl-6-oxo-1,6-dihydropyridin-3-yl)phenyl)cyclopropyl)carbamate-LII

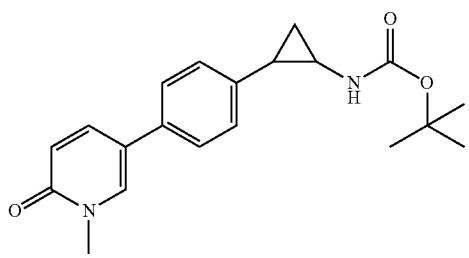 [SMILES: Cn1cc(-c2ccc(C3CC3NC(=O)OC(C)(C)C)cc2)ccc1=O]

To a stirred solution of tert-butyl (2-(4-(6-methoxypyridin-3-yl)phenyl)cyclopropyl)carbamate (LI, 0.85 g, 2.5 mmol) in acetonitrile (5 mL) was added methyl iodide (1.5 mL) and heated at 60° C. for 16 h. The reaction mixture concentrated under reduced pressure and the resultant crude product was triturated with diethyl ether to afford the titled product as light brown solid (LII, 0.80 g, 94%). LC-MS m/z calcd for $C_{20}H_{24}N_2O_3$, 340.2; found 341.2 $[M+H]^+$.

Step 3: 5-(4-(2-aminocyclopropyl)phenyl)-1-methylpyridin-2(1H)-one hydrochloride-B-19

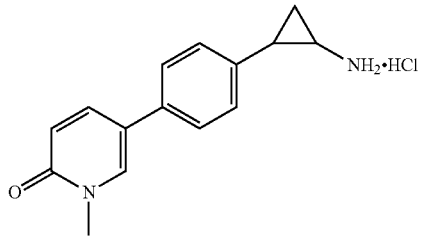

To a stirred solution of tert-butyl (2-(4-(1-methyl-6-oxo-1,6-dihydropyridin-3-yl)phenyl) cyclopropyl) carbamate (LII, 0.85 g, 2.5 mmol) in dioxane (5 mL) was added 20% HCl in dioxane (3 mL) at 0° C. and heated at 60° C. for 16 h. The reaction mixture was concentrated under vacuum to afford the title product as off-white solid (B-19, 0.47 g, 68%). LC-MS m/z calcd for $C_{15}H_{16}N_2O$, 240.1; found 241.1 $[M+H]^+$.

B-20—5-(2-aminocyclopropyl)-1,3,3-trimethylindolin-2-one hydrochloride

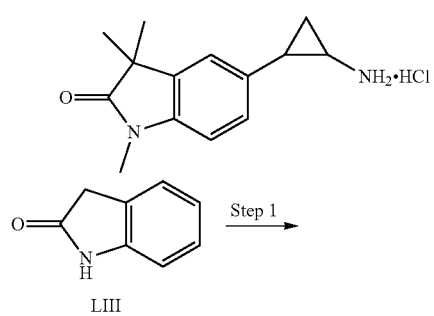

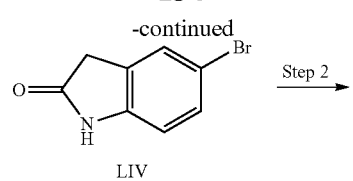

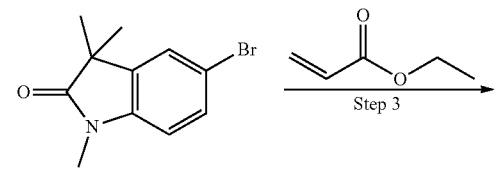

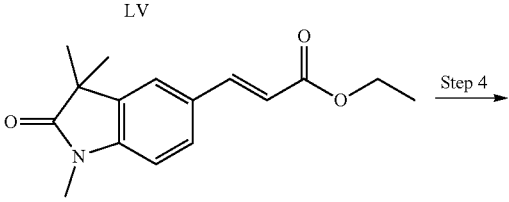

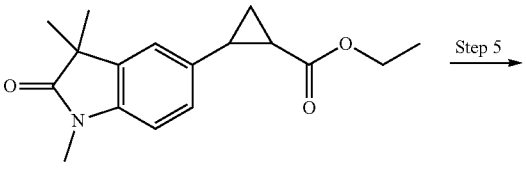

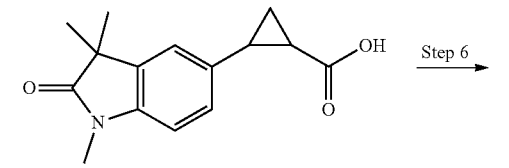

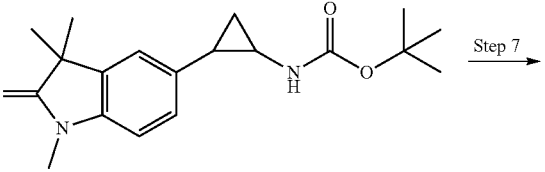

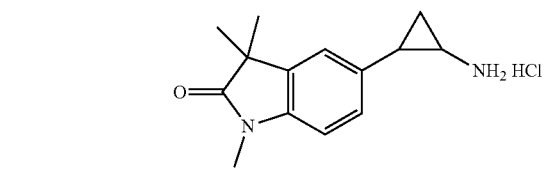

Step-1: 5-bromoindolin-2-one-LIV

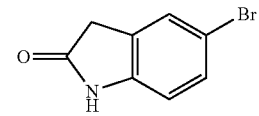 [SMILES: O=C1Cc2cc(Br)ccc2N1]

To a stirred suspension of indolin-2-one (LIII, 4.0 g, 27.0 mmol) in acetonitrile (160 mL), N-bromosuccinimide (6.24 g, 35.1 mmol) was added portion-wise at 0° C. under nitrogen atmosphere and then stirred for 3 h at 15-20° C. The reaction mixture was quenched with ice-water (100 mL) to afford solid. The resultant solid was filtered through sintered funnel, washed with water and dried to afford the title compound as a solid (LIV, 6.0 g, 93%). LC-MS m/z calcd for $C_8H_6BrNO$, 210.9; found 212.0. [M+H]$^+$.

Step 2: 5-Bromo-1,3,3-trimethylindolin-2-one-LV

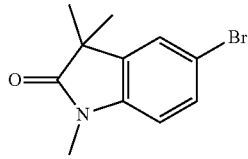

3

To a stirred solution of 5-bromoindolin-2-one (LIV, 7.25 g, 34.36 mmol) in tetrahydrofuran (70 mL) under nitrogen atmosphere, was added sodium hydride (5.9 g, 137.0 mmol) portion-wise at 0° C. After addition of sodium hydride, the reaction was stirred at room temperature for 30 min, then cooled to 0° C. Methyl iodide (8.5 mL, 137.0 mmol) was added, and then allowed to stir at room temperature for 2 h. The reaction mass was cooled to 0° C. and carefully quenched with ice-water. Then the reaction mixture was diluted with water (150 mL) and ethylacetate (150 mL). The organic layer was separated, washed with water, brine solution, dried over sodium sulphate and concentrated under reduced pressure to afford the titled product as brown colour solid (LV, 7.4 g, 85%). LC-MS m/z calcd for $C_{11}H_{12}BrNO$, 253.0; found 254.0 [M+H]$^+$.

Step-3: (E)-ethyl 3-(1,3,3-trimethyl-2-oxoindolin-5-yl)acrylate-LVI

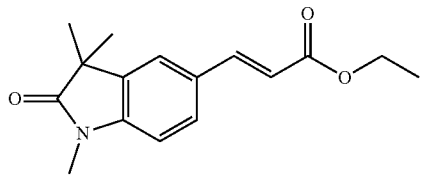

4

To a stirred solution of 5-Bromo-1,3,3-trimethylindolin-2-one (LV, 9.0 g, 35.0 mmol) in triethylamine (25 mL) was added Tetrakis(triphenylphosphine)palladium(0) (1.92 g, 1.75 mmol) and ethyl acrylate (5.59 mL, 52.5 mmol). The reaction mixture was heated at 120° C. for 12 h. The reaction mass was cooled to room temperature and then diluted with ethylacetate (50 mL). The reaction mixture was filtered out through with celite bed. The filtrate was washed with water (100 mL), 1.5N HCl solution (100 mL), water (100 mL), dried over sodium sulphate and then concentrated under reduced pressure to afford the crude product which was purified by column chromatography using ethylacetate-hexane gradient to afford the titled product as yellow solid (LVI, 5.0 g, 70%). LC-MS m/z calcd for $C_{16}H_{19}NO_3$, 273.1; found 274.1 [M+H]$^+$.

Step 4: ethyl 2-(1,3,3-trimethyl-2-oxoindolin-5-yl)cyclopropanecarboxylate-LVII

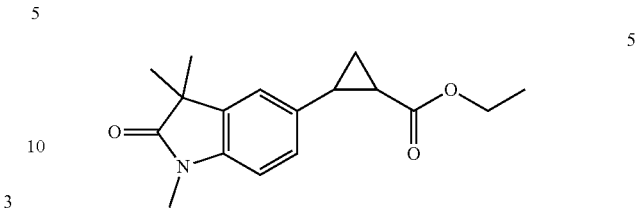

5

To a stirred solution of (E)-ethyl, 3-(1,3,3-trimethyl-2-oxoindolin-5-yl)acrylate (LVI, 2.0 g, 7.2 mmol) in diethyl ether (20 mL) was added Pd(OAc)$_2$ (0.32 g, 1.40 mmol), at 0° C. and stirred for 20 min. A freshly prepared diazomethane (30 eq) in diethyl ether was then added slowly and stirred at room temperature for 16 h. The reaction mixture was filtered through celite bed and washed with dichloromethane. The filtrate was evaporated under reduced pressure to get crude product which was purified by column chromatography using ethylacetate-hexane gradient to afford the titled product as an off white solid (LVII, 1.74 g, 82%). LC-MS m/z calcd for $C_{17}H_{21}NO_3$, 287.1; found 288.1 [M+H]$^+$.

Step-5: 2-(1,3,3-trimethyl-2oxoindolin-5-yl)cyclpropanecarboxylicacid-LVIII

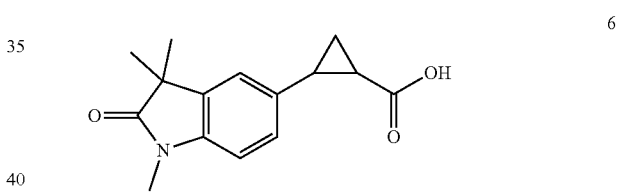

6

To a stirred solution of ethyl 2-(1,3,3-trimethyl-2-oxoindolin-5-yl)cyclopropanecarboxylate (LVII, 1.7 g, 14.0 mmol) in tetrahydrofuran (5 mL), methanol (5 mL) and water (2 mL) was added lithium hydroxide (0.62 g, 14.0 mmol). The reaction mixture was heated at 50° C. for 12 h. The reaction was concentrated under vacuum and then acidified to pH 2 with aqueous solution of 2N HCl. The resultant solid was filteried and dried under vacuum to get the title product as a white colour solid (LVIII, 1.2 g, 79%). LC-MS m/z calcd for $C_{15}H_{17}NO_3$, 259.1; found 260.1 [M+H]$^+$.

Step-6: tert-butyl (2-(1,3,3-trimethyl-2-oxoindolin-5-yl)cyclopropyl)carbamate-LIX

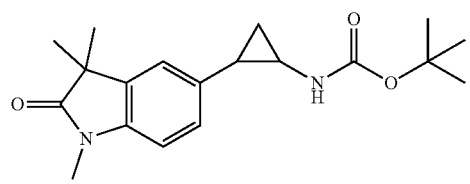

7

To a stirred solution of 2-(1,3,3-trimethyl-2oxoindolin-5-yl)cyclpropanecarboxylicacid (LVIII, 3.0 g, 11.50 mmol) in t-butanol (200 mL) was added triethylamine (2.32 mL, 17.2 mmol) diphenylphosphoryl azide (2.86 mL, 12.6 mmol) and then heated at 80° C. for 48 h. The reaction mixture was concentrated under vacuum to afford the crude product which was purified by column chromatography using ethylacetate-hexane gradient to afford the titled product as yellow solid (LIX, 2.5 g, 65%). LC-MS m/z calcd for $C_{19}H_{26}N_2O_3$, 330.2; found 331.2 $[M+H]^+$.

Step-7: 5-(2-aminocyclopropyl)-1,3,3-trimethylindolin-2-one hydrochloric acid-B-20

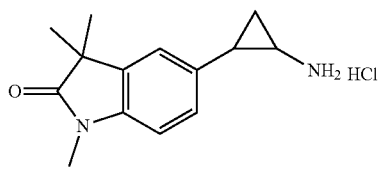 [SMILES: CN1C(=O)C(C)(C)c2cc(C3CC3N)ccc21 ; Cl]

To a stirred solution of tert-butyl (2-(1,3,3-trimethyl-2-oxoindolin-5-yl)cyclopropyl)carbamate (LIX, 12 g, 51.0 mmol) in 1,4-dioxane (50 mL) was added 20% HCl in 4-dioxane (36 mL) at 0° C. and then was heated at 50° C. for 3 h. The reaction mixture was concentrated under vacuum and the resultant solid was titurated with diethyl ether. The solid was filtered out and dried under vacuum to get the titled product as white solid (B-20, 7.7 g, 87%). LC-MS m/z calcd for $C_{14}H_{18}N_2O$, 230.1; found 231.1 $[M+H]^+$.

B-21—2,2,2-trifluoro-N-(2-phenylcyclopropyl)-N-(2-azaspiro[3.3]heptan-6-yl)acetamide hydrochloride

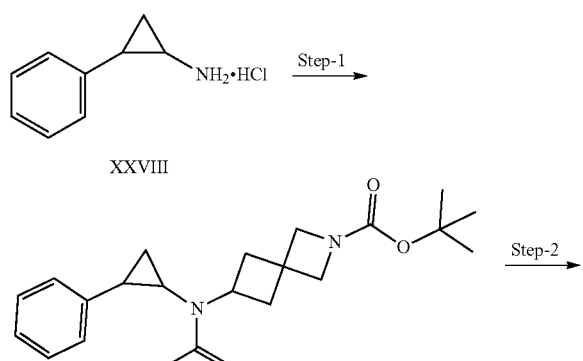

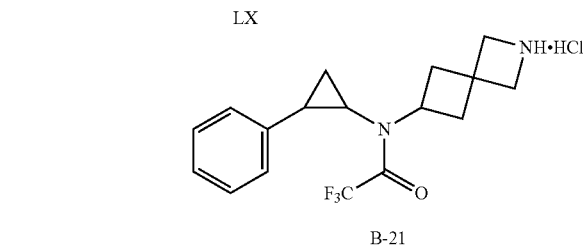

Step-1: tert-butyl 6-(2,2,2-trifluoro-N-(2-phenylcyclopropyl)acetamido)-2-azaspiro[3.3]heptane-2-carboxylate-LX

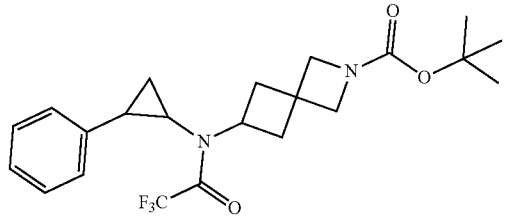 [SMILES: CC(C)(C)OC(=O)N1CC2(CC(N(C(=O)C(F)(F)F)C3CC3c3ccccc3)C2)C1]

To a stirred solution of 2-phenylcyclopropan-1-amine hydrochloride (XXVIII, 0.2 g, 1.17 mmol) and tert-butyl 6-oxo-2-azaspiro[3.3]heptane-2-carboxylate (0.3 g, 1.41 mmol) in DCE (6 mL) was added sodium triacetoxyborohydride (0.89 g, 4.20 mmol) and stirred at room temperature for 0.5 h. Methanol (1 mL) was added and then followed by addition of ethylacetate (10 mL) and 1M potassium carbonate solution and the stirring was continued for 30 min. The organic layer was separated and washed with water, brine solution, dried over sodium sulphate and concentrated under reduced pressure to get the crude. The crude product was diluted with dry dichloromethane (5 mL) and cooled to 0° C. Triethylamine (0.5 mL, 3.51 mmol) and trifluoroacetic anhydride (0.25 mL, 1.70 mmol) were added to it. The reaction mixture was stirred for 30 min. The reaction mixture was diluted with dichloromethane (50 mL) and washed with water, brine solution, dried over sodium sulphate and concentrated under reduced pressure to get crude which was purified by column chromatography using ethylacetate-hexane gradient to afford the titled product as an brown colour liquid (LX, 0.2 g, 40%). LC-MS m/z calcd for $C_{22}H_{27}F_3N_2O_3$, 424.2; found 425.2 $[M+H]^+$.

Step-2: 2,2,2-trifluoro-N-(2-phenylcyclopropyl)-N-(2-azaspiro[3.3]heptan-6-yl)acetamide hydrochloride-Intermediate B-21

To a stirred solution of tert-butyl 6-(2,2,2-trifluoro-N-(2-phenylcyclopropyl)acetamido)-2-azaspiro[3.3]heptane-2-carboxylate (LX, 0.2 g, 0.47 mmol) in 1,4-dioxane (2 mL) was added 20% HCl in 1,4-dioxane (5 mL) and then was refluxed for 10 min. The reaction mixture was concentrated under vacuum and the resultant solid was titurated with diethyl ether. The solid was filtered out and dried under vacuum to get the titled product B-21 as white solid (0.15 g, 98%). LC-MS m/z calcd for $C_{17}H_{19}F_3N_2O$, 324.1; found 325.1 $[M+H]^+$.

B-22—N-(azetidin-3-ylmethyl)-2,2,2-trifluoro-N-(2-(4'-fluoro-[1,1'-biphenyl]-4-yl)cyclopropyl)acetamide hydrochloride

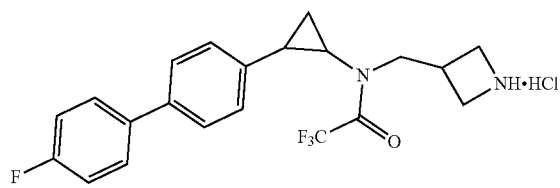

The intermediate B-22 was synthesized starting from intermediate B-12 following procedure given for the synthesis of B-4. LC-MS m/z calcd for $C_{21}H_{20}F_4N_2O$, 392.1; found 393.1 [M+H]$^+$.

B-23—N-(azetidin-3-ylmethyl)-2,2,2-trifluoro-N-(2-(4-(1-methyl-1H-pyrazol-4-yl)phenyl)cyclopropyl)acetamide hydrochloride

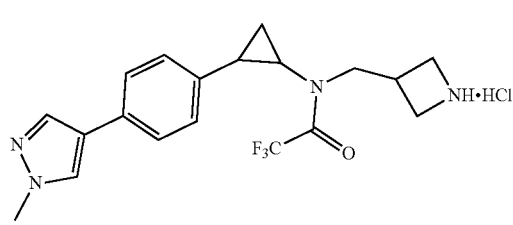

The intermediate B-23 was synthesized starting from intermediate B-7 following procedure given for the synthesis of B-4. LC-MS m/z calcd for $C_{19}H_{21}F_3N_4O$, 378.1; found 379.1 [M+H]$^+$.

B-24—N-(azetidin-3-ylmethyl)-N-(2-(4-(3,5-dimethylisoxazol-4-yl)phenyl)cyclopropyl)-2,2,2-trifluoroacetamide hydrochloride

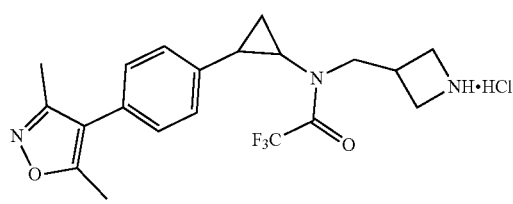

The intermediate B-24 was synthesized starting from intermediate B-8 following procedure given for the synthesis of B-4. LC-MS m/z calcd for $C_{20}H_{22}F_3N_3O_2$, 393.1; found 394.2 [M+H]$^+$.

B-25—N-((1-(2-aminoethyl)piperidin-4-yl)methyl)-2,2,2-trifluoro-N-(2-(4-fluorophenyl)cyclopropyl)acetamide hydrochloride

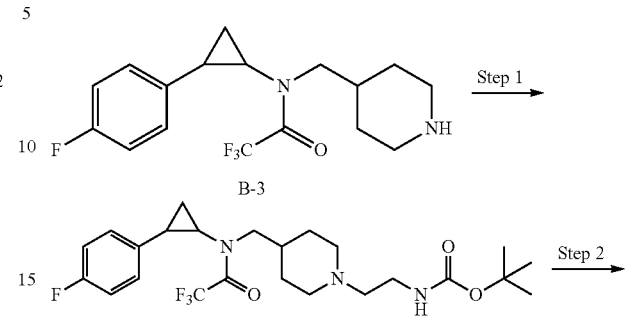

Step 1: tert-butyl (2-(4-((2,2,2-trifluoro-N-(2-(4-fluorophenyl)cyclopropyl)acetamido)methyl)piperidin-1-yl)ethyl)carbamate-LXI

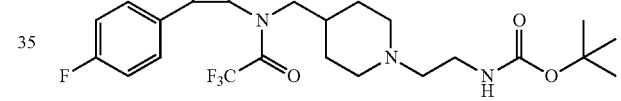

To a solution of 2,2,2-trifluoro-N-(2-(4-fluorophenyl)cyclopropyl)-N-(piperidin-4-ylmethyl)acetamide hydrochloride (B-3, 0.5 g, 1.40 mmol) in acetonitrile (5 mL) was added tert-butyl (2-bromoethyl)carbamate (0.35 g, 1.50 mmol) and N,N-diisopropylethylamine (0.75 mL, 4.2 mmol). Then the reaction mixture was heated at 50° C. for 16 h. After completion of reaction, the reaction was diluted with ethylacetate (50 mL), washed with water, brine solution, dried over sodium sulfate and concentrated under vacuum to afford the crude product which was further purified by flash chromatography using methanol-dichloromethane gradient to result in the titled product as a brown colour liquid (LXI, 0.6 g, 85%). LC-MS m/z calcd for $C_{24}H_{33}F_4N_3O_3$, 487.2; found 488.2 [M+H]$^+$.

Step 2: N-((1-(2-aminoethyl)piperidin-4-yl)methyl)-2,2,2-trifluoro-N-(2-(4-fluorophenyl)cyclopropyl)acetamide hydrochloride-B-25

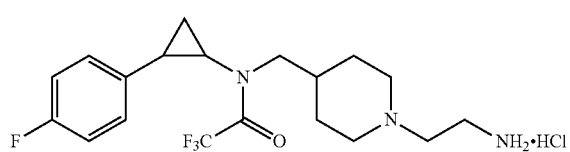

To a stirred solution of tert-butyl (2-(4-((2,2,2-trifluoro-N-(2-(4-fluorophenyl)cyclopropyl)acetamido)methyl)piperidin-1-yl)ethyl)carbamate (LXI, 0.6 g, 1.20 mmol) in dioxane (5 mL) was added 20% HCl in dioxane (3 mL) at 0° C. and stirred for 2 h at room temperature. The reaction mixture was concentrated under vacuum and triturated with diethyl ether. The resultant solid was dried under vacuum to afford the title product as off-white solid (B-25, 0.48 g, quantitative yield). LC-MS m/z calcd for $C_{19}H_{25}F_4N_3O$, 387.2; found 388.2 $[M+H]^+$.

B-26—N-((1-(2-aminoethyl)piperidin-4-yl)methyl)-2,2,2-trifluoro-N-(2-phenylcyclopropyl)acetamide hydrochloride

B-26

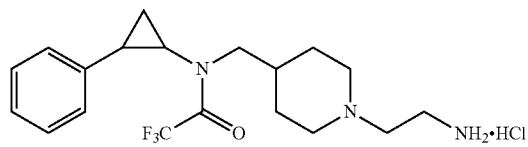

The intermediate B-26 was synthesized starting from 2,2,2-trifluoro-N-(2-phenylcyclopropyl)-N-(piperidin-4-ylmethyl)acetamide and tert-butyl (2-bromoethyl)carbamate by following the experiment procedure of -B-25. LC-MS m/z calcd for $C_{19}H_{26}F_3N_3O$, 369.2; found 370.1 $[M+H]^+$.

B-27—N-((1-(2-aminoethyl)piperidin-4-yl)methyl)-N-(2-(3,4-difluorophenyl) cyclopropyl)-2,2,2-trifluoroacetamide hydrochloride

B-27

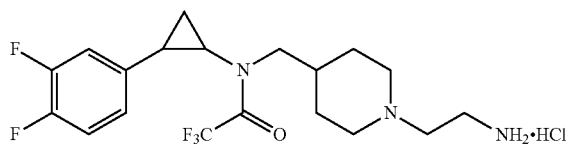

The intermediate B-27 was synthesized starting from N-(2-(3,4-difluorophenyl)cyclopropyl)-2,2,2-trifluoro-N-(piperidin-4-ylmethyl)acetamide and tert-butyl (2-bromoethyl)carbamate by following the experiment procedure of -B-25. LC-MS m/z calcd for $C_{19}H_{22}F_5N_2O$, 389.2; found 390.1 $[M+H]^+$.

Synthesis of Intermediate Esters-I Series

I-2 (E)-3-[4-({tert-Butoxycarbonyl-[2-(4-fluoro-phenyl)-cyclopropyl]-amino}-methyl)-phenyl]-acrylic acid methyl ester (LXII)

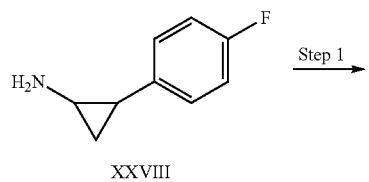

XXVIII

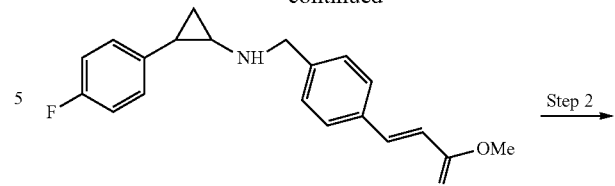

LXII

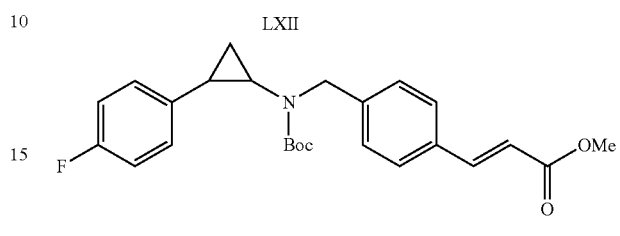

I-2

Step 1: (E)-3-(4-{[2-(4-Fluoro-phenyl)-cyclopropylamino]-methyl}-phenyl)-acrylic acid methyl ester ( )

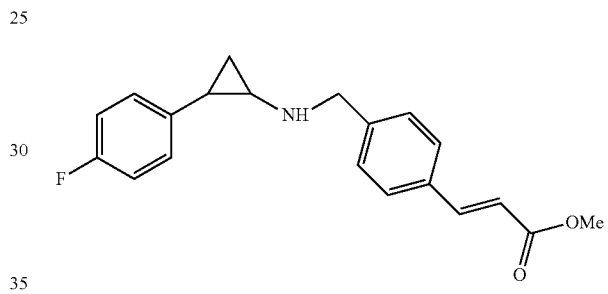

To a stirred solution of 2-(4-fluoro-phenyl)-cyclopropylamine hydrochloride (XXVIII, 0.2 g, 1.06 mmol) in methanol (20 mL) was added (E)-3-(4-formyl-phenyl)-acrylic acid methyl ester (0.24 g, 1.28 mmol) and sodium bicarbonate (0.08 g, 0.95 mmol) and molecular sieves (approx 1 g) at room temperature and the resulting mixture was heated to reflux for 2.5 h. Cooled to 0° C. and sodium borohydride (0.036 g, 0.95 mmol) was added, stirred at room temperature for 1 h. Ice was added and the reaction mixture was filtered. The solvent was evaporated to get the residue. Water was added and extracted with dichloromethane (2×50 mL). The organic portion was washed with water and brine dried over sodium sulphate and concentrated under reduced pressure to afford the crude product which was purified by column chromatography using methanol-dichloromethane gradient to afford the titled product as yellow oil. (LXII, 0.3 g, 90%). LC-MS m/z calcd for $C_{20}H_{20}FNO_2$, 325.1; found 326.3 $[M+H]^+$.

Step 2: (E)-3-[4-({tert-Butoxycarbonyl-[2-(4-fluoro-phenyl)-cyclopropyl]-amino}-methyl)-phenyl]-acrylic acid methyl ester (I-2)

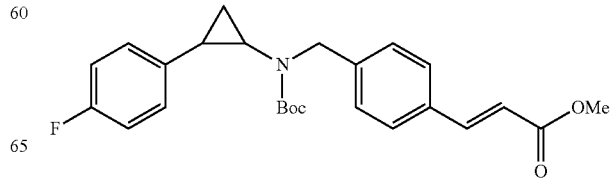

To a stirred solution of (E)-3-(4-{[2-(4-fluoro-phenyl)-cyclopropylamino]-methyl}-phenyl)-acrylic acid methyl ester (XLVI, 0.25 g, 0.76 mmol) in tetrahydrofuran and water mixture (6 mL, 1:1) was added sodium bicarbonate (0.087 g, 2.3 mmol) and Boc anhydride (0.22 mL, 0.92 mmol) at room temperature and the resulting mixture was stirred at that temperature for 2 h. The progress of the reaction was monitored by TLC. The reaction mixture was diluted with ethylacetate and the organic portion was washed with water and brine solution, dried over sodium sulphate and concentrated under reduced pressure to get the crude product which was purified by column chromatography using ethylacetate-hexane gradient to afford the titled product as sticky oil (I-2, 0.19 g, 58%). LC-MS m/z calcd for $C_{25}H_{28}FNO_4$, 425.2; found 326.3 [M-Boc+1]$^+$.

The following compounds were synthesized using procedure for the synthesize of I-2

I-3 methyl (E)-3-(4-(((tert-butoxycarbonyl)(2-(4-((4-fluorobenzyl)oxy)phenyl) cyclopropyl)amino)methyl)phenyl)acrylate

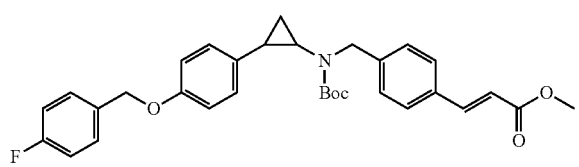 [SMILES: COC(=O)/C=C/c1ccc(CN(C(=O)OC(C)(C)C)C2CC2c2ccc(OCc3ccc(F)cc3)cc2)cc1]

The compound was synthesized using amine B6 and (E)-3-(4-Formyl-phenyl)-acrylic acid methyl ester following the procedure for the synthesis of I-2. LC-MS m/z calcd for $C_{32}H_{34}FNO_5$, 531.2; found 532.2 [M+H]$^+$.

I-4 methyl (E)-3-(4-(4-(((tert-butoxycarbonyl)(2-phenylcyclopropyl)amino)methyl)piperidin-1-yl)phenyl)acrylate

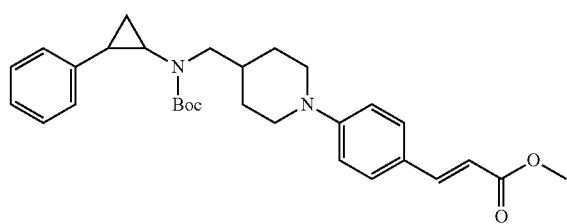 [SMILES: COC(=O)/C=C/c1ccc(N2CCC(CN(C(=O)OC(C)(C)C)C3CC3c3ccccc3)CC2)cc1]

The compound was synthesized using phenylcyclopropyl amine and aldehyde A2 following the procedure for the synthesis of I-2. LC-MS m/z calcd for $C_{30}H_{38}N_2O_4$, 490.3; found 434.2 [M-56]$^+$.

I-5 methyl (E)-3-(4-(((tert-butoxycarbonyl)(2-(4'-chloro-[1,1'-biphenyl]-4-yl)cyclopropyl)amino)methyl)phenyl)acrylate

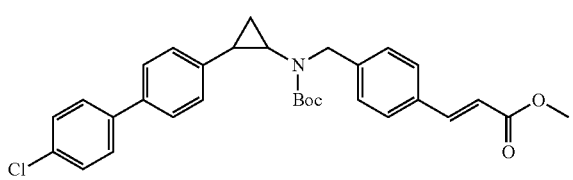 [SMILES: COC(=O)/C=C/c1ccc(CN(C(=O)OC(C)(C)C)C2CC2c2ccc(-c3ccc(Cl)cc3)cc2)cc1]

The compound was synthesized using amine B10 and methyl-4-formyl cinnamic acid ester following the procedure for the synthesis of I-2. LC-MS m/z calcd for $C_{31}H_{32}ClNO_4$, 517.2; found 462.2 [M-56]$^+$.

I-6 methyl (E)-3-(4-(((tert-butoxycarbonyl)(2-(4-(3,5-dimethylisoxazol-4-yl)phenyl)cyclopropyl)amino)methyl)phenyl)acrylate

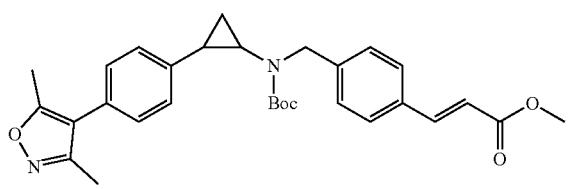 [SMILES: COC(=O)/C=C/c1ccc(CN(C(=O)OC(C)(C)C)C2CC2c2ccc(-c3c(C)noc3C)cc2)cc1]

The compound was synthesized using amine B8 and methyl-4-formyl cinnamic acid ester following the procedure for the synthesis of I-2. LC-MS m/z calcd for $C_{30}H_{34}N_2O_5$, 502.2; found 503.2 [M+H]$^+$.

I-7 methyl (E)-3-(4-(((tert-butoxycarbonyl)(2-(4-(pyrimidin-5-yl)phenyl)cyclopropyl)amino)methyl)phenyl)acrylate

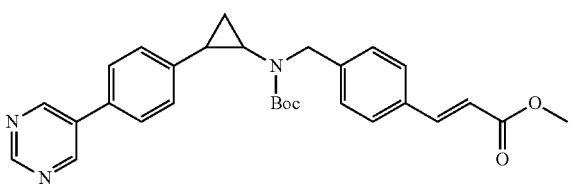 [SMILES: COC(=O)/C=C/c1ccc(CN(C(=O)OC(C)(C)C)C2CC2c2ccc(-c3cncnc3)cc2)cc1]

The compound was synthesized using amine B11 and methyl-4-formyl cinnamic acid ester following the procedure for the synthesis of I-2. LC-MS m/z calcd for $C_{29}H_{31}N_3O_4$, 485.2; found 486.2 [M+H]$^+$.

I-8 methyl 2-(4-(((tert-butoxycarbonyl)(2-(4-fluorophenyl)cyclopropyl)amino)methyl)piperidin-1-yl)pyrimidine-5-carboxylate

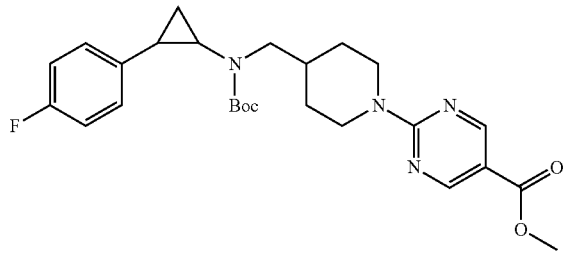 [SMILES: COC(=O)c1cnc(N2CCC(CN(C(=O)OC(C)(C)C)C3CC3c3ccc(F)cc3)CC2)nc1]

The compound was synthesized using 4-fluorophenyl cyclopropyl amine and aldehyde A1 following the procedure for the synthesis of I-2. LC-MS m/z calcd for $C_{26}H_{33}FN_4O_4$, 484.2; found 485.2 [M+H]$^+$.

I-9 methyl 2-(4-((tert-butoxycarbonyl)(2-phenylcyclopropyl)amino)piperidin-1-yl)pyrimidine-5-carboxylate

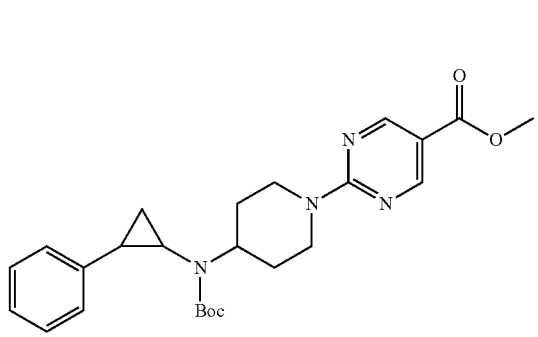 [SMILES: COC(=O)c1cnc(N2CCC(N(C(=O)OC(C)(C)C)C3CC3c3ccccc3)CC2)nc1]

The compound was synthesized using phenylcyclopropyl amine and ketone A3 following the procedure for the synthesis of I-2. LC-MS m/z calcd for $C_{25}H_{32}N_4O_4$, 452.2; found 453.2[M+H]$^+$.

I-10 methyl 2-(4-((tert-butoxycarbonyl)(2-(4-fluorophenyl)cyclopropyl)amino)piperidin-1-yl)pyrimidine-5-carboxylate

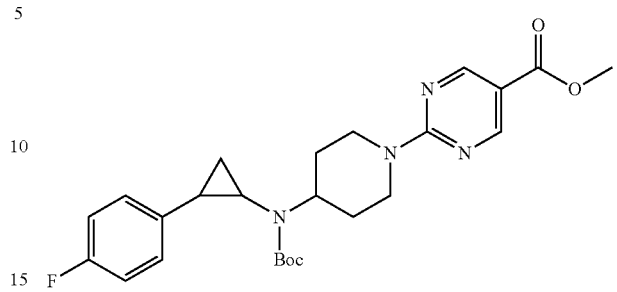

The compound was synthesized using 4-fluorophenylcyclopropyl amine and ketone A3 following the procedure for the synthesis of I-2. LC-MS m/z calcd for $C_{25}H_{31}FN_4O_4$, 470.2; found 471.2 [M+H]$^+$.

I-11 methyl 2-(4-(((tert-butoxycarbonyl)(2-(4-((4-fluorobenzyl)oxy)phenyl)cyclopropyl)amino)methyl)piperidin-1-yl)pyrimidine-5-carboxylate

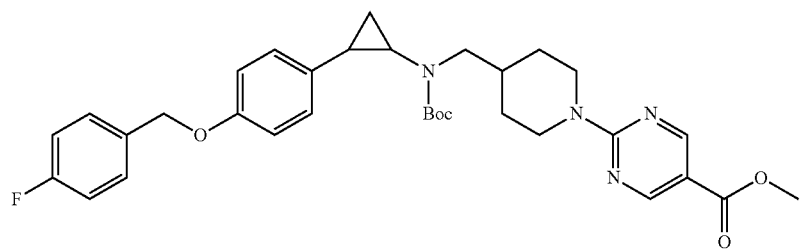 [SMILES: COC(=O)c1cnc(N2CCC(CN(C(=O)OC(C)(C)C)C3CC3c3ccc(OCc4ccc(F)cc4)cc3)CC2)nc1]

The compound was synthesized using amine B-6 and aldehyde A1 following the procedure for the synthesis of I-2. LC-MS m/z calcd for $C_{33}H_{39}FN_4O_5$, 590.3; found 591.2 [M+H]$^+$.

I-12 methyl 2-(4-((tert-butoxycarbonyl)(2-(4-((4-fluorobenzyl)oxy)phenyl)cyclopropyl)amino)piperidin-1-yl)pyrimidine-5-carboxylate

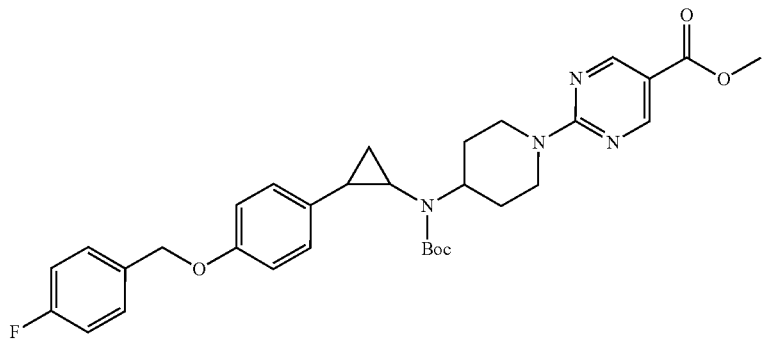 [SMILES: COC(=O)c1cnc(N2CCC(N(C(=O)OC(C)(C)C)C3CC3c3ccc(OCc4ccc(F)cc4)cc3)CC2)nc1]

The compound was synthesized using amine B-6 and ketone A3 following the procedure for the synthesis of I-2. LC-MS m/z calcd for $C_{32}H_{37}FN_4O_5$, 576.2; found 577.3 [M+H]$^+$.

I-13 methyl 2-(4-(((tert-butoxycarbonyl)(2-(4'-chloro-[1,1'-biphenyl]-4-yl)cyclopropyl)amino)piperidin-1-yl)pyrimidine-5-carboxylate

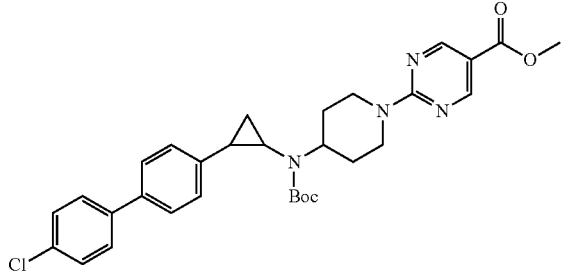 [SMILES: COC(=O)c1cnc(N2CCC(N(C(=O)OC(C)(C)C)C3CC3c3ccc(-c4ccc(Cl)cc4)cc3)CC2)nc1]

The compound was synthesized using amine B-10 and ketone A3 following the procedure for the synthesis of I-2. LC-MS m/z calcd for $C_{31}H_{35}ClN_4O_4$, 562.2; found 563.2 [M+H]$^+$.

I-14 methyl 2-(4-(((tert-butoxycarbonyl)(2-(4'-chloro-[1,1'-biphenyl]-4-yl)cyclopropyl)amino)methyl)piperidin-1-yl)pyrimidine-5-carboxylate

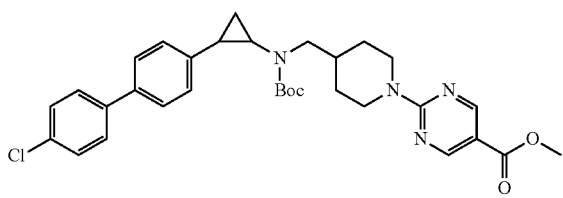 [SMILES: COC(=O)c1cnc(N2CCC(CN(C(=O)OC(C)(C)C)C3CC3c3ccc(-c4ccc(Cl)cc4)cc3)CC2)nc1]

The compound was synthesized using amine B-10 and aldehyde A1 following the procedure for the synthesis of I-2. LC-MS m/z calcd for $C_{32}H_{37}ClN_4O_4$, 576.2; found 577.2 [M+H]$^+$.

I-15 ethyl 2-(4-(((tert-butoxycarbonyl)(2-(4'-fluoro-[1,1'-biphenyl]-4-yl)cyclopropyl)amino)methyl)piperidin-1-yl)pyrimidine-5-carboxylate

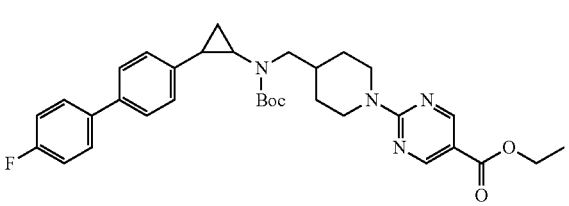 [SMILES: CCOC(=O)c1cnc(N2CCC(CN(C(=O)OC(C)(C)C)C3CC3c3ccc(-c4ccc(F)cc4)cc3)CC2)nc1]

The compound was synthesized using amine B-12 and aldehyde A1 following the procedure for the synthesis of I-2. LC-MS m/z calcd for $C_{33}H_{39}FN_4O_4$, 574.3; found 575.3 [M+H]$^+$.

I-16 methyl 2-(4-(((tert-butoxycarbonyl)(2-(4-(3,5-dimethylisoxazol-4-yl)phenyl)cyclopropyl)amino)methyl)piperidin-1-yl)pyrimidine-5-carboxylate

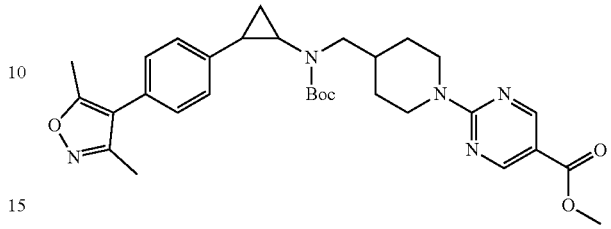

The compound was synthesized using amine B-8 and aldehyde A1 following the procedure for the synthesis of I-2. LC-MS m/z calcd for $C_{31}H_{39}N_5O_5$, 561.2; found 562.2 [M+H]$^+$.

I-17 methyl 2-(4-(((tert-butoxycarbonyl)(2-(4-(pyrimidin-5-yl)phenyl)cyclopropyl)amino) methyl) piperidin-1-yl)pyrimidine-5-carboxylate

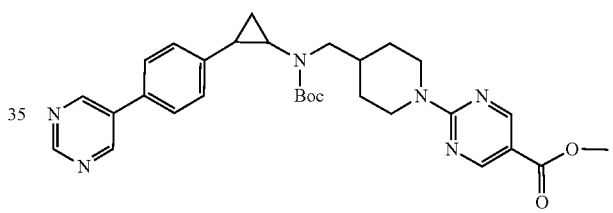

The compound was synthesized using amine B-11 and aldehyde A1 following the procedure for the synthesis of I-2. LC-MS m/z calcd for $C_{30}H_{36}N_6O_4$, 544.3. found 545.2 [M+H]$^+$.

I-18 methyl 2-(4-(((tert-butoxycarbonyl)(2-(4-methoxyphenyl)cyclopropyl)amino)methyl) piperidin-1-yl)pyrimidine-5-carboxylate

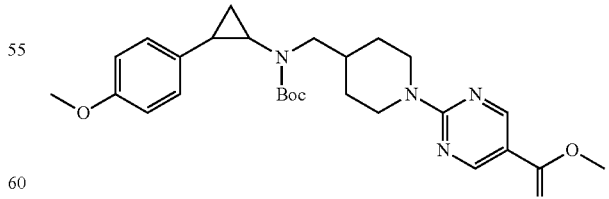

The compound was synthesized using 4-methoxyphenyl cyclopropyl amine and aldehyde A1 following the procedure for the synthesis of I-2. LC-MS m/z calcd for $C_{27}H_{36}N_4O_5$, 496.2. found 497.3 [M+H]$^+$.

I-19 methyl 2-(4-(((tert-butoxycarbonyl)(2-(4-methoxyphenyl)cyclopropyl)amino)piperidin-1-yl)pyrimidine-5-carboxylate

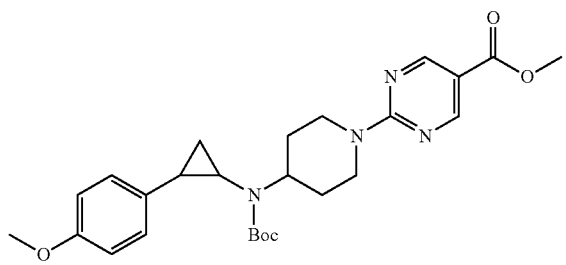

The compound was synthesized using 4-methoxyphenyl cyclopropyl amine and ketone A3 following the procedure for the synthesis of I-2. LC-MS m/z calcd for $C_{26}H_{34}N_4O_5$, 482.2. found 483.2 [M+H]$^+$.

I-20 methyl 2-(4-(((tert-butoxycarbonyl)((1R,2S)-2-(4-fluorophenyl)cyclopropyl)amino) methyl)piperidin-1-yl)pyrimidine-5-carboxylate

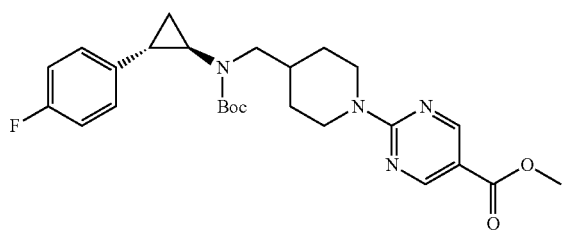 [SMILES: COC(=O)c1cnc(N2CCC(CN(C(=O)OC(C)(C)C)[C@@H]3C[C@H]3c3ccc(F)cc3)CC2)nc1]

The compound was synthesized using 4-fluorophenyl cyclopropyl amine B1 and aldehyde A1 following the procedure for the synthesis of I-2. LC-MS m/z calcd for $C_{26}H_{33}FN_4O_4$, 484.2. found 485.2 [M+H]$^+$.

I-21 methyl 2-(4-(((tert-butoxycarbonyl)((1S,2R)-2-(4-fluorophenyl)cyclopropyl)amino) methyl)piperidin-1-yl)pyrimidine-5-carboxylate

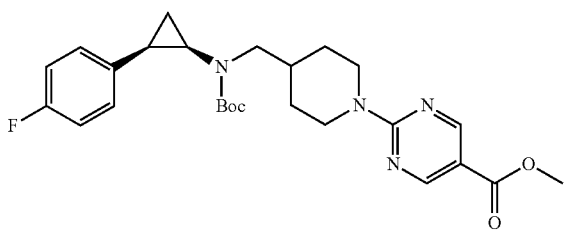 [SMILES: COC(=O)c1cnc(N2CCC(CN(C(=O)OC(C)(C)C)[C@@H]3C[C@@H]3c3ccc(F)cc3)CC2)nc1]

The compound was synthesized using 4-fluorophenyl cyclopropyl amine B2 and aldehyde A1 following the procedure for the synthesis of I-2. LC-MS m/z calcd for $C_{26}H_{33}FN_4O_4$, 484.2. found 485.2 [M+H]$^+$.

I-22 methyl 4-(4-(((tert-butoxycarbonyl)(2-(4-fluorophenyl)cyclopropyl)amino)methyl) piperidin-1-yl)benzoate

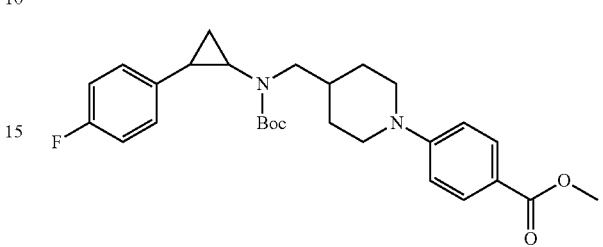

The compound was synthesized using 4-fluorophenyl cyclopropyl amine and aldehyde A2 following the procedure for the synthesis of I-2. LC-MS m/z calcd for $C_{28}H_{35}FN_2O_4$, 482.2. found 483.3 [M+H]$^+$.

I-23 methyl 2-(2-(((tert-butoxycarbonyl)(2-phenylcyclopropyl)amino)methyl)-5,6-dihydroimidazo[1,2-a]pyrazin-7(8H)-yl)pyrimidine-5-carboxylate

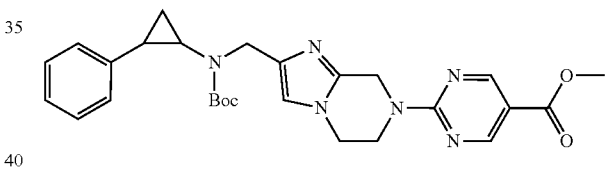

The compound was synthesized using phenylcyclopropyl amine and aldehyde A4 following the procedure for the synthesis of I-2. LC-MS m/z calcd for $C_{27}H_{32}N_6O_4$, 504.2. found 505.2 [M+H]$^+$.

I-24 methyl 2-(2-(((tert-butoxycarbonyl)(2-(4-methoxyphenyl)cyclopropyl)amino)methyl)-5,6-dihydroimidazo[1,2-a]pyrazin-7(8H)-yl)pyrimidine-5-carboxylate

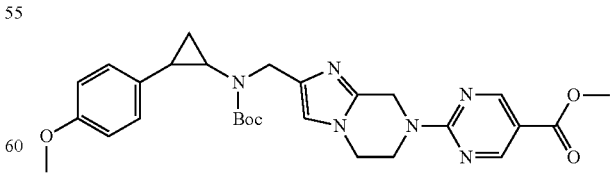

The compound was synthesized using 4-methoxyphenyl-cyclopropyl amine and aldehyde A4 following the procedure for the synthesis of I-2. LC-MS m/z calcd for $C_{28}H_{34}N_6O_5$, 534.2. found 535.2 [M+H]$^+$.

I-25 methyl 2-(2-(((tert-butoxycarbonyl)(2-(4-fluorophenyl)cyclopropyl)amino)methyl)-5,6-dihydroimidazo[1,2-a]pyrazin-7(8H)-yl)pyrimidine-5-carboxylate

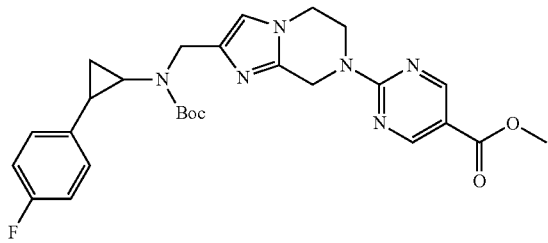 [SMILES: COC(=O)c1cnc(N2CCn3cc(CN(C(=O)OC(C)(C)C)C4CC4c4ccc(F)cc4)nc3C2)nc1]

The compound was synthesized using 4-fluorophenylcyclopropyl amine and aldehyde A4 following the procedure for the synthesis of I-2. LC-MS m/z calcd for $C_{27}H_{31}FN_6O_4$, 522.2. found 523.2 [M+H]$^+$.

I-26 methyl 3-(((2-(4-bromophenyl)cyclopropyl)(tert-butoxycarbonyl)amino)methyl)benzoate

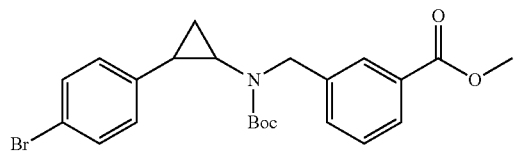 [SMILES: COC(=O)c1cccc(CN(C(=O)OC(C)(C)C)C2CC2c2ccc(Br)cc2)c1]

The compound was synthesized using 4-bromophenylcyclopropyl amine and methyl-3-formyl benzoic acid ester following the procedure for the synthesis of I-2. LC-MS m/z calcd for $C_{23}H_{26}BrNO_4$, 459.1. found 460.1 [M+H]$^+$.

I-27 methyl 3-(((tert-butoxycarbonyl)(2-phenylcyclopropyl)amino)methyl)benzoate

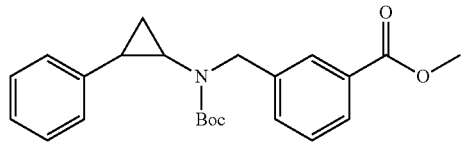 [SMILES: COC(=O)c1cccc(CN(C(=O)OC(C)(C)C)C2CC2c2ccccc2)c1]

The compound was synthesized using phenylcyclopropyl amine and methyl-3-formyl benzoic acid ester following the procedure for the synthesis of I-2. LC-MS m/z calcd for $C_{23}H_{27}NO_4$, 381.2. found 382.1 [M+H]$^+$.

I-28 methyl 4-(((tert-butoxycarbonyl)(2-phenylcyclopropyl)amino)methyl)benzoate

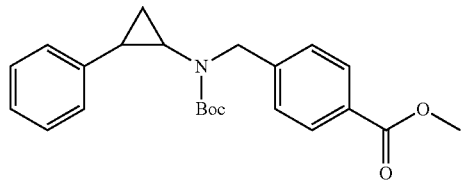 [SMILES: COC(=O)c1ccc(CN(C(=O)OC(C)(C)C)C2CC2c2ccccc2)cc1]

The compound was synthesized using phenylcyclopropyl amine and methyl-4-formyl benzoic acid ester following the procedure for the synthesis of intermediate I-2. LC-MS m/z calcd for $C_{23}H_{27}NO_4$, 381.2. found 382.1 [M+H]$^+$.

I-29 ethyl 6-((tert-butoxycarbonyl)(2-phenylcyclopropyl)amino)hexanoate

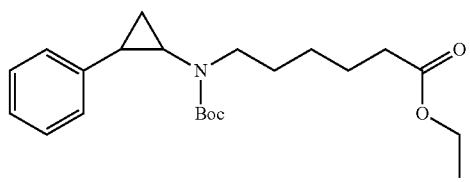 [SMILES: CCOC(=O)CCCCCN(C(=O)OC(C)(C)C)C1CC1c1ccccc1]

The compound was synthesized using phenylcyclopropyl amine and methyl 6-oxohexanoate following the procedure for the synthesis of I-2. LC-MS m/z calcd for $C_{22}H_{33}NO_4$, 375.2. found 276.2 [M-BocH]$^+$.

I-30 ethyl 4-(3-((tert-butoxycarbonyl)(2-(4-fluorophenyl)cyclopropyl)amino)propyl)benzoate

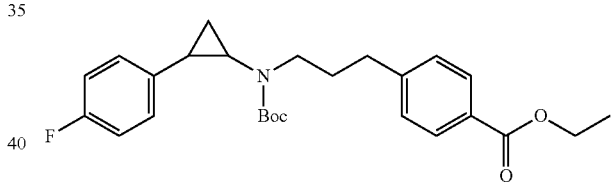

The compound was synthesized using phenylcyclopropyl amine and methyl 4-(3-oxopropyl)benzoate following the procedure for the synthesis of I-2. LC-MS m/z calcd for $C_{26}H_{32}FNO_4$, 441.2. found 386.2 [M-55].

I-31 methyl 7-(4-((((tert-butoxycarbonyl)(2-phenylcyclopropyl)amino)methyl)benzamido) heptanoate

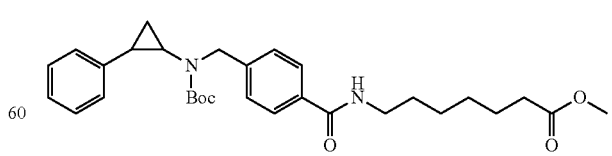

The compound was synthesized using phenylcyclopropyl amine and aldehyde A5 following the procedure for the synthesis of I-2. LC-MS m/z calcd for $C_{30}H_{40}N_2O_5$, 508.3. found 509.3 [M+H]$^+$.

I-32 methyl 7-(4-(((tert-butoxycarbonyl)(2-(4-fluorophenyl)cyclopropyl)amino)methyl) benzamido)heptanoate

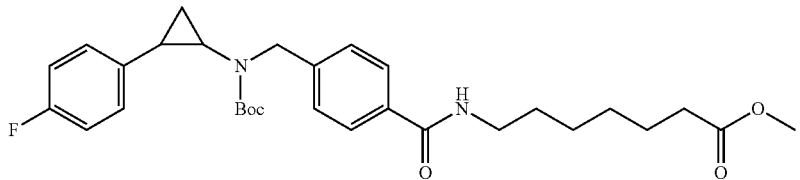 [SMILES: COC(=O)CCCCCCNC(=O)c1ccc(CN(C(=O)OC(C)(C)C)C2CC2c2ccc(F)cc2)cc1]

The compound was synthesized using 4-fluorophenylcyclopropyl amine and aldehyde A5 following the procedure for the synthesis of I-2. LC-MS m/z calcd for $C_{30}H_{39}FN_2O_5$, 526.3. found 527.3 [M+H]$^+$.

I-33 methyl 4-((tert-butoxycarbonyl)(2-phenylcyclopropyl)amino)cyclohexanecarboxylate

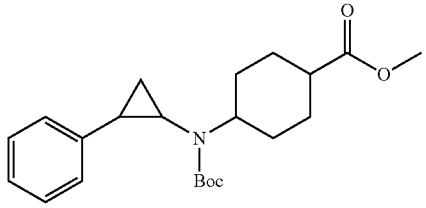 [SMILES: COC(=O)C1CCC(N(C(=O)OC(C)(C)C)C2CC2c2ccccc2)CC1]

The compound was synthesized using phenylcyclopropyl amine and methyl 4-oxocyclohexane-1-carboxylate following the procedure for the synthesis of I-2. LC-MS m/z calcd for $C_{22}H_{31}NO_4$, 373.2. found 374.2 [M+H]$^+$.

I-34 (1S,4R)-methyl 4-((1S)-1-((tert-butoxycarbonyl)(2-phenylcyclopropyl)amino)ethyl)cyclohexane carboxylate

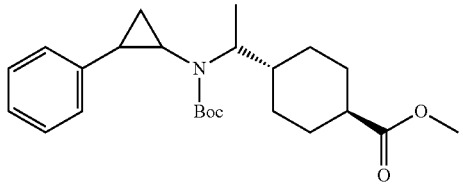 [SMILES: COC(=O)[C@H]1CC[C@H](C(C)N(C(=O)OC(C)(C)C)C2CC2c2ccccc2)CC1]

The compound was synthesized using phenylcyclopropyl amine and methyl (1R,4R)-4-acetylcyclohexane-1-carboxylate following the procedure for the synthesize of I-2 LC-MS m/z calcd for $C_{24}H_{35}NO_4$, 401.2. found 402.2 [M+H]$^+$.

I-35 methyl 4-((4-(((tert-butoxycarbonyl)(2-(4-(1-methyl-6-oxo-1,6-dihydropyridin-3-yl)phenyl)cyclopropyl)amino)methyl)piperidin-1-yl)methyl)benzoate

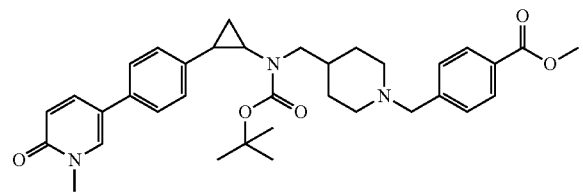 [SMILES: COC(=O)c1ccc(CN2CCC(CN(C(=O)OC(C)(C)C)C3CC3c3ccc(-c4ccc(=O)n(C)c4)cc3)CC2)cc1]

The compound was synthesized using amine B19 and methyl 4-((4-formylpiperidin-1-yl)methyl)benzoate following the procedure for the synthesis of I-2. LC-MS m/z calcd for $C_{35}H_{43}N_3O_5$, 585.3. found 586.3 [M+H]$^+$.

I-36 methyl 4-((4-(((tert-butoxycarbonyl)(2-phenylcyclopropyl)amino)methyl)piperidin-1-yl)methyl)benzoate

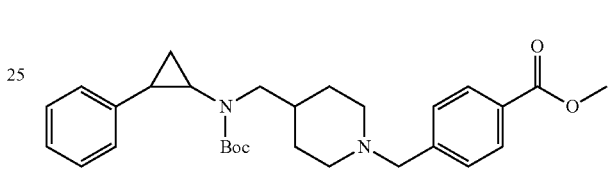

The compound was synthesized using Phenylcyclopropyl amine and methyl 4-((4-formylpiperidin-1-yl)methyl)benzoate following the procedure for the synthesis of I-2. LC-MS m/z calcd for $C_{29}H_{38}N_2O_4$, 478.3. found 479.3 [M+H]$^+$.

I-37 methyl 4-((4-(((tert-butoxycarbonyl)(2-(4-(3,5-dimethylisoxazol-4-yl)phenyl) cyclopropyl)amino)methyl)piperidin-1-yl)methyl)benzoate

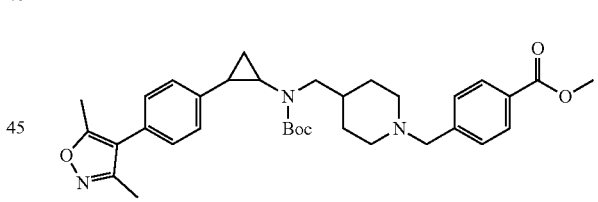

The compound was synthesized using amine B8 and methyl 4-((4-formylpiperidin-1-yl)methyl)benzoate following the procedure for the synthesis of I-2. LC-MS m/z calcd for $C_{34}H_{43}N_3O_5$, 573.3. found 574.3 [M+H]$^+$.

I-38 methyl 4-((4-(((tert-butoxycarbonyl)(2-(4-(pyrimidin-5-yl)phenyl)cyclopropyl)amino) methyl)piperidin-1-yl)methyl)benzoate

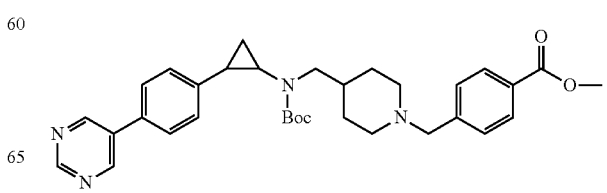

The compound was synthesized using amine B11 and methyl 4-((4-formylpiperidin-1-yl)methyl)benzoate following the procedure for the synthesis of I-2. LC-MS m/z calcd for $C_{33}H_{40}N_4O_4$, 556.3. found 557.3 [M+H]$^+$.

I-39 methyl 6-((4-(((tert-butoxycarbonyl)(2-(4-(3,5-dimethylisoxazol-4-yl)phenyl) cyclopropyl)amino) methyl)piperidin-1-yl)methyl)nicotinate

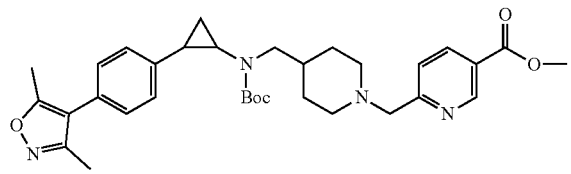 [SMILES: COC(=O)c1ccc(CN2CCC(CN(C(=O)OC(C)(C)C)C3CC3c3ccc(-c4c(C)noc4C)cc3)CC2)nc1]

The compound was synthesized using amine B8 and methyl 6-((4-formylpiperidin-1-yl)methyl)nicotinate following the procedure for the synthesize of I-2. LC-MS m/z calcd for $C_{33}H_{42}N_4O_5$, 574.3. found 575.3 [M+H]$^+$.

I-40 ethyl 4-((4-(((tert-butoxycarbonyl)(2-phenylcyclopropyl)amino)methyl)-1H-pyrazol-1-yl)methyl) benzoate

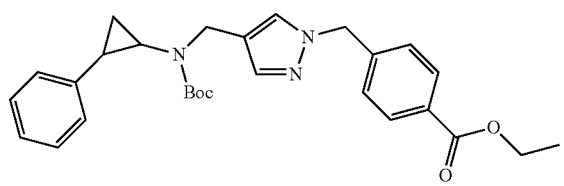 [SMILES: CCOC(=O)c1ccc(Cn2cc(CN(C(=O)OC(C)(C)C)C3CC3c3ccccc3)cn2)cc1]

The compound was synthesized using Phenylcyclopropyl amine and aldehyde A12 following the procedure for the synthesis of I-2. LC-MS m/z calcd for $C_{28}H_{33}N_3O_4$, 475.2. found 476.2 [M+H]$^+$.

I-41 ethyl 4-((4-(((tert-butoxycarbonyl)(2-phenylcyclopropyl)amino)methyl)-1H-1,2,3-triazol-1-yl) methyl)benzoate

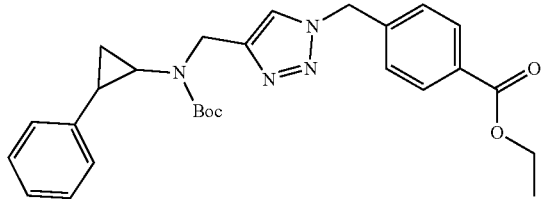 [SMILES: CCOC(=O)c1ccc(Cn2cc(CN(C(=O)OC(C)(C)C)C3CC3c3ccccc3)nn2)cc1]

The compound was synthesized using phenylcyclopropyl amine and aldehyde A7 following the procedure for the synthesis of I-2. LC-MS m/z calcd for $C_{27}H_{32}N_4O_4$, 476.2. found 477.2 [M+H]$^+$.

I-42 methyl 4-(2-(4-(((tert-butoxycarbonyl)(2-phenylcyclopropyl)amino)methyl)piperidin-1-yl)ethyl) benzoate

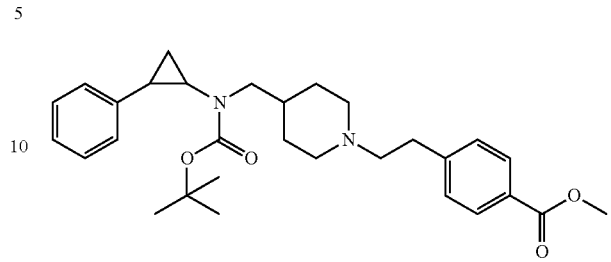

The compound was synthesized using Phenylcyclopropyl amine and aldehyde A15 following the procedure for the synthesis of I-2. LC-MS m/z calcd for $C_{30}H_{40}N_2O_4$, 492.66. found 393.6 [M+H-Boc]$^+$.

I-43 ethyl 4-(3-(4-(((tert-butoxycarbonyl)(2-phenylcyclopropyl)amino)methyl)piperidin-1-yl) propyl) benzoate

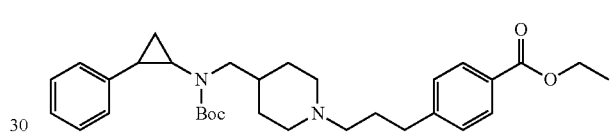

The compound was synthesized using phenylcyclopropyl amine and aldehyde A19 following the procedure for the synthesis of I-2. LC-MS m/z calcd for $C_{32}H_{44}N_2O_4$, 520.3. found 521.3 [M+H]$^+$.

I-44 ethyl 4-(3-(4-((tert-butoxycarbonyl)(2-phenylcyclopropyl)amino)piperidin-1-yl)propyl) benzoate

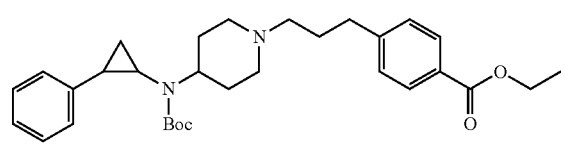 [SMILES: CCOC(=O)c1ccc(CCCN2CCC(N(C(=O)OC(C)(C)C)C3CC3c3ccccc3)CC2)cc1]

The compound was synthesized using phenylcyclopropyl amine and aldehyde A16 following the procedure for the synthesis of I-2. LC-MS m/z calcd for $C_{31}H_{42}N_2O_4$, 506.3. found 507.3 [M+H]$^+$.

I-46 ethyl 4-(3-(6-(2,2,2-trifluoro-N-(2-phenylcyclopropyl)acetamido)-2-azaspiro[3.3]heptan-2-yl)propyl)benzoate

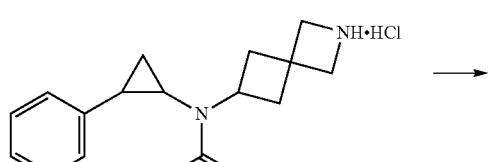

B-21

-continued

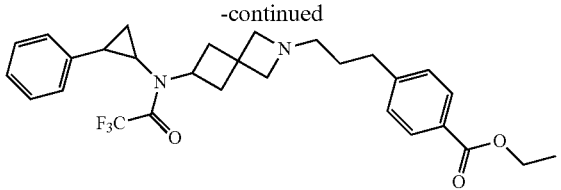

I-46

To a solution of 2,2,2-trifluoro-N-(2-phenylcyclopropyl)-N-(2-azaspiro[3.3]heptan-6-yl)acetamide hydrochloride (B-21, 0.2 g, 0.5 mmol) in acetonitrile (2 mL) was added ethyl 4-(3-bromopropyl)benzoate (0.149 g, 0.5 mmol) and N,N-diisopropylethylamine (0.26 mL, 1.5 mmol). Then the reaction mixture was heated at 60° C. for 16 h. After completion of reaction, the reaction was diluted with ethylacetate (50 mL), washed with water, brine solution, dried over sodium sulfate and concentrated under vacuum to get crude product which was purified by column chromatography using ethylacetate-hexane gradient to afford the titled product as brown gummy solid (I-46, 0.140 g, 49%). LC-MS m/z calcd for $C_{29}H_{33}F_3N_2O_3$, 514.2; found 515.3 [M+H]$^+$.

I-47 ethyl 4-(3-(4-(((tert-butoxycarbonyl)(2-(4-fluorophenyl)cyclopropyl)amino)methyl) piperidin-1-yl)propyl)benzoate

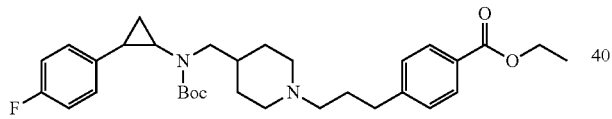

The compound was synthesized using 4-fluorophenylcyclopropyl amine and aldehyde A19 following the procedure for the synthesis of I-2. LC-MS m/z calcd for $C_{32}H_{43}FN_2O_4$, 538.3. found 539.3 [M+H]$^+$.

I-48 ethyl 4-(3-(3-(((tert-butoxycarbonyl)(2-(4-fluorophenyl)cyclopropyl)amino)methyl) azetidin-1-yl)propyl)benzoate

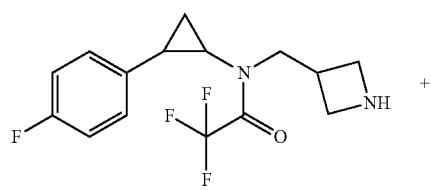

-continued

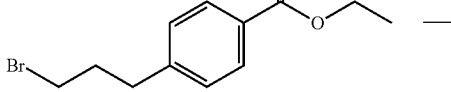

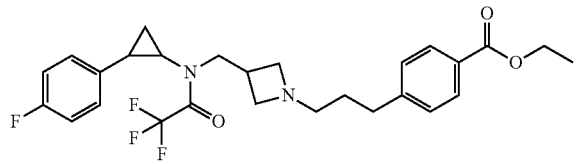

The intermediate I-48 was synthesized using B-4 and ethyl 4-(3-bromopropyl)benzoate following the procedure for the synthesis of I-46. LC-MS m/z calcd for $C_{30}H_{39}FN_2O_4$, 510.3. found 511.3 [M+H]$^+$.

I-49 ethyl 4-(3-(4-(((tert-butoxycarbonyl)(2-(3-fluorophenyl)cyclopropyl)amino)methyl) piperidin-1-yl)propyl)benzoate

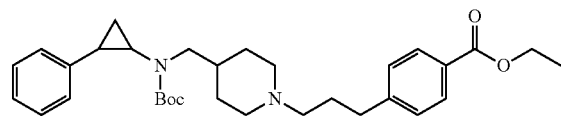

The compound was synthesized using 3-fluorophenylcyclopropyl amine and aldehyde A19 following the procedure for the synthesis of I-2. LC-MS m/z calcd for $C_{32}H_{43}FN_2O_4$, 538.3. found 539.3 [M+H]$^+$.

I-50 ethyl 4-(3-(4-(((tert-butoxycarbonyl)(2-(3,4-difluorophenyl)cyclopropyl)amino) methyl)piperidin-1-yl)propyl)benzoate

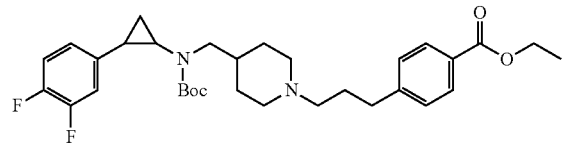 [SMILES: CCOC(=O)c1ccc(CCCN2CCC(CN(C(=O)OC(C)(C)C)C3CC3c3ccc(F)c(F)c3)CC2)cc1]

The compound was synthesized using 3,4-difluorophenylcyclopropyl amine and aldehyde A19 following the procedure for the synthesis of I-2. LC-MS m/z calcd for $C_{32}H_{42}F_2N_2O_4$, 556.3. found 557.3 [M+H]$^+$.

I-51 ethyl 4-(3-(4-(((tert-butoxycarbonyl)(2-(4-methoxyphenyl)cyclopropyl)amino)methyl) piperidin-1-yl)propyl)benzoate

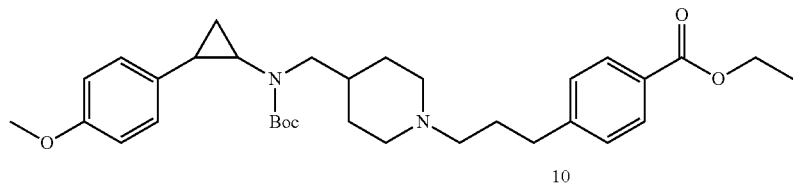

The compound was synthesized using 4-methoxyphenyl-cyclopropyl amine and aldehyde A19 following the procedure for the synthesis of I-2. LC-MS m/z calcd for $C_{33}H_{46}N_2O_5$, 550.3. found 551.3 $[M+H]^+$.

I-52 ethyl 4-(3-(4-(((tert-butoxycarbonyl)(2-(4-((4-fluorobenzyl)oxy)phenyl)cyclopropyl)amino)methyl)piperidin-1-yl)propyl)benzoate

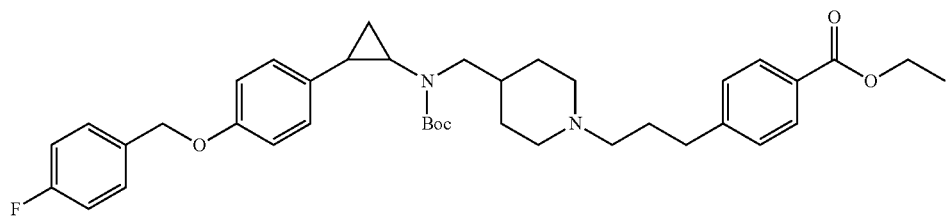 [SMILES: CCOC(=O)c1ccc(CCCN2CCC(CN(C(=O)OC(C)(C)C)C3CC3c3ccc(OCc4ccc(F)cc4)cc3)CC2)cc1]

The compound was synthesized using amine B6 and aldehyde A19 following the procedure for the synthesis of I-2. LC-MS m/z calcd for $C_{39}H_{49}FN_2O_5$, 644.3. found 645.4 $[M+H]^+$.

I-53: ethyl 4-(3-(4-(((tert-butoxycarbonyl)(2-(4-iodophenyl)cyclopropyl)amino)methyl)piperidin-1-yl)propyl)benzoate

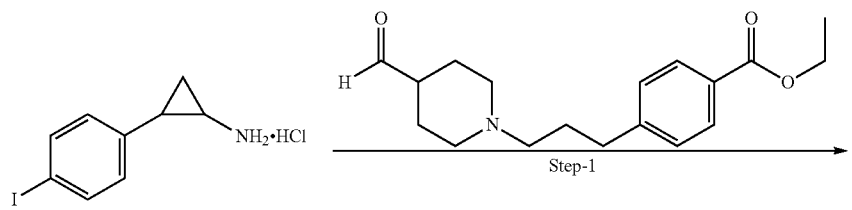

LXIII

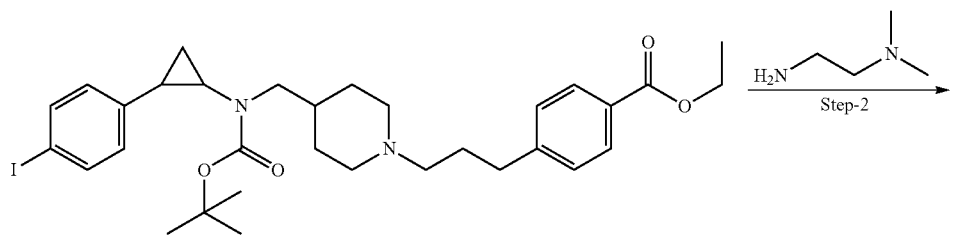

LXIV

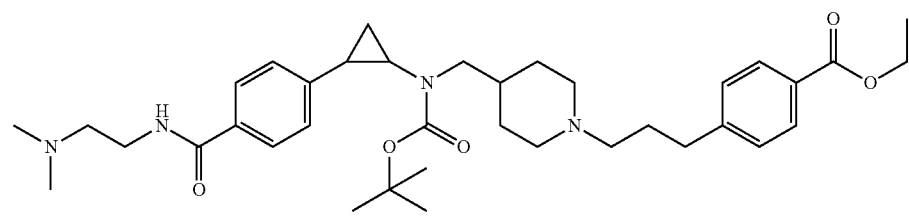

I-53

Step-1

To a stirred solution of 2-(4-iodophenyl)cyclopropan-1-amine hydrochloride (LXIII, 1.0 g, 3.30 mmol) in methanol (50 mL) was added ethyl 4-(3-(4-formylpiperidin-1-yl)propyl)benzoate (I-3, 1.13 g, 3.30 mmol) and sodium bicarbonate (0.25 g, 2.90 mmol) and molecular sieves (approx 2 g) at room temperature and the resulting mixture was heated to reflux for 2 h. Cooled to 0° C., then sodium borohydride (0.12 g, 3.30 mmol) was added and stirred at room temperature for 1 h. Ice was added and the reaction mixture was filtered. The solvent was evaporated to get the residue. Water was added and extracted with ethylacetate (2×200 mL). The organic portion was washed with water, brine, dried over sodium sulphate and concentrated under reduced pressure to afford the crude compound. To a stirred solution of crude compound in mixture of tetrahydrofuran and water (20 mL, 1:1) was added sodium bicarbonate (0.69 g, 8.25 mmol) and Boc anhydride (1.05 mL, 4.90 mmol) at room temperature and the resulting mixture was stirred at that temperature for 2 h. The progress of the reaction was monitored by TLC. The reaction mixture was diluted with ethylacetate and the organic portion was washed with water and brine solution, dried over sodium sulphate and concentrated under reduced pressure to get the crude product which was purified by column chromatography using ethylacetate-hexane gradient to afford the titled product as sticky oil (LXIV, 1 g, 54%), LC-MS m/z calcd for $C_{32}H_{43}IN_2O_4$, 646.2; found 647.1 $[M+H]^+$.

Step-2

To a stirred solution of ethyl 4-(3-(4-(((tert-butoxycarbonyl)(2-(4-iodophenyl)cyclopropyl)amino)methyl)piperidin-1-yl)propyl)benzoate (LXIV, 1 g, 1.5 mmol) in toluene (50 mL) was added N,N-dimethylethane-1,2-diamine (0.16 g, 1.80 mmol) and degassed with argon gas for 10 min. Then, palladium acetate (0.008 g, 0.037 mmol), Bis[(2-diphenylphosphino)phenyl] ether (0.080 g, 0.15), chloroform (0.36 mL, 4.5 mmol) and cesium hydroxide hydrate (2.51 g, 15.0 mmol) was added and heated at 100° C. for 24 h. The reaction mixture was cooled to room temperature. Then, the reaction mixture was filtered through celite, washed with toluene and concentrated under vacuum. The crude product was purified by column chromatography using methanol-dichloromethane gradient to afford the titled product as brown colour oil (I-53, 0.57 g, 58%), LC-MS m/z calcd for $C_{37}H_{54}N_4O_5$, 634.4; found 635.4 $[M+H]^+$.

I-54 ethyl 4-(3-(4-(((tert-butoxycarbonyl)(2-(4-(morpholine-4-carbonyl)phenyl) cyclopropyl)amino)methyl)piperidin-1-yl)propyl)benzoate

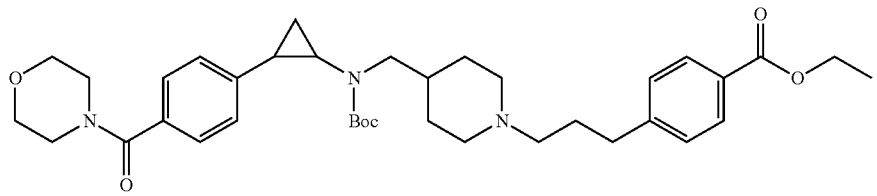 [SMILES: CCOC(=O)c1ccc(CCCN2CCC(CN(C(=O)OC(C)(C)C)C3CC3c3ccc(C(=O)N4CCOCC4)cc3)CC2)cc1]

The compound I-54 was synthesized following the procedure for the synthesis of I-53. LC-MS m/z calcd for $C_{37}H_{51}N_3O_6$, 633.4. found 634.4 $[M+H]^+$.

I-55 ethyl 4-(3-(4-(((tert-butoxycarbonyl)(2-(4-(piperidine-1-carbonyl)phenyl) cyclopropyl)amino)methyl)piperidin-1-yl)propyl)benzoate

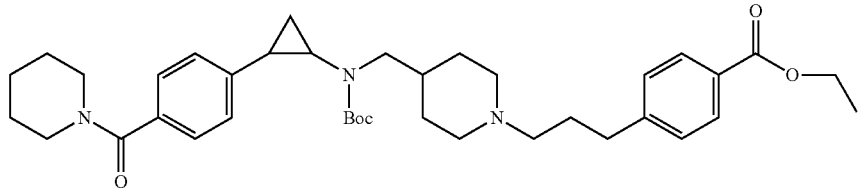 [SMILES: CCOC(=O)c1ccc(CCCN2CCC(CN(C(=O)OC(C)(C)C)C3CC3c3ccc(C(=O)N4CCCCC4)cc3)CC2)cc1]

The compound was synthesized following the procedure for the synthesis of I-53. LC-MS m/z calcd for $C_{38}H_{53}N_3O_5$, 631.4. found 632.4 $[M+H]^+$.

I-56 methyl 4-(3-(4-(((tert-butoxycarbonyl)(2-(4'-chloro-[1,1'-biphenyl]-4-yl)cyclopropyl)amino)methyl)piperidin-1-yl)propyl)benzoate

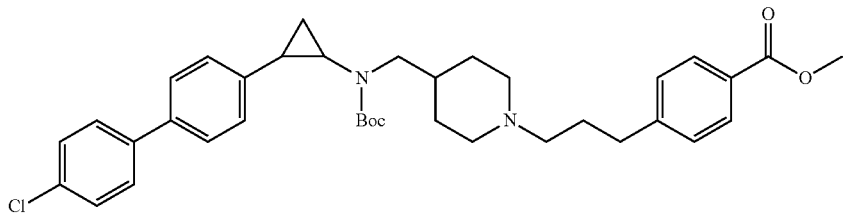 [SMILES: COC(=O)c1ccc(CCCN2CCC(CN(C(=O)OC(C)(C)C)C3CC3c3ccc(-c4ccc(Cl)cc4)cc3)CC2)cc1]

The compound was synthesized using amine B10 and aldehyde A19 following the procedure for the synthesis of I-2. LC-MS m/z calcd for $C_{37}H_{45}ClN_2O_4$, 616.3. found 617.3 [M+H]$^+$.

I-57 ethyl 4-(3-(4-(((tert-butoxycarbonyl)(2-(4'-fluoro-[1,1'-biphenyl]-4-yl)cyclopropyl)amino)methyl)piperidin-1-yl)propyl)benzoate

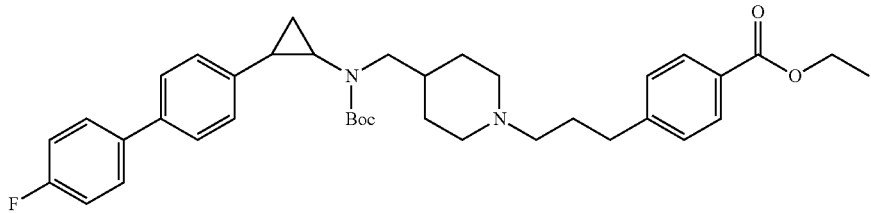 [SMILES: CCOC(=O)c1ccc(CCCN2CCC(CN(C(=O)OC(C)(C)C)C3CC3c3ccc(-c4ccc(F)cc4)cc3)CC2)cc1]

The compound was synthesized using amine B12 and aldehyde A19 following the procedure for the synthesis of I-2. LC-MS m/z calcd for $C_{38}H_{47}FN_2O_4$, 614.3. found 615.3 [M+H]$^+$.

I-58 methyl 4-(3-(3-(((tert-butoxycarbonyl)(2-(4'-fluoro-[1,1'-biphenyl]-4-yl)cyclopropyl)amino)methyl)azetidin-1-yl)propyl)benzoate

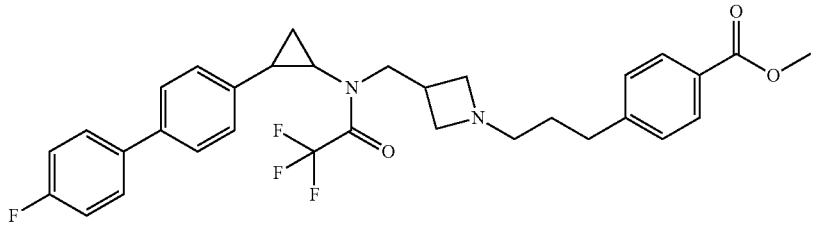 [SMILES: COC(=O)c1ccc(CCCN2CC(CN(C(=O)C(F)(F)F)C3CC3c3ccc(-c4ccc(F)cc4)cc3)C2)cc1]

The compound was synthesized using amine B22 and methyl 4-(3-bromopropyl)benzoate following the procedure for the synthesis of I-46. LC-MS m/z calcd for $C_{32}H_{32}F_4N_2O_3$, 568.2. found 569.2 [M+H]$^+$.

I-59 ethyl 4-(3-(4-(((tert-butoxycarbonyl)(2-(4'-cyano-[1,1'-biphenyl]-4-yl)cyclopropyl)amino)methyl)piperidin-1-yl)propyl)benzoate

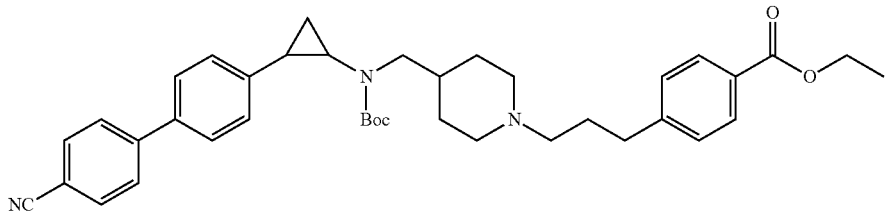 [SMILES: CCOC(=O)c1ccc(CCCN2CCC(CN(C(=O)OC(C)(C)C)C3CC3c3ccc(-c4ccc(C#N)cc4)cc3)CC2)cc1]

The compound was synthesized using amine B13 and aldehyde A19 following the procedure for the synthesis of I-2. LC-MS m/z calcd for $C_{39}H_{47}N_3O_4$, 621.3. found 622.3 [M+H]$^+$.

I-60 ethyl 4-(3-(4-(((tert-butoxycarbonyl)(2-(4-(1-methyl-2-oxo-1,2-dihydropyridin-4-yl)phenyl)cyclopropyl)amino)methyl)piperidin-1-yl)propyl)benzoate

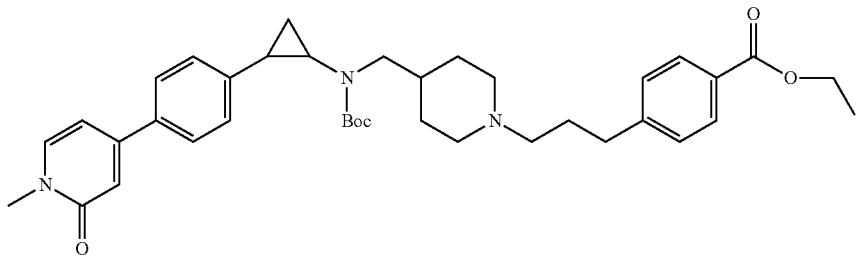 [SMILES: CCOC(=O)c1ccc(CCCN2CCC(CN(C(=O)OC(C)(C)C)C3CC3c3ccc(-c4ccn(C)c(=O)c4)cc3)CC2)cc1]

The compound was synthesized using amine B9 and aldehyde A19 following the procedure for the synthesis of I-2. LC-MS m/z calcd for $C_{38}H_{49}N_3O_5$, 627.3. found 628.3 [M+H]$^+$.

I-61 ethyl 4-(3-(4-(((tert-butoxycarbonyl)(2-(4-(pyrimidin-5-yl)phenyl)cyclopropyl)amino)methyl)piperidin-1-yl)propyl)benzoate

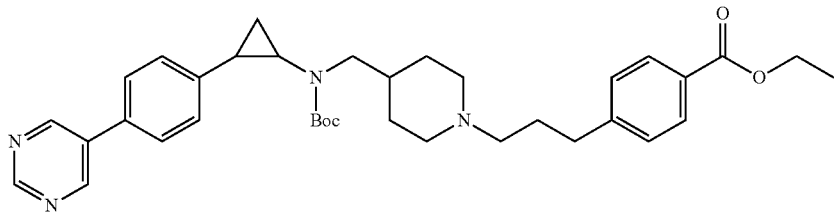 [SMILES: CCOC(=O)c1ccc(CCCN2CCC(CN(C(=O)OC(C)(C)C)C3CC3c3ccc(-c4cncnc4)cc3)CC2)cc1]

The compound was synthesized using amine B11 and aldehyde A19 following the procedure for the synthesis of I-2. LC-MS m/z calcd for $C_{36}H_{46}N_4O_4$, 598.3. found 599.3 [M+H]$^+$.

I-62 ethyl 4-(3-(4-(((tert-butoxycarbonyl)(2-(4-(1-methyl-1H-pyrazol-4-yl)phenyl) cyclopropyl)amino)methyl)piperidin-1-yl)propyl)benzoate

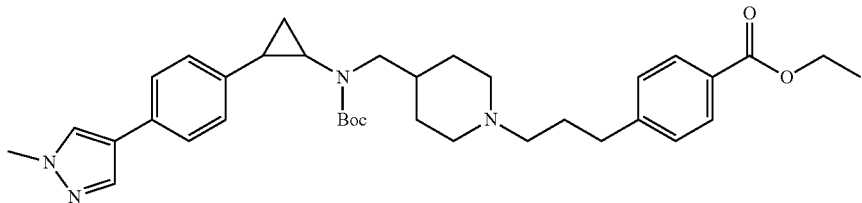 [SMILES: CCOC(=O)c1ccc(CCCN2CCC(CN(C(=O)OC(C)(C)C)C3CC3c3ccc(-c4cnn(C)c4)cc3)CC2)cc1]

The compound was synthesized using amine B7 and aldehyde A19 following the procedure for the synthesis of I-2. LC-MS m/z calcd for $C_{35}H_{46}N_4O_4$, 586.3. found 587.3 [M+H]$^+$.

I-63 ethyl 4-(3-(3-((2,2,2-trifluoro-N-(2-(4-(1-methyl-1H-pyrazol-4-yl)phenyl)cyclopropyl) acetamido)methyl)azetidin-1-yl)propyl)benzoate-Procedure

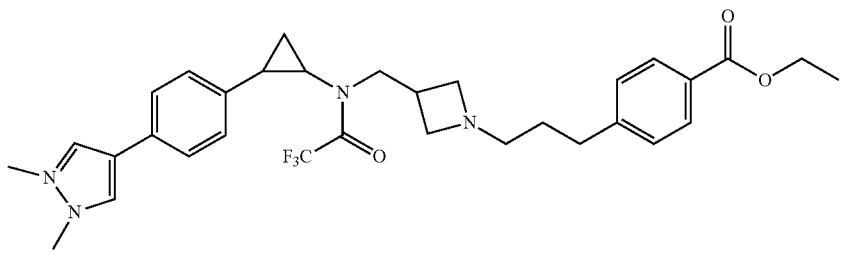

The compound was synthesized using amine B23 and ethyl 4-(3-bromopropyl)benzoate following the procedure for the synthesis of I-46. LC-MS m/z calcd for $C_{31}H_{35}F_3N_4O_3$, 568.2. found 569.2 [M+H]$^+$.

I-64 ethyl 4-(3-(4-(((tert-butoxycarbonyl)(2-(4-(3,5-dimethylisoxazol-4-yl)phenyl)cyclopropyl)amino)methyl)piperidin-1-yl)propyl)benzoate

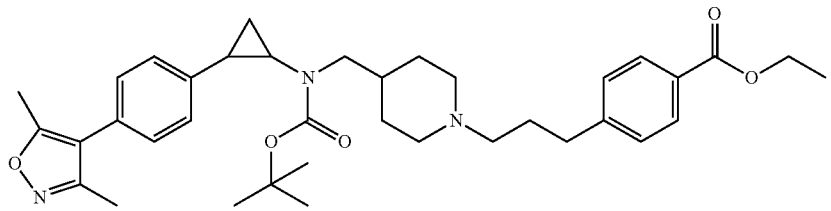 [SMILES: CCOC(=O)c1ccc(CCCN2CCC(CN(C(=O)OC(C)(C)C)C3CC3c3ccc(-c4c(C)noc4C)cc3)CC2)cc1]

The compound was synthesized using amine B8 and aldehyde A19 following the procedure for the synthesis of I-2. LC-MS m/z calcd for $C_{37}H_{49}N_3O_5$, 615.4. found 616.4 [M+H]$^+$.

I-65 ethyl 4-(3-(3-((N-(2-(4-(3,5-dimethylisoxazol-4-yl)phenyl)cyclopropyl)-2,2,2-trifluoroacetamido)methyl)azetidin-1-yl)propyl)benzoate

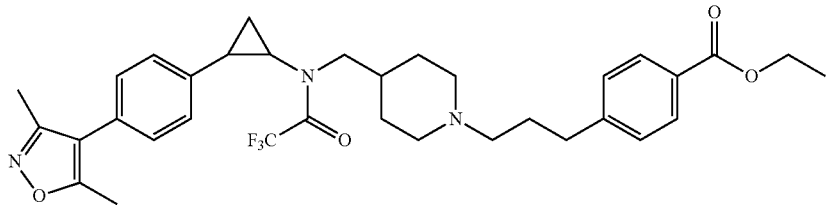 [SMILES: CCOC(=O)c1ccc(CCCN2CCC(CN(C(=O)C(F)(F)F)C3CC3c3ccc(-c4c(C)noc4C)cc3)CC2)cc1]

The compound was synthesized using amine B23 and ethyl 4-(3-bromopropyl)benzoate following the procedure for the synthesis of I-46. LC-MS m/z calcd for $C_{32}H_{36}F_3N_3O_4$, 583.2 found 584.3 $[M+H]^+$.

I-66 ethyl 4-(3-(4-(((tert-butoxycarbonyl)(2-(4-(6-(trifluoromethyl)pyridin-3-yl)phenyl) cyclopropyl)amino)methyl)piperidin-1-yl)propyl)benzoate

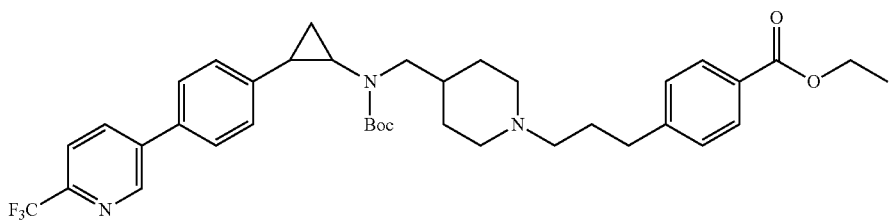 [SMILES: CCOC(=O)c1ccc(CCCN2CCC(CN(C(=O)OC(C)(C)C)C3CC3c3ccc(-c4ccc(C(F)(F)F)nc4)cc3)CC2)cc1]

The compound was synthesized using amine B14 and aldehyde A19 following the procedure for the synthesis of I-2. LC-MS m/z calcd for $C_{38}H_{46}F_3N_3O_4$, 665.3; found 666.3 $[M+H]^+$.

I-67 ethyl 4-(3-(4-(((tert-butoxycarbonyl)(2-(1-isopropyl-1H-pyrazol-4-yl)cyclopropyl)amino)methyl)piperidin-1-yl)propyl)benzoate

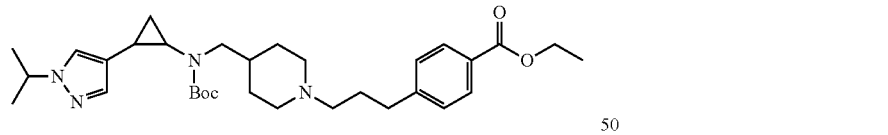

The compound was synthesized using amine B15 and aldehyde A19 following the procedure for the synthesis of I-2. LC-MS m/z calcd for $C_{32}H_{48}N_4O_4$, 552.4; found 553.4 $[M+H]^+$.

I-68 ethyl 4-(3-(4-(((tert-butoxycarbonyl)(2-(1-phenyl-1H-pyrazol-4-yl)cyclopropyl)amino)methyl)piperidin-1-yl)propyl)benzoate

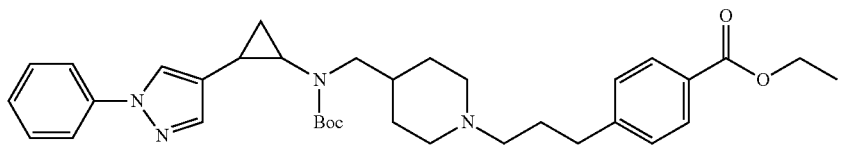 [SMILES: CCOC(=O)c1ccc(CCCN2CCC(CN(C(=O)OC(C)(C)C)C3CC3c3cnn(-c4ccccc4)c3)CC2)cc1]

The compound was synthesized using amine B16 and aldehyde A19 following the procedure for the synthesis of I-2. LC-MS m/z calcd for $C_{35}H_{46}N_4O_4$, 586.4; found 586.4 $[M+H]^+$.

I-69 ethyl 4-(3-(4-(((tert-butoxycarbonyl)(2-(2-methylthiazol-5-yl)cyclopropyl)amino)methyl) piperidin-1-yl)propyl)benzoate

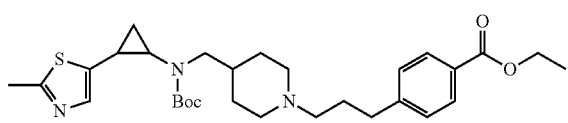 [SMILES: CCOC(=O)c1ccc(CCCN2CCC(CN(C(=O)OC(C)(C)C)C3CC3c3cnc(C)s3)CC2)cc1]

The compound was synthesized using amine B17 and aldehyde A19 following the procedure for the synthesis of I-2. LC-MS m/z calcd for $C_{30}H_{43}N_3O_4S$, 541.3; found 542.3 $[M+H]^+$.

I-70 ethyl 4-(3-(4-(((tert-butoxycarbonyl)(2-(pyridin-3-yl)cyclopropyl)amino)methyl)piperidin-1-yl) propyl)benzoate

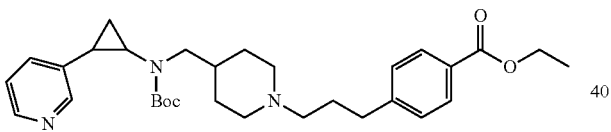

The compound was synthesized using amine B18 and aldehyde A19 following the procedure for the synthesis of I-2. LC-MS m/z calcd for $C_{31}H_{43}N_3O_4$, 521.3; found 522.3 $[M+H]^+$.

I-71 ethyl 4-(3-(2-(((tert-butoxycarbonyl)(2-(4-methoxyphenyl)cyclopropyl)amino)methyl)-5,6-dihydroimidazo[1,2-a]pyrazin-7(8H)-yl)propyl)benzoate

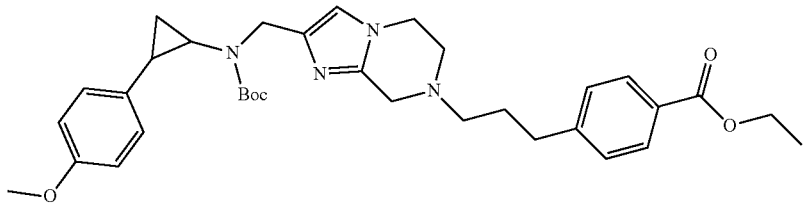 [SMILES: CCOC(=O)c1ccc(CCCN2CCn3cc(CN(C(=O)OC(C)(C)C)C4CC4c4ccc(OC)cc4)nc3C2)cc1]

The compound was synthesized using 4-methoxyphenylcyclopropylamine and aldehyde A18 following the procedure for the synthesis of I-2. LC-MS m/z calcd for $C_{34}H_{44}N_4O_5$, 588.3; found 589.3 $[M+H]^+$.

I-72 ethyl 4-(3-(2-(((tert-butoxycarbonyl)(2-(4-fluorophenyl)cyclopropyl)amino)methyl)-5,6-dihydroimidazo[1,2-a]pyrazin-7(8H)-yl)propyl)benzoate

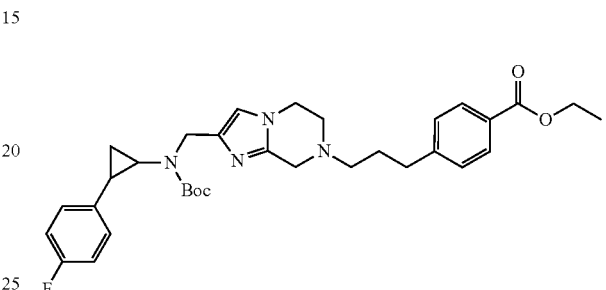

The compound was synthesized using 4-fluorophenylcyclopropylamine and aldehyde A18 following the procedure for the synthesis of I-2. LC-MS m/z calcd for $C_{33}H_{41}FN_4O_4$, 576.3; found 577.3 $[M+H]^+$.

I-73 ethyl 4-(3-(4-(((tert-butoxycarbonyl)(2-(3,4-difluorophenyl)cyclopropyl)amino)methyl)-1H-imidazol-1-yl)propyl)benzoate

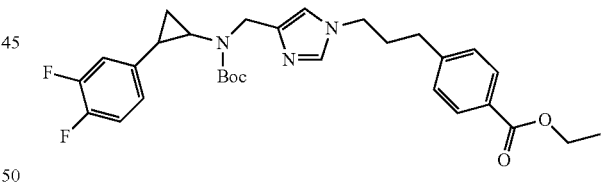

The compound was synthesized using 3,4-difluorophenylcyclopropylamine and aldehyde A8 following the procedure for the synthesis of I-2. LC-MS m/z calcd for $C_{30}H_{35}F_2N_3O_4$, 539.3; found 540.3 $[M+H]^+$.

I-74 ethyl 4-(3-(5-(((tert-butoxycarbonyl)(2-phenyl-cyclopropyl)amino)methyl)-1H-imidazol-1-yl) propyl)benzoate

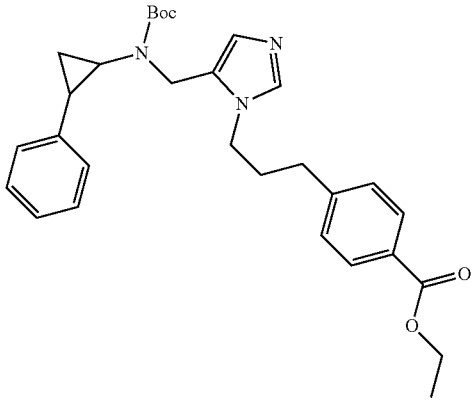 [SMILES: CCOC(=O)c1ccc(CCCn2cncc2CN(C(=O)OC(C)(C)C)C2CC2c2ccccc2)cc1]

The compound was synthesized using phenylcyclopropylamine and aldehyde A9 following the procedure for the synthesis of I-2. LC-MS m/z calcd for $C_{30}H_{37}N_3O_4$, 503.3; found 504.3 $[M+H]^+$.

I-75 ethyl 4-(3-(4-(((tert-butoxycarbonyl)(2-phenyl-cyclopropyl)amino)methyl)-1H-imidazol-1-yl)propyl)benzoate

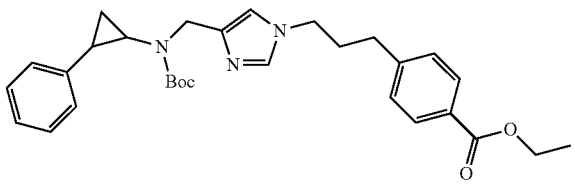 [SMILES: CCOC(=O)c1ccc(CCCn2cnc(CN(C(=O)OC(C)(C)C)C3CC3c3ccccc3)c2)cc1]

The compound was synthesized using phenylcyclopropylamine and aldehyde A8 following the procedure for the synthesis of I-2. LC-MS m/z calcd for $C_{30}H_{37}N_3O_4$, 503.4; found 504.3 $[M+H]^+$.

I-76 ethyl 4-(3-(4-(((2-phenylcyclopropyl)amino)methyl)-1H-pyrazol-1-yl)propyl)benzoate

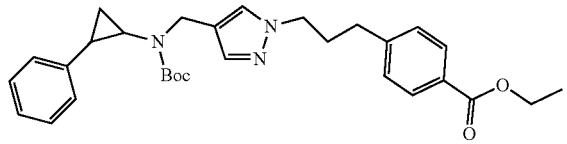 [SMILES: CCOC(=O)c1ccc(CCCn2cc(CN(C(=O)OC(C)(C)C)C3CC3c3ccccc3)cn2)cc1]

The compound was synthesized using phenylcyclopropylamine and aldehyde A11 following the procedure for the synthesis of I-2. LC-MS m/z calcd for $C_{30}H_{37}N_3O_4$, 503.4 found 504.3 $[M+H]^+$.

I-77 ethyl 4-(3-(4-(((tert-butoxycarbonyl)(2-phenyl-cyclopropyl)amino)methyl)-1H-1,2,3-triazol-1-yl) propyl)benzoate

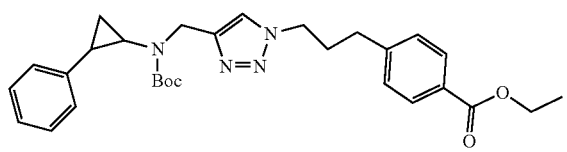 [SMILES: CCOC(=O)c1ccc(CCCn2cc(CN(C(=O)OC(C)(C)C)C3CC3c3ccccc3)nn2)cc1]

The compound was synthesized using phenylcyclopropylamine and aldehyde A28 following the procedure for the synthesis of I-2. LC-MS m/z calcd for $C_{29}H_{36}N_4O_4$, 504.2; found 505.3 $[M+H]^+$.

I-78 ethyl 4-(3-(6-(((tert-butoxycarbonyl)(2-(4-fluorophenyl)cyclopropyl)amino)methyl)-3,4-dihydroisoquinolin-2(1H)-yl)propyl)benzoate

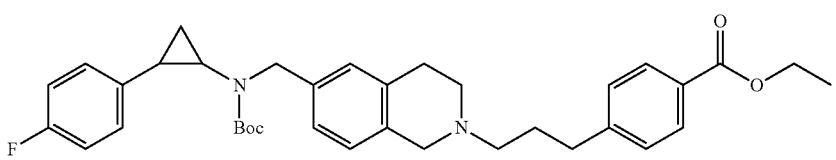 [SMILES: CCOC(=O)c1ccc(CCCN2CCc3cc(CN(C(=O)OC(C)(C)C)C4CC4c4ccc(F)cc4)ccc3C2)cc1]

The compound was synthesized using 4-fluorophenylcyclopropylamine and aldehyde A20 following the procedure for the synthesis of I-2. LC-MS m/z calcd for $C_{36}H_{43}FN_2O_4$, 586.3; found 587.3 $[M+H]^+$.

I-79 methyl 4-((7-(((tert-butoxycarbonyl)(2-(4-fluorophenyl)cyclopropyl)amino)methyl)-3,4-dihydroisoquinolin-2(1H)-yl)methyl)benzoate

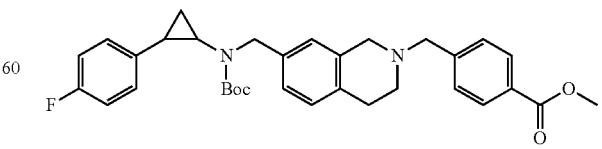

The compound was synthesized using phenylcyclopropylamine and aldehyde A22 following the procedure for the synthesis of I-2. LC-MS m/z calcd for $C_{33}H_{37}FN_2O_4$, 544.2; found 545.3 $[M+H]^+$.

I-80 methyl 4-((2-(((tert-butoxycarbonyl)(2-(4-fluorophenyl)cyclopropyl)amino)methyl)-5,6-dihydroimidazo[1,2-a]pyrazin-7(8H)-yl)methyl)benzoate

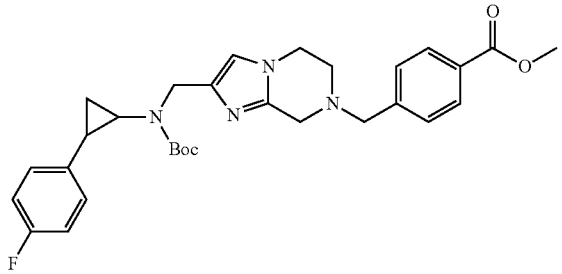 [SMILES: COC(=O)c1ccc(CN2CCn3cc(CN(C(=O)OC(C)(C)C)C4CC4c4ccc(F)cc4)nc3C2)cc1]

The compound was synthesized using 4-fluorophenylcyclopropylamine and aldehyde A14 following the procedure for the synthesis of I-2. LC-MS m/z calcd for $C_{30}H_{35}FN_4O_4$, 534.2; found 535.3 $[M+H]^+$.

I-81 ethyl 4-(3-(4-(((tert-butoxycarbonyl)(2-(1,3,3-trimethyl-2-oxoindolin-5-yl)cyclopropyl)amino)methyl)piperidin-1-yl)propyl)benzoate

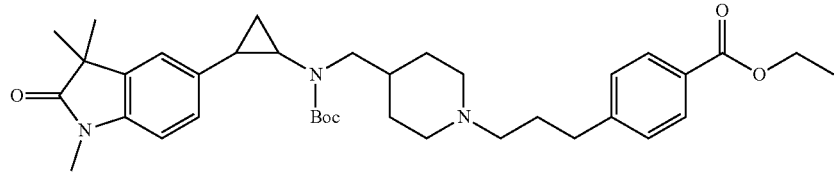 [SMILES: CCOC(=O)c1ccc(CCCN2CCC(CN(C(=O)OC(C)(C)C)C3CC3c3ccc4c(c3)C(C)(C)C(=O)N4C)CC2)cc1]

The compound was synthesized using amine B20 and aldehyde A19 following the procedure for the synthesis of I-2. LC-MS m/z calcd for $C_{37}H_{51}N_3O_5$, 617.4; found 618.4 $[M+H]^+$.

I-82 methyl 4-(3-(4-(((tert-butoxycarbonyl)(2-phenylcyclopropyl)amino)methyl)piperidin-1-yl)-3-oxopropyl)benzoate

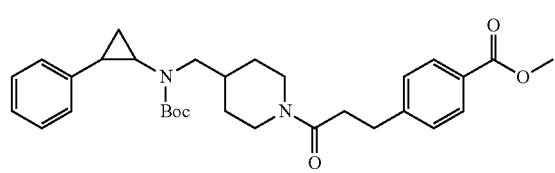 [SMILES: COC(=O)c1ccc(CCC(=O)N2CCC(CN(C(=O)OC(C)(C)C)C3CC3c3ccccc3)CC2)cc1]

The compound was synthesized using phenylcyclopropylamine and aldehyde A29 following the procedure for the synthesis of I-2. LC-MS m/z calcd for $C_{31}H_{40}N_2O_5$, 520.3; found 465.2 $[M-55]^+$.

I-83 methyl 4-(3-(4-(((tert-butoxycarbonyl)(2-phenylcyclopropyl)amino)piperidin-1-yl)-3-oxopropyl)benzoate

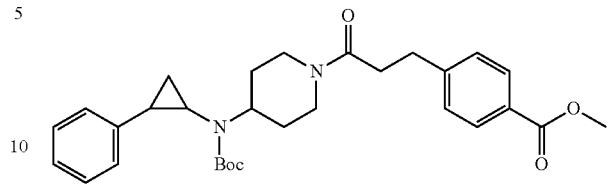

The compound was synthesized using phenylcyclopropylamine and ketone A23 following the procedure for the synthesis of I-2. LC-MS m/z calcd for $C_{30}H_{38}N_2O_5$, 506.3; found 451.2 $[M-55]^+$.

I-84 methyl 4-(2-(4-(((tert-butoxycarbonyl)(2-phenylcyclopropyl)amino)methyl)piperidin-1-yl)-2-oxoethyl)benzoate

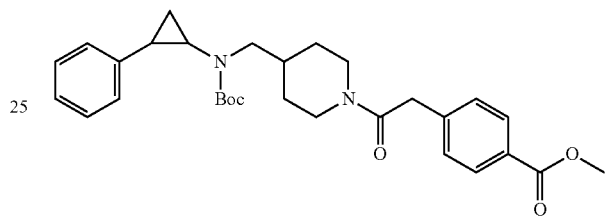

The compound was synthesized using phenylcyclopropylamine and aldehyde A24 following the procedure for the synthesis of I-2. LC-MS m/z calcd for $C_{30}H_{38}N_2O_5$, 506.3; found 451.2 $[M-55]^+$.

I-85 methyl 4-((4-(((tert-butoxycarbonyl)(2-phenylcyclopropyl)amino)methyl)piperidin-1-yl)sulfonyl)benzoate-

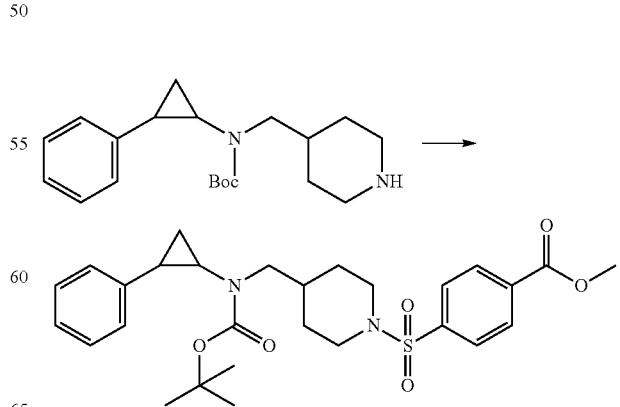

I-85

I-85 4-((4-((2,2,2-trifluoro-N-(2-phenylcyclopropyl)acetamido)methyl)piperidin-1-yl) sulfonyl)benzoic Acid To a stirred solution of tert-butyl (2-phenylcyclopropyl)(piperidin-4-ylmethyl)carbamate (1 g, 3.03 mmol) in dichloromethane (20 mL) was added triethylamine (0.63 mL, 4.5 mmol) and methyl 4-(chlorosulfonyl)benzoate (0.78 g, 3.33 mmol) at 0° C. and stirred at room temperature for 2 h. The reaction mixture was diluted with dichloromethane and washed with 10% aqueous NaHCO$_3$ solution, water, brine solution, dried over sodium sulphate and concentrated under reduced pressure to afford the titled product as off-white solid (I-85, 1.5 g, 92%). LC-MS m/z calcd for C$_{28}$H$_{36}$N$_2$O$_6$S, 528.2; found 429.1 [M-Boc+H]$^+$.

I-86 ethyl 4-((N-(2-(4-((2,2,2-trifluoro-N-(2-phenylcyclopropyl)acetamido)methyl)piperidin-1-yl)ethyl)sulfamoyl)methyl)benzoate-

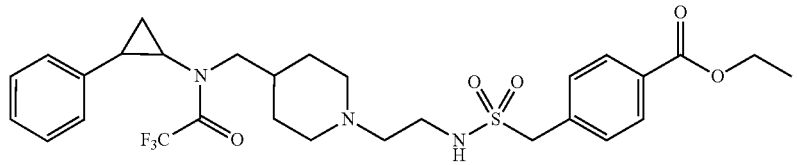 [SMILES: CCOC(=O)c1ccc(CS(=O)(=O)NCCN2CCC(CN(C(=O)C(F)(F)F)C3CC3c3ccccc3)CC2)cc1]

The compound was synthesized using amine B-26 and ethyl 4-((chlorosulfonyl)methyl)benzoate following the procedure for the synthesize of I-85. LC-MS m/z calcd for C$_{28}$H$_{34}$F$_3$N$_3$O$_5$S, 595.2; found 596.3 [M+H]$^+$.

I-87 methyl 4-(N-(2-(4-((2,2,2-trifluoro-N-(2-(4-fluorophenyl)cyclopropyl)acetamido) methyl)piperidin-1-yl)ethyl)sulfamoyl)benzoate

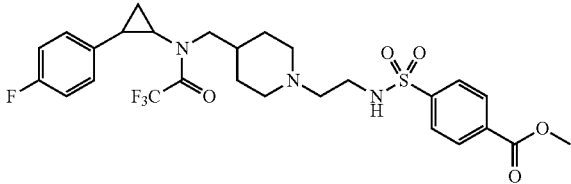 [SMILES: COC(=O)c1ccc(S(=O)(=O)NCCN2CCC(CN(C(=O)C(F)(F)F)C3CC3c3ccc(F)cc3)CC2)cc1]

The compound was synthesized using amine B-25 and methyl 4-(chlorosulfonyl)benzoate following the procedure for the synthesize of I-85. LC-MS m/z calcd for C$_{27}$H$_{31}$F$_4$N$_3$O$_5$S, 585.2; found 586.2 [M+H]$^+$.

I-88 methyl 4-(2-((4-((2,2,2-trifluoro-N-(2-phenylcyclopropyl)acetamido)methyl)piperidin-1-yl) sulfonyl)ethyl)benzoate

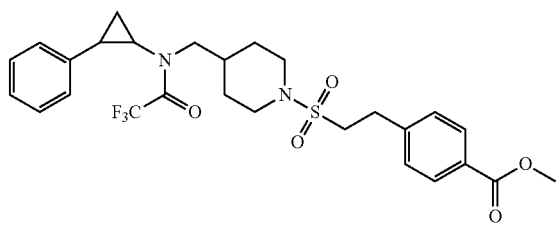 [SMILES: COC(=O)c1ccc(CCS(=O)(=O)N2CCC(CN(C(=O)C(F)(F)F)C3CC3c3ccccc3)CC2)cc1]

The compound was synthesized using 2,2,2-trifluoro-N-(2-phenylcyclopropyl)-N-(piperidin-4-ylmethyl)acetamide hydrochloride and methyl 4-(2-(chlorosulfonyl)ethyl)benzoate following the procedure for the synthesize of I-85. LC-MS m/z calcd for C$_{27}$H$_{31}$F$_3$N$_2$O$_5$S, 552.2; found 553.2 [M+H]$^+$.

I-89 methyl 4-((2-(4-((2,2,2-trifluoro-N-(2-phenylcyclopropyl)acetamido)methyl)piperidin-1-yl)ethyl)carbamoyl)benzoate

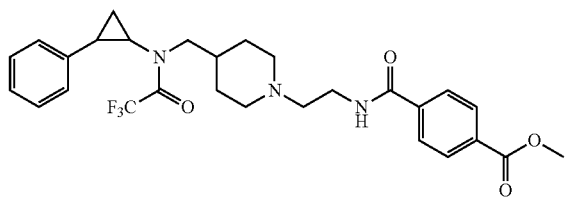 [SMILES: COC(=O)c1ccc(C(=O)NCCN2CCC(CN(C(=O)C(F)(F)F)C3CC3c3ccccc3)CC2)cc1]

The compound was synthesized using amine B-26 and methyl 4-(chlorocarbonyl)benzoate following the procedure for the synthesize of I-85. LC-MS m/z calcd for C$_{28}$H$_{32}$F$_3$N$_3$O$_4$, 531.2; found 532.2 [M+H]$^+$.

I-90 methyl 4-((2-(4-((N-(2-(3,4-difluorophenyl)cyclopropyl)-2,2,2-trifluoroacetamido) methyl)piperidin-1-yl)ethyl)carbamoyl)benzoate

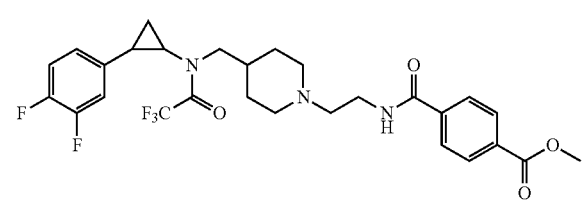 [SMILES: COC(=O)c1ccc(C(=O)NCCN2CCC(CN(C(=O)C(F)(F)F)C3CC3c3ccc(F)c(F)c3)CC2)cc1]

The compound was synthesized using amine B-27 and methyl 4-(chlorocarbonyl)benzoate following the procedure for the synthesize of I-85. LC-MS m/z calcd for C$_{28}$H$_{30}$F$_5$N$_3$O$_4$, 567.2; found 568.2 [M+H]$^+$.

I-91 methyl 4-((4-(N-(tert-butoxycarbonyl)-N-(2-phenylcyclopropyl)glycyl)piperazin-1-yl) methyl)benzoate

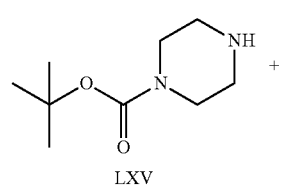

LXV

179

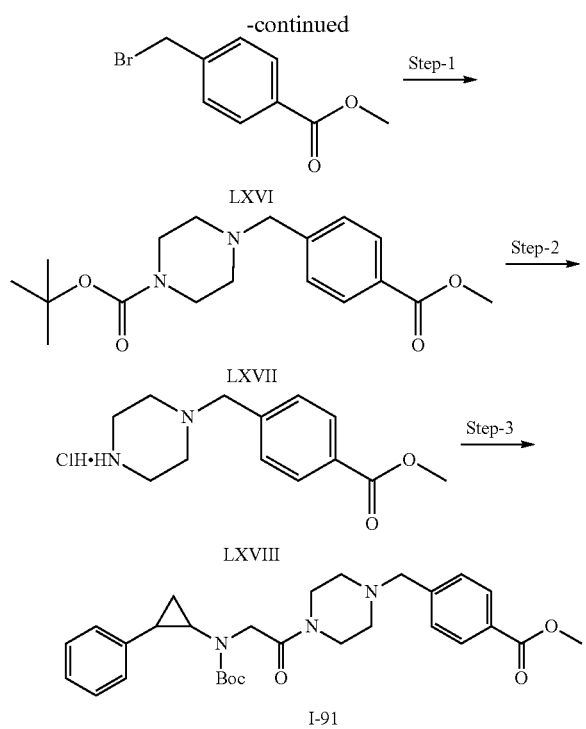

Step-1: tert-butyl 4-(4-(methoxycarbonyl)benzyl)piperazine-1-carboxylate-LXVII

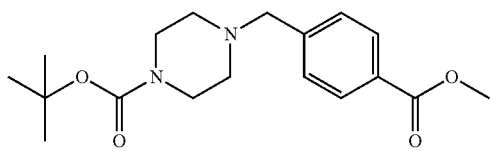 [SMILES: COC(=O)c1ccc(CN2CCN(C(=O)OC(C)(C)C)CC2)cc1]

To a solution of tert-butyl piperazine-1-carboxylate (LXV, 2 g, 10.8 mmol) in acetonitrile (100 mL) was added potassium carbonate (1.7 g, 12.9 mmol) and methyl 4-(bromomethyl)benzoate (LXVI, 2.4 g, 10.8 mmol) and stirred for 24 h at room temperature. After completion of reaction, the reaction was concentrated under vacuum and then diluted with ethylacetate (50 mL). The organic layer was washed with water, brine, dried over sodium sulfate and concentrated under vacuum to get crude product which was purified by flash column chromatography using ethylacetate-hexane gradient to afford the titled product as colourless liquid (LXVII, 2.7 g, 75%). LC-MS m/z calcd for $C_{18}H_{26}N_2O_4$, 334.2; found 335.2 [M+H]$^+$.

Step-2: methyl 4-(piperazin-1-ylmethyl)benzoate hydrochloride-LXVIII

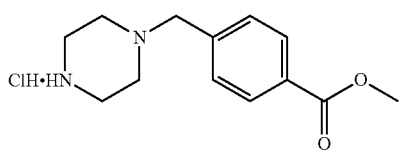

180

To a stirred solution of tert-butyl 4-(4-(methoxycarbonyl)benzyl)piperazine-1-carboxylate (LXVII, 2.7 g, 8.08 mmol) in 1,4-dioxane (50 mL) was added 20% HCl in 1,4-dioxane (50 mL) and was stirred for 16 h. The reaction mixture was concentrated under vacuum. The resultant solid was triturated with diethyl ether. The solid was filtered out and dried under vacuum to get the titled product as white solid (LXVIII, 1.8 g, 75%). LC-MS m/z calcd for $C_{13}H_{18}N_2O_2$, 234.2; found 235.2 [M+H]$^+$.

Step-3: methyl 4-((4-((2-phenylcyclopropyl)glycyl)piperazin-1-yl)methyl)benzoate-I-91

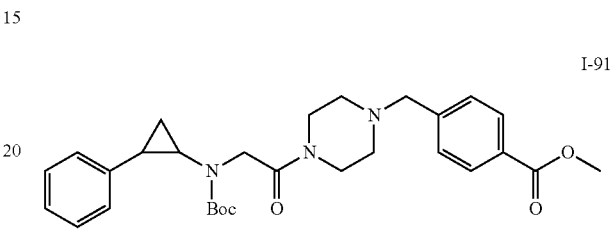

To a stirred solution of N-(tert-butoxycarbonyl)-N-(2-phenylcyclopropyl)glycine (LXVIII, 0.10 g, 0.34 mmol) in dry dichloromethane (10 mL) was added methyl 4-(piperazin-1-ylmethyl)benzoate hydrochloride (0.11 g, 0.37 mmol), then triethylamine (0.24 mL, 1.71 mmol) and cooled to 0° C. T3P (0.6 mL, 0.86 mmol) was added and stirred at room temperature for 16 h. After completion of the reaction, the mixture was quenched with ice-water and extracted with dichloromethane (10 mL×3). The organic layer was washed with water, brine, dried over sodium sulphate and concentrated under reduced pressure to afford the crude product which was purified by column chromatography using methanol-dichloromethane to afford the titled product as gummy solid (I-91, 0.1 g, 57%). LC-MS m/z calcd for $C_{29}H_{37}N_3O_5$, 507.3; found 508.3 [M+H]$^+$.

I-92 methyl 4-((4-(2-((tert-butoxycarbonyl)(2-phenylcyclopropyl)amino)acetyl)piperazin-1-yl)methyl)benzoate

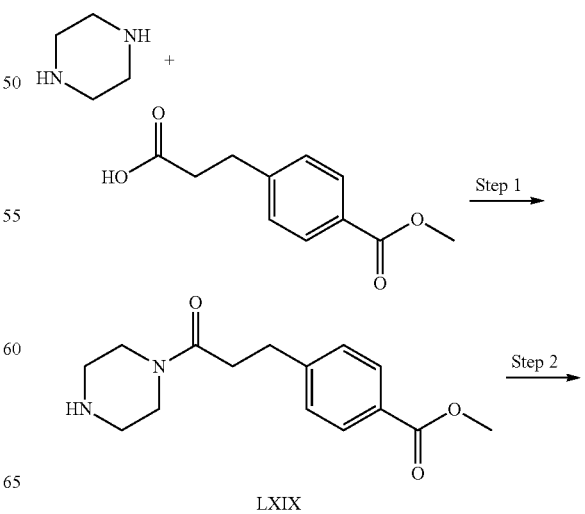

-continued

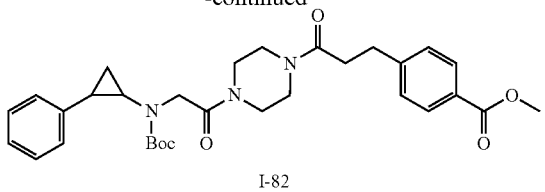

I-82

Step 1: Methyl 4-(3-oxo-3-(piperazin-1-yl)propyl)benzoate-LXIX

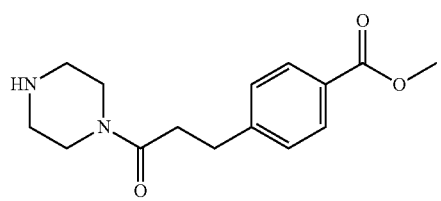 [SMILES: COC(=O)c1ccc(CCC(=O)N2CCNCC2)cc1]

To a stirred solution of 3-(4-(methoxycarbonyl)phenyl)propanoic acid (0.29 g, 1.41 mmol) and piperazine (0.36 g, 4.25 mmol), in dichloromethane (15 mL) was added triethylamine (0.60 g, 4.25 mmol), the reaction was stirred at room temperature for 10 min, then cooled to 0° C. and added propylphosphonic anhydride (1.04 mL, 3.54 mmol), and the resulting mixture was stirred at room temperature for 3 h. The reaction was monitored by TLC, after completion of reaction, the mixture was quenched with ice. The reaction mixture was diluted with water and extracted with dichloromethane (3×25 mL). The organic portion was washed with water and brine, dried over sodium sulphate and concentrated under reduced pressure to get the crude light pale yellow oil (LXIX, 0.37 g, 93%). LC-MS m/z calcd for $C_{15}H_{20}N_2O_3$, 276.2; found 278.3 [M+H]$^+$.

Step 2: methyl 4-(3-(4-(N-(tert-butoxycarbonyl)-N-(2-phenylcyclopropyl)glycyl)piperazin-1-yl)-3-oxopropyl)benzoate-I-92

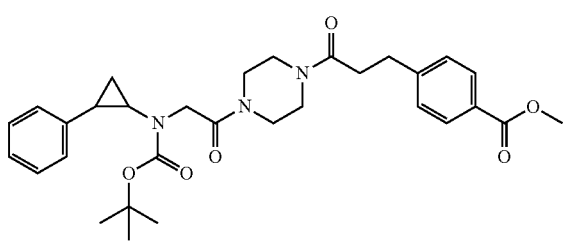 [SMILES: COC(=O)c1ccc(CCC(=O)N2CCN(C(=O)CN(C(=O)OC(C)(C)C)C3CC3c3ccccc3)CC2)cc1]

To a solution of N-(tert-butoxycarbonyl)-N-(2-phenylcyclopropyl)glycine (LXIX, 0.2 g, 0.69 mmol) in dichloromethane (15 mL) was added methyl 4-(3-oxo-3-(piperazin-1-yl)propyl)benzoate (0.23 g, 0.82 mmol), triethyl amine (0.29 mL, 2.05 mmol) to 0° C. and then $T_3P$ was added (0.50 mL, 1.72 mmol). The resulting mixture was stirred at room temperature for 3 h. After completion of reaction, the mixture was diluted with dichloromethane (20 mL). The combined organic layer was washed with water, brine solution, dried over sodium sulphate and concentrated under reduced pressure to afford the title product as stick oil (0.37 g, quantitative yield). LC-MS m/z calcd for $C_{31}H_{39}N_3O_6$, 549.3; found 550.3 [M+H]$^+$.

I-93 methyl 4-(3-(1-(2-((tert-butoxycarbonyl)(2-phenylcyclopropyl)amino)acetyl)piperidin-4-yl)propyl)benzoate

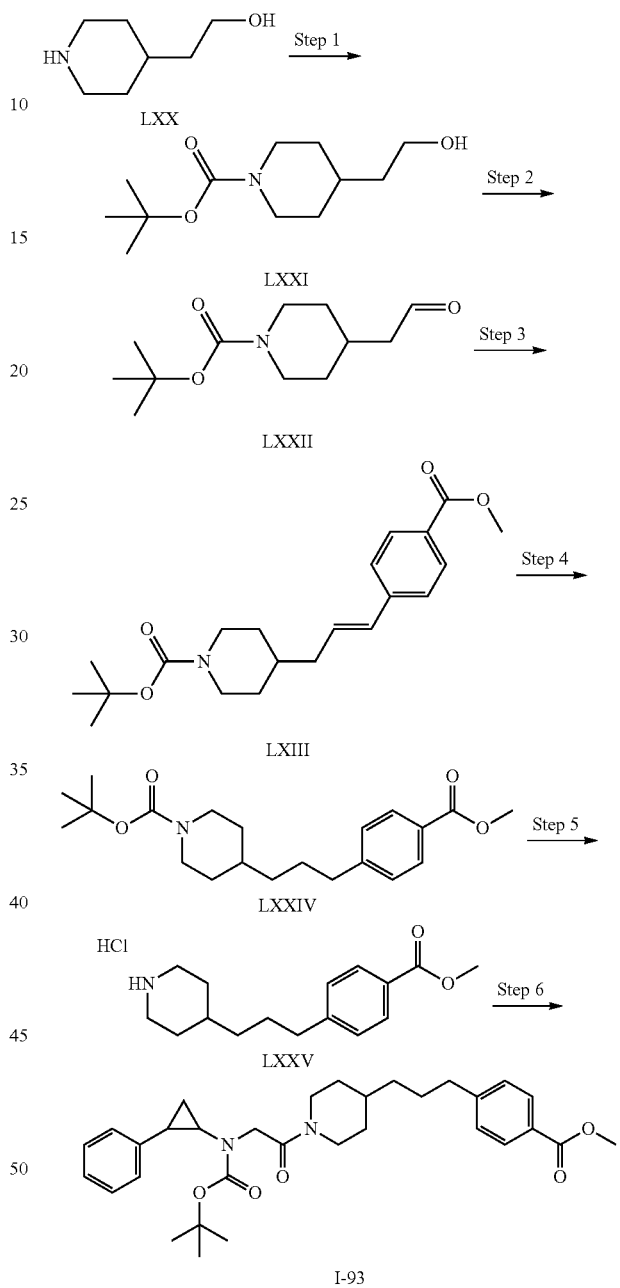

Step 1: tert-butyl 4-(2-hydroxyethyl)piperidine-1-carboxylate (LXXI)

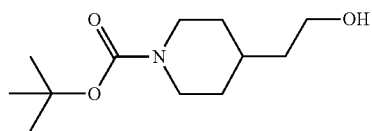

To a stirred solution of 2-(piperidin-4-yl)ethanol (LXX, 1 g, 7.72 mmol) in tetrahydrofuran and water mixture (40 mL, 1:1) was added sodium bicarbonate (1.62 g, 19.32 mmol) and Boc anhydride (2.6 mL, 11.6 mmol) at room temperature and stirred for 3 h. The reaction mixture was diluted with ethyl acetate and the organic portion was washed with water and brine, dried over sodium sulphate and concentrated under reduced pressure to get the crude product which was purified by flash column chromatography using ethylacetate-hexane gradient to afford the titled product as gummy solid (LXXI, 1.6 g, 88%). LC-MS m/z calcd for $C_{12}H_{23}NO_3$, 229.2; found 130.2 [M-Boc]$^+$.

Step 2: tert-butyl
4-(2-oxoethyl)piperidine-1-carboxylate (LXXII)

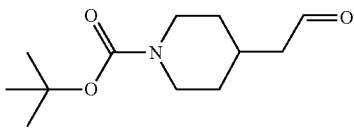

To a stirred solution of tert-butyl 4-(2-hydroxyethyl) piperidine-1-carboxylate (LXXI, 1.5 g, 6.55 mmol) in dry dichloromethane (40 mL) was added Dess-Martin periodinane (3.3 g, 7.86 mmol) at 0° C. and the resulting mixture was stirred at room temperature for 5 h. The reaction mixture was quenched with 10% sodium thiosulphate solution (20 mL) and saturated sodium bicarbonate solution (20 mL) and then extracted with dichloromethane (2×50 mL). The organic portion was washed with saturated sodium bicarbonate solution, water, brine, dried over sodium sulphate and concentrated under reduced pressure to afford the product as yellow semi-solid (LXXII, 0.9 g, 60%).

Step 3: (E)-tert-butyl 4-(3-(4-(methoxycarbonyl) phenyl)allyl)piperidine-1-carboxylate (LXXIII)

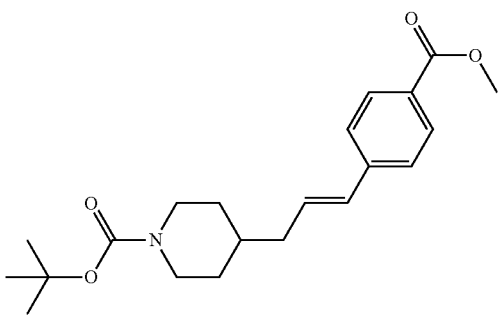 [SMILES: COC(=O)c1ccc(/C=C/CC2CCN(C(=O)OC(C)(C)C)CC2)cc1]

To a stirred solution of methyl 4-((diethoxyphosphoryl) methyl)benzoate (0.9 g, 3.96 mmol) in dry THF (40 mL) was added 60% sodium hydride at 0° C. and stirred for 1 h. Solution of tert-butyl 4-(2-oxoethyl)piperidine-1-carboxylate (LXXII, 1.1 g, 3.96 mmol) in dry THF was added and stirred further 2 h at room temperature. The reaction mixture was quenched with saturated ammonium chloride and then extracted with ethyl acetate (100 mL). The organic portion was washed with water, brine, dried over sodium sulphate and concentrated under reduced pressure to get the crude product which was purified by column chromatography using ethylacetate-hexane gradient to afford the titled product as colourless liquid (LXXIII, 0.7 g, 50%). LC-MS m/z calcd for $C_{21}H_{29}NO_4$, 359.2; found 260.2 [M-Boc+H]$^+$.

Step 4: Tert-butyl 4-(3-(4-(methoxycarbonyl)phenyl)propyl)piperidine-1-carboxylate (LXXIV)

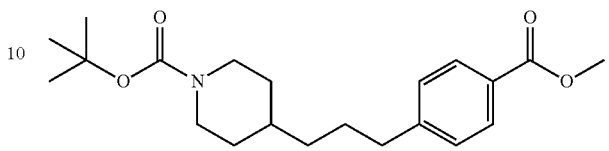

To a stirred solution of (E)-tert-butyl 4-(3-(4-(methoxycarbonyl)phenyl)allyl)piperidine-1-carboxylate (LXXIII, 0.71 g, 1.97 mmol) in methanol (20 mL) was added 10% Pd—C and stirred for 0.5 h in hydrogen balloon at room temperature. The reaction mixture was filtered out through celite and washed with methanol. The filtrate was concentrated under vacuum to afford the title product as colourless sticky solid (LXXIV, 0.71 g, 99%). LC-MS m/z calcd for $C_{21}H_{31}NO_4$, 361.2; found 262.2 [M-Boc+H]$^+$.

Step 5: Methyl 4-(3-(piperidin-4-yl)propyl)benzoate hydrochloride-Intermediate LXXV

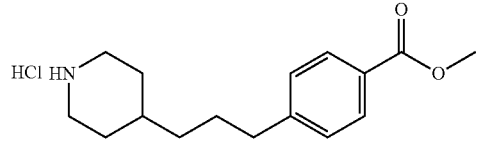 [SMILES: Cl ; COC(=O)c1ccc(CCCC2CCNCC2)cc1]

To a stirred solution of tert-butyl 4-(3-(4-(methoxycarbonyl)phenyl)propyl)piperidine-1-carboxylate (LXXIV, 0.7 g, 1.9 mmol) in dioxane (15 mL) was added 20% HCl in dioxane at 0° C. and stirred for 16 h at room temperature. The reaction mixture was concentrated under vacuum to afford the title product as off-white solid (LXXV, 0.41 g, 72%). LC-MS m/z calcd for $C_{16}H_{23}NO_2$, 261.1; found 262.2 [M+H]$^+$.

Step 6: Methyl 4-(3-(1-(N-(tert-butoxycarbonyl)-N-(2-phenylcyclopropyl)glycyl)piperidin-4-yl)propyl) benzoate-I-93

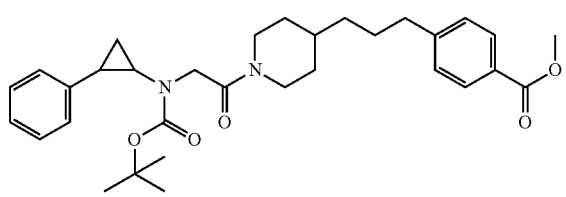 [SMILES: COC(=O)c1ccc(CCCC2CCN(C(=O)CN(C(=O)OC(C)(C)C)C3CC3c3ccccc3)CC2)cc1]

To a stirred solution of N-(tert-butoxycarbonyl)-N-(2-phenylcyclopropyl)glycine (0.1 g, 0.34 mmol) and methyl 4-(3-(piperidin-4-yl)propyl)benzoate hydrochloride (LXXV, 0.11 g, 0.37 mmol) in DMF (2 mL) was added EDC.HCl (0.058 g, 0.37 mmol), HOBt (0.05 g, 0.37 mmol) and DIPEA (0.13 mL, 1.03 mmol) at 0° C. and the resulting mixture was stirred at room temperature for 16 h. The reaction mixture was diluted with water and extracted with ethyl acetate. Organic portion was washed with water and brine, dried over sodium sulphate and concentrated under reduced pressure to get the crude product which was purified by column chromatography using ethylacetate-hexane gradient to afford the titled product as an sticky oil (I-93, 0.12 g, 68%). LC-MS m/z calcd for $C_{32}H_{42}N_2O_5$, 534; found 535 [M+H]$^+$.

I-94 ethyl 4-(3-(4-(((tert-butoxycarbonyl)(2-phenyl-cyclopropyl)amino)methyl)-2-oxopiperidin-1-yl)propyl)benzoate

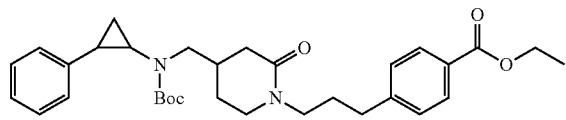 [SMILES: CCOC(=O)c1ccc(CCCN2CCC(CN(C(=O)OC(C)(C)C)C3CC3c3ccccc3)CC2=O)cc1]

The compound was synthesized using phenylcyclopropylamine and aldehyde A17 following the procedure for the synthesis of I-2. LC-MS m/z calcd for $C_{32}H_{42}N_2O_5$, 534.3; found 535.2 [M+H]$^+$.

I-95 methyl 4-(2-((tert-butoxycarbonyl)(2-phenylcyclopropyl)amino)ethoxy)benzoate

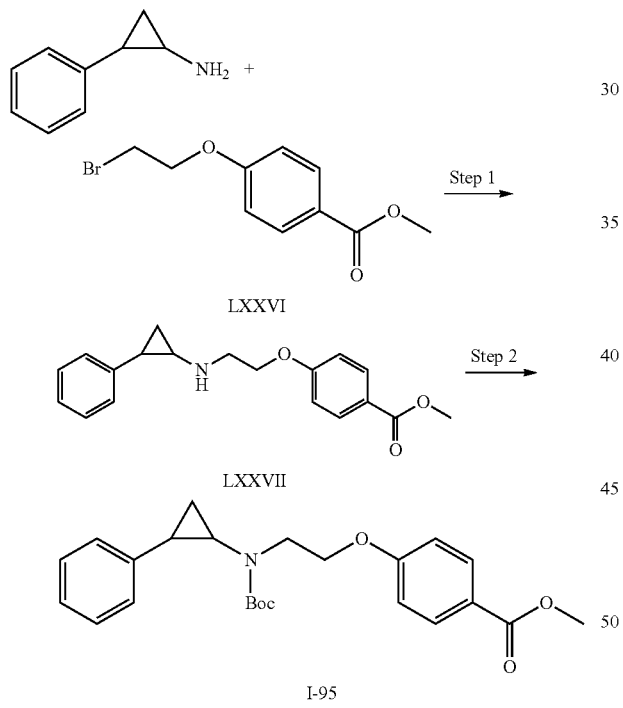

Step 1: Methyl 4-(2-((2-phenylcyclopropyl)amino)ethoxy)benzoate (LXXVII)

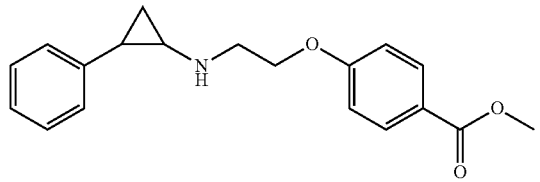 [SMILES: COC(=O)c1ccc(OCCNC2CC2c2ccccc2)cc1]

To a stirred solution of methyl 4-(2-bromoethoxy)benzoate (LXXVI, 0.45 g, 1.77 mmol) in dimethylformamide (15 mL) was added 2-phenylcyclopropanamine (0.5 g, 2.95 mmol) and potassium carbonate (1.22 g, 8.84 mmol) and the resulting mixture was stirred at 60° C. temperature for 12 h. Reaction was monitored by TLC, after completion of reaction, reaction was quenched with ice and the solvent was completely removed to get the residue. Water was added and the residue was extracted with dichloromethane (3×25 mL). The organic portion was washed with water and brine, dried over sodium sulphate and concentrated under reduced pressure to get the crude product which was purified by combi-flash chromatography using ethylacetate-hexane gradient to afford the required product as white solid (LXXVII, 0.32 g, 35%), LC-MS m/z calcd for $C_{19}H_{21}NO_3$, 311.1; found 312.2 [M+H]$^+$.

Step 2: Methyl 4-(2-((tert-butoxycarbonyl)(2-phenylcyclopropyl)amino)ethoxy)benzoate (I-95)

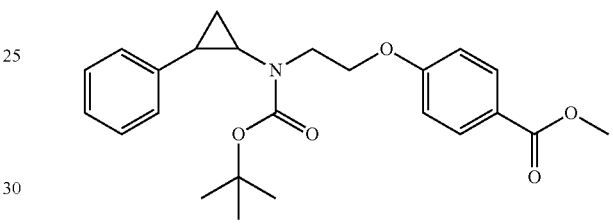

To a stirred solution of methyl 4-(2-((2-phenylcyclopropyl)amino)ethoxy)benzoate (LXXVII, 0.2 g, 0.64 mmol) in tetrahydrofuran and water mixture (14 mL, 1:1) was added sodium bicarbonate (0.16 g, 1.92 mmol) and Boc anhydride (0.16 mL, 0.77 mmol) at room temperature and the resulting mixture was stirred at that temperature for 1 h. The progress of the reaction was monitored by TLC. The reaction mixture was diluted with ethylacetate and the organic portion was washed with water and brine, dried over sodium sulphate and concentrated under reduced pressure to get the crude product which was purified by column chromatography using ethylacetate-hexane gradient to afford the titled product as pale-yellow oil (I-95, 0.16 g, 61%). LC-MS m/z calcd for $C_{24}H_{29}NO_5$, 411.2; found 312.1 [M-Boc+H]$^+$.

I-96 methyl 6-(2-(4-((2,2,2-trifluoro-N-(2-(4-fluorophenyl)cyclopropyl)acetamido)methyl) piperidin-1-yl)ethoxy)nicotinate

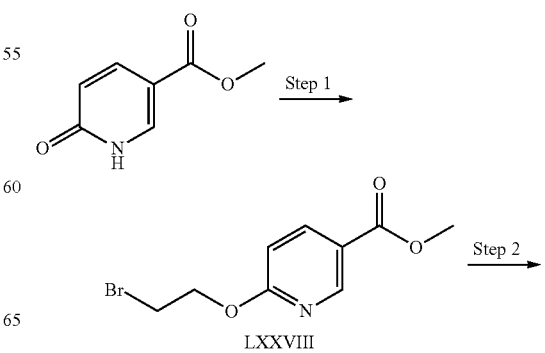

-continued

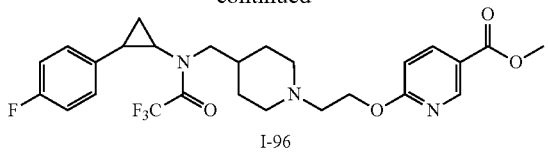

I-96

Step 1: methyl 6-(2-bromoethoxy)nicotinate

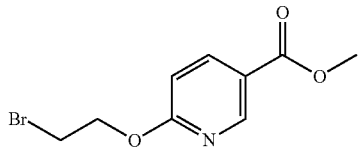

To a solution of methyl 6-hydroxynicotinate (1.2 g, 7.84 mmol) in DMF (10 mL) was added 60% of sodium hydride (0.75 g, 17.25 mmol) at 0° C. Then 1,2-dibromoethane (6.57 mL, 7.84 mmol) was added and then stirred for 16 h at room temperature. After completion of reaction, the reaction was quenched with ice and extracted with ethylacetate (2×50 mL). The combined organic layer was washed with water, brine solution, dried over sodium sulfate and concentrated under vacuum to get crude product which was purified by column chromatography using ethylacetate-hexane gradient to afford the titled product as a white solid (LXXVIII, 0.73 g, 35%). LC-MS m/z calcd for $C_9H_{10}BrNO_3$, 259.0; found 261.0 $[M+H]^+$.

Step 2: methyl 6-(2-(4-((2,2,2-trifluoro-N-(2-(4-fluorophenyl)cyclopropyl)acetamido)methyl)piperidin-1-yl)ethoxy)nicotinate-I-96

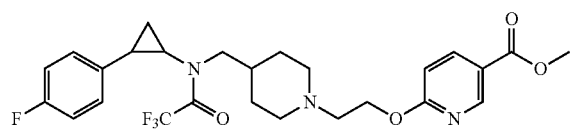 [SMILES: COC(=O)c1ccc(OCCN2CCC(CN(C(=O)C(F)(F)F)C3CC3c3ccc(F)cc3)CC2)nc1]

To a solution of methyl 6-(2-bromoethoxy)nicotinate (LXXVIII, 0.54 g, 2 mmol) in acetonitrile (5 mL) was added 2,2,2-trifluoro-N-(2-(4-fluorophenyl)cyclopropyl)-N-(piperidin-4-ylmethyl)acetamide hydrochloride (B-3, 0.80 g, 2 mmol) and N,N-diisopropylethylamine (1.07 mL, 6 mmol). Then the reaction mixture was heated at 40° C. for 16 h. After completion of reaction, the reaction was diluted with ethyl acetate (50 mL), washed with water, brine, dried over sodium sulfate and concentrated under vacuum to get crude product which was purified by column chromatography using methanol-dichloromethane gradient to afford the titled product as a brown colour liquid (I-96, 0.8 g, 74%). LC-MS m/z calcd for $C_{26}H_{29}F_4N_3O_4$, 523; found 524 $[M+H]^+$.

I-97 methyl 6-(2-(4-((2,2,2-trifluoro-N-(2-phenylcyclopropyl)acetamido)methyl)piperidin-1-yl) ethoxy) nicotinate

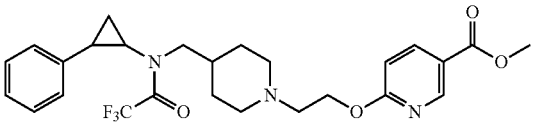

The compound was synthesized using phenylcyclopropylamine following the procedure for the synthesis of I-96. LC-MS m/z calcd for $C_{26}H_{30}F_3N_3O_4$, 505.2; found 506.2 $[M+H]^+$.

I-98 methyl 6-(2-(4-((2,2,2-trifluoro-N-(2-(4'-fluoro-[1,1'-biphenyl]-4-yl)cyclopropyl)acetamido)methyl) piperidin-1-yl)ethoxy)nicotinate

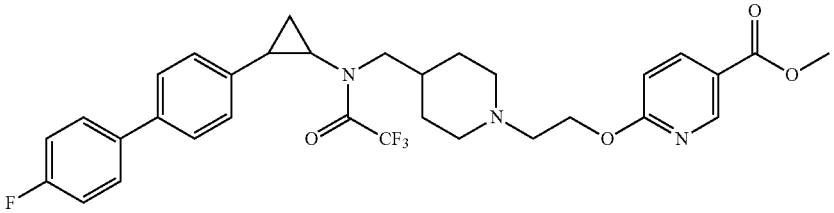 [SMILES: COC(=O)c1ccc(OCCN2CCC(CN(C(=O)C(F)(F)F)C3CC3c3ccc(-c4ccc(F)cc4)cc3)CC2)nc1]

The compound was synthesized using amine B-12 following the procedure for the synthesis of I-96. LC-MS m/z calcd for $C_{32}H_{33}F_4N_3O_4$, 599.2; found 600.2 $[M+H]^+$.

I-99 methyl 4-(2-(4-((2,2,2-trifluoro-N-(2-phenylcyclopropyl)acetamido)methyl)piperidin-1-yl)ethoxy) benzoate

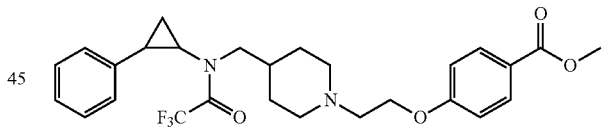

The compound was synthesized using phenylcyclopropylamine following the procedure for the synthesis of I-95. LC-MS m/z calcd for $C_{27}H_{31}F_3N_2O_4$, 504.2; found 505.2 $[M+H]^+$.

I-100 methyl 4-(3-(4-((2,2,2-trifluoro-N-(2-phenylcyclopropyl)acetamido)methyl)piperidin-1-yl) propoxy)benzoate

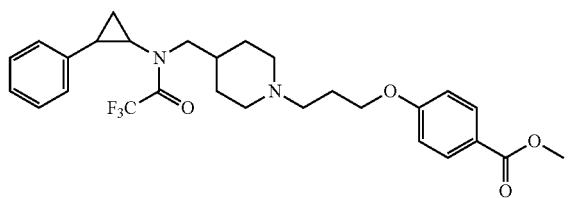 [SMILES: COC(=O)c1ccc(OCCCN2CCC(CN(C(=O)C(F)(F)F)C3CC3c3ccccc3)CC2)cc1]

The compound was synthesized using phenylcyclopropylamine following the procedure for the synthesis of I-95. LC-MS m/z calcd for $C_{28}H_{33}F_3N_2O_4$, 518.2; found 519.2 $[M+H]^+$.

I-101 methyl 4-(3-((tert-butoxycarbonyl)(2-phenylcyclopropyl)amino)propoxy)benzoate

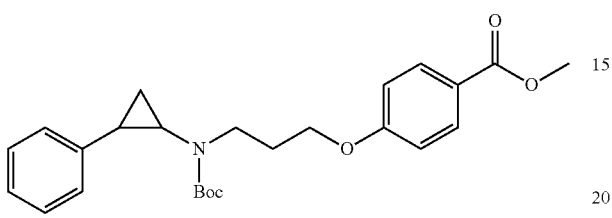

The compound was synthesized using phenylcyclopropylamine following the procedure for the synthesis of I-95. LC-MS m/z calcd for $C_{25}H_{31}NO_5$, 425.2; found 426.1 $[M+H]^+$.

I-102 methyl 2-((2-(4-((2,2,2-trifluoro-N-(2-(4-fluorophenyl)cyclopropyl)acetamido) methyl)piperidin-1-yl)ethyl)amino)pyrimidine-5-carboxylate

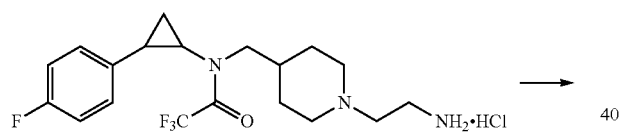

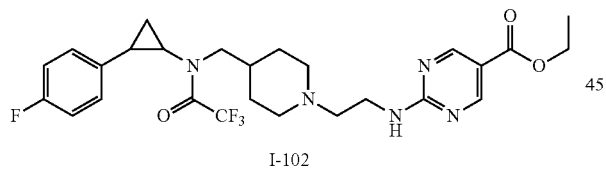

I-102

To a solution of N-((1-(2-aminoethyl)piperidin-4-yl)methyl)-2,2,2-trifluoro-N-(2-(4-fluorophenyl)cyclopropyl)acetamide hydrochloride. (B-25, 0.48 g, 1.60 mmol) in acetonitrile (5 mL) was added methyl 2-(ethylsulfonyl)pyrimidine-5-carboxylate (0.4 g, 1.7 mmol) and N,N-diisopropylethylamine (0.86 mL, 4.8 mmol). Then the reaction mixture was heated at 50° C. for 16 h. After completion of reaction, the reaction was diluted with ethylacetate (50 mL), washed with water, brine solution, dried over sodium sulfate and concentrated under vacuum to get crude product which was purified by column chromatography using methanol-dichloromethane gradient to afford the titled product as brown colour sticky oil (I-102, 0.250 g, 41%). LC-MS m/z calcd for $C_{26}H_{31}F_4N_5O_3$, 537.2; found 538.2 $[M+H]^+$.

I-103 ethyl 5-(2-((tert-butoxycarbonyl)(2-(4-fluorophenyl)cyclopropyl)amino)acetyl)-4,5,6,7-tetrahydrothieno[3,2-c]pyridine-2-carboxylate

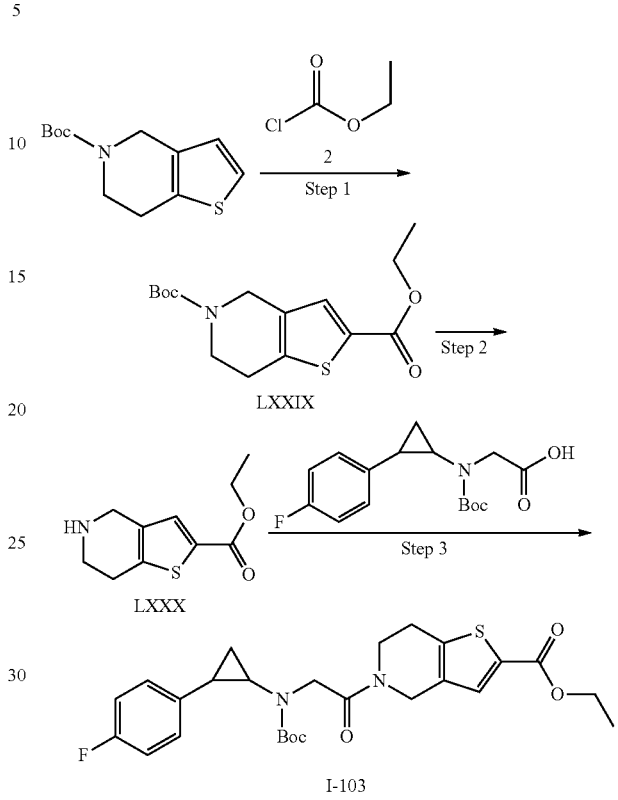

Step 1: 5-(tert-butyl)-2-ethyl-6,7-dihydrothieno[3,2-c]pyridine-2,5(4H)-dicarboxylate LXXIX

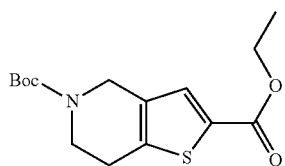 [SMILES: CCOC(=O)c1cc2c(s1)CCN(C(=O)OC(C)(C)C)C2]

To a stirred solution of tert-butyl 6,7-dihydrothieno[3,2-c]pyridine-5(4H)-carboxylate (11.5 g, 48.09 mmol) in tetrahydrofuran (75 mL) was added 1.6M solution of n-butyl lithium in n-hexane (36 mL, 57.71 mmol) at −78° C. and stirred for same temperature for 3 h, ethyl chloroformate (52.19 g, 480.9 mmol) was added drop wise at −78° C. and allowed to stirred for 12 h at room temperature. Progress of reaction followed by TLC. After completion of reaction, the mixture was quenched with ammonium chloride (100 mL) and extracted with ethylacetate. The organic portion was washed with water and brine dried over sodium sulphate and concentrated under reduced pressure to afford the crude product which was purified by column chromatography using ethylacetate-hexane gradient to afford LXXIX as yellowish liquid (3.75 g, 23%). LC-MS m/z calcd for $C_{15}H_{21}NO_4S$, 311.1. found 212.1 $[M-Boc+H]^+$.

Step 2: ethyl 4,5,6,7-tetrahydrothieno[3,2-c]pyridine-2-carboxylate TFA salt LXXX

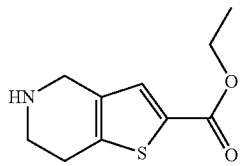

To a stirred solution of 5-(tert-butyl)-2-ethyl-6,7-dihydrothieno[3,2-c]pyridine-2,5(4H)-dicarboxylate (LXXIX, 0.5 g, 1.68 mmol) in dichloromethane (15 mL) was added trifluoroacetic acid (1.5 g, 13.47 mmol) at 0° C. and allowed to stirred for 4 h at room temperature. Progress of reaction was followed by TLC. After completion of reaction, the mixture was concentrated completely and washed with diethyl ether to afford product LXXX as a brown colour liquid (0.50 g, 91%). LC-MS m/z calcd for $C_{10}H_{13}NO_2S$, 211.0. found 212.1 $[M+H]^+$.

Step 3: ethyl 5-(N-(tert-butoxycarbonyl)-N-(2-(4-fluorophenyl)cyclopropyl)glycyl)-4,5,6,7-tetrahydrothieno[3,2-c]pyridine-2-carboxylate I-103

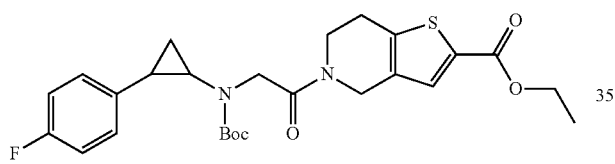

To a stirred solution of ethyl 4,5,6,7-tetrahydrothieno[3,2-c]pyridine-2-carboxylate TFA salt 4 (0.2 g, 0.65 mmol), N-(tert-butoxycarbonyl)-N-(2-(4-fluorophenyl)cyclopropyl) glycine 5 (0.16 g, 0.78 mmol), triethylamine (0.261 g, 2.59 mmol) in dichloromethane (10 mL) was added propylphosphonic anhydride (T3P, 0.514 g, 1.62 mmol) and stirred for 12 h at room temperature. Progress of reaction followed by TLC. After completion, the reaction was quenched with water (20 mL) and extracted with dichloromethane (2×30 mL). The organic portion was washed with water, brine, dried over sodium sulphate and concentrated under reduced pressure to afford the crude product which was purified by column chromatography chromatography using ethylacetate-hexane gradient to afford the titled product I-103 as colourless liquid (0.15 g, 57%). LC-MS m/z calcd for $C_{26}H_{31}FN_2O_5S$, 502.2. found 503.2 $[M+H]^+$.

I-104 methyl 2-(2-((tert-butoxycarbonyl)(2-(4-fluorophenyl)cyclopropyl)amino)acetyl)-1,2,3,4-tetrahydroisoquinoline-7-carboxylate

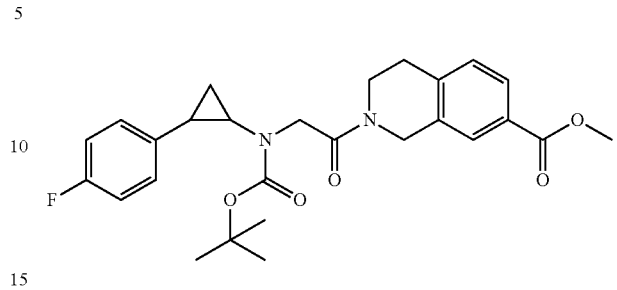

To a stirred solution of methyl 1,2,3,4-tetrahydroisoquinoline-7-carboxylate hydrochloride (0.25 g, 1.1 mmol) and 2-((tert-butoxycarbonyl)(2-(4-fluorophenyl)cyclopropyl) amino)acetic acid (0.34 g, 1.1 mmol) in N,N-dimethylformamide (5 mL), was added EDC.HCl (0.42 g, 2.2 mmol), HOBt (0.18 g, 1.32 mmol) and triethylamine (0.61 mL, 4.4 mmol) at room temperature. The resulting mixture was stirred at that temperature for 16 h. The progress of the reaction was monitored by TLC. After completion, the reaction mixture was diluted with water and extracted with ethylacetate. Organic portion was washed with water and brine, dried over sodium sulphate and concentrated under reduced pressure to get the crude product which was purified by column chromatography using ethylacetate-hexane gradient to afford the titled product as an off-white solid (I-104, 0.25 g, 47%). LC-MS m/z calcd for $C_{27}H_{31}FN_2O_5$, 482.2; found 483.1 $[M+H]^+$.

I-105 ethyl 5-(4-((tert-butoxycarbonyl)(2-(4-fluorophenyl)cyclopropyl)amino)butanoyl)-4,5,6,7-tetrahydrothieno[3,2-c]pyridine-2-carboxylate

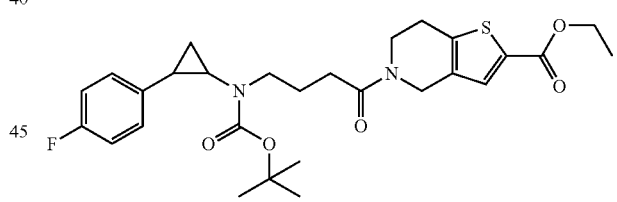

The compound was synthesized using 2-(4-fluorophenyl) cyclopropanamine and A-25 following the procedure for the synthesis of I-2. LC-MS m/z calcd for $C_{28}H_{35}FN_2O_5S$, 530.2; found 531.2 $[M+H]^+$.

I-106 ethyl 5-(4-(4-(((2,2,2-trifluoro-N-(2-(4-fluorophenyl)cyclopropyl)acetamido)methyl) piperidin-1-yl)butanoyl)-4,5,6,7-tetrahydrothieno[3,2-c]pyridine-2-carboxylate

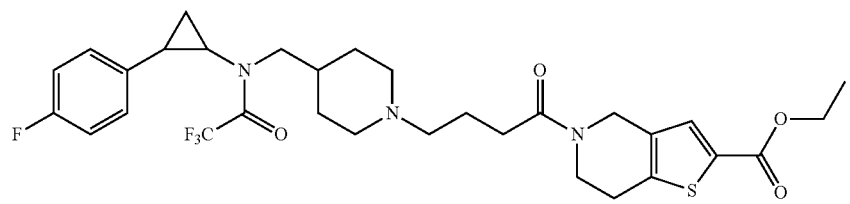 [SMILES: CCOC(=O)c1cc2c(s1)CCN(C(=O)CCCN1CCC(CN(C(=O)C(F)(F)F)C3CC3c3ccc(F)cc3)CC1)C2]

The compound was synthesized using amine B-3 and A25 following the procedure for the synthesis of I-2. LC-MS m/z calcd for $C_{31}H_{37}F_4N_3O_4S$, 623.2; found 624.3 [M+H]⁺.

I-107 ethyl 2-(4-((tert-butoxycarbonyl)(2-(4-fluorophenyl)cyclopropyl)amino)butanoyl)-1,2,3,4-tetrahydroisoquinoline-7-carboxylate

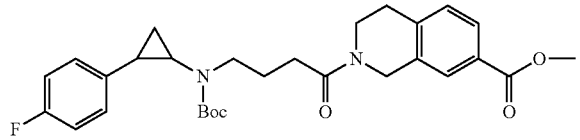 [SMILES: COC(=O)c1ccc2c(c1)CN(C(=O)CCCN(C(=O)OC(C)(C)C)C1CC1c1ccc(F)cc1)CC2]

The compound was synthesized using 2-(4-fluorophenyl)cyclopropanamine and A-26 following the procedure for the synthesis of I-2. LC-MS m/z calcd for $C_{29}H_{35}FN_2O_5$, 510.2; found 511.3 [M+H]⁺.

I-108 methyl 2-(4-((tert-butoxycarbonyl)(2-(4-fluorophenyl)cyclopropyl)amino)butanoyl) isoindoline-5-carboxylate

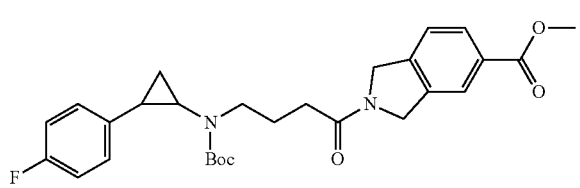 [SMILES: COC(=O)c1ccc2c(c1)CN(C(=O)CCCN(C(=O)OC(C)(C)C)C1CC1c1ccc(F)cc1)C2]

The compound was synthesized using 2-(4-fluorophenyl)cyclopropanamine and A-27 following the procedure for the synthesis of I-2. LC-MS m/z calcd for $C_{28}H_{33}FN_2O_5$, 496.2; found 497.2 [M+H]⁺.

I-109 methyl 2-(4-(4-((2,2,2-trifluoro-N-(2-phenyl-cyclopropyl)acetamido)methyl)piperidin-1-yl)butanoyl)isoindoline-5-carboxylate

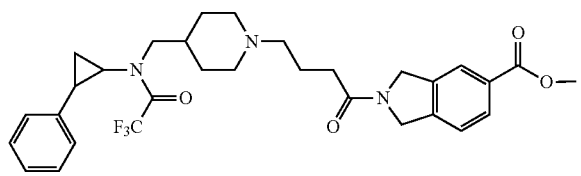 [SMILES: COC(=O)c1ccc2c(c1)CN(C(=O)CCCN1CCC(CN(C(=O)C(F)(F)F)C3CC3c3ccccc3)CC1)C2]

The compound was synthesized using 2,2,2-trifluoro-N-(2-phenylcyclopropyl)-N-(piperidin-4-ylmethyl)acetamide and ketone A27 following the procedure for the synthesis of I-2. LC-MS m/z calcd for $C_{31}H_{36}F_3N_3O_4$, 571.2; found 572.3 [M+H]⁺.

I-110 methyl 2-(3-(4-((2,2,2-trifluoro-N-(2-phenyl-cyclopropyl)acetamido)methyl)piperidin-1-yl)propyl)thiazole-4-carboxylate

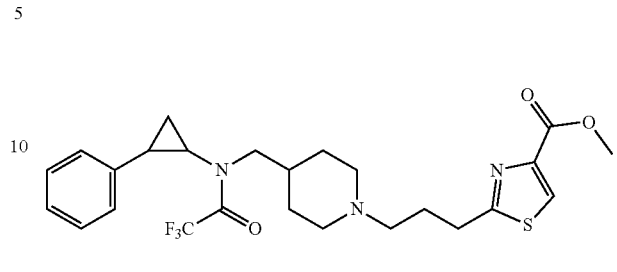

The compound was synthesized using 2,2,2-trifluoro-N-(2-phenylcyclopropyl)-N-(piperidin-4-ylmethyl)acetamide and aldehyde A30 following the procedure for the synthesis of I-2. LC-MS m/z calcd for $C_{25}H_{30}F_3N_3O_3S$, 509.2; found 510.2 [M+H]⁺.

I-111 methyl 2-(3-(4-((2,2,2-trifluoro-N-(2-(4'-fluoro-[1,1'-biphenyl]-4-yl)cyclopropyl) acetamido)methyl)piperidin-1-yl)propyl)thiazole-4-carboxylate

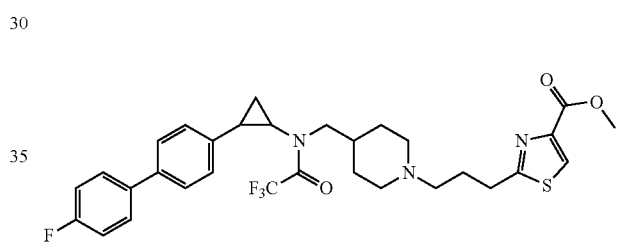

The compound was synthesized using 2,2,2-trifluoro-N-(2-phenylcyclopropyl)-N-(piperidin-4-ylmethyl)acetamide and aldehyde A30 following the procedure for the synthesis of I-2. LC-MS m/z calcd for $C_{31}H_{33}F_4N_3O_3S$, 603.2; found 604.2 [M+H]⁺.

I-112 ethyl 2-(3-(4-((2,2,2-trifluoro-N-(2-phenylcyclopropyl)acetamido)methyl)piperidin-1-yl)propyl)thiazole-5-carboxylate

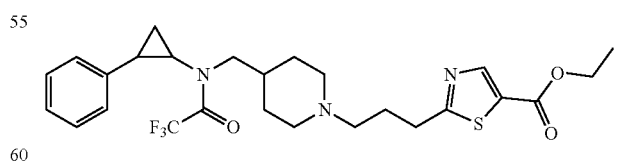

The compound was synthesized using amine 2,2,2-trifluoro-N-(2-phenylcyclopropyl)-N-(piperidin-4-ylmethyl)acetamide and aldehyde A31 following the procedure for the synthesis of I-2. LC-MS m/z calcd for $C_{26}H_{32}F_3N_3O_3S$, 523.2; found 524.2 [M+H]⁺.

I-113 methyl 2-(3-(4-((2,2,2-trifluoro-N-(2-phenyl-cyclopropyl)acetamido)methyl)piperidin-1-yl) propyl)oxazole-4-carboxylate

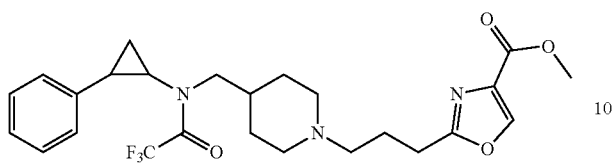

The compound was synthesized using amine 2,2,2-trifluoro-N-(2-phenylcyclopropyl)-N-(piperidin-4-ylmethyl) acetamide and aldehyde A32 following the procedure for the synthesis of I-2. LC-MS m/z calcd for $C_{25}H_{30}F_3N_3O_4$, 493.2; found 494.2 [M+H]$^+$.

I-114 (E)-methyl 4-(3-(4-(((tert-butoxycarbonyl)(2-phenylcyclopropyl)amino)methyl)piperidin-1-yl)-3-oxoprop-1-en-1-yl)benzoate

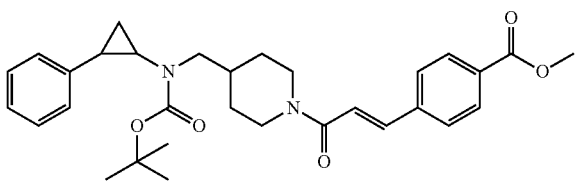

The compound was synthesized using 2-phenylcyclopropanamine hydrochloride and aldehyde A33 following the procedure for the synthesis of I-2. LC-MS m/z calcd for $C_{31}H_{38}N_2O_5$, 518.2; found 519.3 [M+H]$^+$.

I-115 Methyl 4-((E)-3-(4-(((tert-butoxycarbonyl)((1S,2R)-2-(4-fluorophenyl)cyclopropyl)amino) methyl)piperidin-1-yl)-3-oxoprop-1-en-1-yl)benzoate

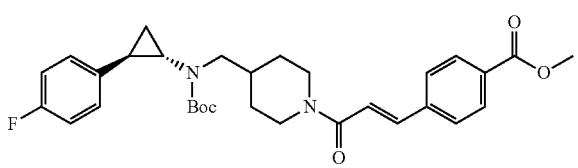 [SMILES: COC(=O)c1ccc(/C=C/C(=O)N2CCC(CN(C(=O)OC(C)(C)C)[C@H]3C[C@@H]3c3ccc(F)cc3)CC2)cc1]

The compound was synthesized using B1 and aldehyde A33 following the procedure for the synthesis of I-2. LC-MS m/z calcd for $C_{31}H_{37}FN_2O_5$, 536.2; found 537.2 [M+H]$^+$.

I-116 (E)-methyl4-(3-(4-(((tert-butoxycarbonyl)(2-(4-(3,5-dimethylisoxazol-4-yl)phenyl) cyclopropyl) amino)methyl)piperidin-1-yl)-3-oxoprop-1-en-1-yl) benzoate

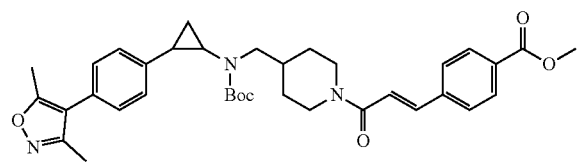 [SMILES: COC(=O)c1ccc(/C=C/C(=O)N2CCC(CN(C(=O)OC(C)(C)C)C3CC3c3ccc(-c4c(C)noc4C)cc3)CC2)cc1]

The compound was synthesized using B8 and aldehyde A33 following the procedure for the synthesis of I-2. LC-MS m/z calcd for $C_{36}H_{43}N_3O_6$, 613.3; found 614.2 [M+H]$^+$.

I-117 (E)-methyl4-(3-(4-(((tert-butoxycarbonyl)(2-(4-(pyrimidin-5-yl)phenyl)cyclopropyl)amino) methyl)piperidin-1-yl)-3-oxoprop-1-en-1-yl)benzoate

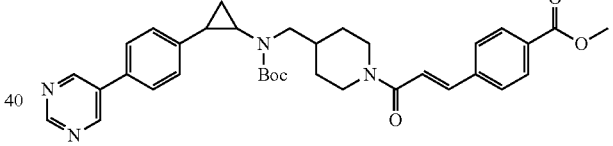

The compound was synthesized using B11 and aldehyde A33 following the procedure for the synthesis of I-2. LC-MS m/z calcd for $C_{35}H_{40}N_4O_5$, 596.3; found 597.3 [M+H]$^+$.

I-118 (E)-methyl4-(3-oxo-3-(3-((2,2,2-trifluoro-N-(2-(4-fluorophenyl)cyclopropyl) acetamido)methyl) azetidin-1-yl)prop-1-en-1-yl)benzoate

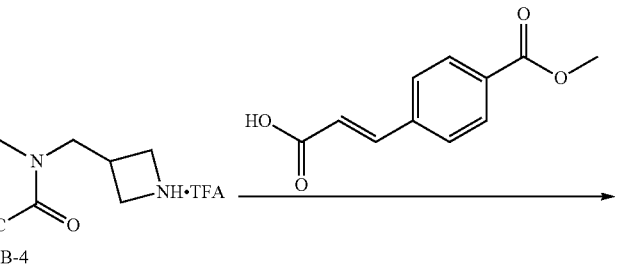

B-4

-continued

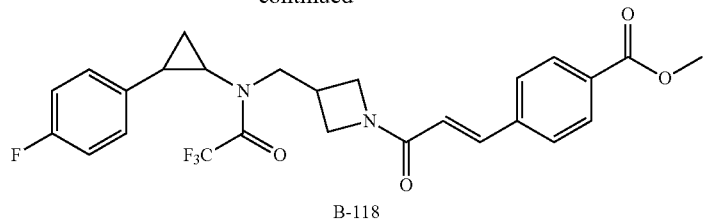

B-118

To a stirred solution of methyl (E)-4-(3-oxo-3-(3-((2,2,2-trifluoro-N-(2-(4-fluorophenyl)cyclopropyl)acetamido)methyl)azetidin-1-yl)prop-1-en-1-yl)benzoate TFA salt (B-4, 0.50 g, 1.51 mmol) and (E)-3-(4-(methoxycarbonyl)phenyl)acrylic acid (0.40 g, 1.97 mmol) in dichloromethane (20 mL), was added HOBt (0.05 g, 0.30 mmol) and triethylamine (0.46 mL, 4.55 mmol) at room temperature and cooled to 0° C. Then, EDC.HCl (0.43 g, 2.27 mmol) was added and stirred for 16 h at room temperature. The reaction mixture was diluted with water and extracted with dichloromethane. The combined organic portion was washed with water, brine, dried over sodium sulphate and concentrated under reduced pressure to get the crude product which was purified by column chromatography using methanol-dichloromethane gradient to afford the titled product as a off-white solid (B-118, 0.49 g, 65%). LC-MS m/z calcd for $C_{26}H_{24}F_4N_2O_4$, 504.2; found 505.2 [M+H]$^+$.

I-119 (E)-methyl4-(3-oxo-3-(3-((2,2,2-trifluoro-N-(2-(4-(1-methyl-1H-pyrazol-4-yl)phenyl) cyclopropyl)acetamido)methyl)azetidin-1-yl)prop-1-en-1-yl)benzoate

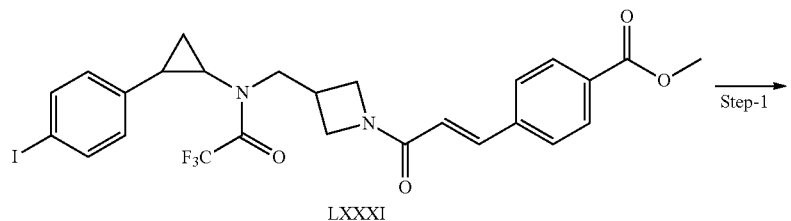

LXXXI

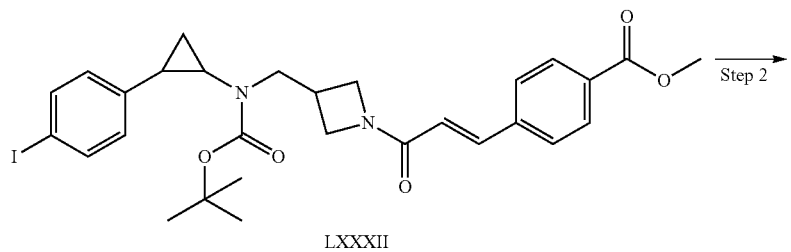

LXXXII

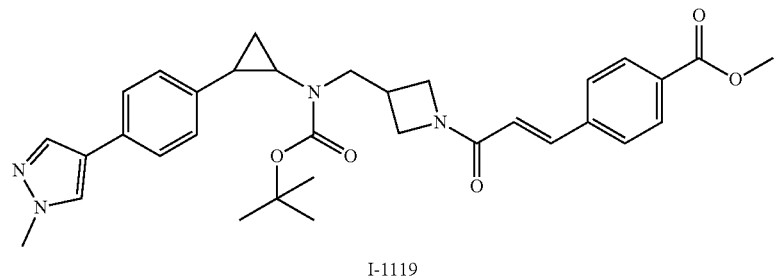

I-1119

Step-1: methyl (E)-4-(3-(3-(((tert-butoxycarbonyl)(2-(4-iodophenyl)cyclopropyl)amino)methyl)azetidin-1-yl)-3-oxoprop-1-en-1-yl)benzoate-LXXXII

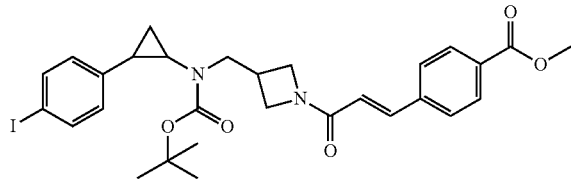 [SMILES: COC(=O)c1ccc(/C=C/C(=O)N2CC(CN(C(=O)OC(C)(C)C)C3CC3c3ccc(I)cc3)C2)cc1]

To a stirred solution of methyl (E)-4-(3-oxo-3-(3-((2,2,2-trifluoro-N-(2-(4-iodophenyl)cyclopropyl)acetamido)methyl)azetidin-1-yl)prop-1-en-1-yl)benzoate (LXXXI, 0.2 g, 0.33 mmol) in methanol (5 mL) was added potassium carbonate (0.1 g, 2.40 mmol) at room temperature and the resulting mixture was stirred at that temperature for 3 h. After completion of the reaction, solvent was evaporated under vacuum. The residue was mixed with tetrahydrofuran-water mixture (6 mL, 1:1). This was followed by addition of Boc anhydride (0.08 mL, 0.39 mmol) and sodium bicarbonate (0.08 g, 0.98 mmol). The reaction mixture was stirred for 2 h at room temperature. The solvent was evaporated and then diluted with dichloromethane. The combined portion was washed with water and brine solution, dried over sodium sulphate and concentrated under reduced pressure to get the crude to afford the titled product as stick oil (LXXXII, 0.25 g, 63%). LC-MS m/z calcd for $C_{29}H_{33}IN_2O_5$, 616.1; found 617.1 $[M+H]^+$.

Step-2: Methyl (E)-4-(3-(3-(((tert-butoxycarbonyl)(2-(4-(1-methyl-1H-pyrazol-4-yl)phenyl)cyclopropyl)amino)methyl)azetidin-1-yl)-3-oxoprop-1-en-1-yl)benzoate-I-119

I-119

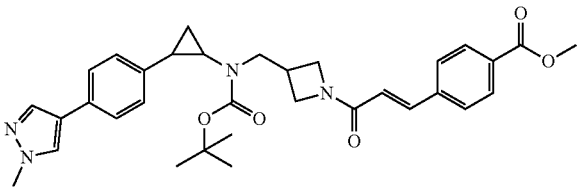

To a stirred solution of methyl (E)-4-(3-(3-(((tert-butoxycarbonyl)(2-(4-iodophenyl)cyclopropyl)amino)methyl)azetidin-1-yl)-3-oxoprop-1-en-1-yl)benzoate (LXXXII, 0.25 g, 0.41 mmol) in DMF (3 mL) was added (1-methyl-1H-pyrazol-4-yl)boronic acid (0.06 g, 0.49 mmol) and potassium carbonate (0.11 g, 0.82 mmol) and then degassed for 5 min. 1,1'-Bis(diphenylphosphino)ferrocene-palladium(II)dichloride dichloromethane complex (0.016 g, 0.02 mmol) was added and heated at 120° C. in microwave for 2 h. Water was added and the residue was extracted with ethylacetate (2×100 mL). The organic portion was washed with water, brine, dried over sodium sulphate and concentrated under reduced pressure to afford the crude product which was purified by column chromatography using methanol-dichloromethane gradient to afford the titled product as sticky oil (I-119, 0.2 g, 86%). LC-MS m/z calcd for $C_{33}H_{38}N_4O_5$, 570.3; found 571.2 $[M+H]^+$.

Synthesis of Acid Intermediates

I-120 (E)-3-(4-(((tert-butoxycarbonyl)(2-(4-fluorophenyl)cyclopropyl)amino)methyl)phenyl)acrylic Acid

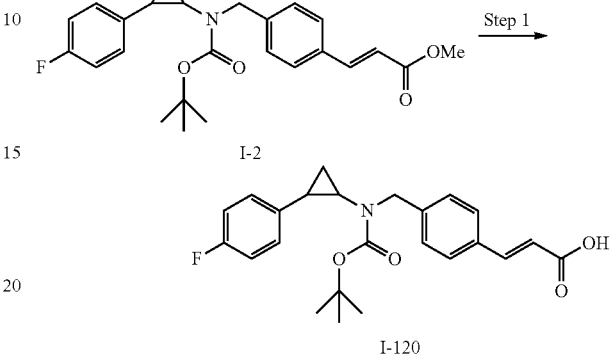

To a stirred solution of (E)-methyl 3-(4-(((tetra-butoxycarbonyl)(2-(4-florophenyl)cyclopropl)amino)methyl)phenyl)acrylate (I-2, 0.38 g, 0.89 mmol) in methanol and water mixture (20 mL, 4:1) was added sodium hydroxide (0.11 g, 2.68 mmol) at room temperature and the resulting mixture was stirred at that temperature for 1 h. The progress of the reaction was monitored by TLC. After completion of reaction, solvent was evaporated and washed with ethylacetate. The reaction mixture was acidified to pH 5 with 2N HCl and extracted with dichloromethane and the organic portion was washed with water, brine solution, dried over sodium sulphate and concentrated under reduced pressure to afford the product as off-white solid (I-120, 0.31 g, 86%). LC-MS m/z calcd for $C_{24}H_{26}FNO_4$, 411.2; found 312.2 $[M-Boc+H]^+$.

I-121 4-(3-(4-(((tert-butoxycarbonyl)(2-phenylcyclopropyl)amino)methyl)piperidin-1-yl)propyl)benzoic Acid

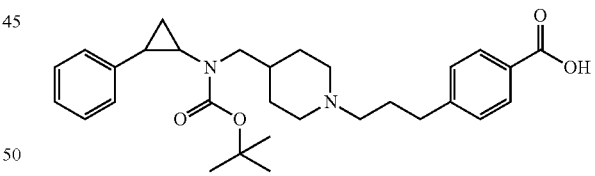

The compound was synthesized using I-43 following the procedure for the synthesis of I-120. LC-MS m/z calcd for $C_{30}H_{40}N_2O_4$, 492.3; found 493.3 $[M+H]^+$.

I-122 4-(3-(4-(((tert-butoxycarbonyl)(2-(4-fluorophenyl)cyclopropyl)amino)methyl)piperidin-1-yl)propyl)benzoic Acid

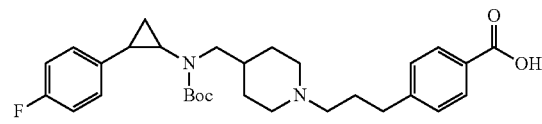 [SMILES: CC(C)(C)OC(=O)N(CC1CCN(CCCc2ccc(C(=O)O)cc2)CC1)C1CC1c1ccc(F)cc1]

The compound was synthesized using I-47 following the procedure for the synthesis of I-120. LC-MS m/z calcd for $C_{30}H_{39}FN_2O_4$, 510.3; found 511.3 $[M+H]^+$.

I-123 4-(3-(4-(((tert-butoxycarbonyl)(2-(4-methoxyphenyl)cyclopropyl)amino)methyl)piperidin-1-yl)propyl)benzoic Acid

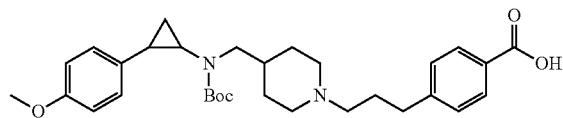 [SMILES: COc1ccc(C2CC2N(CC2CCN(CCCc3ccc(C(=O)O)cc3)CC2)C(=O)OC(C)(C)C)cc1]

The compound was synthesized using I-51 following the procedure for the synthesis of I-120. LC-MS m/z calcd for $C_{31}H_{42}N_2O_5$, 522.3; found 523.3 $[M+H]^+$.

I-124 4-(3-(4-(((tert-butoxycarbonyl)(2-(3,4-difluorophenyl)cyclopropyl)amino)methyl)piperidin-1-yl)propyl)benzoic Acid

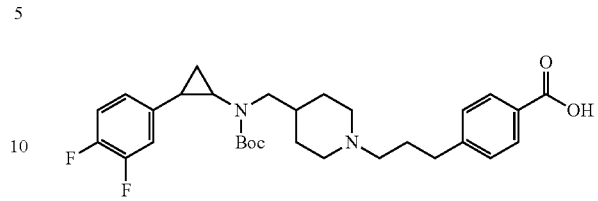

The compound was synthesized using I-50 following the procedure for the synthesis of intermediate I-120. LC-MS m/z calcd for $C_{30}H_{38}F_2N_2O_4$, 528.3; found 529.3 $[M+H]^+$.

I-125 4-(3-(4-(((tert-butoxycarbonyl)(2-(4-(piperidine-1-carbonyl)phenyl)cyclopropyl)amino)methyl)piperidin-1-yl)propyl)benzoic Acid

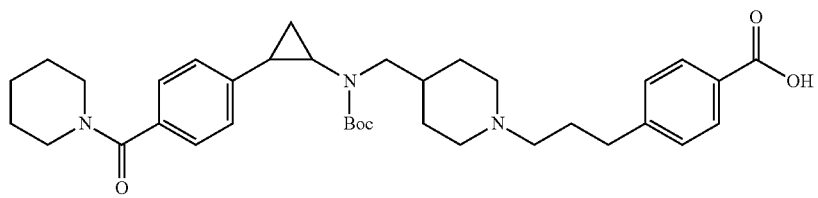 [SMILES: CC(C)(C)OC(=O)N(CC1CCN(CCCc2ccc(C(=O)O)cc2)CC1)C1CC1c1ccc(C(=O)N2CCCCC2)cc1]

The compound was synthesized using I-54 following the procedure for the synthesis of intermediate I-120. LC-MS m/z calcd for $C_{36}H_{49}N_3O_5$, 603.4; found 604.4 $[M+H]^+$.

I-127 4-(3-(6-((tert-butoxycarbonyl)(2-phenylcyclopropyl)amino)-2-azaspiro[3.3]heptan-2-yl)propyl)benzoic Acid

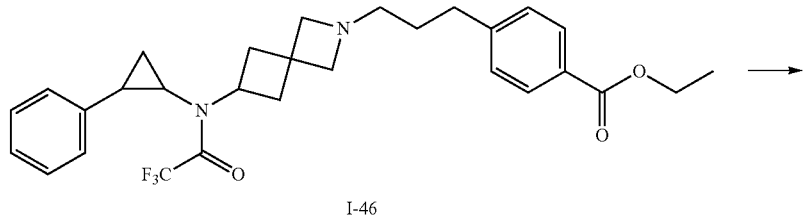

I-46

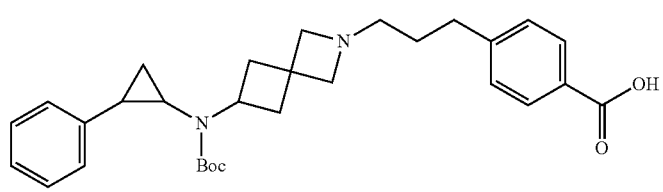

I-127

Step: 4-(3-(6-(((tert-butoxycarbonyl)(2-phenylcyclopropyl)amino)-2-azaspiro[3.3]heptan-2-yl)propyl)benzoic Acid To a stirred solution of ethyl 4-(3-(6-(2,2,2-trifluoro-N-(2-phenylcyclopropyl)acetamido)-2-azaspiro[3.3]heptan-2-yl)propyl)benzoate (0.4 g, 0.77 mmol) in tetrahydrofuran and water mixture (10 mL, 1:1) was added lithium hydroxide (0.097 g, 2.30 mmol) at room temperature and the resulting mixture was stirred at that temperature for 3 h. After disappearance of starting material 1-46, Boc anhydride (0.33 mL, 1.50 mmol) was added and stirred for 2 h at room temperature. The reaction solvent was evaporated and then acidified with 2N HCl solution. The aqueous layer was extracted with dichloromethane (50 mL×2). The combined organic layer was washed with water, brine solution, dried over sodium sulphate and concentrated under reduced pressure to afford the titled product as brown solid (0.31 g, 81%). LC-MS m/z calcd for $C_{30}H_{38}N_2O_4$, 490.3; found 489.3 $[M-H]^+$.

I-128 4-(3-(4-(((tert-butoxycarbonyl)(2-(1-isopropyl-1H-pyrazol-4-yl)cyclopropyl)amino)methyl)piperidin-1-yl)propyl)benzoic Acid

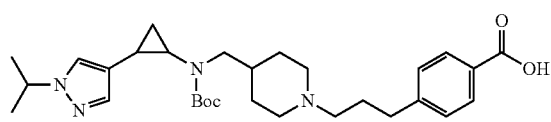 [SMILES: CC(C)n1cc(C2CC2N(CC2CCN(CCCc3ccc(C(=O)O)cc3)CC2)C(=O)OC(C)(C)C)cn1]

The compound was synthesized using I-67 following the procedure for the synthesis of I-120. LC-MS m/z calcd for $C_{30}H_{44}N_4O_4$, 524.3; found 525.4 $[M+H]^+$.

I-129 JBI-XXX-4-(3-(4-(((tert-butoxycarbonyl)(2-(1-phenyl-1H-pyrazol-4-yl)cyclopropyl)amino)methyl)piperidin-1-yl)propyl)benzoic Acid

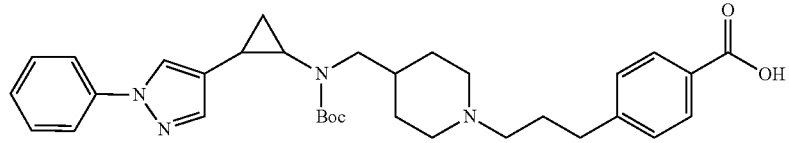 [SMILES: CC(C)(C)OC(=O)N(CC1CCN(CCCc2ccc(C(=O)O)cc2)CC1)C1CC1c1cnn(-c2ccccc2)c1]

The compound was synthesized using I-68 following the procedure for the synthesis of I-120. LC-MS m/z calcd for $C_{33}H_{42}N_4O_4$, 558.3; found 559.3 $[M+H]^+$.

I-130 4-(3-(4-(((tert-butoxycarbonyl)(2-(2-methylthiazol-5-yl)cyclopropyl)amino)methyl)piperidin-1-yl)propyl)benzoic Acid

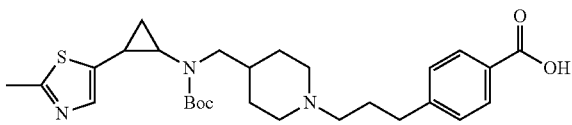 [SMILES: Cc1ncc(C2CC2N(CC2CCN(CCCc3ccc(C(=O)O)cc3)CC2)C(=O)OC(C)(C)C)s1]

The compound was synthesized using I-69 following the procedure for the synthesis of I-120. LC-MS m/z calcd for $C_{28}H_{39}N_3O_4S$, 513.3; found 514.3 $[M+H]^+$.

I-131 4-(3-(4-(((tert-butoxycarbonyl)(2-(pyridin-3-yl)cyclopropyl)amino)methyl)piperidin-1-yl)propyl)benzoic Acid

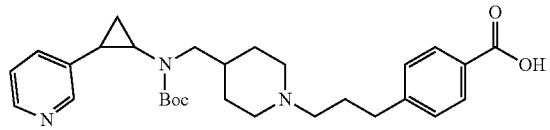 [SMILES: CC(C)(C)OC(=O)N(CC1CCN(CCCc2ccc(C(=O)O)cc2)CC1)C1CC1c1cccnc1]

The compound was synthesized using I-70 following the procedure for the synthesis of I-120. LC-MS m/z calcd for $C_{29}H_{39}N_3O_4$, 493.3; found 494.3 $[M+H]^+$.

I-133 4-(3-(4-((tert-butoxycarbonyl)(2-phenylcyclopropyl)amino)piperidin-1-yl)-3-oxopropyl)benzoic Acid

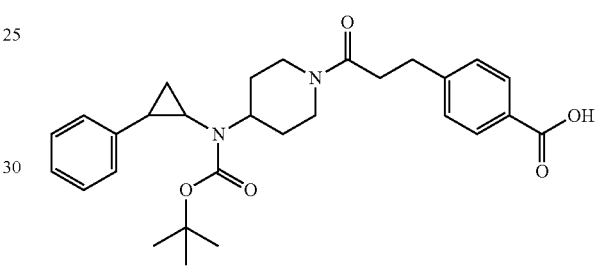

The compound was synthesized using I-83 following the procedure for the synthesis of I-120. LC-MS m/z calcd for $C_{29}H_{36}N_2O_5$, 492.2; found 491.2 $[M-H]^+$.

I-134 4-(3-(4-(((tert-butoxycarbonyl)(2-phenylcyclopropyl)amino)methyl)piperidin-1-yl)-3-oxopropyl)benzoic Acid

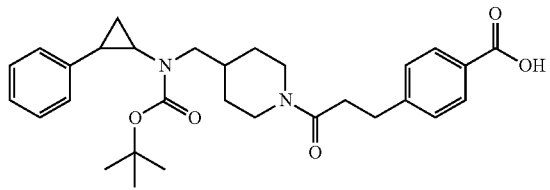 [SMILES: CC(C)(C)OC(=O)N(CC1CCN(C(=O)CCc2ccc(C(=O)O)cc2)CC1)C1CC1c1ccccc1]

The compound was synthesized using I-82 following the procedure for the synthesis of I-120. LC-MS m/z calcd for $C_{30}H_{38}N_2O_5$, 506.2; found 506.3 $[M]^+$.

I-135 4-(3-(4-((((tert-butoxycarbonyl)(2-(3,4-difluorophenyl)cyclopropyl)amino)methyl)-1H-imidazol-1-yl)propyl)benzoic Acid

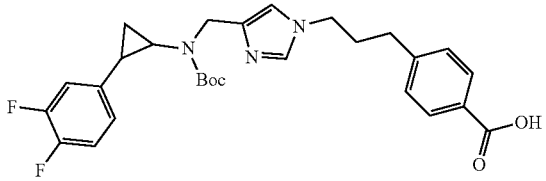 [SMILES: CC(C)(C)OC(=O)N(Cc1cn(CCCc2ccc(C(=O)O)cc2)cn1)C1CC1c1ccc(F)c(F)c1]

The compound was synthesized using I-73 following the procedure for the synthesis of I-120. LC-MS m/z calcd for $C_{28}H_{31}F_2N_3O_4$, 511.2; found 512.2 [M+H]$^+$.

I-136 4-(3-(4-((((tert-butoxycarbonyl)(2-phenylcyclopropyl)amino)methyl)-1H-imidazol-1-yl)propyl)benzoic Acid

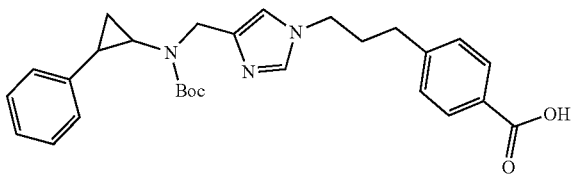

The compound was synthesized using I-75 following the procedure for the synthesis of I-120. LC-MS m/z calcd for $C_{28}H_{33}N_3O_4$, 475.2; found 476.2 [M+H]$^+$.

I-137 4-(3-(4-((((tert-butoxycarbonyl)(2-phenylcyclopropyl)amino)methyl)-1H-1,2,3-triazol-1-yl)propyl)benzoic Acid

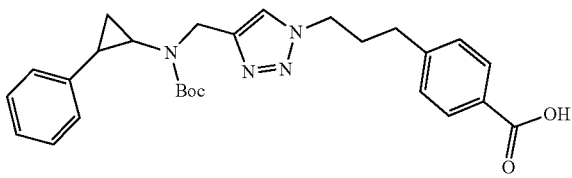 [SMILES: CC(C)(C)OC(=O)N(Cc1cn(CCCc2ccc(C(=O)O)cc2)nn1)C1CC1c1ccccc1]

The compound was synthesized using I-77 following the procedure for the synthesis of I-120. LC-MS m/z calcd for $C_{27}H_{32}N_4O_4$, 476.2; found 477.2 [M+H]$^+$.

I-138 4-(3-(4-((((tert-butoxycarbonyl)(2-phenylcyclopropyl)amino)methyl)-1H-pyrazol-1-yl)propyl)benzoic Acid

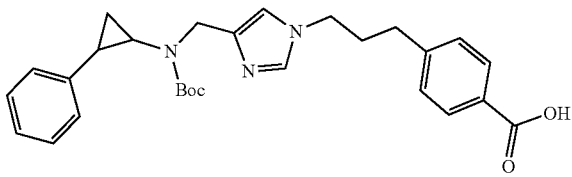 [SMILES: CC(C)(C)OC(=O)N(Cc1cn(CCCc2ccc(C(=O)O)cc2)cn1)C1CC1c1ccccc1]

The compound was synthesized using I-76 following the procedure for the synthesis of I-120. LC-MS m/z calcd for $C_{28}H_{33}N_3O_4$, 475.2; found 476.3 [M+H]$^+$.

I-139 4-(2-(4-((((tert-butoxycarbonyl)(2-phenylcyclopropyl)amino)methyl)piperidin-1-yl)ethyl)benzoic Acid

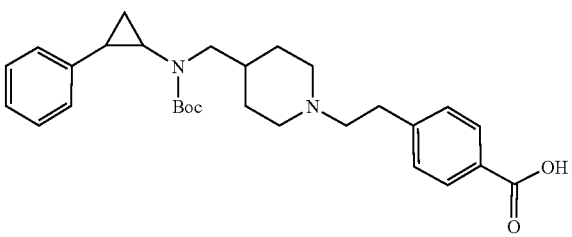 [SMILES: CC(C)(C)OC(=O)N(CC1CCN(CCc2ccc(C(=O)O)cc2)CC1)C1CC1c1ccccc1]

The compound was synthesized using I-42 following the procedure for the synthesis of I-120. LC-MS m/z calcd for $C_{29}H_{38}N_2O_4$, 478.2; found 479.3 [M+H]$^+$.

I-140 4-((4-((((tert-butoxycarbonyl)((1R,2S)-2-phenylcyclopropyl)amino)methyl)piperidin-1-yl)methyl)benzoic Acid

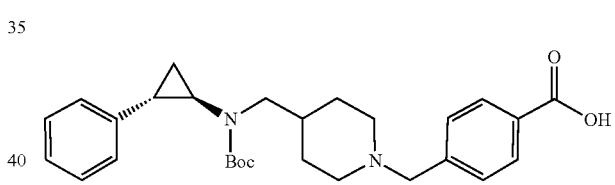

The compound was synthesized using I-36 following the procedure for the synthesis of I-120. LC-MS m/z calcd for $C_{28}H_{36}N_2O_4$, 464.3; found 465.3 [M+H]$^+$.

I-141 4-((4-((((tert-butoxycarbonyl)(2-(4-(1-methyl-6-oxo-1,6-dihydropyridin-3-yl)phenyl)cyclopropyl)amino)methyl)piperidin-1-yl)methyl)benzoic Acid

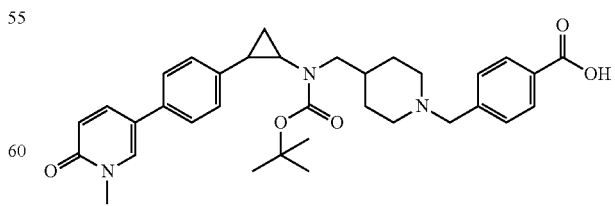

The compound was synthesized using I-35 following the procedure for the synthesis of I-120. LC-MS m/z calcd for $C_{34}H_{41}N_3O_5$, 571.3; found 572.3 [M+H]$^+$.

I-142 4-((4-(((tert-butoxycarbonyl)(2-(4-(1-methyl-1H-pyrazol-4-yl)phenyl)cyclopropyl)amino)methyl)piperidin-1-yl)methyl)benzoic Acid

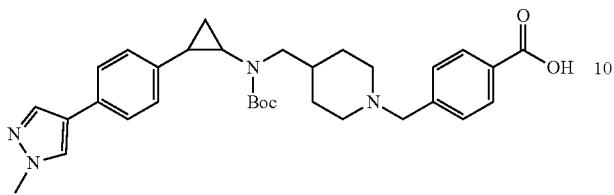

The compound was synthesized following the procedure for the synthesis of intermediate I-120 using the corresponding ester (ester was synthesized using B-7 and methyl 4-((4-formylpiperidin-1-yl)methyl)benzoate using the procedure outlined for synthesis of I-2). LC-MS m/z calcd for $C_{32}H_{40}N_4O_4$, 544.3; found 545.3 [M+H]$^+$.

I-143 4-((4-(((tert-butoxycarbonyl)(2-(4-(3,5-dimethylisoxazol-4-yl)phenyl)cyclopropyl)amino)methyl)piperidin-1-yl)methyl)benzoic Acid

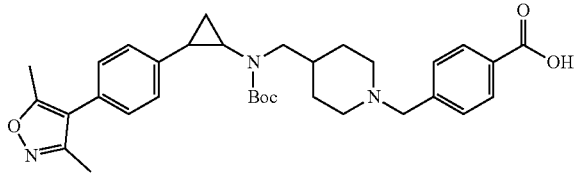 [SMILES: Cc1noc(C)c1-c1ccc(C2CC2N(CC2CCN(Cc3ccc(C(=O)O)cc3)CC2)C(=O)OC(C)(C)C)cc1]

The compound was synthesized using I-37 following the procedure for the synthesis of I-120. LC-MS m/z calcd for $C_{33}H_{41}N_3O_5$, 559.3; found 560.3 [M+H]$^+$.

I-144 4-((4-(((tert-butoxycarbonyl)(2-(4-(pyrimidin-5-yl)phenyl)cyclopropyl)amino)methyl)piperidin-1-yl)methyl)benzoic Acid

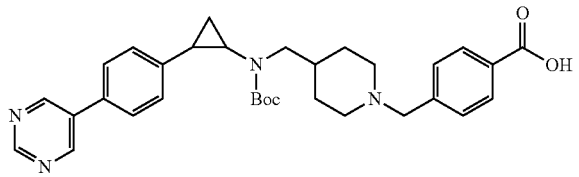 [SMILES: CC(C)(C)OC(=O)N(CC1CCN(Cc2ccc(C(=O)O)cc2)CC1)C1CC1c1ccc(-c2cncnc2)cc1]

The compound was synthesized using I-38 following the procedure for the synthesis of I-120. LC-MS m/z calcd for $C_{32}H_{38}N_4O_4$, 542.2; found 543.3 [M+H]$^+$.

I-145 4-((4-(((tert-butoxycarbonyl)(2-phenylcyclopropyl)amino)methyl)-1H-pyrazol-1-yl)methyl)benzoic Acid

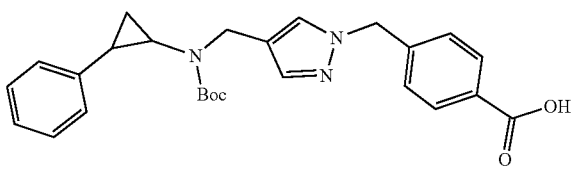 [SMILES: CC(C)(C)OC(=O)N(Cc1cnn(Cc2ccc(C(=O)O)cc2)c1)C1CC1c1ccccc1]

The compound was synthesized using I-40 following the procedure for the synthesis of I-120. LC-MS m/z calcd for $C_{26}H_{29}N_3O_4$, 447.2; found 448.2 [M+H]$^+$.

I-146 4-((4-(((tert-butoxycarbonyl)(2-phenylcyclopropyl)amino)methyl)-1H-1,2,3-triazol-1-yl)methyl)benzoic Acid

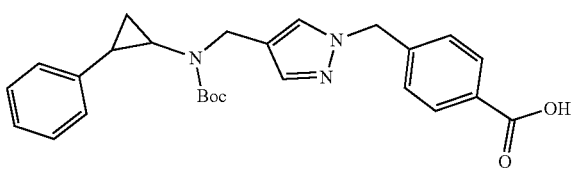 [SMILES: CC(C)(C)OC(=O)N(Cc1cnn(Cc2ccc(C(=O)O)cc2)c1)C1CC1c1ccccc1]

The compound was synthesized using I-41 following the procedure for the synthesis of I-120. LC-MS m/z calcd for $C_{25}H_{28}N_4O_4$, 448.2; found 449.2 [M+H]$^+$.

I-147 4-(2-(4-(((tert-butoxycarbonyl)(2-(4-fluorophenyl)cyclopropyl)amino)methyl)piperidin-1-yl)-2-oxoethyl)benzoic Acid

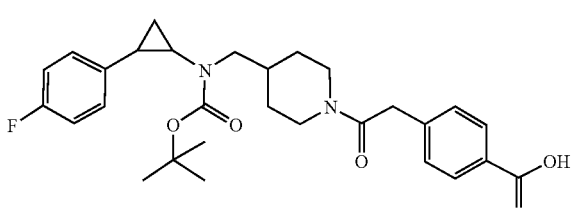

The compound was synthesized following the procedure for the synthesis of intermediate I-120 using the corresponding ester (ester was synthesized using 4-fluorocyclopropylamine and aldehyde A-24 using the procedure outlined for synthesis of I-2). LC-MS m/z calcd for $C_{29}H_{35}FN_2O_5$, 510.2; found 455.2 [M-55]$^+$.

I-148 4-(2-(((tert-butoxycarbonyl)(2-(4-fluorophenyl)cyclopropyl)amino)ethoxy)benzoic Acid

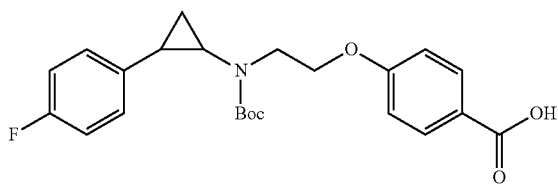 [SMILES: CC(C)(C)OC(=O)N(CCOc1ccc(C(=O)O)cc1)C1CC1c1ccc(F)cc1]

The compound was synthesized following the procedure for the synthesis of intermediate I-120 using the corresponding ester (ester was synthesized using 4-fluorocyclopropylamine and LXXVI, using the procedure outlined for synthesis of I-95). LC-MS m/z calcd for $C_{23}H_{26}FNO_5$, 415.2; found 416.2 $[M+H]^+$.

I-149 6-(2-(4-(((tert-butoxycarbonyl)(2-(4-fluorophenyl)cyclopropyl)amino)methyl)piperidin-1-yl)ethoxy)nicotinic acid

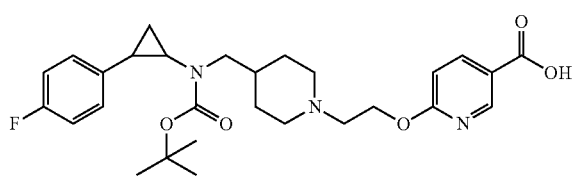 [SMILES: CC(C)(C)OC(=O)N(CC1CCN(CCOc2ccc(C(=O)O)cn2)CC1)C1CC1c1ccc(F)cc1]

The compound was synthesized using I-95 following the procedure for the synthesis of I-120. LC-MS m/z calcd for $C_{28}H_{36}FN_3O_5$, 513.2; found 514.3$[M+H]^+$.

I-150 2-((2-(4-(((tert-butoxycarbonyl)(2-(4-fluorophenyl)cyclopropyl)amino)methyl)piperidin-1-yl)ethyl)amino)pyrimidine-5-carboxylic acid

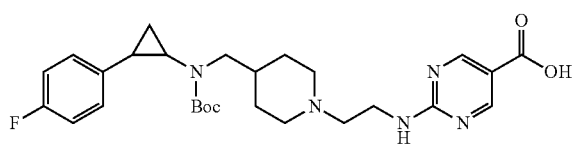 [SMILES: CC(C)(C)OC(=O)N(CC1CCN(CCNc2ncc(C(=O)O)cn2)CC1)C1CC1c1ccc(F)cc1]

The compound was synthesized using I-101 following the procedure for the synthesize of I-120. LC-MS m/z calcd for $C_{27}H_{36}FN_5O_4$, 513.3; found 512.3 $[M-H]^+$.

I-151 5-(N-(tert-butoxycarbonyl)-N-(2-(4-fluorophenyl)cyclopropyl)glycyl)-4,5,6,7-tetrahydrothieno[3,2-c]pyridine-2-carboxylic Acid

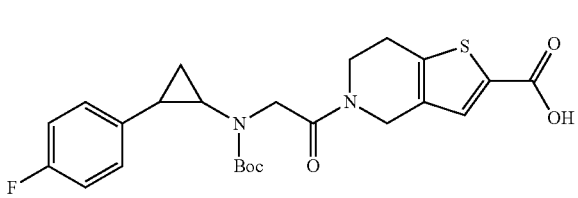 [SMILES: CC(C)(C)OC(=O)N(CC(=O)N1CCc2sc(C(=O)O)cc2C1)C1CC1c1ccc(F)cc1]

The compound was synthesized using I-102 following the procedure for the synthesis of I-120. LC-MS m/z calcd for $C_{24}H_{27}FN_2O_5S$, 474.2; found 475.2 $[M+H]^+$.

I-152 2-(N-(tert-butoxycarbonyl)-N-(2-(4-fluorophenyl)cyclopropyl)glycyl)-1,2,3,4-tetrahydroisoquinoline-7-carboxylic Acid

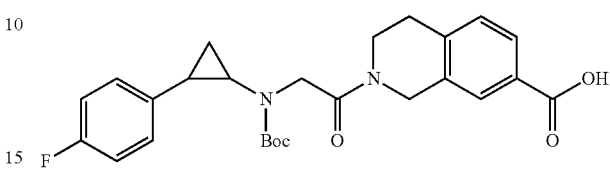

The compound was synthesized using I-103 following the procedure for the synthesis of I-120. LC-MS m/z calcd for $C_{26}H_{29}FN_2O_5$, 468.2; found 469.2 $[M+H]^+$.

I-153 2-(3-(4-(((tert-butoxycarbonyl)(2-phenylcyclopropyl)amino)methyl)piperidin-1-yl)propyl)oxazole-4-carboxylic acid

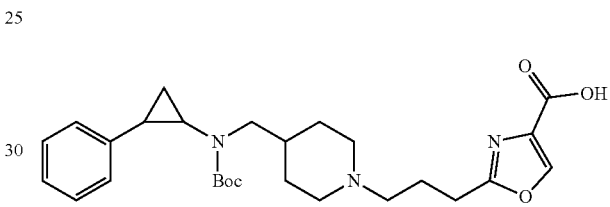

The compound was synthesized using I-112 following the procedure for the synthesis of I-120. LC-MS m/z calcd for $C_{27}H_{37}N_3O_5$, 483.2; found 484.2 $[M+H]^+$.

I-154 2-(3-(4-(((tert-butoxycarbonyl)(2-phenylcyclopropyl)amino)methyl)piperidin-1-yl)propyl)thiazole-5-carboxylic

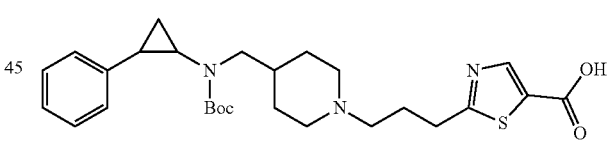

The compound was synthesized using I-111 following the procedure for the synthesis of I-120. LC-MS m/z calcd for $C_{27}H_{37}N_3O_4S$, 499.2; found 500.3 $[M+H]^+$.

I-155 4-((2-((tert-butoxycarbonyl)(2-(4-fluorophenyl)cyclopropyl)amino)acetamido)methyl)benzoic Acid

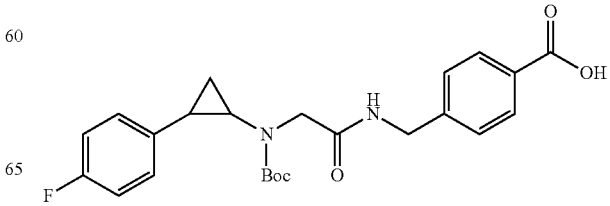

This compound I-155 was synthesized following the procedure for the synthesis of I-120 using the corresponding ester (ester was synthesized using 2-((tert-butoxycarbonyl)(2-(4-fluorophenyl)cyclopropyl)amino)acetic acid and methyl 4-(aminomethyl)benzoate using the procedure outlined for synthesis of I-103). LC-MS m/z calcd for $C_{24}H_{27}FN_2O_5$, 442.2; found 443.2 [M+H]$^+$.

I-156 (E)-4-(3-(4-(((tert-butoxycarbonyl)(2-(4-fluorophenyl)cyclopropyl)amino)methyl)piperidin-1-yl)-3-oxoprop-1-en-1-yl)benzoic acid

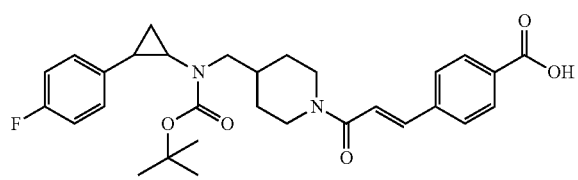 [SMILES: CC(C)(C)OC(=O)N(CC1CCN(C(=O)/C=C/c2ccc(C(=O)O)cc2)CC1)C1CC1c1ccc(F)cc1]

The compound was synthesized using I-114 following the procedure for the synthesis of I-120. LC-MS m/z calcd for $C_{30}H_{35}FN_2O_5$, 522.2; found 523.4 [M+H]$^+$.

I-157 (E)-4-(3-(3-(((2-(4-fluorophenyl)cyclopropyl)amino)methyl)azetidin-1-yl)-3-oxoprop-1-en-1-yl)benzoic acid

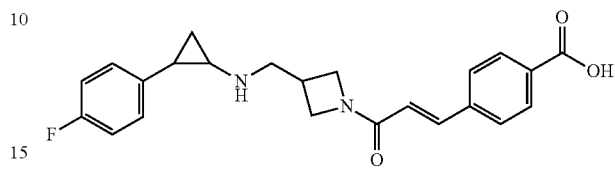

The compound was synthesized using I-117 following the procedure for the synthesis of I-120. LC-MS m/z calcd for $C_{23}H_{23}FN_2O_3$, 394.1; found 395.2 [M+H]$^+$.

I-158 4-((4-((((tert-butoxycarbonyl)(2-(4-fluorophenyl)cyclopropyl)amino)methyl)piperidine-1-carboxamido)methyl)benzoic Acid

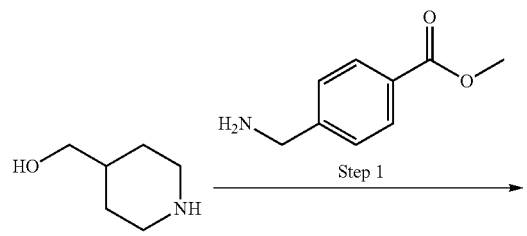

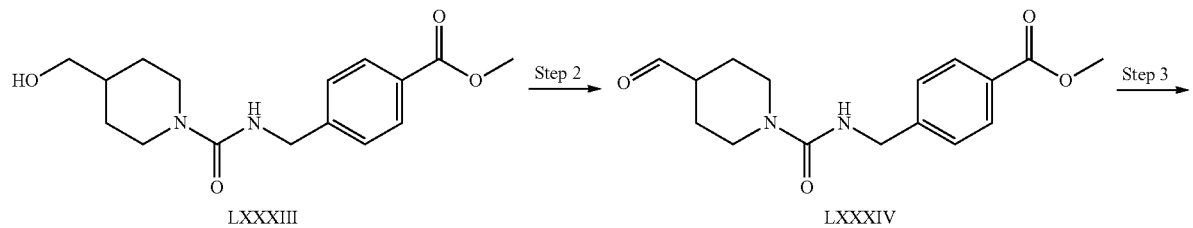

LXXXIII          LXXXIV

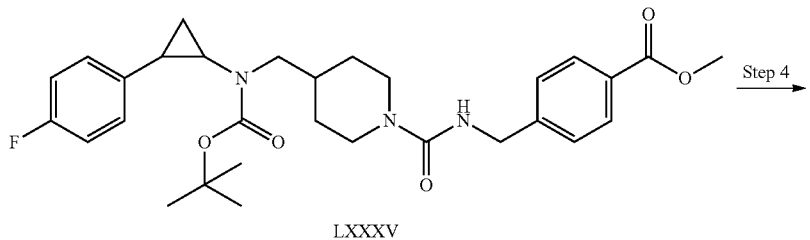

LXXXV

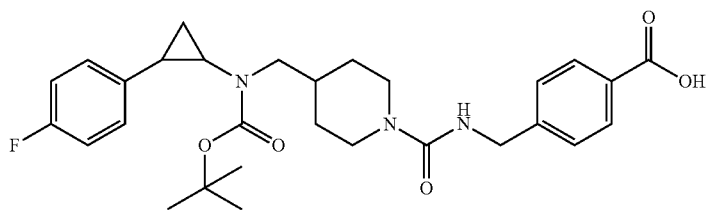

I-158

Step 1: methyl 4-((4-(hydroxymethyl)piperidine-1-carboxamido)methyl)benzoate-LXXXIII

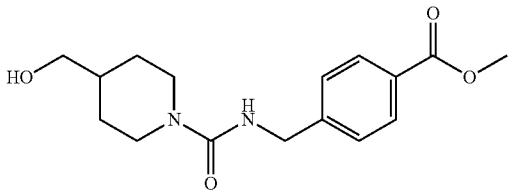 [SMILES: COC(=O)c1ccc(CNC(=O)N2CCC(CO)CC2)cc1]

To a stirred solution of methyl 4-(aminomethyl)benzoate (1.0 g, 6.06 mmol) in water was added carbonyldiimidazole (1.18 g, 7.26 mmol) 0° C. and stirred for 1 h and then warmed to room temperature. Then piperidine-4-ylmethanol (0.84 g, 7.26 mmol) was added and stirring continued for 12 h. The resultant white precipitate was filtrated through sintered funnel. The filtrate was extracted with dichloromethane (2×100 mL) and the combined organic portion was washed with water, brine, dried over sodium sulphate and concentrated under reduced pressure to get the product as off-white solid (LXXXIII, 0.26 g, 49%). LC-MS m/z calcd for $C_{16}H_{22}N_2O_4$, 306.1; found 307.2 [M+H]$^+$.

Step 2: methyl 4-((4-formylpiperidine-1-carboxamido)methyl)benzoate-LXXXIV

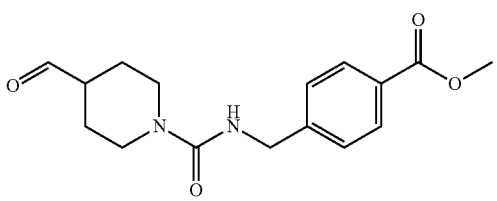 [SMILES: COC(=O)c1ccc(CNC(=O)N2CCC(C=O)CC2)cc1]

To a stirred solution of dimethyl sulphoxide (0.55 ml, 7.84 mmol) in dichloromethane oxalyl chloride (0.45 mL, 5.22 mmol) was slowly added at −78° C. After 30 min stirring, a solution of methyl 4-((4-(hydroxymethyl)piperidine-1-carboxamido)methyl)benzoate (LXXXIII, 0.4 g, 1.30 mmol) was added dropwise. Then the reaction mixture was stirred for 3 h at −78° C. Triethylamine (2.1 mL, 15.68 mmol) was added and stirred for 0.5 h. The reaction mixture was allowed to warm to room temperature. The reaction mixture was diluted with dichloromethane, washed with water, brine, dried over sodium sulphate and concentrated under reduced pressure to get the product as yellow brown oil (LXXXIV, 0.35 g, 89%). LC-MS m/z calcd for $C_{16}H_{20}N_2O_4$, 304.1; found 305.1 [M+H]$^+$.

Step 3: methyl 4-((4-(((tert-butoxycarbonyl)(2-(4-fluorophenyl)cyclopropyl)amino) methyl)piperidine-1-carboxamido)methyl)benzoate-LXXXV

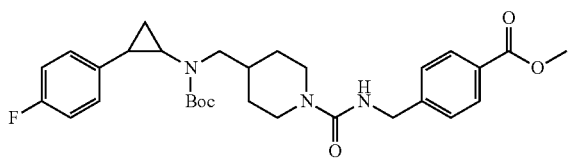 [SMILES: COC(=O)c1ccc(CNC(=O)N2CCC(CN(C(=O)OC(C)(C)C)C3CC3c3ccc(F)cc3)CC2)cc1]

To a stirred solution of 2-(4-flurophenyl)cyclopropylamine hydrochloride (0.2 g, 1.06 mmol) in methanol (15 mL) was added methyl 4-((4-formylpiperidine-1-carboxamido)methyl)benzoate (LXXXIV, 0.39 g, 1.28 mmol), sodium bicarbonate (0.08 g, 0.95 mmol), and molecular sieves (approx 1 g) at room temperature and the resulting mixture was heated to reflux for 2 h. The reaction mixture was cooled to 0° C. and sodium borohydride (0.35 g, 0.95 mmol) was added. Stirring was continued at room temperature for 1 h. Ice-water was added and the reaction mixture was filtered. The solvent was evaporated to get the residue. Water was added to the residue and extracted with dichloromethane (2×50 mL). The combined organic portion were washed with water, brine, dried over sodium sulphate and concentrated under reduced pressure to afford the crude product as brown oil (0.44 g). The crude product was dissolved intetrahydrofuran-water mixture (20 mL, 1:1). Sodium bicarbonate (0.26 g, 3.07 mmol) and Boc anhydride (0.26 mL, 1.25 mmol) were added at room temperature. The resulting mixture was stirred at that temperature for 1 h. The reaction mixture was diluted with ethylacetate and was washed with water, brine solution, dried over sodium sulphate and concentrated under reduced pressure to get the crude product which was purified by column chromatography using methanol-dichloromethane gradient to afford the titled product as brown thick oil (LXXXV, 0.22 g, 40%). LC-MS m/z calcd for $C_{30}H_{38}FN_3O_5$, 539.3; found 540.3 [M+H]$^+$.

Step 4: 4-((4-(((tert-butoxycarbonyl)(2-(4-fluorophenyl)cyclopropyl)amino)methyl) piperidine-1-carboxamido)methyl)benzoic Acid (Intermediate I-158)

I-158

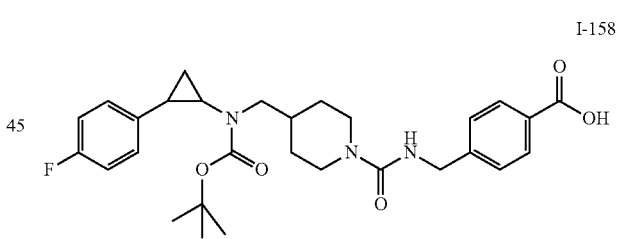

To a stirred solution of methyl 4-((4-(((tert-butoxycarbonyl)(2-(4-fluorophenyl)cyclopropyl)amino)methyl)piperidine-1-carboxamido)methyl)benzoate (LXXXV, 0.22 g, 0.40 mmol), in mixture of tetrahydrofuran-water (6 mL, 1:1), and lithium hydroxide (0.029 g, 1.22 mmol) was added and stirred for 1 h at room temperature. After completion of the reaction, the mixture was evaporated, the residue was diluted with ice-water, and acidified to pH 5 with 2N HCl. The aqueous layer was extracted with dichloromethane (50 mL×2). The combined organic layer was washed with water, brine, dried over sodium sulphate and concentrated under reduced pressure to get the product as off-white solid (I-158, 0.22 g, quantitative yield). LC-MS m/z calcd for $C_{29}H_{36}FN_3O_5$, 525.2; found 526.2 [M+H]$^+$.

I-159 4-(3-(4-(((tert-butoxycarbonyl)(2-phenylcyclopropyl)amino)methyl)-2-oxopiperidin-1-yl)propyl)benzoic Acid

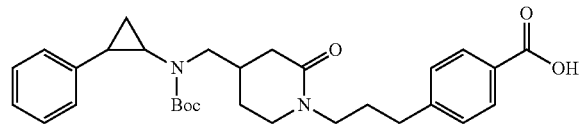 [SMILES: CC(C)(C)OC(=O)N(CC1CCN(CCCc2ccc(C(=O)O)cc2)C(=O)C1)C1CC1c1ccccc1]

The compound was synthesized using I-93 following the procedure for the synthesis of I-120. LC-MS m/z calcd for $C_{30}H_{38}N_2O_5$, 506.2; found 507.2 $[M+H]^+$.

I-160 4-((4-(((tert-butoxycarbonyl)(2-phenylcyclopropyl)amino)methyl)piperidin-1-yl)sulfonyl)benzoic acid

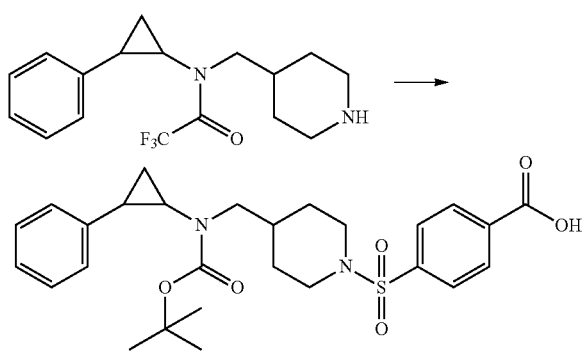

I-160

I-160 4-((4-((2,2,2-trifluoro-N-(2-phenylcyclopropyl)acetamido)methyl)piperidin-1-yl) sulfonyl)benzoic Acid To a stirred solution of 2,2,2-trifluoro-N-(2-phenylcyclopropyl)-N-(piperidin-4-ylmethyl)acetamide (1 g, 2.7 mmol) in dichloromethane (20 mL) was added triethylamine (1.1 mL, 8.10 mmol) and 4-(chlorosulfonyl)benzoic acid (0.66 g, 2.7 mmol) at 0° C. and stirred at room temperature for 2 h. The reaction mixture was concentrated under vacuum. Then the resultant residue was mixed with tetrahydrofuran-water (20 mL, 1:1) and lithium hydroxide (0.28 g, 6.7 mmol) was added at room temperature. After stirring for 3 h, Boc anhydride (0.88 mL, 4 mmol) was added and stirring continued for 2 h at room temperature. The solvent was evaporated and the residue was acidified with 2N HCl and extracted with dichloromethane. The combined organic portion was washed with water, brine, dried over sodium sulphate and concentrated under reduced pressure to afford the titled product as off-white solid (I-160, 1.2 g, 84%). LC-MS m/z calcd for $C_{27}H_{34}N_2O_6S$, 514.2; found 415.1 $[M-Boc+H]^+$.

I-161 4-(((4-(((tert-butoxycarbonyl)(2-phenylcyclopropyl)amino)methyl)piperidin-1-yl)sulfonyl)methyl)benzoic acid-ester Procedure

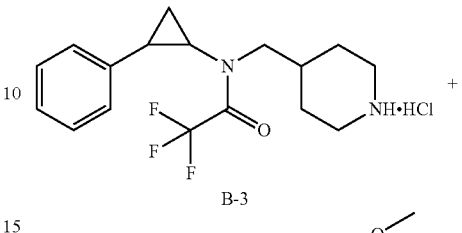

B-3

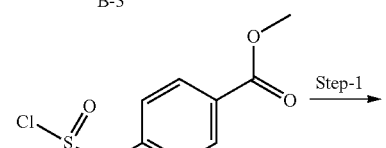

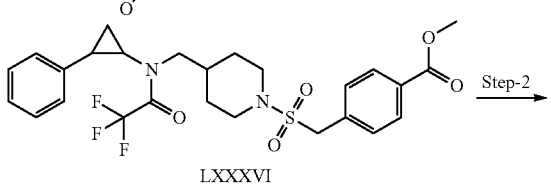

LXXXVI

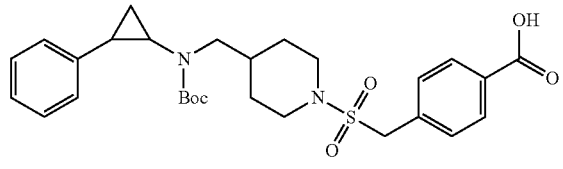

I-161

Step-1

The compound was synthesized using amine B-3 and methyl 4-((chlorosulfonyl)methyl)benzoate following the procedure for the synthesis of I-85.

Step-2

Hydrolysis of ester LXXXVI, followed by protection with (Boc)$_2$O resulted in I-161 as white solid. LC-MS m/z calcd for $C_{28}H_{36}N_2O_6S$, 528.2; found 529.2 $[M+H]^+$.

I-162 4-(2-((4-(((tert-butoxycarbonyl)(2-phenylcyclopropyl)amino)methyl)piperidin-1-yl)sulfonyl)ethyl)benzoic acid

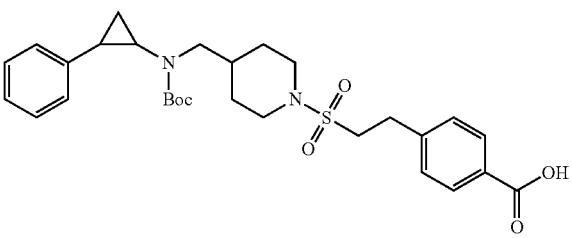 [SMILES: CC(C)(C)OC(=O)N(CC1CCN(S(=O)(=O)CCc2ccc(C(=O)O)cc2)CC1)C1CC1c1ccccc1]

The compound was synthesized using I-88 following the procedure for the synthesis of I-120. LC-MS m/z calcd for $C_{29}H_{38}N_2O_6S$, 542.2; found 543.2 $[M+H]^+$.

Example 1

Synthesis of (E)-3(4(((2(4cyclopropylphenyl)cyclopropl)amino)methyl)phenyl)-N-hydroxyacrylamide (XLIV)

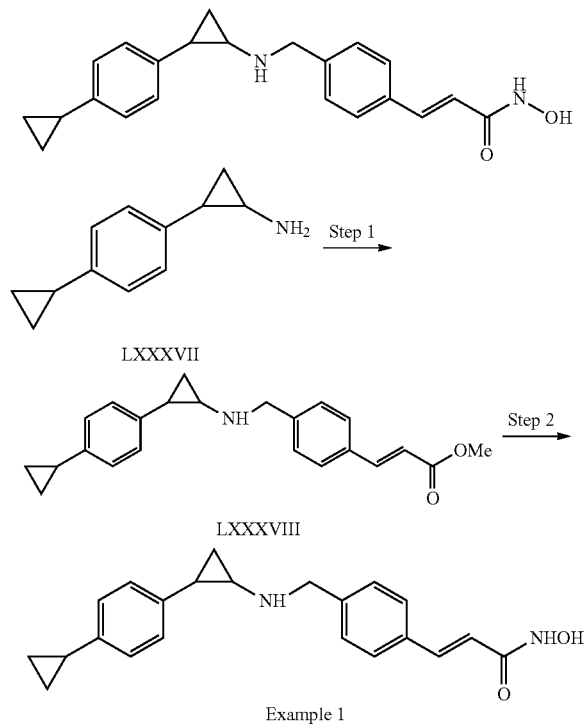

Step-1: (E)-3-(4-{[2-(4-Cyclopropyl-phenyl)-cyclopropylamino]-methyl}-phenyl)-acrylic Acid Methyl Ester (LXXXVIII)

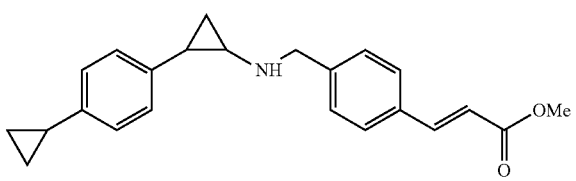 [SMILES: COC(=O)/C=C/c1ccc(CNC2CC2c2ccc(C3CC3)cc2)cc1]

2-(4-Cyclopropyl-phenyl)-cyclopropylamine.HCl (LXXXVII, 0.3 g, 1.43 mmol); which was prepared through cycloproponation of alkene (as described in *Bioorg. Med. Chem. Lett.*, 2008, 18, 3047-3051) was dissolved in dichloroethane and triethylamine (approx 1 mL) was added and stirred for 5 min. The solvent was concentrated under reduced pressure to get the free amine. To a stirred solution of (E)-3-(4-formyl-phenyl)-acrylic acid methyl ester (0.22 g, 1.19 mmol) which was synthesized using reported procedure (*J. Org. Chem.*, 2011, 76(19), 8036-8041) in 1,2-dichloroethane (20 mL) was added to the free cyclopropylamine and the resulting mixture was stirred at 60° C. for 1 h. Cooled to 0° C., sodium triacetoxyborohydride (0.5 g, 2.39 mmol) was added and the resulting mixture was stirred at room temperature for 12 h. The reaction mixture was filtered and the filtrate was diluted with dichloromethane (50 mL). The organic portion was washed with water and brine dried over sodium sulphate and concentrated under reduced pressure to afford the crude. The crude product was purified by column chromatography using ethylacetate-hexane gradient to obtain titled compound as gummy oil (LXXXVIII, 0.22 g, 55%), LC-MS m/z calcd for $C_{23}H_{25}NO_2$, 347.1; found 348.2 $[M+H]^+$.

Step-2: (E)-3-(4-{[2-(4-Cyclopropyl-phenyl)-cyclopropylamino]-methyl}-phenyl)-N-hydroxy-acrylamide—Example 1

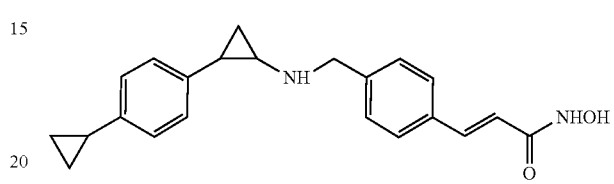

Example 1

To a solution of hydroxylamine hydrochloride (0.79 g, 11.41 mmol) in methanol (5 mL) was added a solution of potassium hydroxide (0.64 g, 11.41 mmol) in methanol (5 mL) at 5-10° C. and stirred at that temperature for 15 min. The formed precipitate was filtered through cotton plug and the filtrate was added to a solution of (E)-3-(4-{[2-(4-cyclopropyl-phenyl)-cyclopropylamino]-methyl}-phenyl)-acrylic acid methyl ester (LXXXVIII, 0.22 g, 0.63 mmol) in methanol at room temperature. The resulting mixture was stirred at room temperature for 3 h. The reaction mixture was diluted with water and extracted with ethylacetate (3×50 mL). The combined organic extract was dried over sodium sulphate and concentrated under reduced pressure to afford the crude product. The crude product was purified through trituration with acetonitrile solvent to afford the titled compound as an off-white solid (Example 1, 0.28 g, 13%). $^1$HNMR (400 MHz, DMSO-$d_6$): δ 10.7 (bs, 1H), 8.98 (bs, 1H), 7.46-7.36 (m, 3H), 7.32 (d, 2H, J=8 Hz), 6.88 (d, 2H, J=7.6 Hz), 6.83 (d, 2H, J=8 Hz), 6.41 (d, 1H, J=16 Hz), 3.75 (s, 2H), 2.91-2.75 (m, 1H), 2.17-2.10 (m, 1H), 1.85-1.72 (m, 2H), 0.96-0.91 (m, 1H), 0.88-0.82 (m, 3H), 0.58-0.53 (m, 2H). LC-MS m/z calcd for $C_{22}H_{24}N_2O_2$, 348.1; found 349.2 $[M+H]^+$. HPLC purity 98.6%.

Example 2

(E)-3-(4-{[2-(4-Fluoro-phenyl)-cyclopropylamino]-methyl}-phenyl)-N-hydroxy-acrylamide TFA Salt

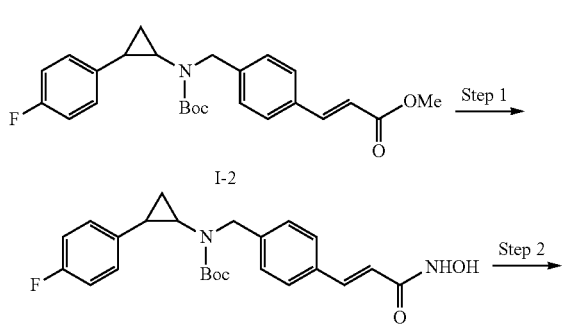

-continued

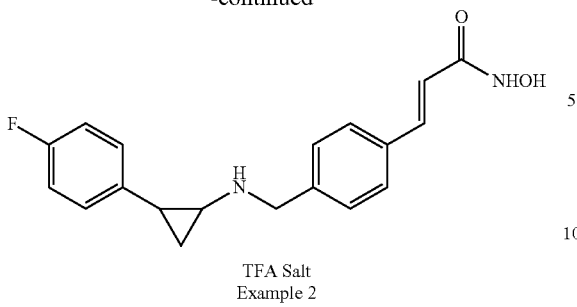

TFA Salt
Example 2

Step 1: [2-(4-Fluoro-phenyl)-cyclopropyl]-[4-((E)-2-hydroxycarbamoyl-vinyl)-benzyl]-carbamic Acid Tert-Butyl Ester (LXXXIX)

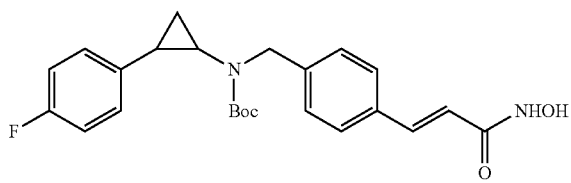

To a solution of hydroxylamine hydrochloride (0.147 g, 2.11 mmol) in methanol was added a solution of potassium hydroxide (0.12 g, 2.11 mmol) in methanol at 5-10° C. and stirred at that temperature for 15 min. The formed precipitate was filtered through cotton plug and the filtrate was added to a solution of (E)-3-[4-({tert-butoxycarbonyl-[2-(4-fluoro-phenyl)-cyclopropyl]-amino}-methyl)-phenyl]-acrylic acid methyl ester (I-2, 0.05 g, 0.12 mmol) in methanol (4 mL) at room temperature. Potassium hydroxide (0.12 g, 2.11 mmol) was added and the resulting mixture was stirred at room temperature for 1 h. The solvent was removed and water was added to the resulting residue. The pH of the aqueous portion was adjusted to 7.0 with 10% acetic acid solution and then extracted with ethylacetate (3×30 mL). The combined organic extract was washed with brine, dried over sodium sulphate and concentrated under reduced pressure to afford the crude product which was triturated with water and dried to afford the title compound as a white solid (LXXXIX, 0.035 g, 73%). LC-MS m/z calcd for $C_{24}H_{27}FN_2O_4$, 426.2; found 427.2 $[M+H]^+$.

Step 2: (E)-3-(4-{[2-(4-Fluoro-phenyl)-cyclopropylamino]-methyl}-phenyl)-N-hydroxy-acrylamide. TFA Salt—Example 2

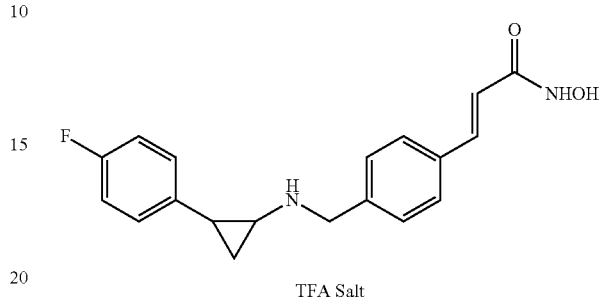

TFA Salt

To a stirred solution of [2-(4-fluoro-phenyl)-cyclopropyl]-[4-((E)-2-hydroxycarbamoyl-vinyl)-benzyl]-carbamic acid tert-butyl ester (LXXXIX, 0.15 g, 0.36 mmol) in dry dichloromethane (2 mL) was added trifluoroacetic acid (2 mL) at 0° C. and the resulting mixture was stirred at that temperature for 1 h. The progress of the reaction was monitored by TLC. The solvent was concentrated under reduced pressure to get the crude product which was purified by reverse-phase HPLC using Chemsil $C_{18}$ (250 mm×4.6 mm×5mic) column with 0.1% TFA in water:ACN to afford the pure product as off-white solid (Example 2, 0.04 g, 26%).

$^1$HNMR (400 MHz, DMSO-$d_6$): δ 10.76 (bs, 1H), 9.18 (bs, 1H), 9.04 (bs, 1H), 7.59 (d, 2H, J=7.6 Hz), 7.52-7.42 (m, 3H), 7.18-7.07 (m, 4H), 6.48 (d, 1H, J=16 Hz), 4.30 (s, 2H), 2.89 (bs, 1H), 2.41-2.32 (m, 1H), 1.45-1.37 (m, 1H), 1.32-1.25 (m, 1H). LC-MS m/z calcd for $C_{19}H_{19}FN_2O_2$, 326.1; found 327.3 $[M+H]^+$. HPLC purity 97.1%.

The following compounds were synthesized using the procedure exemplified in Example 2

Example 3 (E)-3-(4-(((2-(4-((4-fluorobenzyl)oxy)phenyl)cyclopropyl)amino)methyl)phenyl)-N-hydroxyacrylamide TFA Salt

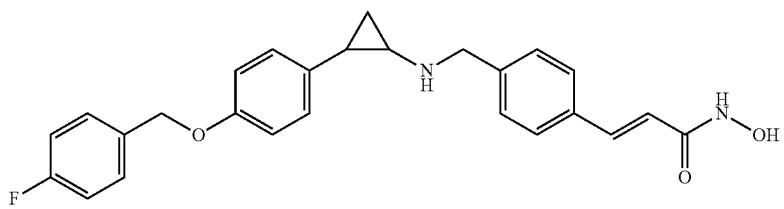 [SMILES: O=C(/C=C/c1ccc(CNC2CC2c2ccc(OCc3ccc(F)cc3)cc2)cc1)NO]

The compound was synthesized using the I-3 following the procedure for Example 2. $^1$HNMR (400 MHz, DMSO-$d_6$): δ 10.75 (bs, 1H), 9.02 (bs, 1H), 7.57-7.55 (m, 2H), 7.49-7.41 (m, 5H), 7.20 (t, 2H, J=9 Hz), 7.00 (d, 2H, J=8.4 Hz), 6.89 (d, 2H, J=8.4 Hz), 6.47 (d, 1H, J=15.6 Hz), 5.04 (s, 2H), 4.19-4.14 (m, 2H), 2.76-2.45 (m, 1H), 2.24-2.15 (m, 1H), 1.31-1.22 (m, 1H), 1.14-1.10 (m, 1H). LC-MS m/z calcd for $C_{26}H_{25}FN_2O_3$, 432.1. found 433.2 $[M+H]^+$. HPLC purity 96.3%.

Example 4 (E)-N-hydroxy-3-(4-(4-(((2-phenylcyclo-propyl)amino)methyl)piperidin-1-yl)phenyl)acrylamide TFA Salt

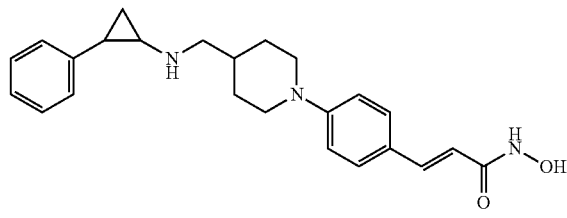 [SMILES: O=C(/C=C/c1ccc(N2CCC(CNC3CC3c3ccccc3)CC2)cc1)NO]

The compound was synthesized using the I-4 following the procedure for Example 2. ¹HNMR (400 MHz, DMSO-$d_6$): δ 10.53 (bs, 1H), 8.78 (bs, 1H), 7.42-7.26 (m, 5H), 7.24-7.15 (m, 3H), 6.94 (d, 2H, J=8.8 Hz), 6.22 (d, 1H, J=15.6 Hz), 5.32 (bs, 1H), 3.86-3.80 (m, 2H), 3.65-3.59 (m, 1H), 3.15-3.11 (m, 1H), 3.08-2.96 (m, 3H), 2.79-2.70 (m, 2H), 2.02-1.96 (m, 1H), 1.90-1.76 (m, 3H), 1.49-1.41 (m, 1H), 0.86-0.80 (m, 1H). LC-MS m/z calcd for $C_{24}H_{29}N_3O_2$, 391.2; found 392.3 $[M+H]^+$. HPLC purity 99.4%.

Example 5 (E)-3-(4-(((2-(4'-chloro-[1,1'-biphenyl]-4-yl)cyclopropyl)amino)methyl)phenyl)-N-hydroxyacrylamide TFA Salt

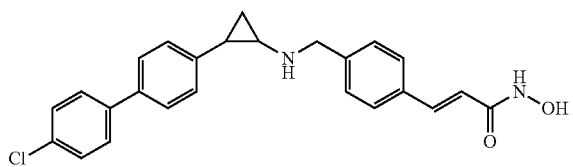 [SMILES: O=C(/C=C/c1ccc(CNC2CC2c2ccc(-c3ccc(Cl)cc3)cc2)cc1)NO]

The compound was synthesized using the I-5 following the procedure for Example 2. ¹HNMR (400 MHz, DMSO-$d_6$): δ 10.75 (s, 1H), 9.20 (bs, 1H), 9.03 (s, 1H), 7.66 (d, 2H, J=8.4 Hz), 7.61-7.56 (m, 4H), 7.50-7.42 (m, 5H), 7.21-7.19 (m, 2H), 6.48 (d, 1H, J=16 Hz), 4.32-4.25 (m, 2H), 1.48-1.32 (m, 2H), 1.25-1.15 (m, 2H). LC-MS m/z calcd for $C_{25}H_{23}ClN_2O_2$, 418.1; found 419.2 $[M+H]^+$. HPLC purity 92.8%.

Example 6 (E)-3-(4-(((2-(4-(3,5-dimethylisoxazol-4-yl)phenyl)cyclopropyl)amino)methyl)phenyl)-N-hydroxyacrylamide TFA Salt

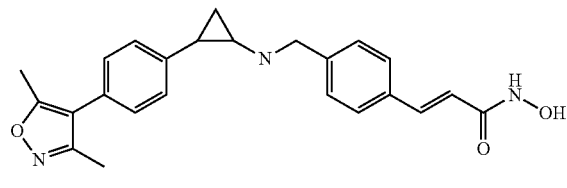

TFA Salt

The compound was synthesized using the I-6 following the procedure for Example 2. ¹HNMR (400 MHz, DMSO-$d_6$): δ 10.74 (s, 1H), 9.25 (bs, 2H), 9.02 (bs, 1H), 7.61 (d, J=7.6 Hz, 2H), 7.50 (d, J=8 Hz, 2H), 7.44 (d, J=15.6 Hz, 1H), 7.28 (d, J=8 Hz, 2H), 7.21 (d, J=8 Hz, 2H), 6.47 (d, J=16 Hz, 1H), 4.32 (s, 2H), 2.96 (m, 1H), 2.55 (m, 1H), 2.36 (s, 3H), 2.18 (s, 3H), 1.50-1.40 (m, 1H), 1.40-1.30 (m, 1H). LC-MS m/z calcd for $C_{24}H_{25}N_3O_3$, 403.2; found 404.2 $[M+H]^+$. HPLC purity 98.8%.

Example 7 (E)-N-hydroxy-3-(4-(((2-(4-(pyrimidin-5-yl)phenyl)cyclopropyl)amino)methyl)phenyl)acrylamide TFA Salt

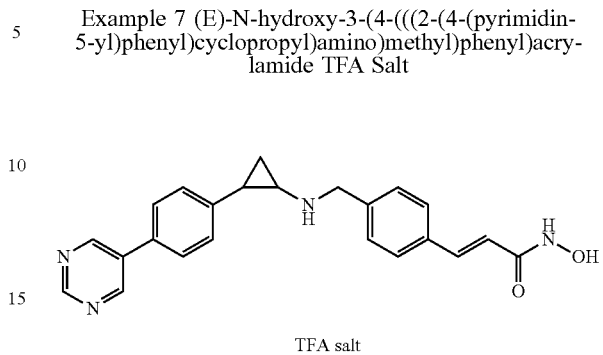

TFA salt

The compound was synthesized using the I-7 following the procedure for Example 2. ¹HNMR (400 MHz, DMSO-$d_6$): δ 10.76 (s, 1H), 9.36 (bs, 2H), 9.25 (bs, 1H), 9.16 (s, 1H), 9.12 (s, 2H), 7.74 (d, J=8.4 Hz, 2H), 7.60 (d, J=8.0 Hz, 2H), 7.50 (d, J=8.0 Hz, 2H), 7.45 (d, J=15.6 Hz, 1H), 7.29 (d, J=8.0 Hz, 2H), 6.48 (d, J=15.6 Hz, 1H), 4.34 (s, 2H), 3.02 (m, 1H), 2.55 (m, 1H), 1.52-1.42 (m, 1H), 1.42-1.34 (m, 1H). LC-MS m/z calcd for $C_{23}H_{22}N_4O_2$, 386.2; found 387.2 $[M+H]^+$. HPLC purity 98.3%.

Example 8 2-(4-(((2-(4-fluorophenyl)cyclopropyl)amino)methyl)piperidin-1-yl)-N-hydroxypyrimidine-5-carboxamide TFA Salt

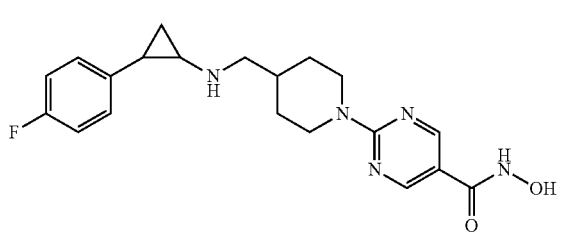 [SMILES: O=C(NO)c1cnc(N2CCC(CNC3CC3c3ccc(F)cc3)CC2)nc1]

The compound was synthesized using the I-8 following the procedure for Example 2. ¹HNMR (400 MHz, DMSO-$d_6$): δ 11.02 (s, 1H), 8.75 (bs, 2H), 8.64 (s, 2H), 7.23-7.20 (dd, J=5.6, 5.6 Hz, 2H), 7.14-7.10 (dd, J=9.2, 8.8 Hz, 2H), 4.70-4.67 (d, J=13.6 Hz, 2H), 3.01-2.92 (m, 5H), 2.44-2.41 (m, 1H), 2.05-1.95 (m, 1H), 1.82-1.79 (m, 2H), 1.47-1.42 (m, 1H), 1.30-1.25 (q, 1H), 1.20-1.12 (m, 2H). LC-MS m/z calcd $[M+H]^+$ 385.2. found 386.2. HPLC purity 99.8%.

Example 9 2-[4-(2-Phenyl-cyclopropylamino)-piperidin-1-yl]-pyrimidine-5-carboxylic Acid Hydroxyamide TFA Salt

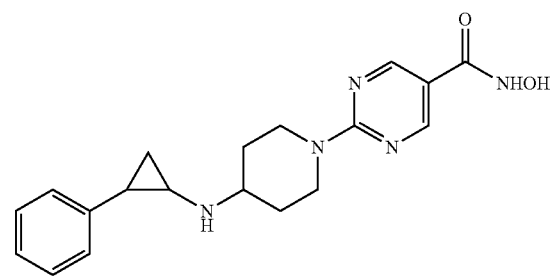

The compound was synthesized using the I-9 following the procedure for Example 2. $^1$HNMR (400 MHz, DMSO-$d_6$): δ 10.96 (bs, 1H), 8.94 (bs, 1H), 7.24-7.18 (m, 2H), 7.12-7.08 (m, 1H), 7.04-7.00 (m, 2H), 4.50-4.4 (m, 2H), 3.20-3.10 (m, 2H), 2.90-2.80 (m, 1H), 2.28-2.20 (m, 2H), 1.88-1.75 (m, 3H), 1.28-1.16 (m, 2H), 0.98-0.92 (m, 2H), 0.86-0.81 (m, 1H). LC-MS m/z calcd for $C_{19}H_{23}N_5O_2$, 353.2; found 354.2 [M+H]$^+$. HPLC purity 99.8%.

Example 10 2-{4-[2-(4-Fluoro-phenyl)-cyclopropylamino]-piperidin-1-yl}-pyrimidine-5-carboxylic acid hydroxyamide TFA salt

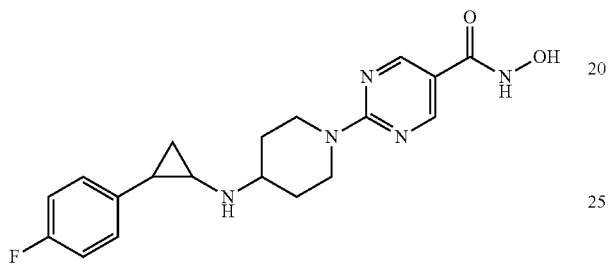

The compound was synthesized using the I-10 following the procedure for Example 2. $^1$HNMR (400 MHz, DMSO-$d_6$): δ 10.95 (bs, 1H), 8.93 (bs, 1H), 8.63 (s, 2H), 7.09-7.01 (m, 4H), 4.50-4.41 (m, 2H), 3.18-3.08 (m, 2H), 2.88-2.80 (m, 1H), 2.25-2.18 (m, 1H), 1.86-1.75 (m, 3H), 1.28-1.15 (m, 3H), 0.99-0.89 (m, 2H). LC-MS m/z calcd for $C_{19}H_{22}FN_5O_2$, 371.1; found 372.1 [M+H]$^+$. HPLC purity 97.7%.

Example 11 2-(4-(((2-(4-((4-fluorobenzyl)oxy)phenyl)cyclopropyl)amino)methyl)piperidin-1-yl)-N-hydroxypyrimidine-5-carboxamide TFA Salt

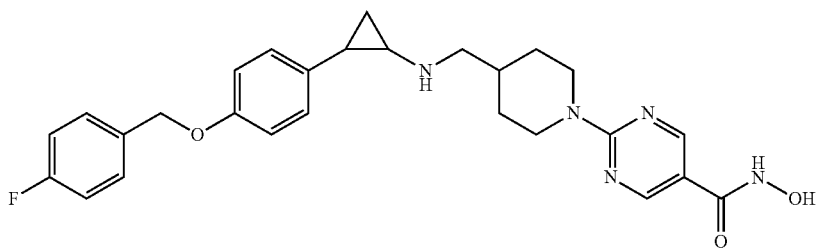 [SMILES: O=C(NO)c1cnc(N2CCC(CNC3CC3c3ccc(OCc4ccc(F)cc4)cc3)CC2)nc1]

The compound was synthesized using the I-11 following the procedure for Example 2. $^1$HNMR (400 MHz, DMSO-$d_6$): δ 11.03 (bs, 1H), 8.97 (bs, 1H), 8.72 (bs, 2H), 8.66 (s, 2H), 7.48-7.45 (m, 2H), 7.23-7.18 (m, 2H), 7.11 (d, 2H, J=8.4 Hz), 6.94 (d, 2H, J=8 Hz), 5.06 (s, 2H), 4.71 (d, 2H, J=12.4 Hz), 3.08-2.85 (m, 6H), 2.40-2.34 (m, 2H), 2.05-1.94 (m, 1H), 1.84-1.77 (m, 2H), 1.42-1.36 (m, 1H), 1.24-1.11 (m, 1H). LC-MS m/z calcd for $C_{27}H_{30}FN_5O_3$, 491.2; found 492.4 [M+H]$^+$. HPLC purity 96.7%.

Example 12 2-(4-((2-(4-((4-fluorobenzyl)oxy)phenyl)cyclopropyl)amino)piperidin-1-yl)-N-hydroxypyrimidine-5-carboxamide TFA Salt

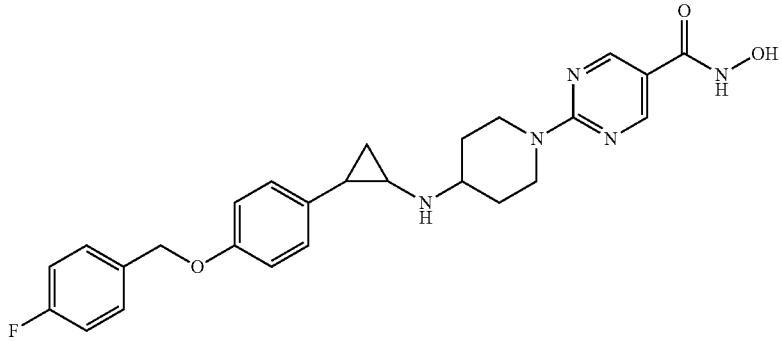 [SMILES: O=C(NO)c1cnc(N2CCC(NC3CC3c3ccc(OCc4ccc(F)cc4)cc3)CC2)nc1]

The compound was synthesized using the I-12 following the procedure for Example 2. ¹HNMR (400 MHz, DMSO-$d_6$): δ 11.07 (bs, 1H), 9.0 (bs, 1H), 8.88 (bs, 1H), 8.84 (bs, 1H), 8.69 (s, 2H), 7.49-7.35 (m, 2H), 7.20 (t, 2H, J=8.8 Hz), 7.11 (d, 2H, J=8.4 Hz), 6.94 (d, 2H, J=8.4 Hz), 5.06 (s, 2H), 4.77 (d, 2H, J=12.8 Hz), 3.63-3.54 (m, 1H), 3.05-2.90 (m, 4H), 2.14-2.08 (m, 2H), 1.52-1.44 (m, 2H), 1.39-1.32 (m, 1H), 1.30-1.23 (m, 1H). LC-MS m/z calcd for $C_{26}H_{28}FN_5O_3$, 477.2; found 476.2 [M−H]⁺. HPLC purity 99.7%.

Example 13 2-(4-((2-(4'-chloro-[1,1'-biphenyl]-4-yl)cyclopropyl)amino)piperidin-1-yl)-N-hydroxypyrimidine-5-carboxamide TFA Salt

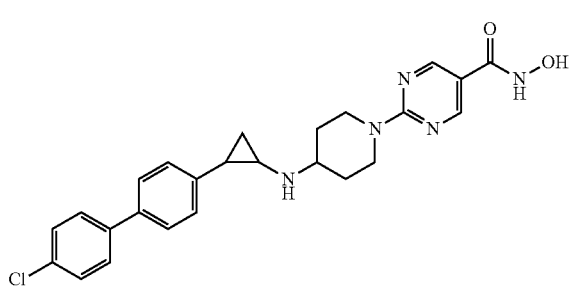 [SMILES: O=C(NO)c1cnc(N2CCC(NC3CC3c3ccc(-c4ccc(Cl)cc4)cc3)CC2)nc1]

The compound was synthesized using the I-13 following the procedure for Example 2. ¹HNMR (400 MHz, DMSO-$d_6$): δ 11.07 (s, 1H), 9.01-8.96 (m, 3H), 8.68 (s, 2H), 7.67 (d, 2H, J=8.4 Hz), 7.61 (d, 2H, J=8.0 Hz), 7.50 (d, 2H, J=8.4 Hz), 7.29 (d, 2H, J=7.6 Hz), 4.78 (d, 2H, J=12.8 Hz), 3.60 (bs, 1H), 3.02 (t, 4H, J=12.4 Hz), 2.13 (d, 2H, J=10.8 Hz), 1.50-1.47 (m, 3H), 1.40-1.38 (m, 1H). LC-MS m/z calcd for $C_{25}H_{26}ClN_5O_2$, 464.1; found 464.2 [M+H]⁺. HPLC purity 98.8%.

Example 14 2-(4-(((2-(4'-chloro-[1,1'-biphenyl]-4-yl)cyclopropyl)amino)methyl)piperidin-1-yl)-N-hydroxypyrimidine-5-carboxamide TFA Salt

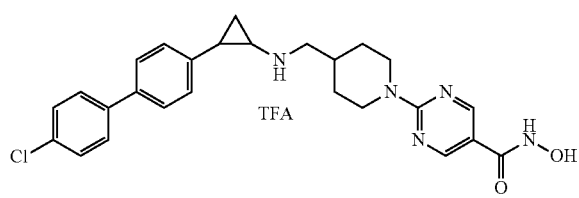 [SMILES: O=C(NO)c1cnc(N2CCC(CNC3CC3c3ccc(-c4ccc(Cl)cc4)cc3)CC2)nc1]

The compound was synthesized using the I-14 following the procedure for Example 2. ¹HNMR (400 MHz, DMSO-$d_6$): δ 11.03 (bs, 1H), 8.97 (bs, 1H), 8.89 (bs, 2H), 8.66 (s, 2H), 7.67 (d, 2H, J=11.2 Hz), 7.61 (d, 2H, J=8 Hz), 7.49 (d, 2H, J=8 Hz), 7.28 (d, 2H, J=7.6 Hz), 4.71 (d, 2H, J=13.2 Hz), 3.09-2.91 (m, 5H), 2.09-1.96 (m, 1H), 1.86-1.78 (m, 2H), 1.52-1.48 (m, 1H), 1.41-1.31 (m, 1H), 1.27-1.12 (m, 3H). LC-MS m/z calcd for $C_{26}H_{28}ClN_5O_2$, 477.1; found 476.4 [M−H]⁺. HPLC purity 98.8%.

Example 15 2-(4-(((2-(4'-fluoro-[1,1'-biphenyl]-4-yl)cyclopropyl)amino)methyl)piperidin-1-yl)-N-hydroxypyrimidine-5-carboxamide TFA Salt

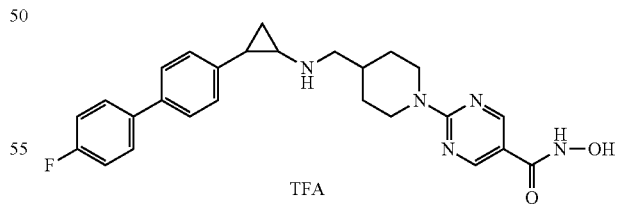

The compound was synthesized using the I-15 following the procedure for Example 2. ¹HNMR (400 MHz, DMSO-$d_6$): δ 11.02 (bs, 1H), 8.96 (bs, 1H), 8.80 (bs, 1H), 8.73 (bs, 1H), 8.65 (s, 2H), 7.69-7.64 (m, 2H), 7.59-7.55 (m, 2H), 7.28-7.23 (m, 4H), 4.74-4.55 (m, 2H), 3.08-2.93 (m, 6H), 2.05-1.96 (m, 1H), 1.84-1.80 (m, 2H), 1.51-1.44 (m, 1H), 1.36-1.32 (m, 1H), 1.24-1.15 (m, 2H). LC-MS m/z calcd for $C_{26}H_{38}FN_5O_2$, 461.2; found 462.2 [M+H]⁺. HPLC purity 99.5%.

Example 16 2-(4-(((2-(4-(3,5-dimethylisoxazol-4-yl)phenyl)cyclopropyl)amino)methyl)piperidin-1-yl)-N-hydroxypyrimidine-5-carboxamide TFA Salt

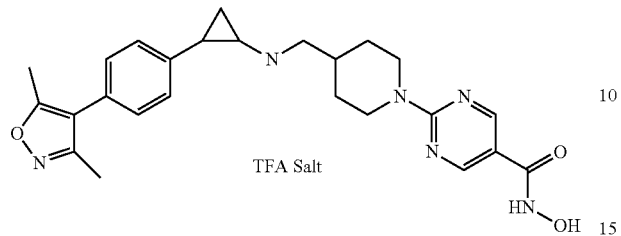

The compound was synthesized using the I-16 following the procedure for Example 2. ¹HNMR (400 MHz, DMSO-$d_6$): δ 11.02 (bs, 1H), 8.95 (bs, 1H), 8.85 (bs, 1H), 8.73 (bs, 1H), 8.65 (s, 2H), 7.31-7.26 (m, 4H), 4.69 (d, J=12.8 Hz, 2H), 3.08-2.92 (m, 5H), 2.55 (m, 1H), 2.35 (s, 3H), 2.18 (s, 3H), 2.06-1.95 (m, 1H), 1.85-1.78 (m, 2H), 1.53-1.45 (m, 1H), 1.40-1.32 (m, 1H), 1.25-1.10 (m, 2H). LC-MS m/z calcd for $C_{25}H_{30}N_6O_3$, 462.2; found 463.2 [M+H]⁺. HPLC purity 99.1%.

Example 17 N-hydroxy-2-(4-(((2-(4-(pyrimidin-5-yl)phenyl)cyclopropyl)amino)methyl)piperidin-1-yl)pyrimidine-5-carboxamide TFA Salt

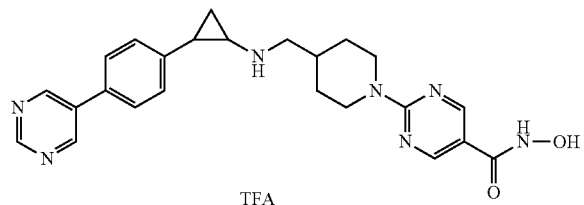 [SMILES: O=C(NO)c1cnc(N2CCC(CNC3CC3c3ccc(-c4cncnc4)cc3)CC2)nc1]

The compound was synthesized using the I-17 following the procedure for Example 2. ¹HNMR (400 MHz, DMSO-$d_6$): δ 11.02 (bs, 1H), 9.16 (s, 1H), 9.12 (s, 2H), 8.90 (bs, 2H), 8.83 (bs, 1H), 8.65 (s, 2H), 7.76 (d, J=8.4 Hz, 2H), 7.35 (d, J=8 Hz, 2H), 4.73-4.67 (m, 2H), 3.08-2.93 (m, 5H), 2.08-1.92 (m, 2H), 1.84-1.78 (m, 2H), 1.54-1.50 (m, 1H), 1.42-1.35 (m, 1H), 1.25-1.13 (m, 2H). LC-MS m/z calcd for $C_{24}H_{27}N_7O_2$, 445.2. found 446.2 [M+H]⁺. HPLC purity 99.8%.

Example 18 N-hydroxy-2-(4-(((2-(4-methoxyphenyl)cyclopropyl)amino)methyl)piperidin-1-yl)pyrimidine-5-carboxamide TFA Salt

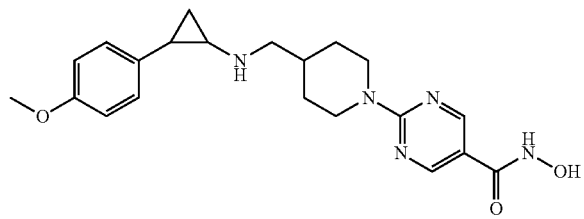 [SMILES: COc1ccc(C2CC2NCC2CCN(c3ncc(C(=O)NO)cn3)CC2)cc1]

The compound was synthesized using the I-18 following the procedure for Example 2. ¹HNMR (400 MHz, DMSO-$d_6$): δ 11.03 (bs, 1H), 8.96 (bs, 1H), 8.79 (bs, 2H), 8.68 (s, 2H), 7.10 (d, 2H, J=8.4 Hz), 6.86 (d, 2H, J=8.8 Hz), 4.77 (d, 2H, J=13.2 Hz), 3.71 (s, 3H), 3.05-2.85 (m, 5H), 2.42-2.32 (m, 1H), 2.05-1.97 (m, 1H), 1.83-1.80 (m, 2H), 1.42-1.37 (m, 1H), 1.24-1.13 (m, 3H). LC-MS m/z calcd for $C_{21}H_{27}N_5O_3$, 397.2; found 398.2 [M+H]⁺. HPLC purity 96.2%.

Example 19 N-hydroxy-2-(4-((2-(4-methoxyphenyl)cyclopropyl)amino)piperidin-1-yl)pyrimidine-5-carboxamide TFA Salt

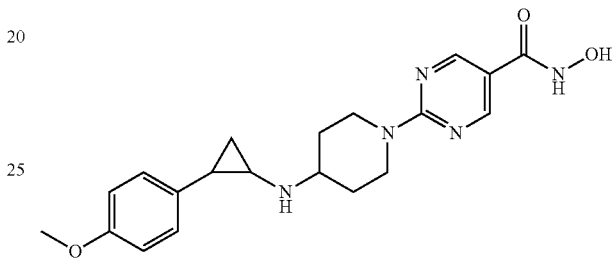

The compound was synthesized using the I-19 following the procedure for Example 2. ¹HNMR (400 MHz, DMSO-$d_6$): δ 11.06 (bs, 1H), 9.04 (bs, 2H), 8.67 (s, 2H), 7.19 (d, 2H, J=8.4 Hz), 6.85 (d, 2H, J=9.2 Hz), 4.78-4.73 (m, 2H), 3.70 (s, 3H), 3.61-3.53 (m, 1H), 3.03-2.96 (m, 2H), 2.92-2.84 (m, 1H), 2.35-2.30 (m, 1H), 2.11-2.04 (m, 2H), 1.51-1.45 (m, 2H), 1.40-1.34 (m, 1H), 1.27-1.21 (m, 1H). LC-MS m/z calcd for $C_{20}H_{25}N_5O_3$, 383.2; found 384.2 [M+H]⁺. HPLC purity 97.1%.

Example 20 2-(4-(((((1R,2S)-2-(4-fluorophenyl)cyclopropyl)amino)methyl)piperidin-1-yl)-N-hydroxypyrimidine-5-carboxamide TFA Salt

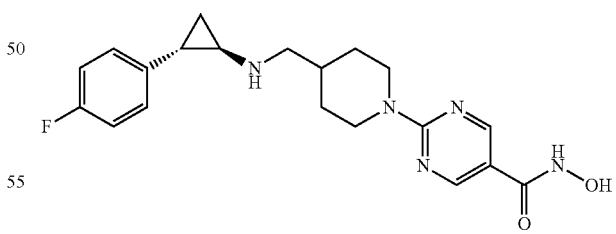

The compound was synthesized using the I-20 following the procedure for Example 2. ¹HNMR (400 MHz, DMSO-$d_6$): δ 11.02 (bs, 1H), 8.95 (bs, 1H), 8.64 (s, 2H), 7.22-7.15 (m, 2H), 7.13-7.06 (m, 2H), 4.72-4.62 (m, 2H), 3.01-2.92 (m, 4H), 2.89-2.81 (m, 1H), 2.35-2.28 (m, 1H), 2.00-1.91 (m, 1H), 1.84-1.76 (m, 2H), 1.40-01.38 (m, 1H), 1.35-1.09 (m, 3H). LC-MS m/z calcd for $C_{20}H_{24}FN_5O_2$[M+H]⁺ 385.1. found 386.2. HPLC purity 98.2%.

Example 21 2-(4-((((1S,2R)-2-(4-fluorophenyl)cyclopropyl)amino)methyl)piperidin-1-yl)-N-hydroxypyrimidine-5-carboxamide TFA Salt

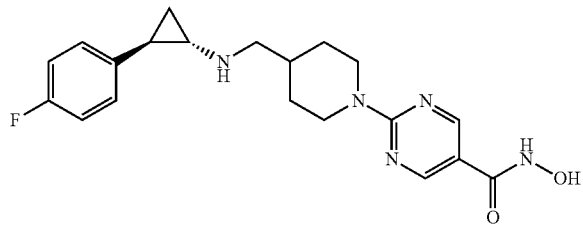 [SMILES: O=C(NO)c1cnc(N2CCC(CN[C@H]3C[C@@H]3c3ccc(F)cc3)CC2)nc1]

The compound was synthesized using the I-21 following the procedure for Example 2. ¹HNMR (400 MHz, DMSO-d$_6$): δ 11.02 (bs, 1H), 8.95 (bs, 1H), 8.64 (s, 2H), 7.22-7.15 (m, 2H), 7.13-7.06 (m, 2H), 4.72-4.62 (m, 2H), 3.01-2.92 (m, 4H), 2.89-2.81 (m, 1H), 2.35-2.28 (m, 1H), 2.00-1.91 (m, 1H), 1.84-1.76 (m, 2H), 1.40-01.38 (m, 1H), 1.35-1.09 (m, 3H). LC-MS m/z calcd for $C_{20}H_{24}FN_5O_2$[M+H]$^+$ 385.1. found 386.1. HPLC purity 98.1%.

Example 22 4-(4-(((2-(4-fluorophenyl)cyclopropyl)amino)methyl)piperidin-1-yl)-N-hydroxybenzamide TFA Salt

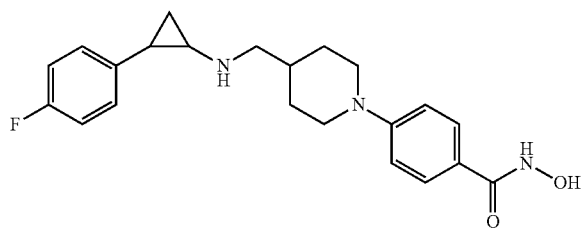 [SMILES: O=C(NO)c1ccc(N2CCC(CNC3CC3c3ccc(F)cc3)CC2)cc1]

The compound was synthesized using the I-22 following the procedure for Example 2. ¹HNMR (400 MHz, DMSO-d$_6$): δ 10.98 (bs, 1H), 8.82 (bs, 2H), 7.61 (d, 2H, J=8.4 Hz), 7.24-7.20 (m, 2H), 7.16-7.08 (m, 2H), 6.92 (d, 2H, J=8.4 Hz), 3.95-3.80 (m, 2H), 3.04-2.90 (m, 3H), 2.79-2.70 (m, 2H), 2.42-2.35 (1H, m), 1.87-1.77 (m, 3H), 1.46-1.41 (m, 1H), 1.34-1.20 (m, 3H). LC-MS m/z calcd for $C_{22}H_{26}FN_3O_2$, 383.2; found 384.2 [M+H]$^+$. HPLC purity 98.0%.

Example 23 N-hydroxy-2-(2-(((2-phenylcyclopropyl)amino)methyl)-5,6-dihydroimidazo[1,2-a]pyrazin-7(8H)-yl)pyrimidine-5-carboxamide TFA Salt

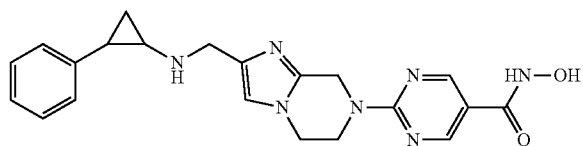 [SMILES: O=C(NO)c1cnc(N2CCn3cc(CNC4CC4c4ccccc4)nc3C2)nc1]

The compound was synthesized using the I-23 following the procedure for Example 2. ¹HNMR (400 MHz, DMSO-d$_6$): δ 8.71 (s, 2H), 7.22-7.15 (m, 2H), 7.09-7.05 (m, 1H), 7.01-6.94 (m, 2H), 6.86 (s, 1H), 4.86 (s, 2H), 4.45-4.38 (m, 2H), 4.02-3.93 (m, 2H), 3.61 (s, 2H), 2.30-2.25 (m, 1H), 1.82-1.75 (m, 1H), 1.02-0.88 (m, 2H). LC-MS m/z calcd for $C_{21}H_{23}N_7O_2$, 405.1; found 406.2 [M+H]$^+$. HPLC purity 98.2%. (3 exchangeable proton merged with solvent)

Example 24 N-hydroxy-2-(2-(((2-(4-methoxyphenyl)cyclopropyl)amino)methyl)-5,6-dihydroimidazo[1,2-a]pyrazin-7(8H)-yl)pyrimidine-5-carboxamide TFA Salt

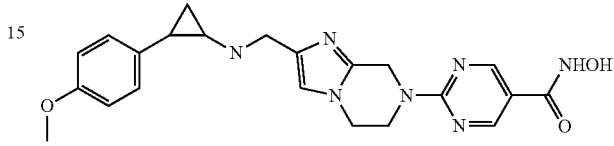

The compound was synthesized using the I-24 following the procedure for Example 2. ¹HNMR (400 MHz, DMSO-d$_6$): δ 11.14 (bs, 1H), 9.22 (bs, 2H), 8.76 (s, 2H), 7.23 (s, 1H), 6.96 (d, 2H, J=8.4 Hz), 6.77 (d, 2H, J=8.4 Hz), 5.03-4.91 (m, 2H), 4.29-4.13 (m, 4H), 4.09-3.98 (m, 2H), 3.67 (s, 3H), 2.83-2.78 (m, 1H), 2.25-2.18 (m, 1H), 1.36-1.29 (m, 1H), 1.23-1.13 (m, 1H). LC-MS m/z calcd for $C_{22}H_{25}N_7O_3$, 435.2. found 436.1[M+H]$^+$. HPLC purity 99.6%.

Example 25 2-(2-(((2-(4-fluorophenyl)cyclopropyl)amino)methyl)-5,6-dihydroimidazo[1,2-a]pyrazin-7(8H)-yl)-N-hydroxypyrimidine-5-carboxamide TFA Salt

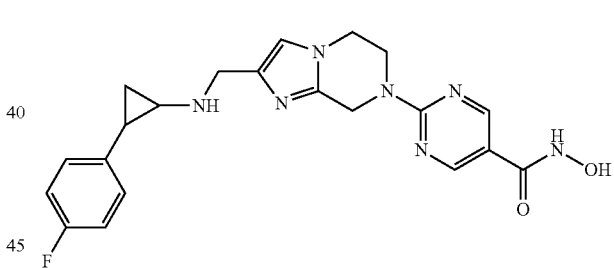

The compound was synthesized using the I-25 following the procedure for Example 2. ¹HNMR (400 MHz, DMSO-d$_6$): δ 11.18 (bs, 1H), 9.28 (bs, 2H), 8.75 (s, 2H), 7.24 (s, 1H), 7.12-7.02 (m, 4H), 4.96 (q, 2H, J=17.2 Hz), 4.25-4.22 (m, 2H), 4.18-4.14 (m, 2H), 4.11-4.00 (m, 2H), 2.87 (t, 1H, J=3.2 Hz), 2.29 (s, 1H), 1.40-1.35 (m, 1H), 1.23 (t, 1H, J=6.8 Hz). LC-MS m/z calcd for $C_{21}H_{22}FN_7O_2$, 423.2; found 424.4 [M+H]$^+$. HPLC purity 99.5%.

Example 26 3-(((2-(4-bromophenyl)cyclopropyl)amino)methyl)-N-hydroxybenzamide TFA Salt

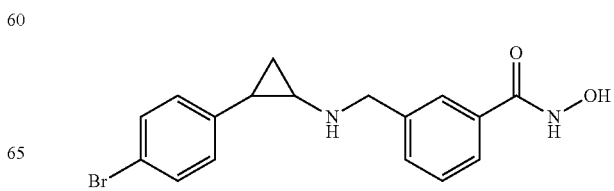

The compound was synthesized using the I-26 following the procedure for Example 2. $^1$HNMR (400 MHz, DMSO-$d_6$): δ 11.09 (bs, 1H), 8.95 (bs, 1H), 7.71 (s, 1H), 7.57 (d, 1H, J=7.6 Hz), 7.41 (d, 1H, J=7.6 Hz), 7.35-7.31 (m, 3H), 6.92 (d, 2H, J=8.4 Hz), 3.77 (s, 2H), 2.92 (bs, 1H), 2.21-2.17 (m, 1H), 1.82-1.78 (m, 1H), 1.04-0.99 (m, 1H), 0.95-0.90 (m, 1H). LC-MS m/z calcd for $C_{17}H_{17}BrN_2O_2$, 360.0; found 361.0 [M+H]$^+$. HPLC purity 98.0%.

Example 27 N-hydroxy-3-(((2-phenylcyclopropyl)amino)methyl)benzamide TFA

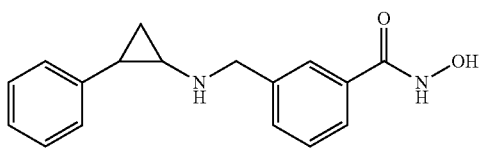 [SMILES: O=C(NO)c1cccc(CNC2CC2c2ccccc2)c1]

The compound was synthesized using the I-27 following the procedure for Example 2. $^1$HNMR (400 MHz, DMSO-$d_6$): δ 11.09 (bs, 1H), 8.95 (bs, 1H), 7.72 (s, 1H), 7.57 (d, 1H, J=7.2 Hz), 7.42 (d, 1H, J=7.6 Hz), 7.33 (t, 1H, J=7.6 Hz), 7.18 (t, 2H, J=7.6 Hz), 7.08 (t, 1H, J=7.6 Hz), 7.0 (d, 2H, J=7.2 Hz), 3.79 (s, 2H), 2.92-2.81 (m, 1H), 2.22-2.20 (m, 1H), 1.86-1.78 (m, 1H), 1.02-0.97 (m, 1H), 0.93-0.84 (m, 1H). LC-MS m/z calcd for $C_{17}H_{18}N_2O_2$ 282.1; found 283.2 [M+H]$^+$. HPLC purity 99.8%.

Example 28 N-hydroxy-4-(((2-phenylcyclopropyl)amino)methyl)benzamide TFA Salt

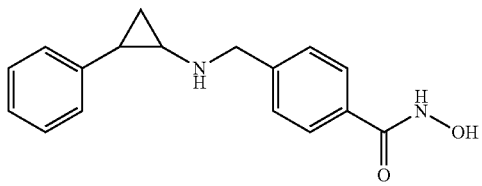 [SMILES: O=C(NO)c1ccc(CNC2CC2c2ccccc2)cc1]

The compound was synthesized using the I-28 following the procedure for Example 2. $^1$HNMR (400 MHz, DMSO-$d_6$): δ 9.20 (bs, 2H), 7.65 (d, 2H, J=7.6 Hz), 7.25 (d, 2H, J=7.2 Hz), 7.18 (t, 2H, J=7.6 Hz), 7.07 (t, 2H, J=7.2 Hz), 6.80 (d, 2H, J=7.6 Hz), 3.75 (s, 2H), 2.88-2.75 (m, 1H), 2.23-2.15 (m, 1H), 1.85-1.75 (m, 1H), 0.98-0.85 (m, 1H). LC-MS m/z calcd for $C_{17}H_{18}N_2O_2$ 282.1; found 283.2 [M+H]$^+$. HPLC purity 99.5%.

Example 29 N-hydroxy-6-((2-phenylcyclopropyl)amino)hexanamide TFA Salt

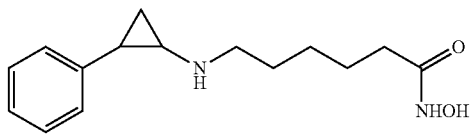

The compound was synthesized using the I-29 following the procedure for Example 2. $^1$HNMR (400 MHz, DMSO-$d_6$): δ 10.31 (bs, 1H), 8.77 (bs, 2H), 7.32-7.25 (m, 2H), 7.23-7.14 (m, 3H), 3.09-3.00 (m, 2H), 2.98-2.91 (m, 1H), 2.42-2.33 (m, 1H), 1.98-1.91 (m, 2H), 1.62-1.38 (m, 5H), 1.32-1.25 (m, 3H). LC-MS m/z calcd for $C_{15}H_{22}N_2O_2$, 263.3; found 263.2 [M+H]$^+$. HPLC purity 96.4%.

Example 30 4-(3-((2-(4-fluorophenyl)cyclopropyl)amino)propyl)-N-hydroxybenzamide TFA Salt

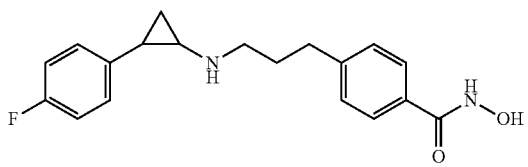 [SMILES: O=C(NO)c1ccc(CCCNC2CC2c2ccc(F)cc2)cc1]

The compound was synthesized using the I-30 following the procedure for Example 2. $^1$HNMR (400 MHz, DMSO-$d_6$): δ 11.12 (s, 1H), 8.94 (bs, 2H), 7.68 (d, 2H, J=8.0 Hz), 7.27 (d, 2H, J=8.0 Hz), 7.20-7.08 (m, 4H), 3.09-3.01 (m, 2H), 2.98-2.91 (m, 1H), 2.72-2.63 (m, 2H), 2.47-2.37 (m, 1H), 1.94-1.86 (m, 2H), 1.43-1.38 (m, 1H), 1.28-1.21 (m, 1H). LC-MS m/z calcd for $C_{19}H_{21}FN_2O_2$, 328.1; found 329.4 [M+H]$^+$. HPLC purity 96.6%.

Example 31 N-(6-Hydroxycarbamoyl-hexyl)-4-[(2-phenyl-cyclopropylamino)-methyl]-benzamide TFA Salt

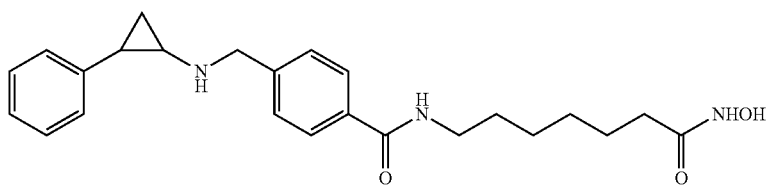

The compound was synthesized using the I-31 following the procedure for Example 2. ¹HNMR (400 MHz, DMSO-d$_6$): δ 10.29 (bs, 1H), 8.63 (bs, 1H), 8.32 (t, 1H, J=5.2 Hz), 7.74 (d, 2H, J=8 Hz), 7.35 (d, 2H, J=8 Hz), 7.20-7.16 (m, 2H), 7.09-7.06 (m, 2H), 6.85 (d, 2H, J=7.6 Hz), 3.79 (s, 2H), 3.34-3.19 (m, 2H), 2.91 (bs, 1H), 2.25-2.17 (m, 1H), 1.92 (t, 1H, J=7.2 Hz), 1.84-1.80 (m, 1H), 1.55-1.42 (m, 4H), 1.32-1.20 (m, 4H), 1.02-0.97 (m, 1H), 0.94-0.89 (m, 1H). LC-MS m/z calcd for C$_{24}$H$_{31}$N$_3$O$_3$, 409.2; found 410.3 [M+H]$^+$. HPLC purity 97.0%.

Example 32 4-(((2-(4-fluorophenyl)cyclopropyl)amino)methyl)-N-(7-(hydroxyamino)-7-oxoheptyl)benzamide TFA Salt

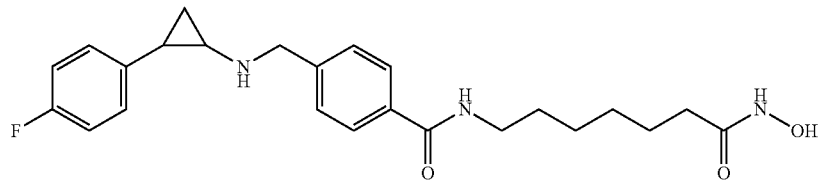 [SMILES: O=C(CCCCCCNC(=O)c1ccc(CNC2CC2c2ccc(F)cc2)cc1)NO]

The compound was synthesized using the I-32 following the procedure for Example 2. ¹HNMR (400 MHz, DMSO-d$_6$): δ 10.30 (bs, 1H), 9.39 (bs, 2H), 8.46-8.44 (m, 1H), 7.86 (d, 2H, J=8.4 Hz), 7.55 (d, 2H, J=8 Hz), 7.19-7.09 (m, 4H), 4.36 (s, 2H), 3.26-3.21 (m, 2H), 2.93-1.88 (m, 1H), 2.44-2.43 (m, 1H), 1.95-1.91 (m, 2H), 1.52-1.41 (m, 5H), 1.31-1.24 (m, 5H). LC-MS m/z calcd for C$_{24}$H$_{30}$FN$_3$O$_3$, 427.2; found 428.5 [M+H]$^+$. HPLC purity 98.6%.

Example 33 4-(2-Phenyl-cyclopropylamino)-cyclohexanecarboxylic Acid Hydroxyamide TFA Salt

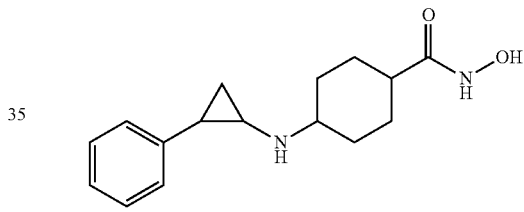

The compound was synthesized using the I-33 following the procedure for Example 2. ¹HNMR (400 MHz, DMSO-d$_6$): δ 10.26 (bs, 1H), 8.54 (bs, 1H), 7.21 (t, 2H, J=7.2 Hz), 7.09 (t, 1H, J=7.2 Hz), 7.00 (d, 2H, J=7.6 Hz), 2.82 (s, 1H), 2.09 (s, 1H), 2.01-1.97 (m, 1H), 1.84-1.59 (m, 5H), 1.50-1.26 (m, 5H), 1.01-0.92 (m, 2H). LC-MS m/z calcd C$_{16}$H$_{22}$N$_2$O$_2$[M+H]$^+$ 275.1. found 275.1. HPLC purity 95%.

Example 34 (1S,4R)—N-hydroxy-4-((1S)-1-((2-phenylcyclopropyl)amino)ethyl)cyclohexanecarboxamide TFA Salt

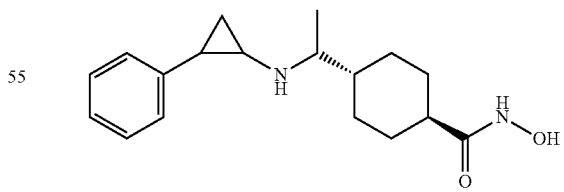

The compound was synthesized using the I-34 following the procedure for Example 2. ¹HNMR (400 MHz, DMSO-d$_6$): δ 10.34 (bs, 1H), 8.76 (bs, 1H), 8.59 (bs, 1H), 7.33-7.27 (m, 2H), 7.24-7.22 (m, 1H), 7.20-7.17 (m, 2H), 3.32-3.23 (m, 1H), 3.00-2.91 (m, 1H), 2.44-2.31 (m, 2H), 1.97-1.89 (m, 1H), 1.72-1.65 (m, 5H), 1.43-1.29 (m, 5H), 1.19-1.00 (m, 3H). LC-MS m/z calcd for C$_{18}$H$_{26}$N$_2$O$_2$, 302.2; found 303.2 [M+H]$^+$. HPLC purity 99.1%.

Example 35 N-hydroxy-4-((4-(((2-(4-(1-methyl-6-oxo-1,6-dihydropyridin-3-yl)phenyl)cyclopropyl)amino)methyl)piperidin-1-yl)methyl)benzamide TFA Salt

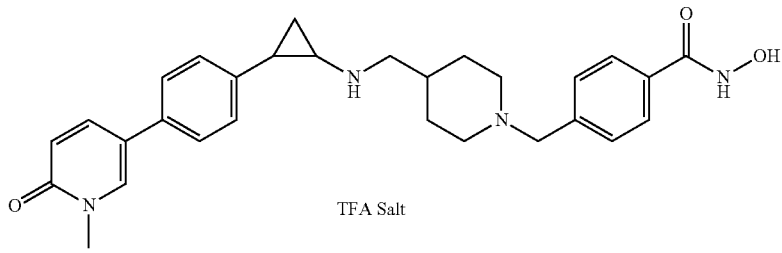 [SMILES: Cn1cc(-c2ccc(C3CC3NCC3CCN(Cc4ccc(C(=O)NO)cc4)CC3)cc2)ccc1=O]

TFA Salt

The compound was synthesized using the I-35 following the procedure for Example 2. $^1$HNMR (400 MHz, DMSO-$d_6$): δ 11.29 (bs, 1H), 9.57 (bs, 1H), 9.00 (bs, 2H), 8.08 (s, 1H), 7.83 (d, J=8.0 Hz, 2H), 7.79-7.76 (m, 1H), 7.55 (d, J=8.0 Hz, 2H), 7.52-7.46 (m, 2H), 7.21 (d, J=8.0 Hz, 2H), 6.46 (d, J=9.2 Hz, 1H), 4.31 (s, 2H), 3.49 (s, 3H), 3.44-3.34 (m, 2H), 3.25-3.10 (m, 1H), 3.05-2.85 (m, 5H), 2.02-1.80 (m, 3H), 1.51-1.27 (m, 4H). LC-MS m/z calcd for $C_{29}H_{34}FN_4O_3$, 486.3; found 487.6 [M+H]$^+$. HPLC purity 99.7%.

Example 36 N-Hydroxy-4-{4-[(2-phenyl-cyclopropylamino)-methyl]-piperidin-1-ylmethyl}-benzamide TFA Salt

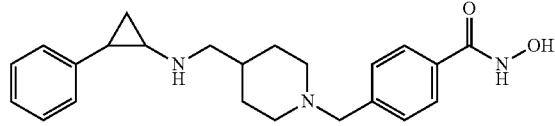 [SMILES: O=C(NO)c1ccc(CN2CCC(CNC3CC3c3ccccc3)CC2)cc1]

The compound was synthesized using the I-36 following the procedure for Example 2. $^1$HNMR (400 MHz, DMSO-$d_6$): δ 10.80 (bs, 1H), 8.95 (bs, 1H), 7.68 (d, 2H, J=8 Hz), 7.33 (d, 2H, J=8 Hz), 7.24-7.17 (m, 2H), 7.12-7.06 (m, 1H), 7.03-6.98 (m, 2H), 3.45 (s, 2H), 2.78-2.72 (m, 2H), 2.46-2.42 (m, 3H), 2.19-2.14 (m, 1H), 1.92-1.84 (m, 2H), 1.78-1.71 (m, 1H), 1.68-1.59 (m, 2H), 1.39-1.30 (m, 1H), 1.16-1.04 (m, 2H), 0.81-0.62 (m, 2H). LC-MS m/z calcd for $C_{23}H_{29}N_3O_2$, 379.2; found 380.2 [M+H]$^+$. HPLC purity 99.8%.

Example 37 4-((4-(((2-(4-(3,5-dimethylisoxazol-4-yl)phenyl)cyclopropyl)amino)methyl)piperidin-1-yl)methyl)-N-hydroxybenzamide TFA salt

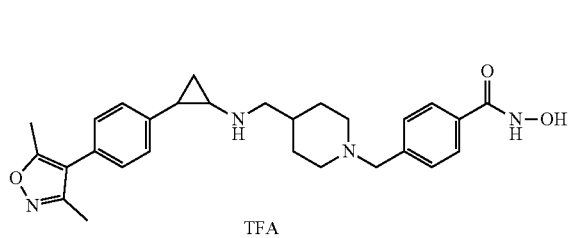 [SMILES: Cc1noc(C)c1-c1ccc(C2CC2NCC2CCN(Cc3ccc(C(=O)NO)cc3)CC2)cc1]

The compound was synthesized using the I-37 following the procedure for Example 2. $^1$HNMR (400 MHz, DMSO-$d_6$): δ 11.28 (bs, 1H), 9.53 (bs, 1H), 9.04-8.84 (bs, 2H), 7.83 (d, J=7.2 Hz, 2H), 7.55 (d, J=7.2 Hz, 2H), 7.32-7.24 (m, 4H), 4.32 (s, 2H), 3.50-3.37 (m, 2H), 3.06-2.92 (m, 5H), 2.35 (s, 3H), 2.18 (s, 3H), 1.98-1.83 (m, 4H), 1.50-1.32 (m, 4H). LC-MS m/z calcd for $C_{28}H_{34}N_4O_3$, 474.3; found 475.3 [M+H]$^+$. HPLC purity 99.9%.

Example 38 N-hydroxy-4-((4-(((2-(4-(pyrimidin-5-yl)phenyl)cyclopropyl)amino)methyl)piperidin-1-yl)methyl)benzamide TFA Salt

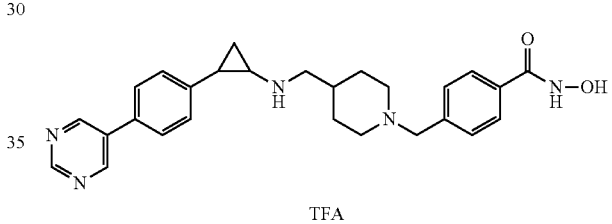

The compound was synthesized using the I-38 following the procedure for Example 2. $^1$HNMR (400 MHz, DMSO-$d_6$): δ 11.27 (bs, 1H), 9.70 (bs, 1H), 9.16 (s, 1H), 9.11 (s, 2H), 9.06 (bs, 1H), 7.82 (d, 2H, J=8.4 Hz), 7.75 (d, 2H, J=8 Hz), 7.55 (d, 2H, J=8 Hz), 7.33 (d, 2H, J=8 Hz), 4.32 (s, 2H), 3.41-3.37 (m, 2H), 3.07-2.92 (m, 5H), 2.00-1.92 (m, 4H), 1.55-1.49 (m, 1H), 1.47-1.33 (m, 3H). LC-MS m/z calcd for $C_{27}H_{31}N_5O_2$, 457.2; found 458.6[M+H]$^+$. HPLC purity 99.0%.

Example 39 6-((4-(((2-(4-(3,5-dimethylisoxazol-4-yl)phenyl)cyclopropyl)amino)methyl)piperidin-1-yl)methyl)-N-hydroxynicotinamide TFA Salt

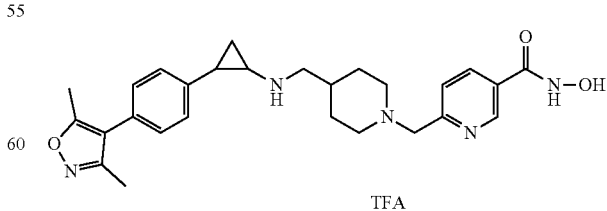

The compound was synthesized using the I-39 following the procedure for Example 2. $^1$HNMR (400 MHz, DMSO-$d_6$): δ 11.45 (bs, 1H), 9.97 (bs, 1H), 9.05 (bs, 2H), 9.00-8.93 (m, 1H), 8.22 (d, 1H, J=7.2 Hz), 7.60 (d, 1H, J=8.4 Hz, 7.33-7.24 (m, 4H), 4.52-4.48 (m, 3H), 3.46-3.40 (m, 2H), 3.11-3.01 (m, 5H), 2.36 (s, 3H), 2.18 (s, 3H), 1.98-1.91 (m, 3H), 1.58-1.48 (m, 3H), 1.38-1.31 (m, 1H). LC-MS m/z calcd for C$_{27}$H$_{33}$N$_5$O$_3$, 475.3. found 476.3 [M+H]$^+$. HPLC purity 99.8%.

Example 40 N-hydroxy-4-((4-(((2-phenylcyclopropyl)amino)methyl)-1H-pyrazol-1-yl)methyl)benzamide TFA Salt

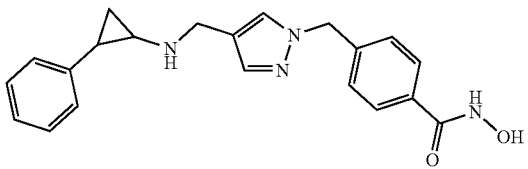 [SMILES: O=C(NO)c1ccc(Cn2cc(CNC3CC3c3ccccc3)cn2)cc1]

The compound was synthesized using the I-40 following the procedure for Example 2. $^1$HNMR (400 MHz, DMSO-d$_6$): δ 11.16 (bs, 1H), 9.01 (bs, 3H), 7.87 (s, 1H), 7.69 (d, 2H, J=8 Hz), 7.54 (s, 1H), 7.32-7.24 (m, 4H), 7.23-7.19 (m, 1H), 7.11 (d, 2H, J=7.2 Hz), 5.36 (s, 2H), 4.18 (s, 2H), 2.92-2.85 (m, 1H), 2.40-2.31 (m, 1H), 1.42-1.36 (m, 1H), 1.32-1.23 (m, 1H). LC-MS m/z calcd for C$_{21}$H$_{22}$N$_4$O$_2$, 362.4; found 363.4 [M+H]$^+$. HPLC purity 99.1%.

Example 41 N-hydroxy-4-((4-(((2-phenylcyclopropyl)amino)methyl)-1H-1,2,3-triazol-1-yl)methyl)benzamide TFA Salt

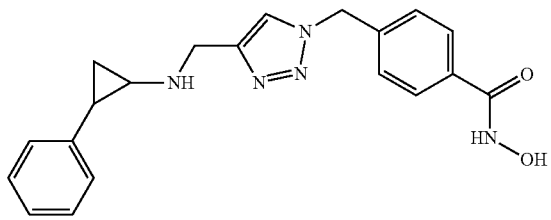 [SMILES: O=C(NO)c1ccc(Cn2cc(CNC3CC3c3ccccc3)nn2)cc1]

The compound was synthesized using the I-41 following the procedure for Example 2. $^1$HNMR (400 MHz, DMSO-d$_6$): δ 11.19 (bs, 1H), 9.39 (bs, 2H), 9.03 (bs, 1H), 8.21 (s, 1H), 7.73 (d, 2H, J=7.6 Hz), 7.35 (d, 2H, J=8 Hz), 7.32-7.24 (m, 2H), 7.22-7.16 (m, 1H), 7.12-7.08 (m, 2H), 5.68 (s, 2H), 4.41 (s, 2H), 3.01-2.95 (m, 1H), 2.41-2.34 (m, 1H), 1.43-1.36 (m, 1H), 1.32-1.22 (m, 1H). LC-MS m/z calcd for C$_{20}$H$_{21}$N$_5$O$_2$, 363.2; found 364.2 [M+H]$^+$. HPLC purity 99.8%.

Example 42 N-hydroxy-4-(2-(4-(((2-phenylcyclopropyl)amino)methyl)piperidin-1-yl)ethyl)benzamide TFA Salt

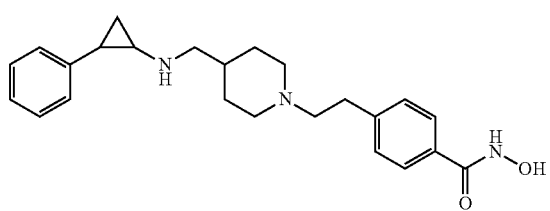 [SMILES: O=C(NO)c1ccc(CCN2CCC(CNC3CC3c3ccccc3)CC2)cc1]

The compound was synthesized using the I-42 following the procedure for Example 2. $^1$HNMR (400 MHz, DMSO-d$_6$): δ 11.17 (bs, 1H), 9.69 (bs, 1H), 9.11 (bs, 2H), 7.72 (d, 2H, J=7.6 Hz), 7.36-7.26 (m, 4H), 7.24-7.20 (m, 1H), 7.15 (d, 2H, J=7.2 Hz), 3.70-3.55 (m, 2H), 3.40-3.15 (m, 3H), 3.10-2.90 (m, 7H), 2.05-1.92 (m, 2H), 1.90-1.78 (m, 1H), 1.55-1.42 (m, 3H), 1.35-1.25 (m, 1H). LC-MS m/z calcd for C$_{24}$H$_{31}$N$_3$O$_2$, 393.5; found 394.5 [M+H]$^+$. HPLC purity 97%

Example 43 N-hydroxy-4-(3-(4-(((2-phenylcyclopropyl)amino)methyl)piperidin-1-yl)propyl)benzamide TFA Salt

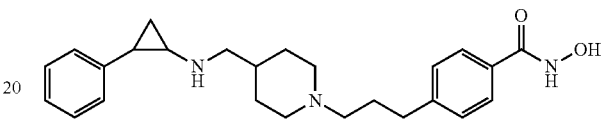

The compound was synthesized using the I-43 following the procedure for Example 2. $^1$HNMR (400 MHz, DMSO-d$_6$): δ 7.66 (d, 2H, J=8.4 Hz), 7.30-7.26 (t, 4H, J=7.6 Hz), 7.22-7.20 (t, 1H, J=6.8 Hz), 7.15 (d, 2H, J=7.6 Hz), 3.53 (m, 2H), 3.15-2.97 (m, 4H), 2.97-2.92 (m, 1H), 2.92-2.80 (m, 2H), 2.69-2.60 (m, 2H), 2.45-2.38 (m, 1H), 2.00-1.88 (m, 5H), 1.46-1.35 (m, 3H), 1.30-1.22 (m, 1H). LC-MS m/z calcd for C$_{25}$H$_{33}$N$_3$O$_2$, 407.2; found 408.3 [M+H]$^+$. HPLC purity 99%.

Example 44 N-hydroxy-4-(3-(4-((2-phenylcyclopropyl)amino)piperidin-1-yl)propyl)benzamide TFA Salt

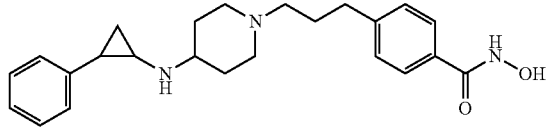 [SMILES: O=C(NO)c1ccc(CCCN2CCC(NC3CC3c3ccccc3)CC2)cc1]

The compound was synthesized using the I-44 following the procedure for Example 2. $^1$HNMR (400 MHz, DMSO-d$_6$): δ 11.13 (bs, 1H), 9.45 (bs, 1H), 9.26 (bs, 2H), 7.69 (d, 2H, J=7.6 Hz), 7.33-7.26 (m, 4H), 7.23-7.21 (m, 1H), 7.19-7.15 (m, 2H), 3.62-3.54 (m, 3H), 3.50-3.41 (m, 2H), 3.35-3.28 (m, 1H), 3.06-2.91 (m, 5H), 2.70-2.61 (m, 1H), 2.25-2.18 (m, 2H), 1.96-1.91 (m, 2H), 1.83-1.72 (m, 1H), 1.48-1.41 (m, 1H), 1.34-1.30 (m, 1H). LC-MS m/z calcd for C$_{24}$H$_{31}$N$_3$O$_2$, 393.2; found 394.2 [M+H]$^+$. HPLC purity 99.6%.

Example 45 N-hydroxy-4-(3-(4-((methyl (2-phenylcyclopropyl)amino) methyl) piperidin-1-yl) propyl) benzamide TFA Salt

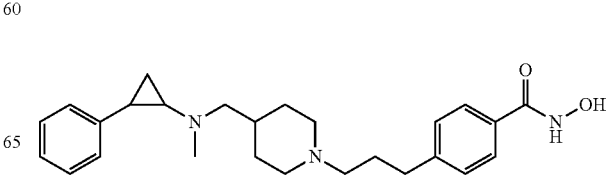

To a stirred solution of example 43 (0.05 g, 0.12 mmol) in methanol (5 mL) was added paraformaldehyde (0.007 g, 0.24 mmol) and TEA (0.037 g, 0.36 mmol) and continue stirred for 1 h at room temperature, sodium borohydride (0.09 g, 0.245 mmol) were added and continue stirred for 30 minute. Reaction mixture was quenched with water (20 mL) and extracted with dichloromethane (2×20 mL). The organic portion was washed with water, brine, dried over sodium sulphate and concentrated under reduced pressure to afford the crude product compound which was purified by reverse-phase HPLC using Chemsil $C_{18}$ (250 mm×4.6 mm×5mic) column with 0.1% TFA in water:ACN to afford (0.02 g, 20%). $^1$HNMR (400 MHz, DMSO-$d_6$): δ 11.16 (s, 1H), 9.35 (bs, 1H), 7.69 (d, J=8.4 Hz, 2H), 7.30-7.10 (m, 7H), 3.53-3.50 (m, 3H), 3.28-2.76 (m, 10H), 2.67-2.63 (m, 3H), 2.04-1.83 (m, 4H), 1.48-1.28 (m, 4H). LC-MS m/z calcd for $C_{26}H_{35}N_3O_2$, 421.3; found 422.5 [M+H]$^+$. HPLC purity 99.5%.

Example 46 N-hydroxy-4-(3-(6-((2-phenylcyclopropyl)amino)-2-azaspiro[3.3]heptan-2-1)propyl)benzamide TFA Salt

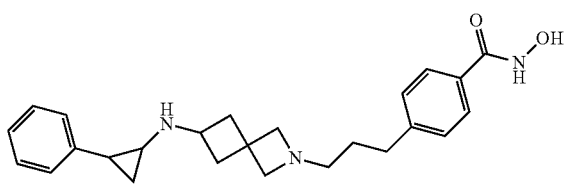 [SMILES: O=C(NO)c1ccc(CCCN2CC3(CC(NC4CC4c4ccccc4)C3)C2)cc1]

The compound was synthesized using the I-46 following the procedure for Example 48. $^1$HNMR (400 MHz, DMSO-$d_6$): δ 11.12 (bs, 1H), 9.97 (bs, 1H), 9.35 (bs, 1H), 9.26 (bs, 1H), 7.68 (d, 2H, J=8 Hz), 7.32-7.24 (m, 4H), 7.23-7.19 (m, 1H), 7.14 (d, 2H, J=7.2 Hz), 4.25-4.19 (m, 2H), 4.14-3.98 (m, 3H), 3.82-3.73 (m, 2H), 3.14-3.02 (m, 2H), 2.89-2.78 (m, 1H), 2.69-2.60 (m, 3H), 2.94-2.84 (m, 2H), 1.79-1.70 (m, 2H), 1.43-1.35 (m, 1H), 1.30-1.26 (m, 1H). LC-MS m/z calcd for $C_{25}H_{31}N_3O_2$, 405.5; found 406.5 [M+H]$^+$. HPLC purity 99.5%.

Example 47 4-[3-(4-{[2-(4-Fluoro-phenyl)-cyclopropylamino]-methyl}-piperidin-1-yl)-propyl]-N-hydroxy-benzamide TFA Salt

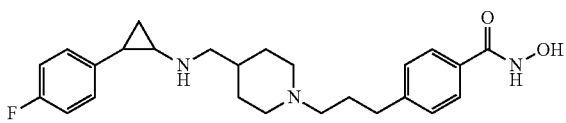 [SMILES: O=C(NO)c1ccc(CCCN2CCC(CNC3CC3c3ccc(F)cc3)CC2)cc1]

The compound was synthesized using the I-47 following the procedure for Example 2. $^1$HNMR (400 MHz, DMSO-$d_6$): δ 11.14 (bs, 1H), 9.27 (bs, 1H), 8.96 (bs, 3H), 7.70 (d, 2H, J=8 Hz), 7.30 (d, 2H, J=8 Hz), 7.26-7.19 (m, 2H), 7.16-7.10 (m, 2H), 3.58-3.46 (m, 2H), 3.08-2.98 (m, 4H), 2.96-2.82 (m, 3H), 2.69-2.63 (m, 2H), 2.00-1.88 (m, 6H), 1.49-1.35 (m, 3H), 1.31-1.24 (m, 1H). LC-MS m/z calcd for $C_{25}H_{32}FN_3O_2$, 425.3; found 426.5 [M+H]$^+$. HPLC purity 97.1%

Example 48 4-(3-(3-(((2-(4-fluorophenyl)cyclopropyl)amino)methyl)azetidin-1-yl)propyl)-N-hydroxy benzamide TFA Salt

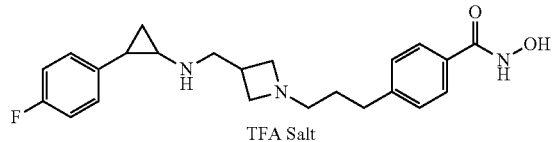 [SMILES: O=C(NO)c1ccc(CCCN2CC(CNC3CC3c3ccc(F)cc3)C2)cc1]

To a solution of hydroxylamine hydrochloride (0.38 g, 5.33 mmol) in methanol was added a solution of potassium hydroxide (0.3 g, 5.33 mmol) in methanol at 5-10° C. and stirred at that temperature for 15 min. The formed precipitate was filtered through cotton plug and the filtrate was added to a solution of ethyl 4-(3-(3-((2,2,2-trifluoro-N-(2-(4-fluorophenyl)cyclopropyl)acetamido)methyl)azetidin-1-yl)propyl)benzoate (I-48, 0.15 g, 0.3 mmol) in methanol (4 mL) at room temperature. Potassium hydroxide (0.3 g, 5.33 mmol) was added and the resulting mixture was stirred at room temperature for 1 h. The solvent was removed and ice-water was added to the resulting residue. The pH of the aqueous portion was adjusted to 7.0 with 10% acetic acid solution. The crude product was extracted with dichloromethane (30 mL×3). The combined organic layer was washed with water, brine, dried over sodium sulphate and concentrated under reduced pressure to get the crude product which was mixed with dichloromethane (5 mL) and trifluoroacetic acid (0.5 mL) was added at 0° C. The reaction mixture was stirred for 10 min at same temperature. The reaction mixture was concentrated under vacuum to get crude TFA salt of product which was purified by reverse-phase HPLC using Chemsil $C_{18}$ (250 mm×4.6 mm×5mic) column with 0.1% TFA in water:ACN to afford the pure product as colourless solid (0.04 g, 34% yield). LC-MS m/z calcd for $C_{23}H_{28}FN_3O_2$, 397.5; found 398.5 [M+H]$^+$.

Example 49 4-(3-(4-(((2-(3-fluorophenyl)cyclopropyl)amino)methyl)piperidin-1-yl)propyl)-N-hydroxybenzamide TFA Salt

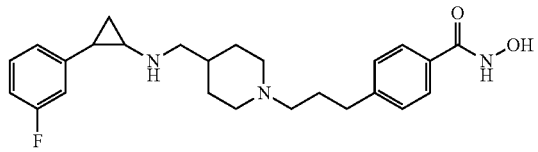 [SMILES: O=C(NO)c1ccc(CCCN2CCC(CNC3CC3c3cccc(F)c3)CC2)cc1]

The compound was synthesized using the I-49 following the procedure for Example 2. $^1$HNMR (400 MHz, DMSO-$d_6$): δ 11.14 (bs, 1H), 9.38 (bs, 1H), 9.07 (bs, 3H), 7.69 (d, 2H, J=8 Hz), 7.36-7.28 (m, 3H), 7.04-7.00 (m, 3H), 3.54-3.50 (m, 2H), 3.28-3.17 (m, 1H), 3.10-2.98 (m, 5H), 2.93-2.82 (m, 2H), 2.70-2.61 (m, 2H), 2.00-1.85 (m, 5H), 1.53-1.30 (m, 3H). LC-MS m/z calcd for $C_{25}H_{32}FN_3O_2$, 425.3; found 426.5 [M+H]$^+$. HPLC purity 99.4%.

Example 50 4-(3-(4-(((2-(3,4-difluorophenyl)cyclopropyl)amino)methyl)piperidin-1-yl)propyl)-N-hydroxybenzamide TFA Salt

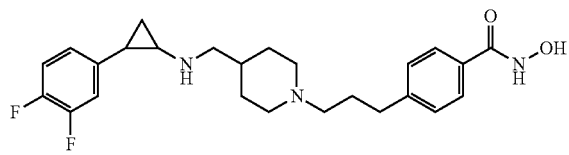 [SMILES: O=C(NO)c1ccc(CCCN2CCC(CNC3CC3c3ccc(F)c(F)c3)CC2)cc1]

The compound was synthesized using the I-50 following the procedure for Example 2. $^1$HNMR (400 MHz, DMSO-$d_6$): δ 11.14 (bs, 1H), 9.06 (bs, 1H), 8.94 (bs, 1H), 7.70 (d, 2H, J=8 Hz), 7.40-7.24 (m, 4H), 7.09-7.03 (m, 1H), 3.58-3.48 (m, 3H), 3.30-3.12 (m, 1H), 3.08-2.97 (m, 5H), 2.93-2.82 (m, 2H), 2.69-2.64 (m, 2H), 1.98-1.86 (m, 5H), 1.48-1.30 (m, 3H). LC-MS m/z calcd for $C_{25}H_{31}F_2N_3O_2$, 443.2. found 444.5 [M+H]$^+$.
HPLC purity 99.6%.

Example 51 N-hydroxy-4-(3-(4-(((2-(4-methoxyphenyl)cyclopropyl)amino)methyl)piperidin-1-yl)propyl)benzamide TFA Salt

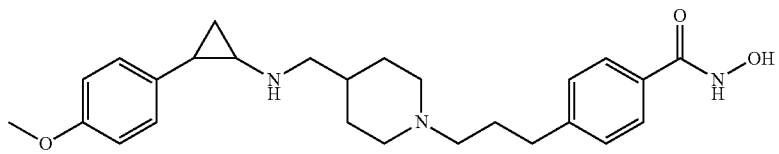 [SMILES: COc1ccc(C2CC2NCC2CCN(CCCc3ccc(C(=O)NO)cc3)CC2)cc1]

The compound was synthesized using the I-51 following the procedure for Example 2. $^1$HNMR (400 MHz, DMSO-$d_6$): δ 11.13 (bs, 1H), 9.35 (bs, 1H), 8.98 (bs, 1H), 7.69 (d, 2H, J=7.6 Hz), 7.29 (d, 2H, J=8.4 Hz), 7.08 (d, 2H, J=8.4 Hz), 6.84 (d, 2H, J=8.4 Hz), 3.70 (s, 3H), 3.53-3.50 (m, 2H), 3.07-3.01 (m, 4H), 2.91-2.86 (m, 3H), 2.67-2.53 (m, 3H), 2.00-1.92 (m, 5H), 1.40-1.38 (m, 3H), 1.22-1.17 (m, 1H). LC-MS m/z calcd for $C_{26}H_{35}N_3O_3$ [M+H]$^+$ 438.2. found 438.3. HPLC purity 99.5%.

Example 52 4-(3-(4-(((2-(4-((4-fluorobenzyl)oxy)phenyl)cyclopropyl)amino)methyl)piperidin-1-yl)propyl)-N-hydroxybenzamide TFA Salt

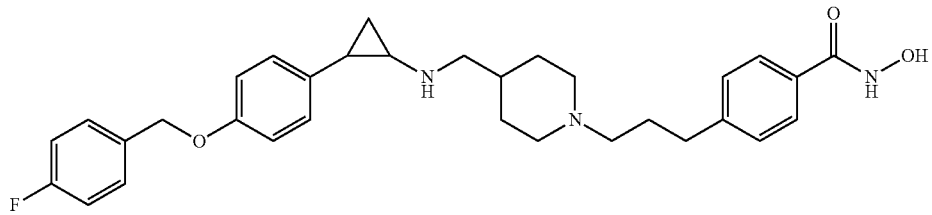 [SMILES: O=C(NO)c1ccc(CCCN2CCC(CNC3CC3c3ccc(OCc4ccc(F)cc4)cc3)CC2)cc1]

The compound was synthesized using the I-52 following the procedure for Example 2. $^1$HNMR (400 MHz, DMSO-$d_6$): δ 11.14 (bs, 1H), 9.10 (bs, 1H), 8.96 (bs, 1H), 8.82 (bs, 2H), 7.71 (d, 2H, J=7.6 Hz), 7.48-7.42 (m, 2H), 7.31 (d, 2H, J=8 Hz), 7.20 (t, 2H, J=8.8 Hz), 7.09 (d, 2H, J=8.4 Hz), 6.93 (d, 2H, J=8.4 Hz), 5.01 (s, 2H), 3.58-3.50 (m, 2H), 3.06-2.97 (m, 4H), 2.92-2.85 (m, 4H), 2.70-2.62 (m, 2H), 2.40-2.35 (m, 1H), 2.00-1.88 (m, 5H), 1.45-1.34 (m, 3H). LC-MS m/z calcd for $C_{32}H_{38}FN_3O_3$, 531.3; found 532.4 [M+H]$^+$. HPLC purity 99.9%.

Example 53 N-hydroxy-4-(3-(4-(((2-(4-(morpholine-4-carbonyl)phenyl)cyclopropyl)amino)methyl)piperidin-1-yl)propyl)benzamide TFA Salt

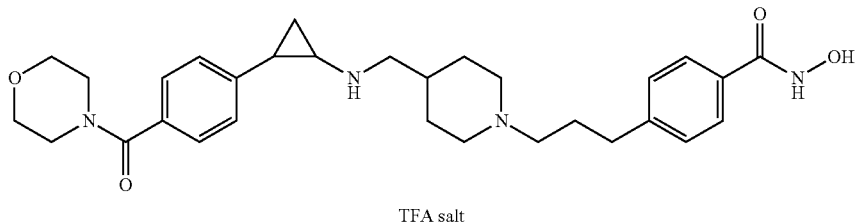 [SMILES: O=C(NO)c1ccc(CCCN2CCC(CNC3CC3c3ccc(C(=O)N4CCOCC4)cc3)CC2)cc1]

TFA salt

The compound was synthesized using the I-54 following the procedure for Example 2. $^1$HNMR (400 MHz, DMSO-$d_6$): δ 11.07 (bs, 1H), 9.41 (bs, 1H), 9.27 (bs, 2H), 7.69 (d, 2H, J=8 Hz), 7.36-7.29 (m, 3H), 7.27-7.22 (m, 3H), 3.65-3.45 (m, 7H), 3.41-3.25 (m, 3H), 3.10-2.98 (m, 5H), 2.96-2.85 (m, 2H), 2.70-2.61 (m, 3H), 2.01-1.85 (m, 5H), 1.78-1.70 (m, 1H), 1.52-1.48 (m, 1H), 1.45-1.31 (m, 2H). LC-MS m/z calcd for $C_{30}H_{40}N_4O_4$, 520.3; found 521.3 [M+H]$^+$; HPLC purity 99.6%.

Example 54 N-hydroxy-4-(3-(4-(((2-(4-(piperidine-1-carbonyl)phenyl)cyclopropyl)amino)methyl)piperidin-1-yl)propyl)benzamide TFA Salt

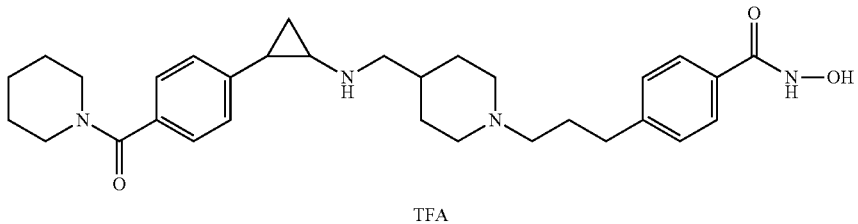 [SMILES: O=C(NO)c1ccc(CCCN2CCC(CNC3CC3c3ccc(C(=O)N4CCCCC4)cc3)CC2)cc1]

TFA

The compound was synthesized using the I-55 following the procedure for Example 2. $^1$HNMR (400 MHz, DMSO-$d_6$): δ 11.14 (bs, 1H), 9.31 (bs, 1H), 9.15 (bs, 3H), 7.70 (d, 2H, J=8.4 Hz), 7.32-7.26 (m, 4H), 7.24-7.20 (m, 2H), 3.56-3.50 (m, 6H), 3.27-3.26 (m, 2H), 3.05-2.85 (m, 5H), 2.93-2.83 (m, 2H), 2.68-2.63 (m, 2H), 2.00-1.90 (m, 5H), 1.62-1.57 (m, 2H), 1.53-1.32 (m, 7H). LC-MS m/z calcd for $C_{31}H_{42}N_4O_3$, 518.3. found 519.3 [M+H]$^+$. HPLC purity 99.4%.

Example 55 N-(2-(dimethylamino)ethyl)-4-(2-(((1-(3-(4-(hydroxycarbamoyl)phenyl)propyl)piperidin-4-yl)methyl)amino)cyclopropyl)benzamide TFA Salt

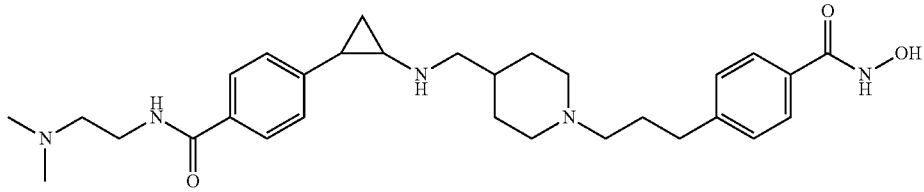 [SMILES: CN(C)CCNC(=O)c1ccc(C2CC2NCC2CCN(CCCc3ccc(C(=O)NO)cc3)CC2)cc1]

The compound was synthesized using the I-53 following the procedure for Example 2. $^1$HNMR (400 MHz, DMSO-$d_6$): δ 11.15 (bs, 1H), 9.51 (bs, 1H), 9.43 (bs, 1H), 9.16 (bs, 2H), 8.65 (bs, 1H), 7.79 (d, 2H, J=8.4 Hz), 7.69 (d, 1H, J=8.0 Hz), 7.62 (d, 1H, J=8.0 Hz), 7.30-7.23 (m, 4H), 3.50-3.48 (m, 4H), 3.28-3.21 (m, 2H), 3.08-2.98 (m, 5H), 2.90-2.81 (m, 8H), 2.69-2.60 (m, 3H), 2.00-1.82 (m, 5H), 1.57-1.50 (m, 1H), 1.46-1.30 (m, 3H). LC-MS m/z calcd for $C_{30}H_{43}N_5O_3$, 521.3; found 522.2 [M+H]$^+$. HPLC purity 99.97%.

Example 56 4-(3-(4-(((2-(4'-chloro-[1,1'-biphenyl]-4-yl)cyclopropyl)amino)methyl)piperidin-1-yl)propyl)-N-hydroxybenzamide TFA Salt

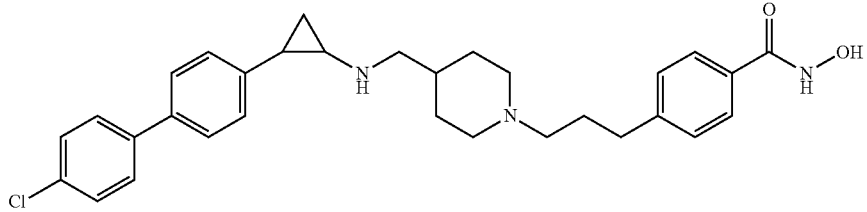 [SMILES: O=C(NO)c1ccc(CCCN2CCC(CNC3CC3c3ccc(-c4ccc(Cl)cc4)cc3)CC2)cc1]

The compound was synthesized using the I-56 following the procedure for Example 2. $^1$HNMR (400 MHz, DMSO-$d_6$): δ 11.13 (bs, 1H), 9.39 (bs, 1H), 9.08 (bs, 2H), 7.70-7.64 (m, 4H), 7.59 (d, 2H, J=8.4 Hz), 7.48 (d, 2H, J=8.4 Hz), 7.30-7.25 (m, 4H), 3.53-3.43 (m, 3H), 3.08-2.97 (m, 5H), 2.89-2.86 (m, 2H), 2.68-2.65 (m, 2H), 2.01-1.90 (m, 5H), 1.52-1.32 (m, 4H). LC-MS m/z calcd for $C_{31}H_{36}ClN_3O_2$, 518.2; found 518.2 [M+H]$^+$. HPLC purity 99.8%.

Example 57 4-(3-(4-(((2-(4'-fluoro-[1,1'-biphenyl]-4-yl)cyclopropyl)amino)methyl)piperidin-1-yl)propyl)-N-hydroxybenzamide TFA Salt

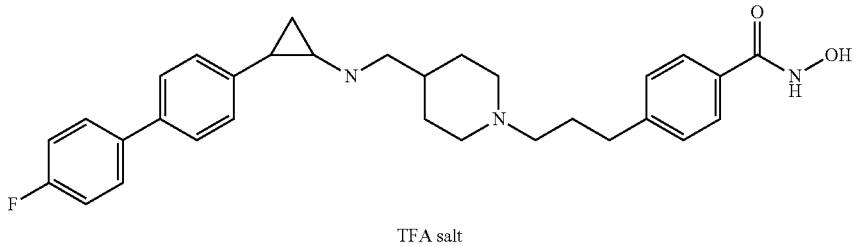 [SMILES: O=C(NO)c1ccc(CCCN2CCC(CNC3CC3c3ccc(-c4ccc(F)cc4)cc3)CC2)cc1]

TFA salt

The compound was synthesized using the I-57 following the procedure for Example 2. $^1$HNMR (400 MHz, DMSO-$d_6$): δ 11.13 (bs, 1H), 9.14 (bs, 1H), 8.92 (bs, 2H), 7.75-7.64 (m, 4H), 7.57 (d, J=8.1 Hz, 2H), 7.35-7.20 (m, 6H), 3.6-3.5 (m, 2H), 3.10-2.96 (m, 5H), 2.94-2.82 (m, 2H), 2.72-2.62 (m, 3H), 2.02-1.86 (m, 5H), 1.54-1.44 (m, 1H), 1.44-1.28 (m, 3H). LC-MS m/z calcd for $C_{31}H_{36}FN_3O_2$, 501.3; found 502.3 [M+H]$^+$. HPLC purity 99.7%.

Example 58 4-(3-(3-(((2-(4'-fluoro-[1,1'-biphenyl]-4-yl)cyclopropyl)amino)methyl)azetidin-1-yl) propyl)-N-hydroxybenzamide TFA Salt

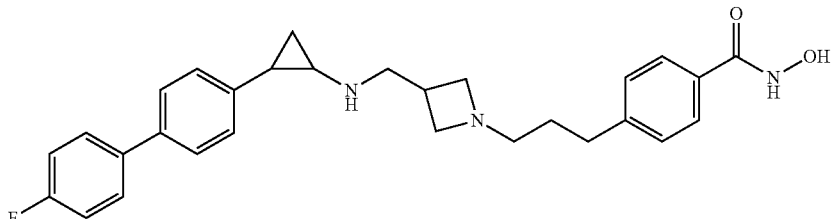

TFA salt

The compound was synthesized using the I-58 following the procedure for Example 48. ¹HNMR (400 MHz, DMSO-d$_6$): δ 11.13 (bs, 1H), 10.05 (bs, 1H), 9.17 (bs, 2H), 9.00 (bs, 1H), 7.70-7.64 (m, 4H), 7.57 (d, 2H, J=8.0 Hz), 7.28-7.24 (m, 6H), 4.25-4.15 (m, 1H), 4.14-4.10 (m, 2H), 3.92-3.81 (m, 2H), 3.48-3.31 (m, 2H), 3.11-3.07 (m, 3H), 2.65-2.61 (m, 2H), 2.48-2.43 (m, 1H), 1.75-1.73 (m, 2H), 1.49-1.41 (m, 1H), 1.39-1.31 (m, 1H). LC-MS m/z calcd for C$_{29}$H$_{32}$FN$_3$O$_2$, 473.5; found 474.5 [M+H]$^+$. HPLC purity 99.8%.

Example 59 4-(3-(4-(((2-(4'-cyano-[1,1'-biphenyl]-4-yl)cyclopropyl)amino)methyl)piperidin-1-yl)propyl)-N-hydroxybenzamide TFA Salt

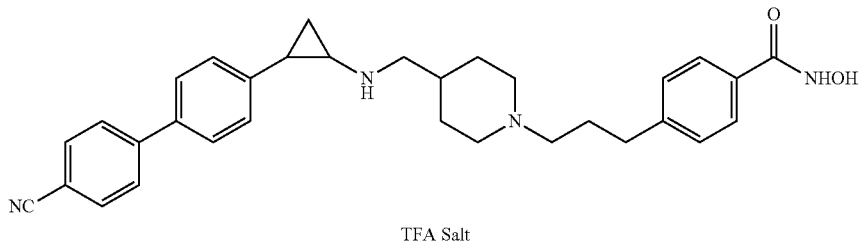

TFA Salt

The compound was synthesized using the I-59 following the procedure for Example 2. ¹HNMR (400 MHz, DMSO-d$_6$): δ 11.13 (bs, 1H), 9.12 (bs, 1H), 8.92 (bs, 2H), 7.97-7.93 (m, 3H), 7.72-7.66 (m, 5H), 7.35-7.24 (m, 4H), 3.70-3.45 (m, 4H), 3.18-2.98 (m, 4H), 3.30-3.16 (bs, 2H), 3.08-2.98 (bs, 4H), 2.95-2.82 (m, 2H), 2.70-2.62 (m, 2H), 2.02-1.90 (m, 4H), 1.55-1.30 (m, 3H). LC-MS m/z calcd for C$_{32}$H$_{36}$N$_4$O$_2$, 508.3; found 527.3[M+H+17]$^+$. HPLC purity 99.8%.

Example 60 N-hydroxy-4-(3-(4-(((2-(4-(1-methyl-2-oxo-1,2-dihydropyridin-4-yl)phenyl)cyclopropyl)amino)methyl)piperidin-1-yl)propyl)benzamide TFA Salt

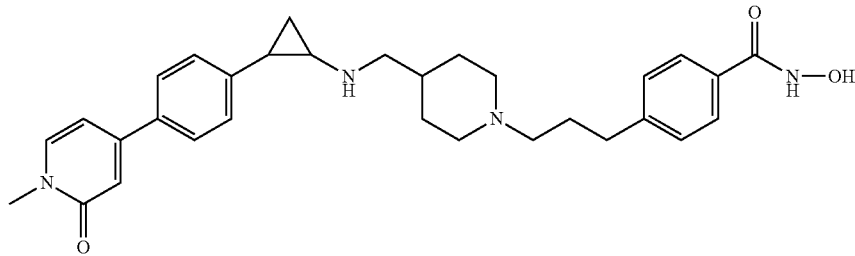

TFA

The compound was synthesized using the I-60 following the procedure for Example 2. ¹HNMR (400 MHz, DMSO-d$_6$): δ 11.14 (bs, 1H), 9.21 (bs, 1H), 8.95 (bs, 3H), 8.07 (s, 1H), 7.81-7.76 (m, 1H), 7.69 (d, J=8.0 Hz, 2H), 7.50 (d, J=8.0 Hz, 2H), 7.30 (d, J=7.6 Hz, 2H), 7.21 (d, J=7.6 Hz, 2H), 6.49 (d, J=9.6 Hz, 1H), 3.56-3.48 (m, 5H), 3.26-3.18 (m, 1H), 3.07-2.97 (m, 5H), 2.92-2.82 (m, 2H), 2.69-2.63 (m, 3H), 2.02-1.94 (m, 5H), 1.48-1.27 (m, 3H). LC-MS m/z calcd for C$_{31}$H$_{38}$N$_4$O$_3$, 514.3. found 513.3[M−H]$^+$. HPLC purity 99.3%.

Example 61 N-hydroxy-4-(3-(4-(((2-(4-(pyrimidin-5-yl)phenyl)cyclopropyl)amino)methyl)piperidin-1-yl)propyl)benzamide TFA Salt

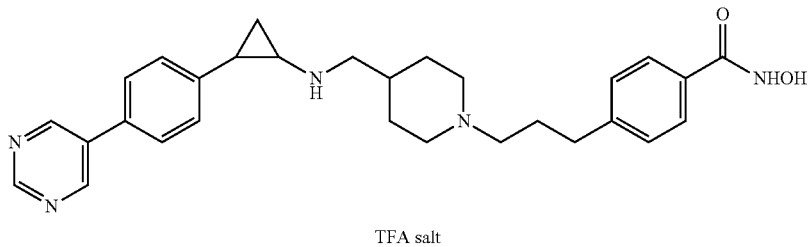

TFA salt

The compound was synthesized using the I-61 following the procedure for Example 2. $^1$HNMR (400 MHz, DMSO-$d_6$): δ 11.14 (s, 1H), 9.24 (bs, 1H), 9.16 (s, 1H), 9.11 (s, 2H), 8.98 (bs, 2H), 7.75 (d, J=8.4 Hz, 2H), 7.69 (d, J=8.0 Hz, 2H), 7.34 (d, J=8.4 Hz, 2H), 7.29 (d, J=8.4 Hz, 1H), 3.52 (d, J=11.6 Hz, 2H), 3.30-3.18 (m, 1H), 3.10-2.98 (m, 5H), 2.95-2.80 (m, 2H), 2.70-2.62 (m, 1H), 2.55 (m, 1H), 2.20-1.70 (m, 5H), 1.58-1.48 (m, 1H), 1.46-1.32 (m, 2H). LC-MS m/z calcd for $C_{29}H_{35}N_5O_2$, 485.2; found 486.2 [M+H]$^+$. HPLC purity 99.7%.

Example 62 N-hydroxy-4-(3-(4-(((2-(4-(1-methyl-1H-pyrazol-4-yl)phenyl)cyclopropyl)amino)methyl)piperidin-1-yl) propyl) benzamide TFA Salt

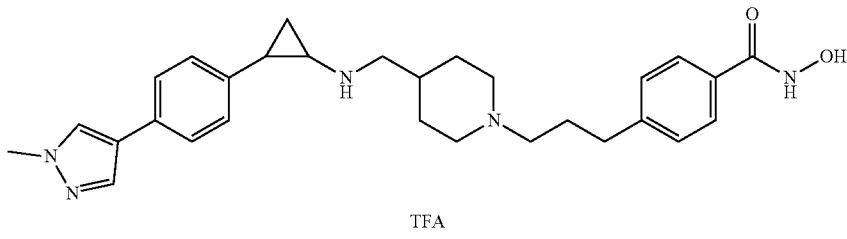 [SMILES: Cn1cc(-c2ccc(C3CC3NCC3CCN(CCCc4ccc(C(=O)NO)cc4)CC3)cc2)cn1]

TFA

The compound was synthesized using the I-62 following the procedure for Example 2. $^1$HNMR (400 MHz, DMSO-$d_6$): 11.13 (s, 1H), 9.17 (s, 1H), 8.91 (s, 2H), 8.07 (s, 1H), 7.80 (s, 1H), 7.70-7.62 (d, J=8 Hz, 2H), 7.48-7.40 (d, J=8.4 Hz, 2H), 7.35-7.20 (d, J=8 Hz, 2H), 7.15-7.10 (d, J=8.4 Hz, 2H), 3.83 (s, 3H), 3.54-3.51 (m, 2H), 3.24-3.19 (m, 1H), 3.02-2.95 (m, 4H), 2.89-2.86 (m, 3H), 2.66 (m, 2H), 2.48-2.30 (m, 1H), 2.05-1.92 (m, 5H), 1.44-1.33 (m, 2H), 1.27-1.22 (m, 1H). LC-MS m/z calcd for $C_{29}H_{37}N_5O_2$, 487.3; found 488.3[M+H]$^+$. HPLC purity 99.8%.

Example 63 N-hydroxy-4-(3-(3-(((2-(4-(1-methyl-1H-pyrazol-4-yl)phenyl)cyclopropyl)amino)methyl)azetidin-1-yl)propyl)benzamide TFA Salt

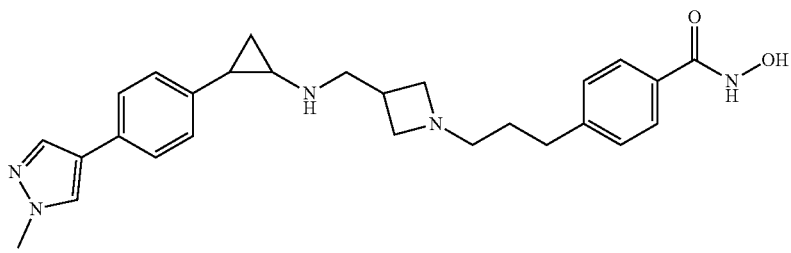

TFA salt

The compound was synthesized using the I-63 following the procedure for Example 48. ¹HNMR (400 MHz, DMSO-d₆): δ 11.13 (bs, 1H), 9.79 (bs, 1H), 8.99 (bs, 2H), 8.08 (s, 1H), 7.81 (s, 1H), 7.69 (d, 2H, J=8.0 Hz), 7.47 (d, 2H, J=8.4 Hz), 7.28-7.23 (m, 2H), 7.14 (d, 2H, J=8 Hz), 4.22-4.14 (m, 1H), 4.11-3.95 (m, 2H), 3.89-3.83 (m, 1H), 3.83 (s, 3H), 3.29-3.01 (m, 5H), 2.92-2.87 (m, 1H), 2.68-2.60 (m, 1H), 2.41-2.30 (m, 2H), 1.70-1.62 (m, 2H), 1.42-1.35 (m, 1H), 1.34-1.26 (m, 1H). LC-MS m/z calcd for $C_{27}H_{33}N_5O_2$, 459.6; found 460.6 [M+H]⁺. HPLC purity 99%.

Example 64 4-(3-(4-(((2-(4-(3,5-dimethylisoxazol-4-yl)phenyl)cyclopropyl)amino)methyl)piperidin-1-yl)propyl)-N-hydroxybenzamide TFA Salt

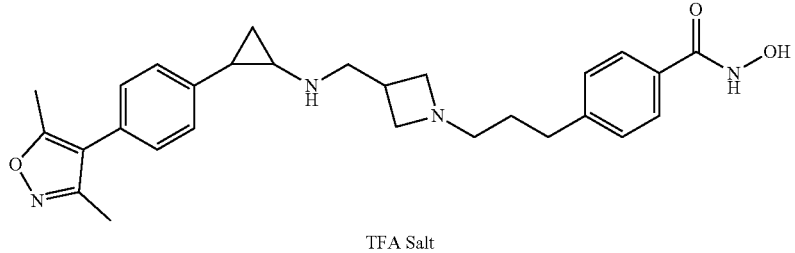 [SMILES: Cc1noc(C)c1-c1ccc(C2CC2NCC2CN(CCCc3ccc(C(=O)NO)cc3)C2)cc1]

TFA Salt

The compound was synthesized using the I-64 following the procedure for Example 2. ¹HNMR (400 MHz, DMSO-d₆): δ11.13 (bs, 1H), 9.14 (bs, 1H), 8.92 (bs, 2H), 7.69 (d, 2H, J=7.6 Hz), 7.32-7.28 (m, 6H), 3.54-3.51 (m, 2H), 3.26-3.20 (m, 1H), 3.08-2.98 (m, 5H), 2.92-2.85 (m, 2H), 2.68-2.64 (m, 2H), 2.35 (s, 3H), 2.18 (s, 3H), 2.01-1.90 (m, 4H), 1.78-1.64 (m, 1H), 1.51-1.47 (m, 1H), 1.40-1.32 (m, 3H). LC-MS m/z calcd for $C_{30}H_{38}N_4O_3$, 502.3; found 503.3[M+H]⁺. HPLC purity 99.5%.

Example 65 3-(3-(3-(((2-(4-(3,5-dimethylisoxazol-4-yl)phenyl)cyclopropyl)amino)methyl)azetidin-1-yl)propyl)-N-hydroxybenzamide TFA Salt

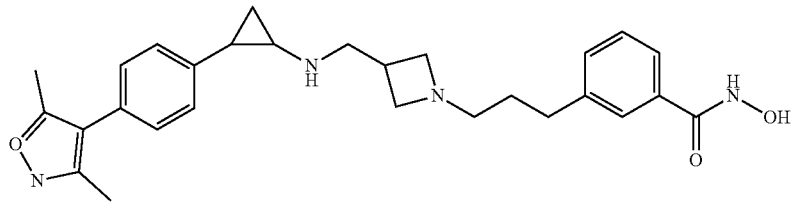

The compound was synthesized using the I-65 following the procedure for Example 48. ¹HNMR (400 MHz, DMSO-d₆): δ 11.13 (bs, 1H), 9.81 (bs, 1H), 8.97 (bs, 3H), 7.69 (d, 2H, J=8.0 Hz), 7.33-7.26 (m, 6H), 4.21-4.18 (m, 1H), 4.12-4.00 (m, 2H), 3.89-3.80 (m, 2H), 3.40-3.32 (m, 2H), 3.29-2.98 (m, 5H), 2.64-2.60 (m, 1H), 2.36 (s, 3H), 2.18 (s, 3H), 1.80-1.73 (m, 2H), 1.44-1.41 (m, 1H), 1.39-1.31 (m, 1H). LC-MS m/z calcd for $C_{28}H_{34}N_4O_3$, 474.6; found 475.6 [M+H]⁺. HPLC purity 99%.

Example 66 N-hydroxy-4-(3-(4-(((2-(4-(6-(trifluoromethyl)pyridin-3-yl)phenyl)cyclopropyl)amino)methyl)piperidin-1-yl)propyl)benzamide TFA Salt

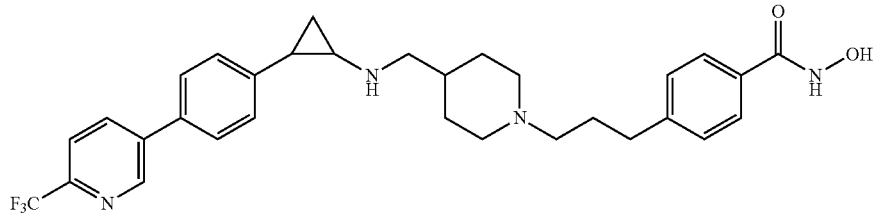 [SMILES: O=C(NO)c1ccc(CCCN2CCC(CNC3CC3c3ccc(-c4ccc(C(F)(F)F)nc4)cc3)CC2)cc1]

The compound was synthesized using the I-66 following the procedure for Example 2. ¹HNMR (400 MHz, DMSO-d$_6$): δ 11.14 (bs, 1H), 9.18 (bs, 1H), 9.07 (s, 1H), 8.99 (bs, 2H), 8.33 (d, 1H, J=8 Hz), 7.96 (d, 1H, J=8.4 Hz), 7.77 (d, 2H, J=8 Hz), 7.70 (d, 1H, J=8 Hz), 7.62 (d, 1H, J=7.6 Hz), 7.35 (d, 2H, J=8 Hz), 7.30 (d, 1H, J=8 Hz), 7.25 (d, 1H, J=8 Hz), 3.55-3.48 (m, 2H), 3.30-3.16 (m, 1H), 3.10-2.84 (m, 2H), 2.69-2.61 (m, 2H), 2.01-1.86 (m, 5H), 1.56-1.50 (m, 1H), 1.45-1.32 (m, 3H). LC-MS m/z calcd for $C_{31}H_{35}F_3N_4O_2$, 552.3; found 553.3 [M+H]$^+$. HPLC purity 99.1%.

Example 67 N-hydroxy-4-(3-(4-(((2-(1-isopropyl-1H-pyrazol-4-yl)cyclopropyl)amino)methyl)piperidin-1-yl)propyl)benzamide TFA Salt

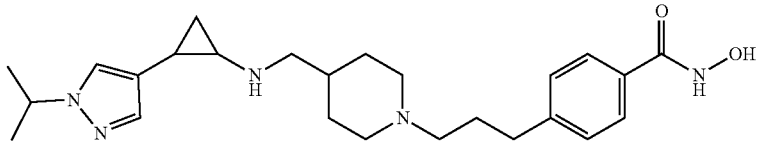 [SMILES: CC(C)n1cc(C2CC2NCC2CCN(CCCc3ccc(C(=O)NO)cc3)CC2)cn1]

The compound was synthesized using the I-67 following the procedure for Example 2. ¹HNMR (400 MHz, DMSO-d$_6$): δ 11.14 (bs, 1H), 9.10 (bs, 1H), 8.78 (bs, 2H), 7.70 (d, 2H, J=8 Hz), 7.61 (s, 1H), 7.31-7.28 (m, 3H), 4.40-4.36 (m, 1H), 3.54-3.50 (m, 2H), 3.30-3.11 (m, 1H), 3.07-2.98 (m, 4H), 2.92-2.76 (m, 4H), 2.24-1.98 (m, 2H), 1.97-1.90 (m, 5H) 1.41-1.30 (m, 8H), 1.10-1.05 (m, 1H). LC-MS m/z calcd for $C_{25}H_{37}N_5O_2$, 439.6; found 440.6 [M+H]$^+$. HPLC purity 99.2%.

Example 68 N-hydroxy-4-(3-(4-(((2-(1-phenyl-1H-pyrazol-4-yl)cyclopropyl)amino)methyl)piperidin-1-yl)propyl)benzamide TFA Salt

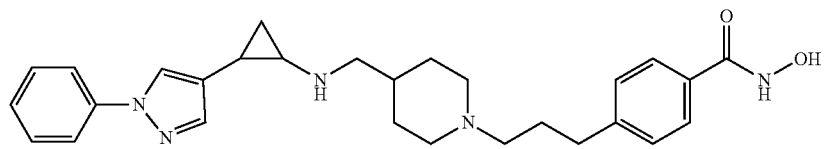 [SMILES: O=C(NO)c1ccc(CCCN2CCC(CNC3CC3c3cnn(-c4ccccc4)c3)CC2)cc1]

The compound was synthesized using the I-68 following the procedure for Example 2. ¹HNMR (400 MHz, DMSO-d$_6$): δ 11.14 (bs, 1H), 8.88 (bs, 3H), 8.36 (s, 1H), 7.75-7.65 (m, 5H), 7.49-7.45 (m, 2H), 7.31-7.26 (m, 3H), 3.55-3.51 (m, 2H), 3.08-2.98 (m, 4H), 2.95-2.84 (m, 3H), 2.71-2.63 (m, 2H), 2.00-1.89 (m, 6H), 1.45-1.34 (m, 3H), 1.25-1.19 (m, 1H). LC-MS m/z calcd for $C_{28}H_{35}N_5O_2$, 473.3; found 474.3 [M+H]$^+$. HPLC purity 99.5%.

Example 69 N-hydroxy-4-(3-(4-(((2-(2-methylthiazol-5-yl)cyclopropyl)amino)methyl)piperidin-1-yl)propyl)benzamide TFA Salt

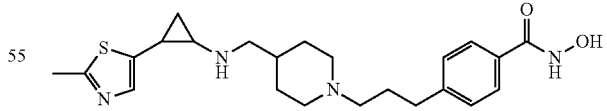

The compound was synthesized using the I-69 following the procedure for Example 2. ¹HNMR (400 MHz, DMSO-d$_6$): δ 11.10 (bs, 1H), 9.36 (bs, 1H), 9.10 (bs, 2H), 7.69 (d, 2H, J=8.4 Hz), 7.42 (s, 1H), 7.29 (d, 2H, J=7.6 Hz), 3.56-3.48 (m, 2H), 3.30-3.16 (m, 1H), 3.06-2.96 (m, 4H), 2.94-2.82 (m, 2H), 2.70-2.64 (m, 2H), 2.62-2.58 (m, 1H), 2.58 (s, 3H), 2.00-1.86 (m, 5H) 1.56-1.46 (m, 1H), 1.42-1.32 (m, 2H), 1.32-1.26 (m, 1H). LC-MS m/z calcd for $C_{23}H_{32}N_4O_2S$, 428.5; found 429.5 [M+H]$^+$.

Example 70 N-hydroxy-4-(3-(4-(((2-(pyridin-3-yl)cyclopropyl)amino)methyl)piperidin-1-yl)propyl)benzamide TFA Salt

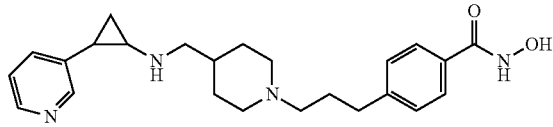 [SMILES: O=C(NO)c1ccc(CCCN2CCC(CNC3CC3c3cccnc3)CC2)cc1]

The compound was synthesized using the I-70 following the procedure for Example 2. $^1$HNMR (400 MHz, DMSO-d$_6$): δ 11.13 (bs, 1H), 9.35 (bs, 1H), 9.11 (bs, 2H), 8.57 (s, 1H), 8.51 (d, 1H, J=4.8 Hz), 7.75-7.67 (m, 3H), 7.49-7.45 (m, 1H), 7.29 (d, 2H, J=8.4 Hz), 3.59-3.53 (m, 2H), 3.08-2.98 (m, 5H), 2.94-2.82 (m, 2H), 2.73-2.67 (m, 2H), 2.02-1.91 (m, 5H), 1.78-1.71 (m, 1H), 1.55-1.51 (m, 1H), 1.45-1.38 (m, 3H). LC-MS m/z calcd for C$_{24}$H$_{32}$N$_4$O$_2$, 408.3; found 409.3 [M+H]$^+$.

Example 71 N-hydroxy-4-(3-(2-(((2-(4-methoxyphenyl)cyclopropyl)amino)methyl)-5,6-dihydroimidazo[1,2-a]pyrazin-7(8H)-yl)propyl)benzamide TFA Salt

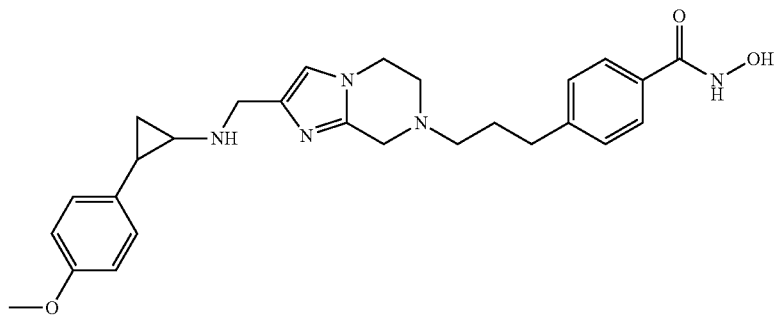 [SMILES: COc1ccc(C2CC2NCc2cn3c(n2)CN(CCCc2ccc(C(=O)NO)cc2)CC3)cc1]

The compound was synthesized using the I-71 following the procedure for Example 2. $^1$HNMR (400 MHz, DMSO-d$_6$): δ 11.18 (bs, 1H), 9.31 (bs, 2H), 7.69 (d, 2H, J=7.6 Hz), 7.31-7.27 (m, 3H), 7.02 (d, 2H, J=9.2 Hz), 6.83 (d, 2H, J=8.4 Hz), 4.40-4.29 (m, 2H), 4.23-4.11 (m, 4H), 3.69 (s, 3H), 3.60-3.50 (m, 2H) 3.16-3.08 (m, 2H), 2.88-2.76 (m, 1H) 2.71-2.65 (m, 2H), 2.32-2.24 (m, 1H), 2.08-1.98 (m, 2H), 1.36-1.31 (m, 1H), 1.22-1.14 (m, 1H). LC-MS m/z calcd for C$_{27}$H$_{33}$N$_5$O$_3$, 475.3; found 474.5 [M–H]$^+$. HPLC purity 99.2%.

Example 72 4-(3-(2-(((2-(4-fluorophenyl)cyclopropyl)amino)methyl)-5,6-dihydroimidazo[1,2-a]pyrazin-7(8H)-yl)propyl)-N-hydroxybenzamide TFA Salt

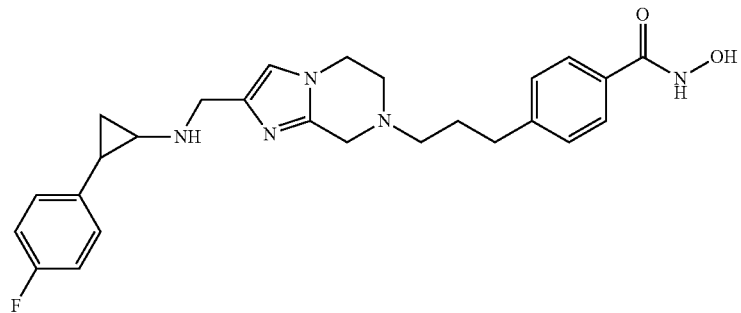 [SMILES: O=C(NO)c1ccc(CCCN2CCn3cc(CNC4CC4c4ccc(F)cc4)nc3C2)cc1]

The compound was synthesized using the I-72 following the procedure for Example 2. $^1$HNMR (400 MHz, DMSO-d$_6$): δ 11.12 (s, 1H), 9.27 (bs, 2H), 7.68 (d, 2H, J=8.0 Hz), 7.29 (d, 2H, J=7.6 Hz), 7.24 (s, 1H), 7.13-7.07 (m, 4H), 4.16-4.12 (m, 2H), 3.89 (bs, 4H), 3.38-3.31 (m, 2H), 2.85 (s, 1H), 2.67 (t, 2H, J=7.2 Hz), 2.31 (d, 1H, J=6.0 Hz), 1.96 (bs, 2H), 1.37 (t, 1H, J=4.4 Hz), 1.24 (s, 1H), 1.21 (s, 2H). LC-MS m/z calcd for C$_{26}$H$_{30}$FN$_5$O$_2$, 463.2; found 464.3 [M+H]$^+$. HPLC purity 99.6%.

Example 73 4-(3-(4-(((2-(3,4-difluorophenyl)cyclopropyl)amino)methyl)-1H-imidazol-1-yl)propyl)-N-hydroxybenzamide TFA Salt

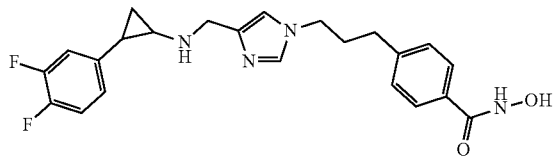 [SMILES: O=C(NO)c1ccc(CCCn2cnc(CNC3CC3c3ccc(F)c(F)c3)c2)cc1]

The compound was synthesized using the I-73 following the procedure for Example 2. $^1$HNMR (400 MHz, DMSO-$d_6$): δ 11.12 (bs, 1H), 9.20 (bs, 2H), 8.05 (s, 1H), 7.67 (d, 1H, J=8.0 Hz), 7.60 (d, 1H, J=7.6 Hz), 7.38-7.17 (m, 5H), 7.00-6.96 (m, 1H), 4.19 (s, 2H), 4.05-3.92 (m, 2H), 2.93-2.89 (m, 1H), 2.58-2.50 (m, 2H), 2.35-2.30 (m, 1H), 2.07-1.98 (m, 2H), 1.43-1.34 (m, 1H), 1.32-1.24 (m, 1H). LC-MS m/z calcd for $C_{23}H_{24}F_2N_4O_2$, 426.2; found 427.2 [M+H]$^+$. HPLC purity 99.4%.

Example 74 N-hydroxy-4-(3-(4-(((2-phenylcyclopropyl)amino)methyl)-1H-imidazol-1-yl)propyl)benzamide TFA Salt

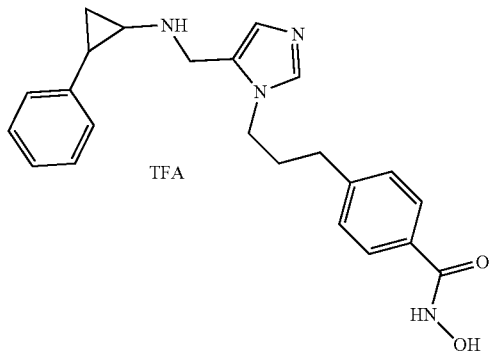 [SMILES: O=C(NO)c1ccc(CCCn2cncc2CNC2CC2c2ccccc2)cc1]

The compound was synthesized using the I-74 following the procedure for Example 2. $^1$HNMR (400 MHz, DMSO-$d_6$): δ 11.13 (bs, 1H), 8.99 (s, 1H), 7.68 (d, 2H, J=8.0 Hz), 7.57 (s, 1H), 7.31-7.24 (m, 4H), 7.22-7.18 (m, 1H), 7.08 (d, 2H, J=7.6 Hz), 4.37 (s, 2H), 4.20-4.16 (m, 2H), 2.92-2.85 (m, 1H), 2.68-2.60 (m, 2H), 2.28-2.21 (m, 1H), 2.12-2.04 (m, 2H), 1.38-1.30 (m, 1H), 1.25-1.18 (m, 1H). LC-MS m/z calcd for $C_{23}H_{26}N_4O_2$, 390.2; found 391.2 [M+H]$^+$. HPLC purity 99.0%.

Example 75 N-hydroxy-4-(3-(4-(((2-phenylcyclopropyl)amino)methyl)-1H-imidazol-1-yl)propyl)benzamide TFA Salt

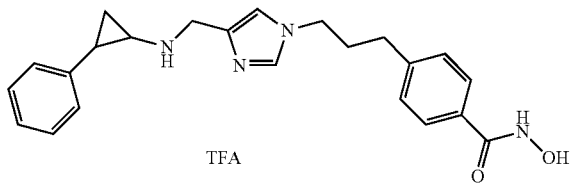 [SMILES: O=C(NO)c1ccc(CCCn2cnc(CNC3CC3c3ccccc3)c2)cc1]

The compound was synthesized using the I-75 following the procedure for Example 2. $^1$HNMR (400 MHz, DMSO-$d_6$): δ 11.14 (bs, 1H), 9.20 (bs, 2H), 8.31 (s, 1H), 7.67 (d, 2H, J=7.6 Hz), 7.46 (s, 1H), 7.27-7.23 (m, 4H), 7.19-7.15 (m, 1H), 7.08 (d, 2H, J=7.2 Hz), 4.30-4.23 (m, 2H), 4.08-4.00 (m, 2H), 2.94-2.90 (m, 1H), 2.59-2.55 (m, 2H), 2.36-2.31 (m, 1H), 2.05-1.98 (m, 2H), 1.42-1.36 (m, 1H) 1.27-1.22 (m, 1H). LC-MS m/z calcd for $C_{23}H_{26}N_4O_2$, 390.2; found 391.2 [M+H]$^+$. HPLC purity 99.7%.

Example 76 N-hydroxy-4-(3-(4-(((2-phenylcyclopropyl)amino)methyl)-1H-pyrazol-1-yl)propyl)benzamide TFA Salt

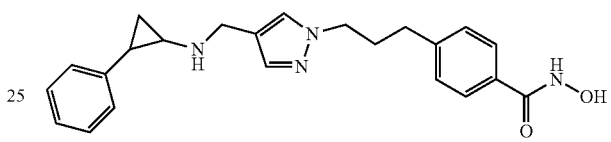

The compound was synthesized using the I-76 following the procedure for Example 2. $^1$HNMR (400 MHz, DMSO-$d_6$): δ 11.11 (bs, 1H), 9.03 (bs, 3H), 7.77 (s, 1H), 7.67 (d, 2H, J=8.4 Hz), 7.52 (s, 1H), 7.29-7.16 (m, 5H), 7.12 (d, 2H, J=7.6 Hz), 4.20-4.17 (m, 2H), 4.07 (t, 2H, J=6.8 Hz), 2.93-2.87 (m, 1H), 2.65-2.53 (m, 2H), 2.37-2.32 (m, 1H), 2.06-1.99 (m, 2H), 1.43-1.37 (m, 1H) 1.31-1.26 (m, 1H). LC-MS m/z calcd for $C_{23}H_{26}N_4O_2$, 390.2; found 391.2 [M+H]$^+$. HPLC purity 99.7%.

Example 77 N-hydroxy-4-(3-(4-(((2-phenylcyclopropyl)amino)methyl)-1H-1,2,3-triazol-1-yl)propyl)benzamide TFA Salt

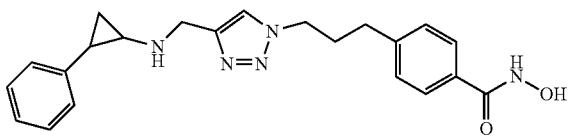 [SMILES: O=C(NO)c1ccc(CCCn2cc(CNC3CC3c3ccccc3)nn2)cc1]

The compound was synthesized using the I-77 following the procedure for Example 2. $^1$HNMR (400 MHz, DMSO-$d_6$): δ 11.12 (bs, 1H), 9.44 (bs, 2H), 8.99 (bs, 1H), 8.16 (s, 1H), 7.68 (d, 2H, J=8.4 Hz), 7.30-7.24 (m, 4H), 7.20-7.16 (m, 1H), 7.11-7.09 (m, 2H), 4.45 (s, 2H), 4.42-4.36 (m, 2H), 2.98-2.95 (m, 1H), 2.60-2.53 (m, 2H), 2.38-2.33 (m, 1H), 2.13-2.05 (m, 2H), 1.43-1.38 (m, 1H) 1.29-1.24 (m, 1H). LC-MS m/z calcd for $C_{22}H_{25}N_5O_2$, 391.4; found 392.4 [M+H]$^+$. HPLC purity 99.6%.

Example 78 4-(3-(6-(((2-(4-fluorophenyl)cyclopropyl)amino)methyl)-3,4-dihydroisoquinolin-2(1H)-yl)propyl)-N-hydroxybenzamide TFA Salt

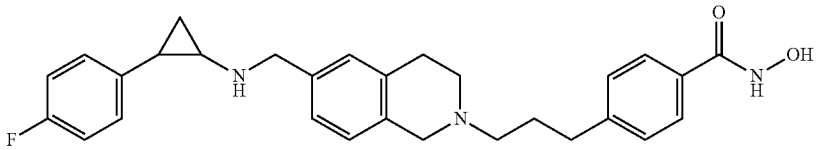 [SMILES: O=C(NO)c1ccc(CCCN2CCc3cc(CNC4CC4c4ccc(F)cc4)ccc3C2)cc1]

The compound was synthesized using the I-78 following the procedure for Example 2. $^1$HNMR (400 MHz, DMSO-$d_6$): δ 11.14 (bs, 1H), 9.91 (bs, 1H), 9.37 (bs, 1H), 9.21 (bs, 1H), 8.95 (bs, 1H), 7.73-7.68 (m, 2H), 7.39-7.28 (m, 4H), 7.24-7.18 (m, 1H), 7.16-7.08 (m, 4H), 4.96-4.77 (m, 1H), 4.32-4.22 (m, 1H), 4.05-3.94 (m, 1H), 3.92-3.84 (m, 1H), 3.78-3.66 (m, 1H), 3.35-3.28 (m, 2H), 3.26-3.27 (m, 2H), 3.07-2.93 (m, 1H), 2.90-2.81 (m, 1H), 2.78-2.68 (m, 2H), 2.28-2.21 (m, 1H), 2.10-2.03 (m, 1H), 1.45-1.36 (m, 1H), 1.32-1.26 (m, 2H). LC-MS m/z calcd for $C_{29}H_{32}FN_3O_2$, 473.2; found 474.2 [M+H]$^+$. HPLC purity 96.9%.

Example 79 4-((7-(((2-(4-fluorophenyl)cyclopropyl)amino)methyl)-3,4-dihydroisoquinolin-2(1H)-yl)methyl)-N-hydroxybenzamide TFA Salt

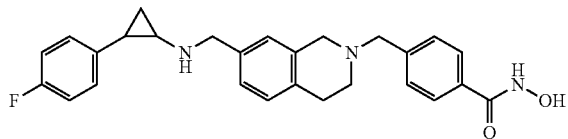 [SMILES: O=C(NO)c1ccc(CN2CCc3ccc(CNC4CC4c4ccc(F)cc4)cc3C2)cc1]

The compound was synthesized using the I-79 following the procedure for Example 2. $^1$HNMR (400 MHz, DMSO-$d_6$): δ 11.28 (bs, 1H), 10.4 (bs, 1H), 9.30 (bs, 1H), 9.19 (bs, 1H), 7.86-7.77 (m, 2H), 7.63-7.56 (m, 2H), 7.37-7.32 (m, 1H), 7.27-7.20 (m, 2H), 7.11-7.09 (m, 4H), 4.56-4.46 (m, 2H), 4.28-4.20 (m, 4H), 3.75-3.66 (m, 2H), 3.13-3.04 (m, 2H), 2.84-2.80 (m, 1H), 2.34-2.30 (m, 1H), 1.41-1.34 (m, 1H), 1.31-1.23 (m, 1H). LC-MS m/z calcd for $C_{27}H_{28}FN_3O_2$, 445.2; found 446.1 [M+H]$^+$. HPLC purity 97.0%.

Example 80 4-((2-(((2-(4-fluorophenyl)cyclopropyl)amino)methyl)-5,6-dihydroimidazo[1,2-a]pyrazin-7(8H)-yl)methyl)-N-hydroxybenzamide TFA Salt

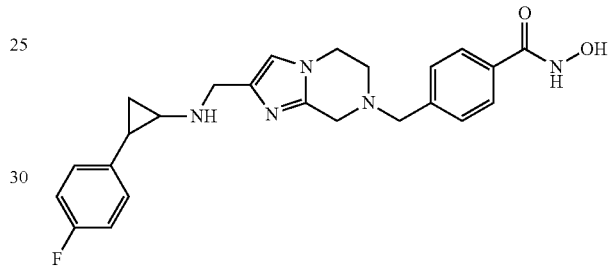

The compound was synthesized using the I-80 following the procedure for Example 2. $^1$HNMR (400 MHz, DMSO-$d_6$): δ 11.17 (s, 1H), 9.14 (bs, 1H), 7.75-7.67 (m, 2H), 7.44-7.39 (m, 2H), 7.22-7.18 (m, 1H), 7.13-7.05 (m, 4H), 4.21-3.71 (m, 8H), 3.09-2.97 (m, 1H), 2.96-2.89 (m, 1H), 2.86-2.81 (m, 1H), 2.32-2.26 (m, 1H), 1.41-1.39 (m, 1H), 1.26-1.19 (m, 2H). LC-MS m/z calcd for $C_{24}H_{26}FN_5O_2$, 436.1; found 436.2 [M+H]$^+$. HPLC purity 99.8%.

Example 81 N-hydroxy-4-(3-(4(((2-(1,3,3,-trimethyl-2-oxoindoline-5-yl)cyclopropyl)amino)methyl)piperidine-1-yl)propyl)benzamide TFA Salt

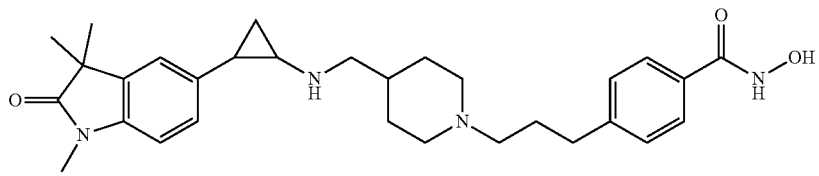 [SMILES: CN1C(=O)C(C)(C)c2cc(C3CC3NCC3CCN(CCCc4ccc(C(=O)NO)cc4)CC3)ccc21]

The compound was synthesized using the I-81 following the procedure for Example 2. $^1$HNMR (400 MHz, DMSO-$d_6$): δ 11.16 (bs, 1H), 9.30 (bs, 1H), 8.98 (bs, 3H), 7.69 (d, 2H, J=8 Hz), 7.29 (d, 2H, J=7.6 Hz), 7.16 (s, 1H), 7.06 (d, 1H, J=8 Hz), 6.92 (d, 1H, J=8 Hz), 3.54-3.50 (m, 2H), 3.09 (s, 3H), 3.07-2.98 (m, 3H), 2.95-2.82 (m, 3H), 2.68-2.63 (m, 2H), 2.46-2.38 (m, 2H), 1.98-1.91 (m, 5H), 1.46-1.36 (m. 3H), 1.29-1.20 (m. 7H). LC-MS m/z calcd for $C_{30}H_{40}N_4O_3$, 504.3; found 505.5 [M+H]$^+$. HPLC purity 99.8%.

Example 82 N-hydroxy-4-(3-oxo-3-(4-(((2-phenylcyclopropyl)amino)methyl)piperidin-1-yl)propyl)benzamide TFA Salt

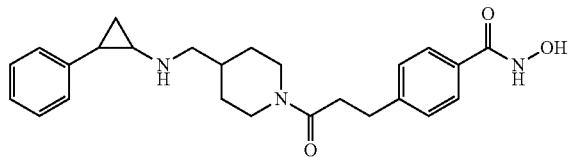 [SMILES: O=C(NO)c1ccc(CCC(=O)N2CCC(CNC3CC3c3ccccc3)CC2)cc1]

The compound was synthesized using the I-82 following the procedure for Example 2. ¹HNMR (400 MHz, DMSO-$d_6$): δ 11.09 (s, 1H), 8.90 (bs, 1H), 8.72 (bs, 2H), 7.64 (d, 2H, J=8.4 Hz), 7.32-7.25 (m, 4H), 7.22-7.19 (m, 1H), 7.19-7.14 (m, 2H), 4.38-4.32 (m, 1H), 3.89-3.83 (m, 1H), 3.00-2.81 (m, 4H), 2.83-2.79 (m, 2H), 2.64-2.61 (m, 3H), 2.59-2.40 (m, 2H), 1.90-1.80 (m, 1H), 1.73-1.66 (m, 2H), 1.46-1.40 (m, 1H), 1.30-1.25 (m, 1H), 1.08-0.95 (m, 1H). LC-MS m/z calcd for $C_{25}H_{31}N_3O_3$, 421.2; found 422.3 [M+H]⁺. HPLC purity 99.5%.

Example 83 N-hydroxy-4-(3-oxo-3-(4-((2-phenylcyclopropyl)amino)piperidin-1-yl)propyl)benzamide TFA Salt

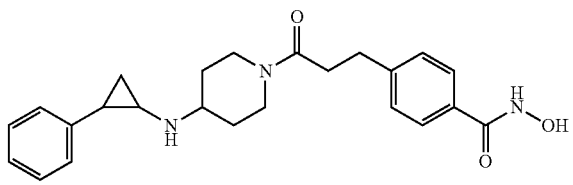 [SMILES: O=C(NO)c1ccc(CCC(=O)N2CCC(NC3CC3c3ccccc3)CC2)cc1]

The compound was synthesized using the I-83 following the procedure for Example 2. ¹HNMR (400 MHz, DMSO-$d_6$): δ 11.1 (bs, 1H), 8.95 (bs, 2H), 7.64 (d, 2H, J=8.4 Hz), 7.32-7.26 (m, 4H), 7.23-7.20 (m, 1H), 7.19-7.15 (m, 2H), 4.46-4.39 (m, 1H), 4.01-3.92 (m, 2H), 3.55-3.40 (m, 1H), 3.04-2.90 (m, 2H), 2.88-2.78 (m, 2H), 2.69-2.61 (m, 2H), 2.59-2.52 (m, 1H), 2.41-2.31 (m, 1H) 2.08-1.95 (m, 2H), 1.45-1.31 (m, 4H). LC-MS m/z calcd for $C_{24}H_{29}N_3O_3$, 407.2; found 408.2 [M+H]⁺. HPLC purity 99.7%.

Example 84 N-hydroxy-4-(2-oxo-2-(4-(((2-phenylcyclopropyl)amino)methyl)piperidin-1-yl)ethyl)benzamide TFA Salt

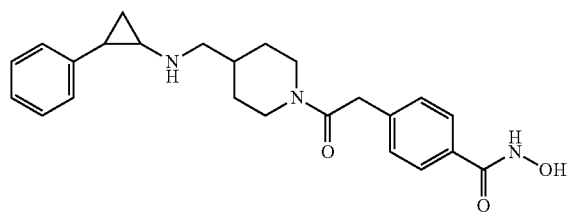 [SMILES: O=C(NO)c1ccc(CC(=O)N2CCC(CNC3CC3c3ccccc3)CC2)cc1]

The compound was synthesized using the I-84 following the procedure for Example 2. ¹HNMR (400 MHz, DMSO-$d_6$): δ 11.13 (bs, 1H), 8.77 (bs, 2H), 7.66 (d, 2H, J=8.4 Hz), 7.34-7.23 (m, 4H), 7.22-7.13 (m, 3H), 4.36-4.33 (m, 1H), 3.97-3.91 (m, 1H), 3.74 (s, 2H), 3.04-2.92 (m, 4H), 2.61-2.52 (m, 1H), 2.41-2.40 (m, 1H), 1.92-1.83 (m, 1H), 1.75-1.63 (m, 2H), 1.46-1.40 (m, 1H), 1.30-1.24 (m, 1H), 1.10-0.92 (m, 2H). LC-MS m/z calcd for $C_{24}H_{29}N_3O_3$, 407.2; found 408.2 [M+1]⁺. HPLC purity 99.8%.

Example 84 A N-hydroxy-4-(2-oxo-2-(4-((((1R,2S)-2-phenylcyclopropyl)amino)methyl)piperidin-1-yl)ethyl)benzamide TFA Salt

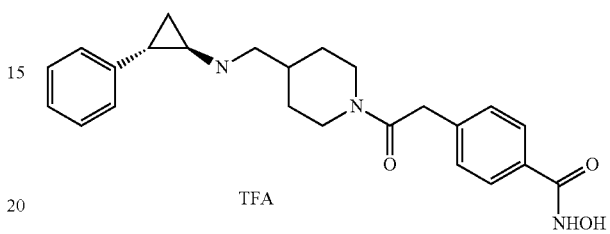

LC-MS m/z calcd for $C_{24}H_{29}N_3O_3$, 407.2; found 408.2 [M+1]+.

Example 84 B N-hydroxy-4-(2-oxo-2-(4-((((1S,2R)-2-phenylcyclopropyl)amino)methyl)piperidin-1-yl)ethyl)benzamide TFA Salt

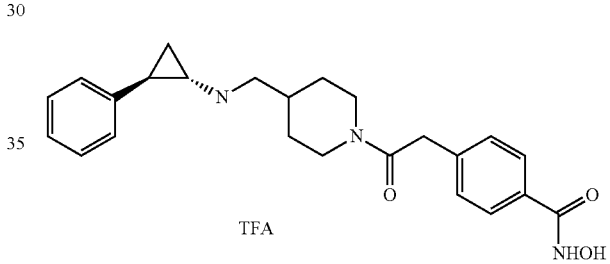

LC-MS m/z calcd for $C_{24}H_{29}N_3O_3$, 407.2; found 408.2 [M+1]⁺.

Example 85 N-hydroxy-4-((4-(((2-phenylcyclopropyl)amino)methyl)piperidin-1-yl)sulfonyl)benzamide TFA Salt

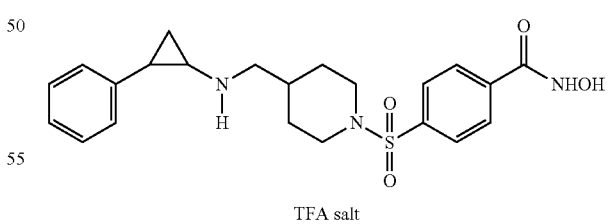

The compound was synthesized using the I-85 following the procedure for Example 2. ¹HNMR (400 MHz, DMSO-$d_6$): δ 11.43 (bs, 1H), 9.21 (bs, 1H), 8.71 (bs, 2H), 7.96 (d, 2H, J=8 Hz), 7.80 (d, 2H, J=8 Hz), 7.30-7.24 (m, 2H), 7.21-7.16 (m, 1H), 7.14-7.10 (m, 2H), 3.71-3.62 (m, 2H), 3.02-2.87 (m, 3H), 2.41-2.32 (m, 1H), 2.31-2.20 (m, 2H), 1.83-1.73 (m, 2H), 1.71-1.59 (m, 1H), 1.42-1.36 (m, 1H), 1.31-1.19 (m, 3H). LC-MS m/z calcd for $C_{22}H_{27}N_3O_4S$, 429.5; found 430.5 [M+1]⁺. HPLC purity 98.5%.

Example 86 N-hydroxy-4-((N-(2-(4-(((2-phenylcyclopropyl)amino)methyl)piperidin-1-yl)ethyl)sulfamoyl)methyl)benzamide TFA Salt

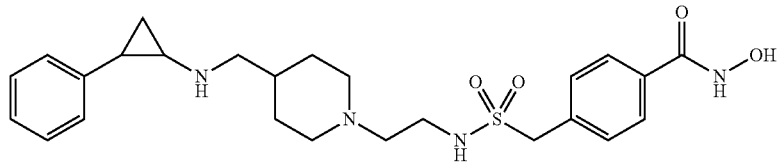 [SMILES: O=C(NO)c1ccc(CS(=O)(=O)NCCN2CCC(CNC3CC3c3ccccc3)CC2)cc1]

The compound was synthesized using the I-86 following the procedure for Example 48. $^1$HNMR (400 MHz, DMSO-$d_6$): δ 11.22 (bs, 1H), 9.33 (bs, 1H), 9.02 (bs, 3H), 7.75 (d, 2H, J=8 Hz), 7.43 (d, 2H, J=8 Hz), 7.32-7.27 (m, 2H), 7.24-7.21 (m, 1H), 7.19-7.14 (m, 2H), 4.47 (s, 2H), 3.56-3.49 (m, 2H), 3.46-3.25 (m, 2H), 3.21-3.09 (m, 3H), 3.06-2.88 (m, 4H), 2.45-2.40 (m, 1H), 2.00-1.85 (m, 3H), 1.51-1.35 (m, 3H), 1.32-1.25 (m, 1H). LC-MS m/z calcd for $C_{25}H_{34}N_4O_4S$, 486.6; found 487.6 [M+H]$^+$. HPLC purity 99.8%.

Example 87 4-(N-(2-(4-(((2-(4-fluorophenyl)cyclopropyl)amino)methyl)piperidin-1-yl)ethyl)sulfamoyl)-N-hydroxybenzamide TFA Salt

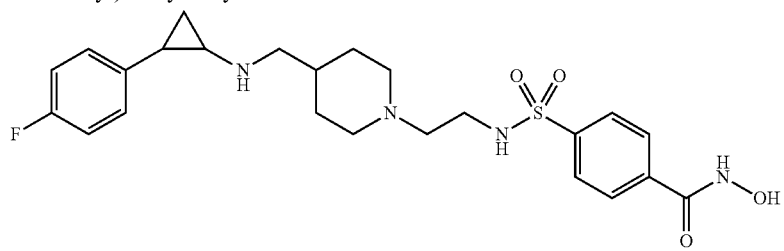

The compound was synthesized using the I-87 following the procedure for Example 48. $^1$HNMR (400 MHz, DMSO-$d_6$): δ 11.42 (bs, 1H), 9.25 (bs, 2H), 8.89 (bs, 2H), 8.08 (bs, 1H), 7.89-7.83 (m, 2H), 7.87 (d, 2H, J=8.4 Hz), 7.27-7.19 (m, 2H), 7.16-7.08 (m, 2H), 3.56-3.48 (m, 3H), 3.22-3.08 (m, 5H), 3.06-2.89 (m, 5H), 1.96-1.81 (m, 4H), 1.48-1.36 (m, 2H), 1.32-1.27 (m, 1H). LC-MS m/z calcd for $C_{24}H_{31}FN_4O_4S$, 490.2; found 491.5 [M+H]$^+$. HPLC purity 99.7%.

Example 88 N-hydroxy-4-(2-((4-(((2-phenylcyclopropyl)amino)methyl)piperidin-1-yl)sulfonyl)ethyl)benzamide TFA Salt

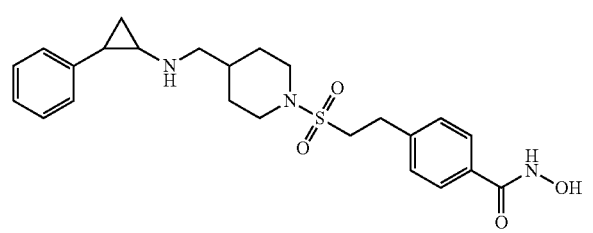 [SMILES: O=C(NO)c1ccc(CCS(=O)(=O)N2CCC(CNC3CC3c3ccccc3)CC2)cc1]

The compound was synthesized using the I-88 following the procedure for Example 2. $^1$HNMR (400 MHz, DMSO-$d_6$): δ 11.14 (bs, 1H), 8.95 (bs, 1H), 8.75 (bs, 2H), 7.66 (d, 2H, J=8 Hz), 7.36 (d, 2H, J=8 Hz), 7.32-7.26 (m, 2H), 7.23-7.15 (m, 3H), 3.64-3.58 (m, 2H), 3.37-3.30 (m, 3H), 3.06-2.94 (m, 5H), 2.82-2.74 (m, 2H), 2.46-2.38 (m, 2H), 1.82-1.76 (m, 3H), 1.48-1.40 (m, 1H), 1.32-1.18 (m, 3H). LC-MS m/z calcd for $C_{24}H_{31}N_3O_4S$, 457.2; found 458.3 [M+H]$^+$. HPLC purity 99.1%.

Example 89 N-hydroxy-N4-(2-(4-(((2-phenylcyclopropyl)amino)methyl)piperidin-1-yl)ethyl)terephthalamide TFA Salt

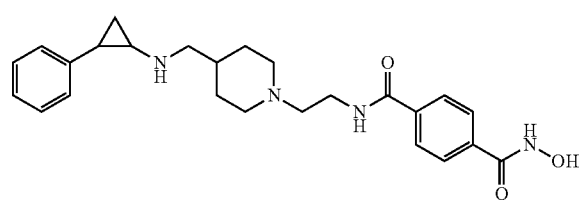 [SMILES: O=C(NO)c1ccc(C(=O)NCCN2CCC(CNC3CC3c3ccccc3)CC2)cc1]

The compound was synthesized using the I-89 following the procedure for Example 48. $^1$HNMR (400 MHz, DMSO-$d_6$): δ 11.32 (bs, 1H), 9.06 (bs, 2H), 8.86 (bs, 1H), 8.81 (bs, 2H), 7.90 (d, 2H, J=8.4 Hz), 7.84 (d, 2H, J=8 Hz), 7.32-7.28 (m, 2H), 7.23-7.21 (m, 1H), 7.18-7.16 (m, 2H), 3.70-3.58 (m, 3H), 3.36-3.30 (m, 1H), 3.28-3.20 (m, 2H), 3.08-2.93 (m, 5H), 2.02-1.84 (m, 4H), 1.49-1.38 (m, 3H), 1.34-1.28 (m, 1H). LC-MS m/z calcd for $C_{25}H_{32}N_4O_3$, 436.3; found 437.5 [M+H]$^+$. HPLC purity 99.7%.

Example 90 N1-(2-(4-(((2-(3,4-difluorophenyl)cyclopropyl)amino)methyl)piperidin-1-yl)ethyl)-N4-hydroxyterephthalamide TFA Salt

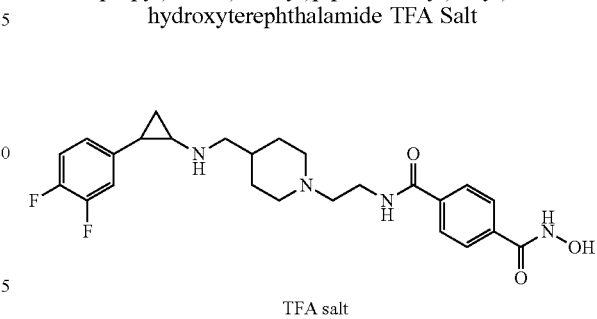

TFA salt

The compound was synthesized using the I-90 following the procedure for Example 48. $^1$HNMR (400 MHz, DMSO-$d_6$): δ 11.32 (bs, 1H), 9.10 (bs, 2H), 8.95 (bs, 1H), 8.81 (bs, 2H), 7.90 (d, 2H, J=8.4 Hz), 7.84 (d, 2H, J=8.4 Hz), 7.40-7.32 (m, 1H), 7.30-7.25 (m, 1H), 7.29-7.45 (m, 1H), 3.67-3.51 (m, 4H), 3.27-3.20 (m, 2H), 3.07-2.94 (m, 5H), 2.00-1.82 (m, 4H), 1.48-1.32 (m, 4H). LC-MS m/z calcd for $C_{25}H_{30}F_2N_4O_3$, 472.2; found 473.5 [M+H]$^+$. HPLC purity 99.4%.

Example 91 N-hydroxy-4-((4-(2-((2-phenylcyclopropyl)amino)acetyl)piperazin-1-yl)methyl)benzamide TFA Salt

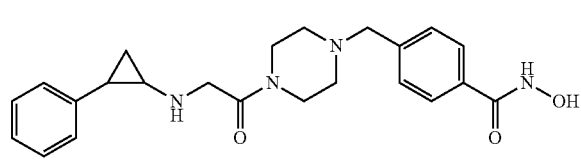 [SMILES: O=C(NO)c1ccc(CN2CCN(C(=O)CNC3CC3c3ccccc3)CC2)cc1]

The compound was synthesized using the I-91 following the procedure for Example 2. $^1$HNMR (400 MHz, DMSO-$d_6$): δ 11.27 (bs, 1H), 9.29 (bs, 2H), 7.82-7.77 (m, 2H), 7.54-7.47 (m, 2H), 7.31-7.24 (m, 2H), 7.22-7.18 (m, 1H), 7.14 (d, 2H, J=6.8 Hz), 4.30-4.20 (m, 5H), 3.81-3.72 (m, 4H), 3.50-3.32 (m, 1H), 2.90-2.81 (m, 2H), 2.01-1.92 (m, 1H), 1.47-1.28 (m, 1H), 1.74-1.51 (m, 1H), 1.27-1.21 (m, 1H). LC-MS m/z calcd for $C_{23}H_{28}N_4O_3$, 408.2; found 409.3 [M+H]$^+$. HPLC purity 98.7%.

Example 92 N-hydroxy-4-(3-oxo-3-(4-(2-((2-phenylcyclopropyl)amino)acetyl)piperazin-1-yl)propyl)benzamide TFA Salt

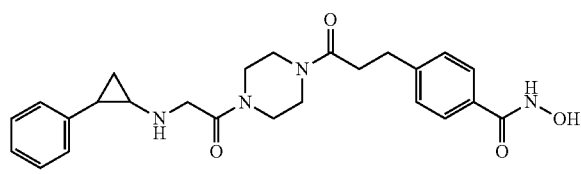 [SMILES: O=C(NO)c1ccc(CCC(=O)N2CCN(C(=O)CNC3CC3c3ccccc3)CC2)cc1]

The compound was synthesized using the I-92 following the procedure for Example 2. $^1$HNMR (400 MHz, DMSO-$d_6$): δ 11.10 (s, 1H), 9.21 (bs, 2H), 8.96 (bs, 1H), 7.64 (d, 2H, J=8.4 Hz), 7.35-7.26 (m, 4H), 7.23-7.18 (m, 1H), 7.18-7.14 (m, 2H), 4.28-4.20 (m, 2H), 3.54-3.35 (m, 8H), 2.88-2.81 (m, 3H), 2.70-2.62 (m, 2H), 1.50-1.44 (m, 1H), 1.30-1.21 (m, 2H). LC-MS m/z calcd for $C_{25}H_{30}N_4O_4$, 450.1; found 451.2 [M+H]$^+$. HPLC purity 92.7%.

Example 93 N-hydroxy-4-(3-(1-(2-((2-phenylcyclopropyl)amino)acetyl)piperidin-4-yl)propyl)benzamide TFA Salt

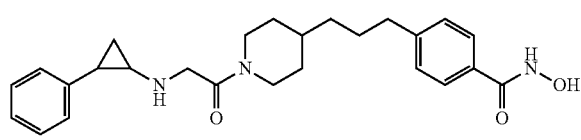 [SMILES: O=C(NO)c1ccc(CCCC2CCN(C(=O)CNC3CC3c3ccccc3)CC2)cc1]

The compound was synthesized using the I-93 following the procedure for Example 2. $^1$HNMR (400 MHz, DMSO-$d_6$): δ 11.09 (s, 1H), 9.11 (bs, 2H), 8.91 (bs, 1H), 7.65 (d, 2H, J=8.2 Hz), 7.29-7.13 (m, 7H), 4.33-4.13 (m, 3H), 3.65-3.62 (m, 1H), 3.31-2.84 (m, 2H), 2.87-2.82 (m, 1H), 2.65-2.57 (m, 3H), 1.73-1.65 (m, 2H), 1.58-1.44 (m, 4H), 1.26-1.16 (m, 3H), 1.06-0.98 (m, 1H), 0.90-0.82 (m, 1H). LC-MS m/z calcd for $C_{26}H_{33}N_3O_3$, 435.2; found 436.2 [M+H]$^+$. HPLC purity 99.9%.

Example 94 N-hydroxy-4-(3-(2-oxo-4-(((2-phenylcyclopropyl)amino)methyl)piperidin-1-yl) propyl) benzamide TFA Salt

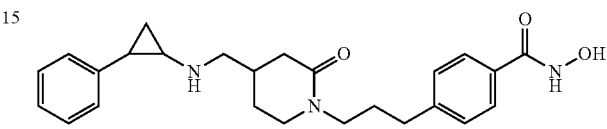

The compound was synthesized using the I-94 following the procedure for Example 2. LC-MS m/z calcd for $C_{25}H_{31}N_3O_3$, 421.5; found 422.5 [M+H]$^+$.

Example 95 N-hydroxy-4-(2-((2-phenylcyclopropyl)amino)ethoxy)benzamide TFA Salt

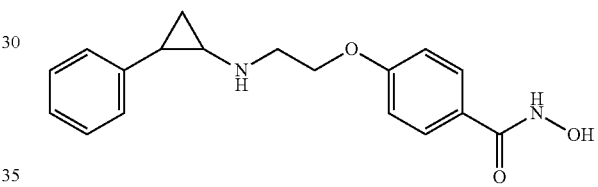

The compound was synthesized using the I-95 following the procedure for Example 2. $^1$HNMR (400 MHz, DMSO-$d_6$): δ 11.06 (bs, 1H), 9.20 (bs, 2H), 7.73 (d, 2H, J=8.8 Hz), 7.29-7.22 (m, 2H), 7.26-7.18 (m, 1H), 7.12 (d, 2H, J=9.2 Hz), 6.99 (d, 2H, J=8.8 Hz), 4.35-4.25 (m, 2H), 3.55-3.48 (m, 2H), 3.08-3.01 (m, 1H), 2.46-2.39 (m, 1H), 1.49-1.43 (m, 1H), 1.34-1.26 (m, 1H). LC-MS m/z calcd for $C_{18}H_{20}N_2O_3$, 312.1; found 313.1 [M+H]$^+$. HPLC purity 99.6%.

Example 96 6-(2-(4-(((2-(4-fluorophenyl)cyclopropyl)amino)methyl)piperidin-1-yl)ethoxy)-N-hydroxynicotinamide TFA Salt

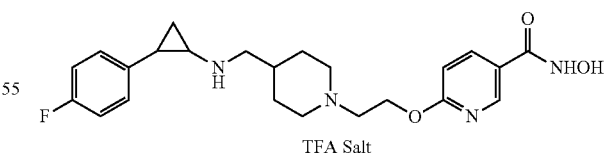

TFA Salt

The compound was synthesized using the I-96 following the procedure for Example 2. $^1$HNMR (400 MHz, DMSO-$d_6$): δ 11.01 (bs, 1H), 9.17 (bs, 1H), 8.94 (bs, 2H), 8.29 (s, 1H), 7.77 (dd, J=9.2, 2.8 Hz, 1H), 7.28-7.18 (m, 2H), 7.13 (t, J=8.8 Hz, 2H), 6.46 (d, J=9.6 Hz, 1H), 4.25-4.35 (m, 2H), 3.72-3.59 (m, 2H), 3.45-3.30 (m, 2H), 3.28-3.14 (m, 1H), 3.08-2.90 (m, 5H), 2.04-1.85 (m, 3H), 1.48-1.24 (m, 4H). LC-MS m/z calcd for $C_{23}H_{29}FN_4O_3$, 428.2; found 429.2 [M+H]$^+$. HPLC purity 99.6%.

Example 97 N-hydroxy-6-(2-(4-(((2-phenylcyclopropyl)amino)methyl)piperidin-1-yl)ethoxy)nicotinamide TFA Salt

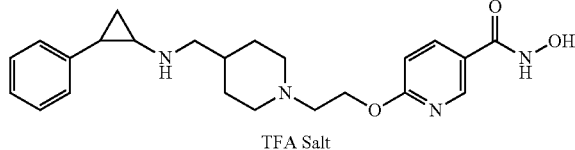 [SMILES: O=C(NO)c1ccc(OCCN2CCC(CNC3CC3c3ccccc3)CC2)nc1]

TFA Salt

The compound was synthesized using the I-97 following the procedure for Example 2. $^1$HNMR (400 MHz, DMSO-$d_6$): δ 11.02 (bs, 1H), 9.26 (bs, 1H), 9.03 (bs, 2H), 8.30 (d, J=1.6 Hz, 1H), 7.77 (dd, J=9.6, 2.4 Hz, 1H), 7.30 (t, J=7.2 Hz, 2H), 7.24-7.16 (m, 3H), 6.46 (d, J=10 Hz, 1H), 4.35-4.28 (m, 2H), 3.80-3.62 (m, 3H), 3.43-3.37 (m, 3H), 3.24-3.12 (m, 1H), 3.08-2.91 (m, 4H), 2.04-1.88 (m, 2H), 1.52-1.35 (m, 3H), 1.33-1.25 (m, 1H). LC-MS m/z calcd for $C_{23}H_{30}N_4O_3$, 410.2; found 411.2 [M+H]$^+$. HPLC purity=98.2%.

Example 98 6-(2-(4-(((2-(4'-fluoro-[1,1'-biphenyl]-4-yl)cyclopropyl)amino)methyl)piperidin-1-yl)ethoxy)-N-hydroxynicotinamide TFA Salt

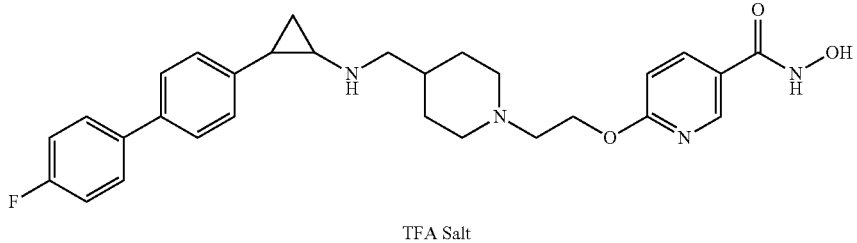 [SMILES: O=C(NO)c1ccc(OCCN2CCC(CNC3CC3c3ccc(-c4ccc(F)cc4)cc3)CC2)nc1]

TFA Salt

The compound was synthesized using the I-98 following the procedure for Example 2. $^1$HNMR (400 MHz, DMSO-$d_6$): δ 11.02 (bs, 1H), 9.14 (bs, 1H), 8.93 (bs, 3H), 8.30 (s, 1H), 7.82-7.75 (m, 1H), 7.70-7.64 (m, 2H), 7.58 (d, J=8.4 Hz, 2H), 7.32-7.24 (m, 4H), 6.46 (d, J=9.2 Hz, 1H), 4.34-4.28 (m, 2H), 3.71-3.65 (m, 3H), 3.26-3.24 (m, 1H), 3.08-2.96 (m, 3H), 2.57-2.54 (m, 3H), 2.02-1.93 (m, 3H), 1.52-1.39 (m, 4H). LC-MS m/z calcd for $C_{29}H_{33}FN_4O_3$, 504.2; found 505.2[M+H]$^+$. HPLC purity 98.2%.

Example 99 N-hydroxy-4-(2-(4-(((2-phenylcyclopropyl)amino)methyl)piperidin-1-yl)ethoxy)benzamide TFA Salt

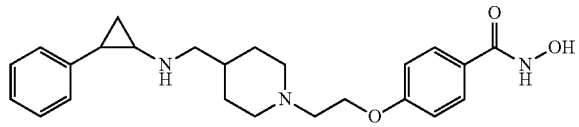 [SMILES: O=C(NO)c1ccc(OCCN2CCC(CNC3CC3c3ccccc3)CC2)cc1]

The compound was synthesized using the I-99 following the procedure for Example 2. $^1$HNMR (400 MHz, DMSO-$d_6$): δ 11.0 (bs, 1H), 9.5 (bs, 1H), 8.9 (bs, 2H), 7.75 (d, 2H, J=8 Hz), 7.32-7.26 (m, 2H), 7.23-7.15 (m, 3H), 7.03 (d, 2H, J=8 Hz), 4.41-4.35 (m, 2H), 3.52-3.45 (m, 2H), 3.35-3.28 (m, 2H), 3.10-2.95 (m, 5H), 2.00-1.91 (m, 3H), 1.51-1.41 (m, 3H), 1.32-1.25 (m, 1H). LC-MS m/z calcd for $C_{24}H_{31}N_3O_3$, 409.2; found 410.2 [M+H]$^+$. HPLC purity 99.1%.

Example 100 N-hydroxy-4-(3-(4-(((2-phenylcyclopropyl)amino)methyl)piperidin-1-yl)propoxy)benzamide TFA Salt

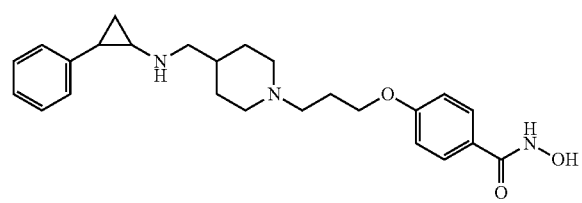 [SMILES: O=C(NO)c1ccc(OCCCN2CCC(CNC3CC3c3ccccc3)CC2)cc1]

The compound was synthesized using the I-100 following the procedure for Example 2.

$^1$HNMR (400 MHz, DMSO-$d_6$): δ 11.04 (s, 1H), 9.12 (bs, 1H), 8.87 (bs, 1H), 7.72 (d, 2H, J=8.4 Hz), 7.34-7.26 (m, 2H), 7.24-7.20 (m, 1H), 7.21-7.15 (m, 2H), 6.96 (d, 2H, J=8.8 Hz), 4.11-4.08 (m, 2H), 3.60-3.51 (m, 2H), 3.23-3.18 (m, 2H), 3.05-3.01 (m, 2H), 2.98-2.92 (m, 2H), 2.45-2.40 (m, 3H), 2.14-2.09 (m, 2H), 1.98-1.93 (m, 3H), 1.48-1.32 (m, 3H), 1.32-1.28 (m, 1H). LC-MS m/z calcd for $C_{25}H_{33}N_3O_3$, 423.2; found 424.2 [M+H]$^+$. HPLC purity 99.2%.

Example 101 N-hydroxy-4-(3-((2-phenylcyclopropyl)amino)propoxy)benzamide TFA Salt

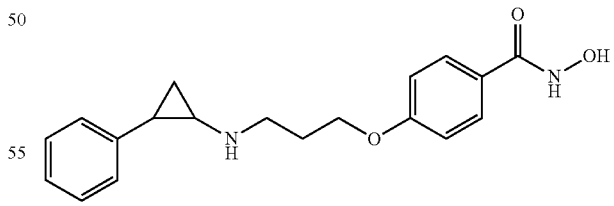

The compound was synthesized using the I-101 following the procedure for Example 2.

$^1$HNMR (400 MHz, DMSO-$d_6$): δ 11.03 (s, 1H), 8.92 (bs, 3H), 7.72 (d, 2H, J=8.9 Hz), 7.31-7.26 (m, 2H), 7.35-7.20 (m, 1H), 7.18-7.14 (m, 2H), 6.96 (m, 2H), 4.13-4.07 (m, 2H), 3.28-3.21 (bs, 2H), 3.06-2.98 (m, 1H), 2.43-2.38 (m, 1H), 2.11-2.03 (m, 2H), 1.49-1.41 (m, 1H), 1.33-1.26 (m, 1H). LC-MS m/z calcd for $C_{19}H_{22}N_2O_3$, 326.3; found 327.3 [M+H]$^+$. HPLC purity 99.7%.

Example 102 2-((2-(4-(((2-(4-fluorophenyl)cyclopropyl)amino)methyl)piperidin-1-yl)ethyl)amino)-N-hydroxypyrimidine-5-carboxamide TFA Salt

TFA Salt

The compound was synthesized using the I-102 following the procedure for Example 2.

$^1$HNMR (400 MHz, DMSO-d$_6$): δ11.07 (bs, 1H), 9.36 (bs, 1H), 9.14 (bs, 2H), 8.66 (s, 2H), 7.87 (bs, 1H), 7.26-7.19 (m, 2H), 7.15-7.08 (m, 2H), 3.72-3.58 (m, 4H), 3.38-3.12 (m, 3H), 3.08-2.88 (m, 5H), 2.00-1.82 (m, 3H) 1.52-1.38 (m, 3H), 1.33-1.20 (m, 1H). LC-MS m/z calcd for C$_{22}$H$_{29}$N$_6$O$_2$, 428.2; found 429.3 [M+H]$^+$. HPLC purity 99.8%.

Example 103 5-(2-((2-(4-fluorophenyl)cyclopropyl)amino)acetyl)-N-hydroxy-4,5,6,7-tetrahydrothieno[3,2-c]pyridine-2-carboxamide TFA Salt

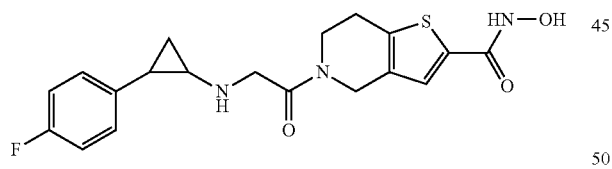

The compound was synthesized using the I-103 following the procedure for Example 2.

$^1$HNMR (400 MHz, DMSO-d$_6$): δ 11.16 (bs, 1H), 9.22 (bs, 2H), 9.06 (bs, 1H), 7.41-7.35 (m, 1H), 7.25-7.16 (m, 2H), 7.13-7.07 (m, 2H) 4.59-4.48 (m, 2H), 4.43-4.29 (m, 2H), 3.85-3.78 (m, 1H), 3.70-3.65 (m, 1H), 2.96-2.90 (m, 1H), 2.88-2.78 (m, 2H), 1.51-1.48 (m, 1H), 1.31-1.20 (m, 1H); LC-MS m/z calcd for C$_{19}$H$_{20}$FN$_3$O$_3$S, 389.1; found 390.1 [M+H]$^+$. HPLC purity 99.3%.

Example 103A 5-(2-(((1R,2S)-2-(4-fluorophenyl)cyclopropyl)amino)acetyl)-N-hydroxy-4,5,6,7-tetrahydrothieno[3,2-c]pyridine-2-carboxamide TFA Salt

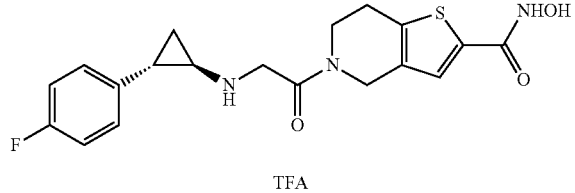

TFA

LC-MS m/z calcd for C$_{19}$H$_{20}$FN$_3$O$_3$S, 389.1; found 390.1 [M+H]$^+$

Example 103B 5-(2-(((1S,2R)-2-(4-fluorophenyl)cyclopropyl)amino)acetyl)-N-hydroxy-4,5,6,7-tetrahydrothieno[3,2-c]pyridine-2-carboxamide TFA Salt

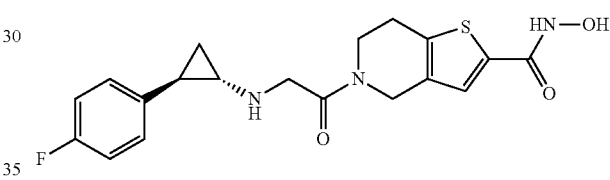

LC-MS m/z calcd for C$_{19}$H$_{20}$FN$_3$O$_3$S, 389.1; found 390.1 [M+H]$^+$

Example 104 2-(2-((2-(4-fluorophenyl)cyclopropyl)amino)acetyl)-N-hydroxy-1,2,3,4-tetrahydroisoquinoline-7-carboxamide TFA Salt

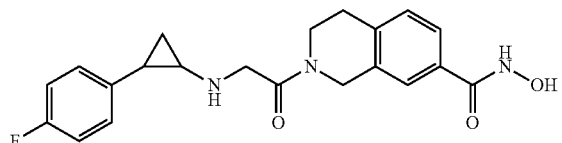

The compound was synthesized using the I-104 following the procedure for Example 2.

$^1$HNMR (400 MHz, DMSO-d$_6$): δ 11.16 (bs, 1H), 9.22 (bs, 2H), 8.96 (bs, 1H), 7.62-7.51 (m, 2H), 7.28-7.15 (m, 3H), 7.13-7.08 (m, 2H), 4.66-4.64 (m, 2H), 4.35-4.31 (m, 2H), 3.75-3.70 (m, 1H), 3.64-3.61 (m, 2H), 2.96-2.91 (m, 1H), 2.89-2.80 (m, 2H), 1.49-1.46 (m, 1H), 1.29-1.25 (m, 1H). LC-MS m/z calcd for C$_{21}$H$_{22}$FN$_3$O$_3$, 383.2; found 384.1 [M+H]$^+$. HPLC purity 99.5%.

Example 104A 2-(2-(((1S,2R)-2-(4-fluorophenyl)cyclopropyl)amino)acetyl)-N-hydroxy-1,2,3,4-tetrahydroisoquinoline-7-carboxamide TFA Salt

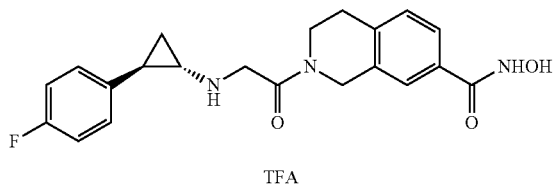

TFA

LC-MS m/z calcd for $C_{21}H_{22}FN_3O_3$, 383.2; found 384.1 [M+H]$^+$.

Example 104B 2-(2-(((1R,2S)-2-(4-fluorophenyl)cyclopropyl)amino)acetyl)-N-hydroxy-1,2,3,4-tetrahydroisoquinoline-7-carboxamide TFA Salt

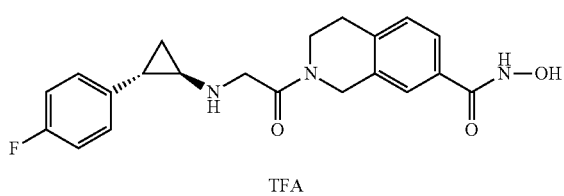 [SMILES: O=C(NO)c1ccc2c(c1)CN(C(=O)CN[C@@H]1C[C@H]1c1ccc(F)cc1)CC2]

TFA

LC-MS m/z calcd for $C_{21}H_{22}FN_3O_3$, 383.2; found 384.1 [M+H]$^+$.

Example 105 5-(4-((2-(4-fluorophenyl)cyclopropyl)amino)butanoyl)-N-hydroxy-4,5,6,7-tetrahydrothieno[3,2-c]pyridine-2-carboxamide TFA Salt

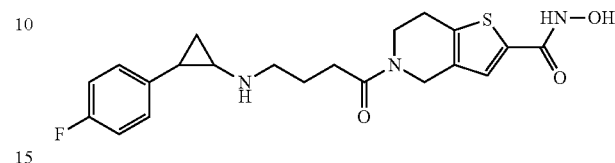

TFA salt

The compound was synthesized using the I-105 following the procedure for Example 2.
$^1$HNMR (400 MHz, DMSO-d$_6$): δ 11.08 (bs, 1H), 9.04 (bs, 1H), 8.84 (bs, 2H), 7.35 (s, 1H), 7.28-7.16 (m, 2H), 7.11 (t, J=8.4 Hz, 2H), 4.50 (s, 2H), 3.80-3.66 (m, 2H), 3.15-3.05 (m, 2H), 3.00-2.90 (m, 1H), 2.92-2.80 (m, 1H), 2.82-2.70 (m, 1H), 2.60-2.51 (m, 2H), 2.42-2.34 (m, 1H), 1.92-1.75 (m, 2H), 1.40 (q, 1H), 1.25 (q, 1H). LC-MS m/z calcd for $C_{21}H_{24}FN_3O_3S$, 417.2; found 418.4 [M+H]$^+$; HPLC purity 99.5%.

Example 106 5-(4-(4-(((2-(4-fluorophenyl)cyclopropyl)amino)methyl)piperidin-1-yl)butanoyl)-N-hydroxy-4,5,6,7-tetrahydrothieno[3,2-c]pyridine-2-carboxamide TFA Salt

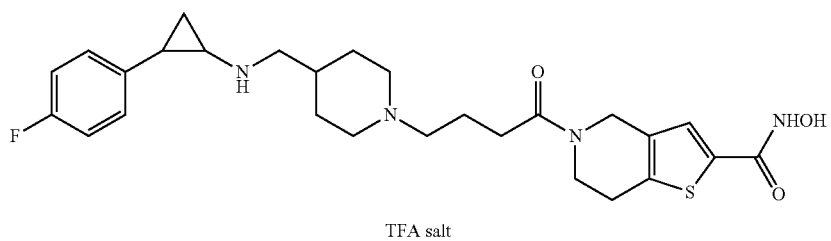

TFA salt

The compound was synthesized using the I-106 following the procedure for Example 48. $^1$HNMR (400 MHz, DMSO-d$_6$): δ 11.04 (bs, 1H), 9.05 (bs, 2H), 8.84 (bs, 2H), 7.34 (s, 1H), 7.22-7.20 (m, 2H), 7.15-7.11 (m, 2H), 4.51 (s, 2H), 3.77-3.70 (m, 2H), 3.55-3.50 (m, 2H), 3.06-3.00 (m, 4H), 2.97-2.86 (m, 4H), 2.77-2.75 (m, 1H), 2.58-2.56 (m, 2H), 2.00-1.86 (m, 6H), 1.48-1.28 (m, 4H). LC-MS m/z calcd for $C_{27}H_{35}FN_4O_3S$, 514.2; found 515.3 [M+H]$^+$. HPLC purity 99.2%.

Example 107 2-(4-((2-(4-fluorophenyl)cyclopropyl)amino)butanoyl)-N-hydroxy-1,2,3,4-tetrahydroisoquinoline-7-carboxamide TFA Salt

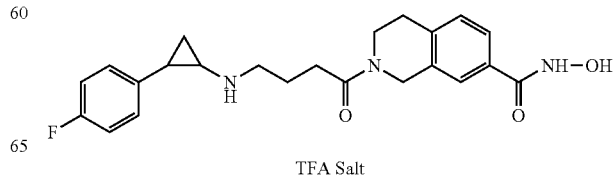

TFA Salt

The compound was synthesized using the I-107 following the procedure for Example 2.

¹HNMR (400 MHz, DMSO-d$_6$): δ 11.13 (bs, 1H), 8.86 (bs, 2H), 8.92 (bs, 2H), 7.59-7.48 (m, 2H), 7.24-7.19 (m, 3H), 7.14-7.06 (t, J=8.4 Hz, 2H), 4.63 (d, J=10 Hz, 2H), 3.69-3.53 (m, 2H), 3.14-3.05 (m, 2H), 2.98-2.95 (m, 2H), 2.82-2.76 (m, 1H), 2.58-2.56 (m, 2H), 2.45-2.38 (m, 1H), 1.90-1.82 (m, 2H), 1.45-1.38 (m, 1H), 1.32-1.24 (m, 1H). LC-MS m/z calcd for C$_{23}$H$_{26}$FN$_3$O$_3$, 411.2; found 412.2 [M+H]$^+$. HPLC purity 99.7%.

The compound was synthesized using the I-109 following the procedure for Example 48. ¹HNMR (400 MHz, DMSO-d$_6$): δ 11.20 (bs, 1H), 9.14 (bs, 2H), 8.88 (bs, 3H), 7.68 (d, 1H, J=8 Hz), 7.43-7.38 (m, 1H), 7.32-7.28 (m, 2H), 7.24-7.16 (m, 3H), 4.84 (s, 2H), 4.66 (s, 2H), 3.60-3.54 (m, 2H), 3.34-3.15 (m, 1H), 3.10-2.88 (m, 8H), 2.01-1.71 (m, 6H), 1.50-1.27 (m, 4H). LC-MS m/z calcd for C$_{28}$H$_{36}$N$_4$O$_3$, 476.3; found 477.6 [M+H]$^+$. HPLC purity 99.6%.

Example 108 2-(4-((2-(4-fluorophenyl)cyclopropyl)amino)butanoyl)-N-hydroxyisoindoline-5-carboxamide TFA Salt

Example 110 N-hydroxy-2-(3-(4-(((2-phenylcyclopropyl)amino)methyl)piperidin-1-yl)propyl)thiazole-4-carboxamide TFA Salt

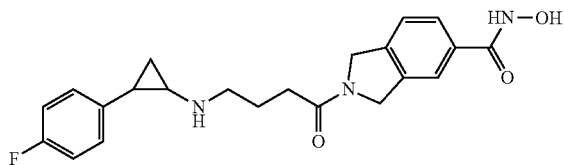 [SMILES: O=C(NO)c1ccc2c(c1)CN(C(=O)CCCNC1CC1c1ccc(F)cc1)C2]

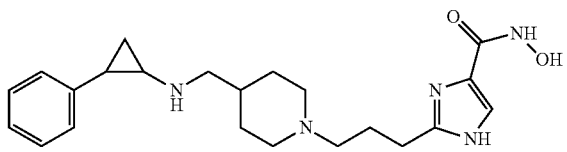

TFA salt

The compound was synthesized using the I-108 following the procedure for Example 2.

¹HNMR (400 MHz, DMSO-d$_6$): δ 11.19 (bs, 1H), 8.79 (bs, 2H), 7.75-7.62 (m, 2H), 7.43-7.35 (m, 1H), 7.25-7.21 (m, 2H), 7.15-7.10 (m, 2H), 4.81 (s, 2H), 4.66 (s, 2H), 3.16-3.10 (m, 2H), 3.02-2.96 (m, 1H), 2.43-2.36 (m, 3H), 1.94-1.88 (m, 2H), 1.44-1.40 (m, 1H), 1.33-1.27 (m, 1H). LC-MS m/z calcd for C$_{22}$H$_{24}$FN$_3$O$_3$, 397.2; found 398.2 [M+H]$^+$. HPLC purity 99.2%.

The compound was synthesized using the I-110 following the procedure for Example 48. ¹HNMR (400 MHz, DMSO-d$_6$): δ 11.32 (bs, 1H), 9.46 (bs, 1H), 9.09 (bs, 2H), 8.10 (s, 1H), 7.32-7.26 (m, 2H), 7.23-7.13 (m, 3H), 3.56-3.51 (m, 2H), 3.30-2.83 (m, 9H), 2.43-2.40 (m, 1H), 2.17-2.08 (m, 2H), 2.06-1.71 (m, 3H), 1.50-1.35 (m, 3H), 1.30-1.25 (m, 1H). LC-MS m/z calcd for C$_{22}$H$_{30}$N$_4$O$_2$S, 414.2; found 415.5 [M+H]$^+$. HPLC purity 99.5%.

Example 109 N-hydroxy-2-(4-(4-(((2-phenylcyclopropyl)amino)methyl)piperidin-1-yl)butanoyl)isoindoline-5-carboxamide TFA Salt

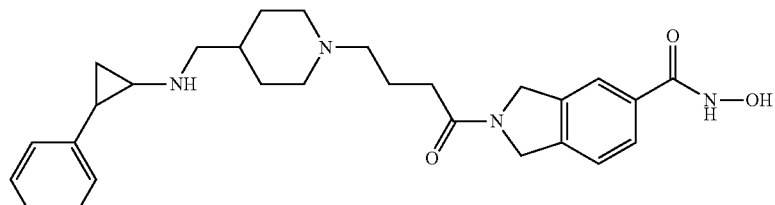

TFA Salt

Example 111 2-(3-(4-(((2-(4'-fluoro-[1,1'-biphenyl]-4-yl)cyclopropyl)amino)methyl)piperidin-1-yl)propyl)-N-hydroxythiazole-4-carboxamide TFA Salt

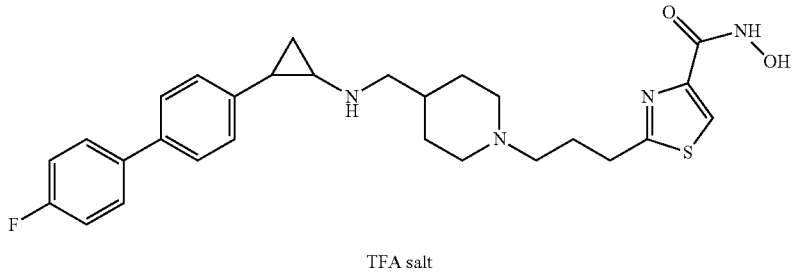 [SMILES: O=C(NO)c1csc(CCCN2CCC(CNC3CC3c3ccc(-c4ccc(F)cc4)cc3)CC2)n1]

TFA salt

The compound was synthesized using the I-111 following the procedure for Example 48. $^1$HNMR (400 MHz, DMSO-d$_6$): δ 10.98 (bs, 1H), 9.13 (bs, 2H), 8.24 (bs, 2H), 8.13 (s, 1H), 7.69-7.64 (m, 2H), 7.58 (d, 2H, J=8.6 Hz), 7.30-7.25 (m, 4H), 3.60-3.55 (m, 2H), 3.19-3.12 (m, 3H), 3.10-3.06 (m, 6H), 2.98-2.86 (m, 3H), 2.18-2.09 (m, 2H), 2.00-1.94 (m, 2H), 1.50-1.44 (m, 1H), 1.42-1.36 (m, 2H). LC-MS m/z calcd for $C_{28}H_{33}FN_4O_2S$, 508.2; found 509.6 [M+H]$^+$. HPLC purity 99.6%.

Example 112 N-hydroxy-2-(3-(4-(((2-phenylcyclopropyl)amino)methyl)piperidin-1-yl)propyl)thiazole-5-carboxamide TFA Salt

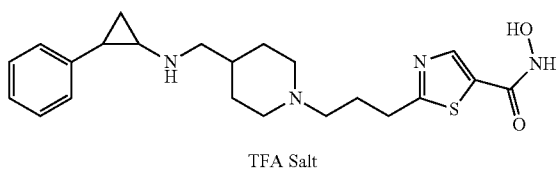 [SMILES: O=C(NO)c1cnc(CCCN2CCC(CNC3CC3c3ccccc3)CC2)s1]

TFA Salt

The compound was synthesized using the I-112 following the procedure for Example 48. $^1$HNMR (400 MHz, DMSO-d$_6$): δ 11.32 (bs, 1H), 9.45 (bs, 1H), 9.09 (bs, 2H), 8.10 (s, 1H), 7.31-7.25 (m, 2H), 7.21-7.15 (m, 3H), 3.56-3.50 (m, 2H), 3.31-3.10 (m, 3H), 3.09-3.02 (m, 3H), 2.97-2.86 (m, 2H), 2.47-2.42 (m, 2H), 2.15-2.07 (m, 2H), 2.00-1.89 (m, 2H), 1.80-1.70 (m, 1H), 1.50-1.35 (m, 3H), 1.32-1.27 (m, 1H). LC-MS m/z calcd for $C_{22}H_{30}N_4O_2S$, 415.2; found 416.5 [M+H]$^+$. HPLC purity 99.3%.

Example 113 N-hydroxy-2-(3-(4-(((2-phenylcyclopropyl)amino)methyl)piperidin-1-yl)propyl)oxazole-4-carboxamide TFA Salt

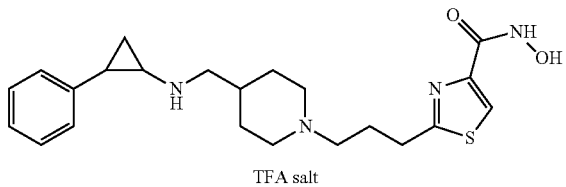 [SMILES: O=C(NO)c1csc(CCCN2CCC(CNC3CC3c3ccccc3)CC2)n1]

TFA salt

The compound was synthesized using the I-113 following the procedure for Example 48. $^1$HNMR (400 MHz, DMSO-d$_6$): δ 10.92 (bs, 1H), 9.49 (bs, 1H), 9.09 (bs, 2H), 8.47 (s, 1H), 7.32-7.14 (m, 5H), 3.60-3.51 (m, 2H), 3.32-3.12 (m, 3H), 3.08-2.81 (m, 6H), 2.15-1.73 (m, 6H), 1.50-1.37 (m, 3H), 1.30-1.23 (m, 1H). LC-MS m/z calcd for $C_{22}H_{30}N_4O_3$, 398.2; found 399.5 [M+H]$^+$. HPLC purity 99.6%.

Example 114 (E)-N-hydroxy-4-(3-oxo-3-(4-(((2-phenylcyclopropyl)amino)methyl)piperidin-1-yl)prop-1-en-1-yl)benzamide TFA Salt

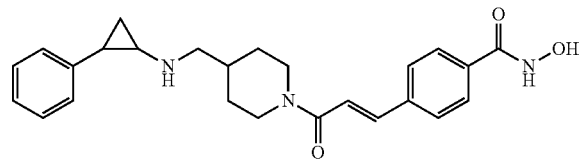 [SMILES: O=C(NO)c1ccc(/C=C/C(=O)N2CCC(CNC3CC3c3ccccc3)CC2)cc1]

The compound was synthesized using the I-114 following the procedure for Example 2.
$^1$HNMR (400 MHz, DMSO-d$_6$): δ 11.24 (bs, 1H), 9.02 (bs, 1H), 8.76 (bs, 2H), 7.79-7.72 (m, 4H), 7.47 (d, 1H, J=15 Hz), 7.33 (d, 1H, J=15 Hz), 7.33-7.27 (m, 2H), 7.22-7.15 (m, 3H), 4.47-4.42 (m, 1H), 4.33-4.27 (m, 1H), 3.11-2.97 (m, 4H), 2.72-2.64 (m, 1H), 2.48-2.38 (m, 1H), 2.00-1.91 (m, 1H), 1.84-1.75 (m, 2H), 1.48-1.41 (m, 1H), 1.33-1.27 (m, 1H), 1.19-1.09 (m, 2H). LC-MS m/z calcd for $C_{25}H_{29}N_3O_3$, 419.2; found 420.2 [M+1]$^+$. HPLC purity 99.8%.

Example 114A N-hydroxy-4-((E)-3-oxo-3-(4-((((1R,2S)-2-phenylcyclopropyl)amino)methyl)piperidin-1-yl)prop-1-en-1-yl)benzamide TFA Salt

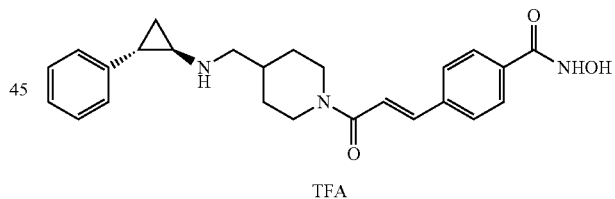

TFA

LC-MS m/z calcd for $C_{25}H_{29}N_3O_3$, 419.2; found 420.2 [M+1]$^+$.

Example 114B N-hydroxy-4-((E)-3-oxo-3-(4-((((1S,2R)-2-phenylcyclopropyl)amino)methyl)piperidin-1-yl)prop-1-en-1-yl)benzamide TFA Salt

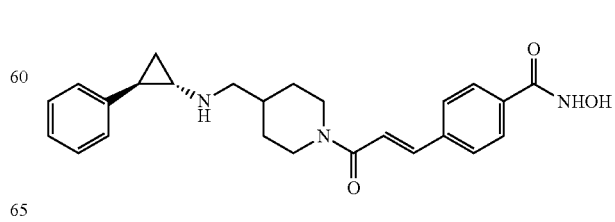

TFA Salt

Example 115 4-((E)-3-(4-((((1S,2R)-2-(4-fluorophenyl)cyclopropyl)amino)methyl)piperidin-1-yl)-3-oxoprop-1-en-1-yl)-N-hydroxybenzamide TFA Salt

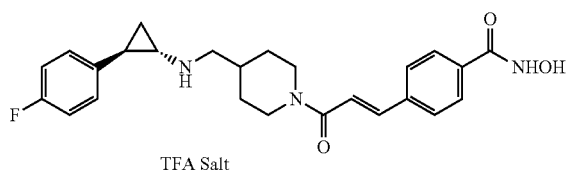

TFA Salt

The compound was synthesized using the I-115 following the procedure for Example 2.

LC-MS m/z calcd for $C_{25}H_{28}FN_3O_3$, 437.5; found 438.5 [M+1]$^+$.

Example 115A 4-((E)-3-(4-((((1R,2S)-2-(4-fluorophenyl)cyclopropyl)amino)methyl)piperidin-1-yl)-3-oxoprop-1-en-1-yl)-N-hydroxybenzamide TFA Salt

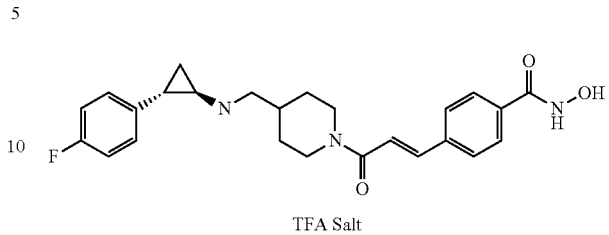

TFA Salt

LC-MS m/z calcd for $C_{25}H_{28}FN_3O_3$, 437.5; found 438.5 [M+1]$^+$.

Example 116 (E)-4-(3-(4-(((2-(4-(3,5-dimethyl-isoxazol-4-yl)phenyl)cyclopropyl)amino)methyl)piperidin-1-yl)-3-oxoprop-1-en-1-yl)-N-hydroxybenzamide TFA Salt

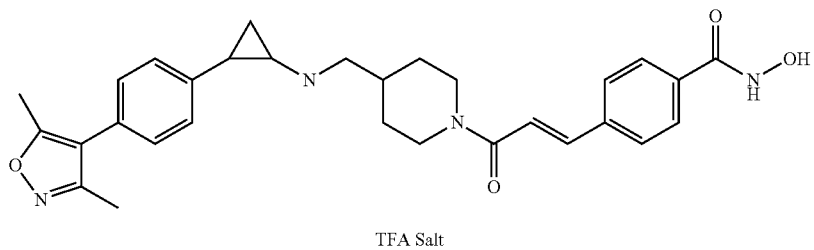 [SMILES: Cc1noc(C)c1-c1ccc(C2CC2NCC2CCN(C(=O)/C=C/c3ccc(C(=O)NO)cc3)CC2)cc1]

TFA Salt

The compound was synthesized using the I-116 following the procedure for Example 2.

$^1$HNMR (400 MHz, DMSO-d$_6$): δ 11.24 (s, 1H), 9.02 (s, 1H), 8.84-8.72 (bs, 2H), 7.76 (m, 4H), 7.48 (d, J=16.0 Hz, 1H), 7.34 (d, J=16.0 Hz, 1H), 7.30-7.26 (m, 4H), 4.4-4.3 (dd, 2H), 3.15-2.98 (m, 4H), 2.75-2.65 (m, 1H), 2.45-2.40 (m, 1H), 2.35 (s, 3H), 2.18 (s, 3H), 2.04-1.9 (m, 1H), 1.88-1.75 (m, 1H), 1.52-1.44 (m, 1H), 1.40-1.30 (q, J=6.8 Hz, 1H), 1.25-1.08 (m, 2H). LC-MS m/z calcd for $C_{30}H_{34}N_4O_4$, 514.2; found 515.2 [M+H]$^+$. HPLC purity 99.8%.

Example 117 (E)-N-hydroxy-4-(3-oxo-3-(4-(((2-(4-(pyrimidin-5-yl)phenyl)cyclopropyl)amino)methyl)piperidin-1-yl)prop-1-en-1-yl)benzamide TFA Salt

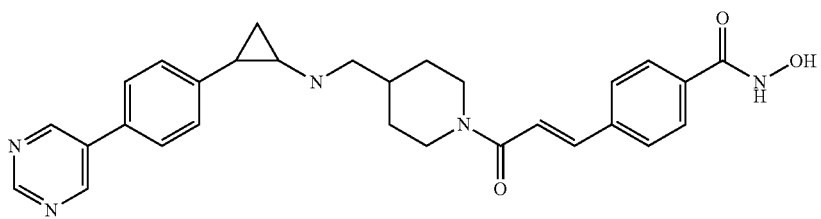

TFA Salt

The compound was synthesized using the I-117 following the procedure for Example 2.

$^1$HNMR (400 MHz, DMSO-$d_6$): δ 11.24 (bs, 1H), 9.16 (s, 1H), 9.11 (s, 2H), 8.92-8.72 (bs, 2H), 7.83-7.73 (m, 4H), 7.69 (d, 2H, J=8.4 Hz), 7.52-7.43 (m, 1H), 7.40-7.33 (m, J=8.4 Hz, 2H), 7.30 (d, J=16 Hz, 1H), 4.55-4.26 (m, 2H), 3.18-3.00 (m, 4H), 2.75-2.60 (m, 2H), 2.05-1.90 (m, 1H), 1.88-1.72 (m, 2H), 1.58-1.48 (m, 1H), 1.42-1.34 (m, 1H), 1.25-1.08 (m, 2H). LC-MS m/z calcd for $C_{29}H_{31}N_5O_3$, 497.2; found 498.2 [M+H]$^+$. HPLC purity 99.6%.

Example 118 (E)-4-(3-(3-(((2-(4-fluorophenyl)cyclopropyl)amino)methyl)azetidin-1-yl)-3-oxoprop-1-en-1-yl)-N-hydroxybenzamide TFA Salt

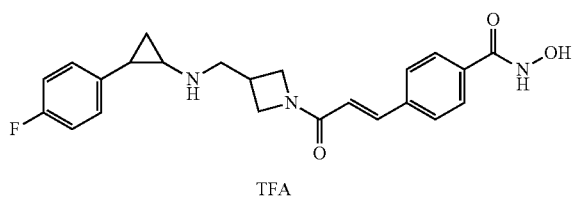 [SMILES: O=C(NO)c1ccc(/C=C/C(=O)N2CC(CNC3CC3c3ccc(F)cc3)C2)cc1]

TFA

The compound was synthesized using the I-118 following the procedure for Example 2.

$^1$HNMR (400 MHz, DMSO-$d_6$): δ 11.25 (bs, 1H), 9.03 (bs, 1H), 8.91 (bs, 2H), 7.81-7.61 (m, 4H), 7.45 (d, J=16 Hz, 1H), 7.26-7.21 (m, 2H), 7.16-7.11 (m, 2H), 6.74 (d, J=15 Hz, 1H), 4.47-4.40 (m, 1H), 4.10-4.02 (m, 2H), 3.81-3.76 (m, 1H), 3.48-3.43 (m, 3H), 3.10-2.93 (m, 2H), 1.44-1.40 (m, 1H), 1.33-1.25 (m, 1H). LC-MS m/z calcd for $C_{23}H_{24}FN_3O_3$, 409.2; found 410.1 [M+H]$^+$. HPLC purity 98.5%.

Example 119 (E)-N-hydroxy-4-(3-(3-(((2-(4-(1-methyl-1H-pyrazol-4-yl)phenyl)cyclopropyl)amino)methyl)azetidin-1-yl)-3-oxoprop-1-en-1-yl)benzamide TFA Salt

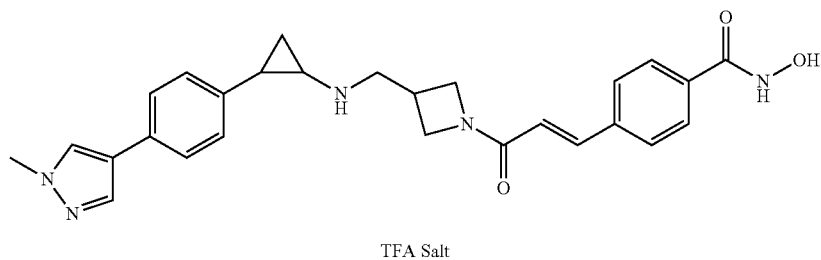 [SMILES: Cn1cc(-c2ccc(C3CC3NCC3CN(C(=O)/C=C/c4ccc(C(=O)NO)cc4)C3)cc2)cn1]

TFA Salt

The compound was synthesized using the I-119 following the procedure for Example 2.

$^1$HNMR (400 MHz, DMSO-$d_6$): δ 11.24 (bs, 1H), 9.01 (bs, 1H), 8.91 (bs, 2H), 8.08 (s, 1H), 7.81 (s, 1H), 7.56-7.70 (m, 4H), 7.50-7.43 (m, 3H), 7.15 (d, 2H, J=8 Hz), 6.74 (d, 1H, J=14 Hz), 4.46-4.38 (m, 1H), 4.08-4.02 (m, 2H), 3.83 (m, 3H), 3.80-3.77 (m, 1H), 3.01-2.94 (m, 2H), 2.47-2.35 (m, 3H), 1.46-1.40 (m, 1H), 1.35-1.28 (m, 1H). LC-MS m/z calcd for $C_{27}H_{29}N_5O_3$, 471.23; found 472.2 [M+H]$^+$. HPLC purity 99.8%.

Example 120 (E)-N-(2-aminophenyl)-3-(4-(((2-4-fluorophenyl)cyclopropyl)amino)methyl)phenyl)acrylamide TFA Salt

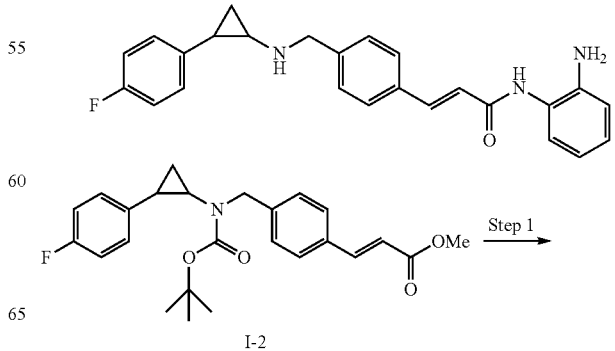

I-2

281

-continued

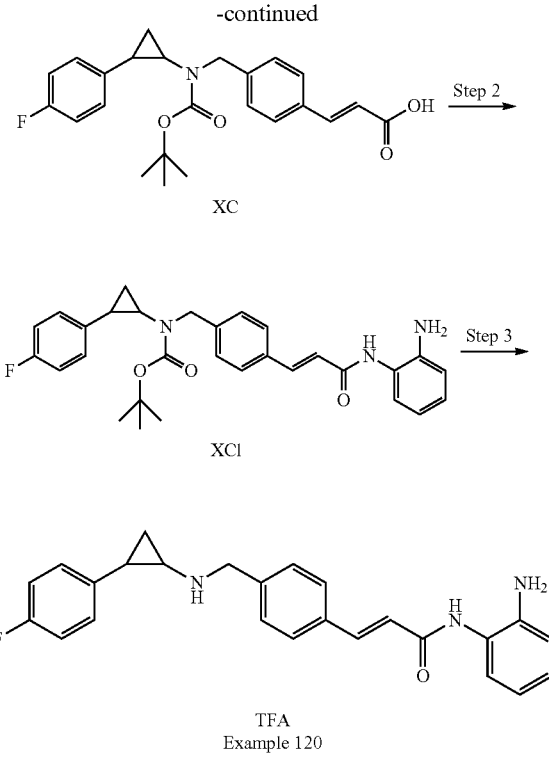

XC

Step 2

XCI

Step 3

TFA
Example 120

Step 1: (E)-3-(4-(((tert-butoxycarbonyl)(2-(4-fluorophenyl)cyclopropyl)amino)methyl)phenyl)acrylic Acid (XC)

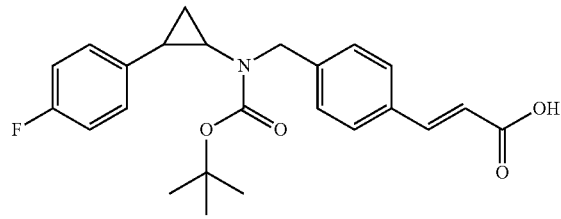 [SMILES: CC(C)(C)OC(=O)N(Cc1ccc(/C=C/C(=O)O)cc1)C1CC1c1ccc(F)cc1]

To a stirred solution of (E)-methyl 3-(4-(((tetra-butoxycarbonyl)(2-(4-florophenyl)cyclopropl)amino)methyl)phenyl)acrylate (I-2, 0.38 g, 0.89 mmol) in methanol and water mixture (20 mL, 4:1) was added sodium hydroxide (0.11 g, 2.68 mmol) at room temperature and the resulting mixture was stirred at that temperature for 1 h. The progress of the reaction was monitored by TLC. After completion of reaction, solvent was evaporated and washed with ethylacetate. The reaction mixture was acidified with 2N HCl and extracted with dichloromethane and the organic portion was washed with water and brine, dried over sodium sulphate and concentrated under reduced pressure to get the crude to afford the titled product as off white solid (XC, 0.31 g, 86.2%), LC-MS m/z calcd for $C_{24}H_{26}FNO_4$, 411.2; found 311.2 [M-Boc]+.

282

Step 2: (E)-tert-butyl 4-(3-((2-aminophenyl)amino)-3-oxoprop-1-en-1-yl)benzyl(2-(4-fluorophenyl)cyclopropyl)carbamate (XCI)

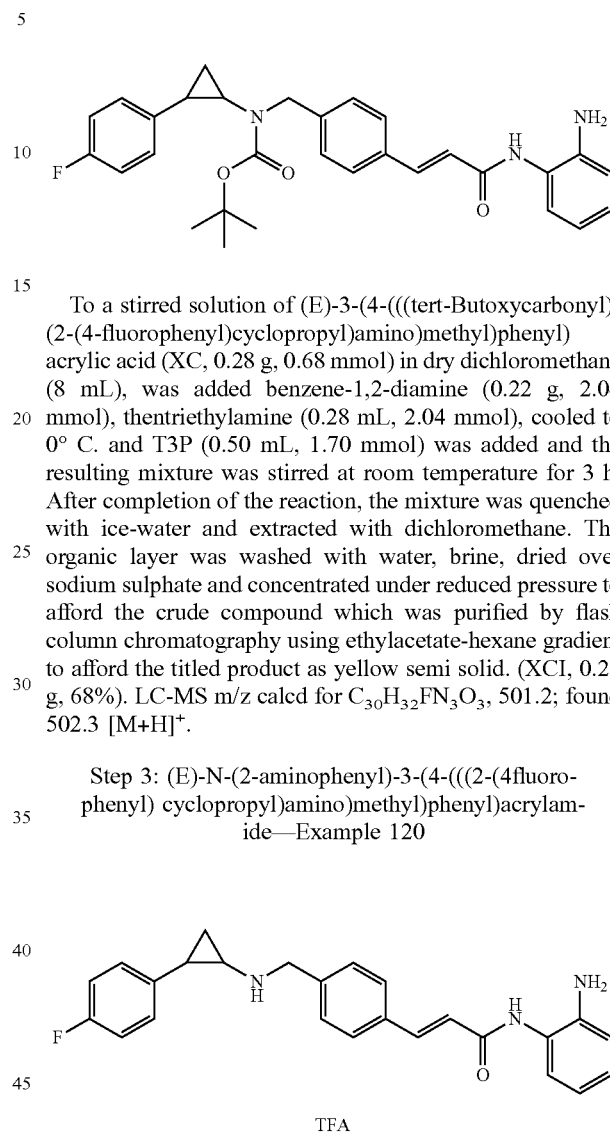

To a stirred solution of (E)-3-(4-(((tert-Butoxycarbonyl)-(2-(4-fluorophenyl)cyclopropyl)amino)methyl)phenyl) acrylic acid (XC, 0.28 g, 0.68 mmol) in dry dichloromethane (8 mL), was added benzene-1,2-diamine (0.22 g, 2.04 mmol), thentriethylamine (0.28 mL, 2.04 mmol), cooled to 0° C. and T3P (0.50 mL, 1.70 mmol) was added and the resulting mixture was stirred at room temperature for 3 h. After completion of the reaction, the mixture was quenched with ice-water and extracted with dichloromethane. The organic layer was washed with water, brine, dried over sodium sulphate and concentrated under reduced pressure to afford the crude compound which was purified by flash column chromatography using ethylacetate-hexane gradient to afford the titled product as yellow semi solid. (XCI, 0.26 g, 68%). LC-MS m/z calcd for $C_{30}H_{32}FN_3O_3$, 501.2; found 502.3 [M+H]+.

Step 3: (E)-N-(2-aminophenyl)-3-(4-(((2-(4fluorophenyl) cyclopropyl)amino)methyl)phenyl)acrylamide—Example 120

To a stirred solution of (E)-tetra-butyl 4(3-((2-aminophenyl)amino)-3-oxoprop-1-en-1-yl)benzyl(2-(4-flurophenyl) cyclopropyl)carbamate (XCI, 0.26 g, 0.52 mmol) in dry dichloromethane (10 mL) was added trifluoro acetic acid (0.63 mL, 8.30 mmol) at 0° C. and the resulting mixture was stirred at room temperature for 1 h. The progress of the reaction was monitored by TLC. The solvent was concentrated under reduced pressure to get the crude product which was purified by reverse-phase HPLC using Chemsil $C_{18}$ (250 mm×4.6 mm×5mic) column with 0.1% TFA in water: ACN to afford the pure product as pale-yellow solid (Example 120: 0.204 g, 96%). $^1$HNMR (400 MHz, DMSO-d$_6$): δ 9.43 (bs, 1H), 9.34 (bs, 2H), 7.65-7.62 (m, 2H), 7.57-7.49 (m, 3H), 7.34-7.30 (m, 1H), 7.19-7.06 (m, 4H), 6.95-6.89 (m, 2H), 6.78-6.74 (m, 1H), 6.62-6.56 (m, 1H), 4.36-4.32 (m, 2H), 2.93-2.89 (m, 1H), 2.46-2.35 (m, 1H), 1.49-1.39 (m, 1H), 1.35-1.25 (m, 1H). LC-MS calcd for $C_{25}H_{24}FN_3O$, 401.2; found 402.4 [M+H]+. HPLC purity 94.8%.

Example 121 N-(2-aminophenyl)-4-(3-(4-(((2-phenylcyclopropyl)amino)methyl)piperidin-1-yl)propyl)benzamide TFA Salt

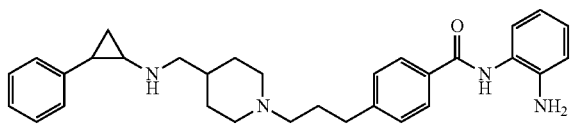 [SMILES: Nc1ccccc1NC(=O)c1ccc(CCCN2CCC(CNC3CC3c3ccccc3)CC2)cc1]

The compound was synthesized using I-121 following the procedure for example 120. $^1$HNMR (400 MHz, DMSO-$d_6$): δ 9.79 (bs, 1H), 9.59 (bs, 1H), 9.13 (bs, 2H), 7.94 (d, 2H, J=7.6 Hz), 7.36 (d, 2H, J=7.6 Hz), 7.31-7.27 (m, 2H), 7.25-7.13 (m, 4H), 7.09-7.01 (m, 1H), 6.93-6.89 (m, 1H), 6.79-6.73 (m, 1H), 3.59-3.48 (m, 2H), 3.08-2.82 (m, 7H), 2.74-2.67 (m, 2H), 2.06-1.87 (m, 6H), 1.50-1.38 (m, 3H), 1.30-1.20 (m, 1H). LC-MS m/z calcd for $C_{31}H_{38}N_4O$, 482.3; found 483.3 $[M+H]^+$. HPLC purity 92.6%.

Example 122 N-(2-aminophenyl)-4-(3-(4-(((2-(4-fluorophenyl)cyclopropyl)amino)methyl)piperidin-1-yl)propyl)benzamide TFA Salt

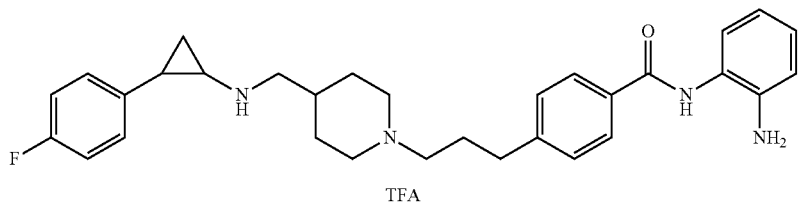 [SMILES: Nc1ccccc1NC(=O)c1ccc(CCCN2CCC(CNC3CC3c3ccc(F)cc3)CC2)cc1]

The compound was synthesized using I-122 following the procedure for example 120. $^1$HNMR (400 MHz, DMSO-$d_6$): δ 9.73 (bs, 1H), 9.60 (bs, 1H), 9.14 (bs, 2H), 7.94 (d, 2H, J=7.6 Hz), 7.36 (d, 2H, J=7.6 Hz), 7.24-7.17 (m, 3H), 7.16-7.08 (m, 2H), 7.05-7.00 (m, 1H), 6.90-6.85 (m, 1H), 6.75-6.68 (m, 1H), 3.56-3.48 (m, 2H), 3.30-3.21 (m, 1H), 3.08-2.98 (m, 4H), 2.95-2.82 (m, 3H), 2.72-2.65 (m, 2H), 2.06-1.87 (m, 5H), 1.50-1.38 (m, 3H), 1.30-1.20 (m, 1H). LC-MS m/z calcd for $C_{31}H_{37}FN_4O$, 500.6; found 501.2 $[M+H]^+$. HPLC purity 92.6%.

Example 123 N-(2-aminophenyl)-4-(3-(4-(((2-(4methoxyphenyl)cyclopropyl)amino)methyl)piperidin-1-yl)propyl)benzamide TFA Salt

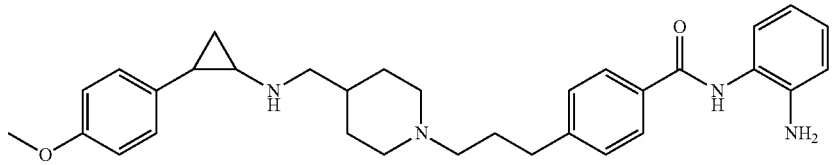 [SMILES: COc1ccc(C2CC2NCC2CCN(CCCc3ccc(C(=O)Nc4ccccc4N)cc3)CC2)cc1]

The compound was synthesized using I-123 following the procedure for example 120. $^1$HNMR (400 MHz, DMSO-$d_6$): δ 9.64 (s, 1H), 9.30 (bs, 1H), 8.92 (bs, 1H), 7.93 (d, 2H J=8 Hz), 7.36 (d, 2H, J=8 Hz), 7.15 (d, 2H, J=7.6 Hz), 7.08 (d, 2H, J=8 Hz), 6.99-6.96 (m, 1H), 6.86-6.81 (m, 2H), 6.65-6.60 (m, 1H), 3.70 (s, 3H), 3.54-3.50 (m, 3H), 3.08-3.00 (m, 4H), 2.94-2.82 (m, 3H), 2.75-2.68 (m, 2H), 2.42-2.34 (m, 1H), 2.04-1.92 (m, 5H), 1.42-1.36 (m, 3H). LC-MS m/z calcd for $C_{32}H_{40}N_4O_2$, 512.3; found 513.3 $[M+H]^+$. HPLC purity 97.2%.

Example 124 N-(2-aminophenyl)-4-(3-(4-(((2-(3,4-difluorophenyl)cyclopropyl)amino)methyl)piperidin-1-yl)propyl)benzamide TFA Salt

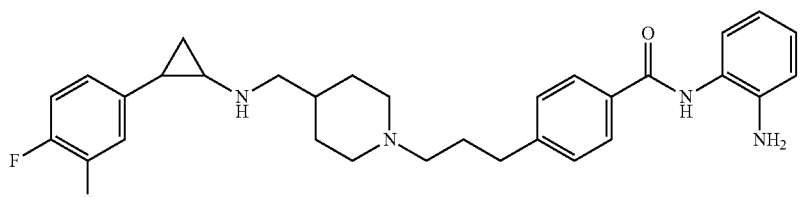

The compound was synthesized using I-124 following the procedure for example 120. ¹HNMR (400 MHz, DMSO-d$_6$): δ 9.71 (bs, 1H), 9.35 (bs, 1H), 9.01 (bs, 2H), 7.94 (d, 2H, J=7.6 Hz), 7.37 (d, 2H, J=7.6 Hz), 7.32-7.26 (m, 1H), 7.18 (d, 1H, J=7.6 Hz), 7.08-6.99 (m, 2H), 6.86 (d, 2H, J=7.6 Hz), 6.72-6.67 (m, 1H), 3.56-3.51 (m, 2H), 3.29-2.82 (m, 8H), 2.74-2.68 (m, 2H), 2.14-1.72 (m, 6H), 1.49-1.31 (m, 3H). LC-MS m/z calcd for $C_{31}H_{36}F_2N_4O$, 518.3. found 519.6 [M+H]⁺. HPLC purity 99.6%.

Example 125 N-(2-aminophenyl)-4-(3-(4-(((2-(4-(piperidine-1-carbonyl)phenyl)cyclopropyl)amino)methyl)piperidin-1-yl)propyl)benzamide TFA Salt

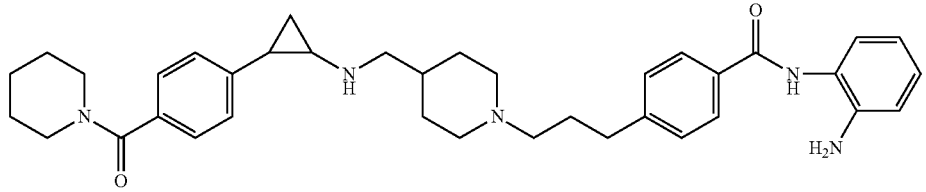 [SMILES: Nc1ccccc1NC(=O)c1ccc(CCCN2CCC(CNC3CC3c3ccc(C(=O)N4CCCCC4)cc3)CC2)cc1]

The compound was synthesized using I-125 following the procedure for example 120. ¹HNMR (400 MHz, DMSO-d$_6$): δ 9.70 (bs, 1H), 8.96 (bs, 1H), 8.90 (bs, 1H), 7.95 (bs, 1H), 7.94 (d, 2H, J=8.4 Hz), 7.37 (d, 2H, J=7.6 Hz), 7.29 (d, 2H, J=8 Hz), 7.23 (d, 2H, J=8 Hz), 7.17 (d, 1H, J=7.6 Hz), 7.01 (t, 1H, J=7.6 Hz), 6.85 (d, 1H, J=8 Hz), 6.73-6.65 (m, 1H), 3.59-3.50 (m, 5H), 3.30-3.17 (m, 3H), 3.09-3.00 (m, 5H), 2.95-2.84 (m, 2H), 2.77-2.67 (m, 2H), 2.05-1.90 (m, 5H), 1.55-1.32 (m, 9H). LC-MS m/z calcd for $C_{37}H_{47}N_5O_2$, 593.4. found 594.4 [M+H]⁺. HPLC purity 99.9%.

Example 126 N-(2-aminophenyl)-4-(3-(3-(((2-(4-fluorophenyl)cyclopropyl)amino)methyl)azetidin-1-yl)propyl)benzamide TFA Salt

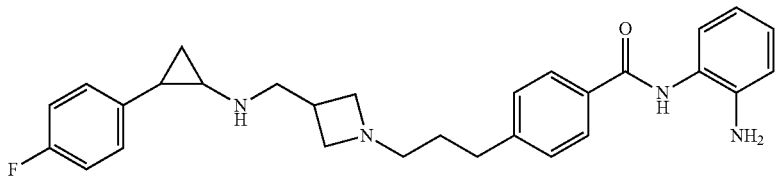

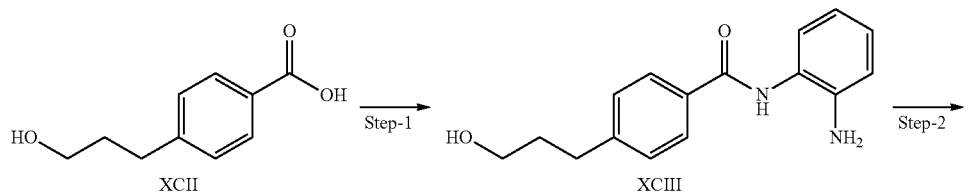

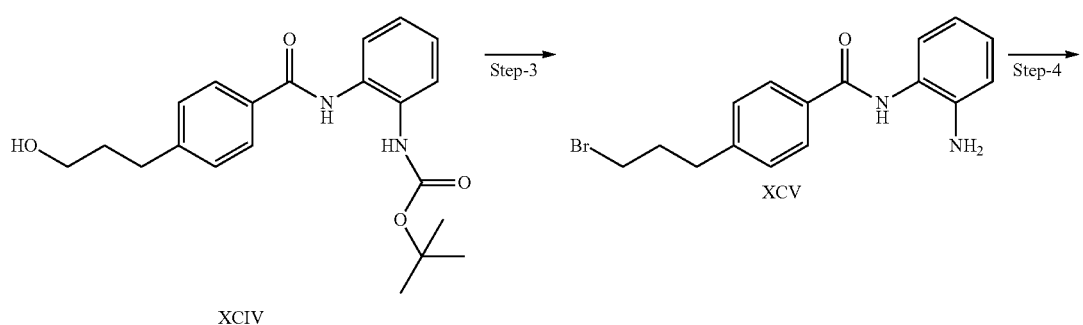

-continued

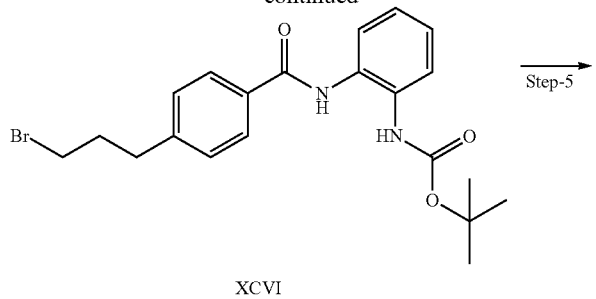

XCVI

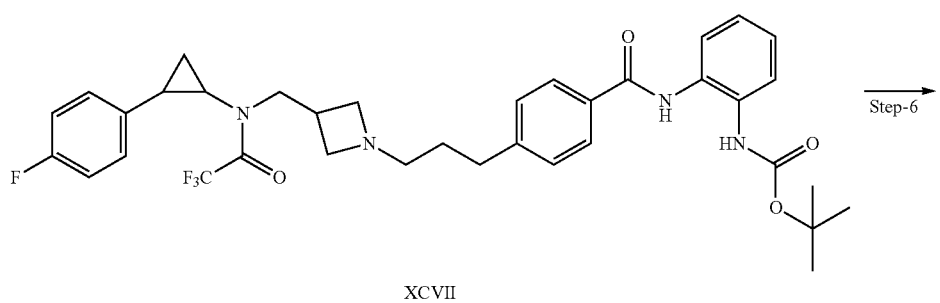

XCVII

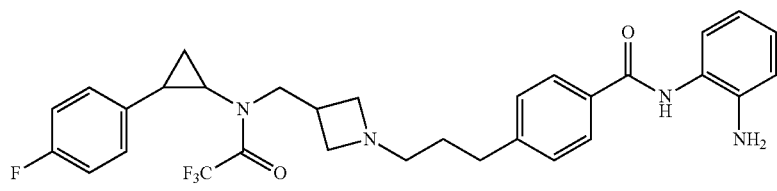

Example 126

Step-1: N-(2-aminophenyl)-4-(3-hydroxypropyl)benzamide-XCIII

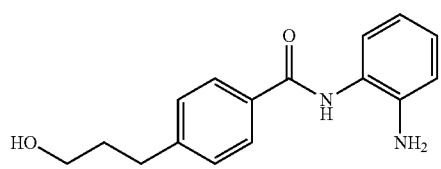 [SMILES: Nc1ccccc1NC(=O)c1ccc(CCCO)cc1]

To a stirred solution of 4-(3-hydroxypropyl)benzoic acid (XCII, 0.7 g, 3.89 mmol) in dry dichloromethane (15 mL) was added benzene-1,2-diamine (1.26 g, 11.66 mmol), triethylamine (1.64 mL, 11.66 mmol) and cooled to 0° C. Then T3P (1.48 mL, 4.66 mmol) was added and the resulting mixture was stirred at room temperature for 3 h. After completion of the reaction, the mixture was quenched with ice water and extracted with dichloromethane. The organic layer was washed with water, brine, dried over sodium sulphate and concentrated under reduced pressure to afford the crude compound which was purified by column chromatography using ethylacetate-hexane gradient to afford the titled product as sticky oil. (XCIII, 0.6 g, 57%). LC-MS m/z calcd for $C_{16}H_{18}N_2O_2$, 270.1; found 271.0 [M+H]$^+$.

Step-2: tert-butyl (2-(4-(3-hydroxypropyl)benzamido)phenyl)carbamate-XCIV

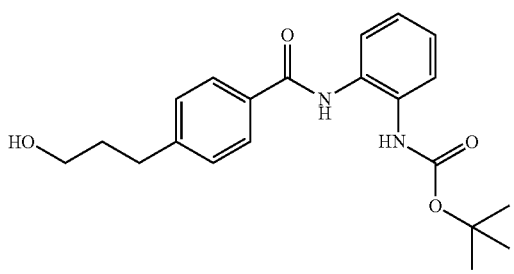 [SMILES: CC(C)(C)OC(=O)Nc1ccccc1NC(=O)c1ccc(CCCO)cc1]

To a stirred solution of N-(2-aminophenyl)-4-(3-hydroxypropyl)benzamide (XCIII, 0.3 g, 0.90 mmol) in tetrahydrofuran-water mixture (1:1, 10 mL) was added sodium bicarbonate (0.227 g, 2.71 mmol) and Boc anhydride (0.23 mL, 1.08 mmol) at room temperature. After 1 h, the reaction mixture was diluted with ethyl acetate and was washed with water, brine, dried over sodium sulphate and concentrated under reduced pressure to get the crude product which was purified by column chromatography using ethylacetate-hexane gradient to afford the titled product as thick oil (XCIV, 0.25 g, 61%). LC-MS m/z calcd for $C_{21}H_{26}N_2O_4$, 370.1; found 371.0 [M+H]$^+$.

Step-3: N-(2-aminophenyl)-4-(3-bromopropyl)benzamide-XCV

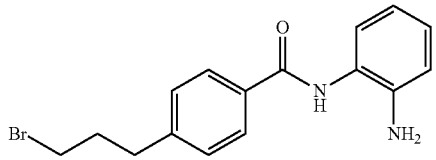 [SMILES: Nc1ccccc1NC(=O)c1ccc(CCCBr)cc1]

To a stirred solution of tert-butyl (2-(4-(3-hydroxypropyl)benzamido)phenyl)carbamate (XCIV, 0.3 g, 0.90 mmol) in dichloromethane (5 mL) was added triphenylphosphine (0.31 g, 0.95 mmol) and tetrabromomethane (0.41 g, 1.09 mmol) at 0° C. After 16 h, the reaction mixture was diluted with dichloromethane and was washed with water, brine solution, dried over sodium sulphate and concentrated under reduced pressure to get the crude product which was purified by column chromatography using ethylacetate-hexane gradient to afford the titled product as thick oil (XCV, 0.17 g, 70%). LC-MS m/z calcd for $C_{16}H_{17}BrN_2O$, 332.0; found 333.1 [M+H]$^+$.

Step-4: tert-butyl (2-(4-(3-bromopropyl)benzamido)phenyl)carbamate-XCVI

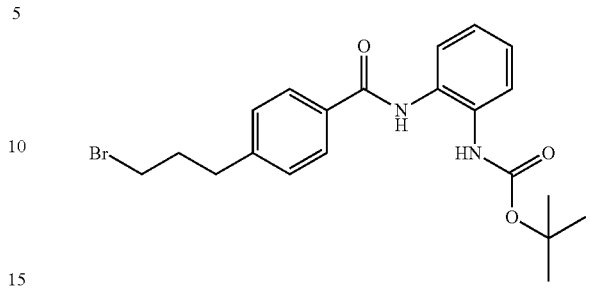

To a stirred solution of N-(2-aminophenyl)-4-(3-bromopropyl)benzamide (XCV, 0.22 g, 0.66 mmol) in tetrahydrofuran-water mixture (1:1, 10 mL) was added sodium bicarbonate (0.16 g, 1.98 mmol) and Boc anhydride (0.17 mL, 0.79 mmol) at room temperature. After 1 h, the reaction mixture was diluted with ethylacetate and was washed with water, brine, dried over sodium sulphate and concentrated under reduced pressure to get the crude product which was purified by column chromatography using ethylacetate-hexane gradient to afford the titled product as thick oil (XCVI, 0.23 g, 82%). LC-MS m/z calcd for $C_{21}H_{25}BrN_2O_3$, 432.1; found 433.0 [M+H]$^+$.

Step-5: tert-butyl(2-(4-(3-(3-((2,2,2-trifluoro-N-(2-(4-fluorophenyl)cyclopropyl)acetamido)methyl)azetidin-1-yl)propyl)benzamido)phenyl)carbamate-XCVII

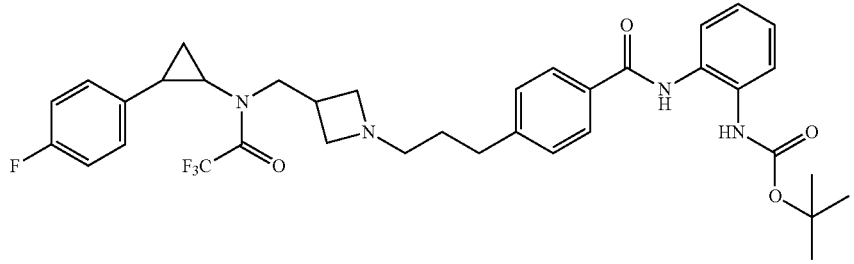 [SMILES: CC(C)(C)OC(=O)Nc1ccccc1NC(=O)c1ccc(CCCN2CC(CN(C(=O)C(F)(F)F)C3CC3c3ccc(F)cc3)C2)cc1]

To a solution of N-(azetidin-3-ylmethyl)-2,2,2-trifluoro-N-(2-(4-fluorophenyl)cyclopropyl)acetamide trifluoroacetate salt (XCVI, 0.18 g, 0.54 mmol) in acetonitrile (5 mL) was added tert-butyl (2-(4-(3-bromopropyl)benzamido)phenyl)carbamate (0.28 g, 0.65 mmol) and N,N-diisopropylethylamine (0.29 mL, 1.61 mmol). Then the reaction mixture was heated at 60° C. for 16 h. After completion of reaction, the reaction was diluted with ethylacetate (50 mL), washed with water, brine solution, dried over sodium sulfate and concentrated under vacuum to get crude product which was purified by column chromatography using methanol-dichloromethane gradient to afford the titled product as brown colour sticky oil (XCVII, 0.13 g, 36%). LC-MS m/z calcd for $C_{36}H_{40}F_4N_4O_4$, 668.3; found 669.1 [M+H]$^+$.

Step-6: N-(2-aminophenyl)-4-(3-(3-(((2-(4-fluorophenyl)cyclopropyl)amino)methyl)azetidin-1-yl)propyl)benzamide TFA Salt—Example 126

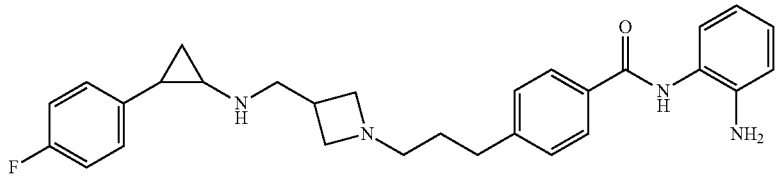 [SMILES: Nc1ccccc1NC(=O)c1ccc(CCCN2CC(CNC3CC3c3ccc(F)cc3)C2)cc1]

To a solution of tert-butyl (2-(4-(3-(3-(((2,2,2-trifluoro-N-(2-(4-fluorophenyl)cyclopropyl) acetamido)methyl)azetidin-1-yl)propyl)benzamido)phenyl)carbamate (XCVII, 0.17 g, 0.25 mmol) in methanol (5 mL) was added potassium carbonate (0.10 g, 0.76 mmol) at room temperature for 16 h. After completion of reaction, the reaction was concentrated under vacuum. The residue was diluted with dichloromethane and cooled to 0° C. TFA (0.46 mL) was added to it and stirred for 1 h at same temperature. The solvent was concentrated under reduced pressure to get the crude product which was purified by reverse-phase HPLC using Chemsil $C_{18}$ (250 mm×4.6 mm×5mic) column with 0.1% TFA in water:ACN to afford the pure product as a colourless solid (Example 126, 0.04 g, 37%). $^{1}$HNMR (400 MHz, DMSO-$d_6$): δ 9.87 (bs, 1H), 9.65 (s, 1H), 9.01 (bs, 2H), 7.93 (d, 2H, J=8 Hz), 7.34 (s, 2H, J=7.6 Hz), 7.25-7.19 (m, 2H), 7.16-7.10 (m, 3H), 6.99 (t, 1H, J=7.6 Hz), 6.81 (d, 1H, J=7.6 Hz), 6.65 (t, 1H, J=7.6 Hz), 4.18 (m, 1H), 4.12-3.95 (m, 2H), 3.90-3.78 (m, 2H), 3.42-3.28 (m, 2H), 3.20-3.02 (m, 4H), 2.95-2.80 (m, 1H), 2.72-2.62 (m, 1H), 1.80-1.68 (m, 2H), 1.42-1.35 (m, 1H), 1.32-1.24 (m, 1H). LC-MS m/z calcd for $C_{29}H_{33}FN_4O$, 472.3; found 473.3 [M+H]$^+$. HPLC purity 99.8%.

Example 127 N-(2-aminophenyl)-4-(3-(6-((2-phenylcyclopropyl)amino)-2-azaspiro[3.3]heptan-2-yl)propyl)benzamide TFA Salt

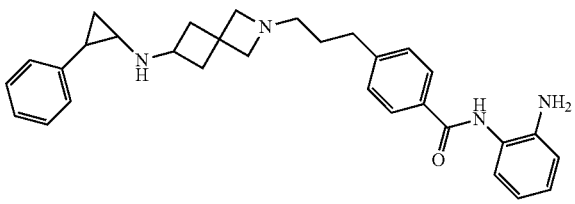 [SMILES: Nc1ccccc1NC(=O)c1ccc(CCCN2CC3(CC(NC4CC4c4ccccc4)C3)C2)cc1]

The compound was synthesized using I-127 following the procedure for example 120. $^{1}$HNMR (400 MHz, DMSO-$d_6$): δ 10.48 (bs, 1H), 9.69 (s, 1H), 8.55 (bs, 2H), 7.93 (d, 2H, J=7.6 Hz), 7.40-7.28 (m, 4H), 7.25-7.14 (m, 4H), 7.00 (t, 1H, J=7.6 Hz), 6.85 (d, 1H, J=7.6 Hz), 6.68 (t, 1H, J=7.2 Hz), 4.38-4.4.26 (m, 1H), 3.75-3.62 (m, 1H), 3.38-3.15 (m, 4H), 3.00-2.96 (m, 2H), 2.78-2.70 (m, 2H), 2.68-2.60 (m, 1H), 2.24-2.04 (m, 3H), 2.00-1.88 (m, 2H), 1.70-1.55 (m, 2H), 1.45-1.32 (m, 1H). LC-MS m/z calcd for $C_{31}H_{36}N_4O$, 480.3; found 481.3 [M+H]$^+$. HPLC purity 99.6%.

Example 128 N-(2-aminophenyl)-4-(3-(4-(((2-(1-isopropyl-1H-pyrazol-4-yl)cyclopropyl)amino)methyl)piperidin-1-yl)propyl)benzamide TFA Salt

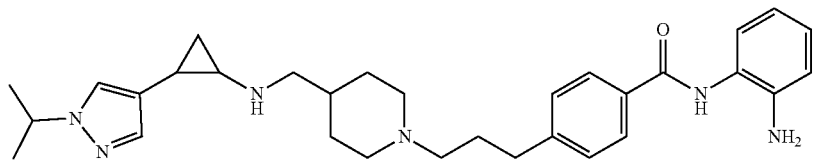 [SMILES: CC(C)n1cc(C2CC2NCC2CCN(CCCc3ccc(C(=O)Nc4ccccc4N)cc3)CC2)cn1]

The compound was synthesized using I-128 following the procedure for example 120. $^{1}$HNMR (400 MHz, DMSO-$d_6$): δ 9.73 (bs, 1H), 9.22 (bs, 1H), 8.34 (bs, 2H), 7.94 (d, 2H, J=7.6 Hz), 7.61 (s, 1H), 7.37 (d, 2H, J=8 Hz), 7.29 (s, 1H), 7.19 (d, 1H, J=7.6 Hz), 7.03 (t, 1H, J=7.6 Hz), 6.88 (d, 1H, J=8 Hz), 6.73 (t, 1H, J=7.2 Hz), 4.42-4.35 (m, 1H), 3.55-3.52 (m, 2H), 3.08-2.98 (m, 4H), 2.96-2.87 (m, 2H), 2.83-2.78 (m, 1H), 2.75-2.68 (m, 2H), 2.23-2.19 (m, 1H), 2.06-1.90 (m, 5H), 1.46-1.40 (m, 9H), 1.21-1.06 (m, 1H). LC-MS m/z calcd for $C_{31}H_{42}N_6O$, 514.3; found 515.3 [M+H]$^+$. HPLC purity 98.8%.

Example 129 N-(2-aminophenyl)-4-(3-(4-(((2-(1-phenyl-1H-pyrazol-4-yl)cyclopropyl)amino)methyl)piperidin-1-yl)propyl)benzamide TFA Salt

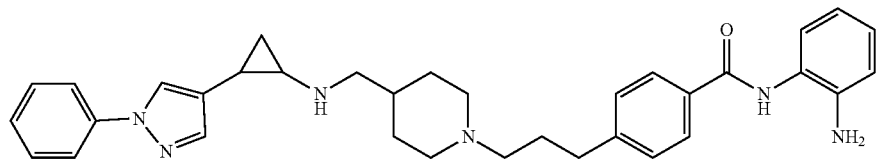 [SMILES: Nc1ccccc1NC(=O)c1ccc(CCCN2CCC(CNC3CC3c3cnn(-c4ccccc4)c3)CC2)cc1]

The compound was synthesized using I-129 following the procedure for example 120. $^1$HNMR (400 MHz, DMSO-$d_6$): δ 9.70 (bs, 1H), 9.54 (bs, 1H), 9.09 (bs, 2H), 8.37 (s, 1H), 7.94 (d, 2H, J=8 Hz), 7.73 (d, 2H, J=8 Hz), 7.65 (s, 1H), 7.47 (t, 2H, J=8 Hz), 7.36 (d, 2H, J=8 Hz), 7.28 (t, 1H, J=7.6 Hz), 7.18 (d, 1H, J=8 Hz), 7.03-6.98 (m, 1H), 6.85 (d, 1H, J=8 Hz), 6.71-6.66 (m, 1H), 3.58-3.51 (m, 2H), 3.10-3.02 (m, 4H), 2.95-2.84 (m, 3H), 2.74-2.68 (m, 2H), 2.38-2.32 (m, 1H), 2.03-1.94 (m, 5H), 1.50-1.41 (m, 3H), 1.25-1.19 (m, 1H). LC-MS m/z calcd for $C_{34}H_{40}N_6O$, 548.3; found 549.3 [M+H]$^+$. HPLC purity 99%.

Example 130 N-(2-aminophenyl)-4-(3-(4-(((2-(2-methylthiazol-5-yl)cyclopropyl)amino)methyl)piperidin-1-yl)propyl)benzamide TFA Salt

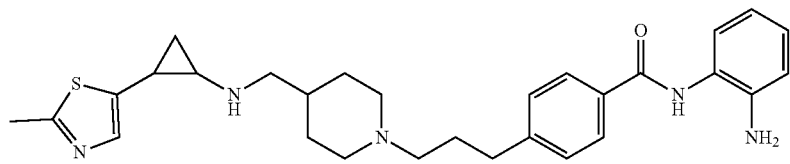 [SMILES: Cc1ncc(C2CC2NCC2CCN(CCCc3ccc(C(=O)Nc4ccccc4N)cc3)CC2)s1]

The compound was synthesized using I-130 following the procedure for example 120. LC-MS m/z calcd for $C_{29}H_{37}N_5OS$, 503.7; found 504.7 [M+H]$^+$.

Example 131 N-(2-aminophenyl)-4-(3-(4-(((2-(pyridin-3-yl)cyclopropyl)amino)methyl)piperidin-1-yl)propyl)benzamide TFA Salt

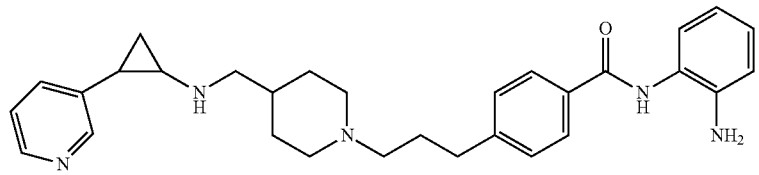 [SMILES: Nc1ccccc1NC(=O)c1ccc(CCCN2CCC(CNC3CC3c3cccnc3)CC2)cc1]

The compound was synthesized using I-131 following the procedure for example 120. LC-MS m/z calcd for $C_{30}H_{37}N_5O$, 483.6; found 484.6 [M+H]$^+$.

Example 132 N-(2-amino-5-fluorophenyl)-4-(3-(4-(((2-(4-fluorophenyl)cyclopropyl)amino)methyl)piperidin-1-yl)propyl)benzamide TFA Salt

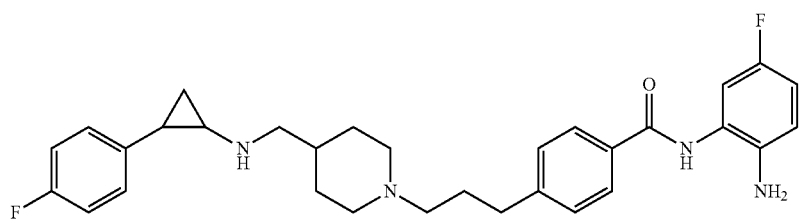 [SMILES: Nc1ccc(F)cc1NC(=O)c1ccc(CCCN2CCC(CNC3CC3c3ccc(F)cc3)CC2)cc1]

The compound was synthesized using I-122 following the procedure for example 120. ¹HNMR (400 MHz, DMSO-d₆): δ 9.53 (s, 1H), 9.42 (bs, 1H), 9.04 (bs, 2H), 7.95 (d, 2H, J=8.0 Hz), 7.34 (d, 2H, J=8.0 Hz), 7.23-7.19 (m, 2H), 7.14-7.06 (m, 3H), 6.55-6.51 (m, 1H), 6.37-6.32 (m, 1H), 3.58-3.50 (m, 2H), 3.30-3.24 (m, 1H), 3.22-3.14 (m, 1H), 3.08-2.98 (m, 3H), 2.95-2.81 (m, 3H), 2.74-2.64 (m, 2H), 2.06-1.85 (m, 5H), 1.46-1.36 (m, 3H), 1.29-1.24 (m, 1H). LC-MS m/z calcd for $C_{31}H_{36}F_2N_4O$, 518.3; found 519.2 [M+H]⁺. HPLC purity 98.6%.

Example 133 N-(2-aminophenyl)-4-(3-oxo-3-(4-((2-phenylcyclopropyl)amino)piperidin-1-yl)propyl)benzamide TFA Salt

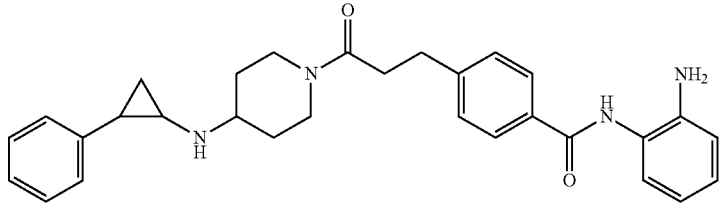 [SMILES: Nc1ccccc1NC(=O)c1ccc(CCC(=O)N2CCC(NC3CC3c3ccccc3)CC2)cc1]

The compound was synthesized using I-133 following the procedure for example 120. ¹HNMR (400 MHz, DMSO-d₆): δ 9.69 (s, 1H), 8.99 (bs, 2H), 7.88 (d, 2H, J=8 Hz), 7.36 (d, 2H, J=8 Hz), 7.31-7.27 (m, 2H), 7.26-7.16 (m, 4H), 7.05-7.00 (m, 1H), 6.88-6.86 (m, 1H), 6.75-6.72 (m, 1H), 4.48-4.41 (m, 1H), 4.03-3.96 (m, 1H), 3.52-3.42 (m, 1H), 3.04-2.97 (m, 2H), 2.90-2.82 (m, 2H), 2.72-2.65 (m, 2H), 2.60-2.52 (m, 1H), 2.42-2.34 (m, 1H), 2.06-2.01 (m, 2H), 1.42-1.30 (m, 4H). LC-MS m/z calcd for $C_{30}H_{34}N_4O_2$ 482.3. found 483.2 [M+H]⁺. HPLC purity 94.3%.

Example 134 N-(2-aminophenyl)-4-(3-oxo-3-(4-(((2-phenylcyclopropyl)amino)methyl)piperidin-1-yl)propyl)benzamide TFA Salt

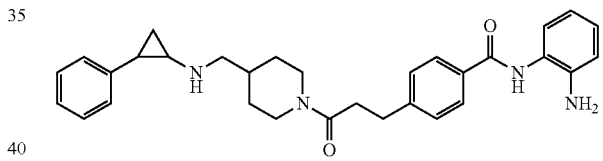

The compound was synthesized using I-134 following the procedure for example 120. ¹HNMR (400 MHz, DMSO-d₆): δ 9.70 (bs, 1H), 8.80 (bs, 2H), 7.88 (d, 2H, J=8 Hz), 7.36 (d, 2H, J=8 Hz), 7.32-7.24 (m, 2H), 7.22-7.12 (m, 4H), 7.05-6.98 (m, 1H), 6.85-6.83 (m, 1H), 6.75-6.70 (m, 1H), 4.37-4.34 (m, 1H), 3.89-3.84 (m, 1H), 3.02-2.82 (m, 3H), 2.80-2.75 (m, 2H), 2.68-2.62 (m, 2H), 2.46-2.37 (m, 2H), 1.92-1.82 (m, 1H), 1.74-1.64 (m, 2H), 1.45-1.42 (m, 1H), 1.33-1.20 (m, 2H), 1.07-0.98 (m, 2H). LC-MS m/z calcd for $C_{31}H_{36}N_4O_2$, 496.3; found 497.4 [M+H]⁺. HPLC purity 96.2%.

Example 135 N-(2-aminophenyl)-4-(3-(4-(((2-(3,4-difluorophenyl)cyclopropyl)amino)methyl)-1H-imidazol-1-yl)propyl)benzamide TFA Salt

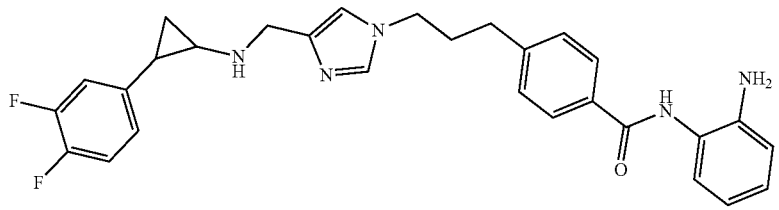 [SMILES: Nc1ccccc1NC(=O)c1ccc(CCCn2cnc(CNC3CC3c3ccc(F)c(F)c3)c2)cc1]

The compound was synthesized using I-135 following the procedure for example 120. $^1$HNMR (400 MHz, DMSO-d$_6$): δ 9.75 (bs, 1H), 8.16 (s, 1H), 7.92 (d, 2H, J=7.6 Hz), 7.42 (s, 1H), 7.37-7.28 (m, 3H), 7.22-7.16 (m, 2H), 7.04 (t, 1H, J=7.6 Hz), 7.02-6.96 (m, 1H), 6.90 (t, 1H, J=8.0 Hz), 6.76 (t, 1H, J=7.6 Hz), 4.22 (s, 2H), 4.06-4.00 (m, 2H), 2.93-2.90 (m, 1H), 2.65-2.60 (m, 2H), 2.37-2.30 (m, 1H), 2.08-2.00 (m, 2H), 1.42-1.38 (m, 1H), 1.33-1.28 (m, 1H). LC-MS m/z calcd for C$_{29}$H$_{29}$F$_2$N$_5$O, 501.2; found 502.2 [M+H]$^+$. HPLC purity 99.5%.

Example 136 N-(2-aminophenyl)-4-(3-(4-(((2-phenylcyclopropyl)amino)methyl)-1H-imidazol-1-yl)propyl)benzamide TFA Salt

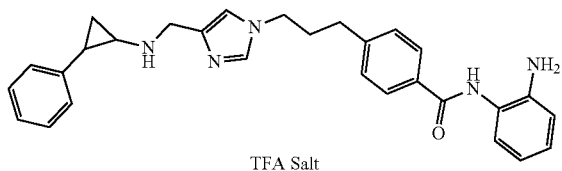 [SMILES: Nc1ccccc1NC(=O)c1ccc(CCCn2cnc(CNC3CC3c3ccccc3)c2)cc1]

TFA Salt

The compound was synthesized using I-136 following the procedure for example 120. $^1$HNMR (400 MHz, DMSO-d$_6$): δ 9.73 (bs, 1H), 9.00 (bs, 1H), 8.09 (s, 1H), 7.92 (d, 2H, J=7.6 Hz), 7.39 (s, 1H), 7.31 (d, 2H, J=7.6 Hz), 7.28-7.24 (m, 2H), 7.20-7.16 (m, 2H), 7.09 (d, 2H, J=7.6 Hz), 7.03 (t, 1H, J=7.6 Hz), 6.88 (d, 1H, J=8 Hz), 6.74 (t, 1H, J=7.2 Hz), 4.23-4.18 (m, 2H), 4.04-4.00 (m, 2H), 2.94-2.88 (m, 1H), 2.64-2.57 (m, 2H), 2.38-2.30 (m, 1H), 2.09-1.99 (m, 2H), 1.43-1.37 (m, 1H), 1.30-1.21 (m, 1H). LC-MS m/z calcd for C$_{29}$H$_{31}$N$_5$O, 465.3; found 466.3 [M+H]$^+$. HPLC purity 99.8%.

Example 137 N-(2-aminophenyl)-4-(3-(4-(((2-phenylcyclopropyl)amino)methyl)-1H-1,2,3-triazol-1-yl)propyl)benzamide TFA Salt

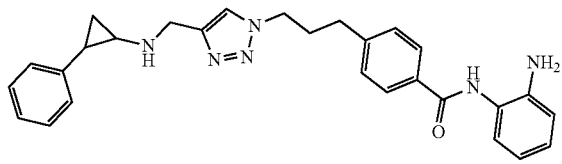 [SMILES: Nc1ccccc1NC(=O)c1ccc(CCCn2cc(CNC3CC3c3ccccc3)nn2)cc1]

The compound was synthesized using I-137 following the procedure for example 120. $^1$HNMR (400 MHz, DMSO-d$_6$): δ 9.71 (bs, 1H), 9.47 (bs, 2H), 8.18 (s, 1H), 7.92 (d, 2H, J=7.6 Hz), 7.32 (d, 2H, J=7.6 Hz), 7.29-7.24 (m, 2H), 7.20-7.16 (m, 2H), 7.11 (d, 2H, J=7.6 Hz), 7.02 (t, 1H, J=7.6 Hz), 6.86 (d, 1H, J=8 Hz), 6.71 (t, 1H, J=7.2 Hz), 4.23-4.18 (m, 2H), 4.04-4.00 (m, 2H), 2.94-2.88 (m, 1H), 2.64-2.57 (m, 2H), 2.38-2.30 (m, 1H), 2.09-1.99 (m, 2H), 1.43-1.37 (m, 1H), 1.30-1.21 (m, 1H). LC-MS m/z calcd for C$_{28}$H$_{30}$N$_6$O, 466.2; found 467.3 [M+H]$^+$. HPLC purity 98.7%.

Example 138 N-(2-aminophenyl)-4-(3-(4-(((2-phenylcyclopropyl)amino)methyl)-1H-pyrazol-1-yl)propyl)benzamide TFA Salt

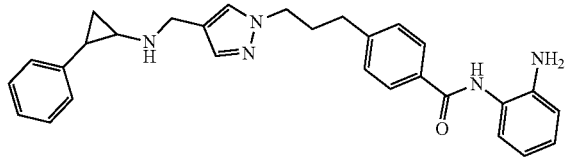 [SMILES: Nc1ccccc1NC(=O)c1ccc(CCCn2cc(CNC3CC3c3ccccc3)cn2)cc1]

The compound was synthesized using I-138 following the procedure for example 120. $^1$HNMR (400 MHz, DMSO-d$_6$): δ 9.69 (bs, 1H), 9.09 (bs, 1H), 9.05 (bs, 1H), 7.91 (d, 2H, J=7.6 Hz), 7.78 (s, 1H), 7.53 (s, 1H), 7.32-7.25 (m, 4H), 7.20 (t, 2H, J=7.6 Hz), 7.12 (d, 2H, J=7.6 Hz), 7.01 (t, 1H, J=7.6 Hz), 6.86 (d, 1H, J=8 Hz), 6.70 (t, 1H, J=7.2 Hz), 4.42-4.17 (m, 2H), 4.10 (t, 2H, J=6.8 Hz), 2.94-2.86 (m, 1H), 2.65-2.57 (m, 2H), 2.40-2.33 (m, 1H), 2.11-2.01 (m, 2H), 1.44-1.37 (m, 1H), 1.32-1.25 (m, 1H). LC-MS m/z calcd for C$_{29}$H$_{31}$N$_5$O, 465.3; found 466.3 [M+H]$^+$. HPLC purity 99%.

Example 139 N-(2-aminophenyl)-4-(2-(4-(((2-phenylcyclopropyl)amino)methyl)piperidin-1-yl)ethyl)benzamide TFA Salt

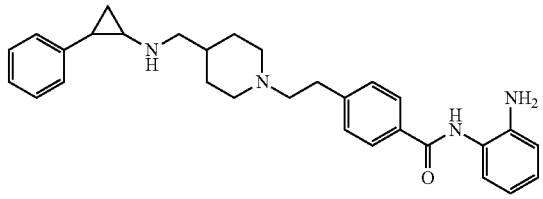 [SMILES: Nc1ccccc1NC(=O)c1ccc(CCN2CCC(CNC3CC3c3ccccc3)CC2)cc1]

The compound was synthesized using I-139 following the procedure for example 120. $^1$HNMR (400 MHz, DMSO-d$_6$): δ 9.64 (bs, 1H), 9.36 (bs, 1H), 8.89 (bs, 2H), 7.96 (d, 2H, J=8.0 Hz), 7.40 (d, 2H, J=8.0 Hz), 7.34-7.28 (m, 2H), 7.23 (d, 1H, J=7.6 Hz), 7.21-7.12 (m, 3H), 6.98 (t, 1H, J=7.6 Hz), 6.80 (d, 1H, J=8.0 Hz), 6.62 (d, 1H, J=8.0 Hz), 3.68-3.60 (m, 2H), 3.36-3.28 (m, 3H), 3.10-3.02 (m, 4H), 3.01-2.92 (m, 3H), 2.04-1.96 (m, 2H), 1.95-1.88 (m, 1H), 1.50-1.40 (m, 3H), 1.34-1.28 (m, 1H). LC-MS m/z calcd for C$_{30}$H$_{36}$N$_4$O, 468.6; found 469.6 [M+H]$^+$. HPLC purity 99%.

Example 140 N-(2-aminophenyl)-4-((4-((((1R,2S)-2-phenylcyclopropyl)amino)methyl)piperidin-1-yl)methyl)benzamide TFA Salt

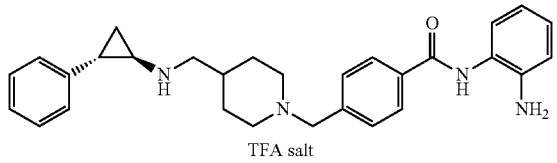 [SMILES: Nc1ccccc1NC(=O)c1ccc(CN2CCC(CN[C@@H]3C[C@H]3c3ccccc3)CC2)cc1]

TFA salt

The compound was synthesized using I-140 following the procedure for example 120. $^1$HNMR (400 MHz, DMSO-d$_6$):

δ 9.75 (s, 1H), 9.64 (bs, 1H), 8.94 (bs, 2H), 8.25 (d, 2H, J=8.0 Hz), 7.62 (d, 2H, J=8 Hz), 7.29 (t, 2H, J=7.2 Hz), 7.25-7.10 (m, 3H), 6.97 (t, 1H, J=7.6 Hz), 6.81 (d, 1H, J=8.0 Hz), 6.72 (t, 1H, J=6.8 Hz), 4.29 (s, 2H), 3.46-3.34 (m, 2H), 3.26-3.10 (m, 1H), 3.06-2.86 (m, 5H), 2.02-1.78 (m, 3H), 1.52-1.34 (m, 3H), 1.32-1.24 (m, 1H). LC-MS m/z calcd for $C_{29}H_{34}N_4O$, 454.2; found 455.2 [M+H]$^+$. HPLC purity 96.5%.

Example 141 N-(2-aminophenyl)-4-((4-(((2-(4-(1-methyl-6-oxo-1,6-dihydropyridin-3-yl)phenyl)cyclopropyl)amino)methyl)piperidin-1-yl)methyl)benzamide TFA Salt

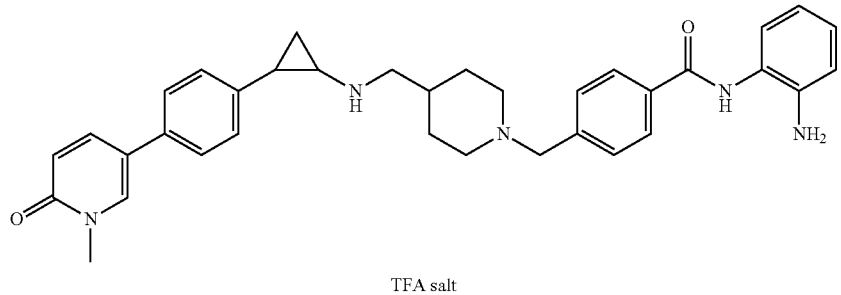 [SMILES: Cn1cc(-c2ccc(C3CC3NCC3CCN(Cc4ccc(C(=O)Nc5ccccc5N)cc4)CC3)cc2)ccc1=O]

TFA salt

The compound was synthesized using I-141 following the procedure for example 120. $^1$HNMR (400 MHz, DMSO-d$_6$): δ 9.86 (bs, 2H), 9.09 (bs, 2H), 8.08-8.60 (m, 3H), 7.79 (dd, J=9.2, 2 Hz, 1H), 7.62 (d, J=8.0 Hz, 2H), 7.49 (d, J=8.0 Hz, 2H), 7.22-7.19 (m, 3H), 7.04 (t, J=7.6 Hz, 1H), 6.89 (d, J=8.0 Hz, 1H), 6.74 (d, J=7.2 Hz, 1H), 6.46 (d, J=9.2 Hz, 1H), 4.37 (s, 2H), 3.49 (s, 3H), 3.42-3.39 (m, 2H), 3.28-3.10 (m, 1H), 3.05-2.94 (m, 5H), 2.02-1.82 (m, 3H), 1.51-1.37 (m, 3H), 1.34-1.27 (m, 1H). LC-MS m/z calcd for $C_{35}H_{39}N_5O_2$, 561.3; found 560.6[M−H]$^+$. HPLC purity 99.9%.

Example 142 N-(2-aminophenyl)-4-((4-(((2-(4-(1-methyl-1H-pyrazol-4-yl)phenyl)cyclopropyl)amino)methyl)piperidin-1-yl)methyl)benzamide TFA Salt

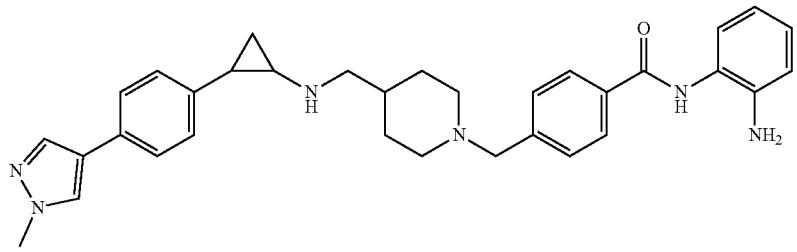

TFA

The compound was synthesized using I-142 following the procedure for example 120. $^1$HNMR (400 MHz, DMSO-d$_6$): δ 9.77 (bs, 1H), 8.89 (bs, 1H), 8.08 (bs, 2H), 8.08 (bs, 3H), 7.81 (s, 1H), 7.61 (d, J=7.6 Hz, 2H), 7.47 (d, J=8 Hz, 2H), 7.17-7.13 (m, 3H), 7.04-6.98 (m, 1H), 6.85-6.80 (m, 1H), 6.68-6.62 (m, 1H), 4.46-4.32 (m, 4H), 3.83 (s, 3H), 3.43-3.38 (m, 2H), 3.25-3.12 (m, 2H), 3.06-2.96 (m, 5H), 1.98-1.84 (m, 3H), 1.46-1.36 (m, 3H), 1.30-1.26 (m, 1H). LC-MS m/z calcd for $C_{35}H_{39}N_5O_2$, 534.3; found 535.2 [M+H]$^+$. HPLC purity 99.8%.

Example 143 N-(2-aminophenyl)-4-((4-(((2-(4-(3,5-dimethylisoxazol-4-yl)phenyl)cyclopropyl)amino)methyl)piperidin-1-yl)methyl)benzamide TFA Salt

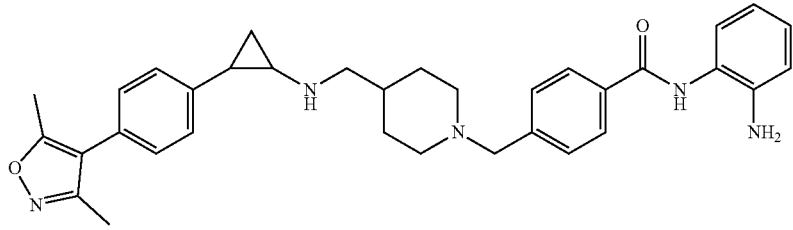

TFA

The compound was synthesized using I-143 following the procedure for example 120. $^1$HNMR (400 MHz, DMSO-$d_6$): δ 9.76 (bs, 1H), 9.69 (bs, 1H), 9.03 (bs, 1H), 8.97 (bs, 1H), 8.07 (d, J=7.2 Hz, 2H), 7.61 (d, J=7.2 Hz, 2H), 7.34-7.25 (m, 4H), 7.16 (d, J=7.6 Hz, 1H), 7.00 (t, J=7.6 Hz, 1H), 6.82 (d, J=8 Hz, 1H), 6.65 (t, J=7.2 Hz, 1H), 4.46-4.32 (m, 2H), 3.45-3.37 (m, 2H), 3.26-3.13 (m, 1H), 3.08-2.91 (m, 5H), 2.36 (s, 3H), 2.18 (s, 3H), 2.00-1.82 (m, 3H), 1.51-1.31 (m, 4H). LC-MS m/z calcd for $C_{35}H_{39}N_5O_2$, 549.3; found 550.3 $[M+H]^+$. HPLC purity 99.6%.

Example 144 N-(2-aminophenyl)-4-((4-(((2-(4-(pyrimidin-5-yl)phenyl)cyclopropyl)amino)methyl)piperidin-1-yl)methyl)benzamide TFA Salt

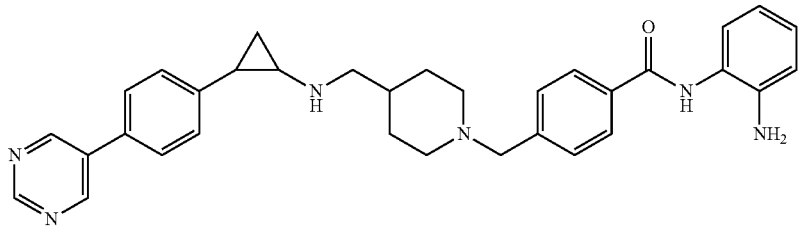

TFA

The compound was synthesized using I-145 following the procedure for example 120. $^1$HNMR (400 MHz, DMSO-$d_6$): δ 9.77 (bs, 1H), 9.66 (bs, 1H), 9.16 (s, 1H), 9.12 (s, 2H), 9.02 (bs, 2H), 8.07 (d, J=7.2 Hz, 2H), 7.76 (d, J=8 Hz, 2H), 7.62 (d, J=8 Hz, 2H), 7.34 (d, J=8 Hz, 2H), 7.16 (d, J=7.6 Hz, 1H), 7.00 (t, J=7.6 Hz, 1H), 6.82 (d, J=7.6 Hz, 1H), 6.65 (t, J=7.6 Hz, 1H), 4.37 (s, 2H), 3.46-3.37 (m, 2H), 3.27-3.12 (m, 1H), 3.10-2.90 (m, 5H), 2.03-1.82 (m, 3H), 1.56-1.37 (m, 4H). LC-MS m/z calcd for $C_{33}H_{36}N_6O$, 532.3; found 533.6 $[M+H]^+$. HPLC purity 99.9%.

Example 145 N-(2-aminophenyl)-4-((4-(((2-phenylcyclopropyl)amino)methyl)-1H-pyrazol-1-yl)methyl)benzamide TFA Salt The compound was synthesized using I-145 following the procedure for example 120. $^1$HNMR (400 MHz, DMSO-$d_6$): δ 9.65 (bs, 1H), 9.02 (bs, 2H), 7.93 (d, 2H, J=7.6 Hz), 7.89 (s, 1H), 7.56 (s, 1H), 7.34-7.25 (m, 4H), 7.23-7.19 (m, 1H), 7.18-7.10 (m, 3H), 6.98 (t, 1H, J=7.6 Hz), 6.81 (d, 1H, J=8 Hz), 6.63 (t, 1H, J=7.2 Hz), 5.41 (s, 2H), 4.19 (s, 2H), 2.94-2.86 (m, 1H), 2.40-2.31 (m, 1H), 1.43-1.37 (m, 1H), 1.32-1.22 (m, 1H). LC-MS m/z calcd for $C_{27}H_{27}N_5O$, 437.2; found 438.3 $[M+H]^+$. HPLC purity 98.7%.

Example 146 N-(2-aminophenyl)-4-((4-(((2-phenylcyclopropyl)amino)methyl)-1H-1,2,3-triazol-1-yl)methyl)benzamide TFA Salt

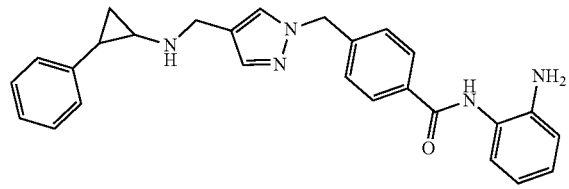 [SMILES: Nc1ccccc1NC(=O)c1ccc(Cn2cc(CNC3CC3c3ccccc3)cn2)cc1]

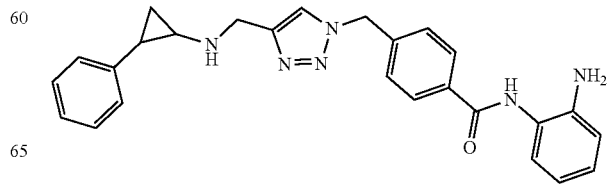

The compound was synthesized using I-146 following the procedure for example 120. $^1$HNMR (400 MHz, DMSO-d$_6$): δ 9.72 (bs, 1H), 9.44 (bs, 2H), 8.24 (s, 1H), 7.97 (d, 2H, J=7.6 Hz), 7.42 (d, 2H, J=8 Hz), 7.31-7.26 (m, 2H), 7.23-7.15 (m, 2H), 7.11 (d, 2H, J=7.2 Hz), 7.00 (t, 1H, J=7.6 Hz), 6.84 (d, 1H, J=8 Hz), 6.67 (t, 1H, J=7.2 Hz), 5.73 (s, 2H), 4.43 (s, 2H), 2.99-2.98 (m, 1H), 2.40-2.37 (m, 1H), 1.44-1.37 (m, 1H), 1.30-1.24 (m, 1H). LC-MS m/z calcd for C$_{26}$H$_{26}$N$_6$O, 438.2; found 439.5 [M+H]$^+$. HPLC purity 98.9%.

Example 147 N-(2-aminophenyl)-4-(2-(4-(((2-(4-fluorophenyl)cyclopropyl)amino)methyl)piperidin-1-yl)-2-oxoethyl)benzamide TFA Salt

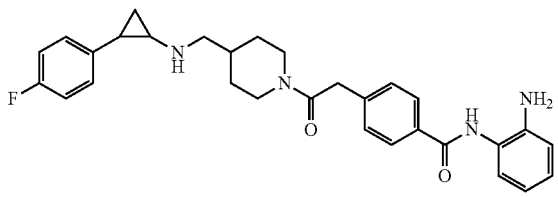 [SMILES: Nc1ccccc1NC(=O)c1ccc(CC(=O)N2CCC(CNC3CC3c3ccc(F)cc3)CC2)cc1]

The compound was synthesized using I-147 following the procedure for example 120. $^1$HNMR (400 MHz, DMSO-d$_6$): δ 9.73 (s, 1H), 8.793 (bs, 2H), 7.91 (d, 2H, J=8.0 Hz), 7.35 (d, 2H, J=8.4 Hz), 7.23-7.19 (m, 3H), 7.14-7.10 (m, 2H), 7.04-7.01 (m, 1H), 6.89-6.87 (m, 1H), 6.76-6.70 (m, 1H), 4.38-4.35 (m, 1H), 3.99-3.96 (m, 1H), 3.79 (s, 2H), 3.05-2.92 (m, 4H), 2.65-2.55 (m, 1H), 2.48-2.42 (m, 1H), 1.92-1.85 (m, 1H), 1.76-1.67 (m, 2H), 1.47-1.39 (m, 1H), 1.32-1.26 (m, 1H), 1.05-0.97 (m, 2H), LC-MS m/z calcd for C$_{30}$H$_{33}$FN$_4$O$_2$, 500.1; found 501.2 [M+H]$^+$. HPLC purity 99.9%.

Example 148 N-(2-aminophenyl)-4-(2-((2-(4-fluorophenyl)cyclopropyl)amino)ethoxy) benzamide TFA Salt

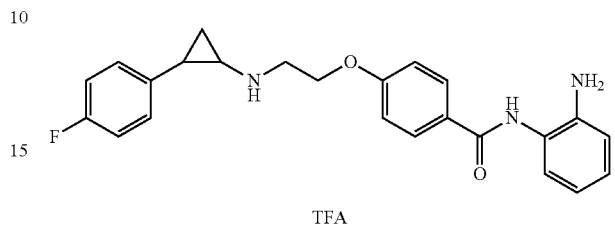

The compound was synthesized using I-148 following the procedure for example 120. $^1$HNMR (400 MHz, DMSO-d$_6$): δ 9.69 (s, 1H), 9.18 (bs, 2H), 7.98 (d, 2H, J=8.8 Hz), 7.21-7.19 (m, 3H), 7.14-7.01 (m, 5H), 6.92-6.88 (m, 1H), 6.78-6.74 (m, 1H), 4.34-4.29 (m, 3H), 3.59-3.51 (m, 2H), 3.09-3.02 (m, 1H), 1.48-1.43 (m, 1H), 1.34-1.29 (m, 1H). LC-MS m/z calcd for C$_{24}$H$_{24}$FN$_3$O$_2$, 405.4; found 406.2 [M+H]$^+$. HPLC purity 99.7%.

Example 149 N-(2-aminophenyl)-6-(2-(4-(((2-(4-fluorophenyl)cyclopropyl)amino)methyl)piperidin-1-yl)ethoxy)nicotinamide TFA Salt

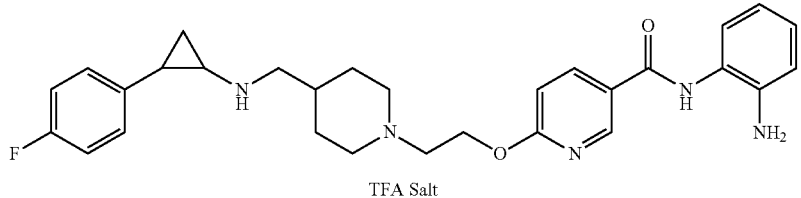 [SMILES: Nc1ccccc1NC(=O)c1ccc(OCCN2CCC(CNC3CC3c3ccc(F)cc3)CC2)nc1]

TFA Salt

The compound was synthesized using I-149 following the procedure for example 120. $^1$HNMR (400 MHz, DMSO-d$_6$): δ 9.48 (s, 1H), 9.29 (bs, 1H), 8.98 (bs, 2H), 8.49 (s, 1H), 8.06 (d, J=7.6 Hz, 1H), 7.25-7.20 (m, 2H), 7.16-7.07 (m, 3H), 6.98 (t, J=7.2 Hz, 1H), 6.80 (d, J=7.6 Hz, 1H), 6.61 (t, J=7.2 Hz, 1H), 6.51 (d, J=9.6 Hz, 1H), 4.40-4.30 (m, 2H), 3.70-3.65 (m, 2H), 3.46-3.39 (m, 2H), 3.30-3.25 (m, 1H), 3.05-2.95 (m, 5H), 2.03-1.95 (m, 3H), 1.49-1.39 (m, 3H), 1.31-1.26 (m, 1H). LC-MS m/z calcd for C$_{29}$H$_{34}$FN$_5$O$_2$, 503.2; found 504.3[M+H]$^+$. HPLC purity 99.6%.

Example 150 N-(-2-aminophenyl)-2-((2-4(((2-(4-flurophenyl)cyclopropyl)amino)methyl)piperdine-1-yl)ethyl)amino)pyrimidine-5-carboxamide TFA Salt

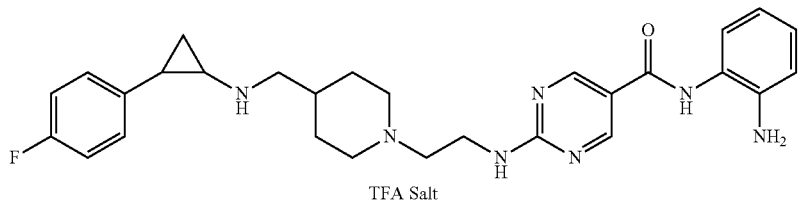 [SMILES: Nc1ccccc1NC(=O)c1cnc(NCCN2CCC(CNC3CC3c3ccc(F)cc3)CC2)nc1]

TFA Salt

The compound was synthesized using I-150 following the procedure for example 120. ¹HNMR (400 MHz, DMSO-d₆): δ 9.68 (bs, 1H), 9.35 (bs, 1H), 9.08 (bs, 2H), 8.88 (s, 2H), 7.98-7.93 (m, 1H), 7.24-7.10 (m, 5H), 7.03 (t, 1H, J=7.2 Hz), 6.88 (d, 1H, J=8 Hz), 6.73 (t, 1H, J=7.6 Hz), 3.76-3.60 (m, 4H), 3.34-3.21 (m, 3H), 3.05-2.92 (m, 4H), 2.46-2.41 (m, 1H), 2.01-1.92 (m, 3H), 1.49-1.40 (m, 3H), 1.30-1.24 (m, 1H). LC-MS m/z calcd for $C_{28}H_{34}FN_7O$, 503.2; found 504.3[M+H]⁺. HPLC purity 99.8%.

Example 151 N-(2-aminophenyl)-5-((2-(4-fluorophenyl)cyclopropyl)glycyl)-4,5,6,7-tetrahydrothieno[3,2-c]pyridine-2-carboxamide TFA Salt

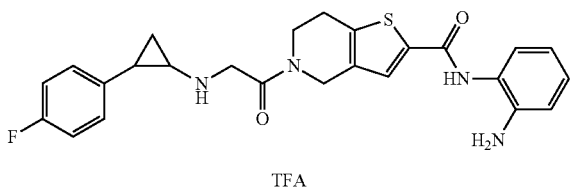 [SMILES: Nc1ccccc1NC(=O)c1cc2c(s1)CCN(C(=O)CNC1CC1c1ccc(F)cc1)C2]

The compound was synthesized using I-151 following the procedure for example 120. ¹HNMR (400 MHz, DMSO-d₆): 9.65 (s, 1H), 9.23 (s, 2H), 7.73-7.71 (m, 1H), 7.22-7.20 (m, 2H), 7.13-7.09 (m, 3H), 6.98 (bs, 1H), 6.80 (bs, 1H), 6.63 (bs, 1H), 4.62 (s, 1H), 4.55 (s, 1H), 4.37-4.35 (m, 2H), 3.70 (s, 2H), 2.97 (s, 2H), 2.85 (s, 2H), 1.48 (bs, 1H), 1.28-1.26 (m, 1H). LC-MS m/z calcd [M+H]⁺ 464.1. found 465.0. HPLC purity 99.0%.

Example 152 N-(2-aminophenyl)-2-(2-((2-(4-fluorophenyl)cyclopropyl)amino)acetyl)-1,2,3,4-tetrahydroisoquinoline-7-carboxamide TFA Salt

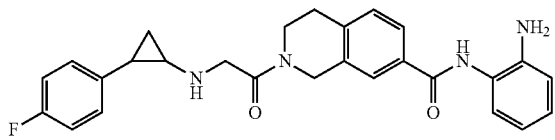 [SMILES: Nc1ccccc1NC(=O)c1ccc2c(c1)CN(C(=O)CNC1CC1c1ccc(F)cc1)CC2]

The compound was synthesized using I-152 following the procedure for example 120. ¹HNMR (400 MHz, DMSO-d₆): δ 9.66 (bs, 1H), 9.26 (bs, 2H), 7.86-7.79 (m, 2H), 7.34-7.32 (d, 1H, J=8.0 Hz), 7.25-7.15 (m, 3H), 7.14-7.07 (m, 2H), 7.02-6.98 (m, 1H), 6.85-6.81 (m, 1H), 6.71-6.64 (m, 1H), 4.74-4.70 (m, 2H), 4.35 (s, 2H), 3.76-3.74 (m, 3H), 3.02-2.96 (m, 1H), 2.90-2.82 (m, 2H), 1.52-1.48 (m, 1H), 1.32-1.26 (m, 1H). LC-MS m/z calcd for $C_{27}H_{27}FN_4O_2$, 458.2; found 459.2 [M+H]⁺. HPLC purity 99.2%.

Example 153 N-(2-aminophenyl)-2-(3-(4-(((2-phenylcyclopropyl)amino)methyl)piperidin-1-yl)propyl)oxazole-4-carboxamide TFA Salt

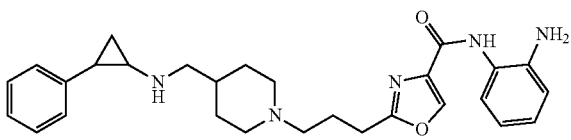 [SMILES: Nc1ccccc1NC(=O)c1coc(CCCN2CCC(CNC3CC3c3ccccc3)CC2)n1]

The compound was synthesized using I-153 following the procedure for example 120. ¹HNMR (400 MHz, DMSO-d₆): δ 9.36 (bs, 2H), 8.94 (bs, 2H), 8.67 (s, 1H), 7.32-7.26 (m, 3H), 7.23-7.15 (m, 3H), 6.98 (t, J=7.6 Hz, 1H), 6.83 (d, J=8 Hz, 1H), 6.66 (t, J=7.2 Hz, 1H), 3.60-3.54 (m, 2H), 3.23-3.14 (m, 3H), 3.07-2.90 (m, 7H), 2.15-2.11 (m, 2H), 2.00-1.94 (m, 3H), 1.49-1.40 (m, 3H), 1.32-1.26 (m, 1H). LC-MS m/z calcd for $C_{28}H_{35}N_5O_2$, 473.3; found 474.3 [M+H]⁺. HPLC purity 99.8%.

Example 154 N-(2-aminophenyl)-2-(3-(4-(((2-phenylcyclopropyl)amino)methyl)piperidin-1-yl)propyl)thiazole-5-carboxamide TFA Salt

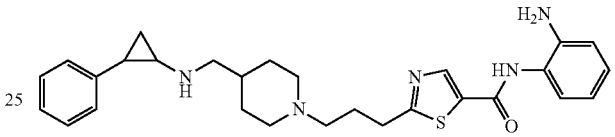

The compound was synthesized using I-154 following the procedure for example 120. ¹HNMR (400 MHz, DMSO-d₆): δ 9.87 (bs, 1H), 9.35 (bs, 1H), 9.00 (bs, 2H), 8.46 (s, 1H), 7.32-7.26 (m, 2H), 7.23-7.09 (m, 4H), 7.02 (t, 1H, J=7.6 Hz), 6.83 (d, 1H, J=8 Hz), 6.66 (t, 1H, J=7.2 Hz), 3.59-3.52 (m, 2H), 3.28-2.88 (m, 9H), 2.46-2.42 (m, 1H), 2.18-2.11 (m, 2H), 2.00-1.94 (m, 3H), 1.49-1.39 (m, 3H), 1.32-1.22 (m, 1H). LC-MS m/z calcd for $C_{28}H_{35}N_5OS$, 489.3; found 490.3 [M+H]⁺. HPLC purity 99.8%.

Example 155 N-(2-aminophenyl)-4-((2-((2-(4-fluorophenyl)cyclopropyl)amino)acetamido)methyl)benzamide TFA Salt

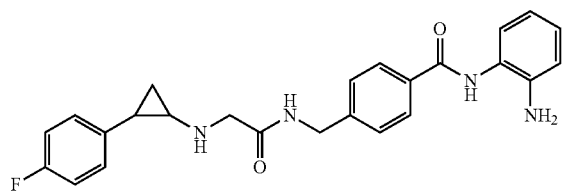 [SMILES: Nc1ccccc1NC(=O)c1ccc(CNC(=O)CNC2CC2c2ccc(F)cc2)cc1]

The compound was synthesized using I-155 following the procedure for example 120. ¹HNMR (400 MHz, DMSO-d₆): δ 9.70 (s, 1H), 9.30 (bs, 2H), 8.97 (s, 1H), 7.94 (d, 2H, J=8 Hz), 7.39 (d, 2H, J=8 Hz), 7.22-7.18 (m, 3H), 7.13-7.09 (m, 2H), 7.03-6.99 (m, 1H), 6.85 (d, 1H, J=7.2 Hz), 4.44 (d, 2H, J=6 Hz), 3.98-3.74 (m, 5H), 2.92 (m, 1H), 1.47-1.45 (m, 1H), 1.30-1.22 (m, 1H). LC-MS m/z calcd for $C_{25}H_{25}FN_4O_2$, 432.2; found 433.0 [M+H]⁺. HPLC purity 99.8%.

Example 156 E)-N-(2-aminophenyl)-4-(3-(4-(((2-(4-fluorophenyl)cyclopropyl)amino)methyl)piperidin-1-yl)-3-oxoprop-1-en-1-yl)benzamide TFA Salt

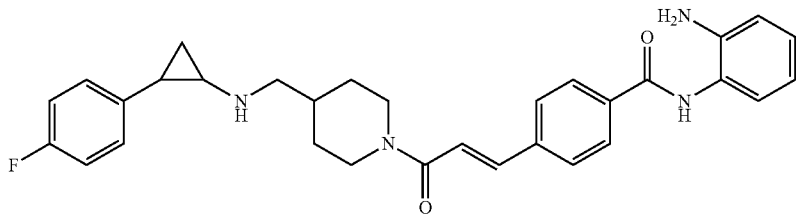 [SMILES: Nc1ccccc1NC(=O)c1ccc(/C=C/C(=O)N2CCC(CNC3CC3c3ccc(F)cc3)CC2)cc1]

The compound was synthesized using I-156 following the procedure for example 120. $^1$HNMR (400 MHz, DMSO-$d_6$): δ 9.81 (s, 1H), 8.85 (bs, 2H), 8.00 (d, 2H, J=7.6 Hz), 7.85 (d, 2H, J=8 Hz), 7.53 (d, 1H, J=15.6 Hz), 7.40 (d, 1H, J=15.6 Hz), 7.25-7.19 (m, 3H), 7.16-7.11 (m, 2H), 7.05-7.02 (m, 1H), 6.89-6.87 (m, 1H), 6.75-6.69 (m, 1H), 4.52-4.28 (m, 2H), 3.17-2.92 (m, 4H), 2.76-2.63 (m, 1H), 2.48-2.45 (m, 1H), 2.03-1.92 (m, 1H), 1.87-1.76 (m, 2H), 1.47-1.43 (m, 1H), 1.32-1.16 (m, 3H). LC-MS m/z calcd for $C_{31}H_{33}FN_4O_2$, 512.6; found 513.2 [M+H]$^+$. HPLC purity 99.7%.

Example 157 (E)-N-(2-aminophenyl)-4-(3-(3-(((2-(4-fluorophenyl)cyclopropyl)amino)methyl)azetidin-1-yl)-3-oxoprop-1-en-1-yl)benzamide TFA Salt

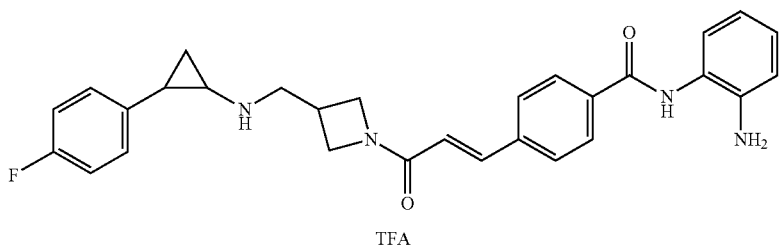 [SMILES: Nc1ccccc1NC(=O)c1ccc(/C=C/C(=O)N2CC(CNC3CC3c3ccc(F)cc3)C2)cc1]

The compound was synthesized using I-157 following the procedure for example 120. $^1$HNMR (400 MHz, DMSO-$d_6$): δ 9.80 (bs, 1H), 8.95 (bs, 2H), 8.00 (d, J=8 Hz, 2H), 7.79 (d, J=8 Hz, 2H), 7.50 (d, J=15.6 Hz, 1H), 7.26-7.21 (m, 5H), 7.05-7.00 (m, 1H), 6.90-6.85 (m, 1H), 6.79 (d, J=16 Hz, 1H), 6.75-6.67 (m, 1H), 4.47-4.42 (m, 1H), 4.10-4.03 (m, 2H), 3.82-3.77 (m, 1H), 3.47-3.38 (m, 2H), 3.03-2.92 (m, 2H), 1.47-1.40 (m, 1H), 1.33-1.27 (m, 1H). LC-MS m/z calcd for $C_{29}H_{29}FN_4O_2$, 484.2; found 485.2 [M+H]$^+$. HPLC purity 99.6%.

Example 158 N-(4-((2-aminophenyl)carbamoyl)benzyl)-4-(((2-(4-fluorophenyl)cyclopropyl)amino)methyl)piperidine-1-carboxamide TFA Salt

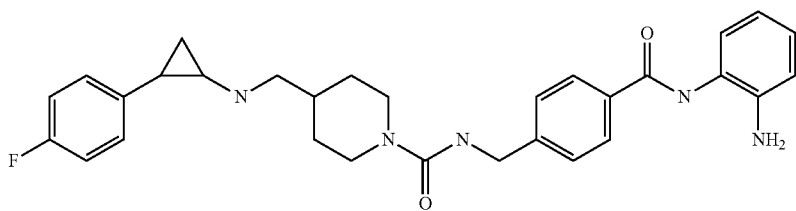 [SMILES: Nc1ccccc1NC(=O)c1ccc(CNC(=O)N2CCC(CNC3CC3c3ccc(F)cc3)CC2)cc1]

The compound was synthesized using I-158 following the procedure for example 120. ¹HNMR (400 MHz, DMSO-$d_6$): δ 9.75 (s, 1H), 8.82 (bs, 2H), 7.91 (d, 2H, J=7.6 Hz), 7.35 (d, 1H, J=8.0 Hz), 7.26-7.18 (m, 3H), 7.16-7.08 (m, 3H), 7.08-7.02 (m, 1H), 6.94-6.88 (m, 1H), 6.79-6.75 (m, 1H), 4.32-4.28 (m, 2H), 4.05-3.94 (m, 2H), 3.07-2.91 (m, 3H), 2.76-2.62 (m, 2H), 2.48-2.43 (bs, 1H), 1.90-1.81 (m, 1H), 1.74-1.63 (m, 2H), 1.46-1.41 (m, 1H), 1.30-1.25 (m, 1H), 1.15-1.00 (m, 2H). LC-MS m/z calcd for $C_{30}H_{34}FN_5O_2$, 515.2; found 516.3 [M+H]⁺. HPLC purity 99.9%.

Example 159 N-(2-aminophenyl)-4-(3-(2-oxo-4-(((2-phenylcyclopropyl)amino)methyl) piperidin-1-yl)propyl)benzamide TFA Salt

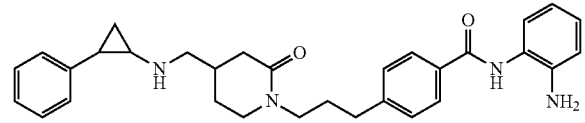 [SMILES: Nc1ccccc1NC(=O)c1ccc(CCCN2CCC(CNC3CC3c3ccccc3)CC2=O)cc1]

The compound was synthesized using I-159 following the procedure for example 120. LC-MS m/z calcd for $C_{31}H_{36}N_4O_2$, 496.6; found 497.6 [M+H]⁺.

Example 160 N-(2-aminophenyl)-4-((4-(((2-phenylcyclopropyl)amino)methyl)piperidin-1-yl)sulfonyl)benzamide TFA Salt

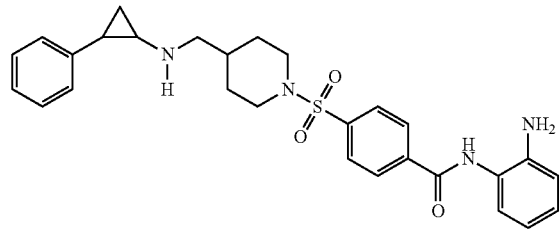 [SMILES: Nc1ccccc1NC(=O)c1ccc(S(=O)(=O)N2CCC(CNC3CC3c3ccccc3)CC2)cc1]

The compound was synthesized using I-160 following the procedure for example 120. ¹HNMR (400 MHz, DMSO-$d_6$): δ 9.88 (bs, 1H), 8.73 (bs, 2H), 8.19 (d, 2H, J=8.0 Hz), 7.85 (d, 2H, J=7.6 Hz), 7.31-7.24 (m, 2H), 7.22-7.11 (m, 4H), 7.02-6.96 (m, 1H), 6.82-6.77 (m, 1H), 6.63-6.59 (m, 1H), 3.72-3.67 (m, 2H), 3.02-2.92 (m, 4H), 2.38-2.32 (m, 1H), 2.28-2.24 (m, 1H), 1.84-1.77 (m, 2H), 1.68-1.61 (m, 1H), 1.43-1.38 (m, 1H), 1.34-1.21 (m, 3H). LC-MS m/z calcd for $C_{28}H_{32}N_4O_3S$, 504.2; found 505.3 [M+H]⁺. HPLC purity 99.4%.

Example 161 N-(2-aminophenyl)-4-(((4-(((2-phenylcyclopropyl)amino)methyl)piperidin-1-yl)sulfonyl) methyl)benzamide TFA Salt

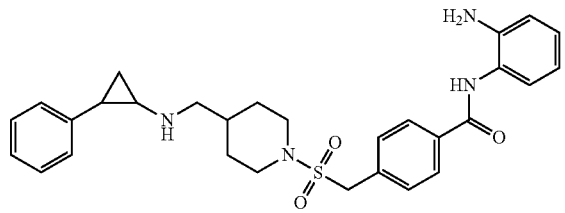 [SMILES: Nc1ccccc1NC(=O)c1ccc(CS(=O)(=O)N2CCC(CNC3CC3c3ccccc3)CC2)cc1]

The compound was synthesized using I-161 following the procedure for example 120. ¹HNMR (400 MHz, DMSO-$d_6$): δ 9.83 (bs, 1H), 8.88 (bs, 2H), 7.98 (d, 2H, J=8.0 Hz), 7.52 (d, 2H, J=7.6 Hz), 7.32-7.26 (m, 2H), 7.23-7.14 (m, 4H), 7.07-7.03 (m, 1H), 6.92-6.88 (m, 1H), 6.78-6.74 (m, 1H), 3.62-3.56 (m, 2H), 3.05-2.94 (m, 3H), 2.79-2.68 (m, 2H), 2.43-2.39 (m, 1H), 1.80-1.70 (m, 3H), 1.46-1.42 (m, 1H), 1.31-1.20 (m, 5H). LC-MS m/z calcd for $C_{29}H_{34}N_4O_3S$, 518.2; found 519.2 [M+H]⁺.

Example 162 N-(2-aminophenyl)-4-(2-((4-(((2-phenylcyclopropyl)amino)methyl)piperidin-1-yl)sulfonyl) ethyl)benzamide TFA

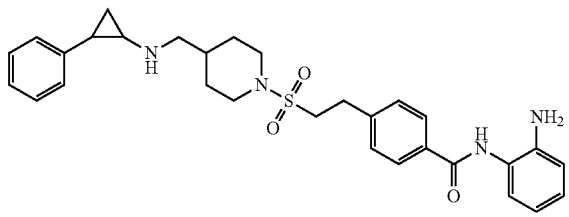 [SMILES: Nc1ccccc1NC(=O)c1ccc(CCS(=O)(=O)N2CCC(CNC3CC3c3ccccc3)CC2)cc1]

The compound was synthesized using I-162 following the procedure for example 120. ¹HNMR (400 MHz, DMSO-$d_6$): δ 9.73 (bs, 1H), 8.85 (bs, 2H), 7.92 (d, 2H, J=8.0 Hz), 7.43 (d, 2H, J=8 Hz), 7.31-7.26 (m, 2H), 7.22-7.14 (m, 4H), 7.04-7.00 (m, 1H), 6.89-6.85 (m, 1H), 6.74-6.68 (m, 1H), 3.65-3.60 (m, 2H), 3.40-2.35 (m, 2H), 3.07-3.00 (m, 4H), 2.98-2.93 (m, 1H), 2.84-2.76 (m, 2H), 2.43-2.40 (m, 1H), 1.82-1.78 (m, 3H), 1.48-1.42 (m, 1H), 1.31-1.20 (m, 3H). LC-MS m/z calcd for $C_{30}H_{36}N_4O_3S$, 532.3; found 533.3 [M+H]⁺. HPLC purity 99.4%.

Biology Methods
TR-FRET Assay for LSD1 (Perkin Elmer)

LSD1 enzyme was produced in house. Tranylcypromine (TCP), LSD1 inhibitor was procured from Selleckchem. LSD1 enzyme, TCP and Biotinylated peptide substrate were diluted in assay buffer just before use. 2× inhibitor (10 μl, diluted in assay buffer) or Assay Buffer, and 5 nMenzyme were added to a 96 well plate and incubated at room temperature for 30 min. 5 μL of biotinylated Histone H3K4me1 peptide (4×) was added to each well and incubated at room temperature (RT) for 1 hour. Stop Solution containing 300 μM tranylcypromine in 1× LANCE Detection Buffer was added to the wells and incubated for 5 min at RT. Then, Detection mix containing 2 nM Eu-Ab and 50 nM ULight-Streptavidin in 1× LANCE Detection Buffer was prepared and added to the reaction mix. This mixture was incubated for 1 hour at room temperature. Readings were taken with the Pherastar Reader in TR-FRET mode (excitation at 337 nm & emission at A-665 nm, B-620 nM).

Histone Deacetylase Assay (BPS Biosciences)

Histone deacetylase assay was done as per manufacturer's instructions. Briefly, assay buffer, 200 uM HDAC substrate (fluorogenic HDAC acetylated peptide substrate for class I HDACs (HDACs 1, 2, and 3) and class 2b HDACs (HDACs 6 and 10) and 1% BSA are taken as a master mix and aliquoted as 40 ul per well. Compounds (10×) were diluted in assay buffer and were added to respective wells of a black 96 well plate. HDAC6 human recombinant enzyme was thawed on ice and 5 μl (7 ng/ul) enzyme was added per well. The plate was incubated at 37° C. for 1 hour. Developer solution was then added (50 μl per well) and incubated at room temperature for 10 minutes. Fluorescence was measured at an excitation wave length of 350-380 nm and emission wavelength of 440-480 nm.

As described above, compounds were tested for LSD1, HDAC1, HDAC2 and HDAC6 enzyme inhibitory activities.

Anticancer Activity: Alamar Blue Assay

Cells were seeded at 5000 cells/per well in 96-well tissue culture plate and incubated at 37° C./5% CO2. After 16-24 hours, fresh media was added to the wells. Compounds were then (1% DMSO conc.) added to the cells at 10 concentrations ranging from 10-0.0005 uM prepared in 3-fold serial dilutions. Cells were incubated for 68-72 h at 37° C./5% CO$_2$. Alamar Blue™ reagent was added and incubated for 1-3 hours at 37° C./5% CO2. Plates were read on fluorescence reader at 540 nm excitation, 590 nm emission wave lengths.

As described above, compounds were tested for anticancer activities in different tumor cell lines and GI$_{50}$ were determined.

Metabolic Stability

The microsomal suspension was prepared by adding liver microsomes to 100 mM potassium phosphate buffer (pH7.4) to give a final protein concentration of 0.5 mg/mL. The stock solution of NCE (10 mM in DMSO) was added to the microsomes to provide a final concentration of 1 μM. Incubations were undertaken with NADPH (1 mM final concentration) for 0, 5, 15 and 30 min at 37° C., after which reactions were quenched with acetonitrile (quench ratio 1:1). Samples were vortexed and centrifuged at 5,000 rpm for 10 min to remove proteins. Supernatant were analyzed on LC-MS/MS.

TABLE 1

Selected list compounds with Enzymatic, cellular activity and metabolic stability

| Compound | LSD1 IC$_{50}$ uM | HDAC6 IC$_{50}$ uM | MM1S EC$_{50}$ uM | Metabolic stability HLM/MLM % remaining in 30 min |
|---|---|---|---|---|
| 1 | 0.083 | ND | ND | 21/5 |
| 2 | 0.057 | ND | 0.023 | 41/19 |
| 3 | 0.020 | ND | 0.104 | 65/<5 |
| 4 | 0.684 | ND | ND | ND |
| 5 | 0.049 | 0.373 | 0.088 | 86/59 |
| 6 | 0.049 | ND | 0.034 | 44/<5 |
| 7 | 0.027 | 0.174 | 0.048 | 70/<5 |
| 8 | 0.040 | 0.088 | 0.007 | 88/52 |
| 9 | 0.101 | ND | 0.004 | 65/50 |
| 10 | 0.221 | ND | 0.009 | 81/55 |
| 11 | 0.019 | ND | 0.018 | 44/14 |
| 12 | 0.778 | 0.136 | 0.011 | 95/85 |
| 13 | 0.044 | ND | 0.024 | 57/23 |
| 14 | 0.367 | ND | 0.008 | 88/82 |
| 15 | 0.095 | 0.134 | 0.012 | ND |
| 16 | 0.089 | ND | 0.017 | 47/25 |
| 17 | 0.128 | 0.398 | 0.017 | 69/57 |
| 18 | 0.150 | ND | 0.003 | 41/28 |
| 19 | 0.309 | ND | 0.007 | 83/71 |
| 20 | 0.100 | 0.072 | 0.003 | 91/69 |
| 21 | 0.115 | 0.091 | 0.009 | 86/51 |
| 22 | 6.4 | 0.171 | 0.044 | 60/38 |
| 23 | 0.778 | 0.136 | 0.011 | 95/85 |
| 24 | 1.160 | ND | 0.009 | 71/74 |
| 25 | 0.840 | ND | 0.011 | 75/85 |
| 26 | 0.020 | ND | ND | 30/13 |
| 27 | 0.016 | >1.00 | ND | 75/51 |
| 28 | 0.023 | 0.264 | ND | 73/35 |
| 29 | 0.178 | 0.819 | ND | >95/90 |
| 30 | 0.119 | 0.202 | 0.045 | 16/51 |
| 31 | 0.111 | ND | ND | 39/18 |
| 32 | 0.070 | ND | 0.017 | 41/22 |
| 33 | 2.250 | >1.00 | ND | ND |
| 34 | 0.031 | >1.00 | 0.094 | 90/79 |
| 35 | 0.034 | 0.199 | 1.429 | ND |
| 36 | 0.011 | 0.235 | ND | 63/53 |
| 37 | 0.043 | 0.141 | 1.731 | 86/55 |
| 38 | 0.053 | 0.169 | 3.642 | 87/>95 |
| 39 | 0.034 | 0.732 | 2.969 | 87/>95 |
| 40 | 0.178 | 0.037 | ND | ND |
| 41 | 0.319 | 0.074 | ND | ND |
| 42 | 0.015 | 0.49 | 0.19 | ND |
| 43 | 0.005 | 0.048 | 0.002 | 40/56 |
| 44 | 0.013 | 0.065 | 0.045 | 71/55 |
| 45 | 0.465 | ND | 0.048 | ND |
| 46 | 0.026 | 0477 | 0.071 | 54/47 |
| 47 | 0.006 | 0.051 | 0.033 | 54/66 |
| 48 | 0.029 | 0.184 | 0.025 | 85/<5 |
| 49 | 0.018 | ND | 0.062 | 48/34 |
| 50 | 0.029 | 0.212 | 0.035 | 86/80 |
| 51 | 0.006 | 0.038 | 0.002 | 74/91 |
| 52 | 0.004 | 0.012 | 0.003 | 79/56 |
| 53 | 0.022 | 0.291 | 0.024 | 89/82 |
| 54 | 0.023 | 0.214 | 0.038 | 65/72 |
| 55 | 0.022 | 0.130 | 0.189 | 40/36 |
| 56 | 0.002 | 0.019 | 0.001 | 87/75 |
| 57 | 0.021 | 0.059 | 0.006 | 92/75 |
| 58 | 0.025 | 0.043 | 0.015 | 85/91 |
| 59 | 0.032 | 0.204 | 0.018 | 76/75 |
| 60 | 0.021 | 0.046 | 0.024 | 73/72 |
| 61 | 0.012 | 0.121 | 0.049 | 77/67 |
| 62 | 0.043 | 0.066 | 0.007 | 77/66 |
| 63 | 0.031 | 1.315 | 0.191 | 86/69 |
| 64 | 0.059 | 0.058 | 0.011 | 82/77 |
| 65 | 0.038 | 0.383 | 0.026 | ND |
| 66 | 0.019 | 0.100 | 0.021 | 79/85 |
| 67 | 0.484 | 0.272 | 0.070 | ND |
| 68 | ND | 0.104 | ND | ND |
| 71 | 1.1 | 0.028 | ND | 73/<5 |
| 72 | 0.730 | 0.018 | 0.343 | 67/<5 |
| 73 | 0.109 | 0.243 | 0.540 | 52/53 |
| 74 | 0.028 | 0.112 | 0.253 | 47/27 |
| 75 | 0.286 | 0.365 | 0.246 | ND |
| 76 | 0.084 | 0.022 | 0.042 | ND |
| 77 | 0.065 | 0.071 | 0.070 | ND |
| 78 | 0.103 | 0.183 | 0.060 | 72/32 |
| 79 | 0.079 | 0.024 | 0.039 | 18/6 |
| 80 | 1.5 | 0.068 | 0.331 | 82/87 |
| 81 | 0.394 | 0.125 | 0.022 | >95/>95 |
| 82 | 0.094 | 0.035 | 0.619 | 77/72 |
| 83 | 0.090 | 0.179 | 0.153 | 69/82 |
| 84 | 0.057 | 0.045 | 0.112 | 78/40 |
| 84A | 0.107 | 0.022 | 0.026 | 78/41 |
| 84B | 0.230 | 0.025 | 0.259 | 75/45 |
| 85 | 0.062 | 0.575 | >10 | ND |
| 86 | 0.018 | 0.554 | 0.676 | 71/58 |
| 87 | 0.025 | 1.061 | 9.107 | ND |
| 88 | ND | 0.077 | ND | ND |
| 89 | 0.020 | 0.720 | 0.311 | ND |
| 90 | 0.021 | 0.170 | 0.339 | 80/93 |
| 91 | 0.332 | 0.138 | 0.468 | 85/79 |
| 92 | 0.273 | 0.115 | 1.4 | 95/91 |
| 93 | 0.072 | 0.187 | 1.04 | 1.040 |
| 95 | 0.033 | 0.350 | 0.144 | 75/55 |
| 96 | 0.022 | 6.608 | >10 | 93/89 |

TABLE 1-continued

Selected list compounds with Enzymatic, cellular activity and metabolic stability

| Compound | LSD1 IC$_{50}$ uM | HDAC6 IC$_{50}$ uM | MM1S EC$_{50}$ uM | Metabolic stability HLM/MLM % remaining in 30 min |
|---|---|---|---|---|
| 97 | 0.033 | >10 | >10 | ND |
| 98 | 0.037 | 5.96 | >10 | ND |
| 99 | 0.004 | 0.051 | 0.027 | 63/76 |
| 100 | 0.023 | ND | 0.017 | 63/57 |
| 101 | 0.197 | 0.152 | 0.029 | 59/29 |
| 102 | 0.022 | 0.075 | 0.005 | >99/>99 |
| 103 | 0.124 | 0.041 | 0.045 | 85/53 |
| 103A | 0.667 | 0.022 | 0.052 | 87/68 |
| 103B | 0.154 | 0.036 | 0.015 | 76/73 |
| 104 | 0.206 | 0.032 | 0.269 | 80/77 |
| 104A | 0.455 | 0.053 | 0.183 | 74/68 |
| 104B | 1.002 | 0.045 | 0.374 | 74/70 |
| 105 | 0.138 | 0.018 | 0.013 | 77/72 |
| 106 | 0.026 | 0.035 | 0.014 | 74/92 |
| 107 | 0.399 | 0.085 | 0.078 | 83/67 |
| 108 | 0.134 | 0.195 | 0.584 | >95/85 |
| 109 | 0.024 | 0.107 | 1.1 | ND |
| 110 | 0.026 | >10 | >10 | 88/95 |
| 111 | 0.022 | 2.98 | 3.065 | 95/91 |
| 112 | 0.022 | 0.517 | 0.063 | ND |
| 113 | 0.026 | >10 | >10 | 78/76 |
| 114 | 0.051 | 0.068 | 0.044 | 83/56 |
| 114A | 0.063 | 0.038 | 0.014 | 67/62 |
| 114B | 0.285 | 0.033 | 0.097 | 73/43 |
| 115 | 0.065 | 0.053 | 0.010 | 75/45 |
| 115A | 0.225 | 0.050 | 0.077 | 59/90 |
| 116 | 0.069 | 0.135 | 0.157 | 63/50 |
| 117 | 0.046 | 0.074 | 0.460 | 80/82 |
| 118 | 0.037 | 0.058 | 0.021 | 77/76 |
| 119 | 0.019 | 0.049 | 0.772 | 72/49 |
| 120 | 0.596 | ND | 0.361 | 27/16 |
| 121 | 0.006 | ND | 0.003 | 36/42 |
| 122 | 0.006 | ND | 0.015 | 77/72 |
| 123 | 0.007 | ND | 0.009 | 82/72 |
| 124 | 0.019 | ND | 0.014 | 73/68 |
| 125 | 0.021 | ND | — | 34/49 |
| 126 | 0.032 | ND | 0.012 | 79/76 |
| 127 | 0.764 | >10 | 0.126 | 17/19 |
| 128 | 0.128 | >10 | 0.070 | ND |
| 129 | ND | >10 | ND | ND |
| 132 | 0.005 | >10 | 0.021 | 81/80 |
| 133 | 0.040 | >10 | ND | 19/9 |
| 134 | 0.042 | >10 | 0.174 | 10/10 |
| 135 | 0.145 | >10 | 0.247 | 2/8 |
| 136 | 0.570 | >10 | 0.174 | 4/3 |
| 137 | 0.139 | >10 | 0.126 | ND |
| 138 | 0.099 | >10 | 0.065 | ND |
| 139 | ND | >10 | ND | ND |
| 140 | 0.002 | >10 | 0.002 | 85/83 |
| 141 | 0.030 | >10 | 0.194 | 88/75 |
| 142 | 0.012 | >10 | 0.120 | 72/52 |
| 143 | 0.037 | >10 | 0.102 | 37/50 |
| 144 | 0.041 | >10 | 0.152 | 68/52 |
| 145 | 0.061 | >10 | 0.123 | ND |
| 146 | 0.069 | >10 | 0.106 | ND |
| 147 | 0.032 | >10 | 0.029 | 48/<5 |
| 148 | 0.024 | >10 | 0.040 | 46/34 |
| 149 | 0.021 | >10 | >10 | ND |
| 150 | 0.016 | >10 | 0.411 | >95/>95 |
| 151 | 0.216 | >10 | 0.345 | 30/18 |
| 152 | 0.306 | >10 | 0.566 | 36/31 |
| 153 | 0.024 | >10 | 0.571 | ND |
| 154 | ND | >10 | ND | ND |
| 155 | 0.271 | >10 | 0.042 | 46/34 |
| 156 | 0.186 | >10 | 0.097 | 58/49 |
| 157 | 0.058 | >10 | 0.167 | 53/63 |
| 158 | 0.171 | >10 | 0.058 | 50/<5 |
| 160 | 0.043 | >10 | 0.178 | ND |

ND: Not determined

TABLE 3

Anticancer profileration (EC$_{50}$ in μM) in different cell lines at 144 hr-

| Compound | HEL-92.1.7 | OCI-AML3 | MV-4-11 | CCRF-CEM | MDAMB231 | A375 |
|---|---|---|---|---|---|---|
| 2 | 0.057 | 0.159 | 0.014 | 0.652 | 0.478 | 1.600 |
| 5 | 0.026 | 0.146 | 0.054 | 0.533 | 1.600 | 2.300 |
| 8 | 0.042 | 0.046 | 0.048 | 0.119 | 0.193 | 0.698 |
| 10 | 0.089 | 0.089 | 0.026 | 0.157 | 0.403 | 0.381 |
| 12 | 0.004 | 0.041 | 0.009 | 0.375 | 1.300 | 2.800 |
| 13 | 0.026 | 0.056 | 0.010 | 0.378 | 1.100 | 1.300 |
| 43 | 0.001 | 0.115 | 0.002 | 0.493 | 0.747 | 1.030 |
| 47 | 0.005 | 0.146 | 0.005 | 1.4 | 0.875 | 3.6 |
| 51 | 0.003 | 0.014 | 0.031 | ND | ND | ND |
| 52 | 0.005 | 0.022 | 0.001 | 0.371 | 0.891 | 1.7 |
| 56 | 0.01 | 0.01 | 0.007 | ND | ND | ND |
| 71 | 6.05 | 0.732 | 0.990 | ND | ND | ND |
| 72 | 4.8 | 0.573 | 0.978 | ND | ND | ND |
| 121 | 0.009 | 0.0007 | 0.004 | ND | ND | ND |

In Vivo PK Studies in Mice

All the animal experiments were approved by Institutional Animal Ethical Committee (IAEC/JDC/2015/72). Male Balb/C mice (n=24) were procured from Vivo Biotech, Hyderabad, India. The animals were housed in Jubilant Biosys animal house facility in a temperature (22±2° C.) and humidity (30-70%) controlled room (15 air changes/hour) with a 12:12 h light:dark cycles, had free access to rodent feed (Altromin Spezialfutter GmbH & Co. KG., Im Seelenkamp 20, D-32791, Lage, Germany) and water for one week before using for experimental purpose. Following ~4 h fast (during the fasting period animals had free access to water) animals were divided into two groups (n=12/group). Group I animals (27-29 g) received NCE orlaly at 10 mg/Kg (strength: 1.0 mg/mL; dose volume: 10 mL/Kg), whereas Group II animals (29-31 g) received NCE intravenously (strength: 0.1 mg/mL; dose volume: 10 mL/Kg) at 2.0 mg/Kg dose. Post-dosing serial blood samples (100 μL, sparse sampling was done and at each time point three mice were used for blood sampling) were collected using Micropipettes (Microcaps®; catalogue number: 1-000-0500) through tail vein into polypropylene tubes containing $K_2$.EDTA solution as an anti-coagulant at 0.25, 0.5, 1, 2, 4, 8, 10 and 24 (for oral study) and 0.12, 0.25, 0.5, 1, 2, 4, 8 and 24 (for intravenous study). Plasma was harvested by centrifuging the blood using Biofuge (Hereaus, Germany) at 1760 g for 5 min and stored frozen at −80±10° C. until analysis. Animals were allowed to access feed 2 h post-dosing.

The criteria for acceptance of the analytical runs encompassed the following: (i) 67% of the QC samples accuracy must be within 85-115% of the nominal concentration (ii) not less than 50% at each QC concentration level must meet the acceptance criteria (US DHHS, FDA, CDER, 2001). Plasma concentration-time data of the compound was analyzed by non-compartmental method using Phoenix WinNonlin Version 6.3 (Pharsight Corporation, Mountain View, Calif.).

TABLE 2

| | | | | In vivo PK data | | | | |
|---|---|---|---|---|---|---|---|---|
| Compound | Dose mg/kg IV/PO | $C_0$- ng/mL IV | $C_{Max}$- ng/mL IV/PO | AUC ng/mL/hr IV/PO | $t_{1/2}$-hr IV/PO | Cl mL/min/Kg IV | $V_d$ L/Kg IV | F % |
| 57 | 2/10 | 260 | 254/217 | 169/677 | 1.71/1.83 | 190 | 28 | 80 |
| 115A | 2/10 | 452 | 452/354 | 301/638 | 0.87/2.78 | 108 | 8 | 43 |
| 142 | 2/50 | 198 | 150/555 | 357/3217 | 12.6/6.7 | 88 | 25 | 36 |
| 61 | 10/50 | 5340 | 2758/771 | 1287/1920 | 2.80/1.48 | 125 | 30 | 30 |

Expression of Biomarkers Assessed by Western Blotting

Cell lysates were prepared in RIPA buffer (150 mM Tris-HCl, 150 mM NaCl, 1% NP-40, 0.5% sodium deoxycholate, 0.1% SDS, 0.5 mM PMSF, 1× protease inhibitor cocktail) and 5-10 ug of protein was loaded for SDS-PAGE. Proteins were then transferred to a nitrocellulose membrane and then probed with respective antibodies. The bands of interest were visualized by chemiluminescence. Antibodies used were $H_3K4$ mono, di and tri methyl from Abcam, Acetyl alpha tubulin and acetyl histone (K9) from Cell signaling technologies.

Expression of Biomarkers Assessed by qPCR

RNA was extracted from cells or tumor samples using the TRI reagent (manufacturer's protocol). Generally 1 μg RNA per sample is used with 10 mM dNTPs and 50 μM Random primers (Thermo). The samples are kept at 65° C. for 5 minutes, then 1 min on ice and then the master mix (5× strand buffer, 0.1M DTT, RNase out inhibitor, Superscript) is added to each sample anth then the RT reaction is completed in a PCR machine (25° C.-5 min, 50° C.-60 min, 70° C.-15 min). The 25-30 ng of cDNA thus prepared is used for the QPCR using respective primers for CD86, CD11b, GFi1B and β actin. The SYBR Green qPCR plate is set up according to the manufacturer's protocols.

Xenograft Studies

Tumor CellImplantation and Randomization of Animals

Five million (5×10$^6$) cells in 100 μl of serum free medium were mixed with equal amount of matrigel and the entire the mixture was injected subcutaneously at the right flank region. The tumors were measured with Vernier calipers periodically after first week of injection. When the tumor volume reached 120-150 mm$^3$ (3-4 weeks after injection) the animals were randomized into different groups so that their tumor volume is approximately similar in all groups.

Determination of In Vivo Efficacy and Tumor Growth Inhibition

For PO dosing, the compounds were prepared in the formulation containing 0.5% Methyl cellulose and 0.01% Tween 80. Animals were dosed with compounds prepared in specific formulations at the required doses. Tumors size and body weights were measured twice or thrice a week. Tumors were harvested at the end of the study after euthanizing the animals according to approved protocols. From the harvested tumor one part was snap frozen and given for PK studies and the other half was homogenized and the lysates were tested for target inhibition using western blotting. Before the tumor was harvested, blood (~200 μL) was collected by ocular bleeding for PK studies. Changes in tumor volume (Δ volumes) for each treated (T) and control (C) group were calculated by subtracting the mean tumor volume on the first day of treatment (starting day) from the mean tumor volume on the specified observation day. These values were used to calculate a percentage growth (% T/C) using the formula:

% T/C=(ΔT/ΔC)×100 where ΔT>0, or

% T/C=(ΔT/ΔTi)×100

Where ΔT<0 and Ti is the mean tumor volume at the start of the experiment.

Percentage tumor growth inhibition was calculated as [100−% T/C].

We claim:

1. A compound of Formula (I) or a stereoisomer, pharmaceutically acceptable salt, complex, hydrate, solvate, tautomer, polymorph, racemic mixture, and optically active form thereof, wherein the compound of Formula (I) is selected from a group consisting of:
   1) (E)-3(4(((2(4cyclopropylphenyl)cyclopropyl)amino) methyl)phenyl)-N-hydroxyacrylamide TFA salt;
   2) (E)-3-(4-{[2-(4-Fluoro-phenyl)-cyclopropylamino]-methyl}-phenyl)-N-hydroxy-acrylamide TFA salt;
   3) (E)-3-(4-(((2-(4-((4-fluorobenzyl)oxy)phenyl)cyclopropyl)amino)methyl)phenyl)-N-hydroxyacrylamide TFA salt;
   4) (E)-N-hydroxy-3-(4-(4-(((2-phenylcyclopropyl) amino)methyl)piperidin-1-yl)phenyl) acrylamide TFA salt;
   5) (E)-3-(4-(((2-(4'-chloro-[1,1'-biphenyl]-4-yl)cyclopropyl)amino)methyl)phenyl)-N-hydroxyacrylamide TFA salt;
   6) (E)-3-(4-(((2-(4-(3,5-dimethylisoxazol-4-yl)phenyl) cyclopropyl)amino)methyl)phenyl)-N-hydroxyacrylamide TFA salt;
   7) (E)-N-hydroxy-3-(4-(((2-(4-(pyrimidin-5-yl)phenyl) cyclopropyl)amino)methyl)phenyl) acrylamide TFA salt;
   8) 2-(4-(((2-(4-fluorophenyl)cyclopropyl)amino)methyl) piperidin-1-yl)-N-hydroxy pyrimidine-5-carboxamide TFA salt;
   9) 2-[4-(2-Phenyl-cyclopropylamino)-piperidin-1-yl]-pyrimidine-5-carboxylicacid hydroxyamide TFA salt;
   10) 2-{4-[2-(4-Fluoro-phenyl)-cyclopropylamino]-piperidin-1-yl}-pyrimidine-5-carboxylic acid hydroxyamide TFA salt;
   11) 2-(4-(((2-(4-((4-fluorobenzyl)oxy)phenyl)cyclopropyl)amino)methyl)piperidin-1-yl)-N-hydroxypyrimidine-5-carboxamide TFA salt;
   12) 2-(4-((2-(4-((4-fluorobenzyl)oxy)phenyl)cyclopropyl)amino)piperidin-1-yl)-N-hydroxypyrimidine-5-carboxamide TFA salt;
   13) 2-(4-((2-(4'-chloro-[1,1'-biphenyl]-4-yl)cyclopropyl) amino)piperidin-1-yl)-N-hydroxypyrimidine-5-carboxamide TFA salt;
   14) 2-(4-(((2-(4'-chloro-[1,1'-biphenyl]-4-yl)cyclopropyl) amino)methyl)piperidin-1-yl)-N-hydroxypyrimidine-5-carboxamide TFA salt;

15) 2-(4-(((2-(4'-fluoro-[1,1'-biphenyl]-4-yl)cyclopropyl)amino)methyl)piperidin-1-yl)-N-hydroxypyrimidine-5-carboxamide TFA salt;
16) 2-(4-(((2-(4-(3,5-dimethylisoxazol-4-yl)phenyl)cyclopropyl)amino)methyl)piperidin-1-yl)-N-hydroxypyrimidine-5-carboxamide TFA salt;
17) N-hydroxy-2-(4-(((2-(4-(pyrimidin-5-yl)phenyl)cyclopropyl)amino)methyl)piperidin-1-yl)pyrimidine-5-carboxamide TFA salt;
18) N-hydroxy-2-(4-(((2-(4-methoxyphenyl)cyclopropyl)amino)methyl)piperidin-1-yl)pyrimidine-5-carboxamide TFA salt;
19) N-hydroxy-2-(4-((2-(4-methoxyphenyl)cyclopropyl)amino)piperidin-1-yl)pyrimidine-5-carboxamide TFA salt;
20) 2-(4-((((1R,2S)-2-(4-fluorophenyl)cyclopropyl)amino)methyl)piperidin-1-yl)-N-hydroxypyrimidine-5-carboxamide TFA salt;
21) 2-(4-((((1S,2R)-2-(4-fluorophenyl)cyclopropyl)amino)methyl)piperidin-1-yl)-N-hydroxypyrimidine-5-carboxamide TFA salt;
22) 4-(4-(((2-(4-fluorophenyl)cyclopropyl)amino)methyl)piperidin-1-yl)-N-hydroxybenzamide TFA salt;
23) N-hydroxy-2-(2-(((2-phenylcyclopropyl)amino)methyl)-5,6-dihydroimidazo[1,2-a]pyrazin-7(8H)-yl)pyrimidine-5-carboxamide TFA salt;
24) N-hydroxy-2-(2-(((2-(4-methoxyphenyl)cyclopropyl)amino)methyl)-5,6-dihydroimidazo[1,2-a]pyrazin-7(8H)-yl)pyrimidine-5-carboxamide TFA salt;
25) 2-(2-(((2-(4-fluorophenyl)cyclopropyl)amino)methyl)-5,6-dihydroimidazo[1,2-a]pyrazin-7(8H)-yl)-N-hydroxypyrimidine-5-carboxamide TFA salt;
26) 3-(((2-(4-bromophenyl)cyclopropyl)amino)methyl)-N-hydroxybenzamide TFA salt;
27) N-hydroxy-3-(((2-phenylcyclopropyl)amino)methyl)benzamide TFA salt;
28) N-hydroxy-4-(((2-phenylcyclopropyl)amino)methyl)benzamide TFA salt;
29) N-hydroxy-6-((2-phenylcyclopropyl)amino)hexanamide TFA salt;
30) 4-(3-((2-(4-fluorophenyl)cyclopropyl)amino)propyl)-N-hydroxybenzamide TFA salt;
31) N-(6-Hydroxycarbamoyl-hexyl)-4-[(2-phenyl-cyclopropylamino)-methyl]-benzamide TFA salt;
32) 4-(((2-(4-fluorophenyl)cyclopropyl)amino)methyl)-N-(7-(hydroxyamino)-7-oxoheptyl)benzamide TFA salt;
33) 4-(2-Phenyl-cyclopropylamino)-cyclohexanecarboxylic acid hydroxyamide TFA salt;
34) (1S,4R)-N-hydroxy-4-((1S)-1-((2phenylcyclopropyl)amino)ethyl)cyclohexanecarboxamide TFA salt;
35) N-hydroxy-4-((4-(((2-(4-(1-methyl-6-oxo-1,6-dihydropyridin-3-yl)phenyl)cyclopropyl)amino)methyl)piperidin-1-yl)methyl)benzamide TFA salt;
36) N-Hydroxy-4-{4-[(2-phenyl-cyclopropylamino)-methyl]-piperidin-1-ylmethyl}-benzamide TFA salt;
37) 4-((4-(((2-(4-(3,5-dimethylisoxazol-4-yl)phenyl)cyclopropyl)amino)methyl)piperidin-1-yl) methyl)-N-hydroxybenzamide TFA salt;
38) N-hydroxy-4-((4-(((2-(4-(pyrimidin-5-yl)phenyl)cyclopropyl)amino)methyl)piperidin-1-yl)methyl)benzamide TFA salt;
39) 6-((4-(((2-(4-(3,5-dimethylisoxazol-4-yl)phenyl)cyclopropyl)amino)methyl)piperidin-1-yl)methyl)-N-hydroxynicotinamide TFA salt;
40) N-hydroxy-4-((4-(((2-phenylcyclopropyl)amino)methyl)-1H-pyrazol-1-yl)methyl) benzamide TFA salt;
41) N-hydroxy-4-((4-(((2-phenylcyclopropyl)amino)methyl)-1H-1,2,3-triazol-1-yl) methyl)benzamide TFA salt;
42) N-hydroxy-4-(4-(((2-phenylcyclopropyl)amino)methyl)piperidin-1-yl)ethyl)benzamide TFA salt;
43) N-hydroxy-4-(3-(4-(((2-phenylcyclopropyl)amino)methyl)piperidin-1-yl)propyl)benzamide TFA salt;
44) N-hydroxy-4-(3-(4-((2-phenylcyclopropyl)amino)piperidin-1-yl)propyl)benzamide TFA salt;
45) N-hydroxy-4-(3-(4-((methyl (2-phenylcyclopropyl) amino) methyl) piperidin-1-yl) propyl)benzamide TFA salt;
46) N-hydroxy-4-(3-(6-((2-phenylcyclopropyl)amino)-2-azaspiro[3.3]heptan-2-1)propyl) benzamide TFA salt;
47) 4-[3-(4-{[2-(4-Fluoro-phenyl)-cyclopropylamino]-methyl}-piperidin-1-yl)-propyl]-N-hydroxy-benzamide TFA salt;
48) 4-(3-(3-(((2-(4-fluorophenyl)cyclopropyl)amino)methyl)azetidin-1-yl)propyl)-N-hydroxy benzamide TFA salt;
49) 4-(3-(4-(((2-(3-fluorophenyl)cyclopropyl)amino)methyl)piperidin-1-yl)propyl)-N-hydroxy benzamide TFA salt;
50) 4-(3-(4-(((2-(3,4-difluorophenyl)cyclopropyl)amino)methyl)piperidin-1-yl)propyl)-N-hydroxybenzamide TFA salt;
51) N-hydroxy-4-(3-(4-(((2-(4-methoxyphenyl)cyclopropyl)amino)methyl)piperidin-1-yl)propyl)benzamide TFA salt;
52) N-hydroxy-4-(3-(4-(((2-(4-(morpholine-4-carbonyl)phenyl)cyclopropyl)amino)methylpiperidin-1-yl)propyl)benzamide TFA salt;
53) N-hydroxy-4-(3-(4-(((2-(4-(morpholine-4-carbonyl)phenyl)cyclopropyl)amino)methyl)piperidin-1-yl)propyl)benzamide TFA salt;
54) N-hydroxy-4-(3-(4-(((2-(4-(piperidine-1-carbonyl)phenyl)cyclopropyl)amino)methyl)piperidin-1-yl)propyl)benzamide TFA salt;
55) N-(2-(dimethylamino)ethyl)-4-(2-(((1-(3-(4-(hydroxycarbamoyl)phenyl)propyl)piperidin-4-yl)methyl)amino)cyclopropyl)benzamide TFA salt;
56) 4-(3-(4-(((2-(4'-chloro-[1,1'-biphenyl]-4-yl)cyclopropyl)amino)methyl)piperidin-1-yl)propyl)-N-hydroxybenzamide TFA salt;
57) 4-(3-(4-(((2-(4'-fluoro-[1,1'-biphenyl]-4-yl)cyclopropyl)amino)methyl)piperidin-1-yl)propyl)-N-hydroxybenzamide TFA salt;
58) 4-(3-(3-(((2-(4'-fluoro-[1,1'-biphenyl]-4-yl)cyclopropyl)amino)methyl)azetidin-1-yl) propyl)-N-hydroxybenzamide;
59) 4-(3-(4-(((2-(4'-cyano-[1,1'-biphenyl]-4-yl)cyclopropyl)amino)methyl)piperidin-1-yl)propyl)-N-hydroxybenzamideTFA salt;
60) N-hydroxy-4-(3-(4-(((2-(4-(1-methyl-2-oxo-1,2-dihydropyridin-4-yl)phenyl)cyclopropyl) amino)methyl)piperidin-1-yl)propyl)benzamide TFA salt;
61) N-hydroxy-4-(3-(4-(((2-(4-(pyrimidin-5-yl)phenyl)cyclopropyl)amino)methyl)piperidin-1-yl)propyl)benzamide TFA salt;
62) N-hydroxy-4-(3-(4-(((2-(4-(1-methyl-1H-pyrazol-4-yl)phenyl)cyclopropyl)amino) methyl)piperidin-1-yl) propyl) benzamide TFA salt;
63) N-hydroxy-4-(3-3-(((2-(4-(1-methyl-1H-pyrazol-4-yl)phenyl)cyclopropyl)amino) methyl) azetidin-1-yl) propyl)benzamide;

64) 4-(3-(4-(((2-(4-(3,5-dimethylisoxazol-4-yl)phenyl)cyclopropyl)amino)methyl)piperidin-1-yl)propyl)-N-hydroxybenzamide TFA salt;
65) 3-(3-(3-(((2-(4-(3,5-dimethylisoxazol-4-yl)phenyl)cyclopropyl)amino)methyl)azetidin-1-yl)propyl)-N-hydroxybenzamide TFA salt;
66) N-hydroxy-4-(3-(4-(((2-(4-(6-(trifluoromethyl)pyridin-3-yl)phenyl)cyclopropyl)amino)methyl)piperidin-1-yl)propyl)benzamide TFA salt;
67) N-hydroxy-4-(3-(4-(((2-(1-isopropyl-1H-pyrazol-4-yl)cyclopropyl)amino)methyl)piperidin-1-yl)propyl)benzamide TFA salt;
68) N-hydroxy-4-(3-(4-(((2-(1-phenyl-1H-pyrazol-4-yl)cyclopropyl)amino)methyl)piperidin-1-yl)propyl)benzamide TFA salt;
69) N-hydroxy-4-(3-(4-(((2-(2-methylthiazol-5-yl)cyclopropyl)amino)methyl)piperidin-1-yl)propyl)benzamide TFA salt;
70) N-hydroxy-4-(3-(4-(((2-(pyridin-3-yl)cyclopropyl)amino)methyl)piperidin-1-yl)propyl) benzamide TFA salt;
71) N-hydroxy-4-(3-(2-(((2-(4-methoxyphenyl)cyclopropyl)amino)methyl)-5,6-dihydroimidazo[1,2-a]pyrazin-7(8H)-yl)propyl)benzamide TFA salt;
72) 4-(3-(2-(((2-(4-fluorophenyl)cyclopropyl)amino)methyl)-5,6-dihydroimidazo[1,2-a]pyrazin-7(8H)-yl)propyl)-N-hydroxybenzamide TFA salt;
73) 4-(3-(4-(((2-(3,4-difluorophenyl)cyclopropyl)amino)methyl)-1H-imidazol-1-yl) propyl)-N-hydroxybenzamide TFA salt;
74) N-hydroxy-4-(3-(4-(((2-phenylcyclopropyl)amino)methyl)-1H-imidazol-1-yl)propyl) benzamide TFA salt;
75) N-hydroxy-4-(3-(4-(((2-phenylcyclopropyl)amino)methyl)-1H-imidazol-1-yl)propyl) benzamide;
76) N-hydroxy-4-(3-(4-(((2-phenylcyclopropyl)amino)methyl)-1H-pyrazol-1-yl)propyl) benzamide TFA salt;
77) N-hydroxy-4-(3-(4-(((2-phenylcyclopropyl)amino)methyl)-1H-1,2,3-triazol-1-yl)propyl)benzamide TFA salt;
78) 4-(3-(6-(((2-(4-fluorophenyl)cyclopropyl)amino)methyl)-3,4-dihydroisoquinolin-2-(1H)-yl)propyl)-N-hydroxybenzamide TFA salt;
79) 4-((7-(((2-(4-fluorophenyl)cyclopropyl)amino)methyl)-3,4-dihydroisoquinolin-2(1H)-yl)methyl)-N-hydroxybenzamide TFA salt;
80) 4-((2-(((2-(4-fluorophenyl)cyclopropyl)amino)methyl)-5,6-dihydroimidazo[1,2-a]pyrazin-7 (8H)-yl)methyl)-N-hydroxybenzamide TFA salt;
81) N-hydroxy-4-(3-(4(((2-(1,3,3,-trimethyl-2-oxoindoline-5-yl)cyclopropyl)amino)methyl) piperidine-1-yl)propyl)benzamide TFA salt;
82) N-hydroxy-4-(3-oxo-3-(4-(((2-phenylcyclopropyl)amino)methyl)piperidin-1-yl)propyl)benzamide TFA salt;
83) N-hydroxy-4-(3-oxo-3-(4-((2-phenylcyclopropyl)amino)piperidin-1-yl)propyl)benzamide TFA salt;
84) N-hydroxy-4-(2-oxo-2-(4-(((2-phenylcyclopropyl)amino)methyl)piperidin-1-yl)ethyl) benzamide TFA salt;
84A. N-hydroxy-4-(2-oxo-2-(4-((((1R,2S)-2-phenylcyclopropyl)amino)methyl)piperidin-1-yl) ethyl)benzamide;
84B. N-hydroxy-4-(2-oxo-2-(4-((((1S,2R)-2-phenylcyclopropyl)amino)methyl)piperidin-1-yl) ethyl)benzamide;
85) N-hydroxy-4-((4-(((2-phenylcyclopropyl)amino)methyl)piperidin-1-yl)sulfonyl) benzamide TFA salt;
86) N-hydroxy-4-((N-(2-(4-(((2-phenylcyclopropyl)amino)methyl)piperidin-1-yl)ethyl) sulfamoyl)methyl)benzamide TFA salt;
87) 4-(N-(2-(4-(((2-(4-fluorophenyl)cyclopropyl)amino)methyl)piperidin-1-yl)ethyl) sulfamoyl)-N-hydroxybenzamide;
88) N-hydroxy-4-(2-((4-(((2-phenylcyclopropyl)amino)methyl)piperidin-1-yl)sulfonyl)ethyl) benzamide TFA salt;
89) N-hydroxy-N4-(2-(4-(((2-phenylcyclopropyl)amino)methyl)piperidin-1-yl)ethyl) terephthalamide TFA salt;
90) N1-(2-(4-(((2-(3,4-difluorophenyl)cyclopropyl)amino)methyl)piperidin-1-yl)ethyl)-N4-hydroxyterephthalamide TFA salt;
91) N-hydroxy-4-((4-(2-((2-phenylcyclopropyl)amino)acetyl)piperazin-1-yl)methyl)benzamide TFA salt;
92) N-hydroxy-4-(3-oxo-3-(4-(2-((2-phenylcyclopropyl)amino)acetyl)piperazin-1-yl)propyl)benzamide TFA salt;
93) N-hydroxy-4-(3-(1-(2-((2-phenylcyclopropyl)amino)acetyl)piperidin-4-yl)propyl)benzamide TFA salt;
94) N-hydroxy-4-(3-2-oxo-4-(((2-phenylcyclopropyl)amino)methyl)piperidin-1-yl) propyl)benzamide TFA salt;
95) N-hydroxy-4-(2-((2-phenylcyclopropyl)amino)ethoxy)benzamide TFA salt;
96) 6-(2-(4-(((2-(4-fluorophenyl)cyclopropyl)amino)methyl)piperidin-1-yl)ethoxy)-N-hydroxynicotinamide TFA salt;
97) N-hydroxy-6-(2-(4-(((2-phenylcyclopropyl)amino)methyl)piperidin-1-yl)ethoxy)nicotinamide TFA salt;
98) 6-(2-(4-(((2-(4'-fluoro-[1,1'-biphenyl]-4-yl)cyclopropyl)amino)methyl)piperidin-1-yl) ethoxy)-N-hydroxynicotinamide TFA salt;
99) N-hydroxy-4-(2-(4-(((2-phenylcyclopropyl)amino)methyl)piperidin-1-yl)ethoxy)benzamide TFA salt;
100) N-hydroxy-4-(3-(4-(((2-phenylcyclopropyl)amino)methyl)piperidin-1-yl)propoxy)benzamide TFA salt;
101) N-hydroxy-4-(3-((2-phenylcyclopropyl)amino)propoxy)benzamide TFA salt;
102) 2-((2-(4-(((2-(4-fluorophenyl)cyclopropyl)amino)methyl)piperidin-1-yl)ethyl)amino)-N-hydroxypyrimidine-5-carboxamide TFA salt;
103) 5-(2-((2-(4-fluorophenyl)cyclopropyl)amino)acetyl)-N-hydroxy-4,5,6,7-tetrahydro thieno[3,2-c]pyridine-2-carboxamide TFA salt;
103A) 5-(2-(((1R,2S)-2-(4-fluorophenyl)cyclopropyl)amino)acetyl)-N-hydroxy-4,5,6,7-tetrahydrothieno[3,2-c]pyridine-2-carboxamide;
103B) 5-(2-(((1S,2R)-2-(4-fluorophenyl)cyclopropyl)amino)acetyl)-N-hydroxy-4,5,6,7-tetrahydrothieno[3,2-c]pyridine-2-carboxamide;
104) 2-(2-((2-(4-fluorophenyl)cyclopropyl)amino)acetyl)-N-hydroxy-1,2,3,4-tetrahydro isoquinoline-7-carboxamide TFA salt;
104A) 2-(2-(((1S,2R)-2-(4-fluorophenyl)cyclopropyl)amino)acetyl)-N-hydroxy-1,2,3,4-tetrahydroisoquinoline-7-carboxamide;
104B) 2-(2-(((1R,2S)-2-(4-fluorophenyl)cyclopropyl)amino)acetyl)-N-hydroxy-1,2,3,4-tetrahydroisoquinoline-7-carboxamide;
105) 5-(4-((2-(4-fluorophenyl)cyclopropyl)amino)butanoyl)-N-hydroxy-4,5,6,7-tetrahydro thieno[3,2-c]pyridine-2-carboxamide TFA salt;

106) 5-(4-(4-(((2-(4-fluorophenyl)cyclopropyl)amino) methyl)piperidin-1-yl)butanoyl)-N-hydroxy-4,5,6,7-tetrahydrothieno[3,2-c]pyridine-2-carboxamide TFA salt;
107) 2-(4-((2-(4-fluorophenyl)cyclopropyl)amino)butanoyl)-N-hydroxy-1,2,3,4-tetrahydro isoquinoline-7-carboxamide TFA salt;
108) 2-(4-((2-(4-fluorophenyl)cyclopropyl)amino)butanoyl)-N-hydroxyisoindoline-5-carboxamide TFA salt;
109) N-hydroxy-2-(4-(4-(((2-phenylcyclopropyl)amino) methyl)piperidin-1-yl)butanoyl) isoindoline-5-carboxamide TFA salt;
110) N-hydroxy-2-(3-(4-(((2-phenylcyclopropyl)amino) methyl)piperidin-1-yl)propyl) thiazole-4-carboxamide TFA salt;
111) 2-(3-(4-(((2-(4'-fluoro-[1,1'-biphenyl]-4-yl)cyclopropyl)amino)methyl)piperidin-1-yl)propyl)-N-hydroxythiazole-4-carboxamide;
112) N-hydroxy-2-(3-(4-(((2-phenylcyclopropyl)amino) methyl)piperidin-1-yl)propyl) thiazole-5-carboxamide TFA salt;
113) N-hydroxy-2-(3-(4-(((2-phenylcyclopropyl)amino) methyl)piperidin-1-yl)propyl) oxazole-4-carboxamide;
114) (E)-N-hydroxy-4-(3-oxo-3-(4-(((2-phenylcyclopropyl)amino)methyl)piperidin-1-yl) prop-1-en-1-yl)benzamide TFA salt;
114A) N-hydroxy-4-((E)-3-oxo-3-(4-((((1R,2S)-2-phenylcyclopropyl)amino)methyl) piperidin-1-yl)prop-1-en-1-yl)benzamide TFA salt;
114B) N-hydroxy-4-((E)-3-oxo-3-(4-((((1S,2R)-2-phenylcyclopropyl)amino)methyl) piperidin-1-yl)prop-1-en-1-yl)benzamide TFA salt;
115) 4-((E)-3-(4-((((1S,2R)-2-(4-fluorophenyl)cyclopropyl)amino)methyl) piperidin-1-yl)-3-oxoprop-1-en-1-yl)-N-hydroxybenzamide TFA salt;
115A) 4-((E)-3-(4-((((1S,2R)-2-(4-fluorophenyl)cyclopropyl)amino)methyl) piperidin-1-yl)-3-oxoprop-1-en-1-yl)-N-hydroxybenzamide TFA salt;
116) (E)-4-(3-(4-(((2-(4-(3,5-dimethylisoxazol-4-yl)phenyl)cyclopropyl)amino)methyl) piperidin-1-yl)-3-oxoprop-1-en-1-yl)-N-hydroxybenzamide TFA salt;
117) (E)-N-hydroxy-4-(3-oxo-3-(4-(((2-(4-(pyrimidin-5-yl)phenyl)cyclopropyl)amino) methyl)piperidin-1-yl) prop-1-en-1-yl)benzamide TFA salt;
118) (E)-4-(3-(3-(((2-(4-fluorophenyl)cyclopropyl) amino)methyl)azetidin-1-yl)-3-oxoprop-1-en-1-yl)-N-hydroxybenzamide TFA salt;
119) (E)-N-hydroxy-4-(3-(3-(((2-(4-(1-methyl-1H-pyrazol-4-yl)phenyl)cyclopropyl)amino)methyl)azetidin-1-yl)-3-oxoprop-1-en-1-yl)benzamide TFA salt;
120) (E)-N-(2-aminophenyl)-3-(4-(((2-(4-fluorophenyl) cyclopropyl)amino)methyl)phenyl)acrylamide TFA salt;
121) N-(2-aminophenyl)-4-(3-(4-(((2-phenylcyclopropyl) amino)methyl)piperidin-1-yl)propyl)benzamide TFA salt;
122) N-(2-aminophenyl)-4-(3-(4-(((2-(4-fluorophenyl) cyclopropyl)amino)methyl)piperidin-1-yl)propyl)benzamide TFA salt;
123) N-(2-aminophenyl)-4-(3-(4-(((2-(4-methoxyphenyl) cyclopropyl)amino)methyl)piperidin-1-yl)propyl)benzamide TFA salt;
124) N-(2-aminophenyl)-4-(3-(4-(((2-(3,4-difluorophenyl)cyclopropyl)amino)methyl) piperidin-1-yl)propyl)benzamide TFA salt;
125) N-(2-aminophenyl)-4-(3-(4-(((2-(4-(piperidine-1-carbonyl)phenyl)cyclopropyl)amino)methyl)piperidin-1-yl)propyl)benzamide TFA salt;
126) N-(2-aminophenyl)-4-(3-(3-(((2-(4-fluorophenyl) cyclopropyl)amino)methyl)azetidin-1-yl) propyl)benzamide TFA salt;
127) N-(2-aminophenyl)-4-(3-(6-((2-phenylcyclopropyl) amino)-2-azaspiro[3.3]heptan-2-yl)propyl)benzamide TFA salt;
128) N-(2-aminophenyl)-4-(3-(4-(((2-(1-isopropyl-1H-pyrazol-4-yl)cyclopropyl)amino)methyl)piperidin-1-yl)propyl)benzamide TFA salt;
129) N-(2-aminophenyl)-4-(3-(4-(((2-(1-phenyl-1H-pyrazol-4-yl)cyclopropyl)amino)methyl)piperidin-1-yl)propyl)benzamide TFA salt;
130) N-(2-aminophenyl)-4-(3-(4-(((2-(2-methylthiazol-5-yl)cyclopropyl)amino)methyl) piperidin-1-yl)propyl) benzamide TFA salt;
131) N-(2-aminophenyl)-4-(3-(4-(((2-(pyridin-3-yl)cyclopropyl)amino)methyl)piperidin-1-yl)propyl)benzamide TFA salt;
132) N-(2-amino-5-fluorophenyl)-4-(3-(4-(((2-(4-fluorophenyl)cyclopropyl)amino)methyl)piperidin-1-yl)propyl)benzamide TFA salt;
133) N-(2-aminophenyl)-4-(3-oxo-3-(4-((2-phenylcyclopropyl)amino)methyl)piperidin-1-yl)propyl)benzamide TFA salt;
134) N-(2-aminophenyl)-4-(3-oxo-3-(4-(((2-phenylcyclopropyl)amino)methyl)piperidin-1-yl)propyl)benzamide TFA salt;
135) N-(2-aminophenyl)-4-(3-(4-(((2-(3,4-difluorophenyl)cyclopropyl)amino)methyl)-1H-imidazol-1-yl)propyl)benzamide TFA salt;
136) N-(2-aminophenyl)-4-(3-(4-(((2-phenylcyclopropyl) amino)methyl)-1H-imidazol-1-yl)propyl)benzamide;
137) N-(2-aminophenyl)-4-(3-(4-(((2-phenylcyclopropyl) amino)methyl)-1H-1,2,3-triazol-1-yl)propyl)benzamide TFA salt;
138) N-(2-aminophenyl)-4-(3-(4-(((2-phenylcyclopropyl) amino)methyl)-1H-pyrazol-1-yl)propyl)benzamide-TFA salt;
139) N-(2-aminophenyl)-4-(2-(4-(((2-phenylcyclopropyl) amino)methyl)piperidin-1-yl) ethyl)benzamide TFA salt;
140) N-(2-aminophenyl)-4-((4-((((1R,2S)-2-phenylcyclopropyl)amino)methyl)piperidin-1-yl) methyl)benzamide TFA salt;
141) N-(2-aminophenyl)-4-((4-(((2-(4-(1-methyl-6-oxo-1,6-dihydropyridin-3-yl)phenyl) cyclopropyl)amino) methyl)piperidin-1-yl)methyl)benzamide TFA salt;
142) N-(2-aminophenyl)-4-((4-(((2-(4-(1-methyl-1H-pyrazol-4-yl)phenyl)cyclopropyl)amino)methyl)piperidin-1-yl)methyl)benzamide TFA salt;
143) N-(2-aminophenyl)-4-((4-(((2-(4-(3,5-dimethylisoxazol-4-yl)phenyl)cyclopropyl)amino) methyl)piperidin-1-yl)methyl)benzamide TFA salt;
144) N-(2-aminophenyl)-4-((4-(((2-(4-(pyrimidin-5-yl) phenyl)cyclopropyl)amino)methyl)piperidin-1-yl) methyl)benzamide TFA salt;
145) N-(2-aminophenyl)-4-((4-(((2-phenylcyclopropyl) amino)methyl)-1H-pyrazol-1-yl)methyl)benzamide TFA salt;
146) N-(2-aminophenyl)-4-((4-(((2-phenylcyclopropyl) amino)methyl)-1H-1,2,3-triazol-1-yl)methyl)benzamide TFA salt;

147) N-(2-aminophenyl)-4-(2-(4-(((2-(4-fluorophenyl)cyclopropyl)amino)methyl)piperidin-1-yl)-2-oxoethyl)benzamide TFA salt;
148) N-(2-aminophenyl)-4-(2-((2-(4-fluorophenyl)cyclopropyl)amino)ethoxy)benzamide TFA salt;
149) N-(2-aminophenyl)-6-(2-(4-(((2-(4-fluorophenyl)cyclopropyl)amino)methyl)piperidin-1-yl)ethoxy)nicotinamide TFA salt;
150) N-(-2-aminophenyl)-2-((2-4(((2-(4-flurophenyl)cyclopropyl)amino)methyl)piperdine-1-yl)ethyl)amino)pyrimidine-5-carboxamide TFA salt;
151) N-(2-aminophenyl)-5-((2-(4-fluorophenyl)cyclopropyl)glycyl)-4,5,6,7-tetrahydrothieno[3,2-c]pyridine-2-carboxamide TFA salt;
152) N-(2-aminophenyl)-2-(2-((2-(4-fluorophenyl)cyclopropyl)amino)acetyl)-1,2,3,4-tetrahydroisoquinoline-7-carboxamide TFA salt;
153) N-(2-aminophenyl)-2-(3-(4-(((2-phenylcyclopropyl)amino)methyl)piperidin-1-yl)propyl)oxazole-4-carboxamide TFA salt;
154) N-(2-aminophenyl)-2-(3-(4-(((2-phenylcyclopropyl)amino)methyl)piperidin-1-yl)propyl)thiazole-5-carboxamide TFA salt;
155) N-(2-aminophenyl)-4-((2-((2-(4-fluorophenyl)cyclopropyl)amino)acetamido) methyl)benzamide TFA salt;
156) (E)-N-(2-aminophenyl)-4-(3-(4-(((2-(4-fluorophenyl)cyclopropyl)amino)methyl)piperidin-1-yl)-3-oxoprop-1-en-1-yl)benzamide TFA salt;
157) (E)-N-(2-aminophenyl)-4-(3-(3-(((2-(4-fluorophenyl)cyclopropyl)amino)methyl)azetidin-1-yl)-3-oxoprop-1-en-1-yl)benzamide TFA salt;
158) N-(4-((2-aminophenyl)carbamoyl)benzyl)-4-(((2-(4-fluorophenyl)cyclopropyl)amino)methyl)piperidine-1-carboxamide TFA salt;
159) N-(2-aminophenyl)-4-(3-(2-oxo-4-(((2-phenylcyclopropyl)amino)methyl)piperidin-1-yl)propyl)benzamide;
160) N-(2-aminophenyl)-4-((4-(((2-phenylcyclopropyl)amino)methyl)piperidin-1-yl)sulfonyl) benzamide TFA salt;
161) N-(2-aminophenyl)-4-(((4-(((2-phenylcyclopropyl)amino)methyl)piperidin-1-yl)sulfonyl)methyl)benzamide TFA salt;
162) N-(2-aminophenyl)-4-(2-((4-(((2-phenylcyclopropyl)amino)methyl)piperidin-1-yl)sulfonyl)ethyl)benzamide TFA salt.

2. A process of preparation of a compound of Formula (I) as claimed in claim 1 or a tautomer, polymorph, stereoisomer, solvate, or pharmaceutically acceptable salt thereof, the process comprising the steps of Scheme 1

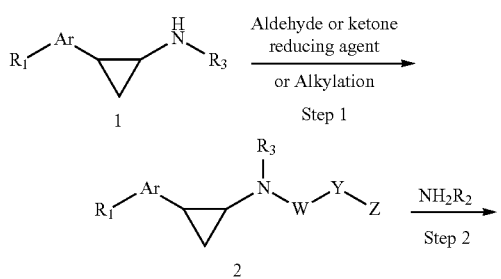

Scheme 1

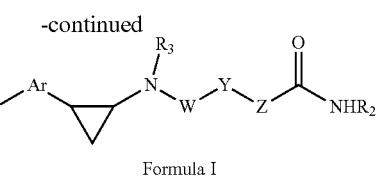

Formula I wherein:
Ar is selected from the group consisting of substituted or unsubstituted $C_{5-6}$aryl, $C_{1-6}$heteroaryl, and $C_{2-10}$heterocyclyl with heteroatoms selected from N, O, S;
W represents a bond or $CR_4R_5$, wherein $R_4$ and $R_5$ are independently selected from the group consisting of hydrogen, and substituted or unsubstituted $C_{1-8}$alkyl;
Y is selected from the group consisting of substituted or unsubstituted $C_{1-8}$alkyl, $C_{5-6}$aryl, $C_{1-6}$heteroaryl, $C_{2-10}$heterocyclyl, $C_{3-8}$cycloalkyl, and —CO—$C_{2-10}$heterocyclyl;
wherein $C_{1-8}$alkyl, $C_{5-6}$aryl, $C_{1-6}$heteroaryl, $C_{2-10}$heterocyclyl, and $C_{3-8}$cycloalkyl, is optionally substituted with one or more of the groups selected from hydrogen, $C_{1-6}$ alkyl, and oxo (=O);
Z represents a bond or is selected from the group consisting of $C_{1-8}$alkyl, $C_{2-8}$alkenyl, $C_{7-12}$-alkylaryl, $C_{7-15}$-arylalkenyl, $C_{2-12}$-alkylheteroaryl, —CO—$C_{7-12}$alkylaryl, —CO—$C_{7-12}$alkenylaryl, —CONR$_6$-$C_{1-8}$ alkyl, CONR$_6$—$C_{5-6}$aryl-, $C_{5-6}$aryl, $C_{1-6}$heteroaryl, $C_{2-10}$ heterocyclyl, —CO—$C_{2-10}$ heterocyclyl, —NR$_6$CO—$C_{5-6}$aryl-, —NR$_6$—$C_{5-6}$aryl, NR$_6$—$C_{1-6}$heteroaryl, —$C_{1-8}$alkyl-O—$C_{5-6}$aryl, —O—$C_{5-6}$aryl, O—$C_{1-6}$heteroaryl, —CONR$_6$-$C_{7-12}$alkylaryl, —SO$_2$—$C_{5-6}$aryl, —SO$_2$—$C_{7-12}$alkylaryl, —NR$_6$SO$_2$—$C_{7-12}$alkyl aryl, $C_{1-8}$alkyl-CONR$_6$—$C_{5-6}$aryl, and OCONR$_6$—$C_{5-6}$aryl;
$R_6$ is selected from the group consisting of hydrogen, and $C_{1-8}$ alkyl;
$R_1$ is selected from the group consisting of hydrogen, halogen, oxo (=O), $C_{1-8}$alkyl, $C_{1-8}$haloalkyl, $C_{1-8}$alkoxy, $C_{3-8}$cycloalkyl, $C_{5-6}$aryl, $C_{2-10}$heterocyclyl, $C_{1-6}$heteroaryl, —C(O)R$_b$, —C(O)NR$_a$R$_b$, and —OR$_a$, wherein R$_a$ and R$_b$ is independently selected from the group consisting of hydrogen, $C_{1-8}$alkyl, $C_{5-6}$aryl, $C_{7-15}$arylalkyl and $C_{2-10}$heterocyclyl with heteroatoms selected from N, O, S; and wherein $C_{1-8}$alkyl, $C_{5-6}$aryl, $C_{1-6}$heteroaryl, $C_{2-10}$heterocyclyl, and $C_{3-8}$cycloalkyl, is optionally substituted with one or more of the groups selected from hydrogen, $C_{1-6}$ alkyl, oxo(=O), halogen, and cyano;
$R_3$ is selected from the group consisting of hydrogen, and substituted or unsubstituted $C_{1-8}$alkyl;
$R_2$ is selected from the group consisting of —OR$_7$ and aniline, wherein aniline is optionally substituted with one or more halogen and $R_7$ is hydrogen;
Step 1 comprises reacting compound 1 with at least one reducing agent or at least one alkylating agent in the presence of inorganic or organic base to obtain a compound 2;
Step 2 comprises hydrolyzing the compound 2 with an inorganic base to obtain an acid;
followed by coupling the acid with at least one activating agent selected from 1-(3-dimethylaminopropyl)-3-ethylcarbodiimide hydrochloride or 1-propylphosphonic anhydride in the presence of 1-hydroxybenzotriazole or triethylamine and at least one substituted amine (NH$_2$R$_2$) to yield the compound of Formula (I).

3. A pharmaceutical composition comprising a compound of Formula (I) or a pharmaceutically acceptable salt thereof as claimed in claim 1 together with a pharmaceutically acceptable carrier, optionally in combination with one or more other pharmaceutical compositions.

4. The pharmaceutical composition as claimed in claim 3, wherein the composition is in the form selected from the group consisting of a tablet, capsule, powder, syrup, solution, aerosol and suspension.

5. A method of inhibiting LSD1 in a cell, comprising treating said cell with an effective amount of a compound as claimed in claim 1, or a pharmaceutically acceptable salt thereof.

6. A method of treating a condition mediated by LSD1 comprising administering to a subject suffering from a condition mediated by LSD1, a therapeutically effective amount of the compound as claimed in claim 1 or a pharmaceutically acceptable salt thereof, or the pharmaceutical composition according to claim 3, wherein the condition is breast cancer, prostate cancer, lung cancer, colon cancer, rectal cancer, brain tumor, non-small cell lung cancer, small cell lung cancer, liver cancer, urinary & bladder cancer, or thyroid cancer.

7. A method of treating a condition mediated by LSD1 comprising administering to a subject suffering from a condition mediated by LSD1, a therapeutically effective amount of the compound as claimed in claim 1 or a pharmaceutically acceptable salt thereof, or the pharmaceutical composition according to claim 3, wherein the condition is acute myelogenous leukemia (AML).

* * * * *